US010278942B2

(12) United States Patent
Josey et al.

(10) Patent No.: US 10,278,942 B2
(45) Date of Patent: May 7, 2019

(54) COMPOSITIONS FOR USE IN TREATING PULMONARY ARTERIAL HYPERTENSION

(71) Applicant: PELOTON THERAPEUTICS, INC., Dallas, TX (US)

(72) Inventors: John A. Josey, Dallas, TX (US); Eli M. Wallace, Richardson, TX (US); Xinlin Du, Irving, TX (US); Barry Goggin, Dallas, TX (US)

(73) Assignee: Peloton Therapeutics, Inc., Dallas, TX (US)

( * ) Notice: Subject to any disclaimer, the term of this patent is extended or adjusted under 35 U.S.C. 154(b) by 0 days.

(21) Appl. No.: 15/556,607

(22) PCT Filed: Mar. 9, 2016

(86) PCT No.: PCT/US2016/021492
§ 371 (c)(1),
(2) Date: Sep. 7, 2017

(87) PCT Pub. No.: WO2016/145032
PCT Pub. Date: Sep. 15, 2016

(65) Prior Publication Data
US 2018/0177754 A1 Jun. 28, 2018

Related U.S. Application Data

(60) Provisional application No. 62/131,783, filed on Mar. 11, 2015.

(51) Int. Cl.
| | | |
|---|---|---|
| *A61K 31/275* | (2006.01) |
| *A61K 31/185* | (2006.01) |
| *A61K 31/47* | (2006.01) |
| *A61P 9/12* | (2006.01) |
| *A61K 31/10* | (2006.01) |
| *A61K 31/381* | (2006.01) |
| *A61K 31/4245* | (2006.01) |
| *A61K 31/435* | (2006.01) |
| *A61K 31/451* | (2006.01) |

(52) U.S. Cl.
CPC .......... *A61K 31/275* (2013.01); *A61K 31/10* (2013.01); *A61K 31/185* (2013.01); *A61K 31/381* (2013.01); *A61K 31/4245* (2013.01); *A61K 31/435* (2013.01); *A61K 31/451* (2013.01); *A61K 31/47* (2013.01); *A61P 9/12* (2018.01)

(58) Field of Classification Search
CPC .... A61K 31/275; A61K 31/435; A61K 31/10; A61K 31/451; A61K 31/381; A61K 31/4245; A61P 9/12
See application file for complete search history.

(56) References Cited

U.S. PATENT DOCUMENTS

| | | |
|---|---|---|
| 4,214,103 A | 7/1980 | Garman et al. |
| 4,364,875 A | 12/1982 | Sehring et al. |
| 4,426,385 A | 1/1984 | Cain |
| 4,505,929 A | 3/1985 | Markley et al. |
| 4,665,097 A | 5/1987 | Cain |
| 4,705,955 A | 11/1987 | Mileikowsky |
| 5,059,609 A | 10/1991 | Eggler et al. |
| 5,644,024 A | 7/1997 | Abrecht et al. |
| 8,003,656 B2 | 8/2011 | Bakthavatchalam et al. |
| 9,796,697 B2 | 10/2017 | Wehn et al. |
| 9,884,843 B2 | 2/2018 | Dixon et al. |
| 2005/0070474 A1 | 3/2005 | Krissansen et al. |
| 2005/0085541 A1 | 4/2005 | Shiohara et al. |
| 2006/0058361 A1 | 3/2006 | Fliri et al. |
| 2006/0128790 A1 | 6/2006 | Chu et al. |
| 2007/0088053 A1 | 4/2007 | Mirzadegan et al. |
| 2007/0155726 A1 | 7/2007 | Arnaiz et al. |
| 2007/0244071 A1 | 10/2007 | Dennis et al. |
| 2007/0265332 A1 | 11/2007 | Ge et al. |
| 2008/0070928 A1 | 3/2008 | Nonoshita et al. |
| 2008/0312313 A1 | 12/2008 | Carballido et al. |
| 2009/0286812 A1 | 11/2009 | Erickson et al. |
| 2009/0325961 A1 | 12/2009 | Duan et al. |
| 2010/0029694 A1 | 2/2010 | Herold et al. |
| 2010/0048537 A1 | 2/2010 | Matsuoka et al. |
| 2010/0168110 A1 | 7/2010 | Chhipa et al. |
| 2011/0054173 A1 | 3/2011 | Brewster et al. |
| 2012/0295937 A1* | 11/2012 | Linehan ............... A61K 31/40 514/315 |
| 2013/0116275 A1 | 5/2013 | Van et al. |
| 2013/0137746 A1 | 5/2013 | Govek et al. |
| 2014/0057914 A1 | 2/2014 | Jones et al. |

(Continued)

FOREIGN PATENT DOCUMENTS

| | | |
|---|---|---|
| CA | 1264763 A | 1/1990 |
| CN | 101058535 A | 10/2007 |

(Continued)

OTHER PUBLICATIONS

Akincioglu, et al. Novel sulfamides as potential carbonic anhydrase isoenzymes inhibitors. Bioorg Med Chem. Mar. 15, 2013;21(6):1379-85. doi: 10.1016/j.bmc.2013.01.019. Epub Jan. 22, 2013.
Bertout, et al. HIF2alpha inhibition promotes p53 pathway activity, tumor cell death, and radiation responses. Proc Natl Acad Sci U S A. Aug. 25, 2009;106(34):14391-6. doi: 10.1073/pnas.0907357106. Epub Aug. 12, 2009.
Bhatt, et al. Hypoxia-inducible factor-2alpha: effect on radiation sensitivity and differential regulation by an mTOR inhibitor. BJU Int. Aug. 2008;102(3):358-63. doi: 10.1111/j.1464-410X.2008.07558.x. Epub Apr. 3, 2008.
Cardoso, et al. Identification of Cys255 in HIF-1α as a novel site for development of covalent inhibitors of HIF-1α/ARNT PasB domain protein-protein interaction. Protein Sci. Dec. 2012;21(12):1885-96. doi: 10.1002/pro.2172. Epub Nov. 9, 2012.

(Continued)

*Primary Examiner* — Sudhakar Katakam
(74) *Attorney, Agent, or Firm* — Wilson Sonsini Goodrich & Rosati

(57) ABSTRACT

The present disclosure provides methods of treating pulmonary arterial hypertension (PAH) in a subject in need thereof. Compositions for use in these methods are also provided.

16 Claims, 29 Drawing Sheets

(56) References Cited

U.S. PATENT DOCUMENTS

| | | |
|---|---|---|
| 2014/0073634 A1 | 3/2014 | Jones et al. |
| 2014/0128365 A1 | 5/2014 | Robl et al. |
| 2014/0148462 A1 | 5/2014 | Eckhardt et al. |
| 2014/0163025 A1 | 6/2014 | Eckhardt et al. |
| 2014/0200218 A1 | 7/2014 | Bellingham et al. |
| 2014/0371319 A1 | 12/2014 | Kazuta et al. |
| 2016/0250216 A1 | 9/2016 | Bruick et al. |
| 2016/0251307 A1 | 9/2016 | Dixon et al. |
| 2016/0368893 A1 | 12/2016 | Dixon et al. |
| 2017/0217891 A1 | 8/2017 | Dixon et al. |
| 2017/0217892 A1 | 8/2017 | Dixon et al. |
| 2018/0140569 A1 | 5/2018 | Josey et al. |
| 2018/0155279 A1 | 6/2018 | Dixon et al. |
| 2018/0162807 A1 | 6/2018 | Dixon et al. |

FOREIGN PATENT DOCUMENTS

| | | |
|---|---|---|
| DE | 705530 C | 4/1941 |
| DE | 2423972 A1 | 1/1975 |
| DE | 3239449 A1 | 5/1983 |
| DE | 3209878 A1 | 9/1983 |
| EP | 0027555 A1 | 4/1981 |
| EP | 2599774 A1 | 6/2013 |
| FR | 1574139 A | 7/1969 |
| GB | 2017087 A | 10/1979 |
| JP | S4872169 A | 9/1973 |
| JP | S57169449 A | 10/1982 |
| JP | S58124758 A | 7/1983 |
| JP | S6351363 A | 3/1988 |
| WO | WO-9324434 A1 | 12/1993 |
| WO | WO-9842671 A1 | 10/1998 |
| WO | WO-0116097 A1 | 3/2001 |
| WO | WO-02086497 A2 | 10/2002 |
| WO | WO-2004113303 A1 | 12/2004 |
| WO | WO-2006027684 A1 | 3/2006 |
| WO | WO-2006083781 A1 | 8/2006 |
| WO | WO-2006125972 A1 | 11/2006 |
| WO | WO-2007071441 A1 | 6/2007 |
| WO | WO-2007099423 A1 | 9/2007 |
| WO | WO-2008157273 A1 | 12/2008 |
| WO | WO-2009093133 A1 | 7/2009 |
| WO | WO-2009109477 A1 | 9/2009 |
| WO | WO-2010058032 A2 | 5/2010 |
| WO | WO-2010068794 A2 | 6/2010 |
| WO | WO-2010079443 A1 | 7/2010 |
| WO | WO-2010103438 A1 | 9/2010 |
| WO | WO-2010137620 A1 | 12/2010 |
| WO | WO-2010141956 A2 | 12/2010 |
| WO | WO-2011105603 A1 | 9/2011 |
| WO | WO-2011121366 A1 | 10/2011 |
| WO | WO-2011124930 A1 | 10/2011 |
| WO | WO-2012123129 A1 | 9/2012 |
| WO | WO-2012170442 A1 | 12/2012 |
| WO | WO-2013011033 A1 | 1/2013 |
| WO | WO-2013040863 A1 | 3/2013 |
| WO | WO-2013057101 A1 | 4/2013 |
| WO | WO-2013064984 A1 | 5/2013 |
| WO | WO-2013110433 A1 | 8/2013 |
| WO | WO-2013133325 A1 | 9/2013 |
| WO | WO-2014078479 A2 | 5/2014 |
| WO | WO-2015035223 A1 | 3/2015 |
| WO | WO-2015095048 A1 | 6/2015 |
| WO | WO-2016144825 A1 | 9/2016 |
| WO | WO-2016144826 A1 | 9/2016 |
| WO | WO-2016145032 A1 | 9/2016 |
| WO | WO-2016145045 A1 | 9/2016 |
| WO | WO-2016145236 A1 | 9/2016 |
| WO | WO-2016168510 A1 | 10/2016 |

OTHER PUBLICATIONS

Carew, et al. ELR510444 inhibits tumor growth and angiogenesis by abrogating HIF activity and disrupting microtubules in renal cell carcinoma. PLoS One. 2012;7(1):e31120. doi: 10.1371/journal.pone.0031120. Epub Jan. 25, 2012.

CAS Registry No. 1050878-94-8 (Sep. 2008).

CAS Registry No. 1062399-04-05 (Oct. 2008).

CAS Registry No. 1090604-08-2 (Dec. 2008).

CAS Registry No. 1119387-77-7 (Mar. 2009).

CAS Registry No. 1147778-06-0 (May 2009).

CAS Registry No. 1386280-55-2 (Aug. 2012).

CAS Registry No. 81614-92-8. (Nov. 1984).

CAS Registry No. 879353-79-4 (Apr. 2006).

CAS Registry No. 903274-78-2 (Aug. 2006).

CAS Registry No. 950051-37-3 (Oct. 2007).

CAS Registry No. 21081-71-0, Database Registry, Chemical Abstracts Services, [retrieved on Mar. 23, 2017], Published 1968.

Co-pending U.S. Appl. No. 15/553,570, filed Aug. 24, 2017.

Co-pending U.S. Appl. No. 15/556,153, filed Sep. 6, 2017.

Co-pending U.S. Appl. No. 15/556,248, filed Sep. 6, 2017.

Co-pending U.S. Appl. No. 15/556,609, filed Sep. 7, 2017.

Co-pending U.S. Appl. No. 15/564,348, filed Oct. 4, 2017.

Co-pending U.S. Appl. No. 15/805,390, filed Nov. 7, 2017.

European Search Report dated Mar. 29, 2017 for EP Application No. 14871152.6.

European Search Report dated Mar. 8, 2017 for EP Application No. 14842085.4.

Giatromanolaki, et al. Relation of hypoxia inducible factor 1 alpha and 2 alpha in operable non-small cell lung cancer to angiogenic/molecular profile of tumours and survival. Br J Cancer. Sep. 14, 2001;85(6):881-90.

Gordan, et al. HIF-2alpha promotes hypoxic cell proliferation by enhancing c-myc transcriptional activity. Cancer Cell. Apr. 2007;11(4):335-47.

He, et al. Downregulating hypoxia-inducible factor-2α improves the efficacy of doxorubicin in the treatment of hepatocellular carcinoma. Cancer Sci. Mar. 2012;103(3):528-34. doi: 10.1111/j.1349-7006.2011.02177.x. Epub Jan. 13, 2012.

Holmquist-Mengelbier, et al. Recruitment of HIF-1alpha and HIF-2alpha to common target genes is differentially regulated in neuroblastoma: HIF-2alpha promotes an aggressive phenotype. Cancer Cell. Nov. 2006;10(5):413-23.

Hu, et al. Differential roles of hypoxia-inducible factor lalpha (HIF-1alpha) and HIF-2alpha in hypoxic gene regulation. Mol Cell Biol. Dec. 2003;23(24):9361-74.

Karoor, et al. Alveolar hypoxia promotes murine lung tumor growth through a VEGFR-2/EGFR-dependent mechanism. Cancer Prev Res (Phila). Aug. 2012;5(8):1061-71. doi: 10.1158/1940-6207.CAPR-12-0069-T. Epub Jun. 14, 2012.

Keith, et al. HIF1α and HIF2α: sibling rivalry in hypoxic tumour growth and progression. Nat Rev Cancer. Dec. 15, 2011;12(1):9-22. doi: 10.1038/nrc3183.

Key, et al. Principles of ligand binding within a completely buried cavity in HIF2alpha PAS-B. J Am Chem Soc. Dec. 9, 2009;131(48):17647-54. doi: 10.1021/ja9073062.

Kim, et al. HIF2alpha cooperates with RAS to promote lung tumorigenesis in mice. J Clin Invest. Aug. 2009;119(8):2160-70.

King, F.D., Biososteres, Conformational restriction, and pro-drugs-case history: An example of a conformational restriction approach. Med. Chem., Principle and Practice (1994), pp. 206-208.

Kondo, et a. Inhibition of HIF2alpha is sufficient to suppress pVHL-defective tumor growth. PLoS Biol. Dec. 2003;1(3):E83, 439-444. Epub Dec. 22, 2003.

Kondo, et al. Inhibition of HIF is necessary for tumor suppression by the von Hippel-Lindau protein. Cancer Cell. Apr. 2002;1(3):237-46.

Koshiji, et al. HIF-1alpha induces cell cycle arrest by functionally counteracting Myc. EMBO J. May 5, 2004;23(9):1949-56. Epub Apr. 8, 2004.

Lee, et al. Acriflavine inhibits HIF-1 dimerization, tumor growth, and vascularization. Proc Natl Acad Sci U S A. Oct. 20, 2009;106(42):17910-5. doi: 10.1073/pnas.0909353106. Epub Oct. 1, 2009.

Li et al. Hypoxia-inducible factors regulate tumorigenic capacity of glioma stem cells. Cancer Cell 15(6):501-513 (2009).

(56) References Cited

OTHER PUBLICATIONS

Lin, et al., Efficient in silico assay of inhibitors of hepatitis c virus RNA-dependent RNA polymerase by structure-based virtual screening and in vitro evaluation. ASSAY and drug development technologies. 9(3): Jun. 2011; pp. 290-298. XP55350132.
Maher, et al. von Hippel-Lindau disease: a clinical and scientific review. Eur J Hum Genet. Jun. 2011;19(6):617-23. doi: 10.1038/ejhg.2010.175. Epub Mar. 9, 2011.
Mandriota, et al. HIF activation identifies early lesions in VHL kidneys: evidence for site-specific tumor suppressor function in the nephron. Cancer Cell. Jun. 2002;1(5):459-68.
Maranchie, et al. The contribution of VHL substrate binding and HIF1-alpha to the phenotype of VHL loss in renal cell carcinoma. Cancer Cell. Apr. 2002;1(3):247-55.
Mazumdar, et al. HIF-2alpha deletion promotes Kras-driven lung tumor development. Proc Natl Acad Sci U S A. Aug. 10, 2010;107(32):14182-7. doi: 10.1073/pnas.1001296107. Epub Jul. 21, 2010.
Miranda, et al. A cyclic peptide inhibitor of HIF-1 heterodimerization that inhibits hypoxia signaling in cancer cells. J Am Chem Soc. Jul. 17, 2013;135(28):10418-25. doi: 10.1021/ja402993u. Epub Jul. 9, 2013.
Morrison and Boyd, Isotope Effects. Org. Chem., 3rd ed., (1974), pp. 353-356.
Nguyen, et al. Epigenetic regulation of hypoxia inducible factor in diseases and therapeutics. Arch Pharm Res. Mar. 2013;36(3):252-63. doi: 10.1007/s12272-013-0058-x. Epub Feb. 26, 2013.
Notice of Allowance dated Oct. 6, 2017 for U.S. Appl. No. 15/439,494.
Notice of Allowance dated Oct. 11, 2017 for U.S. Appl. No. 15/439,308.
Notice of Allowance dated Oct. 19, 2017 for U.S. Appl. No. 14/905,776.
Notice of Allowance dated Nov. 9, 2017 for U.S. Appl. No. 15/037,047.
Office Action dated Mar. 24, 2017 for U.S. Appl. No. 15/037,047.
Office Action dated Apr. 28, 2017 for U.S. Appl. No. 14/905,776.
Office Action dated Aug. 16, 2017 for U.S. Appl. No. 15/037,047.
Office Action dated Sep. 8, 2017 for U.S. Appl. No. 14/905,776.
Office Action dated Nov. 21, 2016 for U.S. Appl. No. 15/037,047.
Office Action dated Dec. 16, 2016 for U.S. Appl. No. 14/905,776.
Owens, et al. Smooth muscle cell hypertrophy versus hyperplasia in hypertension. Proc Natl Acad Sci U S A. Dec. 1981;78(12):7759-63.
Percy, et al. A gain-of-function mutation in the HIF2A gene in familial erythrocytosis. N Engl J Med. Jan. 10, 2008;358(2):162-8. doi: 10.1056/NEJMoa073123.
Percy, et al. Two new mutations in the HIF2A gene associated with erythrocytosis. Am J Hematol. Apr. 2012;87(4):439-42. doi: 10.1002/ajh.23123. Epub Feb. 24, 2012.
PubChem. Compound Summary for CID 21110550. 1-10. Create Date: Dec. 5, 2007. [retrieved on Jan. 20, 2015]. Retrieved from the Internet.<URL:http://pubchem.ncbi.nlm.nih.gov/compound/21110550>. entire document.
PubChem. Compound Summary for CID 825455. 1-11. Create Date: Jul. 9, 2005. [retrieved on Jan. 20, 2015]. Retrieved from the Internet.<URL:http://pubchem.ncbi.nlm.nih.gov/compound/825455>. entire document.
Raval, et al. Contrasting properties of hypoxia-inducible factor 1 (HIF-1) and HIF-2 in von Hippel-Lindau-associated renal cell carcinoma. Mol Cell Biol. Jul. 2005;25(13):5675-86.
Rogers, et al. Development of inhibitors of the PAS-B domain of the HIF-60 transcription factor. J Med Chem. Feb. 28, 2013;56(4):1739-47. doi: 10.1021/jm301847z. Epub Feb. 18, 2013.
Sakairi, et al. Synthesis and SAR studies of bicyclic amine series GPR119 agonists. Bioorganic & Medicinal Chemistry Letters. 2012; 22:5123-5128.
Scheuermann, et al. Allosteric inhibition of hypoxia inducible factor-2 with small molecules. Nat Chem Biol. Apr. 2013;9(4):271-6. doi: 10.1038/nchembio.1185. Epub Feb. 24, 2013.
Scheuermann, et al. Artificial ligand binding within the HIF2alpha PAS-B domain of the HIF2 transcription factor. Proc Natl Acad Sci U S A. Jan. 13, 2009;106(2):450-5. doi: 10.1073/pnas.0808092106. Epub Jan. 7, 2009.
Semenza. Hypoxia-inducible factors: mediators of cancer progression and targets for cancer therapy. Trends Pharmacol Sci. Apr. 2012;33(4):207-14. doi: 10.1016/j.tips.2012.01.005. Epub Mar. 6, 2012.
Shen, et al. The VHL/HIF axis in clear cell renal carcinoma. Semin Cancer Biol. Feb. 2013;23(1):18-25. doi: 10.1016/j.semcancer.2012.06.001. Epub Jun. 13, 2012.
Song et al., Synthesis and Biochemical Evaluation of Thiochromanone Thiosemicarbazone Analogues as Inhibitors of Cathepsin L ACS Med. Chem. Lett.. (2012), vol. 3(6), pp. 450-453.
Svensson, et al., Bromination of bicyclic phenols with SO2 heterocyclic annelated rings, ACTA Pharmaceutica Suecica, Royal Pharmaceutical Institute, Sweden, vol. 12, No. 5-6, Jan. 1, 1975: pp. 401-406.
Talks, et al. The expression and distribution of the hypoxia-inducible factors HIF-1alpha and HIF-2alpha in normal human tissues, cancers, and tumor-associated macrophages. Am J Pathol. Aug. 2000;157(2):411-21.
Tan, et al. Identification of a novel small-molecule inhibitor of the hypoxia-inducible factor 1 pathway. Cancer Res. Jan. 15, 2005;65(2):605-12.
Vanharanta, et al. Epigenetic expansion of VHL-HIF signal output drives multiorgan metastasis in renal cancer. Nat Med. Jan. 2013;19(1):50-6. doi: 10.1038/nm.3029. Epub Dec. 9, 2012.
Xue, et al. Hypoxia-inducible factor-2α activation promotes colorectal cancer progression by dysregulating iron homeostasis. Cancer Res. May 1, 2012;72(9):2285-93. doi: 10.1158/0008-5472.CAN-11-3836. Epub Mar. 14, 2012.
Xue, et al. Hypoxia-inducible factor-2α is essential in activating the COX2/mPGES-1/PGE2 signaling axis in colon cancer. Carcinogenesis. Jan. 2013;34(1):163-9. doi: 10.1093/carcin/bgs313. Epub Oct. 5, 2012.
Zhuang, et al. Somatic HIF2A gain-of-function mutations in paraganglioma with polycythemia. N Engl J Med. Sep. 6, 2012;367(10):922-30. doi: 10.1056/NEJMoa1205119.
Zimmer, et al. Inhibition of hypoxia-inducible factor is sufficient for growth suppression of VHL−/− tumors. Mol Cancer Res. Feb. 2004;2(2):89-95.
Zimmer, et al. Small-molecule inhibitors of HIF-2a translation link its 5'UTR iron-responsive element to oxygen sensing. Mol Cell. Dec. 26, 2008;32(6):838-48. doi: 10.1016/j.molcel.2008.12.004.
Notice of allowance dated Oct. 17, 2018 for U.S. Appl. No. 15/553,570.
Aftab, et al. Differential regulation of pulmonary vascular cell growth by hypoxia-inducible transcription factor-1α and hypoxia-inducible transcription factor-2αα. Am J Respir Cell Mol Biol. Jul. 2013;49(1):78-85. doi: 10.1165/rcmb.2012-0107OC.
Al-Kaabi, et al. Studies on fused 2(1H)-pyridinethiones: new routes for the synthesis of fused 1H-pyrazolo[3,4-b]pyridines and fused thieno[2,3-b]pyridines. Restrived from SN. Database accession No. 1992:633914.
Anonymous: "A Phase 1, Dose-Escalation Trial of PT2385 Tablets in Patients With Advanced Clear Cell Renal Cell Carcinoma—Full Tex View—Clinical Trials.gov", Nov. 19, 2014 (Nov. 19, 2014), XP55486644.
Banker et al. Modern Pharmaceutics. 3rd ed. Marcel Dekker, New York.p. 596 (1996).
Biellmann, et al. Synthesis and reactions of [1,4-dihydropyridinecarboxylic acids]. Tetrahedron (1970), 26(20), 4799-808.
Brusselmans, et al. Heterozygous deficiency of hypoxia-inducible factor-2alpha protects mice against pulmonary hypertension and right ventricular dysfunction during prolonged hypoxia. J Clin Invest. May 2003;111(10):1519-27.
Bundgaard, Design of Prodrugs, chapter 1, p. 1. (Year: 1985).
Catozzi, et al. Synthesis of the Louisianin Alkaloid Family via a 1,2,4-Triazine Inverse-Electron-Demand Diels-Alder Approach. Journal of Organic Chemistry. vol. 74, No. 21, Nov. 6, 2009, pp. 8343-8354.

(56) References Cited

OTHER PUBLICATIONS

Dittmar, et al. (4+2)-Cycloadditionen Der 1.2.4-Triazine-Ein Neuer Weg Zu 4-H-Acepinen. Tetrahedron Letters. El Sevier. Amsterdamn, NL, No. 59, Jan. 1, 1969, pp. 5171-5174.
European search report with written opinion dated Jul. 16, 2018 for EP application No. 16762264.
European search report with written opinion dated Aug. 24, 2018 for EP Application No. 16762394.
Freeman. Reaction of Cyanoacetamide and Some 2-Acylcyclanones. Jan. 1, 1969. pp. 3670-3672.
Gewald, et al. Reaktion von methylenaktiven Nitrilen und Cyanamid mit acylierten Enaminen//Reaction of Methylene Active Nitriles and Cyanamide with Acylated Enamines. Journal Fur Praktische Chemie: Practical Applications and Applied Chemistry: Covering All Aspects of Applied Chemistry, Wiley, DE, vol. 324, No. 6, Jan. 1, 1982, pp. 933-941.
Kozhevnikov, et al. Synthesis of Cyclometallated Platinum Complexes with Substituted Thienylpyridines and Detailed Characterization of Their Luminescence Properties. Inorganic Chemistry, vol. 48, No. 9, Apr. 1, 2009, pp. 4179-4189.
Lone, et al. A Substrate-Free Activity-Based Protein Profiling Screen for the Discovery of Selective PREPL Inhibitors. Journal of the American Chemical Society. vol. 133, No. 30, Aug. 3, 2011 (Aug. 3, 2011), pp. 11665-11674, XP55486936.
Luke, et al. PD-1 pathway inhibitors: the next generation of immunotherapy for advanced melanoma. Oncotarget. Feb. 2015; 6(6): 3479-3492.
McLean, et al. The "inverse electron-demand" Diels-Alder reaction in polymer synthesis. Part 3. Model Diels-Alder reactions of some bis(1,2,4-triazines) with dienophiles and some bis-dienophiles with heterocyclic dienes. XP002782445, retrieved from STN, Database accession No. 1996:608859.
Navarro, et al. American Association for Cancer Research (AACR)—106th Annual Meeting. Philadelphia, Pennsylvania, USA—Apr. 18-22, 2015. Drugs of the Future. vol. 40, No. 5, May 205, p. 341, XP55272384.
Neunhoeffer, et al. Cycloaddition reactions with azabenzenes. XVIII. Synthesis of [2]pyrindines. Heterocycles (1993), 35(2), 1089-101.
Notice of Allowance dated Aug. 13, 2018 for U.S. Appl. No. 15/805,390.
Office action dated Jun. 26, 2018 for U.S. Appl. No. 15/553,570.
Office action dated Aug. 16, 2018 for U.S. Appl. No. 15/564,348.
Office action dated Sep. 17, 2018 for U.S. Appl. No. 15/556,609.
Platonov, et al. Thermolytic reactions of polyfluoroorganic compounds. XXI. Thermolytic reations of hexafluorobenzene and pentafluoropyridine with potassium fluoride and poly(tetrafluoroethylene). XP002782444. Chemical Abstracts Service, Columbus, Ohio, US. Retrieved from STN. Database accession No. 1979:6196.
Prelog, et al. Helvetica Chimica Acta (1946), 29, 1163-9.
Schroder, et al. Non-steroidal anti-inflammatory agents. 6. Anti-inflammatory methanesulfonamides I. European Journal of Medicinal Chemistry, 1982, vol. 17, No. 1, p. 35-42.
Seki, et al. 6,7-Dihydro-5H-2-pyrindines. Retrieved from STN. Database accession No. 1974:3400.
Silverman et al. Chapter 8: Prodrugs and drug delivery systems. In: The Organic Chemistry of Drug Design and Drug Action. San Diego: Academic Press, Inc. p. 352-401 (1992).
Small, W. and Donnelly, E.D. Leibel and Phillips textbook of Radiation oncology. JAMA. 2012; 307(1):93.
U.S. Appl. No. 15/805,390 Office Action dated Apr. 3, 2018.
Vanneman, et al. Combining immunotherapy and targeted therapies in cancer treatment. Nat Rev Cancer. Mar. 22, 2012;12(4):237-51. doi: 10.1038/nrc3237.
Wenzel, et al. beta(2)-adrenoceptor antagonist ICI 118,551 decreases pulmonary vascular tone in mice via a G(i/o) protein/nitric oxide-coupled pathway. Hypertension. Jul. 2009;54(1):157-63. doi: 10.1161/HYPERTENSIONAHA.109.130468. Epub May 26, 2009.
Winter, et al. The Vinylogous Mannich Reaction: An Efficient Access to Substituted Nicotinonitriles. SYNLETT, No. 13, Jan. 1, 2003, pp. 1959-1964.
"Wolff, (ed.), Burger's Medicinal Chemistry and Drug Discovery, Fifth Edition, vol. 1: Principles and Practice, San Diego, California, John Wiley & Sons, 1994, pp. 975-977. (4 pages)".

* cited by examiner

COMPOSITIONS FOR USE IN TREATING PULMONARY ARTERIAL HYPERTENSION

CROSS REFERENCE TO RELATED APPLICATION

This application is a National Stage Entry of PCT/US2016/021492, filed Mar. 9, 2016, which claims the benefit of U.S. Provisional Application No. 62/131,783, filed on Mar. 11, 2015, each incorporated herein by reference in its entirety.

BACKGROUND

An adequate supply of oxygen to tissues is essential in maintaining mammalian cell function and physiology. A deficiency in oxygen supply to tissues is a characteristic of a number of pathophysiologic conditions in which there is insufficient blood flow to provide adequate oxygenation, for example, ischemic disorders, cancer, and atherosclerosis. The hypoxic (low oxygen) environment of tissues activates a signaling cascade that drives the induction or repression of the transcription of a multitude of genes implicated in events such as angiogenesis (neo-vascularization), glucose metabolism, and cell survival/death. A key to this hypoxic transcriptional response lies in the transcription factor, the hypoxia-inducible factor (HIF). HIF is overexpressed in a vast array of cancers through hypoxia-dependent and independent mechanisms and expression is associated with poor patient prognosis.

HIFs consist of an oxygen-sensitive HIFα subunit and constitutively expressed HIFβ subunit. When HIFs are activated, the HIFα and HIF subunits assemble a functional heterodimer (the a subunit heterodimerizes with the β subunit). Both HIFα and HIF have two identical structural characteristics, a basic helix-loop-helix (bHLH) and PAS domains (PAS is an acronym referring to the first proteins, PER, ARNT, SIM, in which this motif was identified). There are three human HIFα subunits (HIF-1α, HIF-2α, and HIF-3α) that are oxygen sensitive. Among the three subunits, HIF-1α is the most ubiquitously expressed and induced by low oxygen concentrations in many cell types. HIF-2α is highly similar to HIF-1α in both structure and function, but exhibits more restricted tissue-specific expression, and might also be differentially regulated by nuclear translocation. HIF-3a also exhibits conservation with HIF-1α and HIF-2α in the HLH and PAS domains. HIFβ (also referred to as ARNT—Aryl Hydrocarbon Receptor Nuclear Translocator), the dimerization partner of the HIFα subunits, is constitutively expressed in all cell types and is not regulated by oxygen concentration.

Pulmonary arterial hypertension (PAH) is a serious, progressive and life-threatening disease of the pulmonary vasculature, characterized by profound vasoconstriction and an abnormal proliferation of smooth muscle cells in the walls of the pulmonary arteries. Severe constriction of the blood vessels in the lungs leads to very high pulmonary arterial pressures. These high pressures make it difficult for the heart to pump blood through the lungs to be oxygenated. Patients with PAH suffer from extreme shortness of breath as the heart struggles to pump against these high pressures. Patients with PAH typically develop significant increases in pulmonary vascular resistance (PVR) and sustained elevations in pulmonary artery pressure (PAP), which ultimately lead to right ventricular failure and death. Patients diagnosed with PAH have a poor prognosis and equally compromised quality of life, with a mean life expectancy of 2 to 5 years from the time of diagnosis if untreated. There is no known cause of PAH, and current treatments only address the symptoms, not the underlying problem.

SUMMARY

In view of the foregoing, there exists a need for improved compounds for treating PAH and related diseases. This disclosure provides compounds, compositions, and methods that address this need, and provide other advantages as well.

In one aspect, the present disclosure provides a method of treating pulmonary arterial hypertension (PAH) in a subject in need thereof. In one embodiment, the method comprises administering a composition comprising an effective amount of a HIF-2α inhibitor to said subject. In some embodiments, the amount of HIF-2α inhibitor is effective in delaying the onset of or reducing the incidence of one or more symptoms of PAH. In some embodiments, the amount of HIF-2α inhibitor is effective in (a) stabilizing pulmonary arterial pressure (PAP) as compared to a PAP trend in the subject prior to treatment, (b) reducing PAP relative to a starting level of PAP in the subject, or (c) reducing right ventricular hypertrophy as measured by Fulton's Index relative to an untreated population of subjects having PAH; wherein the PAP is systolic pulmonary arterial pressure (SPAP) or diastolic pulmonary arterial pressure (DPAP). In some embodiments, the amount of HIF-2α inhibitor is effective in (a) reducing one or more of: pulmonary vascular resistance, pulmonary arterial pressure, systemic arterial pressure, pulmonary capillary wedge pressure, right atrial pressure, and brain natriuretic peptide level; and/or (b) increasing one or more of: mixed venous oxygen saturation, arterial oxygen saturation, cardiac index, six-minute walk distance, and lung diffusion capacity. In some embodiments, the amount of HIF-2α inhibitor is effective in reducing vascular smooth muscle hypertrophy. In some embodiments, the HIF-2α inhibitor inhibits one or more biological effects selected from the group consisting of heterodimerization of HIF-2α to HIF-1β, HIF-2α target gene expression, VEGF gene expression, and VEGF protein secretion. In some embodiments, the HIF-2α inhibitor inhibits heterodimerization of HIF-2α to HIF-1β but not heterodimerization of HIF-la to HIF-1β. In some embodiments, the HIF-2α inhibitor binds the PAS-B domain cavity of HIF-2α. In some embodiments, the HIF-2α inhibitor is a compound of any of the formulas provided herein.

In one aspect, the present invention provides a compound of Formula I:

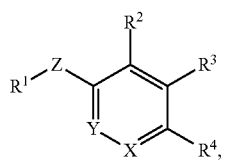

Formula I or a pharmaceutically acceptable salt or prodrug thereof, wherein:
X is $CR^5$ or N;
Y is $CR^6$ or N;
Z is O, S, $CHR^7$, $NR^8$ or absent;
$R^1$ is alkyl, heteroalkyl, cycloalkyl, heterocycloalkyl, aryl, heteroaryl, acyl or cyano;

R² is nitro, carboxaldehyde, carboxyl, ester, amido, cyano, halo, sulfonyl, alkyl, alkenyl, alkynyl or heteroalkyl;

R³ is hydrogen, halo, cyano, alkyl, heteroalkyl, alkenyl, alkynyl, amino, carboxaldehyde, carboxylic acid, oxime, ester, amido or acyl; or R² and R³ taken together form a cyclic moiety;

R⁴ is nitro, halo, cyano, alkyl, cycloalkyl, heteroaryl, carboxyl, sulfinyl, sulfonamidyl, sulfonyl, sulfoximinyl or fluoroalkylsulfonyl; and R⁵, R⁶, R⁷ and R⁸ are independently hydrogen, halo, hydroxy, cyano, alkyl or alkoxy.

In some other embodiments of compounds of Formula I, R¹ is phenyl, monocyclic heteroaryl or bicyclic heteroaryl. In some embodiments, R¹ is phenyl or pyridyl. In yet other embodiments, R¹ is cycloalkyl or heterocycloalkyl. Compounds of Formula I are also provided wherein R¹ is substituted with at least one substituent selected from the group consisting of halo, C₁-C₄ alkyl, C₁-C₄ alkoxy and cyano.

In yet other embodiments of compounds of Formula I, R² and R³ are independently selected from halo, cyano and alkyl. In some further embodiments, R³ is —(CH₂)ₙOH and n is 1, 2 or 3. In still other embodiments, n is 1.

In still other embodiments of compounds of Formula I, R⁴ is cyano, fluoroalkyl, sulfinyl, sulfonamidyl, sulfonyl or sulfoximinyl. In other embodiments, R⁴ is fluoroalkyl or fluoroalkylsulfonyl.

In some embodiments of compounds of Formula I, R² and R³ are independently selected from halo, cyano and alkyl; and R⁴ is cyano, fluoroalkyl, sulfinyl, sulfonamidyl, sulfonyl or sulfoximinyl. In another embodiment, R³ is CH₂OH.

In yet another embodiment, Z is O. In some embodiments, Z is S. In still other embodiments, Z is NR⁸. In another embodiment, Z is CHR⁷. In some embodiments, Z is absent. In some embodiments, X is N and Y is CR⁶. In another embodiment, X is CR⁵ and Y is N. In yet another embodiment, X is N and Y is N. In still another embodiment, X is CR⁵ and Y is CR⁶.

In another aspect, the invention provides a compound of Formula I-A:

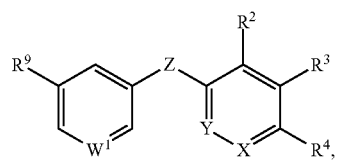

or a pharmaceutically acceptable salt or prodrug thereof, wherein:

X is CR⁵ or N;
Y is CR⁶ or N;
Z is O, S, CHR⁷, NR⁸ or absent;
R² is nitro, carboxaldehyde, carboxylic acid, ester, amido, cyano, halo, sulfonyl or alkyl;
R³ is hydrogen, halo, cyano, alkyl, heteroalkyl, alkenyl, alkynyl, amino, oxime or acyl; or R² and R³ taken together form a cyclic moiety;
R⁴ is nitro, halo, cyano, alkyl, sulfinyl, sulfonamidyl, sulfonyl or sulfoximinyl;
R⁵, R⁶, R⁷ and R⁸ are independently hydrogen, halo, hydroxy, cyano, alkyl or alkoxy;
W¹ is N or CR¹⁰;
R⁹ is cyano, halo, alkyl or alkoxy; and
R¹⁰ is hydrogen, cyano, halo, alkyl or alkoxy.

In another aspect, the invention provides a compound of Formula I-B:

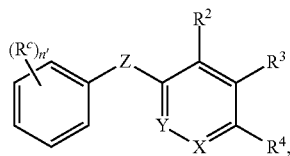

or a pharmaceutically acceptable salt or prodrug thereof, wherein:

X is CR⁵ or N;
Y is CR⁶ or N;
Z is O, S, CHR⁷, NR⁸ or absent;
R² is nitro, carboxaldehyde, carboxylic acid, ester, amido, cyano, halo, sulfonyl or alkyl;
R³ is hydrogen, halo, cyano, alkyl, heteroalkyl, alkenyl, alkynyl, amino, oxime or acyl; or R² and R³ taken together form a cyclic moiety;
R⁴ is nitro, halo, cyano, alkyl, sulfinyl, sulfonamidyl, sulfonyl or sulfoximinyl;
R⁵, R⁶, R⁷ and R⁸ are independently hydrogen, halo, hydroxy, cyano, alkyl or alkoxy;
Rᶜ is hydrogen, cyano, halo, alkyl or alkoxy; and
n' is 0, 1, 2, 3 or 4.

In yet another aspect, the invention provides a compound of Formula I-C:

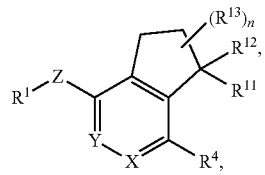

or a pharmaceutically acceptable salt or prodrug thereof, wherein:

X is CR⁵ or N;
Y is CR⁶ or N;
Z is O, S, CHR⁷, NR⁸ or absent;
R¹ is alkyl, heteroalkyl, cycloalkyl, heterocycloalkyl, aryl, heteroaryl, acyl or cyano;
R⁴ is nitro, halo, cyano, alkyl, cycloalkyl, heteroaryl, carboxyl, sulfinyl, sulfonamidyl, sulfonyl, sulfoximinyl or fluoroalkylsulfonyl;
R⁵, R⁶, R⁷ and R⁸ are independently hydrogen, halo, hydroxy, cyano, alkyl or alkoxy;
R¹¹ is hydrogen, hydroxy, alkoxy or amino;
R¹² is hydrogen, alkyl, alkenyl or alkynyl; or R¹¹ and R¹² in combination form oxo or oxime;
each of R¹³ is independently selected from the group consisting of hydrogen, fluoro, chloro, hydroxy, alkyl and heteroalkyl, with the proviso that when R¹³ is hydroxy, n is 1 or 2; or two R¹³s and the carbon atom(s) to which they are attached form a 3- to 8-membered cycloalkyl or heterocycloalkyl moiety; and
n is 0, 1, 2, 3 or 4.

In some other embodiments of compounds of Formula I-C, R¹ is phenyl, monocyclic heteroaryl or bicyclic heteroaryl. In some embodiments, R¹ is phenyl or pyridyl. In yet other embodiments, R¹ is cycloalkyl or heterocycloalkyl. Compounds of Formula I-C are also provided wherein R¹ is substituted with at least one substituent selected from the group consisting of halo, $C_1$-$C_4$ alkyl, $C_1$-$C_4$ alkoxy and cyano.

In still other embodiments of compounds of Formula I-C, $R^4$ is cyano, fluoroalkyl, sulfinyl, sulfonamidyl, sulfonyl or sulfoximinyl. In other embodiments, $R^4$ is fluoroalkyl or fluoroalkylsulfonyl. In some other embodiments, $R^{11}$ is hydroxy or amino. In further embodiments, $R^{11}$ is hydroxy. In yet other embodiments, $R^{12}$ is hydrogen. In yet another embodiment, $R^{13}$ is fluoro and n is 1, 2 or 3.

In some embodiments of compounds of Formula I-C, $R^4$ is cyano, fluoroalkyl, sulfinyl, sulfonamidyl, sulfonyl or sulfoximinyl; $R^{11}$ is hydroxy or amino; and $R^{12}$ is hydrogen. In still another embodiment, $R^{13}$ is fluoro. In yet another embodiment, Z is O. In some embodiments, Z is S. In still other embodiments, Z is $NR^8$. In another embodiment, Z is $CHR^7$. In some embodiments, Z is absent.

In some other embodiments of compounds of Formula I-C, $R^4$ is fluoroalkyl; n is 0, 1, 2 or 3; Z is O; $R^{11}$ is hydroxy; and $R^{12}$ is hydrogen. In still other embodiments, $R^4$ is sulfonyl; n is 0, 1, 2 or 3; Z is O; $R^{11}$ is hydroxy; and $R^{12}$ is hydrogen. In yet other embodiments, $R^1$ is phenyl, pyridyl, cycloalkyl or heterocycloalkyl. In some embodiments, X is N and Y is $CR^6$. In another embodiment, X is $CR^5$ and Y is N. In yet another embodiment, X is N and Y is N.

In still another aspect, the invention provides a compound of Formula I-D, I-E, I-F or I-G:

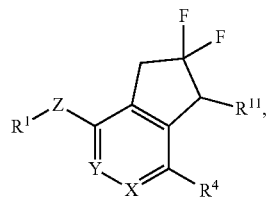

I-D

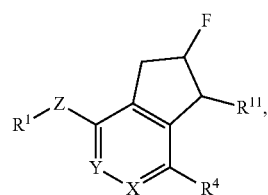

I-E

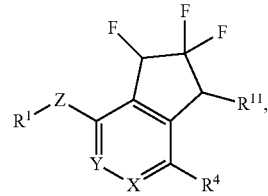

I-F

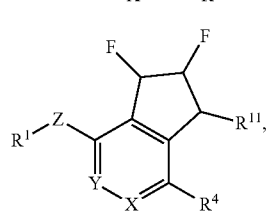

I-G or a pharmaceutically acceptable salt or prodrug thereof, wherein:

X is $CR^5$ or N;

Y is $CR^6$ or N;

Z is O, S, $CHR^7$, $NR^8$ or absent;

$R^1$ is alkyl, heteroalkyl, cycloalkyl, heterocycloalkyl, aryl or heteroaryl;

$R^4$ is nitro, halo, cyano, alkyl, cycloalkyl, heteroaryl, carboxyl, sulfinyl, sulfonamidyl, sulfonyl, sulfoximinyl or fluoroalkylsulfonyl;

$R^5$, $R^6$, $R^7$ and $R^8$ are independently hydrogen, halo, hydroxy, cyano, alkyl or alkoxy; and $R^{11}$ is hydrogen, hydroxy, alkoxy or amino.

In a further aspect, the invention provides a compound of Formula I-H, I-I, I-J or I-K:

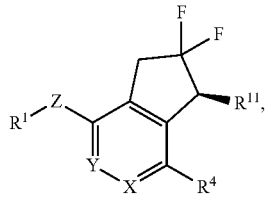

I-H

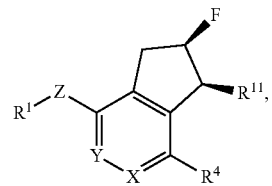

I-I

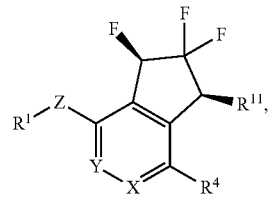

I-J

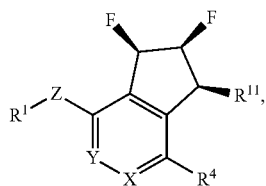

I-K or a pharmaceutically acceptable salt or prodrug thereof, wherein:

X is $CR^5$ or N;

Y is $CR^6$ or N;

Z is O, S, $CHR^7$, $NR^8$ or absent;

$R^1$ is alkyl, heteroalkyl, cycloalkyl, heterocycloalkyl, aryl or heteroaryl;

$R^4$ is nitro, halo, cyano, alkyl, cycloalkyl, heteroaryl, carboxyl, sulfinyl, sulfonamidyl, sulfonyl, sulfoximinyl or fluoroalkylsulfonyl;

$R^5$, $R^6$, $R^7$ and $R^8$ are independently hydrogen, halo, hydroxy, cyano, alkyl or alkoxy; and $R^{11}$ is hydroxy or amino.

In yet another aspect, the invention provides a compound of Formula II:

$$\text{[chemical structure of Formula II with substituents } R^1, Z, R^2, R^{14}, R^{15}, R^{16}, R^{17}, R^{18}, \text{ S=O, and subscript } n'' \text{]}$$

or a pharmaceutically acceptable salt or prodrug thereof, wherein:

Z is O, S, CHR$^7$, NR$^8$ or absent;

R$^1$ is alkyl, heteroalkyl, cycloalkyl, heterocycloalkyl, aryl, heteroaryl, acyl or cyano;

R$^2$ is hydrogen, alkyl, heteroalkyl, alkenyl, alkynyl, nitro, carboxaldehyde, carboxylic acid, ester, amido, cyano, halo or sulfonyl;

R$^{14}$ is hydrogen, deuterium or alkyl;

R$^{15}$ is hydrogen, hydroxy or amino; or R$^{14}$ and R$^{15}$ in combination form oxo or methylene;

R$^{16}$ and R$^{17}$ are independently selected from the group consisting of hydrogen, halo, alkyl, heteroalkyl and cycloalkyl; or R$^{16}$ and R$^{17}$ and the carbon to which they are attached form C$_3$-C$_8$ cycloalkyl or C$_5$-C$_8$ heterocycloalkyl;

R$^{18}$ is O or NR$^{19}$, wherein R$^{19}$ is selected from the group consisting of hydrogen, alkyl and cyano;

n" is 1 or 2; and

R$^7$ and R$^8$ are independently hydrogen, halo, hydroxy, cyano, alkyl or alkoxy.

In another aspect, the invention provides a compound of Formula II-A:

$$\text{[chemical structure of Formula II-A with substituents } R^1, Z, R^2, R^{14}, R^{15}, \text{ F, F, } R^{18}, \text{ S=O]}$$

or a pharmaceutically acceptable salt or prodrug thereof, wherein:

Z is O, S, CHR$^7$, NR$^8$ or absent;

R$^1$ is alkyl, heteroalkyl, cycloalkyl, heterocycloalkyl, aryl, heteroaryl, acyl or cyano;

R$^2$ is hydrogen, alkyl, heteroalkyl, alkenyl, alkynyl, nitro, carboxaldehyde, carboxylic acid, ester, amido, cyano, halo or sulfonyl;

R$^{14}$ is hydrogen, deuterium or alkyl;

R$^{15}$ is hydrogen, hydroxy or amino; or R$^{14}$ and R$^{15}$ in combination form oxo or methylene;

R$^{18}$ is O or NR$^{19}$, wherein R$^{19}$ is selected from the group consisting of hydrogen, alkyl and cyano; and R$^7$ and R$^8$ are independently hydrogen, halo, hydroxy, cyano, alkyl or alkoxy.

In still another aspect, the invention provides a compound of Formula II-B:

$$\text{[chemical structure of Formula II-B with substituents } R^1, Z, R^2, R^{14}, \text{ F, F, } R^{18}, \text{ S=O]}$$

or a pharmaceutically acceptable salt or prodrug thereof, wherein:

Z is O, S, CHR$^7$, NR$^8$ or absent;

R$^1$ is alkyl, heteroalkyl, cycloalkyl, heterocycloalkyl, aryl, heteroaryl, acyl or cyano;

R$^2$ is hydrogen, alkyl, heteroalkyl, alkenyl, alkynyl, nitro, carboxaldehyde, carboxylic acid, ester, amido, cyano, halo or sulfonyl;

R$^{15}$ is hydroxy or amino;

R$^{18}$ is O or NR$^{19}$, wherein R$^{19}$ is selected from the group consisting of hydrogen, alkyl and cyano; and R$^7$ and R$^8$ are independently hydrogen, halo, hydroxy, cyano, alkyl or alkoxy.

In some embodiments, the composition administered to the subject is provided in a unit dose. In some embodiments, the composition is administered orally, intravenously, subcutaneously, intranasally, transdermally, intraperitoneally, intramuscularly, or intrapulmonarily. In some embodiments, a second agent is administered simultaneously or sequentially with the HIF-2α inhibitor. The second agent may form part of the composition. In some embodiments, the second agent is selected from the group consisting of mitotic kinesis inhibitors, JAK2 inhibitors, prostanoids, endothelin receptor antagonists, phosphodiesterase inhibitors, prostacyclin receptor agonists, anticoagulants, diuretics, calcium channel blockers, digoxin, oxygen therapy, nitric oxide therapy, tyrosine kinases, statins, 5-hydroxytryptamine (5-HT) receptor antagonists, phosphatidylinositol 3-kinase inhibitors, soluble guanylate cyclase activators, adrenomedullin, platelet-derived growth factor (PDGF) inhibitors, Rho-kinase inhibitors, and mTOR inhibitors. In some embodiments, the method further comprises (a) measuring a physiological indicator of PAH before and after the administering, and (b) adjusting dosage or discontinuing use of the HIF-2α inhibitor based on results of step (a). In some embodiments, the physiological indicator of PAH is selected from the group consisting of: pulmonary vascular resistance, pulmonary arterial pressure, systemic arterial pressure, mixed venous oxygen saturation, arterial oxygen saturation, cardiac index, pulmonary capillary wedge pressure, right atrial pressure, six-minute walk distance, brain natriuretic peptide level, and lung diffusion capacity.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION

Figure 1:
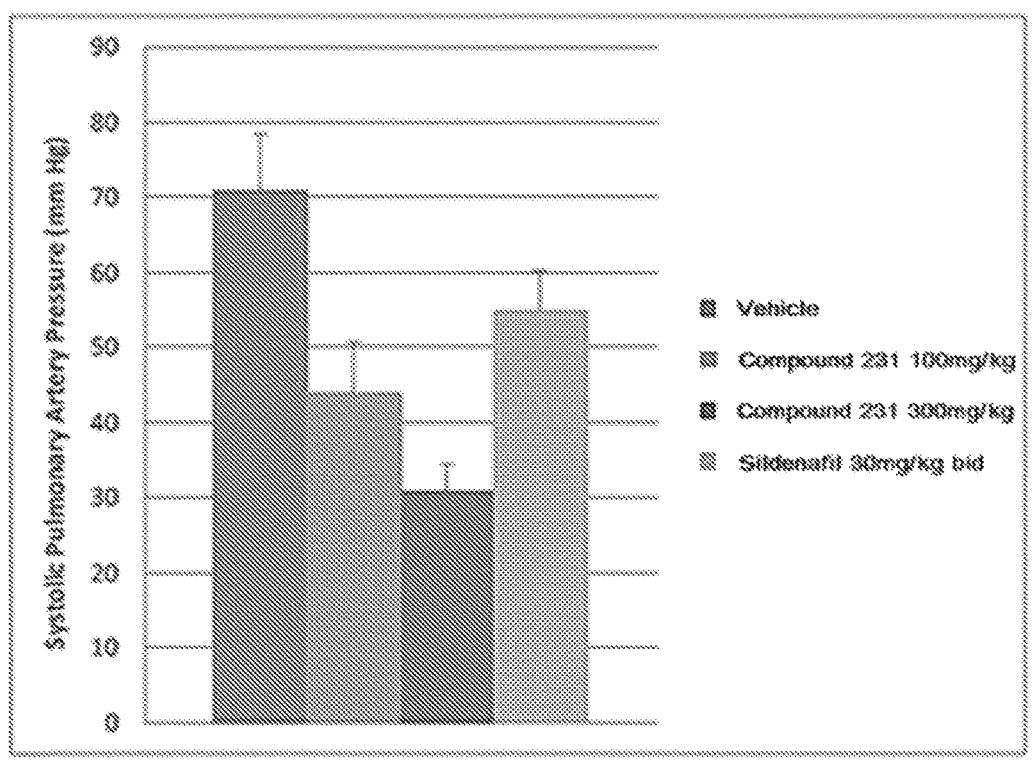
FIG. 1 is a bar graph illustrating effects of HIF-2α inhibitors on reducing systolic pulmonary artery pressure. Bars from left to right correspond to groups listed in the legend from top to bottom. Doses for Compound 231 were in the indicated amount per day (QD).
Figure 2:
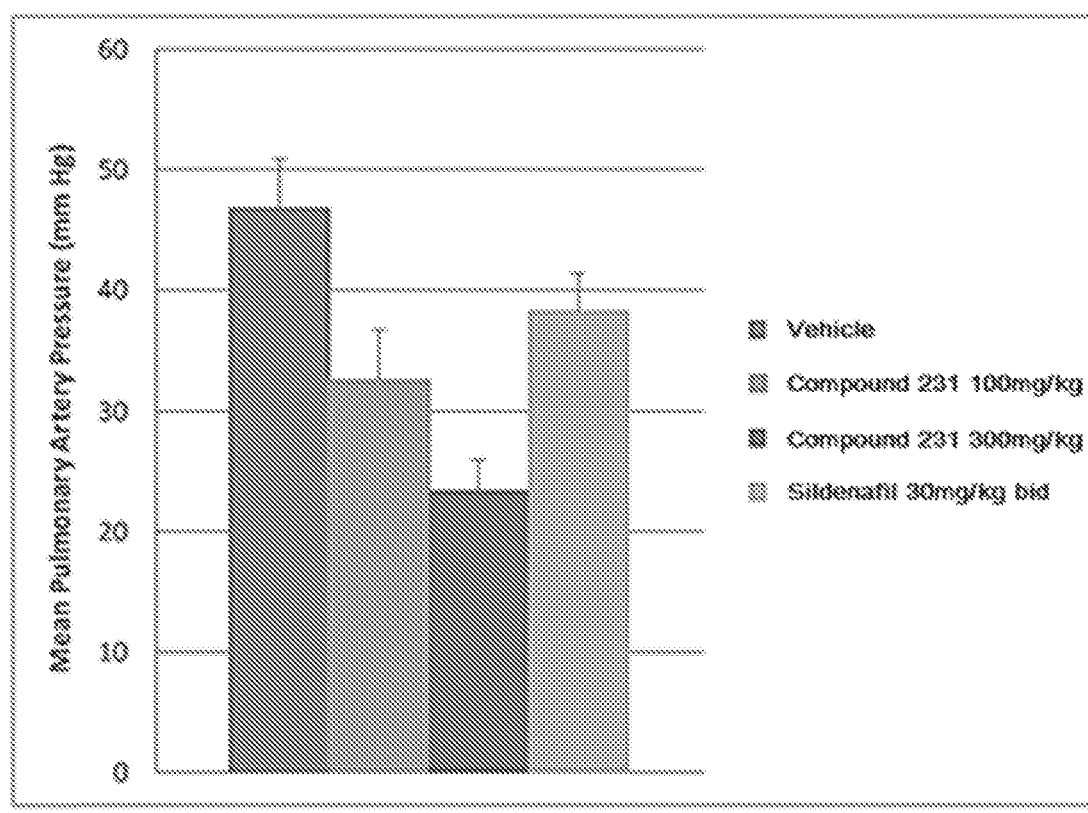
FIG. 2 is a bar graph illustrating effects of HIF-2α inhibitors on mean pulmonary artery pressure. Bars from left to right correspond to groups listed in the legend from top to bottom. Doses for Compound 231 were in the indicated amount per day (QD).
Figure 3:
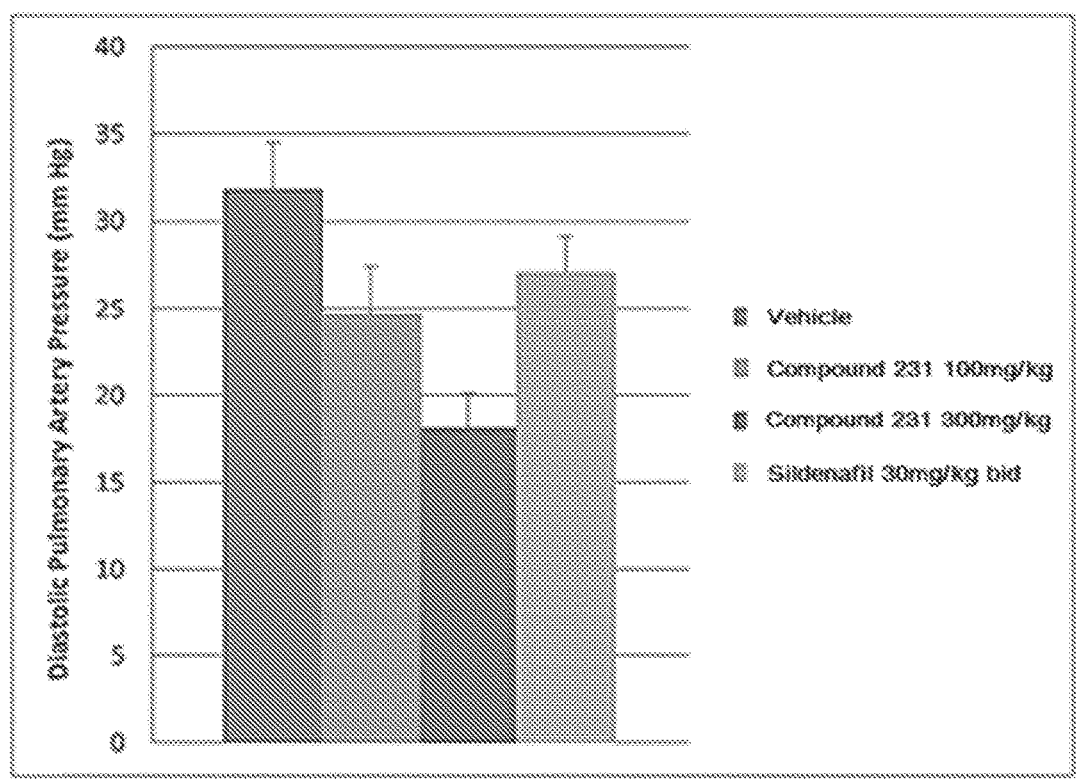
FIG. 3 is a bar graph illustrating effects of HIF-2α inhibitors on reducing diastolic pulmonary artery pressure. Bars from left to right correspond to groups listed in the legend from top to bottom. Doses for Compound 231 were in the indicated amount per day (QD).
Figure 4:
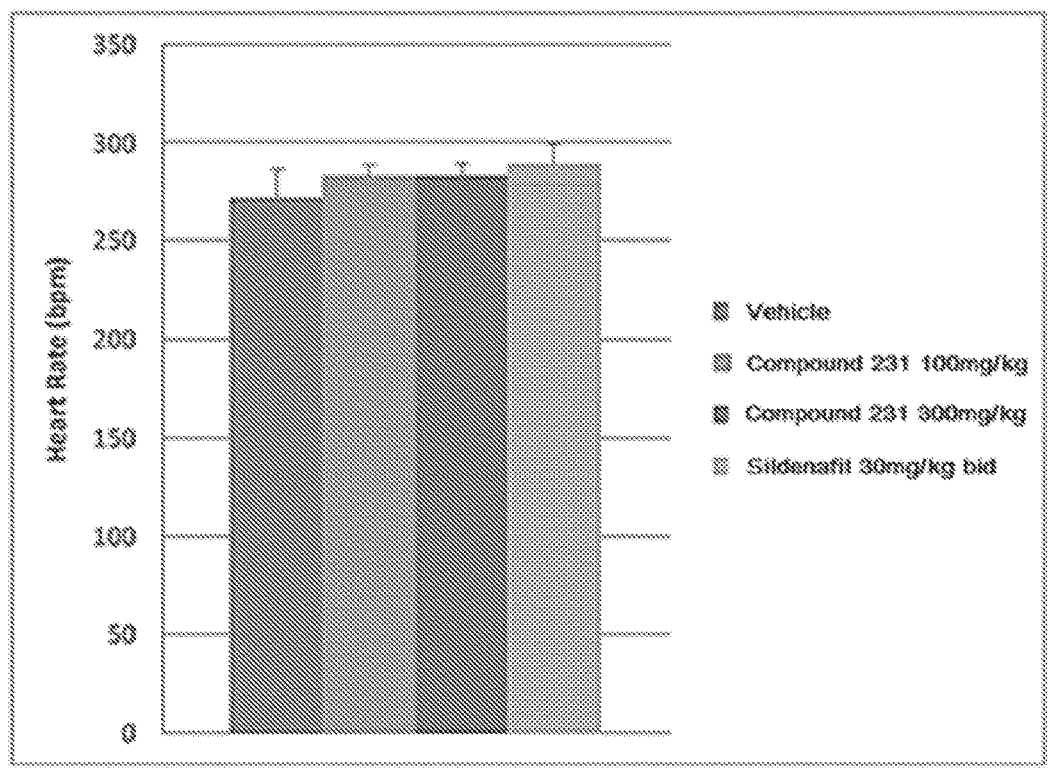
FIG. 4 illustrates effects of HIF-2α inhibitors treatment on heart rate. Bars from left to right correspond to groups listed in the legend from top to bottom. Doses for Compound 231 were in the indicated amount per day (QD).
Figure 5:
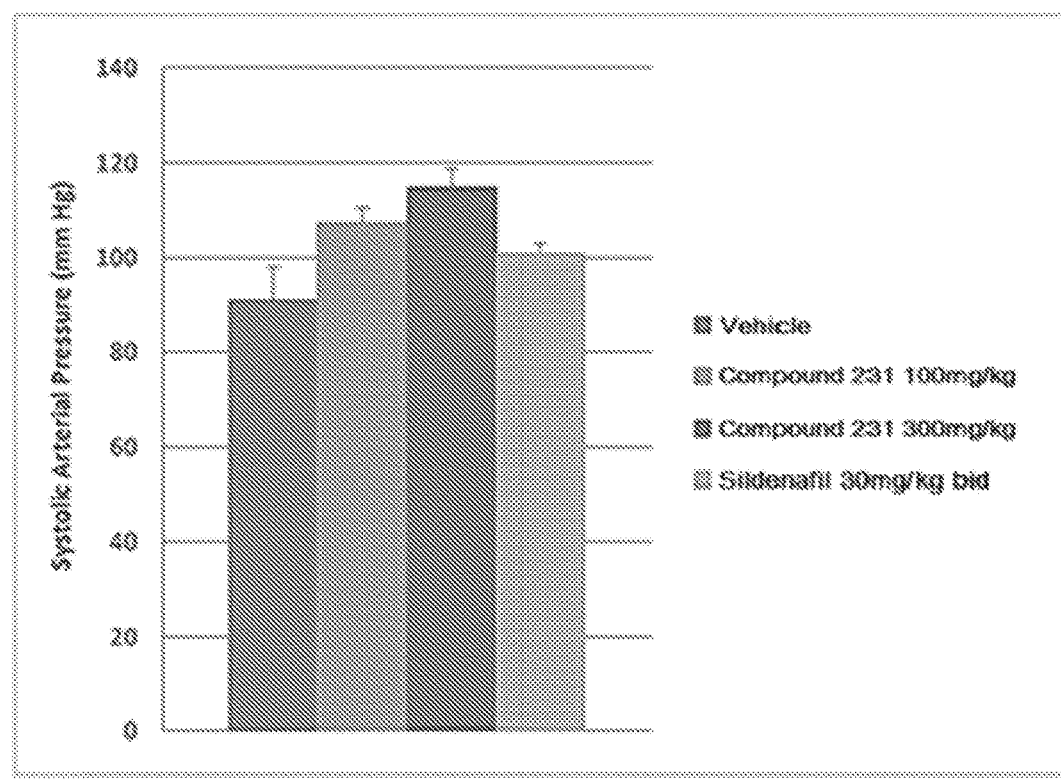
FIG. 5 illustrates effects of HIF-2α inhibitors treatment on systolic arterial pressure. Bars from left to right correspond to groups listed in the legend from top to bottom. Doses for Compound 231 were in the indicated amount per day (QD).
Figure 6:
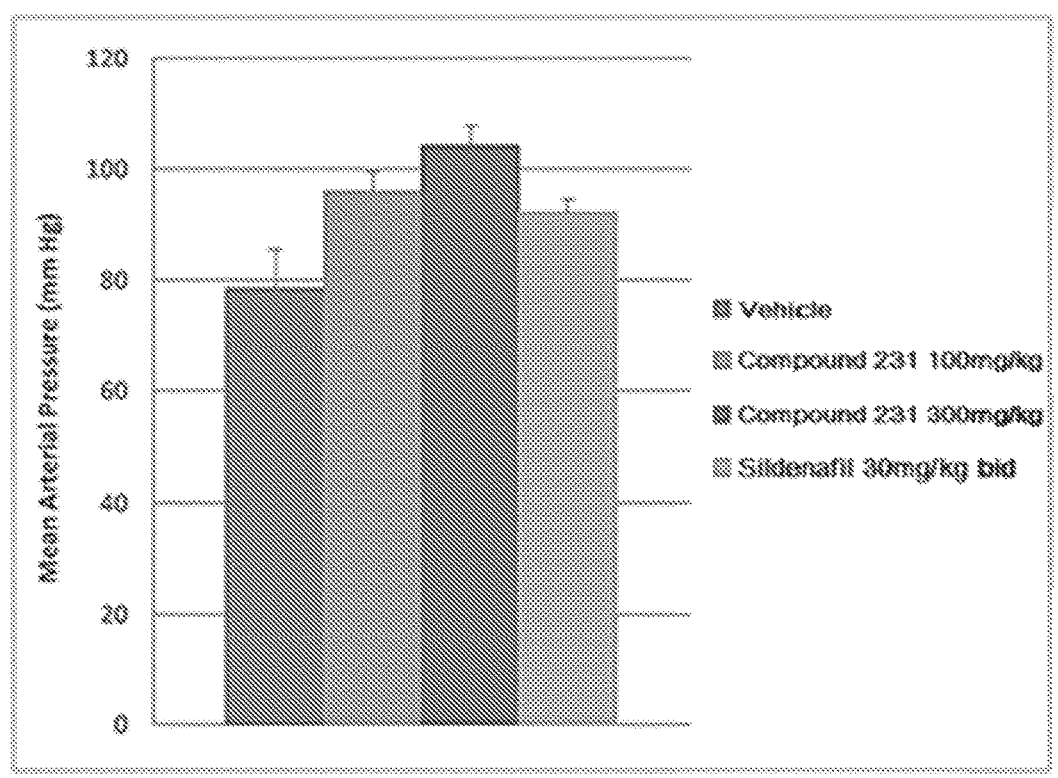
FIG. 6 illustrates effects of HIF-2α inhibitors treatment on mean arterial pressure. Bars from left to right correspond to groups listed in the legend from top to bottom. Doses for Compound 231 were in the indicated amount per day (QD).
Figure 7:
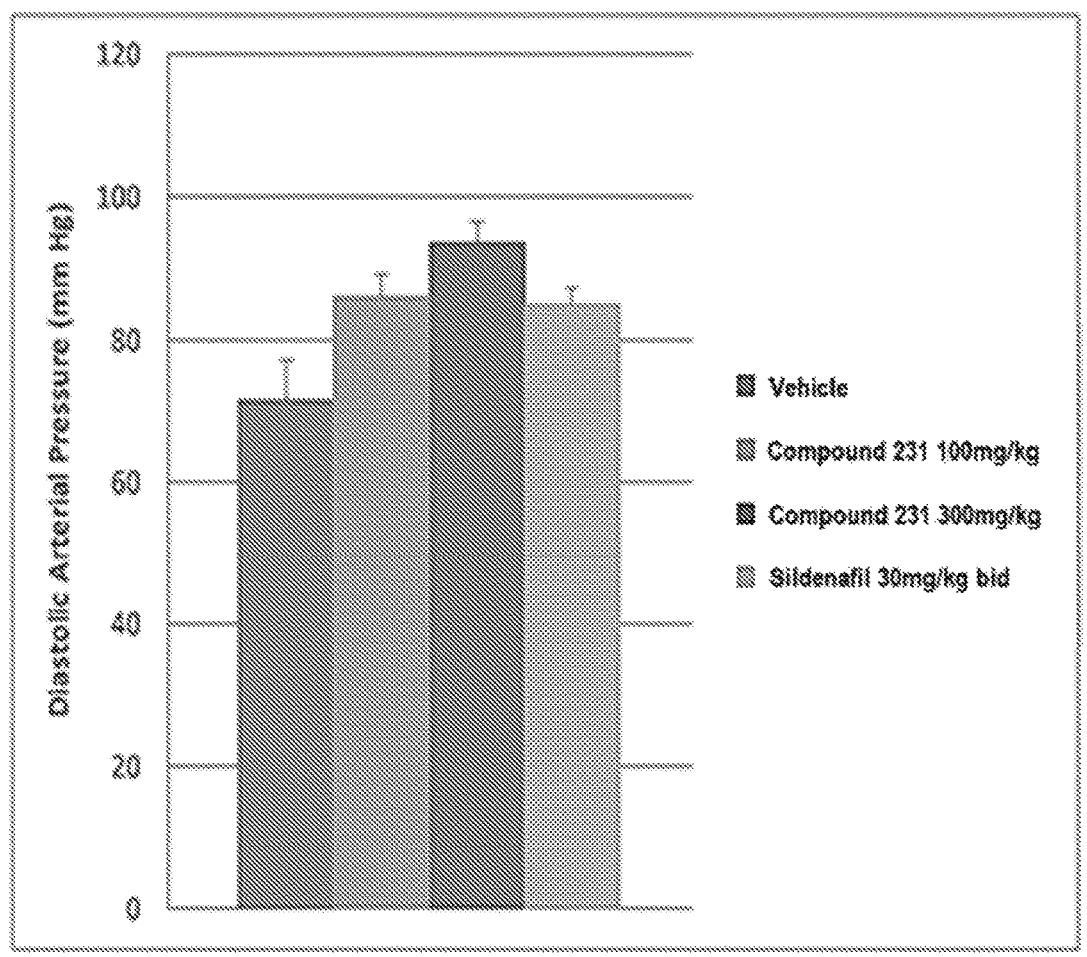
FIG. 7 illustrates effects of HIF-2α inhibitors treatment on diastolic arterial pressure. Bars from left to right correspond to groups listed in the legend from top to bottom. Doses for Compound 231 were in the indicated amount per day (QD).
Figure 8:
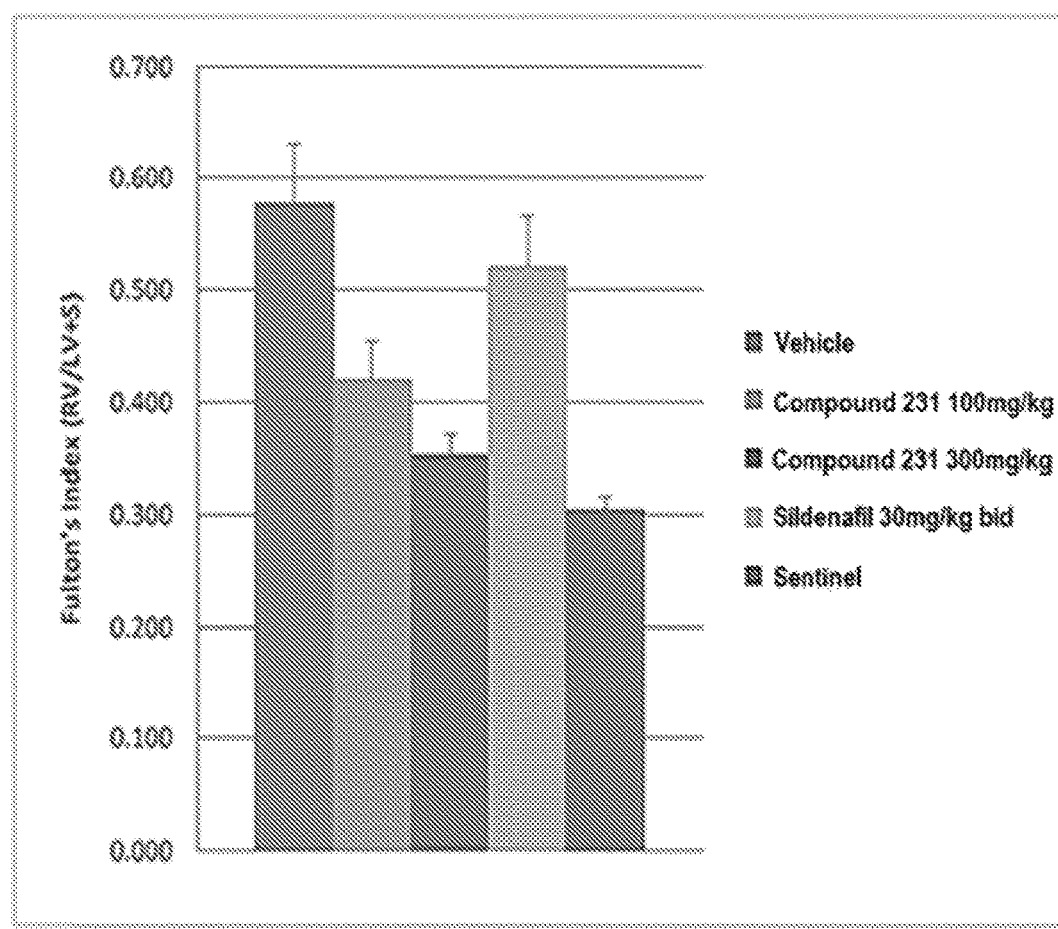
FIG. 8 illustrates effects of HIF-2α inhibitors treatment on Fulton's index (RV/LV+S). Bars from left to right correspond to groups listed in the legend from top to bottom. Doses for Compound 231 were in the indicated amount per day (QD).
Figure 9:
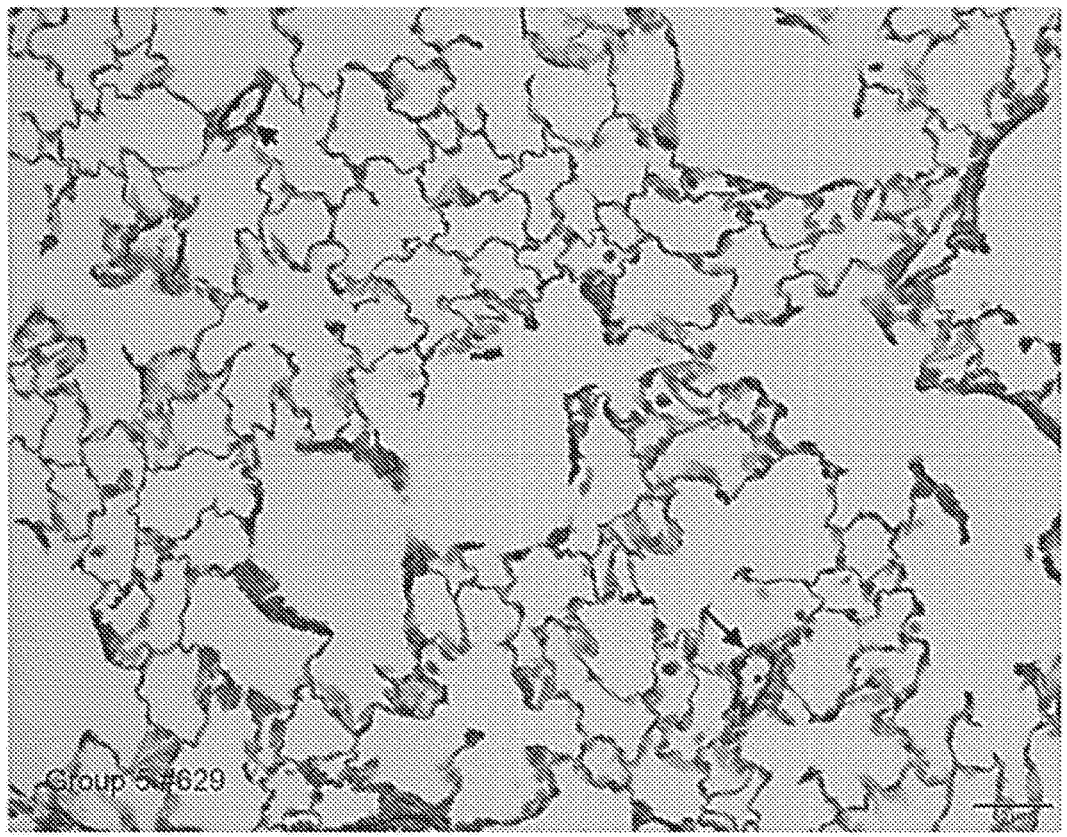
FIG. 9 shows the histopathology of lung tissues in a normal animal. Short arrow points to a completely muscularized arteriole. Long, thin arrow points to a partially muscularized arteriole. The long arrow points to the non-muscularized portion of the partially muscularized arteriole.
Figure 10:
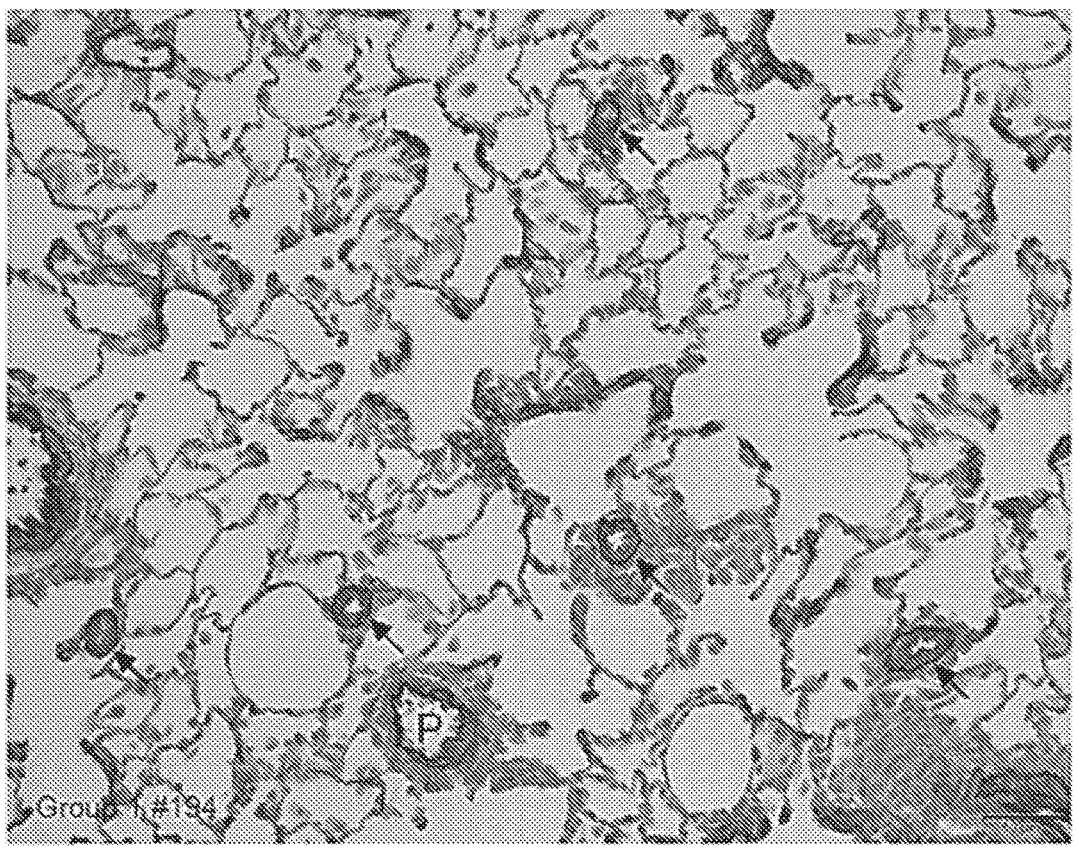
FIG. 10 shows the histopathology of lung tissues in a hypoxia-induced animal treated with a vehicle. Arrows point to completely muscularized arteriole. The letter "P" indicates a partially muscularized arteriole. The arteriolar lumens have thick muscular walls.
Figure 11:
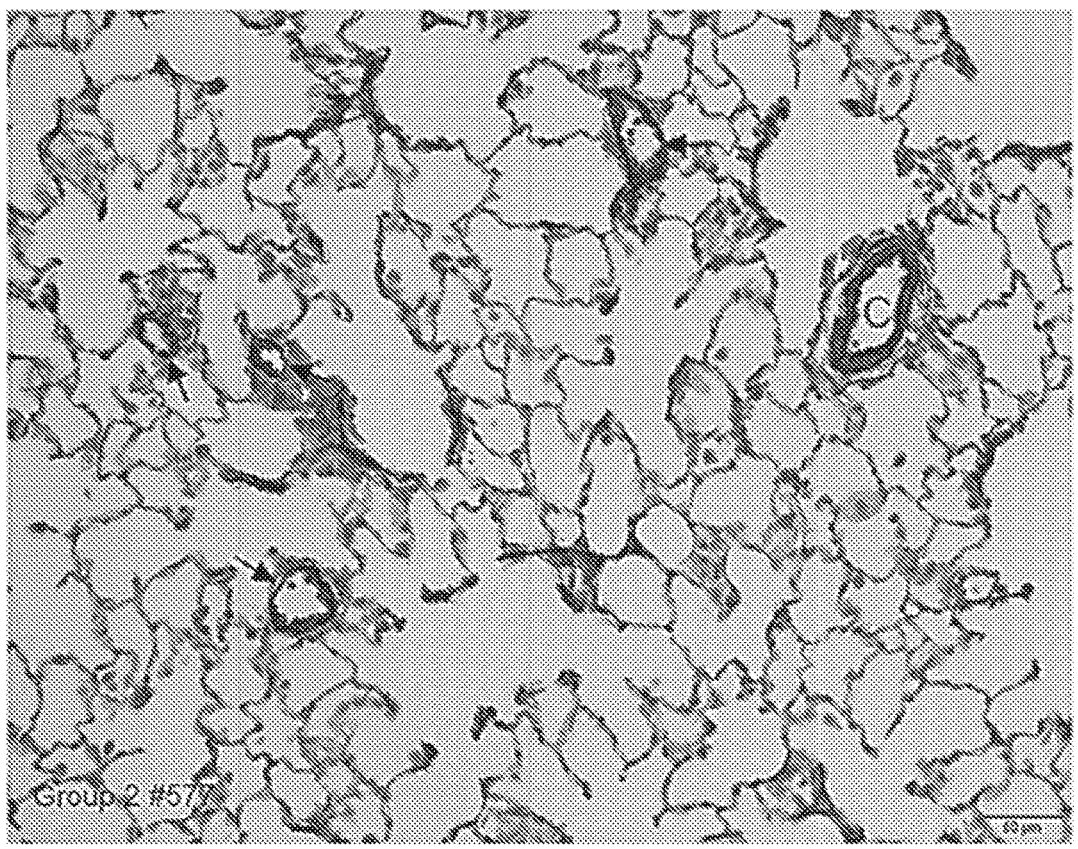
FIG. 11 shows the histopathology of lung tissues in a hypoxia-induced animal treated with 100 mg/kg Compound 231. Arrows point to partially muscularized arterioles. The letter "C" indicates a completely muscularized arteriole. The completely muscularized arteriole has a diameter greater than 50 μm and would not have been included in the categorization of small arterioles. The arrows point to the non-muscularized portion of the partially muscularized arterioles. The arteriolar walls are thinner than those of similarly sized arterioles in FIG. 10.
Figure 12:
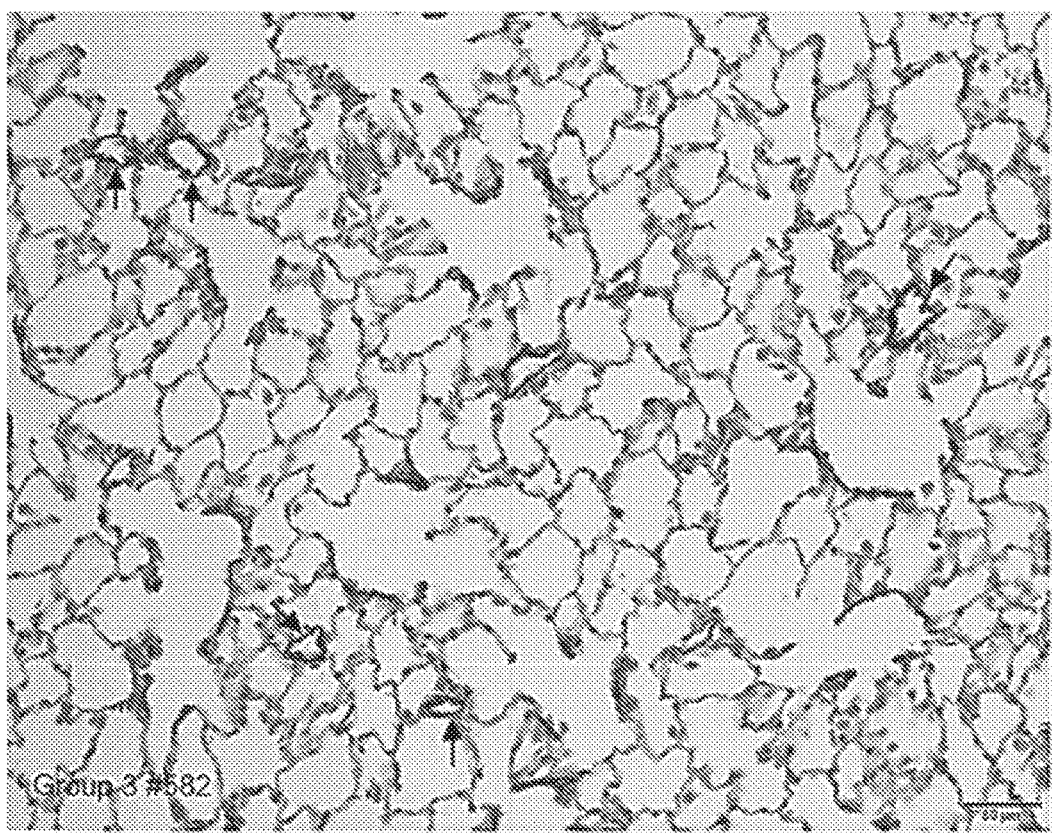
FIG. 12 shows the histopathology of lung tissues in a hypoxia-induced animal treated with 300 mg/kg Compound 231. Arrows point to partially muscularized arterioles. The arrows point to the non-muscularized portion of the partially muscularized arterioles. The arteriolar walls are thinner than those of similar sized arterioles in FIGS. 10 and 11.
Figure 13:
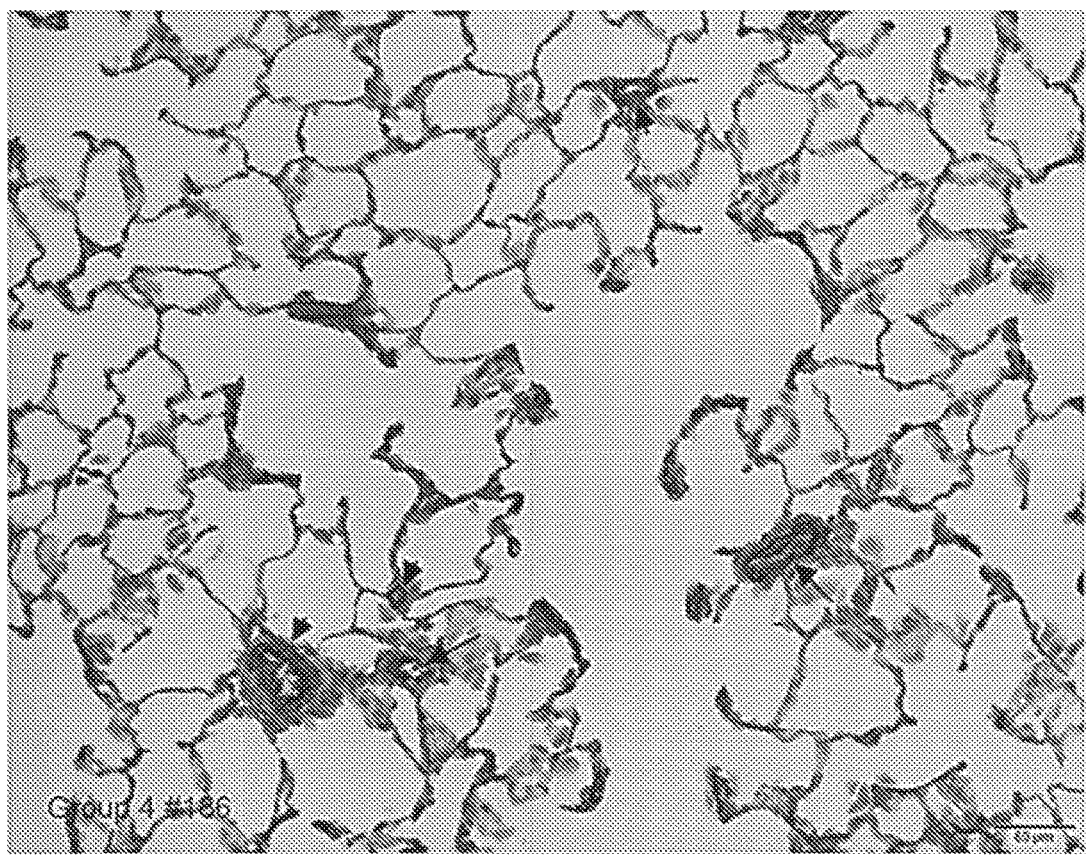
FIG. 13 shows the histopathology of lung tissues in a hypoxia-induced animal treated with 30 mg/kg bid sildenafil. Short arrows point to completely muscularized arterioles. Long arrows point to partially muscularized arterioles. The long arrows point to the non-muscularized portion of the partially muscularized arterioles. The amount of muscular hypertrophy is slightly less than that in FIG. 11.

The term "effective amount" or "therapeutically effective amount" refers herein to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can be determined by one of ordinary skill in the art. The term also applies to a dose that will induce a particular response in target cells, e.g. delaying the onset of or reducing the incidence of one or more symptoms of PAH. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating," or "palliating" and "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of or more of the physiological symptoms associated with the underlying disorder such that an improvement is observed in the patient, notwithstanding that the patient may still be afflicted with the underlying disorder. For prophylactic benefit, the composition may be administered to a patient at risk of developing a particular disease, or to a patient reporting one or more of the physiological symptoms of a disease, even though a diagnosis of this disease may not have been made.

The term "co-administration," "administered in combination with," and their grammatical equivalents, as used herein, encompasses administration of two or more agents to an animal so that both agents and/or their metabolites are present in the animal at the same time. Co-administration includes simultaneous administration in separate composition, administration at different times in separate composition, or administration in a composition in which both agents are present.

"Combination therapy" and "co-therapy" means the administration of a first active agent and at least a second, different active agent as part of a specific treatment regimen intended to provide the beneficial effect from the co-action of the at least two active agents. The beneficial effect of the combination may include, but is not limited to, pharmacokinetic or pharmacodynamic co-action resulting from the combination of therapeutic agents. Administration of therapeutic agents in combination typically is carried out over a defined time period (usually minutes, hours, days or weeks depending upon the combination selected). Combination therapy is not intended to encompass the administration of two or more different therapeutic agents as part of separate monotherapy regimens that incidentally and arbitrarily results in a combination therapy of the invention. Combination therapy includes administration of at least two different therapeutic agents in a sequential manner, wherein each therapeutic agent is administered at a different time, as well as administration of at least two different therapeutic agents in a substantially simultaneous manner. Substantially simultaneous administration can be accomplished, for example, by administering to the subject a single capsule having a fixed ratio of each therapeutic agent or in separate capsules for each of the therapeutic agents. Sequential or substantially simultaneous administration of each therapeutic agent can be effected by any appropriate route, including, but not limited to, oral routes, intravenous routes, intramuscular routes, and direct absorption through mucous membrane tissues. The two different therapeutic agents can be administered by the same route or by different routes. For example, a first therapeutic agent of the combination selected may be administered by intravenous injection while the second therapeutic agent of the combination may be administered orally. Alternatively, for example, all therapeutic agents may be administered orally or all therapeutic agents may be administered by intravenous injection. The sequence in which the therapeutic agents are administered is not critical, unless otherwise stated. Combination therapy also includes the administration of the different therapeutic agents as described above in further combination with other biologically active ingredients and non-drug therapies (e.g., surgery or physical therapy). Where a combination therapy comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The term "pharmaceutically acceptable salt" refers herein to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

As used herein, "agent" or "biologically active agent" refers herein to a biological, pharmaceutical, or chemical compound or other moiety. Non-limiting examples include simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like.

As used herein, "subject" refers to an animal, such as a mammal, for example a human. The methods described herein can be useful in both human therapeutics and veterinary applications. In some embodiments, the patient is a mammal, and in some embodiments, the patient is human.

The term "in vivo" refers to an event that takes places in a subject's body.

The term "in vitro" refers to an event that takes place outside of a subject's body. For example, an in vitro assay encompasses any assay run outside of a subject's body. In vitro assays encompass cell-based assays in which cells alive or dead are employed. In vitro assays also encompass a cell-free assay in which no intact cells are employed.

The term "heterodimerization" as used herein refers to the complex formed by the non-covalent binding of HIF-2α to HIF-1β (ARNT). Heterodimerization of HIF-2α to HIF-1β (ARNT) is required for HIF-2α DNA binding and transcriptional activity and is mediated by the HLH and PAS-B domains. Transcriptional activity following heterodimerization of HIF-2α to HIF-1β (ARNT) can affect four groups of target genes including angiogenic factors, glucose transporters and glycolytic enzymes, survival factors, and invasion factors.

The term "HIF-2α" refers to a monomeric protein that contains three conserved structured domains: basic helix-loop-helix (bHLH), and two Per-ARNT-Sim (PAS) domains designated PAS-A and PAS-B, in addition to C-terminal regulatory regions. "HIF-2α" is also alternatively known by several other names in the scientific literature, most commonly EPAS 1 and MOP2. As a member of the bHLH/PAS family of transcription factors, "HIF-2α" forms an active heterodimeric transcription factor complex by binding to the ARNT (also known as HIF-1β) protein through non-covalent interactions.

The term "HIF-2α PAS-B domain cavity" refers to an internal cavity within the PAS-B domain of HIF-2α. The crystal structure of the PAS-B domain can contain a large (approximately 290 A) cavity in its core. However, the amino acid side chains in the solution structure are dynamic. For example, those side chains can tend to intrude more deeply in the core, and can shrink the cavity to 1 or 2 smaller cavities or can even expand the cavity. The cavity is lined by amino acid residues comprising PHE-244, SER-246, HIS-248, MET-252, PHE-254, ALA-277, PHE-280, TYR-281, MET-289, SER-292, HIS-293, LEU-296, VAL-302, VAL-303, SER-304, TYR-307, MET-309, LEU-319, THR-321, GLN-322, GLY-323, ILE-337, CYS-339, and ASN-341 of HIF-2α PAS-B domain. The numbering system is from the known structures reported in the RCSB Protein Data Bank with PDB code 3H7W. Other numbering systems in the PDB could define the same amino acids, expressed above, that line the cavity.

As described herein "a biological marker", or "a biomarker", generally refers to a measurable indicator of some biological state or condition. Biological markers are often measured and evaluated to examine normal biological processes, pathogenic processes, or pharmacologic responses to a therapeutic intervention. A biomarker may be any molecular structure produced by a cell, expressed inside the cell, accessible on the cell surface, or secreted by the cell. A marker may be any protein, carbohydrate, fat, nucleic acid, catalytic site, or any combination of these such as an enzyme, glycoprotein, cell membrane, virus, cell, organ, organelle, or any uni- or multimolecular structure or any other such structure now known or yet to be disclosed whether alone or in combination.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

"Controlled release" refers to a drug-containing formulation or unit dose form thereof from which release of the drug is not immediate, i.e., with a controlled release formulation, administration does not result in immediate release of all of the drug administered into an absorption pool. The term is used interchangeably with "nonimmediate release" as defined in *Remington: The Science and Practice of Pharmacy, Nineteenth Ed.* (Easton, Pa.: Mack Publishing Company, 1995). In general, controlled release formulations include sustained release and delayed release formulations.

"Sustained release" and "extended release" refers to a drug formulation that provides for gradual release of a drug over an extended period of time, and typically, although not necessarily, results in substantially constant blood levels of a drug over an extended time period.

"Delayed release" refers to a drug formulation that, following administration to a patient, provides a measurable time delay before drug is released from the formulation into the patient's body.

"Dosage form" means any form of a pharmaceutical composition for administration to a subject (typically a human or animal of veterinary interest suffering from a disease or condition to be treated). "Dose" refers to an amount of active agent. "Unit dosage form" refers to a dosage form that contains a fixed amount of active agent. A single tablet or capsule is a unit dosage form. Multiple unit dosage forms can be administered to provide a therapeutically effective dose. A dosage form can include a combination of dosage forms.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

The term "alkyl" refers to a straight or branched hydrocarbon chain radical comprising carbon and hydrogen atoms, containing no unsaturation, and having from one to ten carbon atoms (e.g., $C_1$-$C_{10}$ alkyl). Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated. In some embodiments, it is a $C_1$-$C_4$ alkyl group. Typical alkyl groups include, but are in no way limited to, methyl, ethyl, n-propyl, isopropyl, n-butyl, isobutyl, sec-butyl, tert-butyl, pentyl, isopentyl, neopentyl, hexyl, septyl, octyl, nonyl, decyl, and the like. The alkyl is attached to the rest of the molecule by a single bond, for example, methyl (Me), ethyl (Et), n-propyl, 1-methylethyl, (iso-propyl), n-butyl, n-pentyl, 1,1-dimethylethyl (t-butyl), 3-methylhexyl, 2-methylhexyl, and the like. Unless stated otherwise specifically in the specification, an alkyl group is optionally substituted by one or more of substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —$OR^a$, —$SR^a$, —OC($=$O)$R^a$, —OC($=$O)O$R^a$, —OC($=$O)N($R^a$)$_2$, —N($R^a$), —C($=$O)O$R^a$, —C($=$O)$R^a$, —C($=$O)N($R^a$)$_2$, —N($R^a$)C($=$O)O$R^a$, —N($R^a$)C($=$O)N($R^a$)$_2$, —N($R^a$)C(N$R^a$)N($R^a$)$_2$, —N($R^a$)C($=$O)$R^a$, —N($R^a$)S($=$O)$_t$$R^a$ (where t is 1 or 2), —N($R^a$)S($=$O)$_t$N($R^a$)$_2$ (where t is 1 or 2), —S($=$O)$_t$$R^a$ (where t is 1 or 2), —S($=$O)$_t$N($R^a$)$_2$ (where t is 1 or 2), —PO$_3$($R^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each $R^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "fluoroalkyl" refers to an alkyl group substituted with one or more fluorine atoms. In some embodiments, it is a $C_1$-$C_4$ alkyl group substituted with one or more fluorine atoms. Typical fluoroalkyl groups include, but are in no way limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$.

The term "alkenyl" refers to a straight or branched hydrocarbon chain radical group comprising carbon and hydrogen atoms, containing at least one double bond, and having from two to ten carbon atoms (i.e., $C_2$-$C_{10}$ alkenyl). Whenever it appears herein, a numerical range such as "2 to 10" refers to each integer in the given range; e.g., "2 to 10 carbon atoms" means that the alkenyl group may contain 2 carbon atoms, 3 carbon atoms, etc., up to and including 10 carbon atoms. In certain embodiments, an alkenyl comprises two to eight carbon atoms (i.e., $C_2$-$C_8$ alkenyl). In other embodiments, an alkenyl comprises two to five carbon atoms (i.e., $C_2$-$C_5$ alkenyl). The alkenyl is attached to the rest of the molecule by a single bond, for example, ethenyl (i.e., vinyl), prop-1-enyl, but-1-enyl, pent-1-enyl, penta-1,4-dienyl, and the like. Unless stated otherwise specifically in the specification, an alkenyl group is optionally substituted by one or more of the following substituents: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —$OR^a$, —$SR^a$, —OC($=$O)$R^a$, —OC($=$O)O$R^a$, —OC($=$O)N($R^a$)$_2$, —N($R^a$)$_2$, —C($=$O)O$R^a$, —C($=$O)$R^a$, —C($=$O)N($R^a$)$_2$, —N($R^a$)C($=$O)O$R^a$, —N($R^a$)C($=$O)N($R^a$)$_2$, —N($R^a$)C(N$R^a$)N($R^a$)$_2$, —N($R^a$)C($=$O)$R^a$, —N($R^a$)S($=$O)$_t$$R^a$ (where t is 1 or 2), —N($R^a$)S($=$O)$_t$N($R^a$)$_2$ (where t is 1 or 2), —S($=$O)$_t$$R^a$ (where t is 1 or 2), —S($=$O)$_t$N($R^a$)$_2$ (where t is 1 or 2), —PO$_3$($R^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each $R^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "alkynyl" refers to a straight or branched hydrocarbon chain radical group comprising carbon and hydrogen atoms, containing at least one triple bond, and having from two to ten carbon atoms (i.e., $C_2$-$C_{10}$ alkynyl). In some embodiments, an alkynyl group may contain one or more double bonds. Whenever it appears herein, a numerical range such as "2 to 10" refers to each integer in the given range; e.g., "2 to 10 carbon atoms" means that the alkynyl group may contain 2 carbon atoms, 3 carbon atoms, etc., up to and including 10 carbon atoms. In certain embodiments, an alkynyl comprises two to eight carbon atoms (i.e., $C_2$-$C_8$ alkynyl). In other embodiments, an alkynyl has two to five carbon atoms (i.e., $C_2$-$C_5$ alkynyl). The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —$OR^a$, —$SR^a$, —OC($=$O)$R^a$, —OC($=$O)O$R^a$, —OC($=$O)N($R^a$)$_2$, —N($R^a$)$_2$, —C($=$O)O$R^a$, —C($=$O)$R^a$, —C($=$O)N($R^a$)$_2$, —N($R^a$)C($=$O)O$R^a$, —N($R^a$)C($=$O)N($R^a$)$_2$, —N($R^a$)C(N$R^a$)N($R^a$)$_2$, —N($R^a$)C($=$O)$R^a$, —N($R^a$)S($=$O)$_t$$R^a$ (where t is 1 or 2), —N($R^a$)S($=$O)$_t$N($R^a$)$_2$ (where t is 1 or 2), —S($=$O)$_t$$R^a$ (where t is 1 or 2), —S($=$O)$_t$N($R^a$)$_2$ (where t is 1 or 2), —PO$_3$($R^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each $R^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "aromatic" or "aryl" refers to an aromatic radical with six to ten ring atoms (i.e., $C_6$-$C_{10}$ aromatic or $C_6$-$C_{10}$ aryl) which has at least one ring having a conjugated pi electron system which is carbocyclic (e.g., phenyl, fluorenyl, and naphthyl). Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —$OR^a$, —$SR^a$, —OC($=$O)$R^a$, —OC($=$O)O$R^a$, —OC($=$O)N($R^a$)$_2$, —N($R^a$), —C($=$O)O$R^a$, —C($=$O)$R^a$, —C($=$O)N($R^a$)$_2$, —N($R^a$)C($=$O)O$R^a$, —N($R^a$)C($=$O)N($R^a$)$_2$, —N($R^a$)C(N$R^a$)N($R^a$)$_2$, —N($R^a$)C($=$O)$R^a$, —N($R^a$)S($=$O)$_t$$R^a$ (where t is 1 or 2), —N($R^a$)S (=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

"Aralkyl" or "arylalkyl" refers to an (aryl)alkyl-radical wherein the arylalkyl moiety is attached via the alkyl portion of the moiety. Aryl and alkyl are as disclosed herein and are optionally substituted by one or more of the substituents described as suitable substituents for aryl and alkyl, respectively.

The term "heteroaryl" or, alternatively, "heteroaromatic" refers to a 5- to 18-membered aromatic radical (i.e., $C_5$-$C_{18}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range; e.g., "5 to 18 ring atoms" means that the heteroaryl group may consist of 5 ring atoms, 6 ring atoms, etc., up to and including 18 ring atoms. An N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical, e.g., nitrogen or sulfur, is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzofurazanyl, benzothiazolyl, benzothienyl, benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocyclocta[d]pyrimidinyl, 5,6,7,8,9,10-hexahydrocyclocta[d]pyridazinyl, 5,6,7,8,9,10-hexahydrocyclocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, a heteroaryl moiety is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl. Examples of monocylic heteroaryls include, but are not limited to, imidazolyl, pyridinyl, pyrrolyl, pyrazinyl, pyrimidinyl, thiazolyl, furanyl and thienyl.

Substituted heteroaryl also includes ring systems substituted with one or more oxide substituents, such as pyridinyl N-oxides.

"Heteroarylalkyl" refers to a moiety having a heteroaryl moiety, as described herein, connected to an alkyl moiety, as described herein, wherein the connection to the remainder of the molecule is through the alkyl group. Heteroaryl and alkyl are as disclosed herein and are optionally substituted by one or more of the substituents described as suitable substituents for heteroaryl and alkyl, respectively.

The term "acyl" refers to a —C(=O)R radical, wherein R is alkyl, cycloalkyl, aryl, heteroaryl, heteroalkyl, or heterocycloalkyl, which are as described herein. The R group is attached to the parent structure through the carbonyl functionality. In some embodiments, it is a $C_1$-$C_{10}$ acyl radical which refers to the total number of chain or ring atoms of the alkyl, cycloalkyl, aryl, heteroalkyl, heteroaryl or heterocycloalkyl portion of the acyl group plus the carbonyl carbon of acyl, i.e. ring or chain atoms plus carbonyl. If the R radical is heteroaryl or heterocycloalkyl, the hetero ring or chain atoms contribute to the total number of chain or ring atoms. Unless stated otherwise specifically in the specification, the "R" of an acyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "halo", "halide", or alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoro-alkoxy" refer to haloalkyl and haloalkoxy groups, respectively, in which the halo is fluoro. Examples of fluoroalkyl include, but are not limited to, —CH$_2$F, —CHF$_2$, —CF$_3$, —CF$_2$CH$_3$, —CH$_2$CF$_3$, and —CF$_2$CF$_3$. The alkyl part of the haloalkyl radical may be optionally substituted as defined above for an alkyl group.

The term "cyano" refers to a —CN radical.

The term "alkoxy" refers to an —O-alkyl radical, including from wherein alkyl is as described herein and contains 1 to 10 carbon atoms (i.e., C$_1$-C$_{10}$ alkoxy) of a straight, branched, or cyclic configuration and combinations thereof attached to the parent structure through an oxygen. Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms. In some embodiments, it is a C$_1$-C$_4$ alkoxy group. Examples include methoxy, ethoxy, propoxy, isopropoxy, cyclopropyloxy, cyclohexyloxy and the like. Unless stated otherwise specifically in the specification, an alkoxy moiety may be substituted by one or more of the substituents described as suitable substituents for an alkyl radical.

The term "sp$^3$ hybridized carbon" refers to a carbon atom that is bonded to four other atoms. sp$^3$ hybridization results from the combination of the s orbital and all three p orbitals in the second energy level of carbon. It results in four equivalent orbitals and the geometric arrangement of those four orbitals is tetrahedral.

The term "sulfonyl" refers to a —S(=O)$_2$R$^a$ radical, wherein R$^a$ is selected from the group consisting of alkyl, amino, cycloalkyl, aryl, heteroalkyl, heteroaryl (bonded through a ring carbon) and heterocycloalkyl (bonded through a ring carbon). Unless stated otherwise specifically in the specification, the R$^a$ group may be substituted by one or more of the substituents described as suitable substituents for an alkyl, an aryl or a heteroaryl radical.

The term "sulfoximinyl" refers to a —S(=O)(=NR$^a$)R$^b$ radical, wherein R$^a$ is selected from the group consisting of hydrogen, alkyl, cycloalkyl, aryl, cyano, carbamoyl, acyl, heteroaryl (bonded through a ring carbon) and heterocycloalkyl (bonded through a ring carbon) and R$^b$ is independently selected from the group consisting of alkyl, cycloalkyl, aryl, heteroalkyl, heteroaryl (bonded through a ring carbon) and heterocycloalkyl (bonded through a ring carbon). Unless stated otherwise specifically in the specification, the R$^a$ and R$^b$ groups may be substituted by one or more of the substituents described as suitable substituents for an alkyl, an aryl or a heteroaryl radical.

"Sulfonamide," "sulfonamidyl" or "sulfonamido" refers to a —S(=O)$_2$N(R$^a$)$_2$ radical, wherein each R$^a$ is selected independently from the group consisting of hydrogen, alkyl, heteroalkyl, cycloalkyl, aryl, heteroaryl and heterocycloalkyl. The R$^a$ groups in —N(R$^a$)$_2$ of the —S(=O)$_2$—N(R$^a$) radical may be taken together with the nitrogen to which it is attached to form a 4-, 5-, 6-, or 7-membered ring. In some embodiments, it is a C$_1$-C$_{10}$ sulfonamido, wherein each R$^a$ in sulfonamido contains 1 carbon, 2 carbons, 3 carbons or 4 carbons total. A sulfonamido group is optionally substituted by one or more of the substituents described for alkyl, cycloalkyl, aryl and heteroaryl, respectively.

The term "fluoroalkylsulfonyl" refers to a —S(=O)$_2$R$^a$ radical, wherein R$^a$ is fluoroalkyl. In some embodiments, R$^a$ is C$_1$-C$_4$ alkyl, substituted with one or more fluorines.

The term "cycloalkyl" refers to a monocyclic or polycyclic non-aromatic radical that contains carbon and hydrogen, and may be saturated, or partially unsaturated. Cycloalkyl groups include groups having from 3 to 10 ring atoms (e.g., C$_3$-C$_{10}$ cycloalkyl). Whenever it appears herein, a numerical range such as "3 to 10" refers to each integer in the given range; e.g., "3 to 10 carbon atoms" means that the cycloalkyl group may consist of 3 carbon ring atoms, 4 carbon ring atoms, 5 carbon ring atoms, etc., up to and including 10 carbon ring atoms. In some embodiments, it is a C$_3$-C$_8$ cycloalkyl radical. In some embodiments, it is a C$_3$-C$_5$ cycloalkyl radical. Illustrative examples of cycloalkyl groups include, but are not limited to the following moieties: cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "heterocyclyl" or "heterocycloalkyl" refers to a stable 3- to 18-membered nonaromatic ring (e.g., C$_3$-C$_{18}$ heterocycloalkyl) radical that comprises two to twelve ring carbon atoms and from one to six heteroatoms selected from nitrogen, oxygen and sulfur. Whenever it appears herein, a numerical range such as "3 to 18" refers to each integer in the given range; e.g., "3 to 18 ring atoms" means that the heterocycloalkyl group may consist of 3 ring atoms, 4 ring atoms, etc., up to and including 18 ring atoms. In some embodiments, it is a C$_5$-C$_{10}$ heterocycloalkyl. In some embodiments, it is a C$_4$-C$_{10}$ heterocycloalkyl. In some embodiments, it is a C$_3$-C$_{10}$ heterocycloalkyl. Unless stated otherwise specifically in the specification, the heterocycloalkyl radical may be a monocyclic, bicyclic, tricyclic or tetracyclic ring system, which may include fused or bridged ring systems. The heteroatoms in the heterocycloalkyl radical may be optionally oxidized. One or more nitrogen atoms, if present, may optionally be quaternized. The heterocycloalkyl radical may be partially or fully saturated. The heterocycloalkyl may be attached to the rest of the molecule through any atom of the ring(s). Examples of such heterocycloalkyl radicals include, but are not limited to, 6,7-dihydro-5H-cyclopenta[b]pyridine, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocycloalkyl moiety is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$), —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur and nitrogen, as well as combinations comprising at least one of the foregoing heteroatoms; the other ring, usually with 3 to 7 ring atoms, optionally contains 1-3 heteroatoms independently selected form oxygen, sulfur and nitrogen and is not aromatic.

The terms "heteroalkyl", "heteroalkenyl" and "heteroalkynyl" include optionally substituted alkyl, alkenyl and alkynyl radicals, which respectively have one or more skeletal chain atoms selected from an atom other than carbon, e.g., oxygen, nitrogen, sulfur, phosphorus or combinations thereof. A numerical range, which refers to the chain length in total, may be given. For example, $C_3$-$C_4$ heteroalkyl has a chain length of 3-4 atoms. For example, a —CH$_2$OCH$_2$CH$_3$ radical is referred to as a "$C_4$ heteroalkyl", which includes the heteroatom in the atom chain length description. Connection to the rest of the molecule may be through either a heteroatom or a carbon in the heteroalkyl chain. A heteroalkyl may be a substituted alkyl. The same definition applies to heteroalkenyl or heteroalkynyl. Unless otherwise stated in the specification, a heteroalkyl group may be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$), —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "amino" or "amine" refers to a —N(R$^a$)$_2$ radical group, where each R$^a$ is independently hydrogen, alkyl, heteroalkyl, fluoroalkyl, cycloalkyl, aryl, aralkyl, heterocycloalkyl, heterocycloalkylalkyl, heteroaryl or heteroarylalkyl, unless stated otherwise specifically in the specification. When a —N(R$^a$)$_2$ group has two R$^a$ other than hydrogen, they can be combined with the nitrogen atom to form a 3-, 4-, 5-, 6-, 7- or 8-membered ring. For example, —N(R$^a$)$_2$ is meant to include, but not be limited to, 1-pyrrolidinyl and 4-morpholinyl. Unless stated otherwise specifically in the specification, an amino group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^8$), —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_1$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "substituted amino" also refers to N-oxides of —N(R$^a$) as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

The term "acyloxy" refers to a RC(=O)O— radical wherein R is alkyl, cycloalkyl, aryl, heteroalkyl, heteroaryl or heterocycloalkyl, which are as described herein. In some embodiments, it is a $C_1$-$C_4$ acyloxy radical, which refers to the total number of chain or ring atoms of the alkyl, cycloalkyl, aryl, heteroalkyl, heteroaryl or heterocycloalkyl portion of the acyloxy group plus the carbonyl carbon of acyl, i.e., the other ring or chain atoms plus carbonyl. If the R radical is heteroaryl or heterocycloalkyl, the hetero ring or chain atoms contribute to the total number of chain or ring atoms. Unless stated otherwise specifically in the specification, the "R" of an acyloxy group is optionally substituted by one or more of the following substituents: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$), —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "amide" or "amido" refers to a chemical moiety with formula —C(=O)N(R$^a$)$_2$ or —NR$^a$C(=O)R$^a$, wherein each of R$^a$ is independently selected from the group consisting of hydrogen, alkyl, cycloalkyl, aryl, heteroaryl (bonded through a ring carbon) and heterocycloalkyl. Two R$^a$s may optionally be taken together with the nitrogen to which it is attached to form a 4-10 membered ring. In some embodiments, it is a $C_1$-$C_4$ amido or amide radical, which includes the amide carbonyl in the total number of carbons in the radical. Unless stated otherwise specifically in the specification, an amido group is optionally substituted independently by one or more of the substituents as described herein for alkyl, cycloalkyl, aryl, heteroaryl, or heterocycloalkyl. An amide may be an amino acid or a peptide molecule attached to a compound having an amine or a carboxylic acid moiety, thereby forming a prodrug. Any amine, hydroxy or carboxyl side chain on the compounds described herein can be amidified. The procedures and specific groups to make such amides are known to those of skilled in the art and can readily be found in reference sources such as Wuts, *Greene's Protective Groups in Organic Synthesis*, 5$^{th}$ Ed., Wiley, New York, N.Y., 2014, which is incorporated herein by reference in its entirety.

"Carboxaldehyde" refers to a —C(=O)H radical.

"Carboxyl" refers to a —C(=O)OH radical.

"Ester" refers to a chemical radical of formula —C(=O)OR, where R is selected from the group consisting of alkyl, cycloalkyl, aryl, heteroaryl (bonded through a ring carbon) and heterocycloalkyl (bonded through a ring carbon). Any amine, hydroxy, or carboxyl side chain on the compounds described herein can be esterified. The procedures and specific groups to make such esters are known to those skilled in the art and can readily be found in reference sources such as Wuts, *Greene's Protective Groups in Organic Synthesis*, 5$^{th}$ Ed., Wiley, New York, N.Y., 2014, which is incorporated herein by reference in its entirety. Unless stated otherwise specifically in the specification, an ester group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

"Imino" refers to a =N—R$^a$ radical, wherein R$^a$ is hydrogen, alkyl, heteroalkyl, cycloalkyl, cyano, aryl, heterocycloalkyl or heteroaryl.

"Isocyanato" refers to a —NCO radical.

"Isothiocyanato" refers to a —NCS radical.

"Mercaptyl" refers to an —S(alkyl) or —SH radical.

"Methylene" refers to a =CH$_2$ radical.

"Hydroxy" refers to a —OH radical.

"Oxa" refers to a —O— radical.

"Oxo" refers to a =O radical.

"Nitro" refers to a —NO$_2$ radical.

"Oxime" refers to a =N(—OR) radical, where R is hydrogen or alkyl.

"Sulfinyl" refers to a —S(=O)R radical, where R is selected from the group consisting of alkyl, cycloalkyl, aryl, heteroalkyl, heteroaryl (bonded through a ring carbon) and heterocycloalkyl (bonded through a ring carbon). In some embodiments, R is fluoroalkyl.

"Sulfoxyl" refers to a —S(=O)$_2$OH radical.

"Sulfonate" refers to a —S(=O)$_2$OR radical, where R is selected from the group consisting of alkyl, cycloalkyl, aryl, heteroalkyl, heteroaryl (bonded through a ring carbon) and heterocycloalkyl (bonded through a ring carbon). The R group is optionally substituted by one or more of the substituents described for alkyl, heteroalkyl, cycloalkyl, heterocycloalkyl, aryl, and heteroaryl, respectively.

"Thiocyanato" refers to a —CNS radical.

"Thioxo" refers to a =S radical.

"Moiety" refers to a specific segment or functional group of a molecule. Chemical moieties are often recognized chemical entities embedded in or appended to a molecule.

"Substituted" means that the referenced group may be substituted with one or more additional group(s) individually and independently selected from acyl, alkyl, alkylaryl, heteroalkyl, cycloalkyl, aralkl, heterocycloalkyl, aryl, carbohydrate, carbonate, heteroaryl, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamide, sulfoxyl, sulfonate, urea, and amino, including mono- and di-substituted amino groups and the protected derivatives thereof. The substituents themselves may be substituted, for example, a cycloalkyl substituent may have a halide substituted at one or more ring carbons, and the like. The protecting groups that may form the protective derivatives of the above substituents are known to those of skill in the art and may be found in references such as Wuts, *Greene's Protective Groups in Organic Synthesis*, 5$^{th}$ Ed., Wiley, New York, N.Y., 2014.

The term "optional" or "optionally" means that the subsequently described event or circumstance may or may not occur, and includes instances where the event or circumstance occurs and instances in which it does not. For example, "alkyl optionally substituted with" encompasses both "alkyl" and "alkyl" substituted with groups as defined herein. It will be understood by those skilled in the art, with respect to any group containing one or more substituents, that such groups are not intended to introduce any substitution or substitution patterns which would be deemed unacceptable by one of ordinary skill in the art.

Compounds of the present invention also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof. "Crystalline form," "polymorph," and "novel form" may be used interchangeably herein, and are meant to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

The compounds described herein may exhibit their natural isotopic abundance, or one or more of the atoms may be artificially enriched in a particular isotope having the same atomic number, but an atomic mass or mass number different from the atomic mass or mass number predominantly found in nature. All isotopic variations of the compounds of the present invention, whether radioactive or not, are encompassed within the scope of the present invention. For example, hydrogen has three naturally occurring isotopes, denoted $^1$H (protium), $^2$H (deuterium), and $^3$H (tritium). Protium is the most abundant isotope in nature. Enriching for deuterium may afford certain therapeutic advantages, such as increased in vivo half-life and/or exposure, or may provide a compound useful for investigating in vivo routes of drug elimination and metabolism. Isotopically-enriched compounds may be prepared by conventional techniques well known to those skilled in the art or by processes analogous to those described in the Schemes and Examples herein using appropriate isotopically-enriched reagents and/or intermediates. See Pleiss and Voger, *Synthesis and Applications of Isotopically Labeled Compounds*, Vol. 7, Wiley, ISBN-10: 0471495018, published on Mar. 14, 2001.

"Isomers" are different compounds that have the same molecular formula. "Stereoisomers" are isomers that differ only in the way the atoms are arranged in space. "Enantiomers" are a pair of stereoisomers that are non superimposable mirror images of each other. A 1:1 mixture of a pair of enantiomers is a "racemic" mixture. The term "(±)" is used to designate a racemic mixture where appropriate. "Diastereoisomers" or "diastereomers" are stereoisomers that have at least two asymmetric atoms but are not mirror images of each other. The absolute stereochemistry is specified according to the Cahn-Ingold-Prelog R-S system. When a compound is a pure enantiomer, the stereochemistry at each chiral carbon can be specified by either R or S. Resolved compounds whose absolute configuration is unknown can be designated (+) or (−) depending on the direction (dextro- or levorotatory) in which they rotate plane polarized light at the wavelength of the sodium D line. Certain compounds described herein contain one or more asymmetric centers and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms, mixtures of diastereomers and intermediate mixtures. Optically active (R)- and (S)-isomers can be prepared using chiral synthons or chiral reagents, or resolved using conventional techniques. The optical activity of a compound can be analyzed via any suitable method, including but not limited to chiral chromatography and polarimetry, and the degree of predominance of one stereoisomer over the other isomer can be determined.

Chemical entities having carbon-carbon double bonds or carbon-nitrogen double bonds may exist in Z- or E-form (or cis- or trans-form). Furthermore, some chemical entities may exist in various tautomeric forms. Unless otherwise specified, chemical entities described herein are intended to include all Z-, E- and tautomeric forms as well.

The term "enantiomeric excess," as used herein, is the percent excess of one enantiomer compared to that of the other enantiomer in a mixture, and can be calculated using the following equation: enantiomeric excess=((R−S)/(R+S))×100=% (R*)−% (S*), wherein R and S are the number of moles of each enantiomer in the mixture, and R* and S* are the respective mole fractions of the enantiomers in the mixture. For example, for a mixture with 87% R enantiomer and 13% S enantiomer, the enantiomeric excess is 74%.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

"Protecting group" has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in Wuts, *Greene's Protective Groups in Organic Synthesis*, 5$^{th}$ Ed., Wiley, New York, N.Y., 2014. For example, a hydroxy protected form is where at least one of the hydroxy groups present in a compound is protected with a hydroxy protecting group. Likewise, amines and other reactive groups may similarly be protected.

"Solvate" refers to a compound in physical association with one or more molecules of a pharmaceutically acceptable solvent. It will be understood that the present chemical entities encompass the present chemical entities and solvates of the compound, as well as mixtures thereof.

"Solvent," "organic solvent," and "inert solvent" each means a solvent inert under the conditions of the reaction being described in conjunction therewith, including, for example, benzene, toluene, acetonitrile, tetrahydrofuran ("THF"), dimethylformamide ("DMF"), chloroform, methylene chloride (or dichloromethane), diethyl ether, methanol, N-methylpyrrolidone ("NMP"), pyridine and the like. Unless specified to the contrary, the solvents used in the reactions described herein are inert organic solvents. Unless specified to the contrary, for each gram of the limiting reagent, one cc (or mL) of solvent constitutes a volume equivalent.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples herein below. However, other equivalent separation or isolation procedures can also be used.

When desired, the (R)- and (S)-isomers of the compounds of the present invention, if present, may be resolved by methods known to those skilled in the art, for example by formation of diastereoisomeric salts or complexes which may be separated, for example, by crystallization; via formation of diasteroisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

The compounds described herein can be optionally contacted with a pharmaceutically acceptable acid to form the corresponding acid addition salts. Pharmaceutically acceptable forms of the compounds recited herein include pharmaceutically acceptable salts, chelates, non-covalent complexes, prodrugs, and mixtures thereof. In certain embodiments, the compounds described herein are in the form of pharmaceutically acceptable salts. In addition, if the compound described herein is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range.

Abbreviations used herein have their conventional meaning within the chemical and biological arts.

The following abbreviations and terms have the indicated meanings throughout:

DAST=Diethylaminosulfur trifluoride
DCM=Dichloromethane
MTBE=Methyl t-butyl ether
HATU=O-(7-azabenzotriazol-1-yl)-N,N,N',N'-tetramethyluronium hexafluorophosphate
NBS=N-Bromosuccinimide
NMP=N-Methyl-2-pyrrolidone
e.e. or ee=Enantiomeric excess
PPTS=Pyridinium p-toluenesulfonate
TLC=Thin Layer Chromatography
DMAP=4-Dimethylaminopyridine
DMF=N,N-Dimethylformamide When stereochemistry is not specified, certain small molecules described herein include, but are not limited to, when possible, their isomers, such as enantiomers and diastereomers, mixtures of enantiomers, including racemates, mixtures of diastereomers, and other mixtures thereof, to the extent they can be made by one of ordinary skill in the art by routine experimentation. In those situations, the single enantiomers or diastereomers, i.e., optically active forms, can be obtained by asymmetric synthesis or by resolution of the racemates or mixtures of diastereomers. Resolution of the racemates or mixtures of diastereomers, if possible, can be accomplished, for example, by conventional methods such as crystallization in the presence of a resolving agent, or chromatography, using, for example, a chiral high-pressure liquid chromatography (HPLC) column. Furthermore, a mixture of two enantiomers enriched in one of the two can be purified to provide further optically enriched form of the major enantiomer by recrystallization and/or trituration. In addition, such certain small molecules include Z- and E-forms (or cis- and trans-forms) of certain small molecules with carbon-carbon double bonds or carbon-nitrogen double bonds. Where certain small molecules described herein exist in various tautomeric forms, the term "certain small molecule" is intended to include all tautomeric forms of the certain small molecule.

When "⋯" is drawn across a bond, it denotes where a bond disconnection or attachment occurs. For example, in the chemical structure shown below,

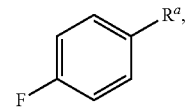

$R^a$ is attached to the para position of a fluorophenyl ring through a single bond. When $R^a$ is phenyl, it can also be drawn as

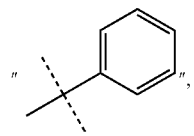

The waved line "∿" means a bond with undefined stereochemistry. For example,

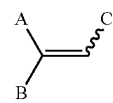

represents a mixture of

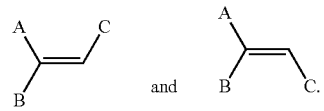

When a bond is drawn across a ring, it means substitution at a non-specific ring atom or position. For example, in the structure shown below,

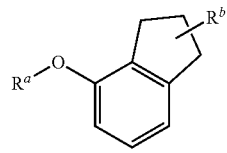

$R^b$ may be attached to any one of the —CH$_2$— in the five-membered ring.

When a bold bond "╱" appears two or more times in the same chemical structure, a mixture of the two cis isomers of the compound is described. For example,

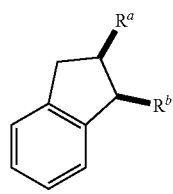

represents a mixture of the two isomers

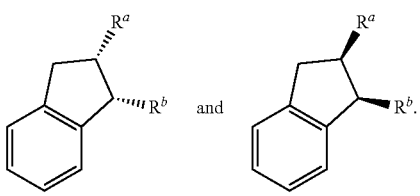

In one aspect, the disclosure provides a method of treating pulmonary arterial hypertension (PAH). In one embodiment, the method comprises administering a composition comprising an effective amount of a HIF-2α inhibitor to said subject. PAH is a life-threatening and progressive disease of various origins characterized by pulmonary vascular remodeling that leads to increased pulmonary vascular resistance and pulmonary arterial pressure, most often resulting in right-sided heart failure. The most common symptom at presentation is breathlessness, with impaired exercise capacity as a hallmark of the disease. PAH includes idopathic PAH, heritable PAH (e.g. BMPR2, ALK1, endoglin), drug-induced PAH, toxin-induced PAH, and PAH associated with another condition (e.g. connective tissue diseases, HIV infection, portal hypertension, congenital heart diseases, schistosomiasis, or chronic hemolytic anemia). Idiopathic PAH occurs in the absence of known risk factors and is the most common form of the disease. The PAH condition treated in accordance with the present disclosure can include any of these PAH conditions.

In general, the median period of survival of PAH after diagnosis, based on an early U.S. National Institutes of Health Registry with prospective follow-up, is less than 3 years for 194 untreated patients with idiopathic or heritable PAH (formerly called primary pulmonary hypertension) with a mean age of 36 years. At present, average survival after diagnosis in adults is estimated at 5 to 7 years, with a similarly poor overall prognosis in children. In some embodiments, the HIF-2α inhibitor is administered in an amount effective to increase average survival among a treated population of subjects, such as by about or more than about 0.5, 1, 2, 3, 4, 5, 6, 7, 8, 9, 10, 15, or more years.

The pathology of PAH can include pathologic changes in the intima, media, and adventitial layers of the vascular wall. Both vascular endothelial and smooth muscle cells have characteristics of abnormal growth, with excess cellular proliferation and apoptosis resistance. These abnormalities in resident vascular cells, in combination with inflammation, excess vasoconstriction, and in situ thrombosis, can contribute to physical narrowing of the distal pulmonary arterioles. Without being bound by any theory, this narrowing can cause increase in pulmonary vascular resistance, which leads to the chronic and progressive elevation of pulmonary arterial pressure. In some cases, PAH can be induced by hypoxia. In some embodiments, the HIF-2α inhibitor is administered in an amount effective to delay, reduce the incidence of, or reduce the severity of one or more such symptoms associated with PAH.

Treating PAH includes treating a subject diagnosed with existing PAH, as well as preventing PAH. In some embodiments, the amount of HIF-2α inhibitor administered to the subject (either in a single dose or over multiple doses) is effective in delaying the onset of or reducing the incidence of one or more symptoms of PAH. The delay or reduction in incidence may be with respect to a reference population, such as an untreated population of subjects having PAH or subjects having PAH but treated with another agent. Delay or reduction in incidence of one or more symptoms of PAH may be a reduction of about or more than about 10%, 20%, 30%, 40%, 50%, 60%, 70%, 80%, 90%, 95%, or more. In some embodiments, delay or reduction in incidence is measured by an increased time in disease progression, such as between the appearance of one or more first symptoms, and the appearance of one or more second symptoms. Delay may be about or more than about days, weeks, months, or years (e.g. 1, 2, 3, 4, 5, 6, 7, or more days; 1, 2, 3, 4, 5, 6, 7, 8, or more weeks; 1, 2, 3, 4, 5, 6, or more months; or 1, 2, 3, 4, 5, or more years). In the case of prevention, the subject may be an individual at risk of developing PAH.

In one embodiment, the amount of HIF-2α inhibitor administered to the subject (either in a single dose or over multiple doses) is effective in (a) stabilizing pulmonary arterial pressure (PAP) as compared to a PAP trend in the subject prior to treatment, or (b) reducing PAP relative to a starting level of PAP in the subject; wherein the PAP is systolic pulmonary arterial pressure (SPAP) or diastolic pulmonary arterial pressure (DPAP). A variety of methods for measuring PAP are available. For example, the PAP can be measured by inserting a catheter into the pulmonary artery. Typically, the mean pressure is 9-18 mmHg, and the wedge pressure measured in the left atrium can be 6-12 mmHg. The wedge pressure may be elevated in left heart failure, mitral valve stenosis, and other conditions, such as sickle cell disease.

PAP in a subject may be stabilized at a level existing at the start of treatment, such as for days, weeks, months or years. In some embodiments, a starting level of PAP in the subject may be reduced by about or more than about 5%, 10%, 15%, 20%, 25%, 30%, 35%, 40%, 45%, 50%, or more. In some embodiments, a rate of PAP increase may be reduced by about or more than about 10%, 20%, 30%, 40%, 50%, 60%, 70%, 80%, 90%, 95%, or more.

The amount of HIF-2α inhibitor administered to the subject (either in a single dose or over multiple doses) can be effective in reducing right ventricular hypertrophy as measured by Fulton's Index relative to an untreated population of subjects having PAH. Fulton's Index is a measure of the ratio between the mass of the right ventricle to the combined mass of the left ventricle and septum (RV/(LV+S)). Mass can be measured directly (e.g. in the context of an animal study) or extrapolated from volume measurements for a live subject (e.g. as determined by echocardiogram). Reduction may be with respect to an untreated population of subjects with PAH. For example, the average reduction in the Fulton Index among a population of PAH subjects treated with a HIF-2α inhibitor as compared to an untreated population of PAH subjects can be about or more than about 5%, 10%, 15%, 20%, 25%, 30%, 35%, 40%, 45%, 50%, or more. In some embodiments, the reduction in Fulton's Index is at least about 20%.

In some embodiments, the amount of HIF-2α inhibitor administered to the subject (either in a single dose or over multiple doses) is effective in reducing a physiological indicator of PAH. The reduction may be measured over a specified period, such as a level of reduction days (e.g. about or more than about 1, 2, 3, 4, 5, 6, 7 or more days), weeks (e.g. 1, 2, 3, 4, 5, 6, or more weeks), months (e.g. 1, 2, 3, 4, 5, 6, 8, 10, or more months), or longer (e.g. 1, 2, 3, 4, 5, or more years) after treatment is initiated (which treatment may be ongoing through the period). Any of a variety of physiological indicators can be measured, such as pulmonary vascular resistance, pulmonary arterial pressure, systemic arterial pressure, mixed venous oxygen saturation, arterial oxygen saturation, cardiac index, pulmonary capillary wedge pressure, right atrial pressure, six-minute walk distance, brain natriuretic peptide level, and lung diffusion capacity. For example, the HIF-2α inhibitor may be present in an amount effective in (a) reducing one or more of: pulmonary vascular resistance, pulmonary arterial pressure, systemic arterial pressure, pulmonary capillary wedge pressure, right atrial pressure, and brain natriuretic peptide level; and/or (b) increasing one or more of: mixed venous oxygen saturation, arterial oxygen saturation, cardiac index, six-minute walk distance, and lung diffusion capacity. The amount of HIF-2α inhibitor may be effective in increasing time to death, increasing time to clinical worsening, reducing incidence of right heart failure, or promoting a favorable change in WHO functional class (see Table 1).

TABLE 1

WHO functional class

| Functional Class | Symptomatic profile |
|---|---|
| I | Patients with pulmonary hypertension but without resulting limitation of physical activity. Ordinary physical activity does not cause dyspnoea or fatigue, chest pain, or near syncope. |
| II | Patients with pulmonary hypertension resulting in slight limitation of physical activity. They are comfortable at rest. Ordinary physical activity causes undue dyspnoea or fatigue, chest pain, or near syncope. |
| III | Patients with pulmonary hypertension resulting in marked limitation of physical activity. They are comfortable at rest. Less than ordinary activity causes undue dyspnoea or fatigue, chest pain, or near syncope. |
| IV | Patients with pulmonary hypertension with inability to carry out any physical activity without symptoms. These patients manifest signs of right heart failure. Dyspnoea and/or fatigue may even be present at rest. Discomfort is increased by any physical activity. |

One physiological indicator of PAH is pulmonary vascular resistance (PVR). The baseline or reference PVR level can be 200 dyn·sec/cm$^5$ or greater, 240 dyn·sec/cm$^5$ or greater, 300 dyn·sec/cm$^5$ or greater, 400 dyn·sec/cm$^5$ or greater, 500 dyn·sec/cm$^5$ or greater, 600 dyn·sec/cm$^5$ or greater, 700 dyn·sec/cm$^5$ or greater, or 800 dyn·sec/cm$^5$ or greater. In some embodiments, a treatment provided herein is efficacious if after treatment has started, the endpoint PVR level of the subject decreases from the baseline or reference PVR level by 70 dyn·sec/cm$^5$ or more, 100 dyn·sec/cm$^5$ or more, 130 dyn·sec/cm$^5$ or more, or 160 dyn·sec/cm$^5$ or more.

Another physiological indicator of PAH is pulmonary arterial pressure (PAP). The baseline or reference PAP level can be 20 mmHg or greater, 25 mmHg or greater, 30 mmHg or greater, 35 mmHg or greater, 40 mmHg or greater, 45 mmHg or greater, 50 mmHg or greater, 60 mmHg or greater, or 70 mmHg or greater. In some embodiments, a treatment provided herein is efficacious if, after treatment has started, the endpoint PAP level of the subject decreases from the baseline or reference PAP level by 0.5 mmHg or more, 1 mmHg or more, 1.5 mmHg or more, 5 mmHg or more, 10 mmHg or more, 20 mmHg or more, 30 mmHg or more, 40 mmHg or more, or 50 mmHg.

Another physiological indicator of PAH is cardiac index (CI). A baseline or reference CI level can be 5 L/min/m$^2$ or lower, 2.5 L/min/m$^2$ or lower, 2 L/min/m$^2$ or lower, 1.5 L/min/m$^2$ or lower, or 1 L/min/m$^2$ or lower. In some embodiments, a treatment provided herein is efficacious if, after treatment has started, the endpoint CI level increases from the baseline or reference CI level by 0.1 or more, 0.2 or more, 0.3 or more, 0.4 or more, 0.5 or more, 1 or more, or 2 or more.

Another physiological indicator of PAH is pulmonary capillary wedge pressure (PCWP). A baseline or reference PCWP level can be 36 mmHg or less, 24 mmHg or less, 18 mmHg or less, 10 mmHg, or 5 mmHg or less. In some embodiments, a treatment provided herein is efficacious if, after treatment has started, the endpoint PCWP level increases from the baseline or reference PCWP level by 0.2 mmHg or more, 0.3 mmHg or more, 0.4 mmHg or more, 0.5 mmHg or more, 0.6 mmHg or more, 1 mmHg or more, or 5 mmHg or more.

Another physiological indicator of PAH is right atrial pressure (RAP). A baseline or reference RAP level can be 4 mmHg or more, 6 mmHg or more, 8 mmHg or more, 10 mmHg or more, 12 mmHg or more, 16 mmHg or more, 20 mmHg or more, or 25 mmHg or more. In some embodiments, a treatment provided herein is efficacious if after treatment has started, the endpoint RAP level of the subject decreases from the baseline or reference RAP level by 5 mmHg or more, 2.5 mmHg or more, 1 mmHg or more, 0.5 mmHg or more, or 0.2 mmHg or more.

Another physiological indicator of PAH is six-minute walk distance (6 MWD). A baseline or reference 6 MWD can be 50 m or less, 100 m or less, 200 m or less, 300 m or less, 400 m or less, or 500 m or less. In some embodiments, a treatment provided herein is efficacious if, after treatment has started, the endpoint 6 MWD of the subject increases from the baseline or reference 6 MWD by 10 m or more, 15 m or more, 20 m or more, 25 m or more, 30 m or more, or 50 m or more; or if the endpoint 6 MWD of the subject increases by 3% or more, 4% or more, 5% or more, 10% or more, or 20% or more of the baseline level.

Another physiological indicator of PAH is brain natriuretic peptide (BNP) level. A baseline or reference BNP level can be 60 pg/mL or higher, 80 pg/mL or higher, 100 pg/mL or higher, 120 pg/mL or higher, 140 pg/mL or higher, 200 pg/mL or higher, 500 pg/mL or higher, or 1000 pg/mL or higher. In some embodiments, a treatment provided herein is efficacious if, after treatment has started, the endpoint BNP level of the subject decreases from the baseline or reference BNP level. For example, the endpoint BNP level of the subject can decrease by 1 pg/mL or more, 2 pg/mL or more, 5 pg/mL or more, 10 pg/mL or more, 20 pg/mL or more, 100 pg/mL or more, 500 pg/mL or more, or 1000 pg/mL or more.

Diffusion of lung capacity (DLCO), or diffusion capacity of CO, can also be used as a physiological indicator of PAH. A baseline or reference DLCO can be 90% or less, 80% or less, 70% or less, 50% or less, 45% or less, or 40% or less. In some embodiments, a treatment provided herein is efficacious if, after treatment has started, the endpoint DLCO is increased from the baseline level. For example, the endpoint DLCO can be increased from the baseline or reference DLCO by 1% or more, 5% or more, 10% or more, 15% or more, 20% or more, or 50% or more.

Average survival rate can be used as a parameter to determine efficacy in a population of one or more subjects. A reference average survival rate can be 95% or lower, 93% or lower, 90% or lower, 86% or lower, 82% or lower, or 78% or lower. The average survival rate can be an average 1-year survival rate. In some embodiments, a treatment provided herein is efficacious in a population of one or more subjects if, after treatment has started, the average survival rate increases. For example, the average survival rate can increase from the reference average survival rate by 1% or more, 2% or more, 5% or more, 10% or more, or 20% or more.

Another physiological indicator of PAH for use in determining efficacy of treatment in a subject is time to death after diagnosis with PAH. A reference time to death can be 1 year or less, 2 years or less, 5 years or less, or 7 years or less. In some embodiments, a treatment provided herein is efficacious if, after treatment has started, the time to death of the subject is higher than the reference time to death. For example, the time to death of the subject can increase from the reference time to death by 0.5 years or more, 1 year or more, 2 years or more, 3 years or more, 4 years or more, 5 years or more, or 6 years or more.

Death can also be used as an endpoint for efficacy of treatment of PAH. With the currently available PAH management methods, the average one-year survival rate of CTD-PAH patients is 86%, the average 1-year survival rate of idiopathic PAH patients is 93%, and the average 1-year survival rate of PAH patients with systemic sclerosis is 82%. The compositions and methods of the invention can increase the survival rate of PAH patients. In one embodiment, after treatment with a HIF-2α inhibitor, an increase in the average 1-year survival rate of PAH patients indicates efficacious treatment. For example, compositions and methods disclosed herein can be effective in increasing the 1-year average survival rate of PAH patients to 82% or greater, 86% or greater, or 93% or greater. In another embodiment, an increase in the time to death after diagnosis of a PAH patient indicates efficacious treatment. For example, a HIF-2α inhibitor of the invention extends the time to death of a PAH patient by at least 1, 2, 3, 4, 5, or 6 years beyond the current average lifespan of PAH patients.

The amount of HIF-2α inhibitor administered to the subject (either in a single dose or over multiple doses) can be effective in reducing vascular smooth muscle hypertrophy, such as with respect to a starting level of hypertrophy in the subject or a reference level of hypertrophy in an untreated population of subjects. The development of ventricular muscle cell hypertrophy can be measured in a variety of ways, including by increase in cell size, induction of a genetic marker of ventricular muscle cell hypertrophy, increase in the assembly of an individual contractile protein such as myosin light chain-2v (MLC-2v) into organized contractile units, accumulating of contractile units, activation of a program of immediate early gene expression, and the induction of genes encoding contractile and embryonic proteins. In some cases, ventricular muscle cell hypertrophy can be measured by determining the expression of an atrial marker, for example, atrial natriuretic factor (ANF). In some embodiments, a measure of vascular smooth muscle hypertrophy is reduced by about or more than about 10%, 20%, 30%, 40%, 50%, 60%, 70%, 80%, 90%, 95%, or more.

Measuring inhibition of biological effects of HIF-2α can comprise performing an assay on a biological sample, such as a sample from a subject. Any of a variety of samples may be selected, depending on the assay. Examples of samples include, but are not limited to blood samples (e.g. blood plasma or serum), exhaled breath condensate samples, bronchoalveolar lavage fluid, sputum samples, urine samples, and tissue samples.

A subject being treated with a HIF-2α inhibitor may be monitored to determine the effectiveness of treatment, and the treatment regimen may be adjusted based on the subject's physiological response to treatment. For example, if inhibition of a biological effect of HIF-2α inhibition is above or below a threshold, the dosing amount or frequency may be decreased or increased, respectively. Alternatively, the treatment regimen may be adjusted to include, remove, or adjust an amount of a second agent. The methods can further comprise continuing the therapy if the therapy is determined to be efficacious. The methods can comprise maintaining, tapering, reducing, or stopping the administered amount of a compound or compounds in the therapy if the therapy is determined to be efficacious. The methods can comprise increasing the administered amount of a compound or compounds in the therapy if it is determined not to be efficacious. Alternatively, the methods can comprise stopping therapy if it is determined not to be efficacious. In some embodiments, treatment with the HIF-2α is discontinued if inhibition of the biological effect is above or below a threshold, such as in a lack of response or an adverse reaction. The biological effect may be a change in any of a variety of physiological indicators of PAH, examples of which are provided herein.

Biological effects for the treatment of HIF-2α inhibitor can be indicated by a variety of methods. For example, it can be evaluated by adjustment of one or more hemodynamic parameters towards a more normal level, for example lowering mean PAP or PVR, PCWP or LVEDP, or raising cardiac index or output versus baseline. It can also be evaluated by improvement of cardiopulmonary efficiency versus baseline, for example increasing exercise capacity, illustratively as measured in a test of 6-minute walking distance (6MWD), or lowering Borg dyspnea index (BDI). In some embodiments, an indicator can be improvement of one or more quality of life parameters versus baseline, for example an increase in score on at least one of the SF-36® health survey functional scales. Another example is general improvement versus baseline in the severity of the condition, for example by movement to a lower WHO functional class. Another example is improvement of clinical outcome following a period of treatment, versus expectation in absence of treatment (e.g., in a clinical trial setting, as measured by comparison with placebo), including improved prognosis, extending time to or lowering probability of clinical worsening, extending quality of life (e.g., delaying progression to a higher WHO functional class or slowing decline in one or more quality of life parameters such as SF-36® health survey parameters), and/or increasing longevity. In some embodiments, a biomarker can be used for the evaluation. For example, adjustment towards a more normal level of one or more molecular markers that can be predictive of clinical outcome (e.g., plasma concentrations of endothelin-1 (ET-1), cardiac troponin T (cTnT) or B-type natriuretic peptide (BNP)).

In general, a HIF-2α inhibitor is a compound that inhibits one or more biological effects of HIF-2α. Examples of biological effects of HIF-2α include, but are not limited to, heterodimerization of HIF-2α to HIF-1β, HIF-2α target gene expression, VEGF gene expression, and VEGF protein secretion. In some embodiments, the HIF-2α inhibitor is selective for HIF-2α, such that the inhibitor inhibits heterodimerization of HIF-2α to HIF-1β but not heterodimerization of HIF-1a to HIF-1β. Such biological effects may be inhibited by about or more than about 10%, 20%, 30%, 40%, 50%, 60%, 70%, 80%, 90%, 95%, or more.

Hypoxia-inducible factors (HIFs), like HIF-2α, are transcription factors that respond to changes in available oxygen in the cellular environment (e.g. a decrease in oxygen, or hypoxia). The HIF signaling cascade mediates the effects of hypoxia, the state of low oxygen concentration, on the cell. Hypoxia often keeps cells from differentiating. However, hypoxia promotes the formation of blood vessels, and is important for the formation of a vascular system in embryos, and cancer tumors. The hypoxia in wounds also promotes the migration of keratinocytes and the restoration of the epithelium. A HIF-2α inhibitor of the present disclosure may be administered in an amount effective in reducing any one or more of such effects of HIF-2α activity.

HIF-2α activity can be inhibited by inhibiting heterodimerization of HIF-2α to HIF-1β (ARNT), such as with inhibitor compounds disclosed herein. A variety of methods for measuring HIF-2α dimerization are available. For example, inhibition of heterodimerization of HIF-2α to HIF-1β (ARNT) may be determined in an Amplified Luminescent Proximity Homogeneous Assay (AlphaScreen). AlphaScreen, an in vitro assay, employs "PAS-B*" variants (R247E HIF-2α and E362R ARNT; Scheuermann et al, PNAS 2009) to assess functional disruption of PAS-PAS interactions in a high throughput screening (HTS) format. Inhibition of heterodimerization may also be determined by a reduction in HIF-2α target gene mRNA expression, and/or co-immunoprecipitation. In some embodiments, a HIF-2α inhibitor inhibits heterodimerization of HIF-2α to HIF-1β (ARNT) with an $IC_{50}$ value not exceeding 30 μM, for example, ranging from 10 to 30 μM, and further, for example, ranging from 1 to 30 μM, as determined by AlphaScreen. In some embodiments, the HIF-2α inhibitor has an $IC_{50}$ value not exceeding 1 μM as determined by AlphaScreen. A further description of methods for determining inhibition of heterodimerization are described in WO2014078479A2. In some embodiments, the HIF-2α inhibitor binds the PAS-B domain cavity of HIF-2α. Binding may be covalent or non-covalent, including but not limited to Van der Waals, hydrogen bond, and electrostatic interaction. In some embodiments, the binding is determined by co-crystallography.

Inhibition of heterodimerization of HIF-2α to HIF-1β (ARNT) may also be determined by a reduction in HIF-2α target gene mRNA expression. mRNA quantitation can be performed using real-time PCR technology. (Wong, et al., "Real-time PCR for mRNA quantitation", 2005. BioTechniques 39, 1: 1-1.). Yet another method for determining inhibition of heterodimerization of HIF-2α to HIF-1β (ARNT) is by co-immunoprecipitation.

As described herein, HIF-2α is a transcription factor that plays important roles in regulating expression of target genes. Non-limiting examples of HIF-2α target gene include HMOX1, SFTPA1, CXCR4, PAI1, BDNF, hTERT, ATP7A, and VEGF. For instance, HIF-2α is an activator of VEGFA. Further non-limiting examples of HIF-2α target genes include HMOX1, EPO, CXCR4, PAI1, CCND1, CLUT1, IL6, and VEGF. A HIF-2α inhibitor of the present disclosure may be administered in an amount effective in reducing expression of any one or more of genes induced by HIF-2α activity. A variety of methods are available for the detection of gene expression level, and include the detection of gene transcription products (polynucleotides) and translation products (polypeptides). For example, gene expression can be detected and quantified at the DNA, RNA or mRNA level. Various methods that have been used to quantify mRNA include in situ hybridization techniques, fluorescent in situ hybridization techniques, reporter genes, RNase protection assays, Northern blotting, reverse transcription (RT)-PCR, SAGE, DNA microarray, tiling array, and RNA-seq. Examples of methods for the detection of polynucleotides include, but are not limited to selective colorimetric detection of polynucleotides based on the distance-dependent optical properties of gold nanoparticles, and solution phase detection of polynucleotides using interacting fluorescent labels and competitive hybridization. Examples for the detection of proteins include, but are not limited to microscopy and protein immunostaining, protein immunoprecipitation, immunoelectrophoresis, western blot, BCA assay, spectrophotometry, mass spectrophotometry and enzyme assay.

In some embodiments, inhibition of HIF-2α is characterized by a decrease in VEGF gene expression. The decrease may be measure by any of a variety of methods, such as those described herein. As a further example, the mRNA expression level of VEGF can be measured by quantitative PCR (QT-PCR), microarray, RNA-seq and nanostring. As another example, an ELISA assay can be used to measure the level VEGF protein secretion.

Pharmaceutical Composition

In one aspect, the HIF-2α inhibitor administered to the subject is a compound of Formula I:

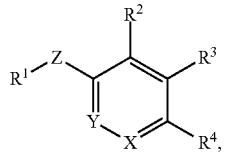

Formula I or a pharmaceutically acceptable salt or prodrug thereof, wherein:

X is $CR^5$ or N;

Y is $CR^6$ or N;

Z is O, S, $CHR^7$, $NR^8$ or absent;

$R^1$ is alkyl, heteroalkyl, cycloalkyl, heterocycloalkyl, aryl, heteroaryl, acyl or cyano;

$R^2$ is nitro, carboxaldehyde, carboxyl, ester, amido, cyano, halo, sulfonyl, alkyl, alkenyl, alkynyl or heteroalkyl;

$R^3$ is hydrogen, halo, cyano, alkyl, heteroalkyl, alkenyl, alkynyl, amino, carboxaldehyde, carboxylic acid, oxime, ester, amido or acyl; or $R^2$ and $R^3$ taken together form a cyclic moiety;

$R^4$ is nitro, halo, cyano, alkyl, cycloalkyl, heteroaryl, carboxyl, sulfinyl, sulfonamidyl, sulfonyl, sulfoximinyl or fluoroalkylsulfonyl; and $R^5$, $R^6$, $R^7$ and $R^8$ are independently hydrogen, halo, hydroxy, cyano, alkyl or alkoxy.

In some embodiments, $R^1$ is phenyl or monocyclic heteroaryl. In some further embodiments, $R^1$ is phenyl or pyridyl, optionally substituted with one or more substituents selected from the group consisting of halo, alkyl, alkoxy and cyano. In a further embodiment, the substituent(s) is selected from the group consisting of halo, $C_1$-$C_4$ alkyl, $C_1$-$C_4$ alkoxy and cyano.

In some embodiments, $R^1$ is bicyclic heteroaryl. In a further embodiment, the bicyclic heteroaryl is substituted with one or more substituents selected from the group consisting of halo, $C_1$-$C_4$ alkyl, $C_1$-$C_4$ alkoxy and cyano.

In some embodiments, $R^1$ is pyridyl N-oxide. In a further embodiment, the pyridyl N-oxide is substituted with one or more substituents selected from the group consisting of halo, $C_1$-$C_4$ alkyl, $C_1$-$C_4$ alkoxy and cyano.

In some embodiments, $R^1$ is

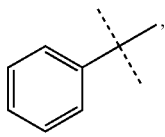

wherein the aryl ring may optionally be substituted with one or more substituents selected from the group consisting of cyano, halo, alkyl and alkoxy. In a further embodiment, the substituent(s) is selected from the group consisting of halo, $C_1$-$C_4$ alkyl, $C_1$-$C_4$ alkoxy and cyano.

In some embodiments, $R^1$ is

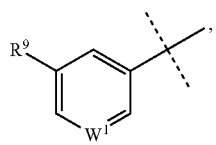

wherein $W^1$ is N or $CR^{10}$, $R^9$ is cyano, halo, alkyl or alkoxy, and $R^{10}$ is hydrogen, cyano, halo, alkyl or alkoxy. In a further embodiment, $R^9$ is cyano, halo, $C_1$-$C_4$ alkyl or $C_1$-$C_4$ alkoxy, and $R^{10}$ is hydrogen, cyano, halo, $C_1$-$C_4$ alkyl or $C_1$-$C_4$ alkoxy.

In some embodiments, $R^1$ is selected from the group consisting of:

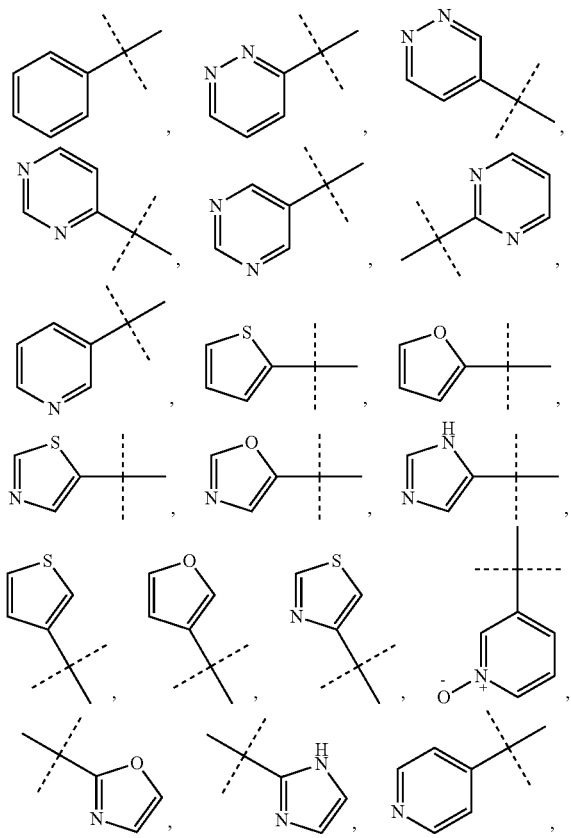

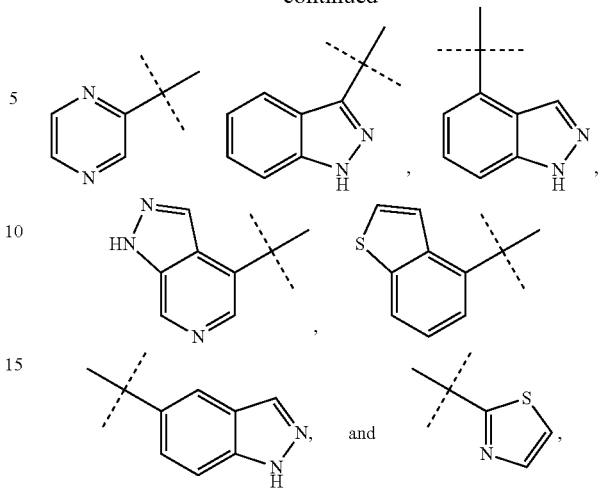

and the rings specified for $R^1$ may optionally be substituted with one or more substituents described for aryl and heteroaryl. In a further embodiment, the substituent(s) is selected from the group consisting of halo, $C_1$-$C_4$ alkyl, $C_1$-$C_4$ alkoxy and cyano.

In some embodiments, $R^1$ is selected from the group consisting of:

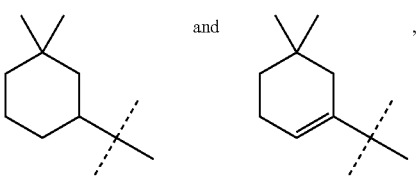

and the rings specified for $R^1$ may optionally be substituted with one or more substituents described for cycloalkyl. In a further embodiment, the substituent(s) is selected from the group consisting of halo, hydroxy, $C_1$-$C_4$ alkyl, $C_1$-$C_4$ alkoxy, cyano and oxo.

In some embodiments, $R^1$ is cycloalkyl. In other embodiments, $R^1$ is heterocycloalkyl. In a further embodiment, $R^1$ is $C_3$-$C_6$ cycloalkyl or $C_3$-$C_6$ heterocycloalkyl. In yet a further embodiment, $R^1$ is cyclobutyl. In some embodiments, said cycloalkyl, cyclobutyl or heterocycloalkyl may optionally be substituted with one or more substituents described for cycloalkyl or heterocycloalkyl. In a further embodiment, the substituent(s) is selected from the group consisting of halo, $C_1$-$C_4$ alkyl, $C_1$-$C_4$ alkoxy and cyano. In another further embodiment, the substituent(s) is at least one fluoro.

In some embodiments, $R^1$ is acyl or cyano. In a further embodiment, $R^1$ is acetyl.

In some embodiments, $R^1$ is alkyl. In a further embodiment, the alkyl is substituted with at least one substituent(s) selected from the group consisting of halo, $C_1$-$C_4$ alkyl, $C_1$-$C_4$ alkoxy and cyano. In another further embodiment, the alkyl is substituted with at least one fluoro. In some embodiments, $R^1$ is heteroalkyl.

In some embodiments, $R^1$ is selected from the group consisting of:

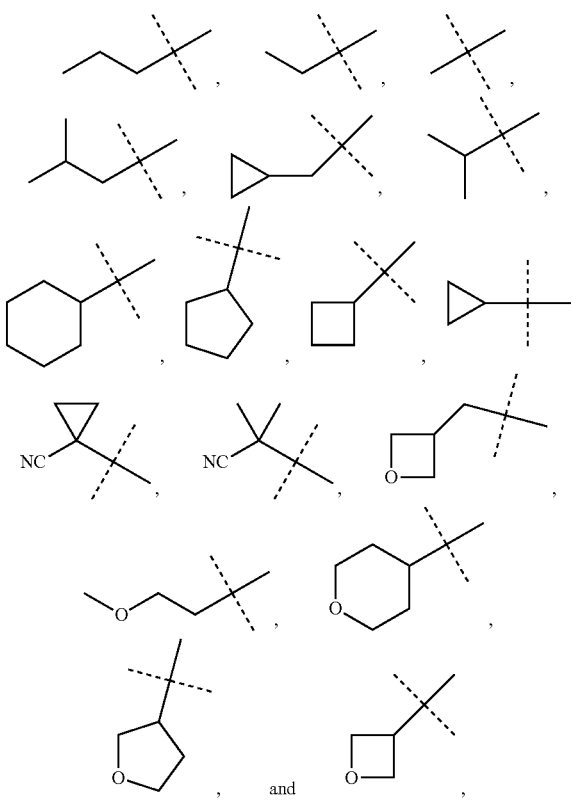

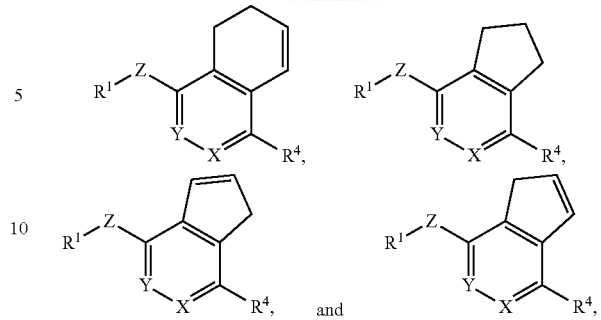

wherein each of the members may optionally be substituted with one or more substituents selected from the group consisting of cyano, halo, alkyl and alkoxy. In a further embodiment, the substituent(s) is selected from the group consisting of fluoro, $C_1$-$C_4$ alkyl, $C_1$-$C_4$ alkoxy and cyano.

In some embodiments, $R^2$ is cyano, halo or alkyl. In some embodiments, $R^2$ is halo or alkyl. In some embodiments, $R^2$ is fluoro, chloro, bromo or iodo. In some embodiments, $R^2$ is fluoroalkyl. In some further embodiments, $R^2$ is —$CH_2F$, —$CHF_2$ or —$CF_3$. In another embodiment, $R^2$ is hydrogen. In some other embodiments, $R^2$ is heteroalkyl, alkenyl or alkynyl.

In some embodiments, $R^3$ is hydrogen, halo, cyano, alkyl, alkenyl, heteroalkyl or acyl; or $R^2$ and $R^3$ taken together form a cyclic moiety. In a further embodiment, $R^3$ is halo, cyano or alkyl. In yet a further embodiment, $R^3$ is —$(CH_2)_n$OH, wherein n is 1, 2 or 3. In still a further embodiment, $R^3$ is —$CH_2OH$.

In some embodiments, $R^2$ and $R^3$ taken together with the atoms to which they are attached form a 5- or 6-membered carbocycle with at least one $sp^3$ hybridized carbon. Representative compounds with the carbocycle include, but are not limited to, the following:

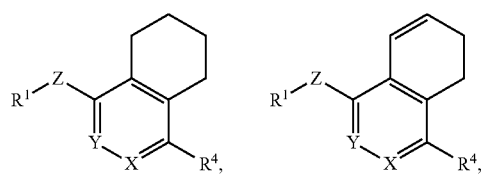

wherein the carbocycle formed by linking $R^2$ and $R^3$ may be optionally substituted with fluoro, chloro, hydroxy, alkyl or heteroalkyl. In a further embodiment, the substituent(s) is selected from the group consisting of halo, $C_1$-$C_4$ alkyl, $C_1$-$C_4$ alkoxy and cyano. In yet other embodiments, the substituent(s) is cycloalkyl or heterocycloalkyl and shares one or more ring atoms with the carbocycle formed by linking $R^2$ and $R^3$. In some embodiments, the substituent(s) is $C_3$-$C_5$ cycloalkyl or $C_3$-$C_5$ heterocycloalkyl. In other embodiments, the substituent is oxo.

In some embodiments, $R^2$ and $R^3$ taken together with the atoms to which they are attached form a 5- or 6-membered heterocycle, including, but not limited to, a lactone or lactol, wherein said heterocycle may be optionally substituted with fluoro, chloro, hydroxy, alkyl or heteroalkyl. In a further embodiment, the substituent(s) is selected from the group consisting of halo, $C_1$-$C_4$ alkyl, $C_1$-$C_4$ alkoxy and cyano.

In some embodiments, $R^4$ is halo, cyano, fluoroalkyl, sulfinyl, sulfonamidyl, sulfonyl, sulfoximinyl or fluoroalkylsulfonyl. In some embodiments, $R^4$ is cyano, fluoroalkyl, sulfonamidyl, sulfinyl, sulfonyl or sulfoximinyl. In some embodiments, $R^4$ is fluoroalkyl, sulfonamidyl, sulfonyl, sulfoximinyl or fluoroalkylsulfonyl. In a further embodiment, $R^4$ is fluoroalkyl. In yet another embodiment, $R^4$ is sulfonyl. In still another embodiment, $R^4$ is fluoroalkylsulfonyl.

In some embodiments, $R^4$ is —$S(=O)_2R^a$, wherein $R^a$ is alkyl or cycloalkyl. In a further embodiment, $R^a$ is $C_1$-$C_4$ alkyl, optionally substituted with one or more fluorines. Suitable examples of fluorine-substituted $C_1$-$C_4$ alkyl include, but are not limited to, —$CH_2F$, —$CHF_2$, —$CF_3$, —$CH_2CF_3$, —$CH_2CHF_2$, —$CH_2CH_2F$, —$CHFCH_3$ and —$CF_2CH_3$. In still a further embodiment, $R^a$ is methyl, optionally substituted with one or more fluorines.

In some embodiments, $R^4$ is —$S(=O)(=NR^b)R^a$, wherein $R^a$ is alkyl or cycloalkyl and $R^b$ is hydrogen, cyano or alkyl. In a further embodiment, $R^a$ is $C_1$-$C_4$ alkyl, optionally substituted with one or more fluorines. Suitable examples of fluorine-substituted $C_1$-$C_4$ alkyl include, but are not limited to, —$CH_2F$, —$CHF_2$, —$CF_3$, —$CH_2CF_3$, —$CH_2CHF_2$, —$CH_2CH_2F$, —$CHFCH_3$ and —$CF_2CH_3$.

In some embodiments, $R^4$ is —$S(=O)_2N(R^a)_2$, wherein each $R^a$ is independently hydrogen, alkyl, heteroalkyl, cycloalkyl or heterocycloalkyl, and at least one $R^a$ is hydrogen. In a further embodiment, both $R^a$s are hydrogen. In another further embodiment, one $R^a$ is hydrogen and the other $R^a$ is $C_1$-$C_4$ alkyl.

In some embodiments, $R^4$ is selected from the group consisting of —CN, —$CF_3$, —$S(=O)CH_3$, —$S(=O)_2CH_3$, —$S(=O)_2CH_2F$, —$S(=O)_2CHF_2$, —$S(=O)_2CF_3$, —$S(=O)_2NH_2$, —$S(=O)_2NHCH_3$, —$S(=O)(=NH)CH_3$, —$S(=O)(=NH)CH_2F$, —$S(=O)(=NH)CHF_2$, —$S(=O)$ (=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, R$^5$ is hydrogen. In some other embodiments, R$^5$ is C$_1$-C$_4$ alkyl or C$_1$-C$_4$ alkoxy. In a further embodiment, R$^5$ is methyl.

In some embodiments, R$^6$ is hydrogen. In some other embodiments, R$^6$ is C$_1$-C$_4$ alkyl or C$_1$-C$_4$ alkoxy. In a further embodiment, R$^6$ is methyl.

In some embodiments, R$^7$ is hydrogen. In some other embodiments, R$^7$ is C$_1$-C$_4$ alkyl or C$_1$-C$_4$ alkoxy. In a further embodiment, R$^7$ is methyl.

In some embodiments, R$^8$ is hydrogen. In some other embodiments, R$^8$ is C$_1$-C$_4$ alkyl or C$_1$-C$_4$ alkoxy. In a further embodiment, R$^8$ is methyl.

In some embodiments, R$^3$ is hydrogen, R$^4$ is —S(=O)$_2$R$^a$ or —S(=O)(=NR$^b$)R$^c$, wherein R$^a$ is fluoroalkyl, R$^b$ is hydrogen, cyano or alkyl and R$^c$ is alkyl. In a further embodiment, R$^1$ is selected from the group consisting of

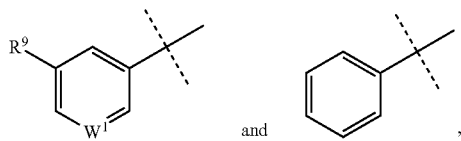

and wherein W$^1$ is N or CR$^{10}$, R$^9$ is cyano, halo, alkyl or alkoxy, and R$^{10}$ is hydrogen, cyano, halo, alkyl or alkoxy; and

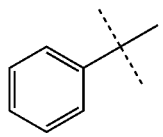

may optionally be substituted with one or more substituents selected from the group consisting of cyano, halo, alkyl and alkoxy. In a further embodiment, the alkyl is C$_1$-C$_4$ alkyl. In another further embodiment, the alkoxy is C$_1$-C$_4$ alkoxy.

In some embodiments, each of R$^2$ and R$^3$ is independently alkyl and R$^4$ is cyano, fluoroalkyl, sulfonamidyl, sulfinyl, sulfonyl, sulfoximinyl or fluoroalkylsulfonyl.

In some embodiments, R$^3$ is —CH$_2$OH. In a further embodiment, R$^4$ is cyano, fluoroalkyl, sulfonamidyl, sulfinyl, sulfonyl, sulfoximinyl or fluoroalkylsulfonyl and R$^5$ is hydrogen. In still a further embodiment, R$^2$ is cyano, halo or alkyl.

In some embodiments, R$^1$ is phenyl or monocyclic heteroaryl; R$^2$ is nitro, halo, cyano or alkyl; R$^3$ is halo, cyano or alkyl; R$^4$ is cyano, fluoroalkyl, sulfonamidyl, sulfinyl, sulfonyl, sulfoximinyl or fluoroalkylsulfonyl. In a further embodiment, R$^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$. In still a further embodiment, R$^5$ is hydrogen.

In some embodiments, R$^1$ is bicyclic heteroaryl; R$^2$ is nitro, halo, cyano or alkyl; R$^3$ is halo, cyano or alkyl; R$^4$ is cyano, fluoroalkyl, sulfonamidyl, sulfinyl, sulfonyl, sulfoximinyl or fluoroalkylsulfonyl; and R$^5$ is hydrogen.

In some embodiments, R$^1$ is phenyl, monocyclic heteroaryl or bicyclic heteroaryl; R$^2$ is halo, cyano or alkyl; R$^3$ is halo, cyano or alkyl; R$^4$ is cyano, fluoroalkyl, sulfonamidyl, sulfinyl, sulfonyl, sulfoximinyl or fluoroalkylsulfonyl; and R$^5$ is hydrogen.

In some embodiments, R$^2$ and R$^3$ together with the atoms to which they are attached form a 5- or 6-membered carbocycle with at least one sp$^3$ hybridized carbon; R$^4$ is cyano, fluoroalkyl, sulfonamidyl, sulfinyl, sulfonyl, sulfoximinyl or fluoroalkylsulfonyl; and R$^5$ is hydrogen. In a further embodiment, R$^1$ is phenyl or monocyclic heteroaryl. In another further embodiment, R$^1$ is bicyclic heteroaryl.

In some embodiments, X is N and Y is CR$^6$. In other embodiments, X is CR$^5$ and Y is N. In still other embodiments, X is N and Y is N. In yet other embodiments, X is CR$^5$ and Y is CR$^6$.

In some embodiments, Z is O. In other embodiments, Z is S. In further embodiments, Z is CHR$^7$. In yet other embodiments, Z is NR$^8$. In some embodiments, Z is absent.

In another aspect, the invention provides a compound of Formula I-A:

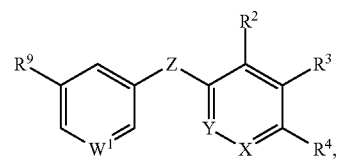

or a pharmaceutically acceptable salt or prodrug thereof, wherein:

X is CR$^5$ or N;

Y is CR$^6$ or N;

Z is O, S, CHR$^7$, NR$^8$ or absent;

R$^2$ is nitro, carboxaldehyde, carboxylic acid, ester, amido, cyano, halo, sulfonyl or alkyl;

R$^3$ is hydrogen, halo, cyano, alkyl, heteroalkyl, alkenyl, alkynyl, amino, oxime or acyl; or R$^2$ and R$^3$ taken together form a cyclic moiety;

R$^4$ is nitro, halo, cyano, alkyl, sulfinyl, sulfonamidyl, sulfonyl or sulfoximinyl; R$^5$, R$^6$, R$^7$ and R$^8$ are independently hydrogen, halo, hydroxy, cyano, alkyl or alkoxy;

W$^1$ is N or CR$^{10}$;

R$^9$ is cyano, halo, alkyl or alkoxy; and

R$^{10}$ is hydrogen, cyano, halo, alkyl or alkoxy.

In some embodiments, R$^2$ is cyano, halo or alkyl. In some embodiments, R$^2$ is halo or alkyl. In some embodiments, R$^2$ is fluoro, chloro, bromo or iodo. In some embodiments, R$^2$ is fluoroalkyl. In some further embodiments, R$^2$ is —CH$_2$F, —CHF$_2$ or —CF$_3$.

In some embodiments, R$^3$ is hydrogen, halo, cyano, alkyl, alkenyl, heteroalkyl or acyl; or R$^2$ and R$^3$ taken together form a cyclic moiety. In a further embodiment, R$^3$ is halo, cyano or alkyl. In yet a further embodiment, R$^3$ is —(CH$_2$)—OH, wherein n is 1, 2 or 3. In still a further embodiment, R$^3$ is —CH$_2$OH.

In some embodiments, R$^2$ and R$^3$ taken together with the atoms to which they are attached form a 5- or 6-membered carbocycle with at least one sp$^3$ hybridized carbon. Representative compounds with the carbocycle include, but are not limited to, the following:

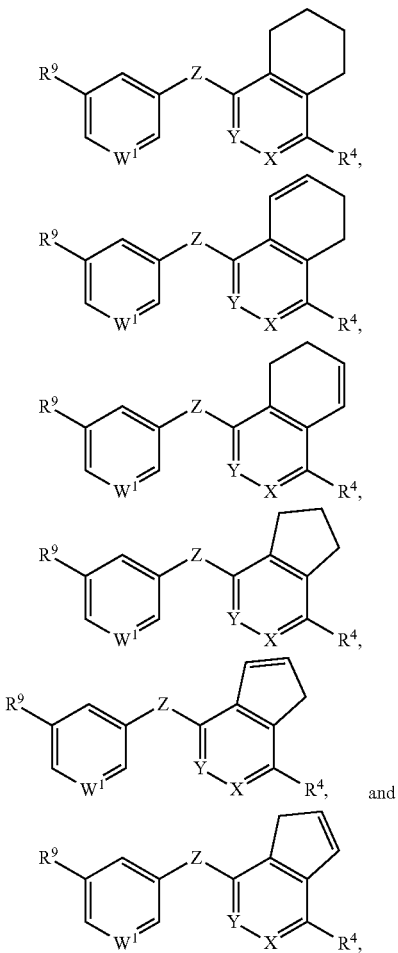

wherein the carbocycle formed by linking $R^2$ and $R^3$ may be optionally substituted with fluoro, chloro, hydroxy, alkyl or heteroalkyl. In a further embodiment, the substituent(s) is selected from the group consisting of halo, $C_1$-$C_4$ alkyl, $C_1$-$C_4$ alkoxy and cyano. In yet other embodiments, the substituent(s) is cycloalkyl or heterocycloalkyl and shares one or more ring atoms with the carbocycle formed by linking $R^2$ and $R^3$. In some embodiments, the substituent(s) is $C_3$-$C_5$ cycloalkyl or $C_3$-$C_5$ heterocycloalkyl. In other embodiments, the substituent is oxo.

In some embodiments, $R^2$ and $R^3$ taken together with the atoms to which they are attached form a 5- or 6-membered heterocycle, including, but not limited to, a lactone or lactol, wherein said heterocycle may be optionally substituted with fluoro, chloro, hydroxy, alkyl or heteroalkyl. In a further embodiment, the substituent(s) is selected from the group consisting of halo, $C_1$-$C_4$ alkyl, $C_1$-$C_4$ alkoxy and cyano.

In some embodiments, $R^4$ is halo, cyano, fluoroalkyl, sulfinyl, sulfonamidyl, sulfonyl, sulfoximinyl or fluoroalkylsulfonyl. In some embodiments, $R^4$ is cyano, fluoroalkyl, sulfonamidyl, sulfinyl, sulfonyl or sulfoximinyl. In some embodiments, $R^4$ is fluoroalkyl, sulfonamidyl, sulfonyl or sulfoximinyl. In a further embodiment, $R^4$ is fluoroalkyl. In yet another embodiment, $R^4$ is sulfonyl. In still another embodiment, $R^4$ is fluoroalkylsulfonyl.

In some embodiments, $R^4$ is —S(=O)$_2$R$^a$, wherein R$^a$ is alkyl or cycloalkyl. In a further embodiment, R$^a$ is $C_1$-$C_4$ alkyl, optionally substituted with one or more fluorines.

Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$. In still a further embodiment, R$^a$ is methyl, optionally substituted with one or more fluorines.

In some embodiments, $R^4$ is —S(=O)(=NR$^b$)R$^a$, wherein R$^a$ is alkyl or cycloalkyl and R$^b$ is hydrogen, cyano or alkyl. In a further embodiment, R$^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$.

In some embodiments, $R^4$ is —S(=O)$_2$N(R$^a$)$_2$, wherein each R$^a$ is independently hydrogen, alkyl, heteroalkyl, cycloalkyl or heterocycloalkyl, and at least one R$^a$ is hydrogen. In a further embodiment, both R$^a$s are hydrogen. In another further embodiment, one R$^a$ is hydrogen and the other R$^a$ is $C_1$-$C_4$ alkyl.

In some embodiments, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, $R^5$ is hydrogen. In some other embodiments, $R^5$ is $C_1$-$C_4$ alkyl or $C_1$-$C_4$ alkoxy. In a further embodiment, $R^5$ is methyl.

In some embodiments, $R^6$ is hydrogen. In some other embodiments, $R^6$ is $C_1$-$C_4$ alkyl or $C_1$-$C_4$ alkoxy. In a further embodiment, $R^6$ is methyl.

In some embodiments, $R^7$ is hydrogen. In some other embodiments, $R^7$ is $C_1$-$C_4$ alkyl or $C_1$-$C_4$ alkoxy. In a further embodiment, $R^7$ is methyl.

In some embodiments, $R^8$ is hydrogen. In some other embodiments, $R^8$ is $C_1$-$C_4$ alkyl or $C_1$-$C_4$ alkoxy. In a further embodiment, $R^8$ is methyl.

In some embodiments, $R^9$ is cyano, halo, $C_1$-$C_4$ alkyl or $C_1$-$C_4$ alkoxy.

In some embodiments, $R^{10}$ is hydrogen, cyano, halo, $C_1$-$C_4$ alkyl or $C_1$-$C_4$ alkoxy.

In some embodiments, $R^2$ and $R^3$ taken together with the atoms to which they are attached form a 5- or 6-membered carbocycle with at least one sp$^3$ hybridized carbon and $R^4$ is cyano, fluoroalkyl, sulfonamidyl, sulfonyl, sulfonyl, sulfoximinyl or fluoroalkylsulfonyl.

In some embodiments, $R^3$ is —CH$_2$OH and $R^4$ is cyano, fluoroalkyl, sulfonamidyl, sulfonyl or sulfoximinyl. In a further embodiment, $R^5$ is hydrogen. In still a further embodiment, $R^2$ is cyano, halo or alkyl.

In some embodiments, $R^2$ is halo, cyano or alkyl; $R^3$ is CH$_2$OH; $R^4$ is cyano, fluoroalkyl, sulfonamidyl, sulfonyl or sulfoximinyl. In a further embodiment, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, X is N and Y is CR$^6$. In other embodiments, X is CR$^5$ and Y is N. In still other embodiments, X is N and Y is N. In yet other embodiments, X is CR$^5$ and Y is CR$^6$.

In some embodiments, Z is O. In other embodiments, Z is S. In further embodiments, Z is CHR$^7$. In yet other embodiments, Z is NR$^8$. In some embodiments, Z is absent.

In another aspect, the invention provides a compound of Formula I-B:

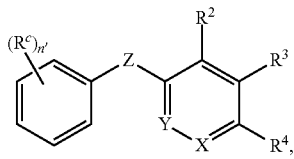

or a pharmaceutically acceptable salt or prodrug thereof, wherein:

X is CR$^5$ or N;
Y is CR$^6$ or N;
Z is O, S, CHR$^7$, NR$^8$ or absent;
R$^2$ is nitro, carboxaldehyde, carboxylic acid, ester, amido, cyano, halo, sulfonyl or alkyl;
R$^3$ is hydrogen, halo, cyano, alkyl, heteroalkyl, alkenyl, alkynyl, amino, oxime or acyl; or R$^2$ and R$^3$ taken together form a cyclic moiety;
R$^4$ is nitro, halo, cyano, alkyl, sulfinyl, sulfonamidyl, sulfonyl or sulfoximinyl;
R$^5$, R$^6$, R$^7$ and R$^8$ are independently hydrogen, halo, hydroxy, cyano, alkyl or alkoxy;
R$^c$ is hydrogen, cyano, halo, alkyl or alkoxy; and
n' iso, 1, 2, 3 or 4.

In some embodiments, R$^2$ is cyano, halo or alkyl. In some embodiments, R$^2$ is halo or alkyl. In some embodiments, R$^2$ is fluoro, chloro, bromo or iodo. In some embodiments, R$^2$ is fluoroalkyl. In some further embodiments, R$^2$ is —CH$_2$F, —CHF$_2$ or —CF$_3$.

In some embodiments, R$^3$ is hydrogen, halo, cyano, alkyl, alkenyl, heteroalkyl or acyl; or R$^2$ and R$^3$ taken together form a cyclic moiety. In a further embodiment, R$^3$ is halo, cyano or alkyl. In yet a further embodiment, R$^3$ is —(CH$_2$)$_n$OH, wherein n is 1, 2 or 3.

In some embodiments, R$^2$ and R$^3$ taken together with the atoms to which they are attached form a 5- or 6-membered carbocycle with at least one sp$^3$ hybridized carbon. Representative compounds with the carbocycle include, but are not limited to, the following:

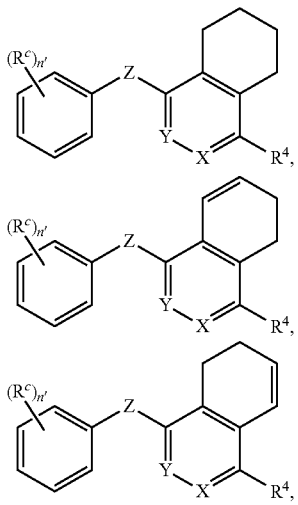

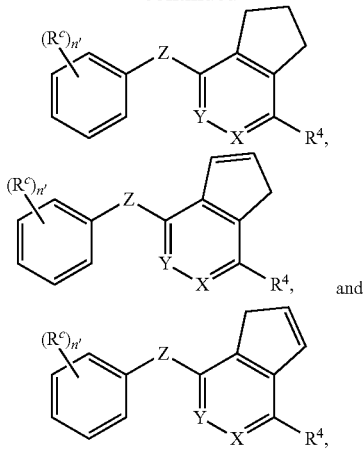

wherein the carbocycle formed by linking R$^2$ and R$^3$ may be optionally substituted with fluoro, chloro, hydroxy, alkyl or heteroalkyl. In a further embodiment, the substituent(s) is selected from the group consisting of halo, C$_1$-C$_4$ alkyl, C$_1$-C$_4$ alkoxy and cyano. In yet other embodiments, the substituent(s) is cycloalkyl or heterocycloalkyl and shares one or more ring atoms with the carbocycle formed by linking R$^2$ and R$^3$. In some embodiments, the substituent(s) is C$_3$-C$_5$ cycloalkyl or C$_3$-C$_5$ heterocycloalkyl. In other embodiments, the substituent is oxo.

In some embodiments, R$^2$ and R$^3$ taken together with the atoms to which they are attached form a 5- or 6-membered heterocycle, including, but not limited to, a lactone or lactol, wherein said heterocycle may be optionally substituted with fluoro, chloro, hydroxy, alkyl or heteroalkyl. In a further embodiment, the substituent(s) is selected from the group consisting of halo, C$_1$-C$_4$ alkyl, C$_1$-C$_4$ alkoxy and cyano.

In some embodiments, R$^3$ is hydrogen, R$^4$ is —S(=O)$_2$R$^a$ or —S(=O)(=NR$^b$)R$^d$, wherein R$^a$ is fluoroalkyl, R$^b$ is hydrogen, cyano or alkyl and R$^d$ is alkyl.

In some embodiments, R$^4$ is halo, cyano, fluoroalkyl, sulfinyl, sulfonamidyl, sulfonyl, sulfoximinyl or fluoroalkylsulfonyl. In some embodiments, R$^4$ is cyano, fluoroalkyl, sulfonamidyl, sulfinyl, sulfonyl or sulfoximinyl. In some embodiments, R$^4$ is fluoroalkyl, sulfonamidyl, sulfonyl or sulfoximinyl. In a further embodiment, R$^4$ is fluoroalkyl. In yet another embodiment, R$^4$ is sulfonyl. In still another embodiment, R$^4$ is fluoroalkylsulfonyl.

In some embodiments, R$^4$ is —S(=O)$_2$R$^a$, wherein R$^a$ is alkyl or cycloalkyl. In a further embodiment, R$^a$ is C$_1$-C$_4$ alkyl, optionally substituted with one or more fluorines. Suitable examples of fluorine-substituted C$_1$-C$_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$. In still a further embodiment, R$^a$ is methyl, optionally substituted with one or more fluorines.

In some embodiments, R$^4$ is —S(=O)(=NR$^b$)R$^a$, wherein R$^a$ is alkyl or cycloalkyl and R$^b$ is hydrogen, cyano or alkyl. In a further embodiment, R$^a$ is C$_1$-C$_4$ alkyl, optionally substituted with one or more fluorines. Suitable examples of fluorine-substituted C$_1$-C$_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$.

In some embodiments, R$^4$ is —S(=O)$_2$—N(R$^a$)$_2$, wherein each R$^a$ is independently hydrogen, alkyl, heteroalkyl, cycloalkyl or heterocycloalkyl, and at least one R$^a$ is hydrogen. In a further embodiment, both $R^a$s are hydrogen. In another further embodiment, one $R^a$ is hydrogen and the other $R^a$ is $C_1$-$C_4$ alkyl.

In some embodiments, $R^4$ is selected from the group consisting of —CN, —$CF_3$, —S(=O)$CH_3$, —S(=O)$_2CH_3$, —S(=O)$_2CH_2F$, —S(=O)$_2CHF_2$, —S(=O)$_2CF_3$, —S(=O)$_2NH_2$, —S(=O)$_2NHCH_3$, —S(=O)(=NH)$CH_3$, —S(=O)(=NH)$CH_2F$, —S(=O)(=NH)$CHF_2$, —S(=O)(=NH)$CF_3$, —S(=O)(=N—CN)$CH_3$, —S(=O)(=N—CN)$CH_2F$, —S(=O)(=N—CN)$CHF_2$ and —S(=O)(=N—CN)$CF_3$.

In some embodiments, $R^5$ is hydrogen. In some other embodiments, $R^5$ is $C_1$-$C_4$ alkyl or $C_1$-$C_4$ alkoxy. In a further embodiment, $R^5$ is methyl.

In some embodiments, $R^6$ is hydrogen. In some other embodiments, $R^6$ is $C_1$-$C_4$ alkyl or $C_1$-$C_4$ alkoxy. In a further embodiment, $R^6$ is methyl.

In some embodiments, $R^7$ is hydrogen. In some other embodiments, $R^7$ is $C_1$-$C_4$ alkyl or $C_1$-$C_4$ alkoxy. In a further embodiment, $R^7$ is methyl.

In some embodiments, $R^8$ is hydrogen. In some other embodiments, $R^8$ is $C_1$-$C_4$ alkyl or $C_1$-$C_4$ alkoxy. In a further embodiment, $R^8$ is methyl.

In some embodiments, $R^2$ and $R^3$ taken together with the atoms to which they are attached form a 5- or 6-membered carbocycle with at least one sp$^3$ hybridized carbon and $R^4$ is cyano, fluoroalkyl, sulfonamidyl, sulfinyl, sulfonyl, sulfoximinyl or fluoroalkylsulfonyl. In a further embodiment, $R^4$ is selected from the group consisting of —CN, —$CF_3$, —S(=O)$CH_3$, —S(=O)$_2CH_3$, —S(=O)$_2CH_2F$, —S(=O)$_2$ $CHF_2$, —S(=O)$_2CF_3$, —S(=O)$_2NH_2$, —S(=O)$_2NHCH_3$, —S(=O)(=NH)$CH_3$, —S(=O) (=NH)$CH_2F$, —S(=O)(=NH)$CHF_2$, —S(=O)(=NH) $CF_3$, —S(=O)(=N—CN)$CH_3$, —S(=O)(=N—CN) $CH_2F$, —S(=O)(=N—CN)$CHF_2$ and —S(=O)(=N—CN)$CF_3$.

In some embodiments, $R^3$ is —$CH_2OH$ and $R^4$ is fluoroalkyl, sulfonamidyl, sulfonyl, sulfinyl or sulfoximinyl. In a further embodiment, $R^5$ is hydrogen. In still a further embodiment, $R^2$ is cyano, halo or alkyl.

In some embodiments, $R^2$ is halo, cyano or alkyl; $R^3$ is $CH_2OH$; $R^4$ is fluoroalkyl, sulfonamidyl, sulfonyl, sulfinyl or sulfoximinyl. In a further embodiment, $R^4$ is selected from the group consisting of —$CF_3$, —S(=O)$CH_3$, —S(=O)$_2CH_3$, —S(=O)$_2CH_2F$, —S(=O)$_2CHF_2$, —S(=O)$_2CF_3$, —S(=O)$_2NH_2$, —S(=O)$_2NHCH_3$, —S(=O)(=NH)$CH_3$, —S(=O)(=NH)$CH_2F$, —S(=O) (=NH)$CHF_2$, —S(=O)(=NH)$CF_3$, —S(=O)(=N—CN) $CH_3$, —S(=O)(=N—CN)$CH_2F$, —S(=O)(=N—CN) $CHF_2$ and —S(=O)(=N—CN)$CF_3$.

In some embodiments, X is N and Y is $CR^6$. In other embodiments, X is $CR^5$ and Y is N. In still other embodiments, X is N and Y is N. In yet other embodiments, X is $CR^5$ and Y is $CR^6$.

In some embodiments, Z is O. In other embodiments, Z is S. In further embodiments, Z is $CHR^7$. In yet other embodiments, Z is $NR^8$. In some embodiments, Z is absent.

In some embodiments, $R^e$ is cyano, halo, $C_1$-$C_4$ alkyl or $C_1$-$C_4$ alkoxy.

In yet another aspect, the invention provides a compound of Formula I-C:

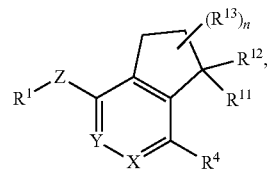

or a pharmaceutically acceptable salt or prodrug thereof, wherein:

X is $CR^5$ or N;

Y is $CR^6$ or N;

Z is O, S, $CHR^7$, $NR^8$ or absent;

$R^1$ is alkyl, heteroalkyl, cycloalkyl, heterocycloalkyl, aryl, heteroaryl, acyl or cyano;

$R^4$ is nitro, halo, cyano, alkyl, cycloalkyl, heteroaryl, carboxyl, sulfinyl, sulfonamidyl, sulfonyl, sulfoximinyl or fluoroalkylsulfonyl;

$R^5$, $R^6$, $R^7$ and $R^8$ are independently hydrogen, halo, hydroxy, cyano, alkyl or alkoxy;

$R^{11}$ is hydrogen, hydroxy, alkoxy or amino;

$R^{12}$ is hydrogen, alkyl, alkenyl or alkynyl; or $R^{11}$ and $R^{12}$ in combination form oxo or oxime;

each of $R^{13}$ is independently selected from the group consisting of hydrogen, fluoro, chloro, hydroxy, alkyl and heteroalkyl, with the proviso that when $R^{13}$ is hydroxy, n is 1 or 2; or two $R^{13}$s and the carbon atom(s) to which they are attached form a 3- to 8-membered cycloalkyl or heterocycloalkyl moiety; and n is 0, 1, 2, 3 or 4.

In some embodiments, $R^1$ is phenyl or monocyclic heteroaryl. In some further embodiments, $R^1$ is phenyl or pyridyl, optionally substituted with one or more substituents selected from the group consisting of halo, alkyl, alkoxy and cyano. In a further embodiment, $R^1$ is

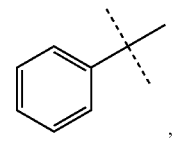

wherein the aryl ring is optionally substituted with one or more substituents selected from the group consisting of cyano, halo, alkyl and alkoxy. In another further embodiment, $R^1$ is

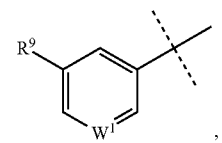

wherein $W^1$ is N or $CR^{10}$, $R^9$ is cyano, halo, alkyl or alkoxy, and $R^{10}$ is hydrogen, cyano, halo, alkyl or alkoxy.

In some embodiments, $R^1$ is bicyclic heteroaryl.

In some embodiments, $R^1$ is selected from the group consisting of:

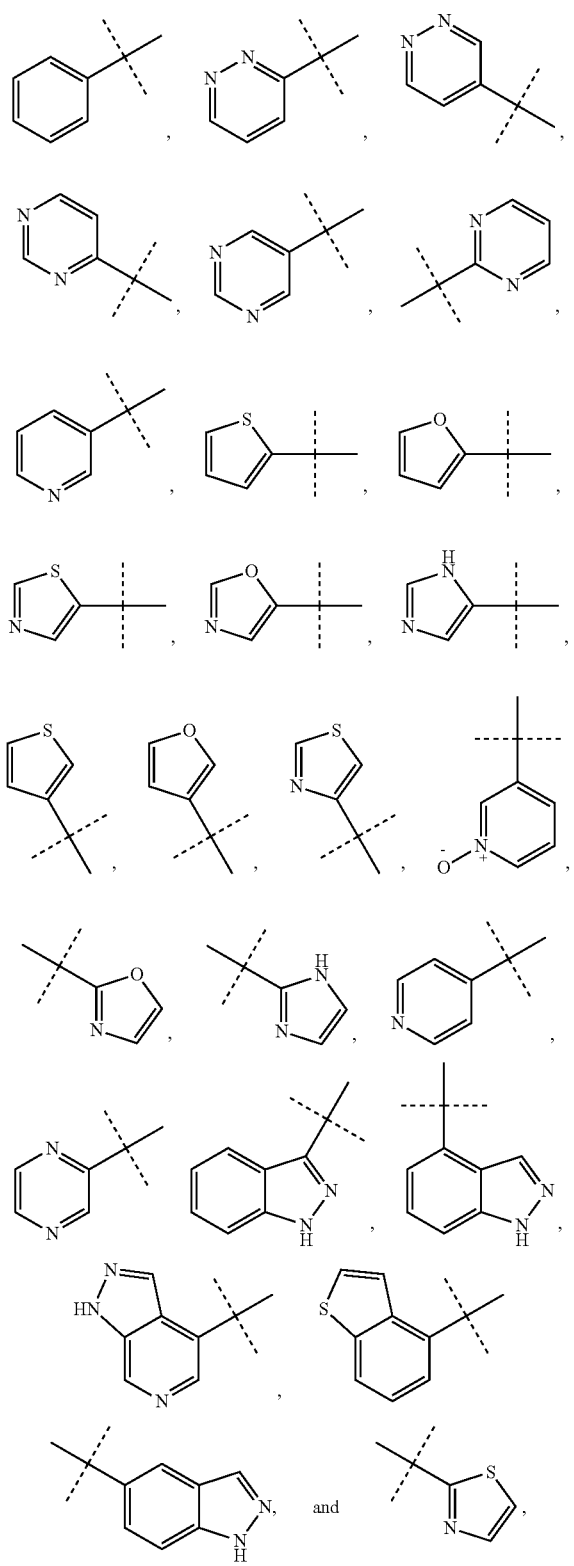

and the rings specified for R¹ may optionally be substituted with one or more substituents described for aryl and heteroaryl. In a further embodiment, the substituent(s) is selected from the group consisting of halo, $C_1$-$C_4$ alkyl, $C_1$-$C_4$ alkoxy and cyano.

In some embodiments, R¹ is selected from the group consisting of:

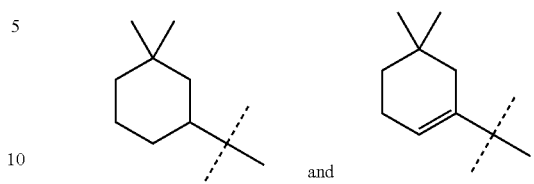

and the rings specified for R¹ may optionally be substituted with one or more substituents described for cycloalkyl. In a further embodiment, the substituent(s) is selected from the group consisting of halo, hydroxy, $C_1$-$C_4$ alkyl, $C_1$-$C_4$ alkoxy, cyano and oxo.

In some embodiments, R¹ is cycloalkyl. In other embodiments, R¹ is heterocycloalkyl. In a further embodiment, R¹ is $C_3$-$C_6$ cycloalkyl or $C_3$-$C_6$ heterocycloalkyl. In yet a further embodiment, R¹ is cyclobutyl. In some embodiments, said cycloalkyl, cyclobutyl or heterocycloalkyl may optionally be substituted with one or more substituents described for cycloalkyl or heterocycloalkyl. In a further embodiment, the substituent(s) is selected from the group consisting of halo, $C_1$-$C_4$ alkyl, $C_1$-$C_4$ alkoxy and cyano. In another further embodiment, the substituent(s) is at least one fluoro.

In some embodiments, R¹ is acyl or cyano. In a further embodiment, R¹ is acetyl.

In some embodiments, R¹ is alkyl. In a further embodiment, the alkyl is substituted with at least one substituent(s) selected from the group consisting of halo, $C_1$-$C_4$ alkyl, $C_1$-$C_4$ alkoxy and cyano. In another further embodiment, the alkyl is substituted with at least one fluoro. In some embodiments, R¹ is heteroalkyl.

In some embodiments, R¹ is selected from the group consisting of:

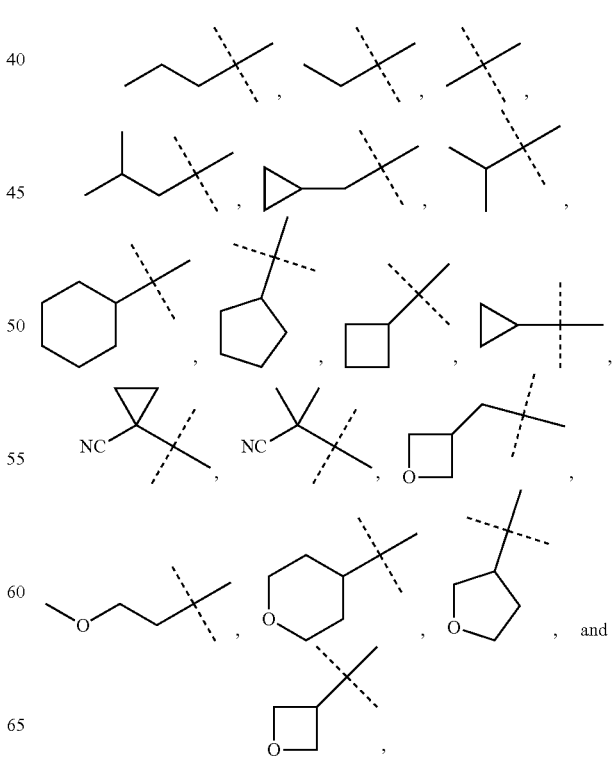

wherein each of the members may optionally be substituted with one or more substituents selected from the group consisting of cyano, halo, alkyl and alkoxy. In a further embodiment, the substituent(s) is selected from the group consisting of fluoro, $C_1$-$C_4$ alkyl, $C_1$-$C_4$ alkoxy and cyano.

In some embodiments, $R^4$ is cyano, fluoroalkyl, sulfinyl, sulfonamidyl, sulfonyl or sulfoximinyl. In some embodiments, $R^4$ is fluoroalkyl, sulfonamidyl, sulfinyl, sulfonyl or sulfoximinyl. In a further embodiment, $R^4$ is fluoroalkyl. In yet another embodiment, $R^4$ is sulfonyl. In still another embodiment, $R^4$ is fluoroalkylsulfonyl.

In some embodiments, $R^4$ is —S(=O)$_2$R$^a$, wherein R$^a$ is alkyl or cycloalkyl. In a further embodiment, R$^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$. In still a further embodiment, R$^a$ is methyl, optionally substituted with one or more fluorines.

In some embodiments, $R^4$ is —S(=O)(=NR$^b$)R$^a$, wherein R$^a$ is alkyl or cycloalkyl and R$^b$ is hydrogen, cyano or alkyl. In a further embodiment, R$^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$.

In some embodiments, $R^4$ is —S(=O)$_2$N(R$^a$)$_2$, wherein each R$^a$ is independently hydrogen, alkyl, heteroalkyl, cycloalkyl or heterocycloalkyl, and at least one R$^a$ is hydrogen. In another further embodiment, one R$^a$ is hydrogen and the other R$^a$ is $C_1$-$C_4$ alkyl.

In some embodiments, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, $R^5$ is hydrogen or alkyl. In some other embodiments, $R^5$ is $C_1$-$C_4$ alkyl or $C_1$-$C_4$ alkoxy. In a further embodiment, $R^5$ is methyl.

In some embodiments, $R^6$ is hydrogen or alkyl. In some other embodiments, $R^6$ is $C_1$-$C_4$ alkyl or $C_1$-$C_4$ alkoxy. In a further embodiment, $R^6$ is methyl.

In some embodiments, $R^7$ is hydrogen or alkyl. In some other embodiments, $R^7$ is $C_1$-$C_4$ alkyl or $C_1$-$C_4$ alkoxy. In a further embodiment, $R^7$ is methyl.

In some embodiments, $R^8$ is hydrogen or alkyl. In some other embodiments, $R^8$ is $C_1$-$C_4$ alkyl or $C_1$-$C_4$ alkoxy. In a further embodiment, $R^8$ is methyl.

In some embodiments, $R^{11}$ is hydroxy or amino. In a further embodiment, $R^{11}$ is hydroxy. In another further embodiment, $R^{11}$ is amino.

In some embodiments, $R^{12}$ is hydrogen. In some other embodiments, $R^{12}$ is alkyl or alkenyl.

In some embodiments, $R^{13}$ is fluoro. In a further embodiment, n is 1, 2 or 3. In a further embodiment, two $R^{13}$s in combination form oxo, oxime or methylene. In still further embodiments, two $R^{13}$s and the carbon atom(s) to which they are attached form a 3- to 8-membered cycloalkyl or heterocycloalkyl moiety.

In some embodiments, $R^1$ is monocyclic aryl or monocyclic heteroaryl and $R^{11}$ is hydroxy or amino. In a further embodiment, $R^{13}$ is fluoro. In still a further embodiment, n is 1, 2 or 3.

In some embodiments, $R^1$ is phenyl or monocyclic heteroaryl, $R^{11}$ is hydroxy or amino, $R^{13}$ is fluoro, n is 1, 2 or 3, and $R^5$ is hydrogen.

In some embodiments, $R^1$ is bicyclic heteroaryl and $R^{11}$ is hydroxy or amino. In a further embodiment, $R^{13}$ is fluoro. In still a further embodiment, n is 1, 2 or 3.

In some embodiments, $R^1$ is bicyclic heteroaryl, $R^{11}$ is hydroxy or amino, $R^{13}$ is fluoro, n is 1, 2 or 3, and $R^5$ is hydrogen.

In some embodiments, $R^4$ is cyano, fluoroalkyl, sulfonamidyl, sulfinyl, sulfonyl, sulfoximinyl or fluoroalkylsulfonyl, and $R^{11}$ is hydroxy or amino. In a further embodiment, $R^{12}$ is hydrogen. In another further embodiment, $R^{13}$ is fluoro. In still a further embodiment, n is 1, 2 or 3.

In some embodiments, $R^4$ is cyano, fluoroalkyl, sulfonamidyl, sulfinyl, sulfonyl, sulfoximinyl or fluoroalkylsulfonyl; $R^{11}$ is hydroxy or amino; $R^{13}$ is fluoro; n is 1, 2 or 3; and $R^5$ is hydrogen. In a further embodiment, $R^{12}$ is hydrogen.

In some embodiments $R^{11}$ is hydroxy or amino and $R^{12}$ is hydrogen. In a further embodiment, $R^{13}$ is fluoro. In still a further embodiment, n is 1, 2 or 3.

In some embodiments $R^{11}$ is hydroxy or amino, $R^{12}$ is hydrogen, $R^{13}$ is fluoro, n is 1, 2 or 3, and $R^5$ is hydrogen. In a further embodiment, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, $R^4$ is fluoroalkyl; n is 0, 1, 2 or 3; Z is O; $R^{11}$ is hydroxy; and $R^{12}$ is hydrogen.

In some embodiments, $R^4$ is sulfonyl or fluoroalkylsulfonyl; n is 0, 1, 2 or 3; Z is O; $R^{11}$ is hydroxy; and $R^{12}$ is hydrogen.

In some embodiments, X is N and Y is CR$^6$. In other embodiments, X is CR$^5$ and Y is N. In still other embodiments, X is N and Y is N. In yet other embodiments, X is CR$^5$ and Y is CR$^6$.

In some embodiments, Z is O. In other embodiments, Z is S. In further embodiments, Z is CHR$^7$. In yet other embodiments, Z is NR$^8$. In some embodiments, Z is absent.

In still another aspect, the invention provides a compound of Formula I-D, I-E, I-F or I-G:

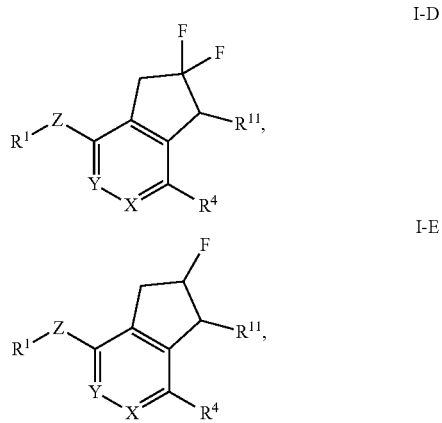

-continued

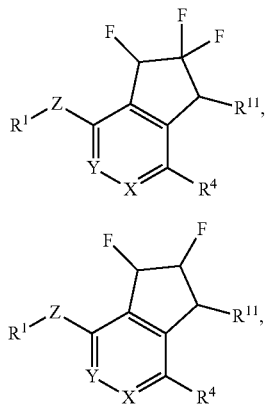

or a pharmaceutically acceptable salt or prodrug thereof, wherein:

X is $CR^5$ or N;

Y is $CR^6$ or N;

Z is O, S, $CHR^7$, $NR^8$ or absent;

$R^1$ is alkyl, heteroalkyl, cycloalkyl, heterocycloalkyl, aryl or heteroaryl;

$R^4$ is nitro, halo, cyano, alkyl, cycloalkyl, heteroaryl, carboxyl, sulfinyl, sulfonamidyl, sulfonyl, sulfoximinyl or fluoroalkylsulfonyl;

$R^5$, $R^6$, $R^7$ and $R^8$ are independently hydrogen, halo, hydroxy, cyano, alkyl or alkoxy; and $R^{11}$ is hydrogen, hydroxy, alkoxy or amino.

In some embodiments, $R^1$ is monocyclic aryl or monocyclic heteroaryl. In some further embodiments, $R^1$ is phenyl or pyridyl, optionally substituted with one or more substituents selected from the group consisting of halo, alkyl, alkoxy and cyano. In a further embodiment, $R^1$ is

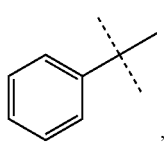

wherein the aryl ring is optionally substituted with one or more substituents selected from the group consisting of cyano, halo, alkyl and alkoxy. In another further embodiment, $R^1$ is

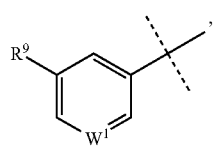

wherein $W^1$ is N or $CR^{10}$, $R^9$ is cyano, halo, alkyl or alkoxy, and $R^{10}$ is hydrogen, cyano, halo, alkyl or alkoxy.

In some embodiments, $R^1$ is bicyclic heteroaryl having at least one N atom.

In some embodiments, $R^1$ is selected from the group consisting of:

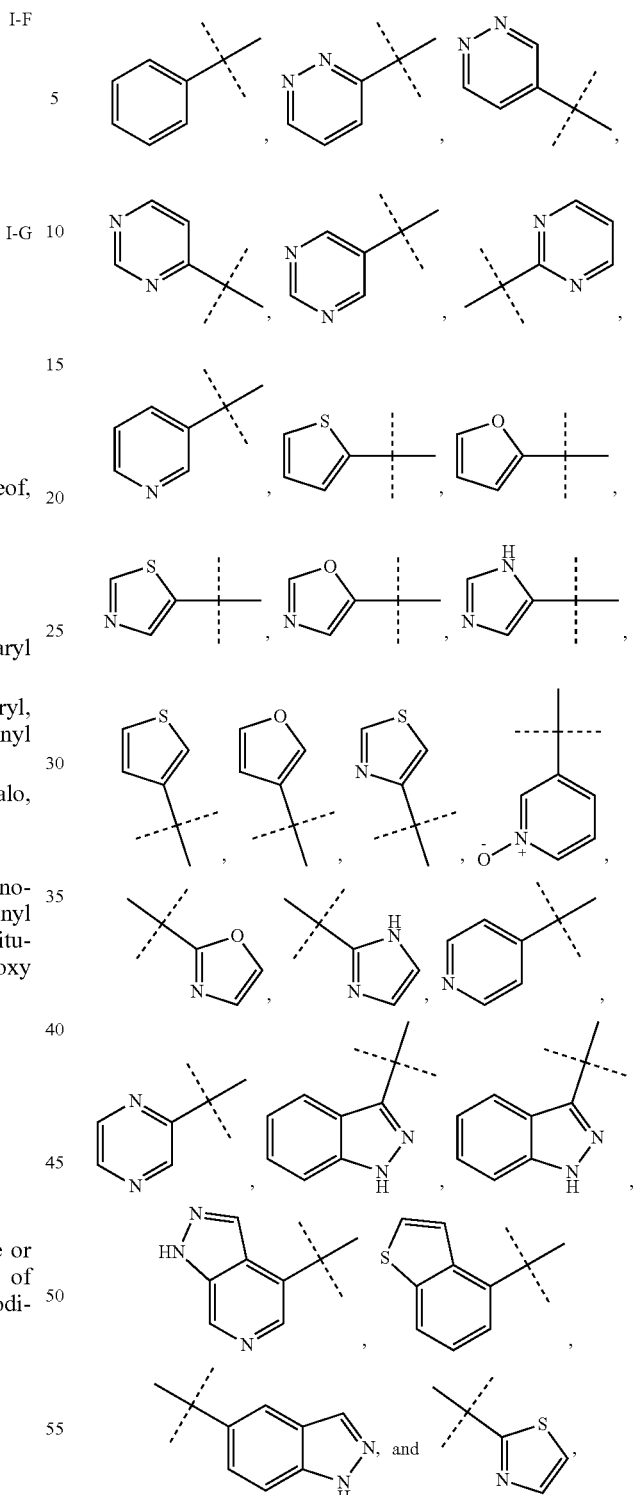

and the rings specified for $R^1$ may optionally be substituted with one or more substituents described for aryl and heteroaryl. In a further embodiment, the substituent(s) is selected from the group consisting of halo, $C_1$-$C_4$ alkyl, $C_1$-$C_4$ alkoxy and cyano.

In some embodiments, $R^1$ is selected from the group consisting of:

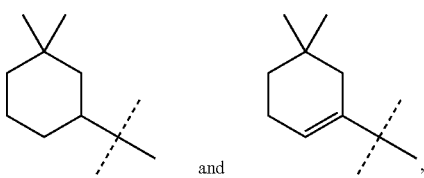

and the rings specified for $R^1$ may optionally be substituted with one or more substituents described for cycloalkyl. In a further embodiment, the substituent(s) is selected from the group consisting of halo, hydroxy, $C_1$-$C_4$ alkyl, $C_1$-$C_4$ alkoxy, cyano and oxo.

In some embodiments, $R^1$ is cycloalkyl. In other embodiments, $R^1$ is heterocycloalkyl. In a further embodiment, $R^1$ is $C_3$-$C_6$ cycloalkyl or $C_3$-$C_6$ heterocycloalkyl. In yet a further embodiment, $R^1$ is cyclobutyl. In some embodiments, said cycloalkyl, cyclobutyl or heterocycloalkyl may optionally be substituted with one or more substituents described for cycloalkyl or heterocycloalkyl. In a further embodiment, the substituent(s) is selected from the group consisting of halo, $C_1$-$C_4$ alkyl, $C_3$-$C_4$ alkoxy and cyano. In another further embodiment, the substituent(s) is at least one fluoro.

In some embodiments, $R^1$ is acyl or cyano. In a further embodiment, $R^1$ is acetyl.

In some embodiments, $R^1$ is alkyl. In a further embodiment, the alkyl is substituted with at least one substituent(s) selected from the group consisting of halo, $C_1$-$C_4$ alkyl, $C_1$-$C_4$ alkoxy and cyano. In another further embodiment, the alkyl is substituted with at least one fluoro. In some embodiments, $R^1$ is heteroalkyl.

In some embodiments, $R^1$ is selected from the group consisting of:

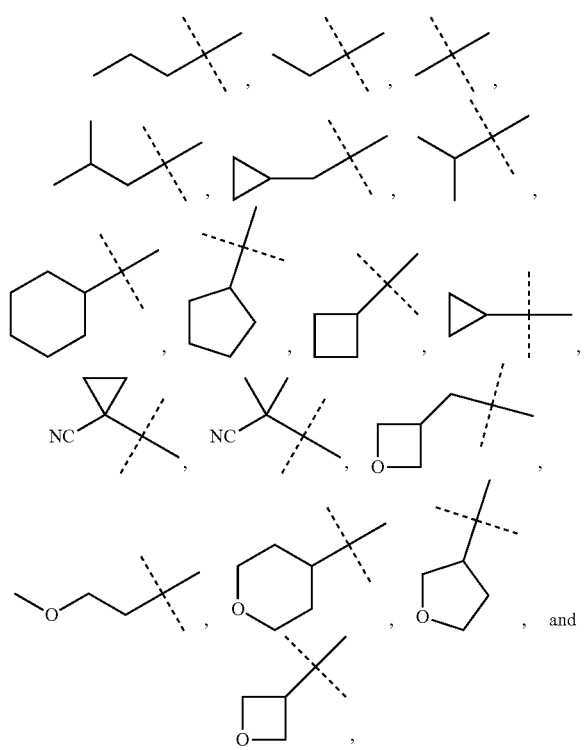

wherein each of the members may optionally be substituted with one or more substituents selected from the group consisting of cyano, halo, alkyl and alkoxy. In a further embodiment, the substituent(s) is selected from the group consisting of fluoro, $C_1$-$C_4$ alkyl, $C_1$-$C_4$ alkoxy and cyano.

In some embodiments, $R^4$ is cyano, fluoroalkyl, sulfinyl, sulfonamidyl, sulfonyl or sulfoximinyl. In some embodiments, $R^4$ is fluoroalkyl, sulfonamidyl, sulfinyl, sulfonyl or sulfoximinyl. In a further embodiment, $R^4$ is fluoroalkyl. In yet another embodiment, $R^4$ is sulfonyl. In still another embodiment, $R^4$ is fluoroalkylsulfonyl.

In some embodiments, $R^4$ is —S(=O)$_2$R$^a$, wherein R$^a$ is alkyl or cycloalkyl. In a further embodiment, R$^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$.

In some embodiments, $R^4$ is —S(=O)(=NR$^b$)R$^a$, wherein R$^a$ is alkyl or cycloalkyl and R$^b$ is hydrogen, cyano or alkyl. In a further embodiment, R$^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$.

In some embodiments, $R^4$ is —S(=O)$_2$N(R$^a$)$_2$, wherein each R$^a$ is independently hydrogen, alkyl, heteroalkyl, cycloalkyl or heterocycloalkyl, and at least one R$^a$ is hydrogen. In another further embodiment, both R$^a$s are hydrogen. In a further embodiment, one R$^a$ is hydrogen and the other R$^a$ is $C_1$-$C_4$ alkyl.

In some embodiments, $R^4$ is selected from the group consisting of —CN, —CF$_3$, S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, $R^5$ is hydrogen or alkyl. In some other embodiments, $R^5$ is $C_1$-$C_4$ alkyl or $C_1$-$C_4$ alkoxy. In a further embodiment, $R^5$ is methyl.

In some embodiments, $R^6$ is hydrogen or alkyl. In some other embodiments, $R^6$ is $C_1$-$C_4$ alkyl or $C_1$-$C_4$ alkoxy. In a further embodiment, $R^6$ is methyl.

In some embodiments, $R^7$ is hydrogen or alkyl. In some other embodiments, $R^7$ is $C_1$-$C_4$ alkyl or $C_1$-$C_4$ alkoxy. In a further embodiment, $R^7$ is methyl.

In some embodiments, $R^8$ is hydrogen or alkyl. In some other embodiments, $R^8$ is $C_1$-$C_4$ alkyl or $C_1$-$C_4$ alkoxy. In a further embodiment, $R^8$ is methyl.

In some embodiments, $R^{11}$ is hydroxy. In another further embodiment, $R^{11}$ is amino.

In some embodiments, $R^1$ is phenyl or monocyclic heteroaryl and $R^{11}$ is hydroxy or amino.

In some embodiments, $R^1$ is bicyclic heteroaryl and $R^{11}$ is hydroxy or amino. In a further embodiment, X is CR$^5$ and $R^5$ is hydrogen. In another further embodiment, $R^5$ is alkyl. In still a further embodiment, $R^5$ is $C_1$-$C_4$ alkyl.

In some embodiments $R^1$ is bicyclic heteroaryl and $R^4$ is cyano, fluoroalkyl, sulfinyl, sulfonamidyl, sulfonyl or sulfoximinyl. In a further embodiment, X is CR$^5$ and $R^5$ is hydrogen. In another further embodiment, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)

(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments R$^1$ is bicyclic heteroaryl; R$^4$ is cyano, fluoroalkyl, sulfonamidyl, sulfonyl or sulfoximinyl; R$^{11}$ is hydroxy or amino; and X is CR$^5$ or N; and R$^5$ is hydrogen. In a further embodiment, R$^{11}$ is hydroxy. In another further embodiment, R$^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments R$^1$ is phenyl or monocyclic heteroaryl and R$^4$ is cyano, fluoroalkyl, sulfinyl, sulfonamidyl, sulfonyl or sulfoximinyl. In a further embodiment, X is CR$^5$ and R$^5$ is hydrogen. In another further embodiment, R$^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments R$^1$ is phenyl or monocyclic heteroaryl; R$^4$ is cyano, fluoroalkyl, sulfinyl, sulfonamidyl, sulfonyl or sulfoximinyl; R$^{11}$ is hydroxy or amino; and X is CR$^5$ or N; and R$^5$ is hydrogen. In a further embodiment, R$^{11}$ is hydroxy. In another further embodiment, R$^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, X is N and Y is CR$^6$. In other embodiments, X is CR$^5$ and Y is N. In still other embodiments, X is N and Y is N. In yet other embodiments, X is CR$^5$ and Y is CR$^6$.

In some embodiments, Z is O. In other embodiments, Z is S. In further embodiments, Z is CHR$^7$. In yet other embodiments, Z is NR$^8$. In some embodiments, Z is absent.

In a further aspect, the invention provides a compound of Formula I-H, I-I, I-J or I-K:

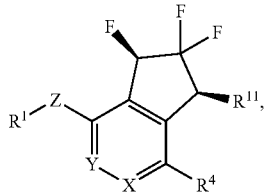

I-H

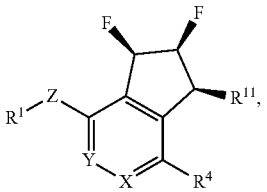

I-I

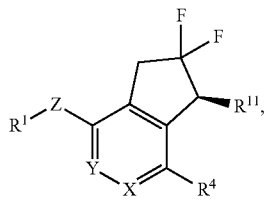

I-J

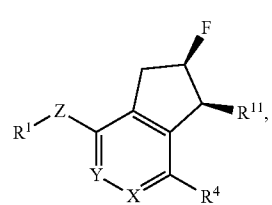

I-K or a pharmaceutically acceptable salt or prodrug thereof, wherein:

X is CR$^5$ or N;

Y is CR$^6$ or N;

Z is O, S, CHR$^7$, NR$^8$ or absent;

R$^1$ is alkyl, heteroalkyl, cycloalkyl, heterocycloalkyl, aryl or heteroaryl;

R$^4$ is nitro, halo, cyano, alkyl, cycloalkyl, heteroaryl, carboxyl, sulfinyl, sulfonamidyl, sulfonyl, sulfoximinyl or fluoroalkylsulfonyl;

R$^5$, R$^6$, R$^7$ and R$^8$ are independently hydrogen, halo, hydroxy, cyano, alkyl or alkoxy; and R$^{11}$ is hydroxy or amino.

In some embodiments, R$^1$ is monocyclic aryl or monocyclic heteroaryl. In some further embodiments, R$^1$ is phenyl or pyridyl, optionally substituted with one or more substituents selected from the group consisting of halo, alkyl, alkoxy and cyano. In a further embodiment, R$^1$ is

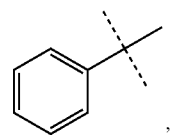

wherein the aryl ring is optionally substituted with one or more substituents selected from the group consisting of cyano, halo, alkyl and alkoxy. In another further embodiment, R$^1$ is

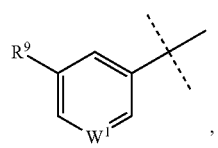

wherein W$^1$ is N or CR$^{10}$, R$^9$ is cyano, halo, alkyl or alkoxy, and R$^{10}$ is hydrogen, cyano, halo, alkyl or alkoxy.

In some embodiments, R$^1$ is bicyclic heteroaryl.

In some embodiments, R$^1$ is selected from the group consisting of:

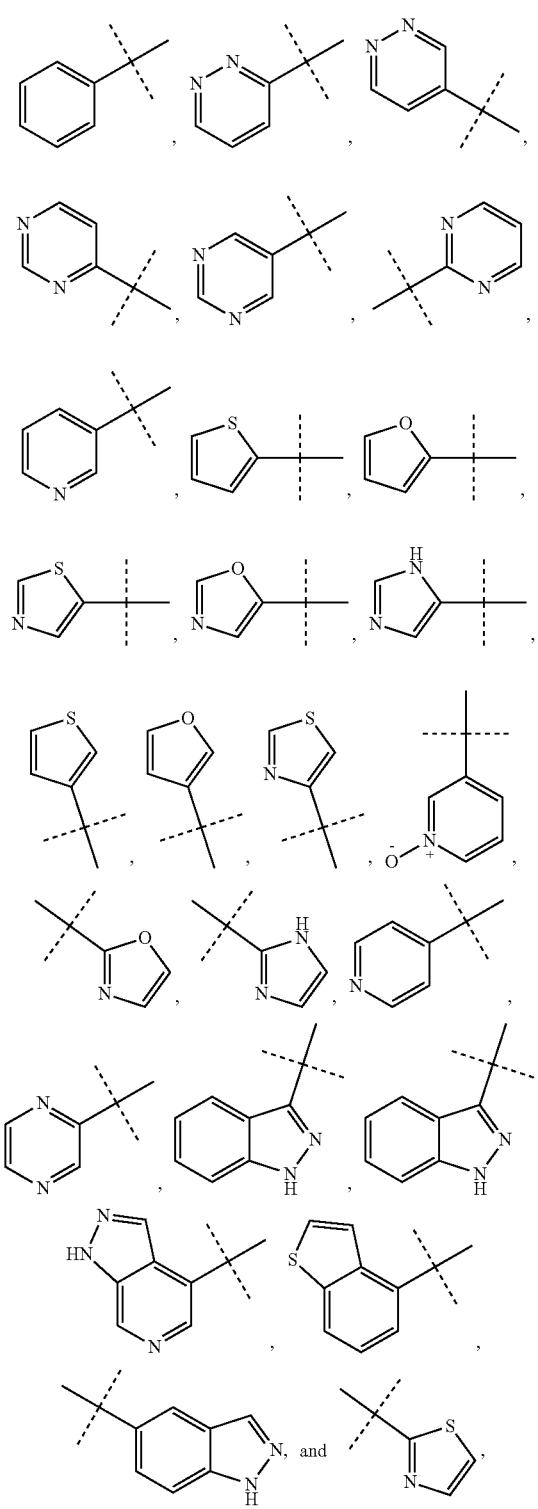

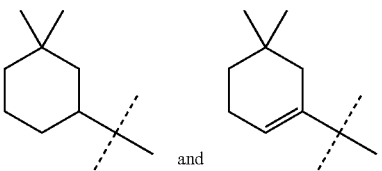

and the rings specified for $R^1$ may optionally be substituted with one or more substituents described for cycloalkyl. In a further embodiment, the substituent(s) is selected from the group consisting of halo, hydroxy, $C_1$-$C_4$ alkyl, $C_1$-$C_4$ alkoxy, cyano and oxo.

In some embodiments, $R^1$ is cycloalkyl. In other embodiments, $R^1$ is heterocycloalkyl. In a further embodiment, $R^1$ is $C_3$-$C_6$ cycloalkyl or $C_3$-$C_6$ heterocycloalkyl. In yet a further embodiment, $R^1$ is cyclobutyl. In some embodiments, said cycloalkyl, cyclobutyl or heterocycloalkyl may optionally be substituted with one or more substituents described for cycloalkyl or heterocycloalkyl. In a further embodiment, the substituent(s) is selected from the group consisting of halo, $C_1$-$C_4$ alkyl, $C_1$-$C_4$ alkoxy and cyano. In another further embodiment, the substituent(s) is at least one fluoro.

In some embodiments, $R^1$ is acyl or cyano. In a further embodiment, $R^1$ is acetyl.

In some embodiments, $R^1$ is alkyl. In a further embodiment, the alkyl is substituted with at least one substituent(s) selected from the group consisting of halo, $C_1$-$C_4$ alkyl, $C_1$-$C_4$ alkoxy and cyano. In another further embodiment, the alkyl is substituted with at least one fluoro. In some embodiments, $R^1$ is heteroalkyl.

In some embodiments, $R^1$ is alkyl. In a further embodiment, the alkyl is substituted with at least one substituent(s) selected from the group consisting of halo, $C_1$-$C_4$ alkyl, $C_1$-$C_4$ alkoxy and cyano. In another further embodiment, the alkyl is substituted with at least one fluoro. In some embodiments, $R^1$ is heteroalkyl.

In some embodiments, $R^1$ is selected from the group consisting of:

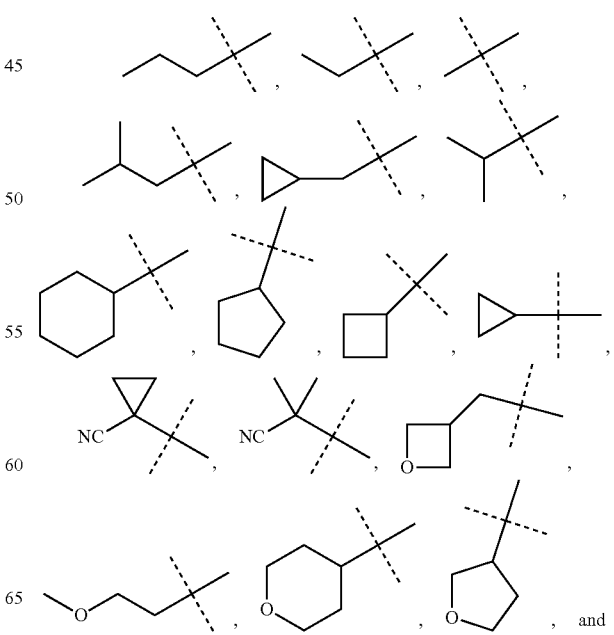

and the rings specified for $R^1$ may optionally be substituted with one or more substituents described for aryl and heteroaryl. In a further embodiment, the substituent(s) is selected from the group consisting of halo, $C_1$-$C_4$ alkyl, $C_1$-$C_4$ alkoxy and cyano.

In some embodiments, $R^1$ is selected from the group consisting of:

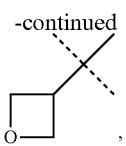, wherein each of the members may optionally be substituted with one or more substituents selected from the group consisting of cyano, halo, alkyl and alkoxy. In a further embodiment, the substituent(s) is selected from the group consisting of fluoro, $C_1$-$C_4$ alkyl, $C_1$-$C_4$ alkoxy and cyano.

In some embodiments, $R^4$ is cyano, fluoroalkyl, sulfinyl, sulfonamidyl, sulfonyl or sulfoximinyl. In a further embodiment, $R^4$ is fluoroalkyl. In yet another embodiment, $R^4$ is sulfonyl. In still another embodiment, $R^4$ is fluoroalkylsulfonyl.

In some embodiments, $R^4$ is —S(=O)$_2$$R^a$, wherein $R^a$ is alkyl or cycloalkyl. In a further embodiment, $R^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$. In still a further embodiment, $R^a$ is methyl, optionally substituted with one or more fluorines.

In some embodiments, $R^4$ is —S(=O)(=N$R^b$)$R^a$, wherein $R^a$ is alkyl or cycloalkyl and $R^b$ is hydrogen, cyano or alkyl. In a further embodiment, $R^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$.

In some embodiments, $R^4$ is —S(=O)$_2$N($R^a$)$_2$, wherein each $R^a$ is independently hydrogen, alkyl, heteroalkyl, cycloalkyl or heterocycloalkyl, and at least one $R^a$ is hydrogen. In another further embodiment, both $R^a$s are hydrogen. In a further embodiment, one $R^a$ is hydrogen and the other $R^a$ is $C_1$-$C_4$ alkyl.

In some embodiments, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, $R^5$ is hydrogen or alkyl. In some other embodiments, $R^5$ is $C_1$-$C_4$ alkyl or $C_1$-$C_4$ alkoxy. In a further embodiment, $R^5$ is methyl.

In some embodiments, $R^6$ is hydrogen or alkyl. In some other embodiments, $R^6$ is $C_1$-$C_4$ alkyl or $C_1$-$C_4$ alkoxy. In a further embodiment, $R^6$ is methyl.

In some embodiments, $R^7$ is hydrogen or alkyl. In some other embodiments, $R^7$ is $C_1$-$C_4$ alkyl or $C_1$-$C_4$ alkoxy. In a further embodiment, $R^7$ is methyl.

In some embodiments, $R^8$ is hydrogen or alkyl. In some other embodiments, $R^8$ is $C_1$-$C_4$ alkyl or $C_1$-$C_4$ alkoxy. In a further embodiment, $R^8$ is methyl.

In some embodiments, $R^{11}$ is hydroxy. In another further embodiment, $R^{11}$ is amino.

In some embodiments, $R^1$ is phenyl or monocyclic heteroaryl and $R^{11}$ is hydroxy or amino.

In some embodiments, $R^1$ is bicyclic heteroaryl and $R^{11}$ is hydroxy or amino. In a further embodiment, X is CR$^5$ and $R^5$ is hydrogen. In another further embodiment, $R^5$ is alkyl. In still a further embodiment, $R^5$ is $C_1$-$C_4$ alkyl.

In some embodiments $R^1$ is bicyclic heteroaryl and $R^4$ is cyano, fluoroalkyl, sulfinyl, sulfonamidyl, sulfonyl or sulfoximinyl. In a further embodiment, X is CR$^5$ and $R^5$ is hydrogen. In another further embodiment, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments $R^1$ is bicyclic heteroaryl; $R^4$ is cyano, fluoroalkyl, sulfinyl, sulfonamidyl, sulfonyl or sulfoximinyl; $R^{11}$ is hydroxy or amino; and X is CR$^5$ or N; and $R^5$ is hydrogen. In a further embodiment, $R^{11}$ is hydroxy. In another further embodiment, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments $R^1$ is phenyl or monocyclic heteroaryl and $R^4$ is cyano, fluoroalkyl, sulfinyl, sulfonamidyl, sulfonyl or sulfoximinyl. In a further embodiment, X is CR$^5$ and $R^5$ is hydrogen. In another further embodiment, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments $R^1$ is phenyl or monocyclic heteroaryl; $R^4$ is cyano, fluoroalkyl, sulfinyl, sulfonamidyl, sulfonyl or sulfoximinyl; $R^{11}$ is hydroxy or amino; and X is CR$^5$ or N; and $R^5$ is hydrogen. In a further embodiment, $R^{11}$ is hydroxy. In another further embodiment, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, X is N and Y is CR$^6$. In other embodiments, X is CR$^5$ and Y is N. In still other embodiments, X is N and Y is N. In yet other embodiments, X is CR$^5$ and Y is CR$^6$.

In some embodiments, Z is O. In other embodiments, Z is S. In further embodiments, Z is CHR$^7$. In yet other embodiments, Z is NR$^8$. In some embodiments, Z is absent.

In some embodiments, a compound of any one of Formulae I-H-I-K may have an enantiomeric excess of at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or even higher. In some embodiments, a compound of any one of Formulae I-H-I-K may have an enantiomeric excess of about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99%.

In yet another aspect, the invention provides a compound of Formula II:

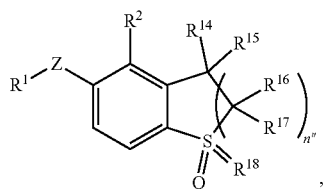

or a pharmaceutically acceptable salt or prodrug thereof, wherein:

Z is O, S, CHR$^7$, NR$^8$ or absent;

R$^1$ is alkyl, heteroalkyl, cycloalkyl, heterocycloalkyl, aryl, heteroaryl, acyl or cyano;

R$^2$ is hydrogen, alkyl, heteroalkyl, alkenyl, alkynyl, nitro, carboxaldehyde, carboxylic acid, ester, amido, cyano, halo or sulfonyl;

R$^{14}$ is hydrogen, deuterium or alkyl;

R$^{15}$ is hydrogen, hydroxy or amino; or R$^{14}$ and R$^{15}$ in combination form oxo or methylene;

R$^{16}$ and R$^{17}$ are independently selected from the group consisting of hydrogen, halo, alkyl, heteroalkyl and cycloalkyl; or R$^{16}$ and R$^{17}$ and the carbon to which they are attached form C$_3$-C$_8$ cycloalkyl or C$_5$-C$_8$ heterocycloalkyl;

R$^{18}$ is O or NR$^{19}$, wherein R$^{19}$ is selected from the group consisting of hydrogen, alkyl and cyano;

n″ is 1 or 2; and

R$^7$ and R$^8$ are independently hydrogen, halo, hydroxy, cyano, alkyl or alkoxy.

In some embodiments, R$^1$ is alkyl, cycloalkyl, heterocycloalkyl, aryl or heteroaryl. In some embodiments, R$^1$ is cycloalkyl, heterocycloalkyl, aryl or heteroaryl. In some embodiments, R$^1$ is heterocycloalkyl, aryl or heteroaryl. In some embodiments, R$^1$ is cycloalkyl, aryl or heteroaryl. In some embodiments, R$^1$ is aryl or heteroaryl. In a further embodiment, R$^1$ is phenyl. In another further embodiment, R$^1$ is pyridyl. In a still further embodiment, the phenyl or pyridyl is substituted with at least one substituent selected from the group consisting of halo, alkoxy, cyano and alkyl.

In some embodiments, R$^1$ is selected from the group consisting of cyclobutyl, cyclohexyl, tetrahydrofuranyl and tetrahydropyranyl.

In some embodiments, R$^1$ is

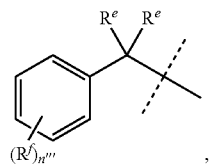

wherein each of R$^e$ is independently hydrogen or C$_1$-C$_4$ alkyl, or two R$^e$s and the carbon atom to which they are attached form a 4- to 8-membered cyclic moiety; each of R$^f$ is independently selected from the group consisting of halo, alkoxy, cyano and alkyl; and n‴ is 0, 1, 2, 3 or 4. In some further embodiments, the 4- to 8-membered cyclic moiety is an all carbon or heterocyclic ring system.

In some embodiments, R$^1$ is selected from the group consisting of:

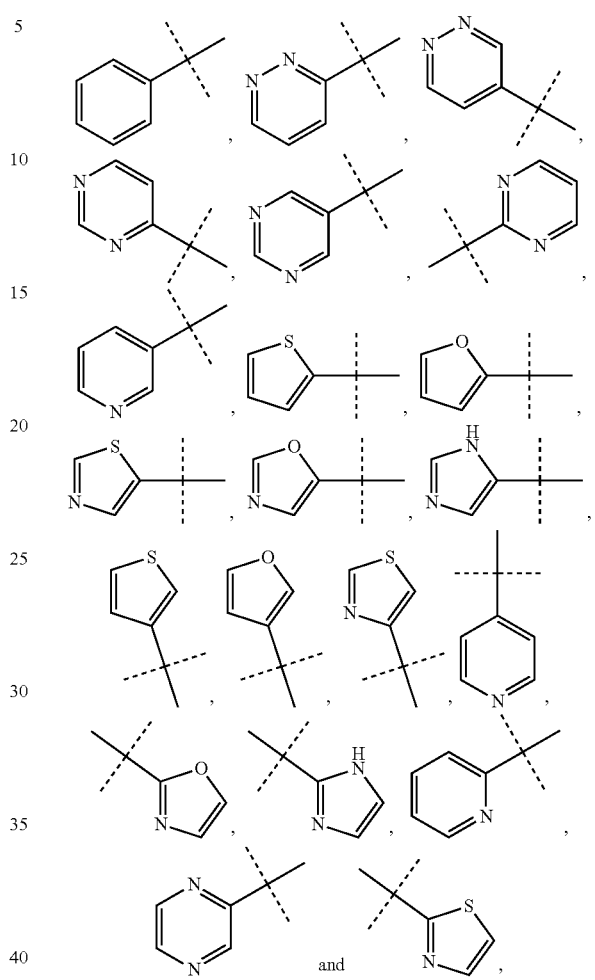

and the rings specified for R$^1$ may optionally be substituted by one or more substituents described for aryl and heteroaryl. In a further embodiment, the substituent(s) is selected from the group consisting of halo, C$_1$-C$_4$ alkyl, C$_1$-C$_4$ alkoxy and cyano.

In some embodiments, R$^1$ is cycloalkyl. In other embodiments, R$^1$ is heterocycloalkyl. In a further embodiment, R$^1$ is C$_3$-C$_6$ cycloalkyl or C$_3$-C$_6$ heterocycloalkyl. In yet a further embodiment, R$^1$ is cyclobutyl. In some embodiments, said cycloalkyl, cyclobutyl or heterocycloalkyl may optionally be substituted with one or more substituents described for cycloalkyl or heterocycloalkyl. In a further embodiment, the substituent(s) is selected from the group consisting of halo, C$_1$-C$_4$ alkyl, C$_1$-C$_4$ alkoxy and cyano. In another further embodiment, the substituent(s) is at least one fluoro.

In some embodiments, R$^1$ is acyl or cyano. In a further embodiment, R$^1$ is acetyl.

In some embodiments, R$^1$ is alkyl. In a further embodiment, the alkyl is substituted with at least one substituent(s) selected from the group consisting of halo, C$_1$-C$_4$ alkyl, C$_1$-C$_4$ alkoxy and cyano. In another further embodiment, the alkyl is substituted with at least one fluoro. In some embodiments, R$^1$ is heteroalkyl.

In some embodiments, $R^1$ is selected from the group consisting of:

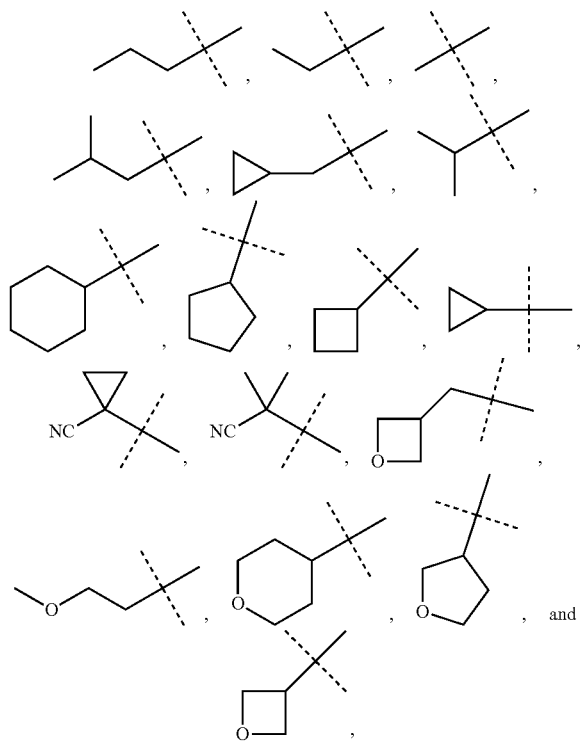

wherein each of the members may optionally be substituted with one or more substituents selected from the group consisting of cyano, halo, alkyl and alkoxy. In a further embodiment, the substituent(s) is selected from the group consisting of fluoro, $C_1$-$C_4$ alkyl, $C_1$-$C_4$ alkoxy and cyano.

In some embodiments, $R^2$ is nitro, cyano, halo, alkyl, heteroalkyl, alkynyl or alkenyl. In some embodiments, $R^2$ is cyano, halo, alkyl, heteroalkyl or alkynyl. In some embodiments, $R^2$ is cyano, halo or alkyl. In some embodiments, $R^2$ is halo or alkyl. In a further embodiment, $R^2$ is fluoroalkyl. In a still further embodiment, $R^2$ is $C_1$-$C_4$ fluoroalkyl. Exemplary $C_1$-$C_4$ fluoroalkyl includes, but is not limited to, —$CH_2F$, —$CHF_2$, —$CF_2CH_3$ and the like.

In some embodiments, $R^{14}$ is hydrogen or deuterium. In some embodiments, $R^{14}$ is alkyl. In a further embodiment, $R^{14}$ is $C_1$-$C_4$ alkyl.

In some embodiments, $R^{15}$ is hydroxy or amino. In some embodiments, $R^{15}$ is hydroxy. In some embodiments, $R^{15}$ is amino. In a further embodiment, $R^{15}$ is $NH_2$.

In some embodiments, each of $R^{16}$ and $R^{17}$ is independently hydrogen or fluoro. In some embodiments, each of $R^{16}$ and $R^{17}$ is hydrogen. In some embodiments, each of $R^{16}$ and $R^{17}$ is fluoro. In some embodiments, at least one of $R^{16}$ and $R^{17}$ is fluoro.

In some embodiments, $R^{18}$ is O, N—CN, or NH. In some embodiments, $R^{18}$ is O. In some embodiments, $R^{18}$ is NH. In some embodiments, $R^{18}$ is N—CN.

In some embodiments, $R^{14}$ is hydrogen and $R^{15}$ is hydroxy or amino. In some further embodiments, $R^1$ is aryl or heteroaryl. In a further embodiment, $R^2$ is cyano, halo or alkyl. In a still further embodiment, $R^{16}$ and $R^{17}$ are fluoro.

In some embodiments, $R^{15}$ is hydroxy or amino and $R^2$ is cyano, halo or alkyl. In a further embodiment, $R^2$ is fluoroalkyl. In a still further embodiment, at least one $R^{16}$ and $R^{17}$ is fluoro. In a yet still further embodiment, n" is 1.

In some embodiments, $R^{18}$ is O or NH and $R^{14}$ is hydrogen. In some further embodiments, $R^1$ is aryl or heteroaryl. In a further embodiment, $R^2$ is cyano, halo or alkyl. In a still further embodiment, at least one of $R^{16}$ and $R^{17}$ is fluoro.

In some embodiments, n" is 1. In some further embodiments, $R^{15}$ is hydroxy or amino and $R^{16}$ and $R^{17}$ are fluoro. In a further embodiment, $R^1$ is aryl or heteroaryl. In a still further embodiment, $R^1$ is phenyl or pyridyl, optionally substituted with one or more substituents selected from the group consisting of halo, alkoxy, cyano and alkyl.

In another aspect, the invention provides a compound of Formula II-A:

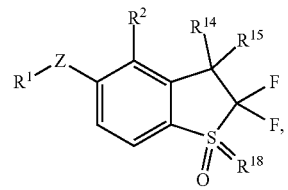

or a pharmaceutically acceptable salt or prodrug thereof, wherein:
Z is O, S, $CHR^7$, $NR^8$ or absent;
$R^1$ is alkyl, heteroalkyl, cycloalkyl, heterocycloalkyl, aryl, heteroaryl, acyl or cyano;
$R^2$ is hydrogen, alkyl, heteroalkyl, alkenyl, alkynyl, nitro, carboxaldehyde, carboxylic acid, ester, amido, cyano, halo or sulfonyl;
$R^{14}$ is hydrogen, deuterium or alkyl;
$R^{15}$ is hydrogen, hydroxy or amino; or $R^{14}$ and $R^{15}$ in combination form oxo or methylene;
$R^{18}$ is O or $NR^{19}$, wherein $R^{19}$ is selected from the group consisting of hydrogen, alkyl and cyano; and
$R^7$ and $R^8$ are independently hydrogen, halo, hydroxy, cyano, alkyl or alkoxy.

In some embodiments, $R^1$ is alkyl, cycloalkyl, heterocycloalkyl, aryl or heteroaryl. In some embodiments, $R^1$ is cycloalkyl, heterocycloalkyl, aryl or heteroaryl. In some embodiments, $R^1$ is heterocycloalkyl, aryl or heteroaryl. In some embodiments, $R^1$ is cycloalkyl, aryl or heteroaryl. In some embodiments, $R^1$ is aryl or heteroaryl. In a further embodiment, $R^1$ is phenyl. In another further embodiment, $R^1$ is pyridyl. In a still further embodiment, the phenyl or pyridyl is substituted with at least one substituent selected from the group consisting of halo, alkoxy, cyano and alkyl.

In some embodiments, $R^1$ is selected from the group consisting of cyclobutyl, cyclohexyl, tetrahydrofuranyl and tetrahydropyranyl.

In some embodiments, $R^1$ is

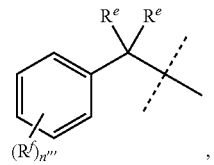

wherein each of $R^e$ is independently hydrogen or $C_1$-$C_4$ alkyl, or two $R^e$s and the carbon atom to which they are attached form a 4- to 8-membered cyclic moiety; each of $R^f$ is independently selected from the group consisting of halo, alkoxy, cyano and alkyl; and n''' is 0, 1, 2, 3 or 4. In some further embodiments, the 4- to 8-membered cyclic moiety is an all carbon or heterocyclic ring system.

In some embodiments, $R^1$ is selected from the group consisting of:

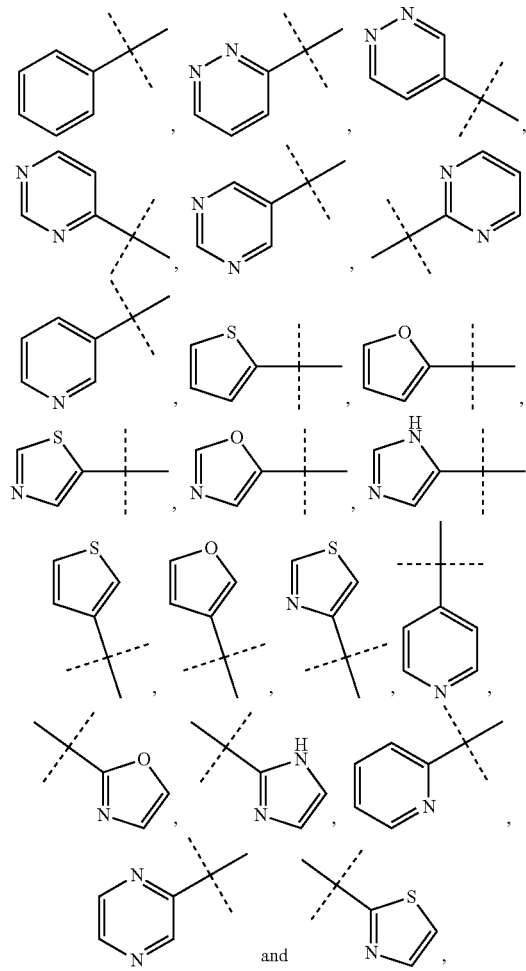

and the rings specified for $R^1$ may optionally be substituted by one or more substituents described for aryl and heteroaryl. In a further embodiment, the substituent(s) is selected from the group consisting of halo, $C_1$-$C_4$ alkyl, $C_1$-$C_4$ alkoxy and cyano.

In some embodiments, $R^1$ is cycloalkyl. In other embodiments, $R^1$ is heterocycloalkyl. In a further embodiment, $R^1$ is $C_3$-$C_6$ cycloalkyl or $C_3$-$C_6$ heterocycloalkyl. In yet a further embodiment, $R^1$ is cyclobutyl. In some embodiments, said cycloalkyl, cyclobutyl or heterocycloalkyl may optionally be substituted with one or more substituents described for cycloalkyl or heterocycloalkyl. In a further embodiment, the substituent(s) is selected from the group consisting of halo, $C_1$-$C_4$ alkyl, $C_1$-$C_4$ alkoxy and cyano. In another further embodiment, the substituent(s) is at least one fluoro.

In some embodiments, $R^1$ is acyl or cyano. In a further embodiment, $R^1$ is acetyl.

In some embodiments, $R^1$ is alkyl. In a further embodiment, the alkyl is substituted with at least one substituent(s) selected from the group consisting of halo, $C_1$-$C_4$ alkyl, $C_1$-$C_4$ alkoxy and cyano. In another further embodiment, the alkyl is substituted with at least one fluoro. In some embodiments, $R^1$ is heteroalkyl.

In some embodiments, $R^1$ is selected from the group consisting of:

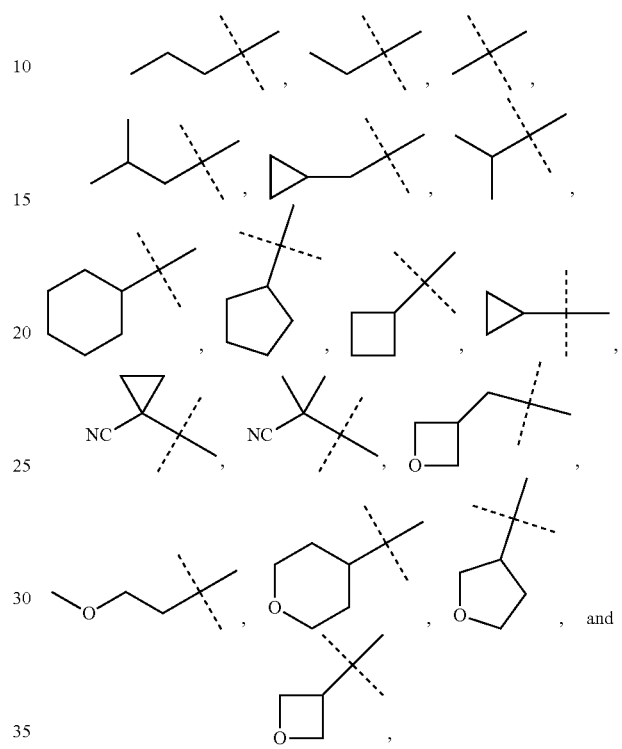

wherein each of the members may optionally be substituted with one or more substituents selected from the group consisting of cyano, halo, alkyl and alkoxy. In a further embodiment, the substituent(s) is selected from the group consisting of fluoro, $C_1$-$C_4$ alkyl, $C_1$-$C_4$ alkoxy and cyano.

In some embodiments, $R^2$ is nitro, cyano, halo, alkyl, heteroalkyl, alkynyl or alkenyl. In some embodiments, $R^2$ is cyano, halo, alkyl, heteroalkyl or alkynyl. In some embodiments, $R^2$ is cyano, halo or alkyl. In some embodiments, $R^2$ is halo or alkyl. In a further embodiment, $R^2$ is fluoroalkyl. In a still further embodiment, $R^2$ is $C_1$-$C_4$ fluoroalkyl. Exemplary $C_1$-$C_4$ fluoroalkyl includes, but is not limited to, —$CH_2F$, —$CHF_2$, —$CF_2CH_3$ and the like.

In some embodiments, $R^{14}$ is hydrogen or deuterium. In some embodiments, $R^{14}$ is alkyl. In a further embodiment, $R^{14}$ is $C_1$-$C_4$ alkyl.

In some embodiments, $R^{15}$ is hydroxy or amino. In some embodiments, $R^{15}$ is hydroxy. In some embodiments, $R^{15}$ is amino. In a further embodiment, $R^{15}$ is $NH_2$.

In some embodiments, $R^{18}$ is O, N—CN, or NH. In some embodiments, $R^{18}$ is O. In some embodiments, $R^{18}$ is NH. In some embodiments, $R^{18}$ is N—CN.

In some embodiments, $R^{18}$ is O or NH and $R^{14}$ is hydrogen. In some further embodiments, $R^1$ is aryl or heteroaryl. In a further embodiment, $R^2$ is cyano, halo or alkyl. In a still further embodiment, at least one of $R^{16}$ and $R^{17}$ is fluoro.

In still another aspect, the invention provides a compound of Formula II-B:

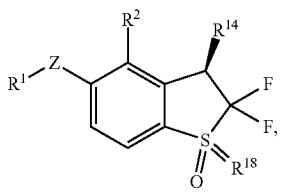

or a pharmaceutically acceptable salt or prodrug thereof, wherein:

Z is O, S, $CHR^7$, $NR^8$ or absent;
$R^1$ is alkyl, heteroalkyl, cycloalkyl, heterocycloalkyl, aryl, heteroaryl, acyl or cyano;
$R^2$ is hydrogen, alkyl, heteroalkyl, alkenyl, alkynyl, nitro, carboxaldehyde, carboxylic acid, ester, amido, cyano, halo or sulfonyl;
$R^{15}$ is hydroxy or amino;
$R^{18}$ is O or $NR^{19}$, wherein $R^{19}$ is selected from the group consisting of hydrogen, alkyl and cyano; and
$R^7$ and $R^8$ are independently hydrogen, halo, hydroxy, cyano, alkyl or alkoxy.

In some embodiments, $R^1$ is alkyl, cycloalkyl, heterocycloalkyl, aryl or heteroaryl. In some embodiments, $R^1$ is cycloalkyl, heterocycloalkyl, aryl or heteroaryl. In some embodiments, $R^1$ is heterocycloalkyl, aryl or heteroaryl. In some embodiments, $R^1$ is cycloalkyl, aryl or heteroaryl. In some embodiments, $R^1$ is aryl or heteroaryl. In a further embodiment, $R^1$ is phenyl. In another further embodiment, $R^1$ is pyridyl. In a still further embodiment, the phenyl or pyridyl is substituted with at least one substituent selected from the group consisting of halo, alkoxy, cyano and alkyl.

In some embodiments, $R^1$ is selected from the group consisting of cyclobutyl, cyclohexyl, tetrahydrofuranyl and tetrahydropyranyl.

In some embodiments, $R^1$ is

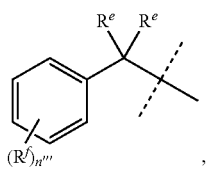

wherein each of $R^e$ is independently hydrogen or $C_1$-$C_4$ alkyl, or two $R^e$s and the carbon atom to which they are attached form a 4- to 8-membered cyclic moiety; each of $R^f$ is independently selected from the group consisting of halo, alkoxy, cyano and alkyl; and n''' is 0, 1, 2, 3 or 4. In some further embodiments, the 4- to 8-membered cyclic moiety is an all carbon or heterocyclic ring system.

In some embodiments, $R^1$ is selected from the group consisting of:

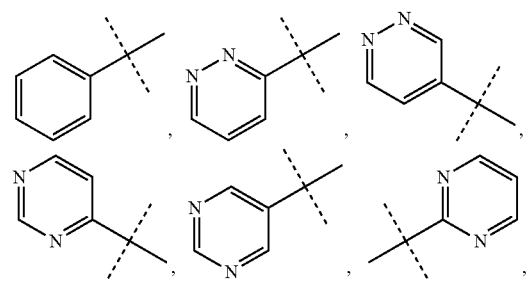

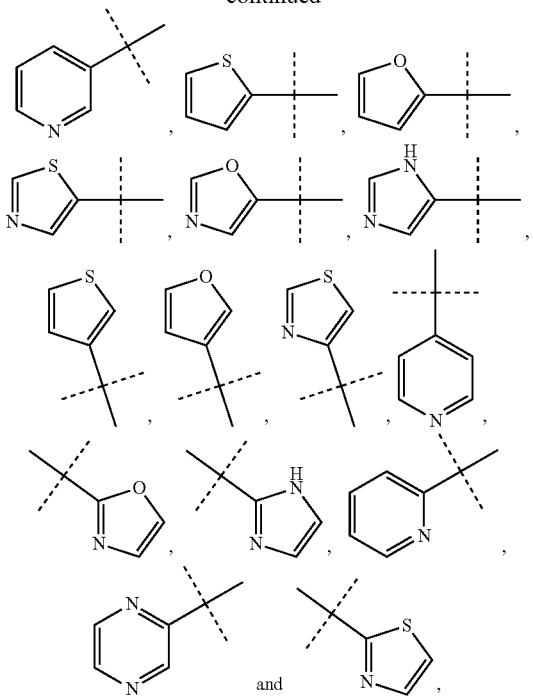

and the rings specified for $R^1$ may optionally be substituted by one or more substituents described for aryl and heteroaryl. In a further embodiment, the substituent(s) is selected from the group consisting of halo, $C_1$-$C_4$ alkyl, $C_1$-$C_4$ alkoxy and cyano.

In some embodiments, $R^1$ is cycloalkyl. In other embodiments, $R^1$ is heterocycloalkyl. In a further embodiment, $R^1$ is $C_3$-$C_6$ cycloalkyl or $C_3$-$C_6$ heterocycloalkyl. In yet a further embodiment, $R^1$ is cyclobutyl. In some embodiments, said cycloalkyl, cyclobutyl or heterocycloalkyl may optionally be substituted with one or more substituents described for cycloalkyl or heterocycloalkyl. In a further embodiment, the substituent(s) is selected from the group consisting of halo, $C_1$-$C_4$ alkyl, $C_1$-$C_4$ alkoxy and cyano. In another further embodiment, the substituent(s) is at least one fluoro.

In some embodiments, $R^1$ is acyl or cyano. In a further embodiment, $R^1$ is acetyl.

In some embodiments, $R^1$ is alkyl. In a further embodiment, the alkyl is substituted with at least one substituent(s) selected from the group consisting of halo, $C_1$-$C_4$ alkyl, $C_1$-$C_4$ alkoxy and cyano. In another further embodiment, the alkyl is substituted with at least one fluoro. In some embodiments, $R^1$ is heteroalkyl.

In some embodiments, $R^1$ is selected from the group consisting of:

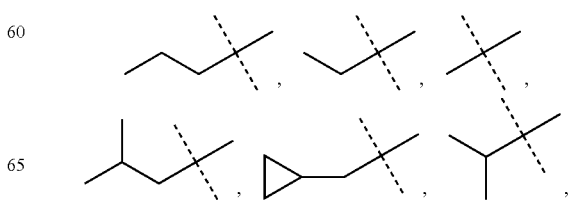

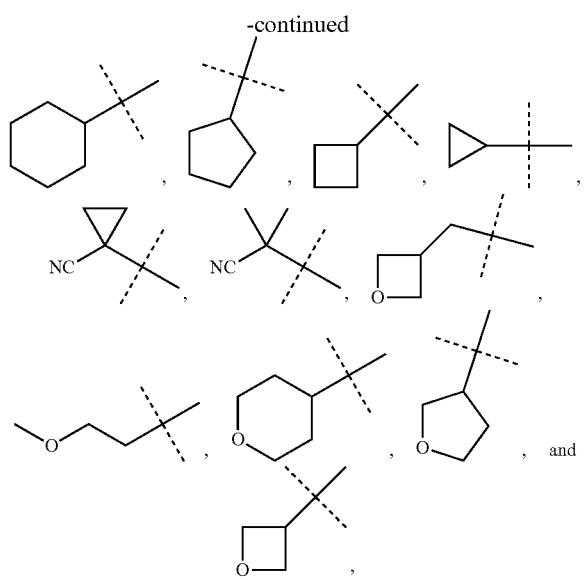

wherein each of the members may optionally be substituted with one or more substituents selected from the group consisting of cyano, halo, alkyl and alkoxy. In a further embodiment, the substituent(s) is selected from the group consisting of fluoro, $C_1$-$C_4$ alkyl, $C_1$-$C_4$ alkoxy and cyano.

In some embodiments, $R^2$ is nitro, cyano, halo, alkyl, heteroalkyl, alkynyl or alkenyl. In some embodiments, $R^2$ is cyano, halo, alkyl, heteroalkyl or alkynyl. In some embodiments, $R^2$ is cyano, halo or alkyl. In some embodiments, $R^2$ is halo or alkyl. In a further embodiment, $R^2$ is fluoroalkyl. In a still further embodiment, $R^2$ is $C_1$-$C_4$ fluoroalkyl. Exemplary $C_1$-$C_4$ fluoroalkyl includes, but is not limited to, —$CH_2F$, —$CHF_2$, —$CF_2CH_3$ and the like.

In some embodiments, $R^{15}$ is hydroxy. In some embodiments, $R^{15}$ is amino. In a further embodiment, $R^{15}$ is $NH_2$.

In some embodiments, $R^{18}$ is O, N—CN, or NH. In some embodiments, $R^{18}$ is O. In some embodiments, $R^{18}$ is NH. In some embodiments, $R^{18}$ is N—CN.

In some embodiments, a compound of Formula II-B may have an enantiomeric excess of at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99%. In a further embodiment, the compound has an enantiomeric excess of at least about 90%.

In another aspect, the present disclosure provides a compound or pharmaceutically acceptable salt or prodrug thereof, selected from the group consisting of the compounds given in Table 2.

The chemical entities described herein can be synthesized according to one or more illustrative schemes herein and/or techniques known in the art. Materials used herein are either commercially available or prepared by synthetic methods generally known in the art. These schemes are not limited to the compounds listed in the examples or by any particular substituents, which are employed for illustrative purposes.

Although various steps are described and depicted in Schemes 1-27, the steps in some cases may be performed in a different order than the order shown in Schemes 1-27. Various modifications to these synthetic reaction schemes may be made and will be suggested to one skilled in the art having referred to the disclosure contained in this Application.

Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

In general, compounds of the invention may be prepared by the following reaction schemes:

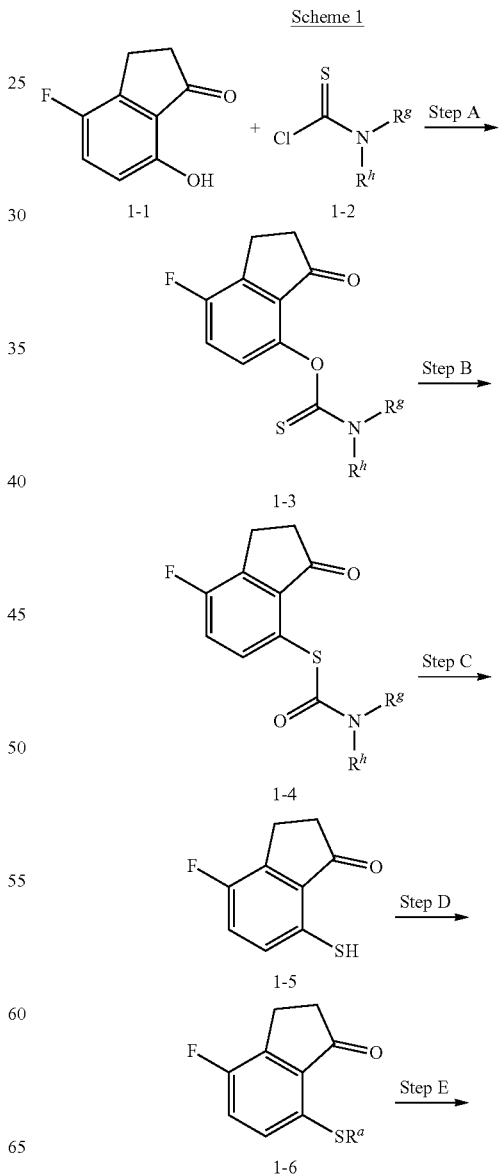

Scheme 1

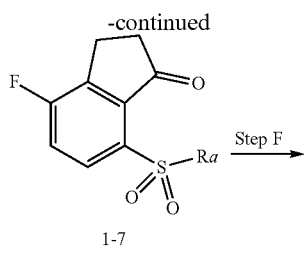

1-7

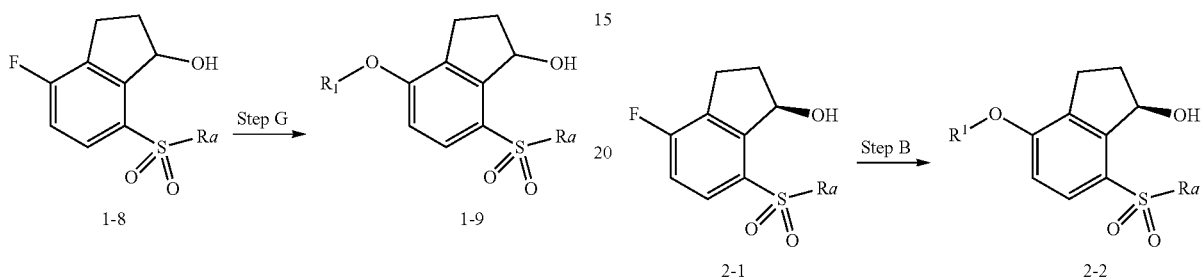

1-8  1-9

In some embodiments, a compound of Formula 1-9 can be prepared according to steps outlined in Scheme 1. The synthesis starts with phenol 1-1. Reaction of 1-1 with chloride 1-2 (wherein $R^g$ and $R^h$ are independently alkyl) provides intermediate 1-3. The reaction may be carried out in a suitable organic solvent in the presence of a base. Suitable bases for the reaction include, but are not limited to, organic bases, for example, triethylamine, N,N-diisopropylethylamine, 1,4-diazabicyclo[2.2.2]octane, and inorganic bases, for example, sodium hydroxide, cesium carbonate, cesium bicarbonate, sodium carbonate, and potassium carbonate. A compound of Formula 1-3 is then subjected to a rearrangement reaction to give a compound of Formula 1-4. Elevated temperature may be needed for the rearrangement to occur. The temperature may be in a range of 100° C. to 300° C. In some embodiments, the temperature is in a range of 180° C. to 240° C. Hydrolysis of a compound of Formula 1-4 provides thiophenol 1-5, which is alkylated to provide a compound if Formula 1-6. A variety of alkyl groups may be introduced in Step D. In some embodiments, $R^a$ is a $C_1$-$C_4$ alkyl. In a further embodiment, $R^a$ is a $C_1$-$C_4$ fluoroalkyl. Oxidation of a compound of Formula 1-6 may be accomplished by a variety of methods known in the art, including, but not limited to, $RuCl_3$ catalyzed oxidation in the presence of $NaIO_4$, oxidation with m-chloroperoxybenzoic acid (mCPBA) and oxidation with Oxone®. Ketone 1-7 is then reduced to give alcohol 1-8, which then undergoes a nucleophilic aromatic substitution (SNAr) reaction with a suitable substrate $R^1OH$ to give a compound of Formula 1-9. Temperatures for carrying out the SNAr reaction may depend on the reactivity of both $R^1OH$ and/or compound 1-8. The reaction may be carried out in a temperature range from about room temperature to 200° C. In some embodiments, the temperature range is from room temperature to 60° C. In some other embodiments, the temperature range is from 60° C. to 100° C. In some other embodiments, the temperature range is from 100° C. to 200° C.

Scheme 2

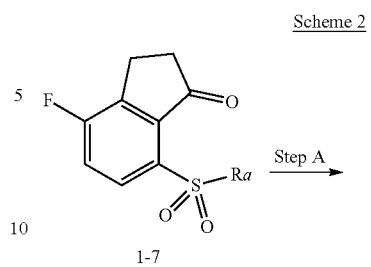

1-7

2-1  2-2

In some other embodiments, a compound of Formula 1-9 can be prepared asymmetrically to give a compound of Formula 2-2 (Scheme 2). For example, direct asymmetric reduction of ketone 1-7 (Step A) may be accomplished chemically or enzymatically. For a recent review on enzymatic reduction of ketones, see Moore, et al. *Acc. Chem. Res.* 40: 1412-1419, 2007. Examples of chemical asymmetric reduction of ketones include, but are not limited to, Corey-Bakshi-Shibata (CBS) reduction, asymmetric hydrogenation and asymmetric transfer hydrogenation. In some embodiments, the asymmetric transfer hydrogenation is catalyzed by ruthenium. For examples of methods and catalysts for ruthenium catalyzed transfer hydrogenation, see U.S. Pat. Nos. 6,184,381 and 6,887,820. Exemplary catalysts for asymmetric transfer hydrogenation include, but are not limited to, the following (shown as the R, R configuration):

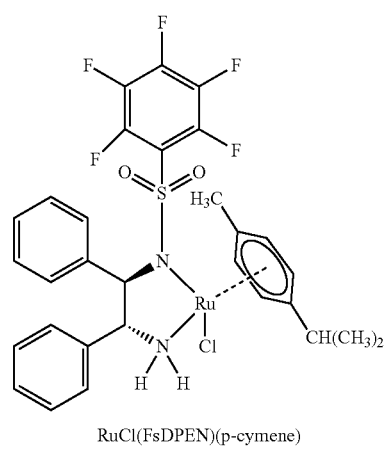

RuCl(FsDPEN)(p-cymene)

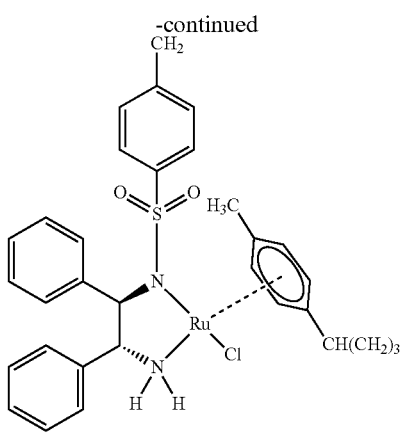

RuCl(TsDPEN)(p-cymene)

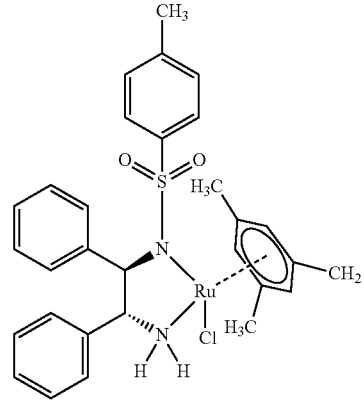

RuCl(TsDPEN)(mesitylene)

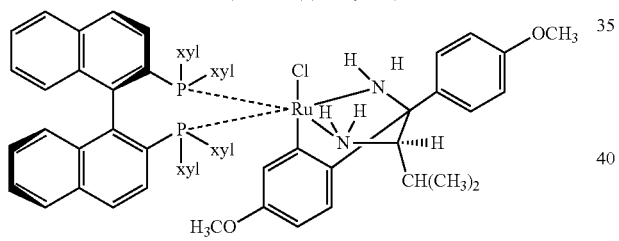

RUCY™

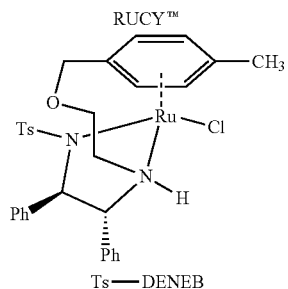

Ts—DENEB

The asymmetric transfer hydrogenation may be carried out at or below room temperature. In some embodiments, the asymmetric transfer hydrogenation is carried out at about 4° C. The alcohol product may have an enantiomeric excess of at least 90%, at least 91%, at least 92%, at least 93%, at least 94%, at least 95%, at least 96%, at least 97%, or even higher. It is well understood by one skilled in the art that changing the catalyst configuration will lead to a product with the opposite configuration. Chiral alcohol 2-1 can be coupled with a suitable substrate, for example, a phenol, to give a compound of Formula 2-2 without significant loss of enantiomeric excess. The loss of enantiomeric excess (ee) in the coupling step for 2-2 may be less than about 1%, less than about 2%, less than about 3%, less than about 4%, less than about 5%, less than about 6% or less than about 8%.

Scheme 3

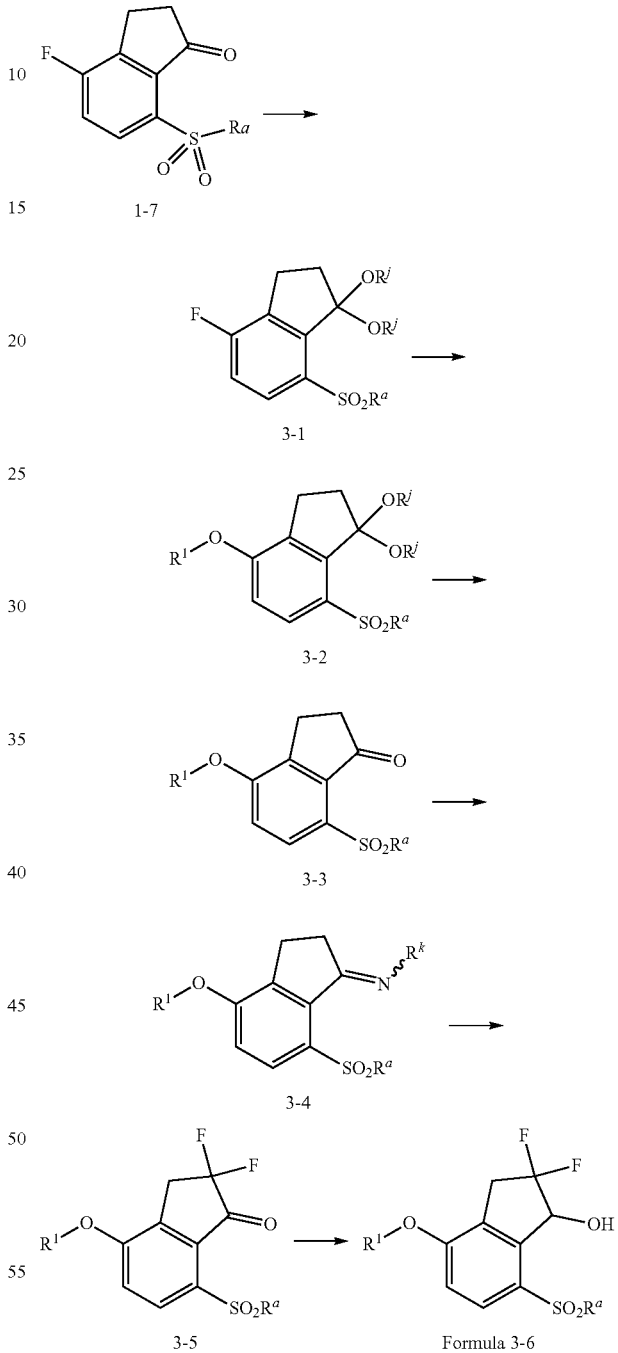

In some embodiments, a compound of Formula 3-6 may be prepared according to Scheme 3. The ketone in 1-7 is protected as a ketal to give a compound of Formula 3-1, wherein each of $R^i$ and $R^j$ is independently an alkyl group. In addition, $R^i$ and $R^j$ may optionally be connected to form a cyclic ketal. Exemplary structures of ketal 3-1 include, but are not limited to, the following:

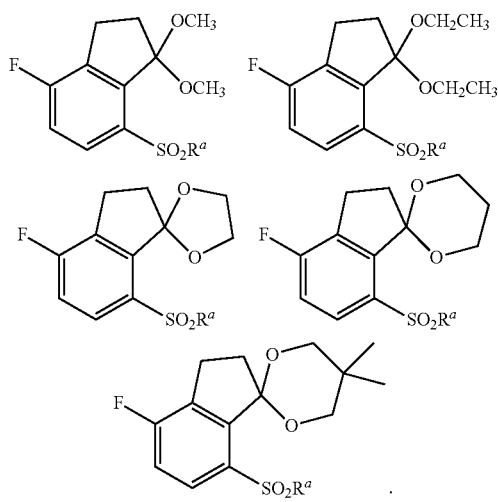

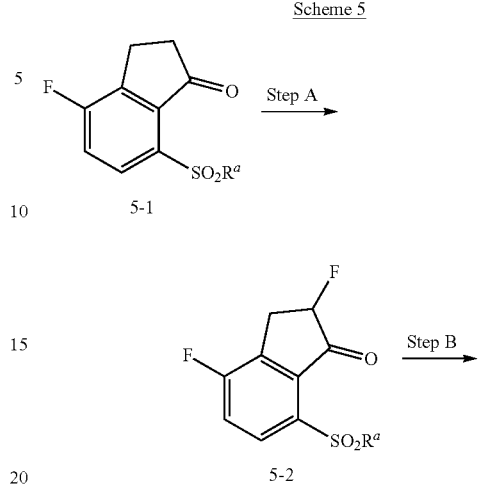

A compound of Formula 3-1 and a suitable R¹OH may undergo a nucleophilic aromatic substitution reaction (SNAr) to give biaryl ether 3-2. As described in Step G of Scheme 1, the reaction temperature of the SNAr reaction may depend on the reactivity of the aryl halide (i.e. compound 3-1) and/or R¹OH. Ketone 3-3, resulting from the deprotection of ketal 3-2, is condensed with an amine to form imine 3-4, wherein $R^k$ is alkyl. The imine functional group in a compound of Formula 3-4 may exist as a mixture of E and Z isomers. Fluorination of 3-4 can be accomplished with a fluorinating reagent, for example, 1-(chloromethyl)-4-fluoro-1,4-diazoniabicyclo[2.2.2]octane ditetrafluoroborate, to give difluoroketone 3-5 after acid hydrolysis. Finally, reduction of ketone 3-5 with a hydride donor gives a compound of Formula 3-6.

Scheme 4

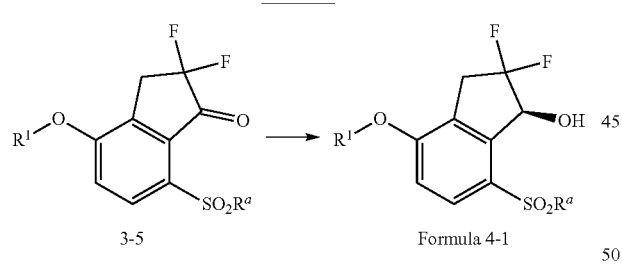

A compound of Formula 4-1 (Scheme 4) can be prepared asymmetrically following the general procedure described above in Scheme 2. In some embodiments, the asymmetric reduction gives a compound of Formula 4-1 with an enantiomeric excess of at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or even higher. The enantiomeric excess of a compound of Formula 2-2 or 4-1 may be determined by chiral HPLC or Mosher ester analysis. For determination of ee with Mosher ester, see Hoye, et al. *Natural Protocol*, 2: 2451, 2007.

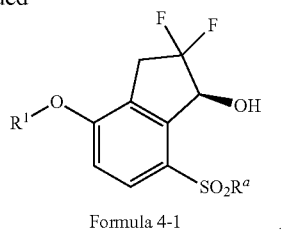

Formula 4-1

Alternatively, a compound of Formula 4-1 may be prepared according to Scheme 5. Ketone 5-1 is fluorinated to give monofluoroketone 5-2, which is then converted to a silylenol ether, e.g., TBS enol ether 5-3. Other silyl protecting groups may also be used, for example, triisopropylsilyl or diphenyl-t-butylsilyl. The resulting enol ether is further fluorinated to give difluoroketone 5-4, which undergoes an asymmetric reduction, such as asymmetric transfer hydrogenation as described herein, to give chiral alcohol 5-5. Protection of the hydroxy moiety, followed by SNAr reaction and deprotection of the alcohol, provides a compound of Formula 4-1.

Scheme 6

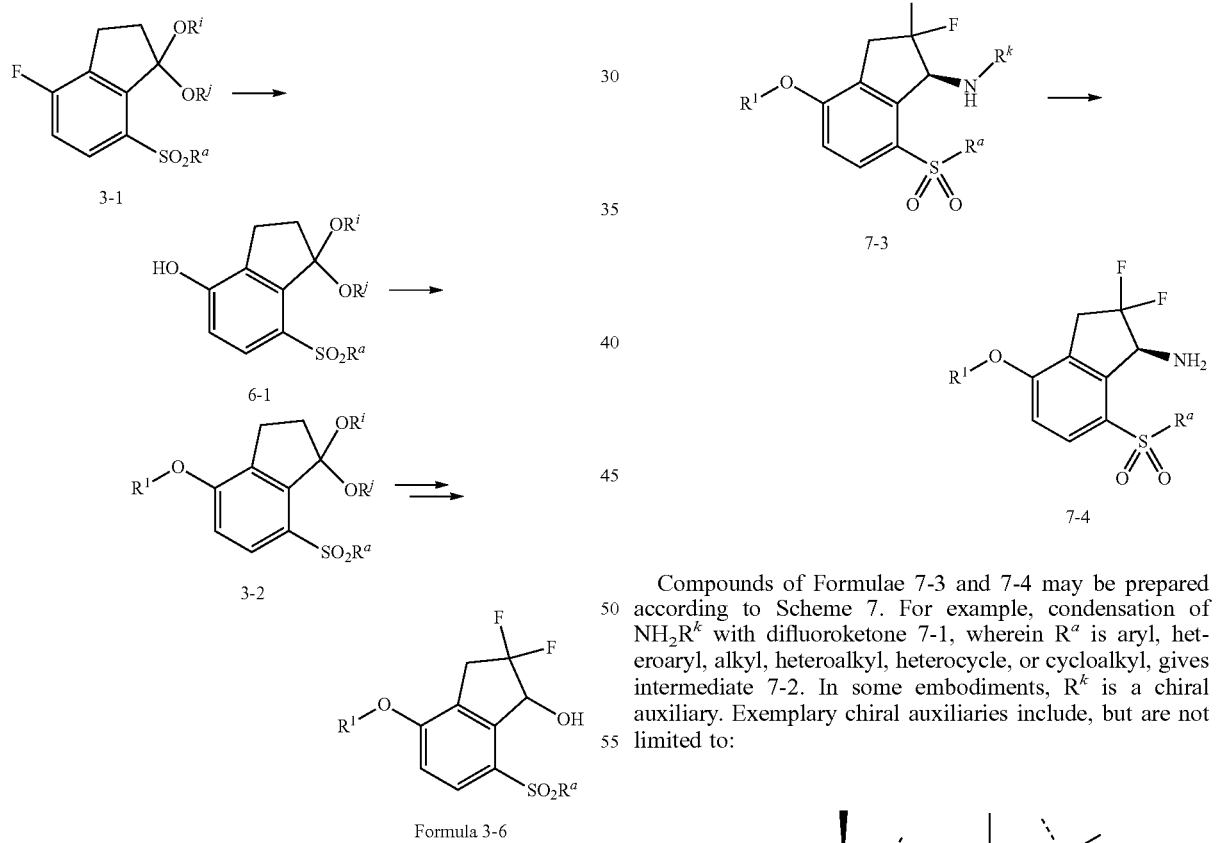

Alternatively, a compound of Formula 3-6 can be prepared according to Scheme 6. Treatment of aryl halide 3-1 with a hydroxide source gives phenol 6-1. Suitable hydroxide sources include, but are not limited to, sodium hydroxide and potassium hydroxide. Suitable solvents for the reaction include, but are not limited to, DMSO, DMA, DMF and EtOH. Phenol 6-1 can react with a suitable halide via an SNAr reaction to give ether 3-2, which can be converted to a compound of Formula 3-6 as described in Scheme 3.

Scheme 7

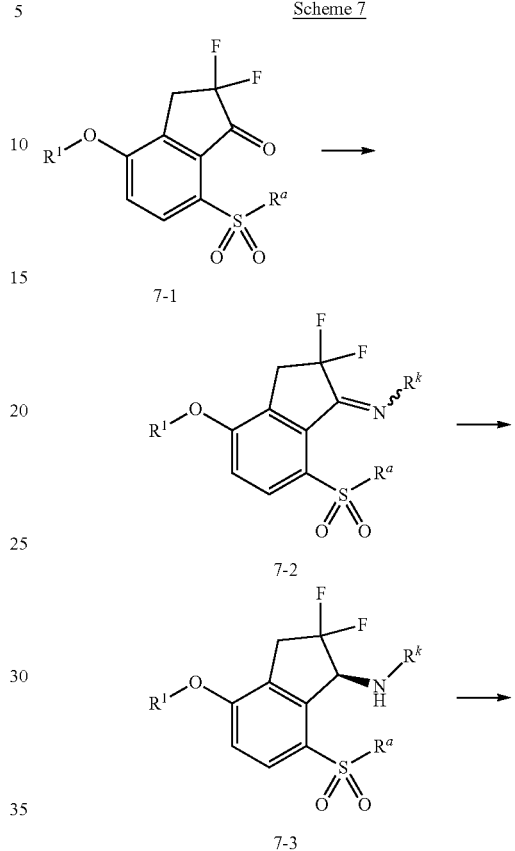

Compounds of Formulae 7-3 and 7-4 may be prepared according to Scheme 7. For example, condensation of $NH_2R^k$ with difluoroketone 7-1, wherein $R^a$ is aryl, heteroaryl, alkyl, heteroalkyl, heterocycle, or cycloalkyl, gives intermediate 7-2. In some embodiments, $R^k$ is a chiral auxiliary. Exemplary chiral auxiliaries include, but are not limited to:

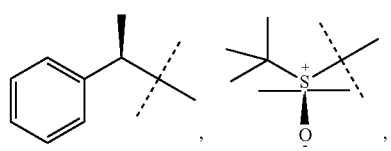

and enantiomers thereof. Hydride reduction of intermediate 7-2 yields 7-3. At this stage, the chiral auxiliary may be cleaved under appropriate conditions, e.g., hydrogenation or acid treatment, to give chiral secondary amine 7-4. In some other embodiments, when a compound of Formula 7-3 is desirable and $R^k$ is not hydrogen, asymmetric hydrogenation or asymmetric transfer hydrogenation is applied on intermediate 7-2 to give a compound of Formula 7-3. For a review on asymmetric hydrogenation and asymmetric transfer hydrogenation, see Iwao Ojima ed. *Catalytic Asymmetric Synthesis*, Wiley-VCH, Inc., 2000, ISBN 0-471-29805-0.

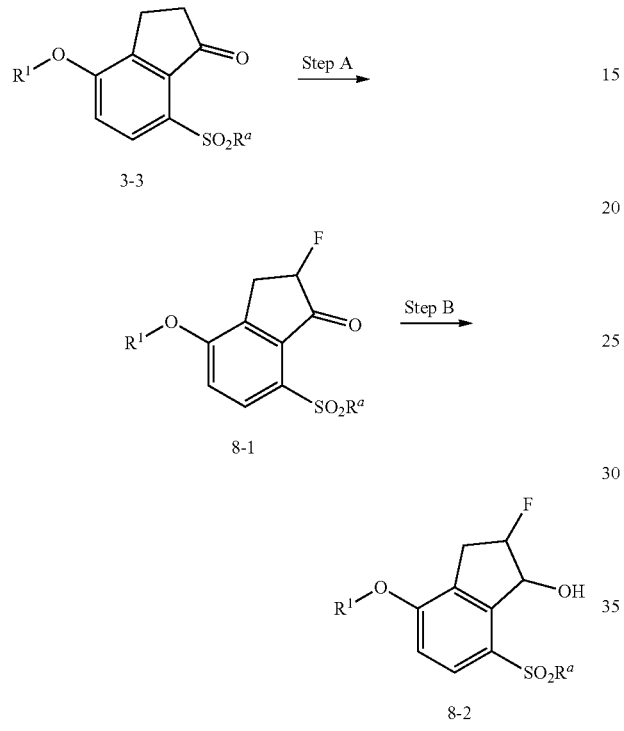

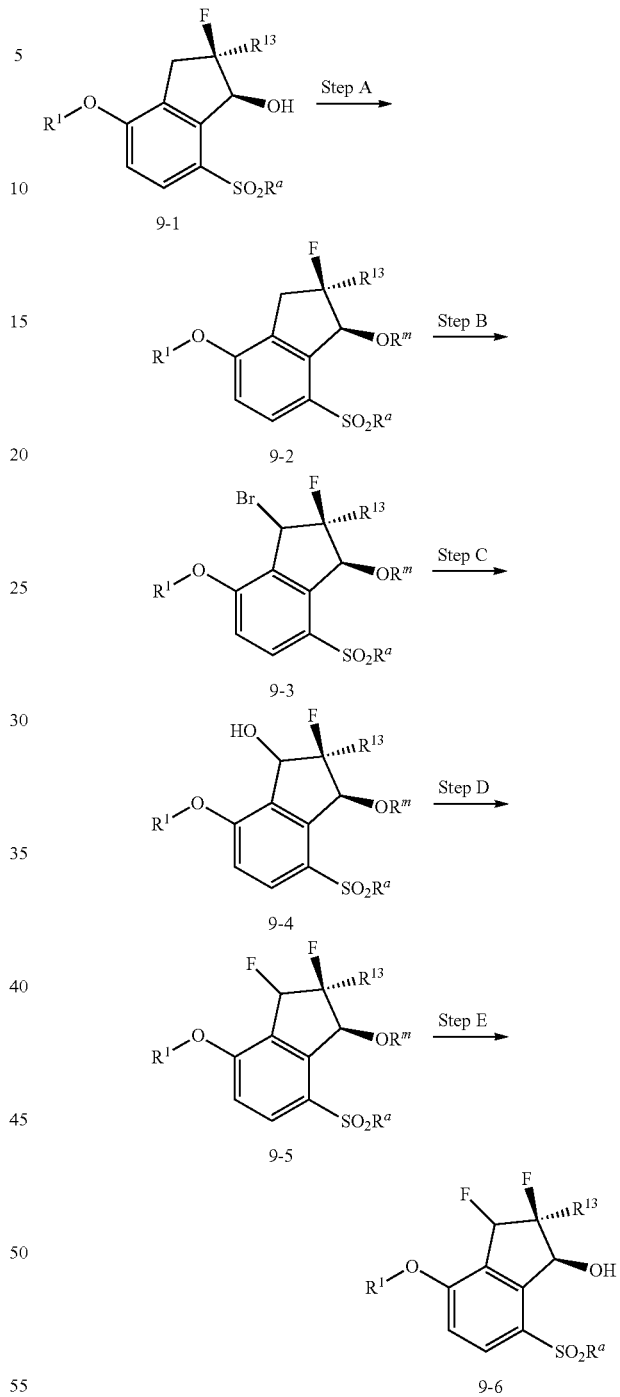

In some embodiments, a compound of Formula 8-2 can be prepared according to Scheme 8. For example, ketone 3-3 is monofluorinated to give a monofluoroketone of Formula 8-1. The monofluorination can be achieved with a variety of fluorinating reagents, e.g., N-Fluoro-O-benzenedisulfonimide, acetyl hypofluorite, Accufluor®, Selectfluor®, Selectfluor® II, or N-fluorobenzenesulfonimide, in the presence or absence of a base. A compound of Formula 8-1 is reduced to give a compound of Formula 8-2. In some cases, the reduction is highly diastereoselective to give a compound of Formula 8-2 with greater than 80%, greater than 82%, greater than 84%, greater than 86%, greater than 88%, greater than 90%, greater than 92%, greater than 94%, greater than 96% or even greater than 96% diastereoselectivity. In some cases, the reduction is highly enantioselective to give a compound of Formula 8-2 with greater than 80%, greater than 82%, greater than 84%, greater than 86%, greater than 88%, greater than 90%, greater than 92%, greater than 94%, greater than 96% or even greater than 96% enantioselectivity. Reduction conditions to achieve high enantioselectivity include, but are not limited to, asymmetric transfer hydrogenation and enzymatic reduction as described herein.

In some embodiments, a compound of Formula 9-6 may be prepared according to Scheme 9, wherein $R^{13}$ is hydrogen, alkyl or fluoro. The hydroxy group of compound 9-1 may be protected, for example, with an acyl or methoxymethyl ether (MOM) group, to give a compound of Formula 9-2. Benzylic bromination in Step B may be carried out with a bromide source, e.g., N-bromosuccinimide, in the presence of a radical initiator, e.g., 2,2'-azobis(2-methylpropionitrile) (AIBN) or benzyol peroxide. The bromide of compound 9-3 can be replaced with a hydroxy group in a solvent comprising water in the presence of a silver salt, e.g., Ag$_2$CO$_3$ or AgClO$_4$ or AgBF$_4$. Finally, fluorination of a compound of Formula 9-4 followed by deprotection gives a compound of Formula 9-6. In some cases, direct benzylic oxidation may be used for converting a compound of Formula 9-2 to a compound of Formula 9-4, thus bypassing an intermediate bromination step.

In some embodiments, a compound of Formula 10-7 can be prepared according to Scheme 10. For example, a compound of Formula 10-3 may be prepared from a compound of Formula 3-2 following a similar sequence as outlined in Scheme 9. Further functional group manipulations lead to a compound of Formula 10-7.

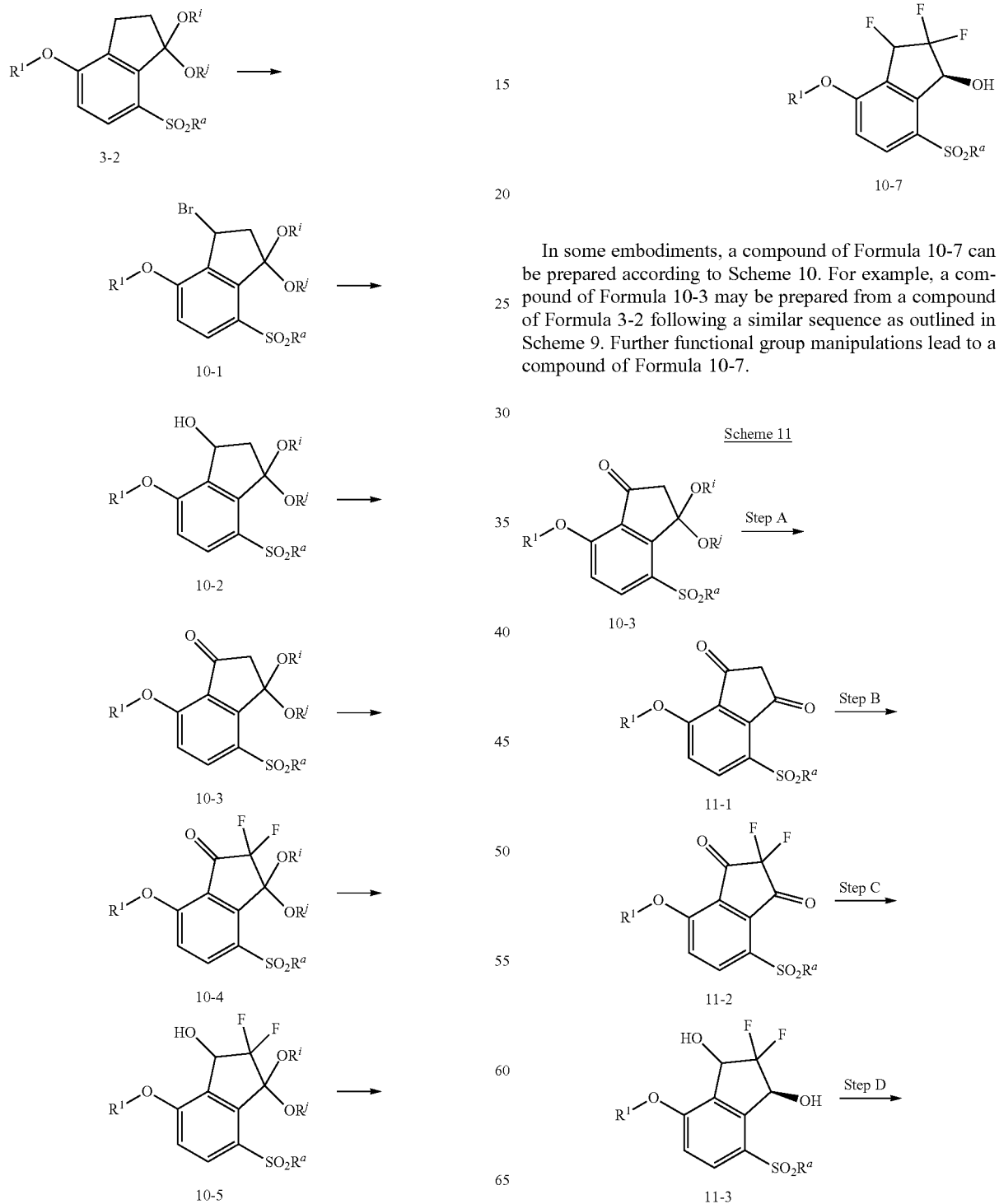

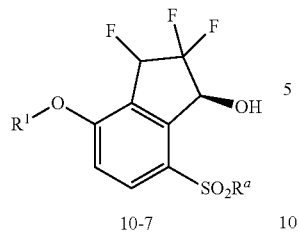

10-7

Alternatively, a compound of Formula 10-3 can be deprotected to give diketone 11-1, which is fluorinated to give difluorodiketone 11-2. Asymmetric reduction of 11-2 provides diol 11-3. In some embodiments, a fluorination step is performed to give a compound of Formula 10-7.

Scheme 12

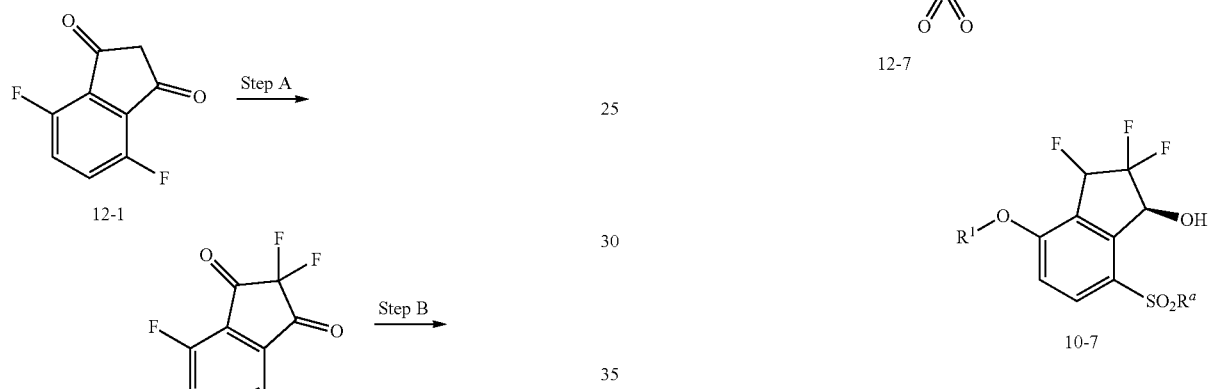

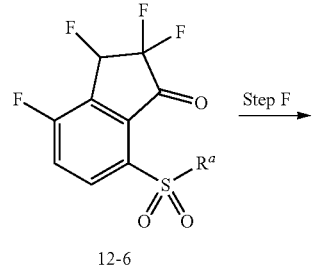

12-6

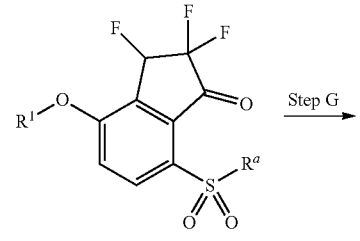

12-7

10-7

Alternatively, a compound of Formula 10-7 may be prepared according to Scheme 12. For example, difluoroketone 12-2 is reduced to give hydroxyketone 12-3. The reduction maybe enantioselective under transfer hydrogenation conditions with a Ru-catalysis as described herein. One of the aryl fluorines may be selectively displaced with an alkyl thiol to give a compound of Formula 12-4. Oxidation, fluorination, nucleophilic aromatic substitution (SNAr) and asymmetric reduction give a compound of Formula 10-7.

Scheme 13

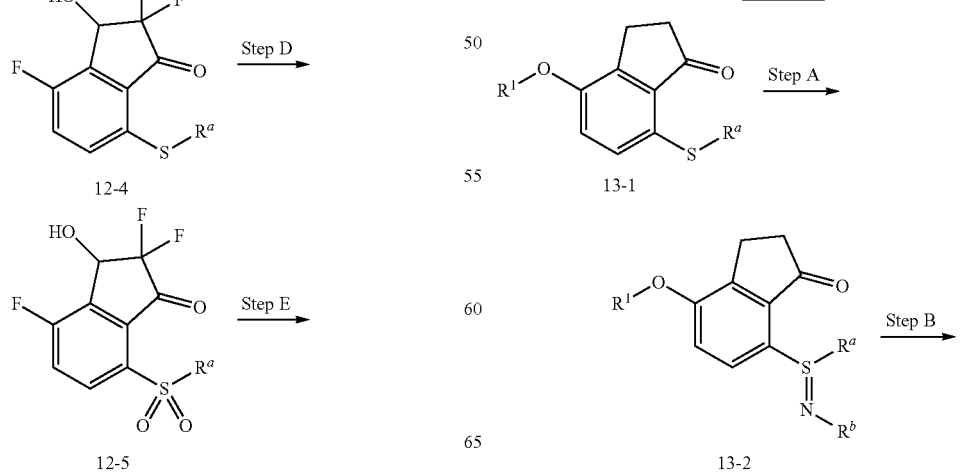

87

-continued

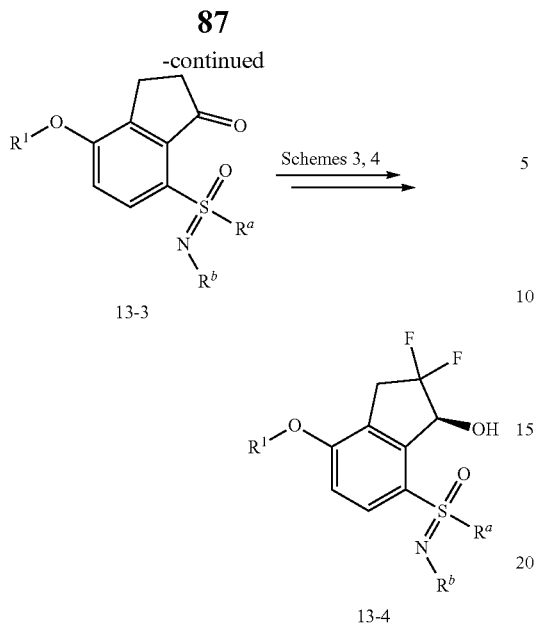

13-3

13-4

In some embodiments, a compound of Formula 13-4 can be prepared according to Scheme 13. An aryl sulfide of Formula 13-1 is treated with $H_2N$—$R^b$ and an oxidant, e.g., diacetoxyiodobenzene or dipivaloyloxyiodobenzene, in a suitable solvent, such as acetonitrile, to obtain aryl sulfinimide 13-2. In some embodiments, wherein $R^a$ is fluoroalkyl, the addition of rhodium(II) acetate or $Rh_2(esp)_2$ catalyst along with magnesium oxide is helpful in Step A. Oxidation of aryl sulfinimide 13-2 to substituted sulfoximine 13-3 may be accomplished with catalytic ruthenium (III) chloride and sodium periodate in a suitable solvent, such as a mixture of water, acetonitrile, and carbon tetrachloride. Substituted sulfoximine 13-3 is then manipulated similarly as described in Schemes 3 and 4 to afford sulfoximines of Formula 13-4 as a diastereomeric mixture. The diastereomers may be separated by column chromatography.

Scheme 14

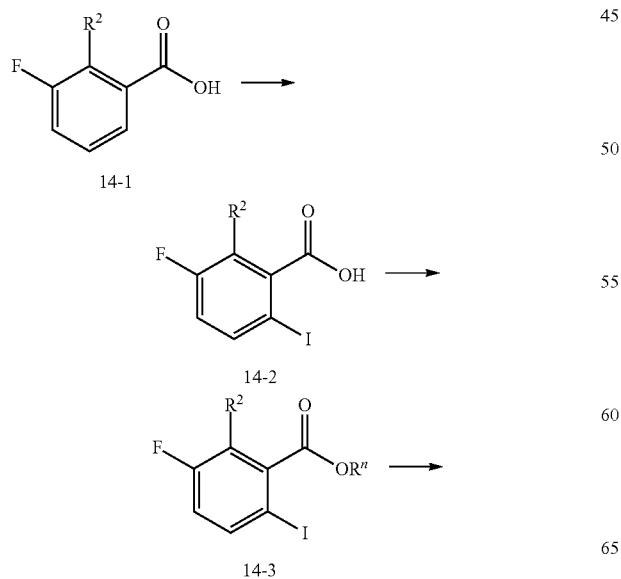

14-1

14-2

14-3

88

-continued

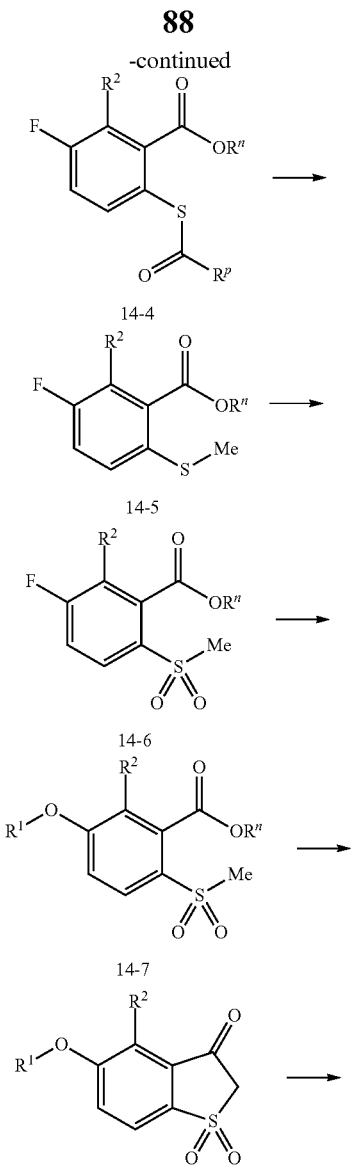

14-4

14-5

14-6

14-7

14-8

14-9

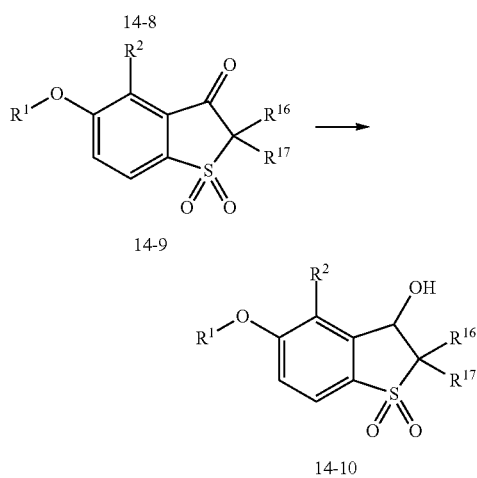

14-10

In some embodiments, a compound of Formula 14-10 can be prepared according to steps outlined in Scheme 14, wherein $R^1$ is alkyl, heteroalkyl, cycloalkyl, heterocycloalkyl, aryl or heteroaryl; $R^2$ is halo, cyano, alkyl, alkenyl or alkynyl; and $R^{16}$ and $R^{17}$ are fluoro or alkyl, or $R^{16}$ and $R^{17}$ and the carbon to which they are attached form $C_3$-$C_8$ cycloalkyl or $C_5$-$C_8$ heterocycloalkyl. The synthesis commences with compounds of Formula 14-1. Orthoiodination of 14-1 provides compound 14-2. The reaction may be carried out in a suitable organic solvent in the presence of iodine and a palladium catalyst at an elevated temperature, if needed. After esterification of 14-2, the resulting ester 14-3 may undergo a transition-metal catalyzed coupling reaction with a thioate, e.g., potassium ethanethioate or sodium ethanethioate, to give compounds of Formula 14-4. Suitable transition-metal catalysts include, but are not limited to, $Pd(PPh_3)_4$, $Pd_2(dba)_3$ chloroform complex or $Pd(OAc)_2$, in the presence or absence of a suitable ligand. Hydrolysis of a compound of Formula 14-4 followed by alkylation of the resulting thiophenol intermediate with an alkyl halide, e.g., methyl iodide, gives a compound of Formula 14-5. The hydrolysis and alkylation may be carried out in a one-pot procedure without purification. In some embodiments, this is carried out by treating a compound of Formula 14-4 with a carbonate base in a suitable solvent at or near room temperature for a period ranging from 0.1 to 24 hours, followed by addition of an alkyl halide. Carbonate bases include, but are not limited to, sodium carbonate, potassium carbonate, cesium carbonate, potassium bicarbonate and cesium bicarbonate. Oxidation of a compound of Formula 14-5 to give a compound of Formula 14-6 may be accomplished by a variety of methods known in the art, including, but not limited to, $RuCl_3$ catalyzed oxidation in the presence of $NaIO_4$, oxidation with m-chloroperoxybenzoic acid (mCPBA), and oxidation with Oxone®. A compound of Formula 14-6 is then subjected to a nucleophilic aromatic substitution (SNAr) reaction with $R^1OH$ (wherein $R^1$ is alkyl, aryl or heteroaryl) to give a compound of Formula 14-7. Temperature for carrying out the SNAr reaction may depend on the reactivity of both $R^1OH$ and/or a compound of Formula 14-6. The reaction may be carried out at a temperature ranging from −10° C. to 200° C. In some embodiments, the temperature range is from 30° C. to 120° C. In some other embodiments, the temperature range is from 0° C. to room temperature. Cyclization of a compound of Formula 14-7 may be effected with a base, e.g., sodium hydride, in a suitable solvent to yield a compound of Formula 14-8. After the cyclization, a variety of $R^{16}$ and $R^{17}$ groups may be introduced. In some embodiments, a compound of Formula 14-8 is difluorinated to give a compound of Formula 14-9, formed by treatment with a fluorinating agent, e.g., 1-(chloromethyl)-4-fluoro-1,4-diazo niabicyclo [2.2.2]octane ditetrafluoroborate (Selectfluor®), in the presence of suitable base, e.g., sodium carbonate. Reduction of a compound of Formula 14-9 yields a compound of Formula 14-10. In some embodiments, the reduction is carried out with a hydride, e.g., sodium borohydride and sodium triacetoxyborohydride, to give a racemic mixture. In some embodiments, an asymmetric reduction is carried out as described above (see Scheme 2) to give an enantiomer having an enantiomeric excess as disclosed herein.

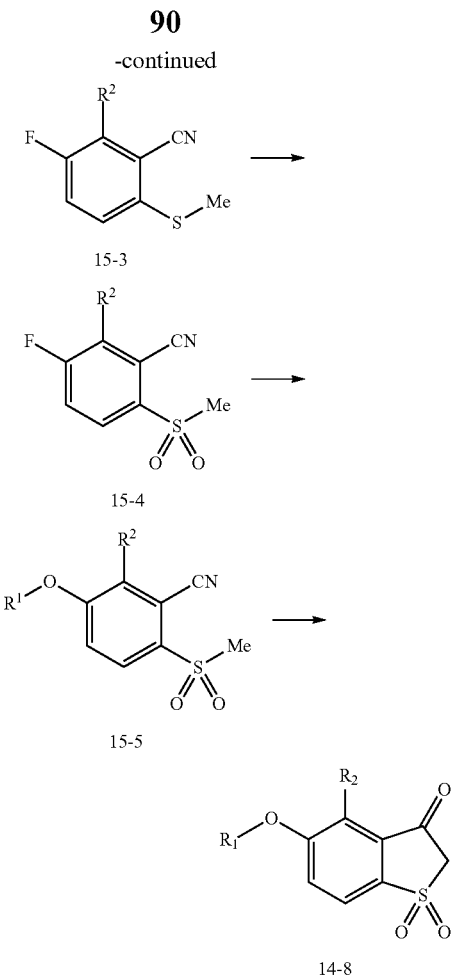

Alternatively, a compound of Formula 14-8 may be prepared according to Scheme 15. For example, lithiation of a compound of Formula 15-1 followed by trapping of the resulting lithio intermediate with a suitable electrophile gives a compound of Formula 15-2. In some embodiments, the electrophile is N,N-dimethylformamide and $R^2$ is —CHO. In a further embodiment, —CHO is converted to —$CHF_2$ through addition of a fluorinating reagent, e.g., diethylaminosulfur trifluoride. One of the fluorines in a compound of Formula 15-2 may be selectively displaced with a thiomethoxide, e.g., sodium thiomethoxide, to give compounds of Formula 15-3. The reaction temperature may be in a range of −50 to 40° C. In some embodiments, the temperature is at or about 0° C. Oxidation of a compound of Formula 15-3, followed by SNAr reaction with $R^1OH$ and base-mediated cyclization provides a compound of Formula 14-8.

Scheme 15

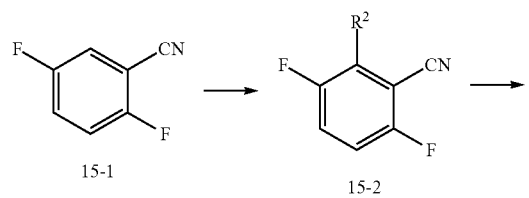

Scheme 16

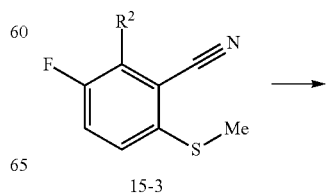

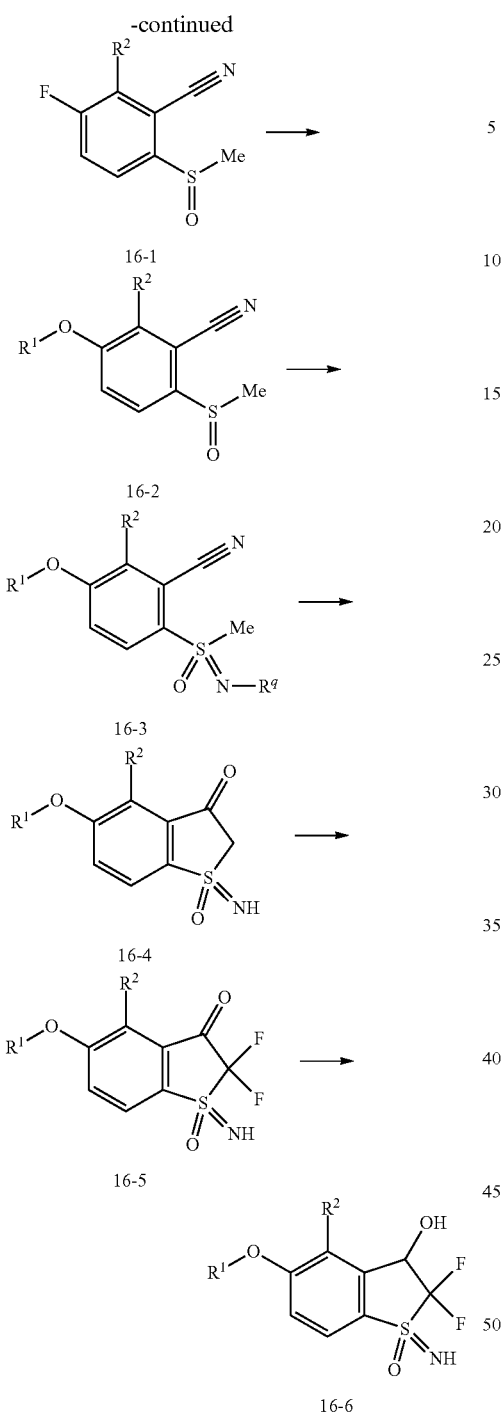

compound of Formula 16-3 through a transition-metal catalyzed insertion of a suitable nitrogen donor. Suitable transition-metal catalysts include, but are not limited to, copper and rhodium catalysts, e.g., bis(rhodium(α,α,α',α'-tetramethyl-1,3-benezenedipropionic acid)) and dirhodium tetraacetate. Suitable nitrogen donors include, but are not limited to, PhI=NNs, cyanamide, and fluoroalkylamides, e.g., trifluoromethyl acetamide. Cyclization of a compound of Formula 16-3 to give a compound of Formula 16-4 may be achieved with a base, e.g., sodium hydride, at about room temperature. Finally, reduction of a compound of Formula 16-5 as outlined in Scheme 14 provides a compound of Formula 16-6. A compound of Formula 16-6 may exist as a mixture of diastereomers and/or enantiomers. Diastereomers may be separated by conventional column chromatography, while enantiomers may be separated by chiral column chromatography.

Scheme 17

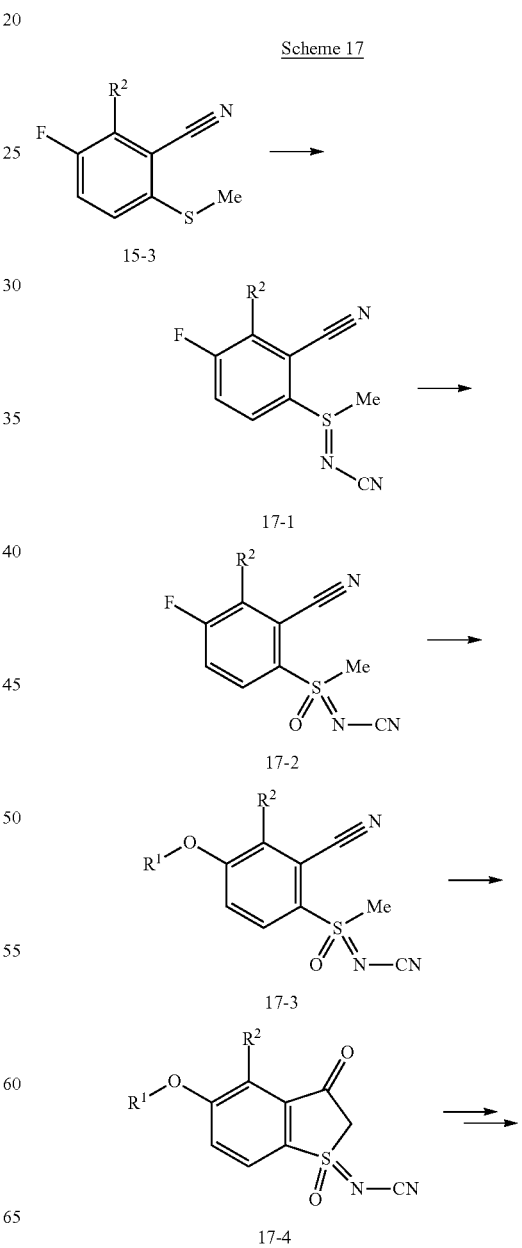

In some embodiments, a compound of Formula 16-6 may be prepared according to Scheme 16. Oxidation of a compound of Formula 15-3 gives a compound of Formula 16-1. The oxidation may be accomplished with Oxone® or mCPBA. The amount of oxidant used for the oxidation may be about 1.5 equivalent, about 1.4 equivalent, about 1.3 equivalent, about 1.2 equivalent, about 1.1 equivalent or about 1.0 equivalent. SNAr reaction of a compound of Formula 16-1 with $R^1OH$ (wherein $R^1$ is alkyl, heteroalkyl, cycloalkyl, heterocycloalkyl, aryl or heteroaryl) in the presence of a base gives a compound of Formula 16-2. At this stage, a sulfoximine moiety may be installed to give a

93

-continued

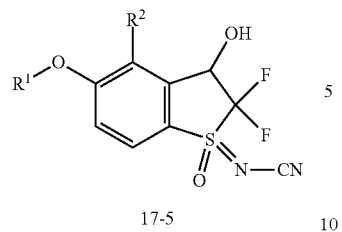

17-5

In some embodiments, a compound of Formula 17-5 can be prepared according to Scheme 17. Reaction of a compound of Formula 15-3 with cyanamide in the presence of an oxidant, e.g., (diacetoxyiodo)benzene, affords a compound of Formula 15-1. Further oxidation of a compound of Formula 15-1 provides a compound of Formula 15-2, which undergoes SNAr reaction, cyclization and reduction to give a compound of Formula 17-5.

94

-continued

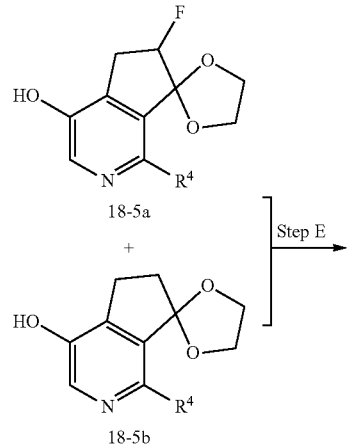

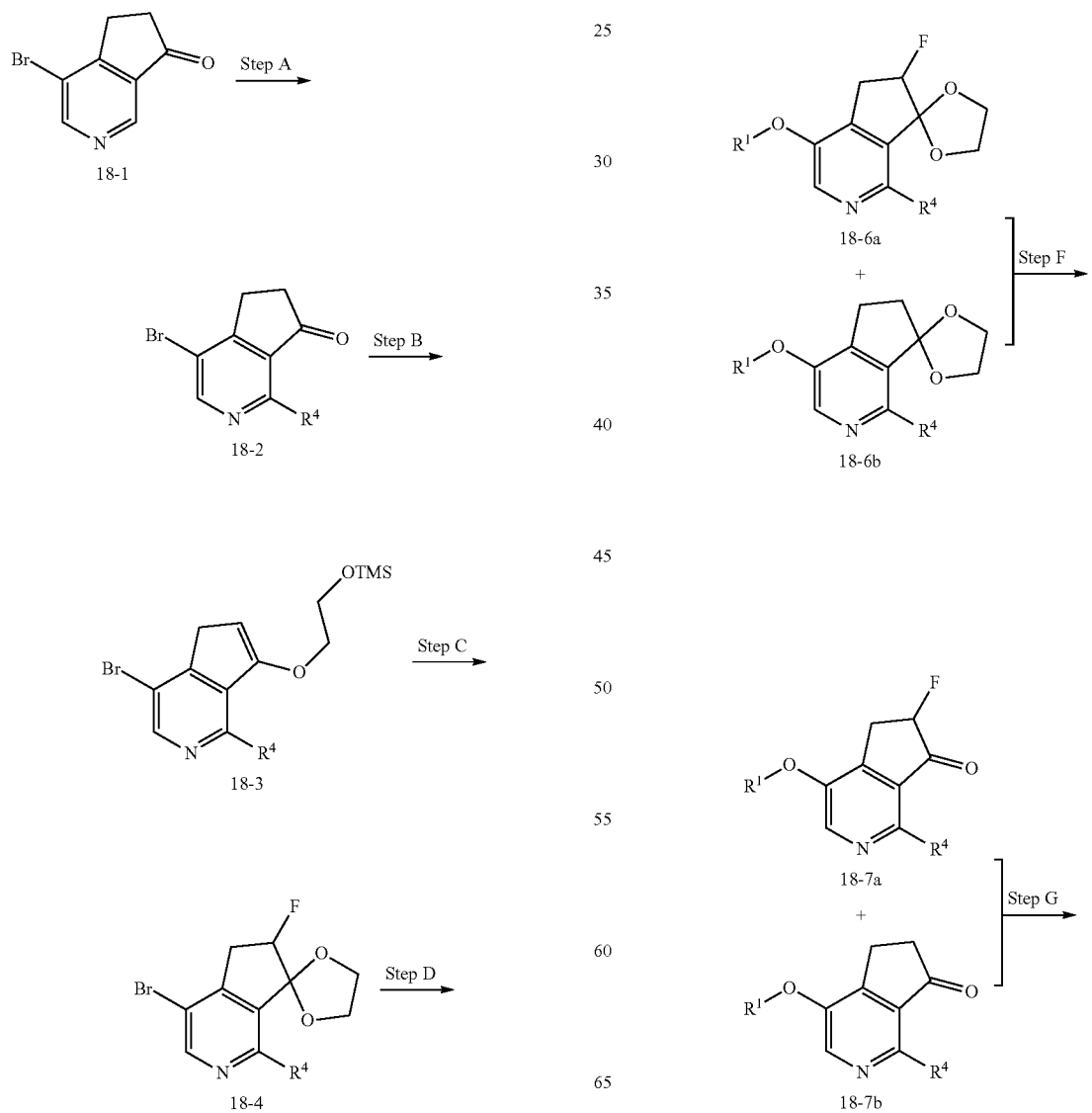

-continued

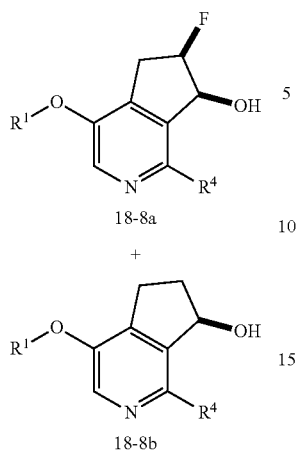

In some embodiments, compounds of Formula 18-8a and 18-8b may be prepared according to Scheme 18. For example, pyridine 18-1 may be converted to alkylaryl derivative 18-2 in Step A, wherein $R^4$ is, for example, trifluoromethyl. The ketone may be converted to protected enol ether 18-3, then fluorinated to give fluoroketal 18-4. Treatment of a compound of Formula 18-4 with a suitable hydroxide source as described in Scheme 6 gives a mixture of phenols 18-5a and 18-5b. The phenols can undergo an SNAr reaction with a suitable halide to give aryl ethers of Formulae 18-6a and 18-6b, which may be deprotected to give the resultant ketones. In some embodiments, a compound of Formula 18-7 is reduced with a hydride source to give a racemic mixture. In other embodiments, an asymmetric reduction is carried out as described in Scheme 2, affording alcohols 18-8a and 18-8b, separable by methods known to one skilled in the art, such as, for example, conventional column chromatography.

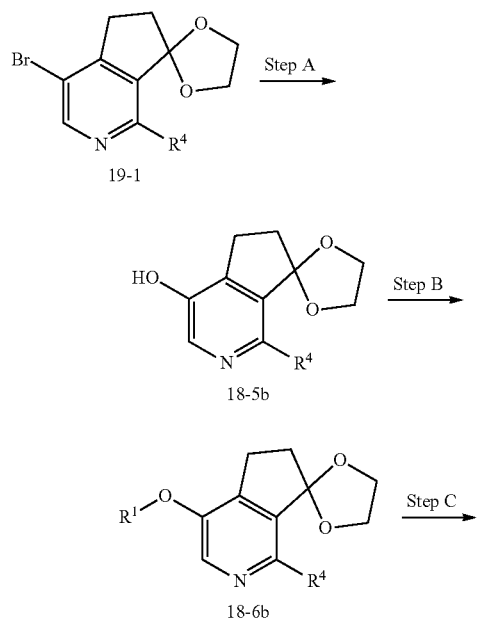

Alternatively, a compound of Formula 18-8a can be prepared according to Scheme 19. For example, conversion of a compound of Formula 19-1 to a phenol is followed by coupling to form an aryl ether and deprotection to give a ketone of Formula 18-7b as described above. Ketone 18-7b is converted to silyl enol ether 19-5 using a suitable silyl protecting group, including, for example, tert-butyldimethylsilyl, triisopropylsilyl or diphenyl-t-butylsilyl. The resulting silyl enol ether is fluorinated to give fluoroketone 18-7a, which undergoes an asymmetric reduction, such as asymmetric transfer hydrogenation as described herein, to give chiral alcohol 18-8a.

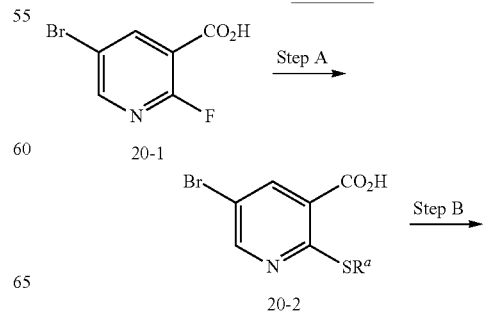

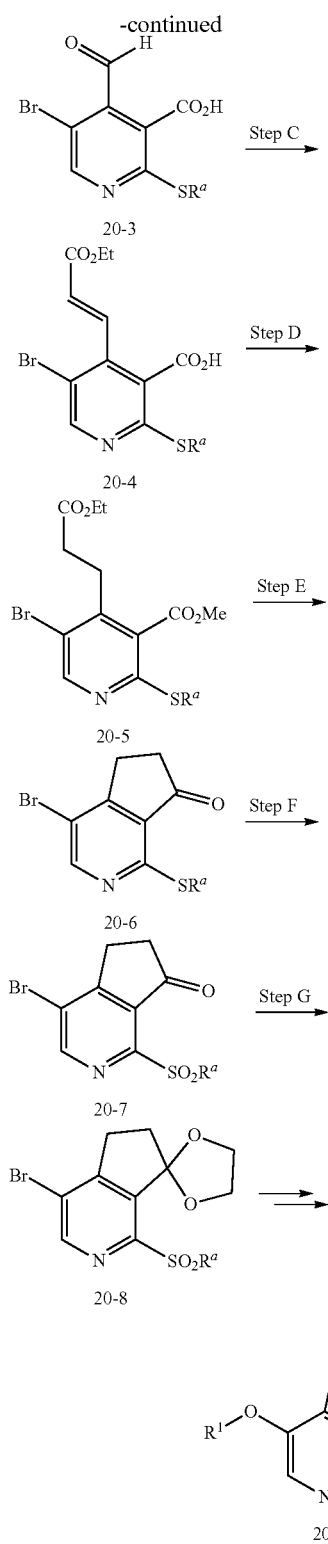

boxylation to give ketone 20-6. Oxidation of a compound of Formula 20-6 to give a compound of Formula 20-7 may be accomplished by a variety of methods known in the art, including, but not limited to, RuCl$_3$ catalyzed oxidation in the presence of NaIO$_4$, oxidation with m-chloroperoxybenzoic acid (mCPBA) and oxidation with Oxone®. Protection of the ketone, for example, as the cyclic ketal (20-8) is followed by the general procedure outlined in Scheme 19 to give a compound of Formula 20-9.

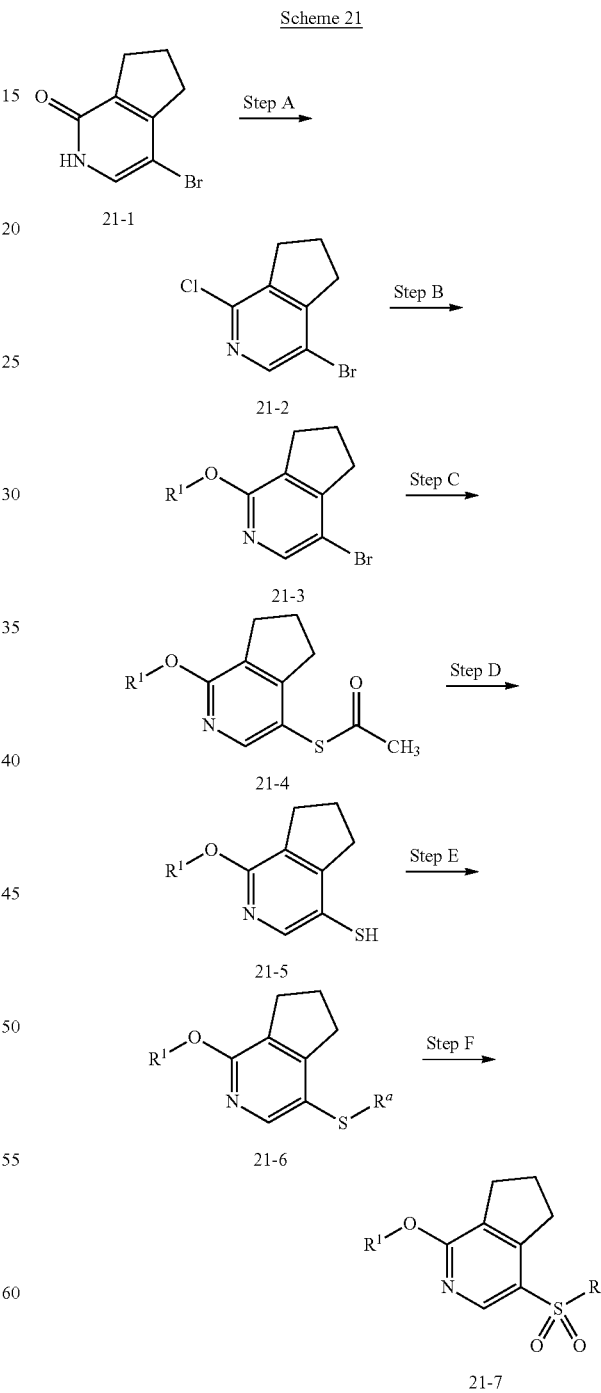

Scheme 21

A compound of Formula 20-9 can be prepared following the general procedure outlined in Scheme 20, wherein the aryl fluoride of a compound of Formula 20-1 is displaced with an alkyl thiol to give 20-2. Formation of benzaldehyde 20-3 may be followed by, for example, a Wittig reaction, to give alkene 20-4, which is reduced to an alkane of Formula 20-5 under suitable conditions. In some embodiments, a Dieckmann condensation reaction is followed by a decar- In some embodiments, a compound of Formula 21-7 may be prepared according to Scheme 21. Formation of a chloropyridine of Formula 21-2 may be followed by an SNAr reaction with a suitable alcohol of formula R¹OH as described above to give a compound of Formula 21-3. Aryl bromide 21-3 may undergo a transition-metal catalyzed coupling reaction with a thioate to give a compound of Formula 21-4, analogously to the procedure detailed in Scheme 14. Hydrolysis, alkylation with a suitable alkyl halide and oxidation affords a compound of Formula 21-7.

Scheme 22

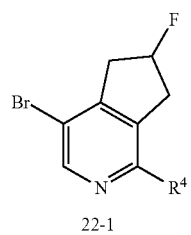

22-1

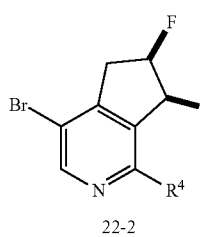

22-2   22-3

In some embodiments, a ketone of Formula 22-1 may be reduced to give 22-2, optionally with high enantioselectivity using asymmetric transfer hydrogenation or enzymatic reduction conditions as described herein. A compound of Formula 22-2 and a suitable coupling partner, including, but not limited to, a boronic acid of formula R¹B(OH)₂, may undergo a coupling reaction to give a compound of Formula 22-3.

Scheme 23

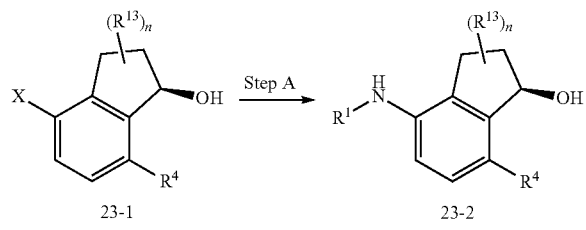

23-1   23-2

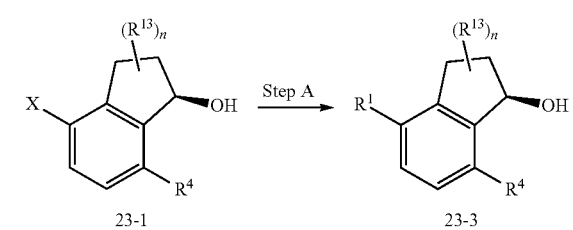

23-1   23-3

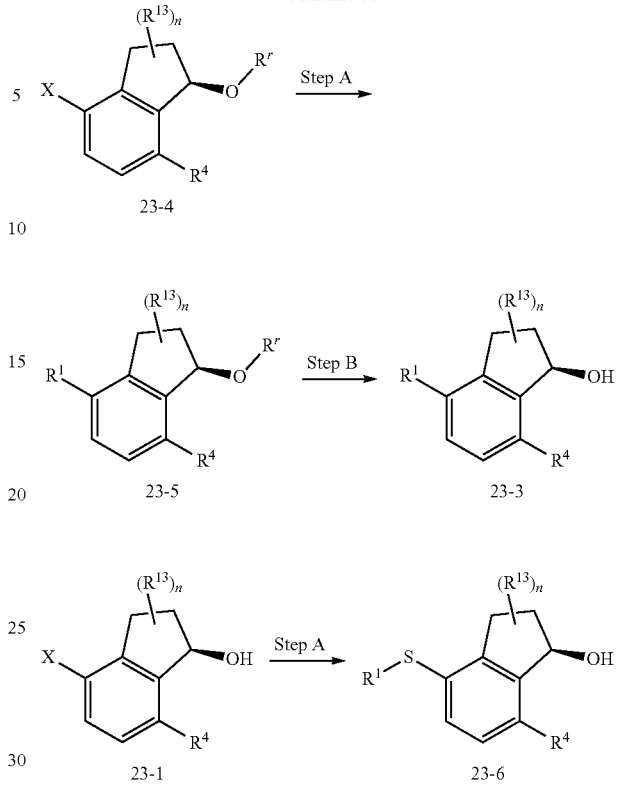

23-4

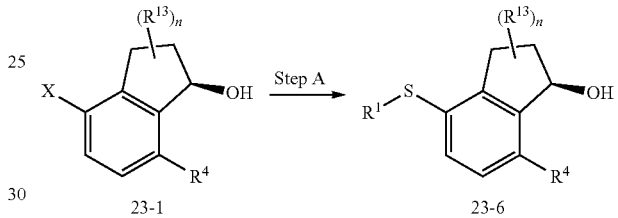

23-5   23-3

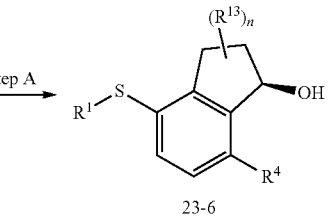

23-1   23-6

In some embodiments, R¹ can be coupled to a compound of Formula 23-1 or 23-4 via a reaction scheme represented generally in Scheme 23. In some embodiments, wherein Z is NR⁸, an aryl halide of Formula 23-1 is coupled to a suitably substituted amine, i.e. NHR¹R⁸, via a Buchwald-Hartwig amination to give a compound of Formula 23-2. In a further embodiment, Step A is a cross coupling reaction, including, but not limited to, a Stille, Negishi or Suzuki reaction, wherein an aryl halide of Formula 23-1 is combined with an appropriate reactant containing R¹ and a suitable catalyst to afford a compound of Formula 23-3. In other embodiments, a compound of Formula 23-4 undergoes an SNAr reaction and a subsequent deprotection to give a compound of Formula 23-3. R¹ in a compound of Formula 23-5 may be, for example, morpholine, wherein a C—N bond connects said morpholine to the aryl ring. In still other embodiments, Z is S, and R¹S— is attached to a compound of Formula 23-1 via an SNAr reaction to give a compound of Formula 23-6.

Scheme 24

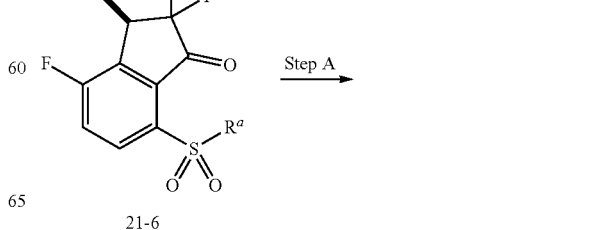

21-6

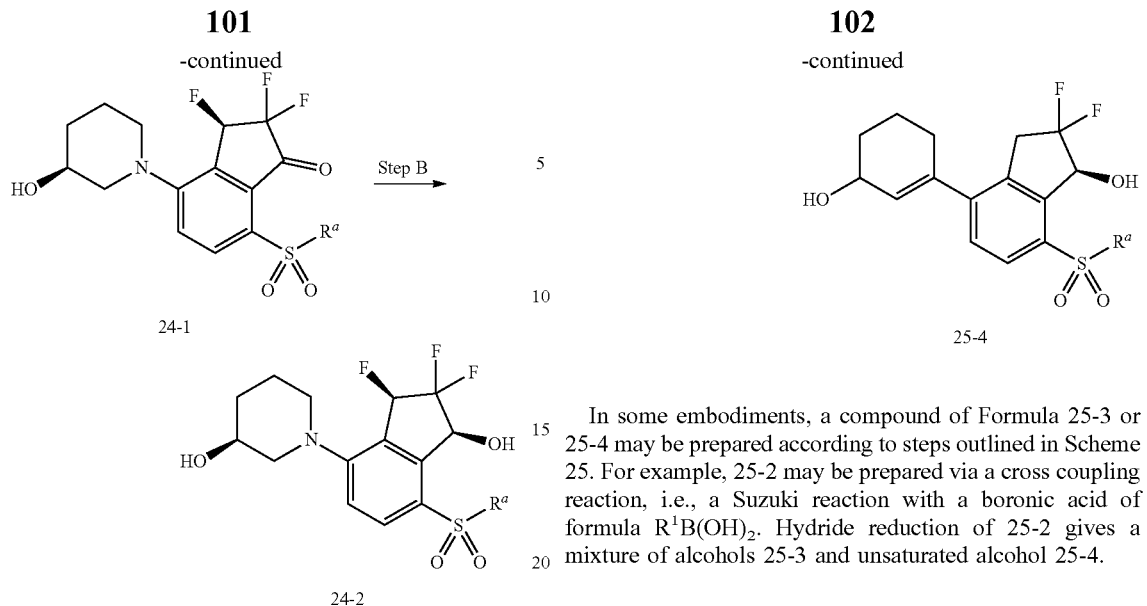

24-1

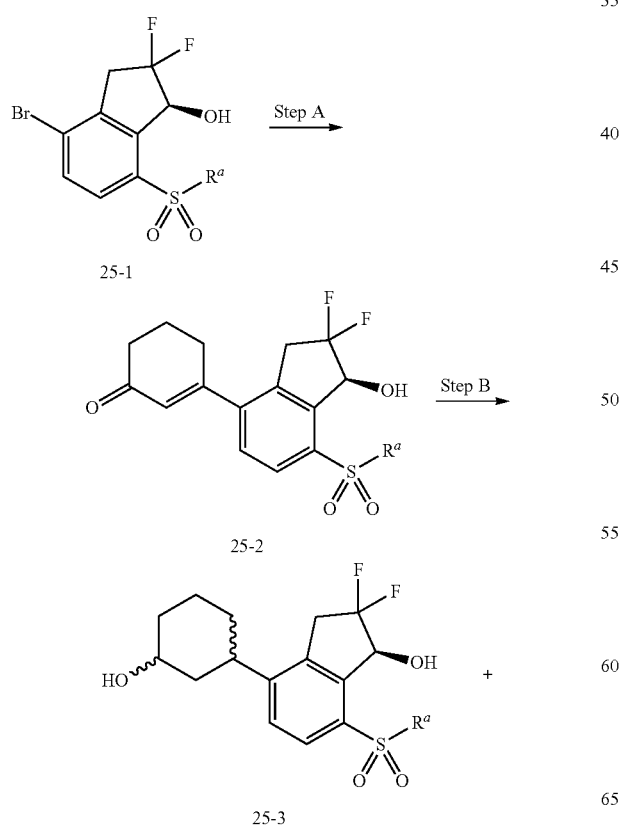

24-2

In some additional embodiments, a compound of Formula 24-2 can be prepared according to steps outlined in Scheme 24. A compound of Formula 12-6 is prepared via an asymmetric variation of the sequence presented in Scheme 12, then reacted with an amine, i.e. (3S)-3-piperidinol hydrochloride, to give a compound of Formula 24-1. Asymmetric reduction as described above gives a compound of Formula 24-2.

Scheme 25

25-4

In some embodiments, a compound of Formula 25-3 or 25-4 may be prepared according to steps outlined in Scheme 25. For example, 25-2 may be prepared via a cross coupling reaction, i.e., a Suzuki reaction with a boronic acid of formula $R^1B(OH)_2$. Hydride reduction of 25-2 gives a mixture of alcohols 25-3 and unsaturated alcohol 25-4.

Scheme 26

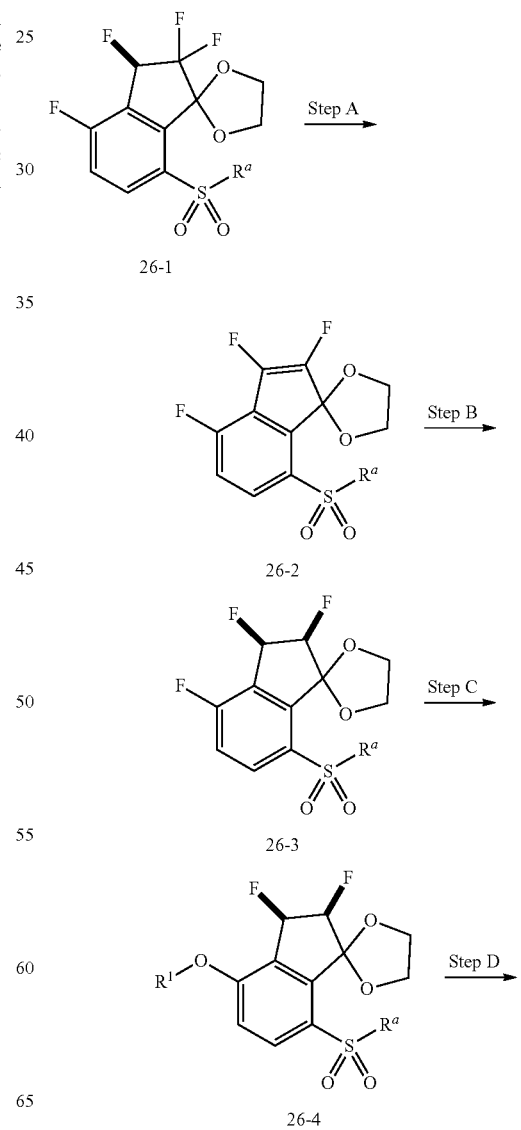

-continued

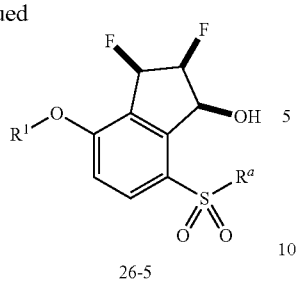

26-5

In some embodiments, a compound of Formula 26-5 can be synthesized according to Scheme 26. For example, treatment of compound 26-1 with base can provides difluoroalkene 26-2. The amount of base may be about 1 equivalent to avoid byproduct formation. The olefin in 26-2 may be hydrogenated to give a compound of Formula 26-3 with cis difluoro configuration. At this stage, an alkoxy group can be introduced by displacement of the aryl fluoride in 26-3 by an alcohol in the presence of a base. Finally, deprotection followed by reduction of the resulting ketone provides a compound of Formula 26-5. Intermediate 26-3 may be separated, for example, by chiral column chromatography, to give both enantiomers, each of which can be functionalized as outlined in Scheme 26 to provide either enantiomer of a compound of Formula 26-5.

Scheme 27

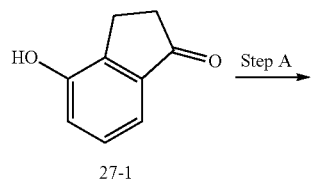

27-1

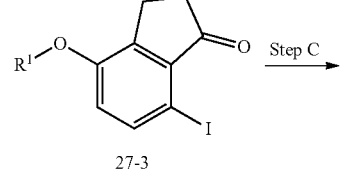

27-2

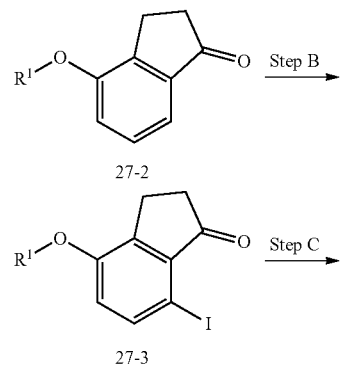

27-3

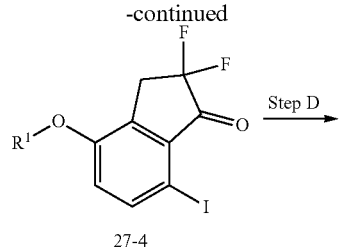

27-4

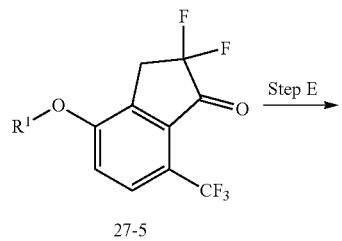

27-5

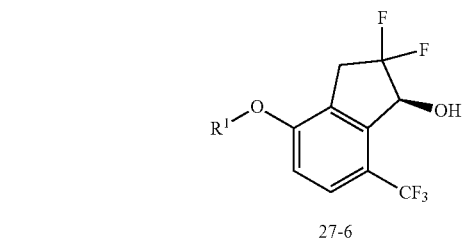

27-6

In some embodiments, a compound of Formula 27-6 may be synthesized according to Scheme 27. For example, alkylation of compound 27-1 provides a compound of Formula 27-2, wherein $R^1$ is alkyl, cycloalkyl, or heterocycloalkyl. A compound of Formula 27-2 can be selectively iodinated to give aryl iodide 27-3. A compound of Formula 27-3 can be difluorinated as previously described. Installation of a $CF_3$ group followed by asymmetric reduction provides a compound of Formula 27-6.

In some other embodiments, a compound of a formula given in Table 2 is synthesized according to one of the general routes outlined in Schemes 1-27, Examples 1-32 or by methods generally known in the art.

TABLE 2

| No. | Structure | Mass Characterization | $^1$H NMR Data |
|---|---|---|---|
| 1 | ![structure] | 393 (M + H) | (400 MHz, CDCl$_3$): δ 7.81 (d, 1H), 7.00-6.89 (m, 3H), 6.73-6.71 (m, 1H), 6.35 (t, 1H), 5.66-5.65 (m, 1H), 3.19-3.13 (m, 2H), 2.96-2.90 (m, 1H), 2.50-2.40 (m, 1H), 2.30-2.24 (m, 1H) |

TABLE 2-continued

| No. | Structure | Mass Characterization | $^1$H NMR Data |
|---|---|---|---|
| 2 | (3,5-difluorophenoxy indanol with SO$_2$CF$_2$H) | 377 (M + H) | (400 MHz, CDCl$_3$): δ 7.81 (d, 1H), 6.96 (d, 1H), 6.73-6.68 (m, 1H), 6.62-6.61 (m, 2H), 6.36 (t, 1H), 5.66-5.65 (m, 1H), 3.22-3.10 (m, 2H), 2.96-2.90 (m, 1H), 2.50-2.40 (m, 1H), 2.29-2.24 (m, 1H) |
| 3 | (5-chloropyridin-3-yloxy indanol with SO$_2$CF$_2$H) | 376, 378 (M + H) | (400 MHz, CDCl$_3$): δ 8.49 (s, 1H), 8.36 (s, 1H), 7.81 (d, 1H), 7.44-7.43 (m, 1H), 6.89 (d, 1H), 6.36 (t, 1H), 5.67-5.66 (m, 1H), 3.23-3.16 (m, 2H), 2.99-2.92 (m, 1H), 2.51-2.42 (m, 1H), 2.32-2.25 (m, 1H) |
| 4 | (5-cyanopyridin-3-yloxy indanol with SO$_2$CF$_2$H) | 367 (M + H) | (400 MHz, CDCl$_3$): δ 8.76 (s, 1H), 8.66 (s, 1H), 7.86 (d, 1H), 7.65-7.64 (m, 1H), 6.93 (d, 1H), 6.38 (t, 1H), 5.71-5.65 (m, 1H), 3.20-3.16 (m, 2H), 2.96-2.90 (m, 1H), 2.50-2.42 (m, 1H), 2.37-2.24 (m, 1H) |
| 5 | (5-fluoropyridin-3-yloxy indanol with SO$_2$CF$_2$H) | 360 (M + H) | (400 MHz, CDCl$_3$): δ 8.41 (s, 1H), 8.32 (s, 1H), 7.82 (d, 1H), 7.22-7.17 (m, 1H), 6.92 (d, 1H), 6.37 (t, 1H), 5.70-5.60 (m, 1H), 3.23-3.18 (m, 2H), 2.99-2.97 (m, 1H), 2.54-2.40 (m, 1H), 2.34-2.22 (m, 1H) |
| 6 | (3-methoxy-5-fluorophenoxy indanol with SO$_2$CF$_2$H) | 433 (M − H + 46) | (400 MHz, CDCl$_3$): δ 7.77 (d, 1H), 6.91 (d, 1H), 6.54-6.50 (m, 1H), 6.42-6.38 (m, 2H), 6.39 (t, 1H), 5.67-5.63 (m, 1H), 3.80 (s, 3H), 3.23-3.15 (m, 2H), 2.99-2.92 (m, 1H), 2.50-2.45 (m, 1H), 2.30-2.23 (m, 1H) |
| 7 | Compound 7a (3-chloro-5-fluorophenoxy methylindanol with SO$_2$CF$_2$H); Compound 7b (diastereomer) | 7a, 429, 431 (M + Na) 7b, 429, 431 (M + Na) | 7a: (400 MHz, CDCl$_3$): δ 7.81 (d, 1H), 7.01-6.98 (m, 1H), 6.91-6.89 (m, 2H), 6.75-6.71 (m, 1H), 6.34 (t, 1H), 5.58-5.53 (m, 1H), 3.48-3.40 (m, 1H), 3.22 (d, 1H), 2.66-2.59 (m, 1), 1.98-1.93 (m, 1H), 1.46 (d, 3H) 7b: (400 MHz, CDCl$_3$): δ 7.81 (d, 1H), 7.01-6.97 (m, 1H), 6.92 (d, 1H), 6.89-6.88 (m, 1H), 6.73-6.69 (m, 1H), 6.38 (t, 1H), 5.70-5.67 (m, 1H), 3.71-3.64 (m, 1H), 3.25 (d, 1H), 2.47-2.41 (m, 1H), 2.14-2.06 (m, 1H), 1.36 (d, 3H) |

TABLE 2-continued

| No. | Structure | Mass Characterization | $^1$H NMR Data |
|---|---|---|---|
| 8 | 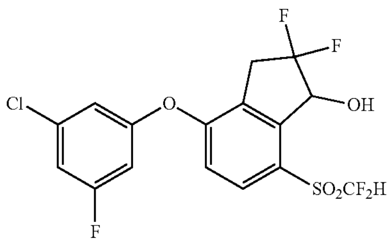 | 429, 431 (M + H) | (400 MHz, CDCl$_3$): δ 7.90 (d, 1H), 7.06-7.03 (m, 1H), 6.98 (d, 1H), 6.94-6.92 (m, 1H), 6.78-6.74 (m, 1H), 6.42 (t, 1H), 5.50 (d, 1H), 3.61-3.43 (m, 2H), 3.24 (s, 1H) |
| 9 | 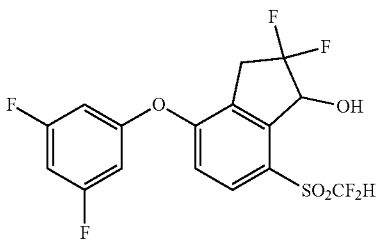 | 413 (M + H) | (400 MHz, CDCl$_3$): δ 7.90 (d, 1H), 7.01 (d, 1H), 6.80-6.73 (m, 1H), 6.70-6.63 (m, 2H), 6.43 (t, 1H), 5.50 (m, 1H), 3.60-3.43 (m, 2H), 3.30 (d, 1H) |
| 10 | 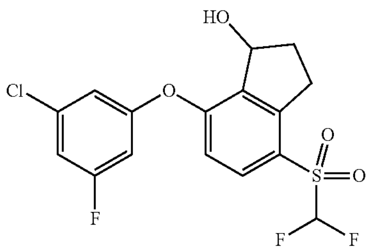 [SMILES: O=S(=O)(c1ccc(Oc2cc(F)cc(Cl)c2)c2c1CCC2O)C(F)F] | 375, 377 (M − OH) | (400 MHz, CDCl$_3$): δ 7.85 (d, 1H), 7.04-7.00 (m, 1H), 6.97-6.95 (m, 1H), 6.84-6.77 (m, 2H), 6.18 (t, 1H), 5.58-5.53 (m, 1H), 3.59-3.50 (m, 1H), 3.34-3.26 (m, 1H), 2.60-2.50 (m, 1H), 2.31 (d, 1H), 2.21-2.13 (m, 1H) |
| 11 | 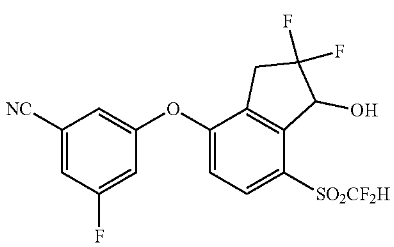 | 437 (M + NH$_4$) | (400 MHz, CDCl$_3$): δ 7.94 (d, 1H), 7.33-7.29 (m, 1H), 7.23-7.21 (m, 1H), 7.13-7.09 (m, 1H), 7.00 (d, 1H), 6.43 (t, 1H), 5.51 (d, 1H), 3.60-3.43 (m, 2H), 3.30 (br s, 1H) |
| 12 | 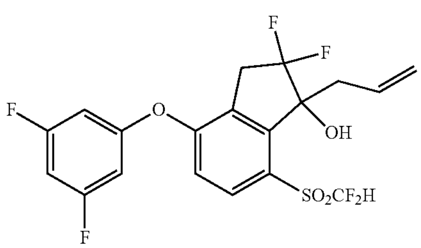 | 451 (M − H) | (400 MHz, CDCl$_3$): δ 8.01 (d, 1H), 6.97 (d, 1H), 6.82-6.55 (m, 4H), 5.76-5.64 (m, 1H), 5.35-5.26 (m, 2H), 3.54-3.44 (m, 2H), 3.31-3.18 (m, 1H), 3.06-2.96 (m, 2H) |
| 13 | 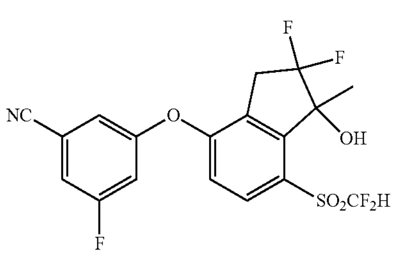 | 451 (M + NH$_4$) | (400 MHz, CDCl$_3$): δ 8.0 (d, 1H), 7.33-7.30 (m, 1H), 7.23-7.21 (m, 1H), 7.13-7.09 (m, 1H), 6.92 (d, 1H), 6.62 (m, 1H), 3.58-3.49 (m, 2H), 3.34-3.20 (m, 1H), 1.84-1.82 (m, 3H) |

TABLE 2-continued

| No. | Structure | Mass Characterization | $^1$H NMR Data |
|---|---|---|---|
| 14 | 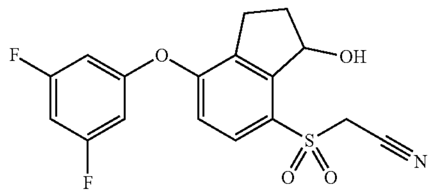 [SMILES: N#CCS(=O)(=O)c1ccc(Oc2cc(F)cc(F)c2)c2c1C(O)CC2] | 364 (M − H) | (400 MHz, CDCl$_3$): δ 7.9 (d, 1H), 6.97 (d, 1H), 6.73-6.67 (m 1H), 6.64-6.58 (m, 1H), 5.83-5.79 (m, 1H), 6.57-6.53 (m, 1H), 4.22 (d, 1H), 3.20-3.10 (m, 1H), 2.95-2.85 (m, 2H), 2.60-2.50 (m, 1H), 2.25-2.16 (m, 1H) |
| 15 | 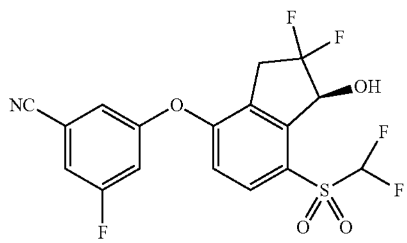 [SMILES: N#Cc1cc(F)cc(Oc2ccc(S(=O)(=O)C(F)F)c3c2CC(F)(F)[C@H]3O)c1] | 420 (M + H) | (400 MHz, CDCl$_3$): δ 7.94 (d, 1H), 7.33-6.98 (m, 4H), 6.44 (t, 1H), 5.51 (d, 1H), 3.61-3.45 (m, 2H) |
| 16 | 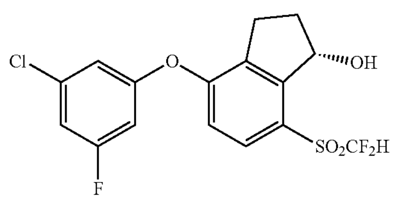 | 437/439 (M − H + 46) | (400 MHz, CDCl$_3$): δ 7.81 (d, 1H), 7.00-6.98 (m, 1H), 6.94 (d, 1H), 6.89-6.88 (m, 1H), 6.74-6.71 (m, 1H), 6.35 (t, 1H), 5.67-5.65 (m, 1H), 3.21-3.13 (m, 2H), 2.96-2.89 (m, 1H), 2.50-2.41 (m, 1H), 2.30-2.23 (m, 1H) |
| 17 | 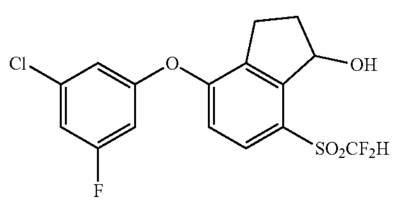 | 393 (M + H) | |
| 18 | 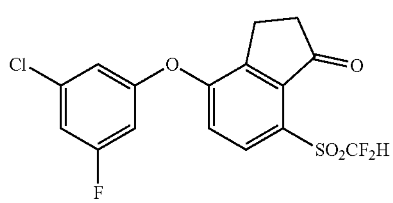 | 391, 393 (M + H) | (400 MHz, CDCl$_3$): δ 8.15 (d, 1H), 7.14 (d, 1H), 7.12 (t, 1H), 7.07-7.04 (m, 1H), 6.96-6.93 (m, 1H), 6.80-6.76 (m, 1H), 3.23-3.20 (m, 2H), 2.90-2.87 (m, 2H) |
| 19 | 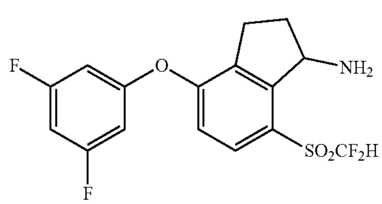 | 376 (M + H) | (400 MHz, CDCl$_3$): δ 7.81 (d, 1H), 6.92 (d, 1H), 6.72-6.67 (m, 1H), 6.62 (t, 1H), 6.63-6.59 (m, 2H), 4.96-4.94 (H, 1H), 3.18-3.10 (m, 1H), 2.99-2.92 (m, 1H), 2.51-2.41 (m, 1H), 2.30-2.00 (m, 3H) |
| 20 | 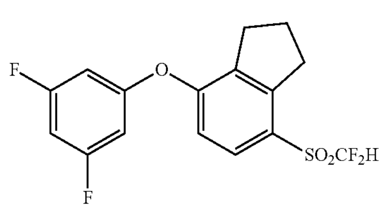 | 361 (M + H) | (400 MHz, CDCl$_3$): δ 7.76 (d, 1H), 6.87 (d, 1H), 6.69-6.63 (m, 1H), 6.60-6.55 (m, 2H), 6.18 (t, 1H), 3.37 (t, 2H), 2.93 (t, 2H), 2.20-2.17 (m, 2H) |

TABLE 2-continued

| No. | Structure | Mass Characterization | ¹H NMR Data |
|---|---|---|---|
| 21 | 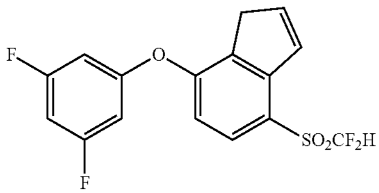 | 359 (M + H) | (400 MHz, CDCl₃): δ 7.88 (d, 1H), 7.47-7.45 (m, 1H), 6.93-6.90 (m, 2H), 6.71-6.60 (m, 3H), 6.22 (t, 1H), 3.49-3.48 (m, 1H) |
| 22 | 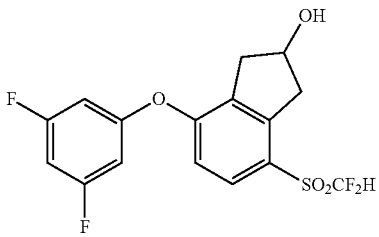 | 421 (M − H + 46) | (400 MHz, CDCl₃): δ 7.79 (d, 1H), 6.90 (d, 1H), 6.72-6.66 (m, 1H), 6.64-6.57 (m, 2H), 6.19 (t, 1H), 4.85-4.81 (m, 1H), 3.60-3.44 (m, 3H), 3.21-2.99 (m, 2H) |
| 23 | 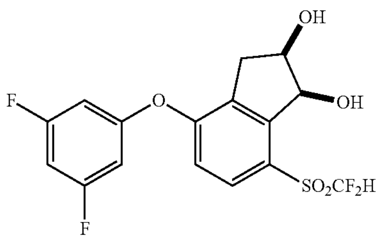 | 437 (M − H + 46) | (400 MHz, CDCl₃): δ 7.83 (d, 1H), 6.98 (d, 1H), 6.74-6.69 (m, 1H), 6.64-6.62 (m, 2H), 6.36 (t, 1H), 5.37 (brs, 1H), 4.65-4.63 (m, 1H), 3.45-3.39 (m, 2H), 2.92-2.88 (m, 1H) |
| 24 | 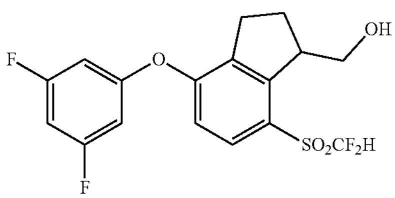 | 391 (M + H) | (400 MHz, CDCl₃): δ 7.77 (d, 1H), 6.90 (d, 1H), 6.71-6.65 (m, 1H), 6.62-6.36 (m, 2H), 6.23 (t, 1H), 3.94-3.71 (m, 3H), 2.97-2.89 (m, 2H), 2.84 (s, 1H), 2.40-2.22 (m, 2H) |
| 25 | 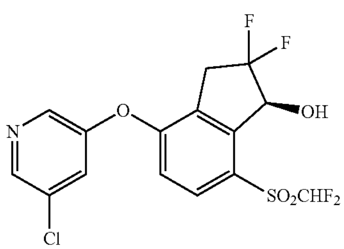 | 410, 412 (M + H) | (400 MHz, CDCl₃) δ 8.55-8.54 (m, 1H), 8.40-8.39 (m, 1H), 7.91 (d, 1H), 7.52-7.49 (m, 1H), 6.93 (d, 1H), 6.44 (t, 1H), 5.53-5.49 (m, 1H), 3.64-3.48 (m, 2H), 3.35 (d, 1H) |
| 26 | 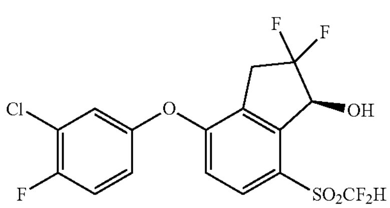 | 473, 475 (M − H + 46) | (400 MHz, CDCl₃): δ 7.86 (d, 1H), 7.26-7.22 (m, 2H), 7.05-6.95 (m, 1H), 6.86 (d, 1H), 6.41 (t, 1H), 5.51-5.47 (m, 1H), 3.58-3.51 (m, 2H), 3.26 (brd s, 1H) |
| 27 | 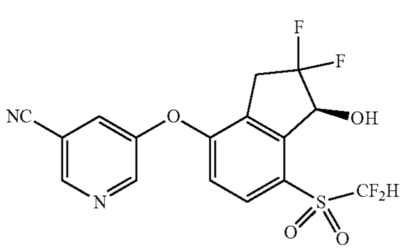 [SMILES: N#Cc1cncc(Oc2ccc(S(=O)(=O)C(F)F)c3c2CC(F)(F)[C@H]3O)c1] | 403 (M + H) | (400 MHz, CDCl₃): δ 8.82 (s, 1H), 8.71 (s, 1H), 7.95 (d, 1H), 7.73-7.71 (m, 1H), 6.95 (d, 1H), 6.44 (t, 1H), 5.55-5.50 (m, 1H), 3.60-3.51 (m, 2H), 3.29 (d, 1H) |

TABLE 2-continued

| No. | Structure | Mass Characterization | ¹H NMR Data |
|---|---|---|---|
| 28 | 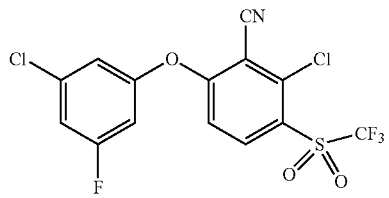 [SMILES: N#Cc1c(Oc2cc(F)cc(Cl)c2)ccc(S(=O)(=O)C(F)(F)F)c1Cl] | 412, 414 (M − H) | (400 MHz, CDCl$_3$): δ 8.27 (d, 1H), 7.17-7.14 (m, 1H), 7.03-7.02 (m, 1H), 6.97 (d, 1H), 6.88-6.85 (m, 1H) |
| 29 | 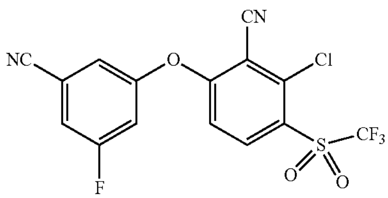 [SMILES: N#Cc1cc(F)cc(Oc2ccc(S(=O)(=O)C(F)(F)F)c(Cl)c2C#N)c1] | 403/405 (M − H) | (400 MHz, CDCl$_3$): δ 8.31 (d, 1H), 7.44-7.41 (m, 1H), 7.32-7.31 (m, 1H), 7.24-7.20 (m, 1H), 6.97 (d, 1H) |
| 30 | 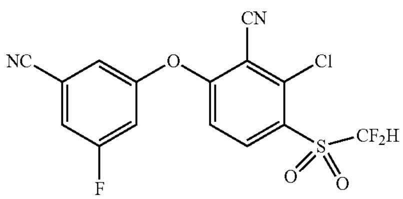 [SMILES: N#Cc1cc(F)cc(Oc2ccc(S(=O)(=O)C(F)F)c(Cl)c2C#N)c1] | 385, 387 (M − H) | (400 MHz, CDCl$_3$): δ 8.28 (d, 1H), 7.42-7.40 (m, 1H), 7.31-7.26 (m, 1H), 7.22-7.19 (m, 1H), 6.97 (d, 1H), 6.45 (t, 1H) |
| 31 | 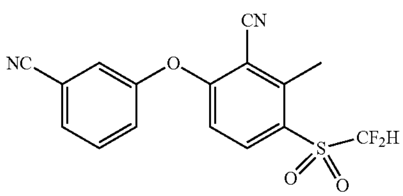 [SMILES: Cc1c(S(=O)(=O)C(F)F)ccc(Oc2cccc(C#N)c2)c1C#N] | [M − H] 374 | (400 MHz, CDCl$_3$): δ 8.14 (d, 1H), 7.67-7.61 (m, 2H), 7.48-7.47 (m, 1H), 6.80 (d, 1H), 6.24 (t, 1H), 2.98 (s, 3H) |
| 32 | 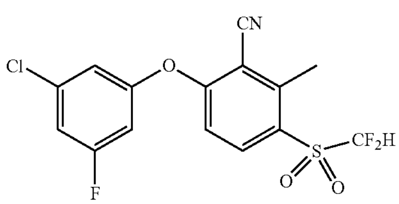 [SMILES: Cc1c(S(=O)(=O)C(F)F)ccc(Oc2cc(F)cc(Cl)c2)c1C#N] | [M − 1] 374 | (400 MHz, CDCl$_3$): δ 8.15 (d, 1H), 7.12-7.08 (m, 1H), 7.01-6.99 (m, 1H), 6.89 (d, 1H), 6.85-6.81 (m, 1H), 6.24 (t, 1H), 2.97 (s, 3H) |
| 33 | 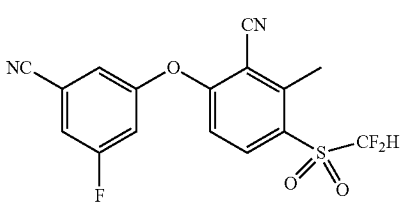 [SMILES: Cc1c(S(=O)(=O)C(F)F)ccc(Oc2cc(F)cc(C#N)c2)c1C#N] | [M − H] 365 | (400 MHz, CDCl$_3$): δ 8.20 (d, 1H), 7.39-7.35 (m, 1H), 7.29-7.27 (m, 1H), 7.20-7.16 (m, 1H), 6.90 (d, 1H), 6.26 (t, 1H), 2.90 (s, 3H) |
| 34 | 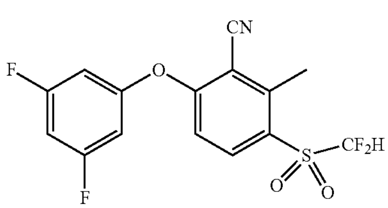 [SMILES: Cc1c(S(=O)(=O)C(F)F)ccc(Oc2cc(F)cc(F)c2)c1C#N] | [M − H] 358 | (400 MHz, CDCl$_3$): δ 8.15 (d, 1H), 6.91 (d, 1H), 6.85-6.79 (m, 1H), 6.77-6.70 (m, 2H), 6.24 (t, 1H), 2.97 (s, 3H) |

TABLE 2-continued

| No. | Structure | Mass Characterization | ¹H NMR Data |
|---|---|---|---|
| 35 | 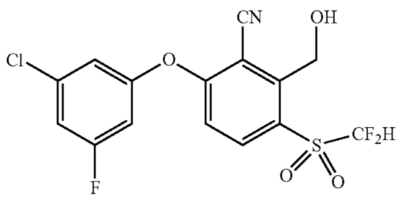 [SMILES: N#Cc1c(Oc2cc(F)cc(Cl)c2)ccc(S(=O)(=O)C(F)F)c1CO] | [M − H] 391 | (400 MHz, CDCl$_3$): δ 8.07 (d, 1H), 7.13-7.05 (m, 1H), 7.04-6.95 (m, 2H), 6.89-6.85 (m, 1H), 6.26 (t, 1H), 5.60 (s, 2H) |
| 36 | 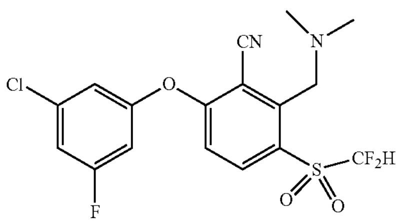 [SMILES: CN(C)Cc1c(S(=O)(=O)C(F)F)ccc(Oc2cc(F)cc(Cl)c2)c1C#N] | [M + H] 419 | (400 MHz, CDCl$_3$): δ 8.29 (d, 1H), 7.13-7.09 (m, 1H), 7.02 (t, 1H), 7.01-6.99 (m, 1H), 6.96 (d, 1H), 6.86-6.82 (m, 1H), 4.11 (s, 2H), 2.34 (s, 6H) |
| 37 | 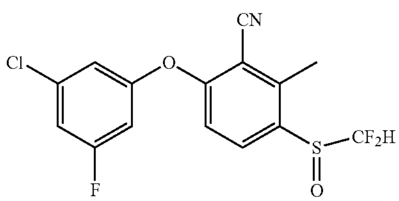 [SMILES: Cc1c(S(=O)C(F)F)ccc(Oc2cc(F)cc(Cl)c2)c1C#N] | [M − H] 358 | (400 MHz, CDCl$_3$): δ 8.07 (d, 1H), 7.07-7.03 (m, 1H), 7.01 (d, 1H), 6.96-6.94 (m, 1H), 6.81-6.77 (m, 1H), 6.15 (t, 1H), 2.68 (s, 3H) |
| 38 | 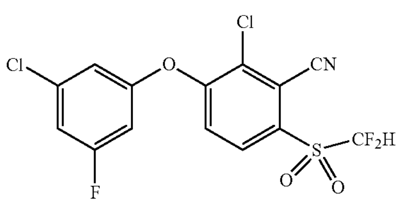 [SMILES: N#Cc1c(S(=O)(=O)C(F)F)ccc(Oc2cc(F)cc(Cl)c2)c1Cl] | [M − H + 18] 413 | (400 MHz, CDCl$_3$): δ 8.03 (d, 1H), 7.24 (d, 1H), 7.12-7.08 (m, 1H), 6.96-6.94 (m, 1H), 6.81-6.77 (m, 1H), 6.41 (t, 1H) |
| 39 | 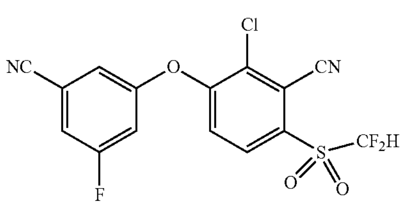 [SMILES: N#Cc1cc(F)cc(Oc2ccc(S(=O)(=O)C(F)F)c(C#N)c2Cl)c1] | [M − H + 18] 404 | (400 MHz, CDCl$_3$): δ 8.09 (d, 1H), 7.37-7.34 (m, 1H), 7.29 (d, 1H), 7.22-7.21 (m, 1H), 7.14-7.10 (m, 1H), 6.43 (t, 1H) |
| 40 | 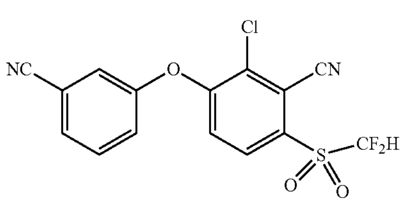 [SMILES: N#Cc1cccc(Oc2ccc(S(=O)(=O)C(F)F)c(C#N)c2Cl)c1] | [M − H + 18] 386 | (400 MHz, CDCl$_3$): δ 8.03 (d, 1H), 7.68-7.62 (m, 2H), 7.45-7.43 (m, 1H), 7.40-7.36 (m, 1H), 7.17 (d, 1H), 6.41 (t, 1H) |
| 41 | 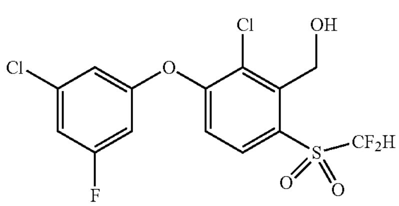 [SMILES: O=S(=O)(c1ccc(Oc2cc(F)cc(Cl)c2)c(Cl)c1CO)C(F)F] | [M − H + 46] 445 | (400 MHz, CDCl$_3$): δ 8.01 (d, 1H), 7.06 (d, 1H), 7.04-7.01 (m, 1H), 6.91-6.88 (m, 1H), 6.76-6.71 (m, 1H), 6.47 (t, 1H), 5.21 (d, 2H), 2.69 (t, 1H) |

TABLE 2-continued

| No. | Structure | Mass Characterization | ¹H NMR Data |
|---|---|---|---|
| 42 | 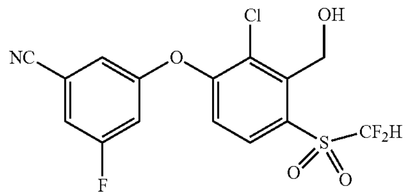 [SMILES: N#Cc1cc(F)cc(Oc2ccc(S(=O)(=O)C(F)F)c(CO)c2Cl)c1] | [M − H + 46] 436 | (400 MHz, CDCl$_3$): δ 8.06 (d, 1H), 7.28-7.25 (m, 1H), 7.15-7.12 (m, 2H), 7.07-7.03 (m, 1H), 6.50 (t, 1H), 5.21 (d, 2H), 2.70 (t, 1H) |
| 43 | 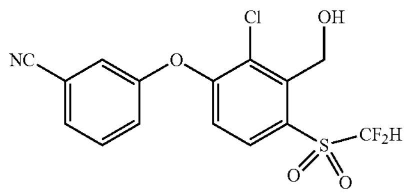 [SMILES: N#Cc1cccc(Oc2ccc(S(=O)(=O)C(F)F)c(CO)c2Cl)c1] | [M − H + 46] 418 | (400 MHz, CDCl$_3$): δ 8.00 (d, 1H), 7.59-7.56 (m, 1H), 7.38-7.37 (m, 1H), 7.36-7.31 (m, 1H), 7.00 (d, 1H), 6.48 (t, 1H), 5.22 (d, 2H), 2.71 (t, 1H) |
| 44 | 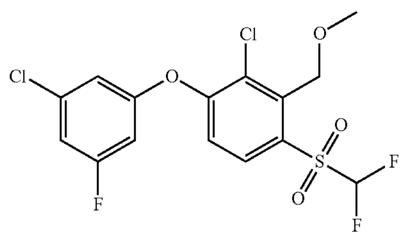 [SMILES: COCc1c(S(=O)(=O)C(F)F)ccc(Oc2cc(F)cc(Cl)c2)c1Cl] | [M − H + 46] 445 | (400 MHz, CDCl$_3$): δ 8.01 (d, 1H), 7.06 (d, 1H), 7.04-7.01 (m, 1H), 6.91-6.88 (m, 1H), 6.76-6.71 (m, 1H), 6.47 (t, 1H), 5.21 (d, 2H), 2.69 (t, 1H) |
| 45 | 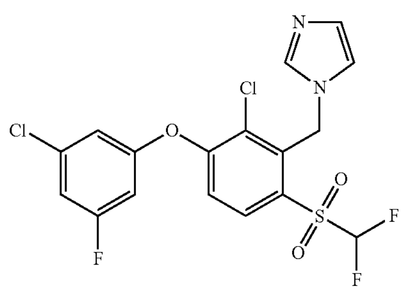 [SMILES: O=S(=O)(c1ccc(Oc2cc(F)cc(Cl)c2)c(Cl)c1Cn1ccnc1)C(F)F] | [M + H] 451 | (400 MHz, CDCl$_3$): δ 8.06 (d, 1H), 7.67 (s, 1H), 7.12-7.03 (m, 4H), 6.93 (s, 1H), 6.77 (br d, 1H), 5.92 (t, 1H), 5.76 (d, 2H) |
| 46 | 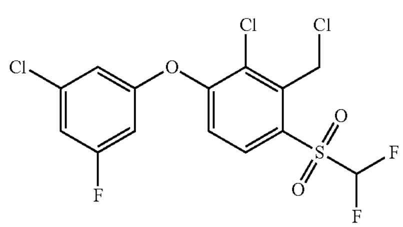 [SMILES: O=S(=O)(c1ccc(Oc2cc(F)cc(Cl)c2)c(Cl)c1CCl)C(F)F] | [M − H + 46] 463 | (400 MHz, CDCl$_3$): δ 8.03 (d, 1H), 7.07 (d, 1H), 7.06-7.03 (m, 1H), 6.93-6.91 (m, 1H), 6.78-6.74 (m, 1H), 6.42 (t, 1H), 5.26 (d, 2H) |
| 47 | 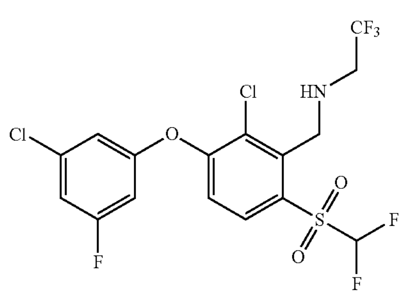 [SMILES: O=S(=O)(c1ccc(Oc2cc(F)cc(Cl)c2)c(Cl)c1CNCC(F)(F)F)C(F)F] | [M + H] 482 | (400 MHz, CDCl$_3$): δ 8.04 (d, 1H), 7.05-7.01 (m, 2H), 6.90-6.89 (m, 1H), 6.75-6.71 (m, 1H), 6.67 (s, 1H), 6.43 (t, 1H), 4.50 (br s, 2H) 3.40-3.30 (m, 2H) |

TABLE 2-continued

| No. | Structure | Mass Characterization | ¹H NMR Data |
|---|---|---|---|
| 48 | 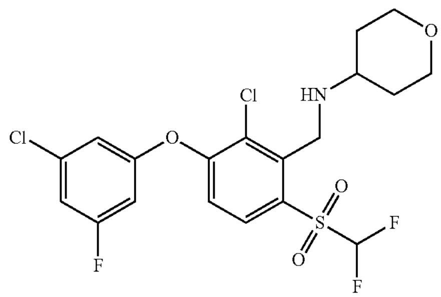 [SMILES: O=S(=O)(c1ccc(Oc2cc(F)cc(Cl)c2)c(Cl)c1CNC1CCOCC1)C(F)F] | [M + H] 484 | (400 MHz, CDCl$_3$): δ 8.04 (d, 1H), 7.07 (t, 2H), 7.03-6.99 (m, 2H), 6.89-6.87 (m, 1H), 6.74-6.70 (m, 1H), 4.40 (s, 2H), 4.05-3.98 (m, 2H) 3.48-3.40 (m, 2H), 2.89-2.81 (m, 1H), 1.97-1.90 (m, 2H), 1.52-1.41 (m, 3H) |
| 49 | 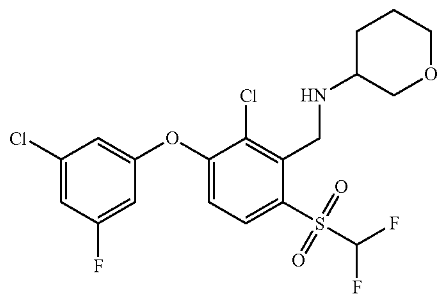 [SMILES: O=S(=O)(c1ccc(Oc2cc(F)cc(Cl)c2)c(Cl)c1CNC1CCCOC1)C(F)F] | [M + H] 484 | (400 MHz, CDCl$_3$): δ 8.04 (d, 1H), 7.09 (t, 2H), 7.03-7.00 (m, 2H), 6.89-6.88 (m, 1H), 6.74-6.70 (m, 1H), 4.40 (s, 2H), 3.94-3.89 (m, 1H) 3.78-3.71 (m, 1H), 3.56-3.49 (m, 1H), 3.39-3.33 (m, 1H), 2.86-2.79 (m, 1H), 2.06-1.97 (m, 1H), 1.80-1.72 (m, 1H), 1.66-1.46 (m, 3H) |
| 50 | 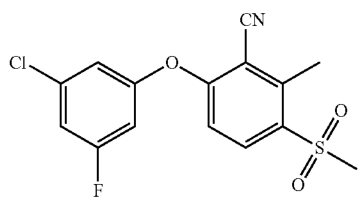 [SMILES: Cc1c(S(C)(=O)=O)ccc(Oc2cc(F)cc(Cl)c2)c1C#N] | [M − H] 338 | (400 MHz, CDCl$_3$): δ 8.20 (d, 1H), 7.08-7.04 (m, 1H), 6.96-6.94 (m, 1H), 6.87 (d, 1H), 6.81-6.77 (m, 1H), 3.12 (s, 3H), 2.97 (s, 3H) |
| 51 | 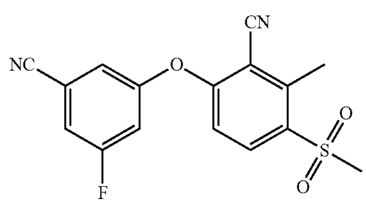 [SMILES: Cc1c(S(C)(=O)=O)ccc(Oc2cc(F)cc(C#N)c2)c1C#N] | [M − H] 329 | (400 MHz, CDCl$_3$): δ 8.25 (d, 1H), 7.33-7.30 (m, 1H), 7.22-7.20 (m, 1H), 7.16-7.12 (m, 1H), 6.93-6.89 (m, 1H), 3.13 (s, 3H), 2.98 (s, 3H) |
| 52 | 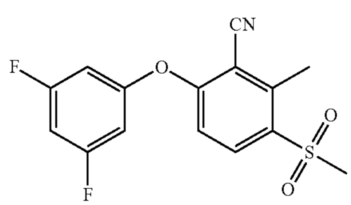 [SMILES: Cc1c(S(C)(=O)=O)ccc(Oc2cc(F)cc(F)c2)c1C#N] | [M − H] 322 | (400 MHz, CDCl$_3$): δ 8.20 (d, 1H), 6.91-6.88 (m, 1H), 6.81-6.75 (m, 1H), 6.72-6.65 (m, 2H), 3.12 (s, 3H), 2.97 (s, 3H) |
| 53 | 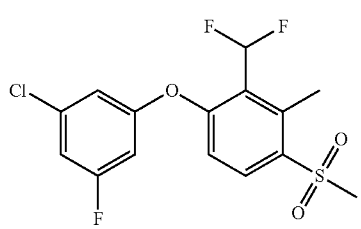 [SMILES: Cc1c(S(C)(=O)=O)ccc(Oc2cc(F)cc(Cl)c2)c1C(F)F] | [M − H] 363 | (400 MHz, CDCl$_3$): δ 8.18 (br d, 1H), 7.26 (t, 1H), 7.01-6.97 (m, 1H), 6.89-6.84 (m, 2H), 6.71-6.67 (m, 1H), 3.15 (s, 3H), 2.95 (t, 3H) |

TABLE 2-continued

| No. | Structure | Mass Characterization | ¹H NMR Data |
|---|---|---|---|
| 54 | 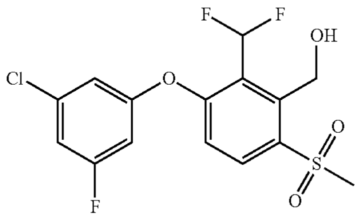 [SMILES: CS(=O)(=O)c1ccc(Oc2cc(F)cc(Cl)c2)c(C(F)F)c1CO] | [M − H + 46] 425 | (400 MHz, CDCl$_3$): δ 8.21 (d, 1H), 7.31 (t, 1H), 7.03-6.98 (m, 2H), 6.89-6.87 (m, 1H), 6.74-6.70 (m, 1H), 5.27 (d, 2H), 3.30 (s, 3H), 2.96-2.91 (m, 1H) |
| 55 | 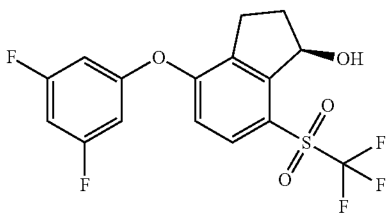 [SMILES: O=S(=O)(c1ccc(Oc2cc(F)cc(F)c2)c2c1[C@H](O)CC2)C(F)(F)F] | [M − H] 393 | (400 MHz, CDCl$_3$): δ 7.84 (d, 1H), 6.95 (d, 1H), 6.76-6.70 (m, 1H), 6.66-6.60 (m, 2H), 5.65-5.60 (m, 1H), 3.25-3.15 (m, 2H), 3.00-2.92 (m, 1H) 2.47-2.28 (m, 2H) |
| 56 | 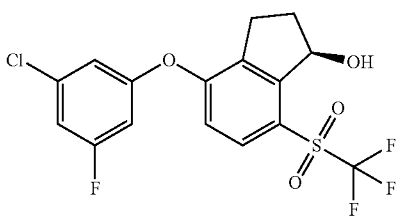 [SMILES: O=S(=O)(c1ccc(Oc2cc(F)cc(Cl)c2)c2c1[C@H](O)CC2)C(F)(F)F] | [M − H + 46] 455 | (400 MHz, CDCl$_3$): δ 7.84 (d, 1H), 7.03-6.99 (m, 1H), 6.93 (d, 1H), 6.92-6.90 (m, 1H), 6.75-6.71 (m, 1H), 5.65-5.61 (m, 1H), 3.24-3.15 (m, 2H), 3.01-2.92 (m, 1H) 2.47-2.28 (m, 2H) |
| 57 | 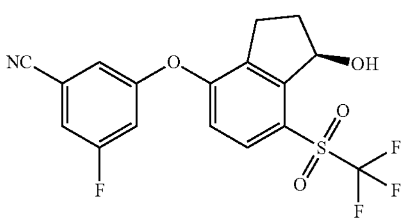 [SMILES: N#Cc1cc(F)cc(Oc2ccc(S(=O)(=O)C(F)(F)F)c3c2CC[C@H]3O)c1] | [M − H + 46] 446 | (400 MHz, CDCl$_3$): δ 7.88 (d, 1H), 7.28-7.25 (m, 2H), 7.19-7.17 (m, 1H), 7.09-7.05 (m, 1H), 6.96 (d, 1H), 5.66-5.62 (m, 1H), 3.23-3.13 (m, 2H), 2.99-2.90 (m, 1H) 2.47-2.29 (m, 2H) |
| 58 | 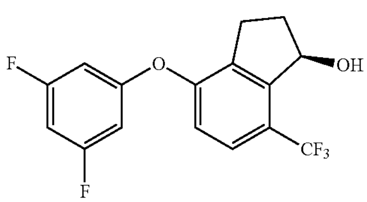 | [M − H] 329 | (400 MHz, CDCl$_3$): δ 7.53-7.49 (m, 1H), 6.98-6.95 (m, 1H), 6.62-6.55 (m, 1H), 6.53-6.46 (m, 2H), 5.53 (br s, 1H), 3.11-3.01 (m, 1H), 2.84-2.76 (m, 1H), 2.41-2.31 (m, 1H) 2.25-2.18 (m, 1H), 2.04 (br s, 1H) |
| 59 | 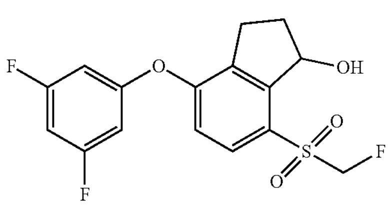 [SMILES: O=S(=O)(CF)c1ccc(Oc2cc(F)cc(F)c2)c2c1C(O)CC2] | [M − H + 46] 403 | (400 MHz, CDCl$_3$): δ 7.81 (d, 1H), 6.97 (d, 1H), 6.70-6.64 (m, 1H), 6.61-6.55 (m, 2H), 5.70-5.66 (m, 1H), 5.41-5.14 (m, 2H), 3.29 (d, 1H), 3.18-3.09 (m, 1H), 2.92-2.83 (m, 1H), 2.51-2.42 (m, 1H) 2.27-2.19 (m, 1H) |
| 60 | 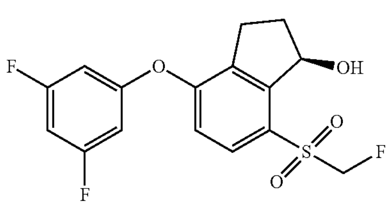 [SMILES: O=S(=O)(CF)c1ccc(Oc2cc(F)cc(F)c2)c2c1[C@H](O)CC2] | [M − H + 46] 403 | (400 MHz, CDCl$_3$): δ 7.81 (d, 1H), 6.97 (d, 1H), 6.70-6.64 (m, 1H), 6.61-6.55 (m, 2H), 5.70-5.66 (m, 1H), 5.42-5.13 (m, 2H), 3.30 (d, 1H), 3.18-3.09 (m, 1H), 2.92-2.83 (m, 1H), 2.51-2.42 (m, 1H) 2.27-2.19 (m, 1H) |

TABLE 2-continued

| No. | Structure | Mass Characterization | ¹H NMR Data |
|---|---|---|---|
| 61 | 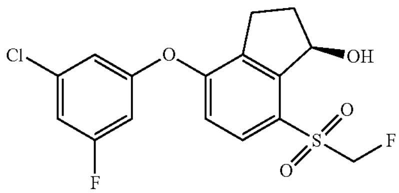 [SMILES: O=S(=O)(CF)c1ccc(Oc2cc(F)cc(Cl)c2)c2c1[C@H](O)CC2] | [M − H + 46] 419 | (400 MHz, CDCl₃): δ 7.81 (d, 1H), 6.97-6.93 (m, 2H), 6.87-6.85 (m, 1H), 6.71-6.67 (m, 1H), 5.71-5.66 (m, 1H), 5.42-5.13 (m, 2H), 3.30 (d, 1H), 3.18-3.09 (m, 1H), 2.92-2.84 (m, 1H), 2.51-2.41 (m, 1H) 2.28-2.19 (m, 1H) |
| 62 | 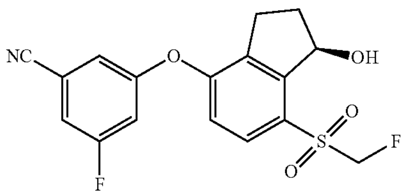 [SMILES: N#Cc1cc(F)cc(Oc2ccc(S(=O)(=O)CF)c3c2CC[C@H]3O)c1] | [M − H + 46] 410 | (400 MHz, CDCl₃): δ 7.85 (d, 1H), 7.23-7.19 (m, 2H), 7.13-7.11 (m, 1H), 7.04-7.00 (m, 1H), 6.98 (d, 1H), 5.72-5.67 (m, 1H), 5.44-5.12 (m, 2H), 3.29 (d, 1H), 3.16-3.07 (m, 1H), 2.90-2.81 (m, 1H), 2.52-2.42 (m, 1H), 2.29-2.20 (m, 1H) |
| 63 | 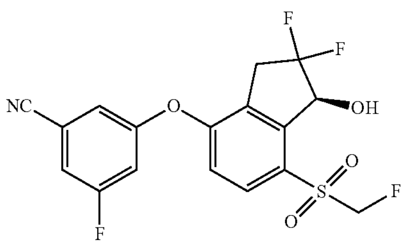 [SMILES: N#Cc1cc(F)cc(Oc2ccc(S(=O)(=O)CF)c3c2CC(F)(F)[C@H]3O)c1] | [M − H + 46] 446 | (400 MHz, CDCl₃): δ 7.93 (d, 1H), 7.30-7.26 (m, 1H), 7.20-7.19 (m, 1H), 7.10-7.07 (m, 1H), 7.00 (d, 1H), 5.59-5.13 (m, 3H), 3.58-3.38 (m, 1H) |
| 64 | 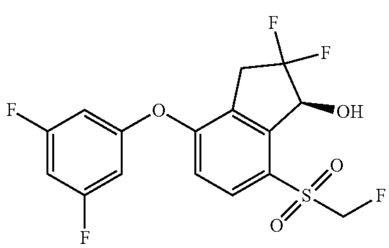 [SMILES: O=S(=O)(CF)c1ccc(Oc2cc(F)cc(F)c2)c2c1[C@H](O)C(F)(F)C2] | [M − H + 46] 439 | (400 MHz, CDCl₃): δ 7.90 (d, 1H), 7.01 (d, 1H), 6.77-6.71 (m, 1H), 6.67-6.60 (m, 2H), 5.58-5.12 (m, 3H), 3.58-3.38 (m, 3H) |
| 65 | 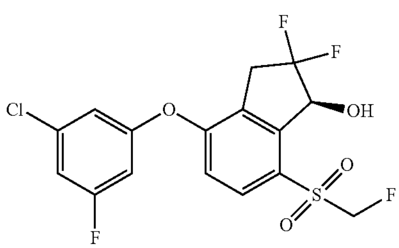 [SMILES: O=S(=O)(CF)c1ccc(Oc2cc(F)cc(Cl)c2)c2c1[C@H](O)C(F)(F)C2] | [M − H + 46] 455 | (400 MHz, CDCl₃): δ 7.90 (d, 1H), 7.03-7.00 (m, 1H), 6.98 (d, 1H), 6.91-6.90 (m, 1H), 6.76-6.72 (m, 1H), 5.58-5.12 (m, 3H), 3.59-3.39 (m, 3H) |
| 66 | 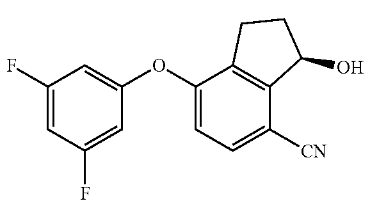 [SMILES: N#Cc1ccc(Oc2cc(F)cc(F)c2)c2c1[C@H](O)CC2] | [M − H] 286 | (400 MHz, CDCl₃): δ 7.55-7.52 (m, 1H), 6.90 (d, 1H), 6.65-6.60 (m, 1H), 6.55-6.49 (m, 2H), 5.56-5.51 (m, 1H), 3.08-3.00 (m, 1H), 2.80-2.71 (m, 1H), 2.68-2.64 (m, 1H) 2.60-2.50 (m, 1H), 2.17-2.08 (m, 1H) |
| 67 | 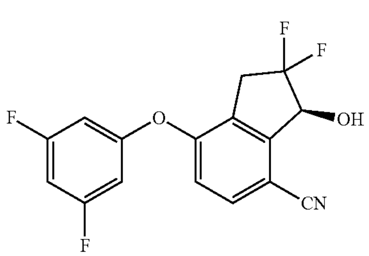 [SMILES: N#Cc1ccc(Oc2cc(F)cc(F)c2)c2c1[C@H](O)C(F)(F)C2] | [M − H + 46] 368 | (400 MHz, CDCl₃): δ 7.62 (d, 1H), 6.94 (d, 1H), 6.72-6.67 (m, 1H), 6.61-6.54 (m, 2H), 5.36-5.30 (m, 1H), 3.54-3.30 (m, 2H), 3.13-3.10 (m, 1H) |

TABLE 2-continued

| No. | Structure | Mass Characterization | ¹H NMR Data |
|---|---|---|---|
| 68 | 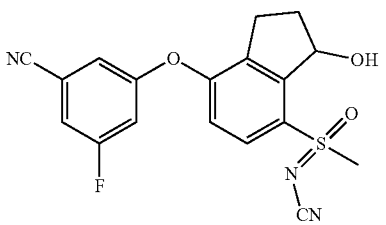 [SMILES: CS(=O)(=NC#N)c1ccc(Oc2cc(F)cc(C#N)c2)c2c1C(O)CC2] | [M + H] 372 | (400 MHz, CDCl₃): δ 7.87 (d, 1H), 7.25-7.22 (m, 1H), 7.15-7.13 (m, 1H), 7.08-6.97 (m, 2H), 5.86-5.80 (m, 1H), 3.51 (s, 3H), 3.19-3.06 (m, 2H), 2.95-2.78 (m, 1H), 2.65-2.55 (m, 1H), 2.27-2.14 (m, 1H) |
| 69 | 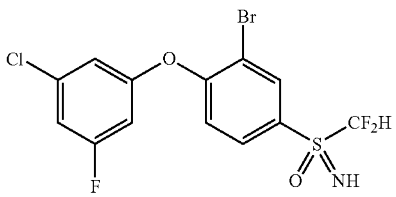 [SMILES: N=S(=O)(c1ccc(Oc2cc(F)cc(Cl)c2)c(Br)c1)C(F)F] | 414, 416, 418 (M + H) | (400 MHz, CDCl₃): δ 8.34 (d, 1H), 7.96 (m, 1H), 7.08 (d, 1H), 6.99 (m, 1H), 6.86 (m, 1H), 6.70 (m, 1H), 6.16 (t, 1H), 3.35 (br s, 1H) |
| 70 | 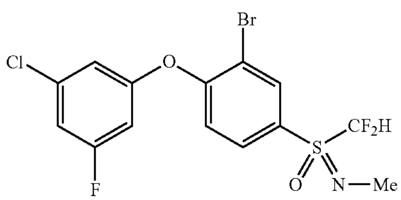 [SMILES: CN=S(=O)(c1ccc(Oc2cc(F)cc(Cl)c2)c(Br)c1)C(F)F] | 428, 430, 432 (M + H) | (400 MHz, CDCl₃): δ 8.26 (d, 1H), 7.87 (m, 1H), 7.07 (d, 1H), 6.98 (m, 1H), 6.86 (m, 1H), 6.70 (m, 1H), 6.22 (t, 1H), 2.98 (s, 3H) |
| 71 | 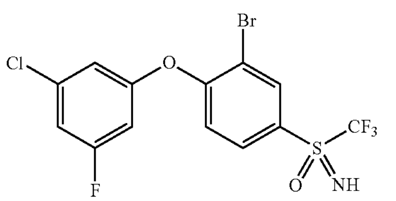 [SMILES: N=S(=O)(c1ccc(Oc2cc(F)cc(Cl)c2)c(Br)c1)C(F)(F)F] | 430, 432, 434 (M − H) | (400 MHz, CDCl₃): δ 8.42 (d, 1H), 8.03 (m, 1H), 7.07 (d, 1H), 7.01 (m, 1H), 6.89 (m, 1H), 6.73 (m, 1H), 3.65 (br s, 1H) |
| 72 | 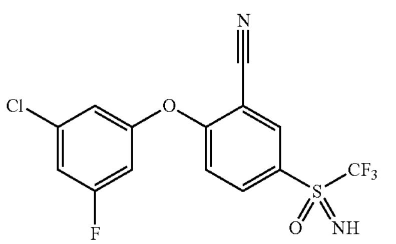 [SMILES: N#Cc1cc(S(=N)(=O)C(F)(F)F)ccc1Oc1cc(F)cc(Cl)c1] | 377, 379 (M − H) | (400 MHz, CDCl₃): δ 8.47 (d, 1H), 8.23 (m, 1H), 7.12 (m, 1H), 7.07 (d, 1H), 7.00 (m, 1H), 6.84 (m, 1H), 3.74 (br s, 1H) |
| 73 | 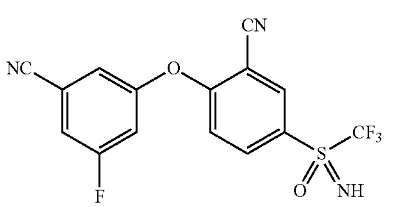 [SMILES: N#Cc1cc(F)cc(Oc2ccc(S(=N)(=O)C(F)(F)F)cc2C#N)c1] | 368 (M − H) | (400 MHz, CDCl₃): δ 8.50 (d, 1H), 8.28 (m, 1H), 7.38 (m, 1H), 7.30 (m, 1H), 7.20 (m, 1H), 7.09 (d, 1H), 3.78 (br s, 1H) |
| 74 | 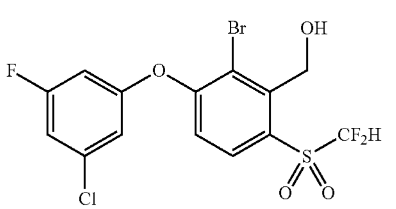 [SMILES: O=S(=O)(c1ccc(Oc2cc(F)cc(Cl)c2)c(Br)c1CO)C(F)F] | 462, 464, 466 (M + NH₄) | (400 MHz, CDCl₃): δ 8.06 (d, 1H), 7.04-6.99 (m, 2H), 6.90 (m, 1H), 6.73 (m, 1H), 6.48 (t, 1H), 5.25 (d, 2H), 2.69 (t, 1H) |

TABLE 2-continued

| No. | Structure | Mass Characterization | $^1$H NMR Data |
|---|---|---|---|
| 75 | [structure] | 464, 466, 468 (M − H) | (400 MHz, CDCl$_3$): δ 8.33 (d, 1H), 7.03 (m, 1H), 6.98 (d, 1H), 6.90 (m, 1H), 6.74 (m, 1H), 3.88 (br s, 1H) |
| 76 | [structure] | 441, 443, 445 (M + H) | (400 MHz, CDCl$_3$): δ 8.00 (d, 1H), 7.36 (d, 1H), 7.03 (m, 1H), 6.87 (m, 1H), 6.72 (m, 1H), 6.33 (t, 1H) |
| 77 | [structure] | 432, 434 (M + H) | (400 MHz, CDCl$_3$): δ 8.06 (d, 1H), 7.42 (d, 1H), 7.28 (m, 1H), 7.12 (m, 1H), 7.03 (m, 1H), 6.36 (t, 1H) |
| 78 | [structure] | 401 (M + NH$_4$) | (400 MHz, CDCl$_3$): δ 7.86 (d, 1H), 7.16 (m, 1H), 7.04 (m, 1H), 6.97 (d, 1H), 6.37 (t, 1H), 5.69-5.65 (m, 1H), 3.21-3.11 (m, 2H), 2.92 (m, 1H), 2.51-2.41 (m, 1H), 2.32-2.23 (m, 1H) |
| 79 | [structure] | | (400 MHz, CDCl$_3$): δ 8.16 (d, 1H), 7.43 (m, 1H), 7.34-7.32 (m, 1H), 7.24-7.21 (m, 1H), 7.06 (d, 1H), 2.79 (s, 3H) |
| 80 | [structure] | 453, 455 (M + NH$_4$) | (400 MHz, CDCl$_3$): δ 8.11 (d, 1H), 7.28-7.23 (m, 1H), 7.15-7.13 (m, 1H), 7.09 (d, 1H), 7.05 (m, 1H), 6.50 (t, 1H), 5.25 (d, 2H), 2.69 (t, 1H) |

TABLE 2-continued

| No. | Structure | Mass Characterization | ¹H NMR Data |
|---|---|---|---|
| 81 | 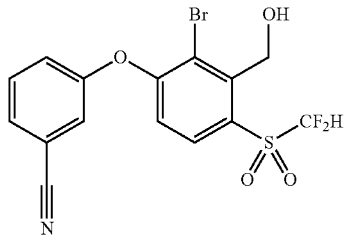 [SMILES: N#Cc1cccc(Oc2ccc(S(=O)(=O)C(F)F)c(CO)c2Br)c1] | 435, 437 (M + NH₄) | (400 MHz, CDCl₃): δ 8.05 (d, 1H), 7.59-7.56 (m, 2H), 7.39-7.37 (m, 1H), 7.36-7.31 (m, 1H), 6.95 (d, 1H), 6.48 (t, 1H), 5.26 (d, 2H), 2.70 (t, 1H) |
| 82 | 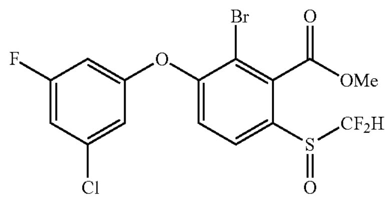 [SMILES: COC(=O)c1c(S(=O)C(F)F)ccc(Oc2cc(F)cc(Cl)c2)c1Br] | 457, 459, 461 | (400 MHz, CDCl₃): δ 8.05 (d, 1H), 7.28 (d, 1H), 6.96 (m, 1H), 6.83-6.81 (m, 1H), 6.66 (m, 1H), 6.58 (m, 1H), 4.04 (t, 3H) |
| 83 | 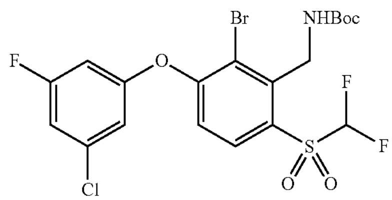 [SMILES: CC(C)(C)OC(=O)NCc1c(S(=O)(=O)C(F)F)ccc(Oc2cc(F)cc(Cl)c2)c1Br] | 488, 490, 492 [MH⁺-C₄H₈] | (400 MHz, CDCl₃): δ 8.04 (d, 1H), 7.02 (m, 1H), 6.99 (d, 1H), 6.90-6.88 (m, 1H), 6.73 (m, 1H), 6.62 (br t, 1H), 5.22 (br s, 1H), 4.95 (d, 2H), 1.45 (s, 9H) |
| 84 | 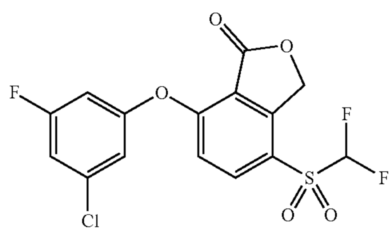 [SMILES: O=C1OCc2c(S(=O)(=O)C(F)F)ccc(Oc3cc(F)cc(Cl)c3)c21] | 393, 395 (M + H) | (400 MHz, CDCl₃): δ 8.07 (d, 1H), 7.11 (m, 1H), 7.04-6.99 (m, 2H), 6.87 (m, 1H), 6.26 (t, 1H), 5.61 (d, 2H) |
| 85 | 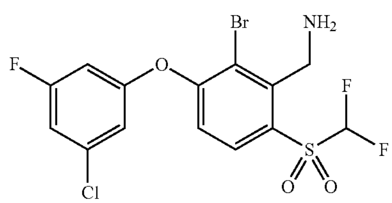 [SMILES: NCc1c(S(=O)(=O)C(F)F)ccc(Oc2cc(F)cc(Cl)c2)c1Br] | 444, 446, 448 (M + H) | (400 MHz, CDCl₃): δ 8.04 (d, 1H), 7.02 (m, 1H), 6.97 (d, 1H), 6.89 (m, 1H), 6.73 (m, 1H), 6.66 (t, 1H), 4.45 (br s, 2H) |
| 86 | 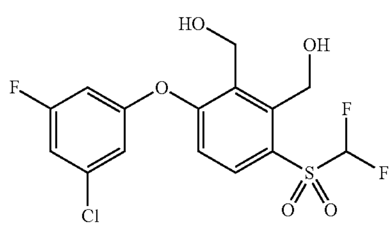 [SMILES: O=S(=O)(c1ccc(Oc2cc(F)cc(Cl)c2)c(CO)c1CO)C(F)F] | 486, 488, 490 (M + H) | (400 MHz, CDCl₃): δ 8.04 (d, 1H), 7.03 (m, 1H), 6.99 (d, 1H), 6.90 (m, 1H), 6.74 (m, 1H), 6.66 (t, 1H), 6.11 (br s, 1H), 5.05 (d, 2H), 2.00 (s, 3H) |
| 87 | 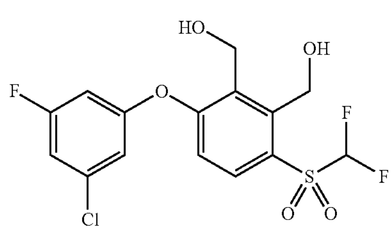 [SMILES: O=S(=O)(c1ccc(Oc2cc(F)cc(Cl)c2)c(CO)c1CO)C(F)F] | 379, 381 (M + H − 16) | (400 MHz, CDCl₃): δ 8.07 (d, 1H), 7.02 (d, 1H), 7.00 (m, 1H), 6.90-6.88 (m, 1H), 6.75-6.71 (m, 1H), 6.46 (t, 1H), 5.18 (d, 2H), 5.01 (d, 2H), 3.01 (t, 1H), 2.76 (t, 1H) |

TABLE 2-continued

| No. | Structure | Mass Characterization | $^1$H NMR Data |
|---|---|---|---|
| 88 | 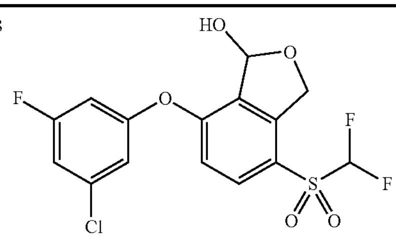 | 377, 379 (M + H − 16) | (400 MHz, CDCl$_3$): δ 7.89 (d, 1H), 7.03 (m, 1H), 6.97-6.94 (m, 2H), 6.80 (m, 1H), 6.67 (m, 1H), 6.20 (t, 1H), 5.57 (m, 1H), 5.39 (d, 1H), 3.33 (d, 1H) |
| 89 | 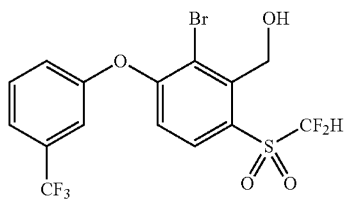 [SMILES: O=S(=O)(c1ccc(Oc2cccc(C(F)(F)F)c2)c(Br)c1CO)C(F)F] | 478, 480 (M + NH$_4$) | (400 MHz, CDCl$_3$): δ 8.01 (d, 1H), 7.63-7.55 (m, 2H), 7.41-7.38 (m, 1H), 7.28 (m, 1H), 6.90 (d, 1H), 6.47 (t, 1H), 5.26 (d, 2H), 2.73 (t, 1H) |
| 90 | 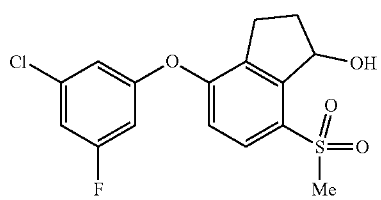 [SMILES: CS(=O)(=O)c1ccc(Oc2cc(F)cc(Cl)c2)c2c1C(O)CC2] | 339, 341 (M + H − 16) | (400 MHz, CDCl$_3$): δ 7.80 (d, 1H), 6.95 (d, 1H), 6.93 (m, 1H), 6.84-6.82 (m, 1H), 6.66 (m, 1H), 5.68 (m, 1H), 3.64 (d, 1H), 3.20 (s, 3H), 3.15-3.06 (m, 1H), 2.83 (m, 1H), 2.53-2.43 (m, 1H), 2.27-2.18 (m, 1H) |
| 91 | 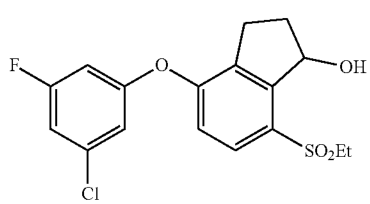 | 353, 355 (M − OH) | (400 MHz, CDCl$_3$): δ 7.74 (d, 1H), 6.95-6.92 (m, 2H), 6.84-6.82 (m, 1H), 6.66 (m, 1H), 5.65-5.60 (m, 1H), 3.70 (d, 1H), 3.35-3.19 (m, 2H), 3.15-3.06 (m, 1H), 2.83 (m, 1H), 2.49-2.39 (m, 1H), 2.27-2.19 (m, 1H), 1.34 (t, 3H) |
| 92 | 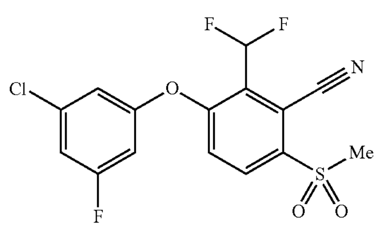 [SMILES: CS(=O)(=O)c1ccc(Oc2cc(F)cc(Cl)c2)c(C(F)F)c1C#N] | 393, 395 (M + NH$_4$) | (400 MHz, CDCl$_3$): δ 8.29-8.25 (m, 1H), 7.27-7.23 (m, 1H), 7.22 (t, 1H), 7.10-7.06 (m, 1H), 6.93-6.91 (m, 1H), 6.76 (m, 1H), 3.35 (s, 3H) |
| 93 | 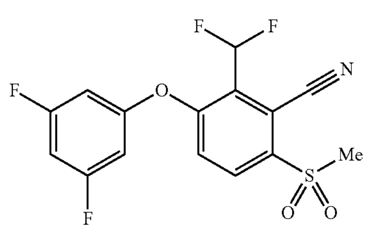 [SMILES: CS(=O)(=O)c1ccc(Oc2cc(F)cc(F)c2)c(C(F)F)c1C#N] | 377 (M + NH$_4$) | (400 MHz, CDCl$_3$): δ 8.29-8.25 (m, 1H), 7.29-7.25 (m, 1H), 7.22 (t, 1H), 6.80 (tt, 1H), 6.69-6.63 (m, 2H), 3.35 (s, 3H) |
| 94 | 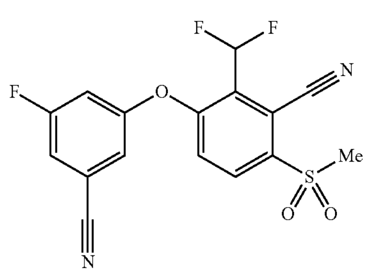 [SMILES: CS(=O)(=O)c1ccc(Oc2cc(F)cc(C#N)c2)c(C(F)F)c1C#N] | 384 (M + NH$_4$) | (400 MHz, CDCl$_3$): δ 8.34-8.30 (m, 1H), 7.35-7.32 (m, 1H), 7.29-7.25 (m, 1H), 7.21 (t, 1H), 7.21-7.18 (m, 1H), 7.11 (m, 1H), 3.36 (s, 3H) |

TABLE 2-continued

| No. Structure | Mass Characterization | $^1$H NMR Data |
|---|---|---|
| 95 | 379 (M + NH$_4$) | (400 MHz, CDCl$_3$): δ 7.98 (d, 1H), 7.17 (m, 1H), 7.05-7.03 (m, 1H), 6.97 (m, 1H), 6.95 (d, 1H), 5.44-5.39 (m, 1H), 3.72 (m, 1H), 3.25 (s, 3H), 3.04-2.95 (m, 1H), 2.58-2.47 (m, 1H), 2.29-2.22 (m, 1H), 2.16-2.03 (m, 1H), 1.91-1.73 (m, 2H) |
| 96 | | (400 MHz, CDCl$_3$): δ 7.85 (d, 1H), 6.94 (d, 1H), 6.93-6.90 (m, 1H), 6.74-6.73 (m, 1H), 6.61-6.57 (m, 1H) |
| 97 | | (400 MHz, CDCl$_3$): δ 7.68 (d, 1H), 6.99-6.94 (m, 2H), 6.85-6.84 (m, 1H), 6.71-6.67 (m, 1H) |
| 98 | (M − H) 456, 458 | (400 MHz, CDCl$_3$): δ 8.12 (d, 1H), 7.18 (d, 1H), 7.14-7.11 (m, 1H), 6.97-6.96 (m, 1H), 6.82-6.79 (m, 1H) |
| 99 | (M + NH$_4$) 448 | (400 MHz, CDCl$_3$): δ 8.12 (d, 1H), 7.69-7.63 (m, 2H), 7.46-7.45 (m, 1H), 7.41-7.38 (m, 1H), 7.11 (d, 1H) |
| 100 | (M + NH$_4$) 466 | (400 MHz, CDCl$_3$): δ 8.17 (d, 1H), 7.39-7.36 (m, 1H), 7.24-7.23 (m, 1H), 7.22 (d, 1H), 7.16-7.13 (m, 1H) |
| 101 | | (400 MHz, CDCl$_3$): δ 10.31 (s, 1H), 7.99 (d, 1H), 7.10 (d, 1H), 7.10-7.07 (m, 1H), 6.96-6.94 (m, 1H), 6.81-6.77 (m, 1H) |

TABLE 2-continued

| No. | Structure | Mass Characterization | ¹H NMR Data |
|---|---|---|---|
| 102 | 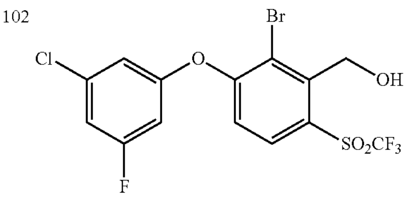 | | (400 MHz, CDCl$_3$): δ 7.77 (d, 1H), 7.16 (d, 1H), 7.00-6.97 (m, 1H), 6.83-6.82 (m, 1H), 6.70-6.67 (m, 1H), 5.43 (s, 2H) |
| 103 | 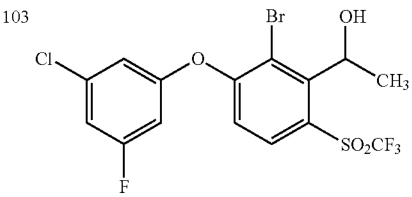 | (M − H) 475, 477 | (400 MHz, CDCl$_3$): δ 8.11 (d, 1H), 7.06-7.03 (m, 1H), 6.95 (d, 1H), 6.92-6.91 (m, 1H), 6.77-6.74 (m, 1H), 5.88 (m, 1H), 3.38 (d, 1H), 1.81 (d, 3H) |
| 104 | 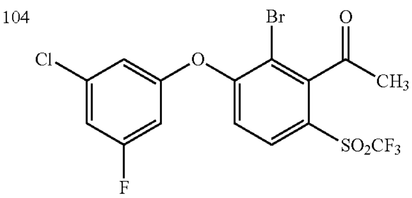 | (M + H) 474.8/ 476.7 | (400 MHz, CDCl$_3$): δ 7.97-7.94 (m, 1H), 7.10-7.07 (m, 1H), 7.01 (d, 1H), 6.80-6.77 (m, 1H), 2.71 (s, 3H) |
| 105 | 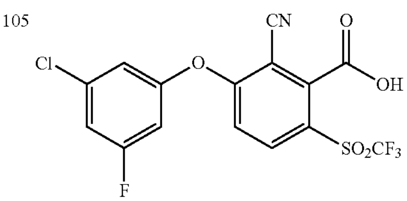 | (M + H) 424, 426 | (400 MHz, CDCl$_3$): δ 8.35 (d, 1H), 7.84 (brd s, 1H), 7.26 (d, 1H), 7.15-7.12 (m, 1H), 7.04-7.03 (m, 1H), 6.89-6.86 (m, 1H) |
| 106 | 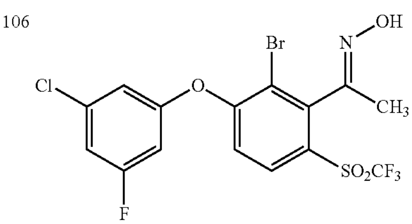 | (M + H) 492, 494 | (400 MHz, CDCl$_3$): δ 7.95-7.94 (m, 1H), 7.09-7.06 (m, 1H), 7.01 (d, 1H), 6.96-6.95 (m, 1H), 6.80-6.77 (m, 1H), 2.70 (s, 3H) |
| 107 | 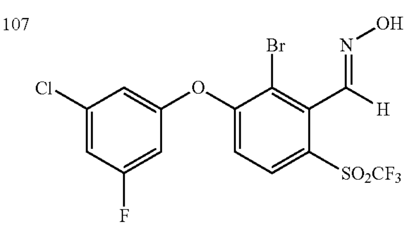 | (M + H) 476, 478 | (400 MHz, CDCl$_3$): δ 8.39 (s, 1H), 8.07 (d, 1H), 7.07 (d, 1H), 7.07-7.04 (m, 1H), 6.94-6.93 (m, 1H), 6.79-6.76 (m, 1H) |
| 108 | 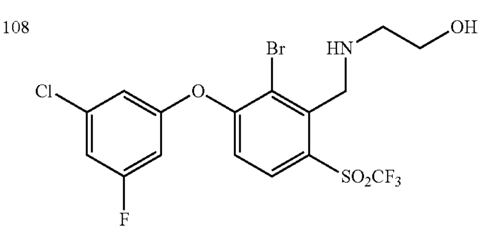 | (M + H) 506, 508 | (400 MHz, CDCl$_3$): δ 8.07 (d, 1H), 7.06-7.03 (m, 1H), 6.98 (d, 1H), 6.93-6.92 (m, 1H), 6.78-6.74 (m, 1H), 4.32 (s, 2H), 3.72 (t, 2H), 2.97 (t, 2H) |

TABLE 2-continued

| No. | Structure | Mass Characterization | ¹H NMR Data |
|---|---|---|---|
| 109 | 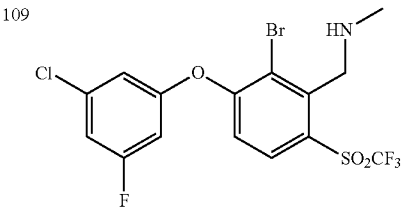 | (M + H) 476, 478 | (400 MHz, CDCl$_3$): δ 8.06 (d, 1H), 7.05-7.02 (m, 1H), 6.97 (d, 1H), 6.91-6.90 (m, 1H), 6.76-6.72 (m, 1H), 4.25 (s, 2H), 2.57 (s, 3H) |
| 110 | 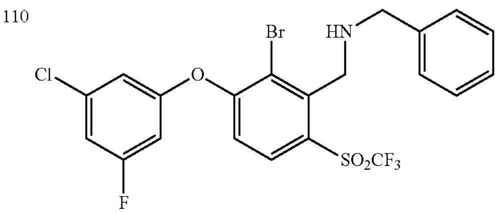 | (M + H) 552, 554 | (400 MHz, CDCl$_3$): δ 8.04 (d, 1H), 7.39-7.31 (m, 4H), 7.28-7.23 (m, 1H), 7.05-7.02 (m, 1H), 6.94 (d, 1H), 6.91-6.89 (m, 1H), 6.75-6.72 (m, 1H), 4.30 (s, 2H), 3.96 (s, 2H). |
| 111 | 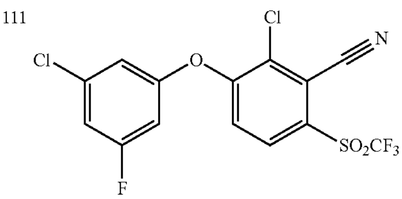 | (M + NH$_4$) 431, 433 | (400 MHz, CDCl$_3$): δ 8.08 (d, 1H), 7.23 (d, 1H), 7.14-7.11 (m, 1H), 6.98-6.96 (m, 1H), 6.83-6.79 (m, 1H) |
| 112 | 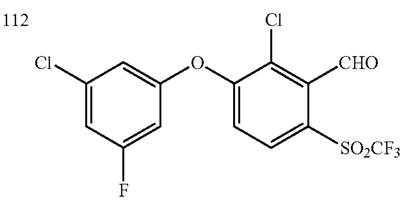 | | (400 MHz, CDCl$_3$): δ 10.43 (s, 1H), 7.96 (d, 1H), 7.15 (d, 1H), 7.09-7.07 (m, 1H), 6.95-6.94 (m, 1H), 6.80-6.77 (m, 1H) |
| 113 | 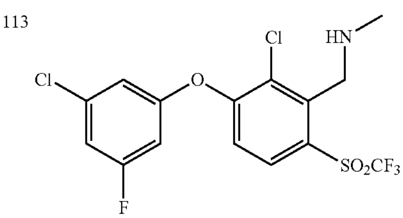 | (M + H) 432, 434 | (400 MHz, CDCl$_3$): δ 8.02 (d, 1H), 7.05-7.02 (m, 1H), 7.01 (d, 1H), 6.91-6.90 (m, 1H), 6.76-6.72 (m, 1H), 4.22 (s, 2H), 2.56 (s, 3H) |
| 114 | 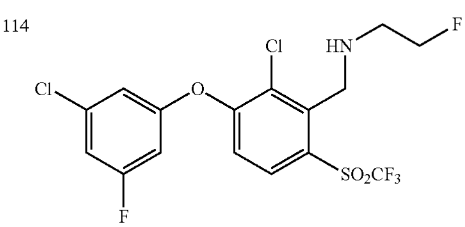 | (M + H) 464, 466 | (400 MHz, CDCl$_3$): δ 8.02 (d, 1H), 7.06-7.03 (m, 1H), 7.01 (d, 1H), 6.92 (m, 1H), 6.77-6.73 (m, 1H), 4.64 (t, 1H), 4.52 (t, 1H), 4.34 (s, 2H), 3.11-3.09 (m, 1H), 3.04-3.02 (m, 1H) |
| 115 | 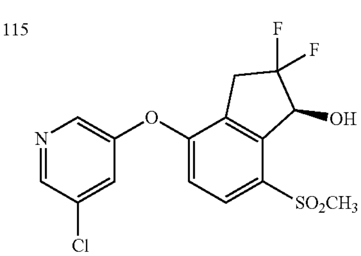 | (M + H) 376, 378 | (400 MHz, CDCl$_3$): δ 8.50-8.49 (m, 1H), 8.36-8.35 (m, 1H), 7.89 (d, 1H), 7.43 (t, 1H), 6.93 (d, 1H), 5.62-5.58 (m, 1H), 3.62-3.40 (m, 3H), 3.22 (s, 3H) |

TABLE 2-continued

| No. | Structure | Mass Characterization | ¹H NMR Data |
|---|---|---|---|
| 116 | 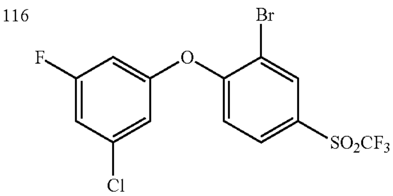 | 431 (M − H) | (400 MHz, CDCl₃): δ 8.30 (d, 1H), 7.93 (m, 1H), 7.08-7.02 (m, 2H), 6.93-6.91 (m, 1H), 6.78-6.74 (m, 1H) |
| 117 | 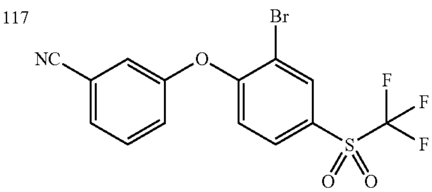 | 404 (M − H) | |
| 118 | 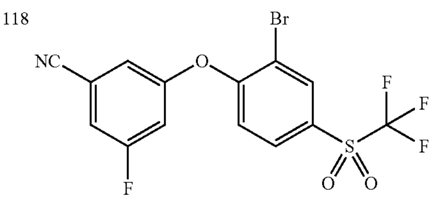 | 422 (M − H) | |
| 119 | 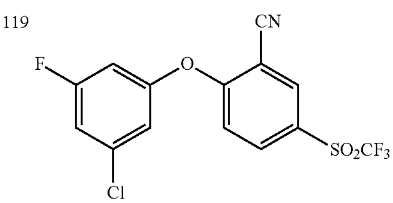 | 379 (M − H) | (400 MHz, CDCl₃): δ 8.35 (d, 1H), 8.13 (m, 1H), 7.16-7.13 (m, H), 7.11 (d, 1H), 7.03-7.01 (m, 1H), 6.88-6.85 (m, 1H) |
| 120 | 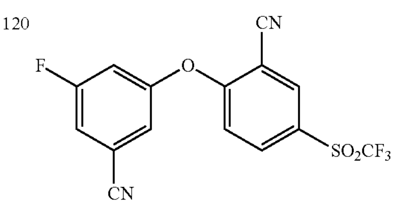 | 369 (M − H) | |
| 121 | 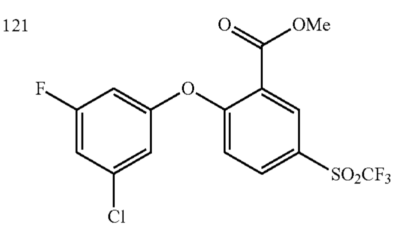 | 411 (M − H) | (400 MHz, CDCl₃): δ 8.58 (d, 1H), 8.10-8.07 (m, 1H), 7.14 (d, 1H), 7.03-7.00 (m, 1H), 6.91-6.90 (m, 1H), 6.77-6.73 (m, 1H), 3.94 (s, 3H) |
| 122 | 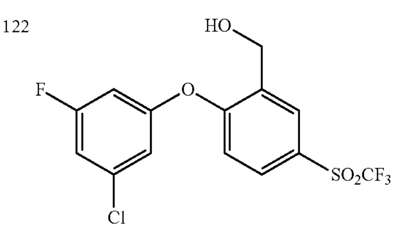 | 383 (M − H) | |

TABLE 2-continued

| No. | Structure | Mass Characterization | $^1$H NMR Data |
|---|---|---|---|
| 123 | 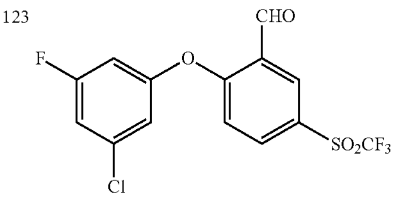 | | |
| 124 | 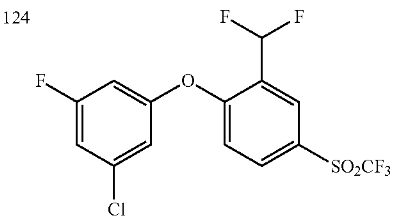 | | (400 MHz, CDCl$_3$): δ 8.35-8.34 (m, 1H), 8.09-8.05 (m, 1H), 7.17-6.90 (m, 4H), 6.82-6.78 (m, 1H) |
| 125 | 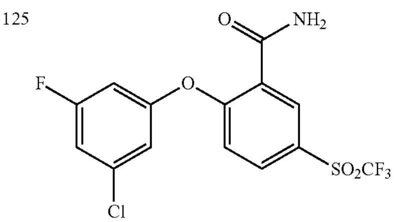 | 396 (M − H) | (400 MHz, CDCl$_3$): δ 8.95 (d, 1H), 8.07-8.04 (m, 1H), 7.21 (br s, 1H), 7.15-7.12 (m, 1H), 7.05 (d, 1H), 7.02-7.01 (m, 1H), 6.86-6.83 (m, 1H), 6.01 (br s, 1H) |
| 126 | 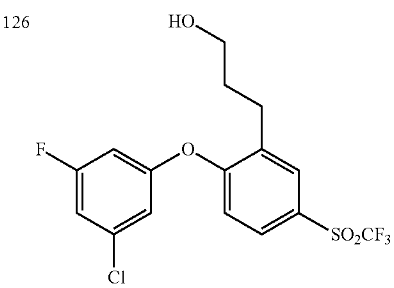 | 457 (M + HCO$_2^-$) | (400 MHz, CDCl$_3$): δ 7.96 (d, 1H), 7.84 (m, 1H), 7.02-6.98 (m, 2H), 6.88-6.87 (m, 1H), 6.73-6.69 (m, 1H), 3.74-3.60 (m, 2H), 2.91-2.87 (m, 2H), 1.97-1.90 (m, 2H), 1.40-1.37 (m, 1H) |
| 127 | 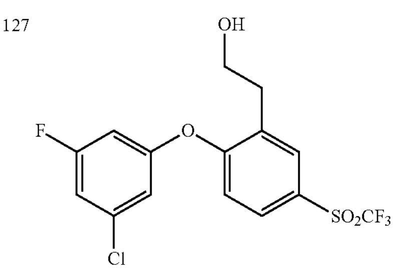 | 397 (M − H) | (400 MHz, CDCl$_3$): δ 8.02 (d, 1H), 7.86 (m, 1H), 7.02-6.99 (m, 2H), 6.89-6.87 (m, 1H), 6.74-6.70 (m, 1H), 3.98-3.93 (m, 2H), 3.06 (t, 2H), 1.50-1.47 (m, 1H) |
| 128 | 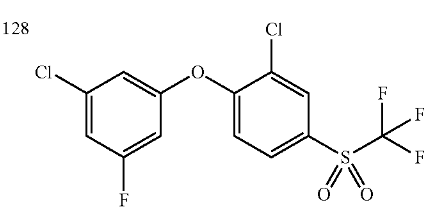 | 387 (M − H) | |

TABLE 2-continued

| No. | Structure | Mass Characterization | ¹H NMR Data |
|---|---|---|---|
| 129 | 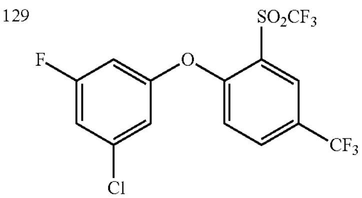 | 421 (M − H) | (400 MHz, CDCl$_3$): δ 8.39-8.38 (m, 1H), 7.98-7.95 (m, 1H), 7.15 (d, 1H), 7.08-7.05 (m, 1H), 6.95-6.94 (m, 1H), 6.80-6.77 (m, 1H) |
| 130 | 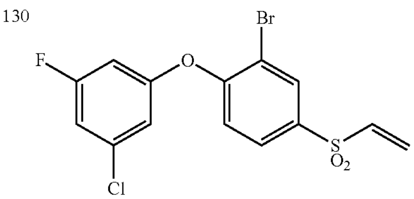 | 389 (M − H) | (400 MHz, CDCl$_3$): δ 8.18 (d, 1H), 7.83-7.80 (m, 1H), 7.07 (d, 1H), 6.97-6.94 (m, 1H), 6.82-6.81 (m, 1H), 6.70-6.64 (m, 2H), 6.54-6.50 (m, 1H), 6.13-6.11 (m, 1H) |
| 131 | 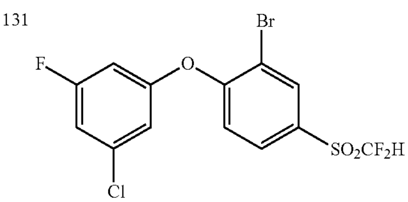 | 413 (M − H) | (400 MHz, CDCl$_3$): δ 8.26 (d, 1H), 7.89-7.87 (m, 1H), 7.07 (d, 1H), 7.04-7.00 (m, 1H), 6.90-6.89 (m, 1H), 6.75-6.72 (m, 1H), 6.21 (t, 1H) |
| 132 | 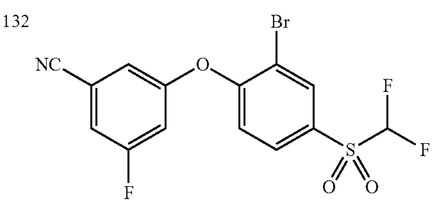 | 404 (M − H) | (400 MHz, CDCl$_3$): δ 8.30 (d, 1H), 7.95-7.93 (m, 1H), 7.27-7.25 (m, 1H), 7.15-7.13 (m, 2H), 7.06-7.03 (m, 1H), 6.24 (t, 1H) |
| 133 | 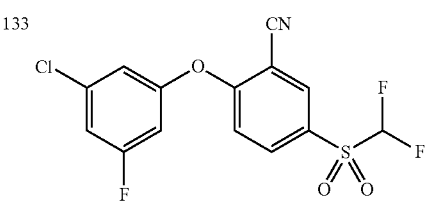 | 360 (M − H) | (400 MHz, CDCl$_3$): δ 8.34 (d, 1H), 8.15-8.12 (m, 1H), 7.40-7.37 (m, 1H), 7.31-7.29 (m, 1H), 7.22-7.19 (m, 1H), 7.10 (d, 1H), 6.26 (t, 1H) |
| 134 | 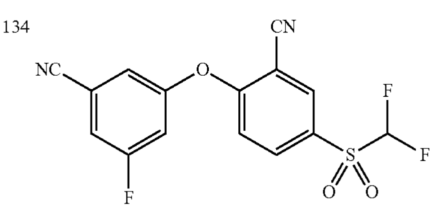 | 351 (M − H) | (400 MHz, CDCl$_3$): δ 8.34 (d, 1H), 8.15-8.12 (m, 1H), 7.40-7.37 (m, 1H), 7.31-7.29 (m, 1H), 7.22-7.19 (m, 1H), 7.10(d, 1H), 6.26 (t, 1H) |
| 135 | 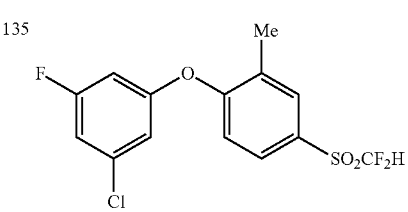 | 349 (M − H) | (400 MHz, CDCl$_3$): δ 7.86 (d, 1H), 7.80-7.77 (m, 1H), 7.01 (d, 1H), 6.98-6.95 (m, 1H), 6.84-6.83 (m, 1H), 6.69-6.65 (m, 1H), 6.19 (t, 1H), 2.39 (s, 3H) |

TABLE 2-continued

| No. | Structure | Mass Characterization | ¹H NMR Data |
|---|---|---|---|
| 136 | (3-fluoro-5-cyanophenoxy)(2-methyl-4-(difluoromethylsulfonyl)phenyl) ether | 340 (M − H) | (400 MHz, CDCl$_3$): δ 7.93 (d, 1H), 7.85-7.82 (m, 1H), 7.23-7.20 (m, 1H), 7.11-7.09 (m, 1H), 7.04 (d, 1H), 7.03-6.98 (m, 1H), 6.21 (t, 1H), 2.39 (s, 3H) |
| 137 | (3-fluoro-5-chlorophenoxy)(2-bromo-4-(fluoromethylsulfonyl)phenyl) ether | 395 (M − H) | (400 MHz, CDCl$_3$): δ 8.25 (d, 1H), 7.89-7.86 (m, 1H), 7.09 (d, 1H), 7.00-6.97 (m, 1H), 6.87-6.86 (m, 1H), 6.72-6.69 (m, 1H), 5.17 (d, 2H) |
| 138 | (3-fluoro-5-chlorophenoxy)(2-bromo-4-(methylsulfonyl)phenyl) ether | 377 (M − H) | |
| 139 | (3-fluoro-5-chlorophenoxy)(2-cyano-4-(methylsulfonyl)phenyl) ether | 370 (M + HCO$_2^-$) | (400 MHz, CDCl$_3$): δ 8.29-8.28 (m, 1H), 8.09-8.06 (m, 1H), 7.10-7.06 (m, 2H), 6.97-6.96 (m, 1H), 6.83-6.79 (m, 1H), 3.10 (s, 3H) |
| 140 | (3-chloro-5-fluorophenoxy)(2-methyl-3-bromo-4-(trifluoromethylsulfonyl)phenyl) ether | 445 (M − H) | (400 MHz, CDCl$_3$): δ 8.07 (d, 1H), 7.03-7.00 (m, 1H), 6.94 (d, 1H), 6.87-6.86 (m, 1H), 6.72-6.68 (m, 1H), 2.52 (s, 3H) |
| 141 | (3-cyano-5-fluorophenoxy)(2-methyl-3-bromo-4-(trifluoromethylsulfonyl)phenyl) ether | 438 (M + H) | |
| 142 | (3-cyano-5-fluorophenoxy)(2-methyl-3-(3-hydroxyprop-1-ynyl)-4-(trifluoromethylsulfonyl)phenyl) ether | 412 (M − H) | (400 MHz, CDCl$_3$): δ 8.00 (d, 1H), 7.26-7.23 (m, 1H), 7.12-7.11 (m, 1H), 7.03-6.99 (m, 1H), 6.97 (d, 1H), 4.62 (d, 2H), 2.49 (s, 3H), 1.96-1.91 (m, 1H) |

TABLE 2-continued

| No. | Structure | Mass Characterization | $^1$H NMR Data |
|---|---|---|---|
| 143 | 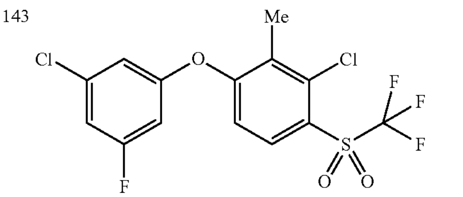 | 401 (M − H) | (400 MHz, CDCl$_3$): δ 8.03 (d, 1H), 7.03-7.00 (m, 1H), 6.90 (d, 1H), 6.88-6.86 (m, 1H), 6.72-6.69 (m, 1H), 2.47 (s, 3H) |
| 144 | 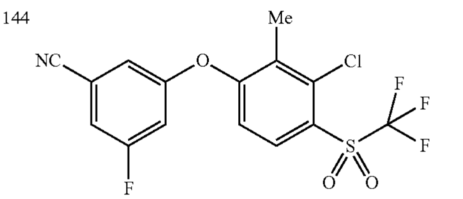 | 392 (M − H) | (400 MHz, CDCl$_3$): δ 8.05 (m, 1H), 7.29-7.26 (m, 1H), 7.14 (s, 1H), 7.05-7.02 (m, 1H), 6.94-6.91 (m, 1H), 2.46 (s, 3H) |
| 145 | 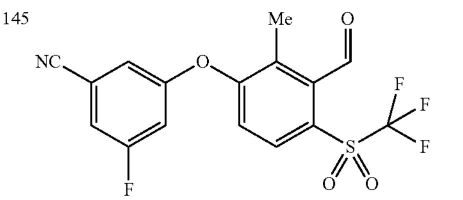 | 386 (M − H) | (400 MHz, CDCl$_3$): δ 10.62 (s, 1H), 7.97 (d, 1H), 7.30-7.27 (m, 1H), 7.16-7.15 (m, 1H), 7.10 (d, 1H), 7.07-7.03 (m, 1H), 2.40 (s, 3H) |
| 146 | 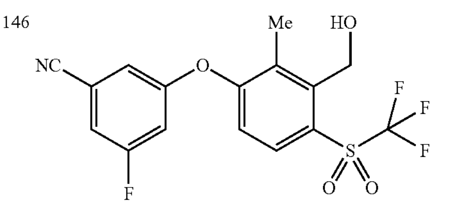 | 434 (M + HCO$_2^-$) | (400 MHz, CDCl$_3$): δ 8.01 (d, 1H), 7.26-7.23 (m, 1H), 7.12-7.11 (m, 1H), 7.03-6.99 (m, 2H), 4.99 (d, 2H), 2.50 (s, 3H) |
| 147 | 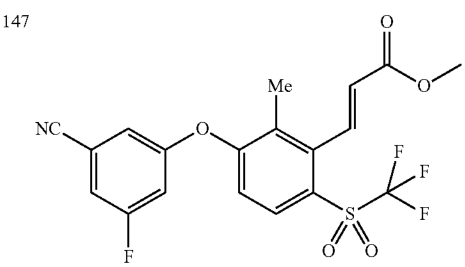 | 442 (M − H) | (400 MHz, CDCl$_3$): δ 8.02 (s, 1H), 7.99 (d, 1H), 7.28-7.25 (m, 1H), 7.16-7.15 (m, 1H), 7.07-7.05 (m, 1H), 6.98 (d, 1H), 6.03 (d, 1H), 3.85 (s, 3H), 2.34 (s, 3H) |
| 148 | 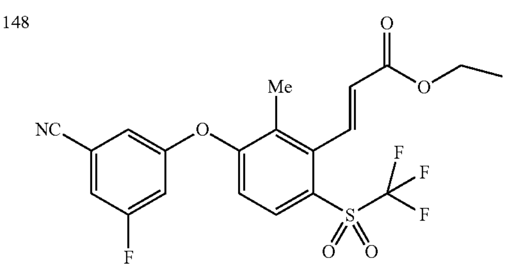 | 458 (M + H) | (400 MHz, CDCl$_3$): δ 8.02 (s, 1H), 7.99 (d, 1H), 7.28-7.25 (m, 1H), 7.16-7.15 (m, 1H), 7.07-7.03 (m, 1H), 6.98 (d, 1H), 6.02 (d, 1H), 4.31 (q, 2H), 2.34 (s, 3H), 1.36 (t, 3H) |

TABLE 2-continued
| No. | Structure | Mass Characterization | ¹H NMR Data |
|---|---|---|---|
| 149 | 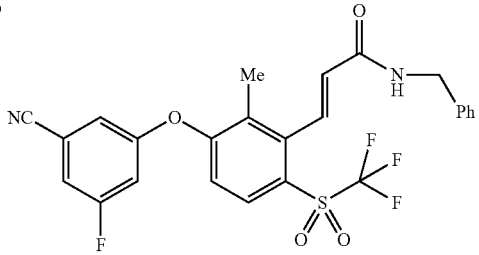 | 519 (M + H) | (400 MHz, CDCl₃): δ 8.01 (d, 1H), 7.79 (d, 1H), 7.39-7.29 (m, 5H), 7.27-7.24 (m, 1H), 7.14-7.13 (m, 1H), 7.06-7.03 (m, 1H), 6.97 (d, 1H), 6.06-6.02 (m, 2H), 4.60 (d, 2H), 2.33 (s, 3H) |
| 150 | 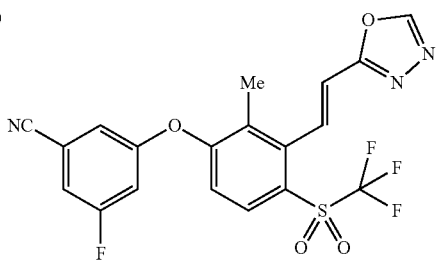 | 454 (M + H) | (400 MHz, CDCl₃): δ 8.47 (d, 1H), 8.05 (d, 1H), 7.98 (d, 1H), 7.31-7.27 (m, 1H), 7.19-7.18 (m, 1H), 7.10-7.07 (m, 1H), 7.01 (d, 1H), 6.72 (d, 1H), 2.42 (s, 3H) |
| 151 | 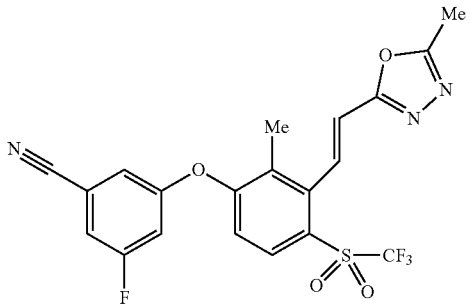 [SMILES: Cc1nnc(/C=C/c2c(S(=O)(=O)C(F)(F)F)ccc(Oc3cc(F)cc(C#N)c3)c2C)o1] | 468 (M + H) | (400 MHz, CDCl₃): δ 8.03 (d, 1H), 7.85 (d, 1H), 7.30-7.27 (m, 1H), 7.18-7.17 (m, 1H), 7.09-7.05 (m, 1H), 6.99 (d, 1H), 6.62 (d, 1H), 2.63 (s, 3H), 2.40 (s, 3H) |
| 152 | 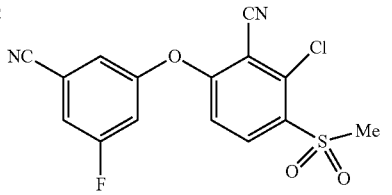 | 349 (M − H) | (400 MHz, CDCl₃): δ 8.32 (d, 1H), 7.38-7.35 (m, 1H), 7.26-7.25 (m, 1H), 7.18-7.15 (m, 1H), 6.97 (d, 1H), 3.30 (s, 3H) |
| 153 | 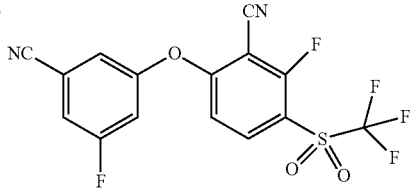 [SMILES: N#Cc1cc(F)cc(Oc2ccc(S(=O)(=O)C(F)(F)F)c(F)c2C#N)c1] | 396 (M − H) | (400 MHz, CDCl₃): δ 8.01 (d, 1H), 7.22 (d, 1H), 7.09-7.05 (m, 1H), 6.94-6.92 (m, 1H), 6.80-6.77 (m, 1H) |
| 154 | 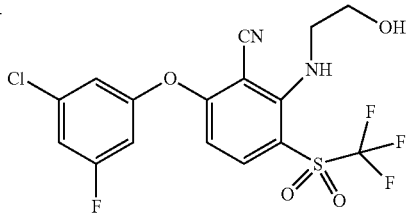 | 437 (M − H) | (400 MHz, CDCl₃): δ 7.44-7.40 (m, 1H), 7.33 (m, 1H), 7.15 (d, 1H), 6.91-6.88 (m, 1H), 6.74-6.73 (m, 1H), 6.62-6.58 (m, 1H), 3.95-3.91 (m, 2H), 3.44-3.40 (m, 2H), 1.71-1.69 (m, 1H) |

TABLE 2-continued

| No. | Structure | Mass Characterization | ¹H NMR Data |
|---|---|---|---|
| 155 | 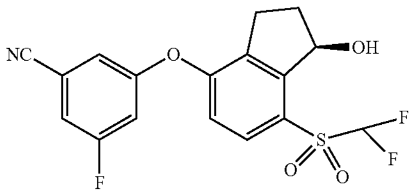 [SMILES: N#Cc1cc(F)cc(Oc2ccc(S(=O)(=O)C(F)F)c3c2CC[C@H]3O)c1] | 428 (M + HCO$_2^-$) | (400 MHz, CDCl$_3$): δ 7.85 (d, 1H), 7.26-7.24 (m, 1H), 7.17-7.15 (m, 1H), 7.06-7.03 (m, 1H), 6.97 (d, 1H), 6.37 (t, 3H), 5.68-5.65 (m, 1H), 3.20-3.11 (m, 2H), 2.94-2.87 (m, 1H), 2.51-2.41 (m, 1H), 2.31-2.25 (m, 1H) |
| 156 | 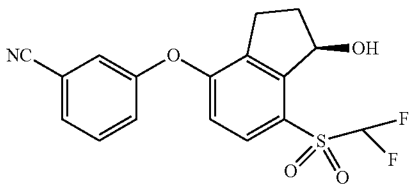 [SMILES: N#Cc1cccc(Oc2ccc(S(=O)(=O)C(F)F)c3c2CC[C@H]3O)c1] | 410 (M + HCO$_2^-$) | (400 MHz, CDCl$_3$): δ 7.80 (d, 1H), 7.56-7.54 (m, 2H), 7.39-7.30 (m, 2H), 6.88-6.84 (m, 1H), 6.38 (t, 1H), 5.68-5.66 (m, 1H), 3.22-3.13 (m, 2H), 2.98-2.90 (m, 1H), 2.50-2.41 (m, 1H), 2.32-2.22 (m, 1H) |
| 157 | 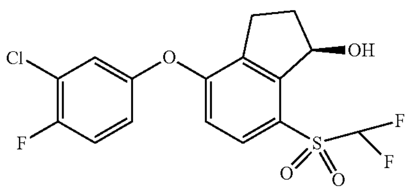 [SMILES: O=S(=O)(c1ccc(Oc2ccc(F)c(Cl)c2)c2c1[C@H](O)CC2)C(F)F] | 437 (M + HCO$_2^-$) | |
| 158 | 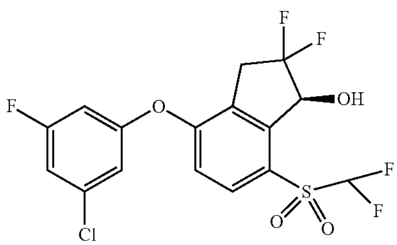 [SMILES: O=S(=O)(c1ccc(Oc2cc(F)cc(Cl)c2)c2c1[C@H](O)C(F)(F)C2)C(F)F] | 473 (M + HCO$_2^-$) | (400 MHz, CDCl$_3$): δ 7.90 (d, 1H), 7.06-7.03 (m, 1H), 6.99 (d, 1H), 6.94-6.93 (m, 1H), 6.78-6.75 (m, 1H), 6.43 (t, 1H), 5.52-5.48 (m, 1H), 3.64-3.43 (m, 2H), 3.29 (s, 1H) |
| 159 | 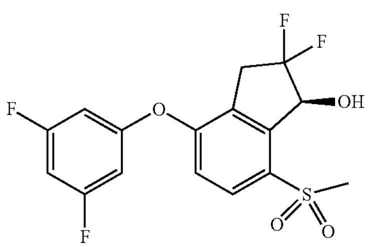 | 421 (M + HCO$_2^-$) | (400 MHz, CDCl$_3$): δ 7.89 (d, 1H), 7.01 (d, 1H), 6.74-6.68 (m, 1H), 6.62-6.58 (m, 2H), 5.61-5.57 (m, 1H), 3.54-3.40 (m, 3H), 3.22 (s, 3H) |
| 160 | 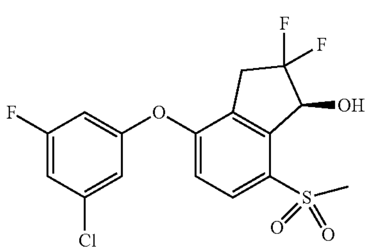 [SMILES: CS(=O)(=O)c1ccc(Oc2cc(F)cc(Cl)c2)c2c1[C@H](O)C(F)(F)C2] | 393 (M + H) | (400 MHz, CDCl$_3$): δ 7.90-7.87 (m, 1H), 7.01-6.97 (m, 2H), 6.88-6.87 (m, 1H), 6.73-6.69 (m, 1H), 5.61-5.57 (m, 1H), 3.57-3.37 (m, 3H), 3.22 (s, 3H) |
| 161 | 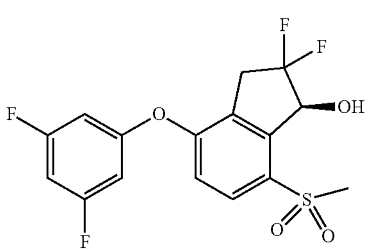 | 421 (M + HCO$_2^-$) | (400 MHz, CDCl$_3$): δ 7.89 (d, 1H), 7.01 (d, 1H), 6.74-6.68 (m, 1H), 6.62-6.58 (m, 2H), 5.61-5.57 (m, 1H), 3.54-3.40 (m, 3H), 3.22 (s, 3H) |

TABLE 2-continued

| No. | Structure | Mass Characterization | $^1$H NMR Data |
|---|---|---|---|
| 162 | 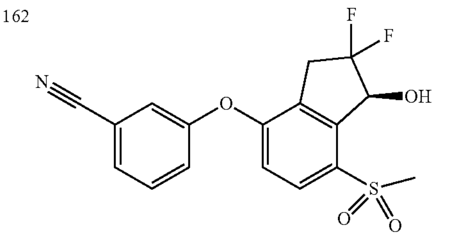 | 410 (M + HCO$_2^-$) | |
| 163 | 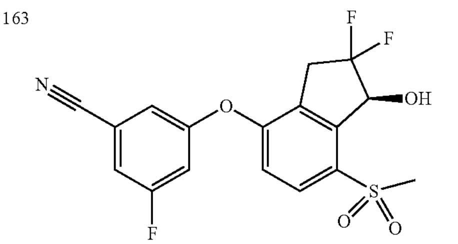 | 428 (M + HCO$_2^-$) | (400 MHz, CDCl$_3$): δ 7.93 (d, 1H), 7.27-7.24 (m, 1H), 7.15-7.14 (m, 1H), 7.07-7.03 (m, 1H), 7.00 (d, 1H), 5.63-5.58 (m, 1H), 3.56-3.35 (m, 3H), 3.24 (s, 3H) |
| 164 | 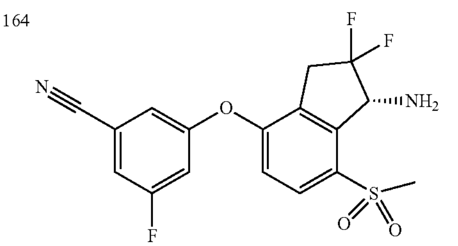 | 383 (M + H) | (400 MHz, CDCl$_3$): δ 7.93-7.91 (m, 1H), 7.25-7.22 (m, 1H), 7.14-7.13 (m, 1H), 7.06-7.02 (m, 1H), 6.96 (d, 1H), 4.97-4.93 (m, 1H), 3.55-3.37 (m, 2H), 3.32 (s, 3H) |
| 165 | 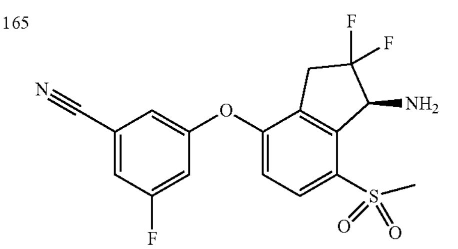 | 383 (M + H) | (400 MHz, CDCl$_3$): δ 7.93-7.91 (m, 1H), 7.25-7.22 (m, 1H), 7.14-7.13 (m, 1H), 7.06-7.02 (m, 1H), 6.96 (d, 1H), 4.97-4.93 (m, 1H), 3.55-3.37 (m, 2H), 3.32 (s, 3H) |
| 166 | 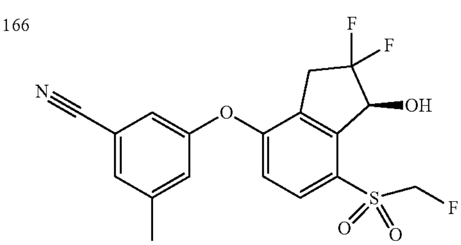 | [M − H + 46]: 442 | (400 MHz, CDCl$_3$) δ 7.87 (d, 1H), 7.38 (br s, 1H), 7.16 (br d, 1H), 6.88 (d, 1H), 5.58-5.12 (m, 3H), 3.59-3.44 (m, 3H) |
| 167 | 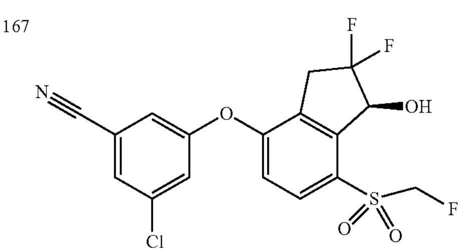 | [M − H + 46]: 462 | (400 MHz, CDCl$_3$) δ 7.92 (d, 1H), 7.36-7.33 (m, 1H), 7.32-7.27 (m, 1H), 6.97 (d, 1H), 5.58-5.12 (m, 3H), 3.62-3.38 (m, 3H) |

TABLE 2-continued

| No. | Structure | Mass Characterization | ¹H NMR Data |
|---|---|---|---|
| 168 | 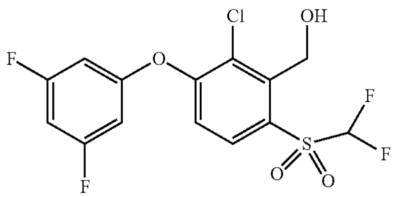 [SMILES: O=S(=O)(c1ccc(Oc2cc(F)cc(F)c2)c(Cl)c1CO)C(F)F] | [M − H + 46]: 429 | (400 MHz, CDCl$_3$) δ 8.01 (d, 1H), 7.09 (d, 1H), 6.77-6.67 (m, 1H), 6.64-6.61 (m, 2H), 6.47 (t, 1H), 5.21 (d, 2H), 2.70 (t, 1H) |
| 169 | 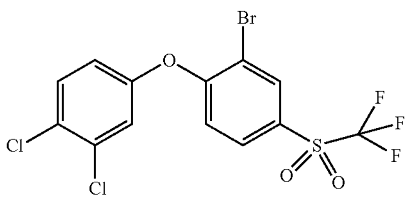 [SMILES: O=S(=O)(c1ccc(Oc2ccc(Cl)c(Cl)c2)c(Br)c1)C(F)(F)F] | | (400 MHz, CDCl$_3$): δ 8.30 (d, 1H), 7.89 (d, 1H), 7.54 (d, 1H), 7.26 (s, 1H), 6.99 (m, 2H) |
| 170 | 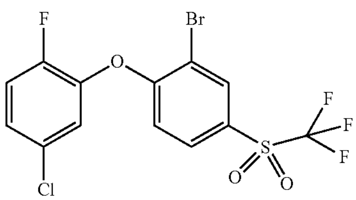 | | (400 MHz, CDCl$_3$): δ 8.30 (s, 1H), 7.88 (d, 1H), 7.21-7.31 (m, 3H), 6.90 (d, 1H) |
| 171 | 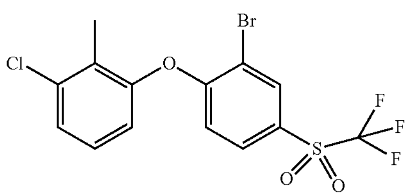 [SMILES: Cc1c(Cl)cccc1Oc1ccc(S(=O)(=O)C(F)(F)F)cc1Br] | | (400 MHz, d$_6$-DMSO): δ 8.40 (d, 1H), 8.02 (d, 1H), 7.45 (d, 1H), 7.35 (t, 1H), 7.20 (d, 1H), 6.95 (d, 1H), 2.13 (s, 3H) |
| 172 | 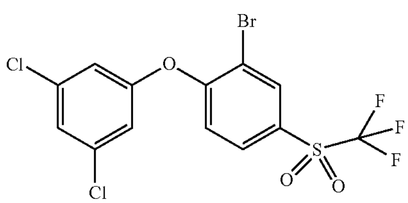 [SMILES: O=S(=O)(c1ccc(Oc2cc(Cl)cc(Cl)c2)c(Br)c1)C(F)(F)F] | | (400 MHz, CDCl$_3$): δ 8.30 (d, 1H), 7.93 (d, 1H), 7.31 (d, 1H), 7.04 (m, 3H) |
| 173 | 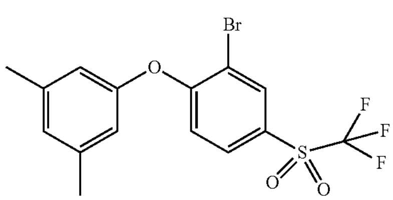 [SMILES: Cc1cc(C)cc(Oc2ccc(S(=O)(=O)C(F)(F)F)cc2Br)c1] | | (400 MHz, CDCl$_3$): δ 8.26 (d, 1H), 7.81 (d, 1H), 6.95 (s, 1H), 6.91 (d, 1H), 6.74 (s, 2H), 2.35 (s, 6H) |
| 174 | 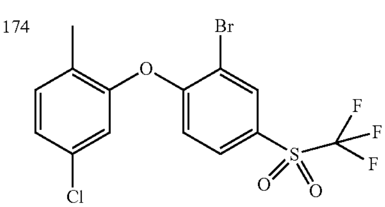 | | (400 MHz, CDCl$_3$): δ 8.29 (d, 1H), 7.84 (d, 1H), 7.22-7.27 (m, 2H), 7.06 (s, 1H), 6.78 (d, 1H), 2.16 (s, 3H) |

TABLE 2-continued

| No. | Structure | Mass Characterization | ¹H NMR Data |
|---|---|---|---|
| 175 | 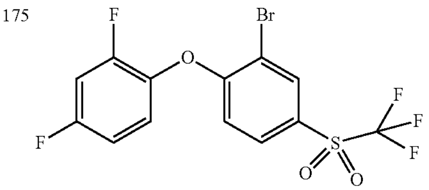 | | (400 MHz, d$_6$-DMSO): δ 8.40 (s, 1H), 8.03 (d, 1H), 7.58 (m, 2H), 7.23 (m, 1H), 7.11 (d, 1H) |
| 176 | 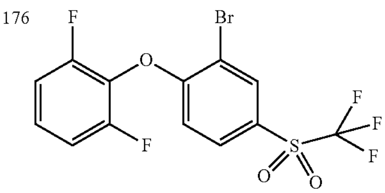 | | (400 MHz, d$_6$-DMSO): δ 8.30 (s, 1H), 7.88 (d, 1H), 7.27-7.32 (m, 1H), 7.08-7.14 (m, 2H), 6.85 (d, 1H) |
| 177 | 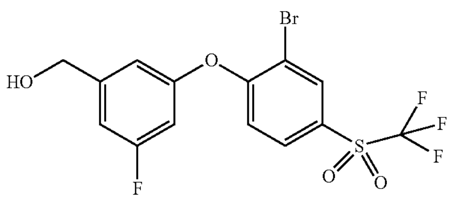 [SMILES: O=S(=O)(c1ccc(Oc2cc(F)cc(CO)c2)c(Br)c1)C(F)(F)F] | | (400 MHz, CDCl$_3$): δ 8.29 (d, 1H), 7.87 (m, 1H), 7.06 (d, 1H), 7.02 (d, 1H), 6.94 (d, 1H), 6.77 (m, 1H), 4.75 (d, 2H), 1.83 (t, 1H) |
| 178 | 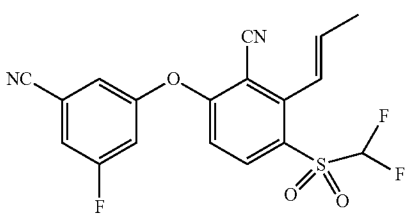 [SMILES: C/C=C/c1c(S(=O)(=O)C(F)F)ccc(Oc2cc(F)cc(C#N)c2)c1C#N] | 391 (M − H) | (400 MHz, CDCl$_3$): δ 8.18 (d, 1H), 7.38-7.35 (m, 1H), 7.29-7.27 (m, 1H), 7.21-7.18 (m, 1H), 7.07-7.02 (m, 1H), 6.90 (d, 1H), 6.56-6.47 (m, 1H), 6.22 (t, 1H), 2.08-2.06 (m, 1H) |
| 179 | 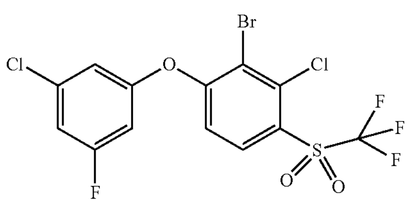 [SMILES: O=S(=O)(c1ccc(Oc2cc(F)cc(Cl)c2)c(Br)c1Cl)C(F)(F)F] | | (400 MHz, CDCl$_3$): δ 8.13 (d, 1H), 7.08-7.05 (m, 1H), 6.95-6.93 (m, 2H), 6.79-6.76 (m, 1H) |
| 180 | 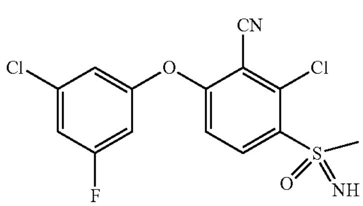 [SMILES: CS(=N)(=O)c1ccc(Oc2cc(F)cc(Cl)c2)c(C#N)c1Cl] | 359, 361 (M + H) | (400 MHz, CDCl$_3$): δ 8.33 (d, 1H), 7.09 (m, 1H), 6.97-6.95 (m, 1H), 6.94 (d, 1H), 6.81 (m, 1H), 3.32 (s, 3H), 2.94 (br s, 1H) |
| 181 | 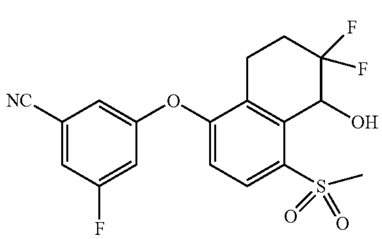 [SMILES: CS(=O)(=O)c1ccc(Oc2cc(F)cc(C#N)c2)c2c1C(O)C(F)(F)CC2] | | (400 MHz, CDCl$_3$): δ 8.04 (d, 1H), 7.23 (m, 1H), 7.12-7.10 (m, 1H), 7.03-6.99 (m, 1H), 6.07 (d, 1H), 5.54-5.49 (m, 1H), 3.68 (m, 1H), 3.26 (s, 3H), 3.20 (m, 1H), 2.97-2.86 (m, 1H), 2.63-2.45 (m, 1H), 2.35-2.25 (m, 1H) |

TABLE 2-continued

| No. | Structure | Mass Characterization | ¹H NMR Data |
|---|---|---|---|
| 182 | 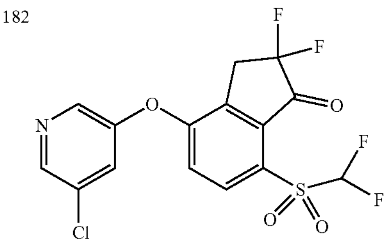 | (M + H) 410/412 | |
| 183 | 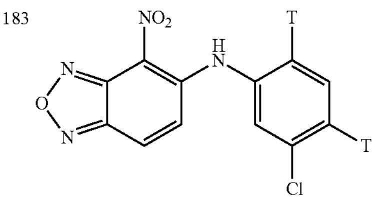 | 478 mCi | |
| 184 | 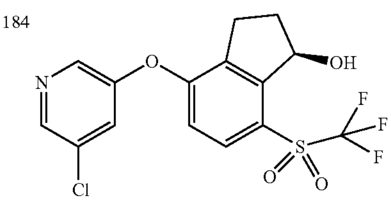 | [M + H] 394 | (400 MHz, CDCl$_3$): δ 8.47 (d, 1H), 8.35 (d, 1H), 7.82 (d, 1H), 7.45 (t, 1H), 6.88 (d, 1H), 5.64-5.59 (m, 1H), 3.30-3.15 (m, 2H), 3.02-2.93 (m, 1H) 2.46-2.26 (m, 2H) |
| 185 | 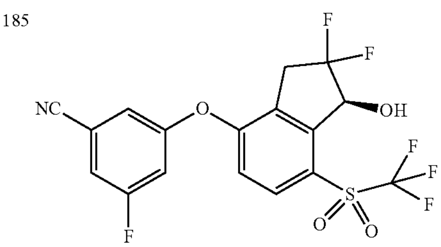 | [M − H] 436 | (400 MHz, CDCl$_3$): δ 7.95 (d, 1H), 7.35-7.31 (m, 1H), 7.26-7.23 (m, 1H), 7.15-7.11 (m, 1H), 6.99 (d, 1H), 5.46-5.39 (m, 1H), 3.63-3.41 (m, 2H), 3.36 (d, 1H) |
| 186 | 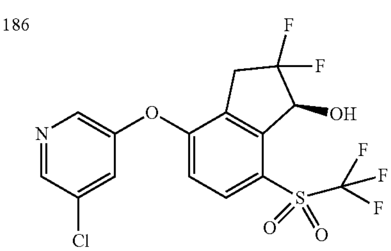 | [M + H] 430 | (400 MHz, CDCl$_3$): δ 8.55 (d, 1H), 8.40 (d, 1H), 7.91 (d, 1H), 7.52 (t, 1H), 6.94 (d, 1H), 5.46-5.40 (m, 1H), 3.85 (d, 1H), 3.66-3.47 (m, 2H) |
| 187 | 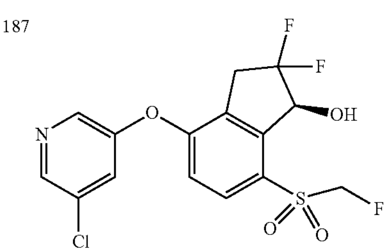 | [M + H] 394 | (400 MHz, CDCl$_3$): δ 8.51 (d, 1H), 8.37 (d, 1H), 7.90 (d, 1H), 7.48 (t, 1H), 6.93 (d, 1H), 5.61-5.11 (m, 3H), 3.94 (d, 1H), 3.62-3.42 (m, 2H) |

TABLE 2-continued
| No. | Structure | Mass Characterization | ¹H NMR Data |
|---|---|---|---|
| 188 | 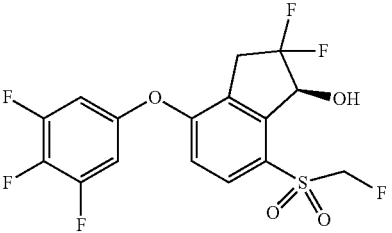 [SMILES: O=S(=O)(CF)c1ccc(Oc2cc(F)c(F)c(F)c2)c2c1[C@H](O)C(F)(F)C2] | [M − H + 46] 457 | (400 MHz, CDCl$_3$): δ 7.89 (d, 1H), 6.94 (d, 1H), 6.82-6.71 (m, 2H), 5.59-5.11 (m, 3H), 3.59-3.38 (m, 3H) |
| 189 | 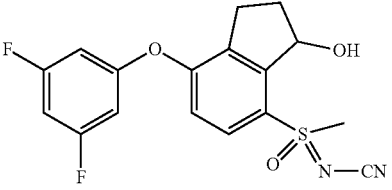 [SMILES: CS(=O)(=NC#N)c1ccc(Oc2cc(F)cc(F)c2)c2c1C(O)CC2] | [M + H] 365 | (400 MHz, CDCl$_3$): δ 7.88-7.80 (m, 1H), 6.97 (d, 1H), 6.72-6.65 (m, 1H), 6.63-6.55 (m, 2H), 5.83-5.76 (m, 1H), 3.57 (s, 1H), 3.51 (s, 3H), 3.18-3.07 (m, 1H), 2.93-2.79 (m, 1H), 2.60-2.47 (m, 1H), 2.23-2.11 (m, 1H) |
| 190 | 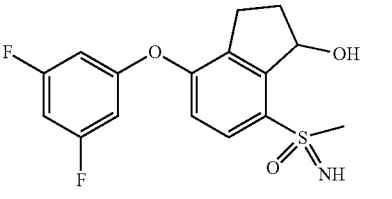 [SMILES: CS(=N)(=O)c1ccc(Oc2cc(F)cc(F)c2)c2c1C(O)CC2] | [M + H] 340 | (400 MHz, CDCl$_3$): δ 7.89-7.81 (m, 1H), 6.99-6.94 (m, 1H), 6.66-6.60 (m, 1H), 6.57-6.51 (m, 2H), 5.66-5.59 (m, 1H), 3.28 (s, 3H), 3.24 (s, 1H), 3.15-3.01 (m, 1H), 2.87-2.71 (m, 1H), 2.55-2.41 (m, 1H), 2.27-2.13 (m, 1H) |
| 191 | 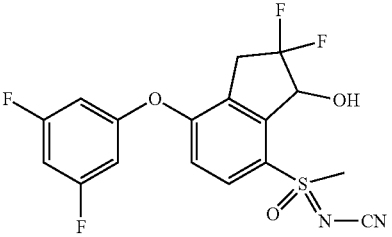 [SMILES: CS(=O)(=NC#N)c1ccc(Oc2cc(F)cc(F)c2)c2c1C(O)C(F)(F)C2] | [M + H] 401 | (400 MHz, CDCl$_3$): δ 7.98-7.91 (m, 1H), 7.04-7.01 (m, 1H), 6.80-6.73 (m, 1H), 6.69-6.61 (m, 2H), 5.73-5.63 (m, 1H), 3.60 (s, 1H), 3.58-3.40 (m, 5H) |
| 192 | 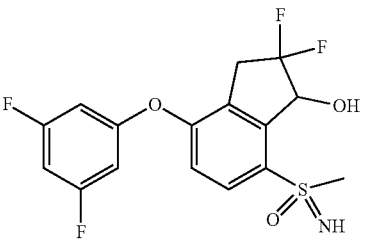 [SMILES: CS(=N)(=O)c1ccc(Oc2cc(F)cc(F)c2)c2c1C(O)C(F)(F)C2] | [M + H] 376 | (400 MHz, CDCl$_3$): δ 7.96-7.89 (m, 1H), 7.03-6.98 (m, 1H), 6.73-6.66 (m, 1H), 6.63-6.55 (m, 2H), 5.62-5.56 (m, 1H), 5.47-5.41 (m, 1H), 3.57-3.30 (m, 2H), 3.28 (s, 3H) 3.24-2.88 (m, 1H) |
| 193 | 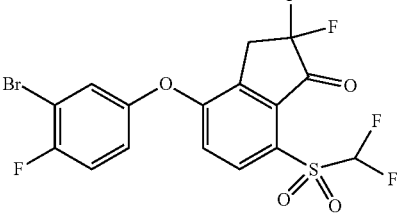 | | (400 MHz, CDCl$_3$) δ 8.18 (d, 1H), 7.41-7.39 (m, 1H), 7.30-7.26 (m, 1H), 7.13-7.05 (m, 2H), 6.91 (t, 1H), 3.67 (t, 2H) |

TABLE 2-continued

| No. | Structure | Mass Characterization | ¹H NMR Data |
|---|---|---|---|
| 194 | 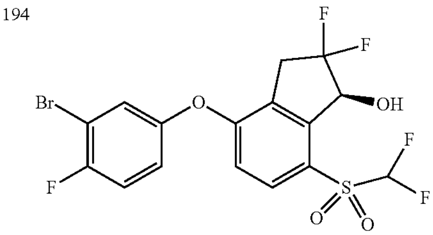 | (M + HCOOH − H): 517, 519 | (400 MHz, CDCl$_3$) δ 7.86 (d, 1H), 7.37-7.35 (m, 1H), 7.25-7.21 (m, 1H), 7.08-7.04 (m, 1H), 6.86 (d, 1H), 6.41 (t, 1H), 5.51-5.47 (m, 1H), 3.63-3.47 (m, 2H), 3.25 (d, 1H) |
| 195 | 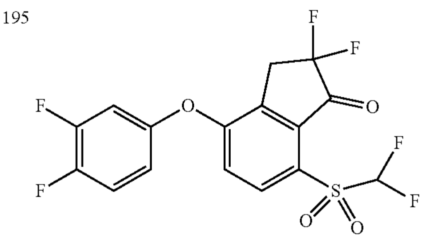 | | (400 MHz, CDCl$_3$) δ 8.16 (d, 1H), 7.32 (q, 1H), 7.13 (d, 1H), 7.06-7.02 (m, 1H), 6.93-6.91 (m, 1H), 6.90 (t, 1H), 3.67 (t, 2H) |
| 196 | 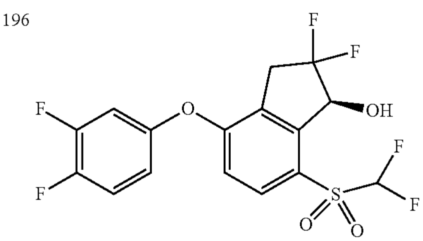 | (M + HCOOH − H) 457 | (400 MHz, CDCl$_3$) δ 7.86 (d, 1H), 7.30-7.24 (m, 1H), 7.02-6.97 (m, 1H), 6.89-6.86 (m, 2H), 6.41 (t, 1H), 5.51-5.47 (m, 1H), 3.63-3.47 (m, 2H), 3.27 (d, 1H) |
| 197 | 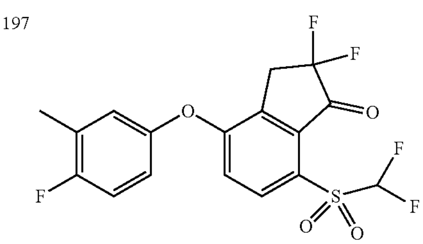 | | (400 MHz, CDCl$_3$) δ 8.14 (d, 1H), 7.15-7.05 (m, 2H), 6.99-6.91 (m, 2H), 6.92 (t, 1H), 3.67 (t, 2H), 2.33 (m, 3H) |
| 198 | 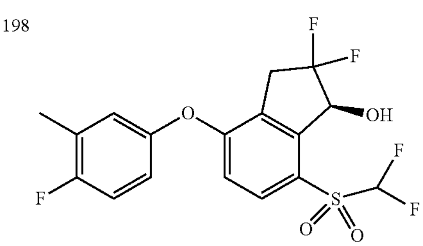 | (M + HCOOH − H) 453 | (400 MHz, CDCl$_3$) δ 7.82 (d, 1H), 7.09 (t, 1H), 6.93-6.88 (m, 2H), 6.82 (d, 1H), 6.40 (t, 1H), 5.48 (m, 1H), 3.63-3.48 (m, 2H), 3.25 (d, 1H), 2.31 (m, 3H) |
| 199 | 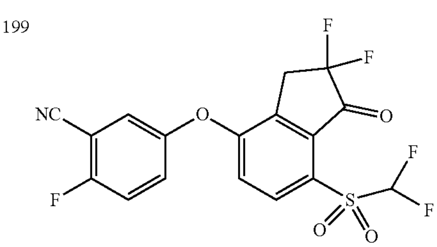 | | (400 MHz, CDCl$_3$) δ 8.20 (d, 1H), 7.47-7.38 (m, 3H), 7.11 (d, 1H), 6.92 (t, 1H), 3.68 (t, 2H) |

TABLE 2-continued

| No. | Structure | Mass Characterization | ¹H NMR Data |
|---|---|---|---|
| 200 | 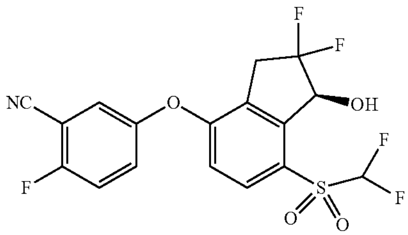 [SMILES: N#Cc1cc(Oc2ccc(S(=O)(=O)C(F)F)c3c2CC(F)(F)[C@H]3O)ccc1F] | (M + HCOOH − H) 464 | (400 MHz, CDCl$_3$) δ 7.89 (d, 1H), 7.41-7.32 (m, 3H), 6.85 (d, 1H), 6.43 (t, 1H), 5.57-5.48 (m, 1H), 3.59-3.49 (m, 2H), 3.29 (d, 1H) |
| 201 | 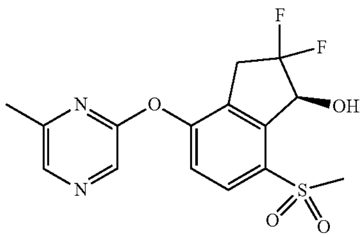 | (M + HCOOH − H) 401 | (400 MHz, CDCl$_3$) δ 8.31 (s, 1H), 8.28 (s, 1H), 7.94 (d, 1H), 7.33 (d, 1H), 5.61-5.58 (m, 1H), 3.57 (d, 1H), 3.51-3.28 (m, 2H), 3.24 (s, 3H), 2.44 (s, 3H) |
| 202 | 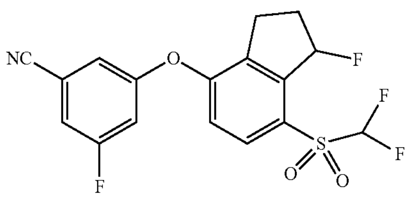 [SMILES: N#Cc1cc(F)cc(Oc2ccc(S(=O)(=O)C(F)F)c3c2CCC3F)c1] | (M + HCOOH − H) 428 | (400 MHz, CDCl$_3$) δ 7.95 (d, 1H), 7.28-7.26 (m, 1H), 7.18 (brd s, 1H), 7.08-7.03 (m, 2H), 6.64-6.47 (m, 1H), 6.34 (t, 1H), 3.23-3.14 (m, 1H), 3.04-2.95 (m, 1H), 2.57-2.42 (m, 2H) |
| 203 | 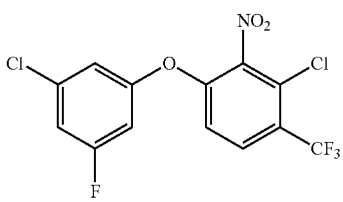 [SMILES: O=[N+]([O-])c1c(Oc2cc(F)cc(Cl)c2)ccc(C(F)(F)F)c1Cl] | | (400 MHz, CDCl$_3$) δ 7.78-7.75 (m, 1H), 7.05-7.02 (m, 1H), 7.00-6.98 (m, 1H), 6.93-6.92 (m, 1H), 6.78-6.75 (m, 1H) |
| 204 | 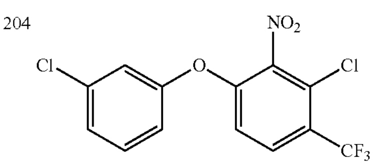 | 350, 352, 354 (M − H) | (400 MHz, CDCl$_3$): δ 7.71 (d, 1H), 7.38 (t, 1H), 7.31-7.26 (m, 1H), 7.14 (t, 1H), 7.03-7.00 (m, 1H), 6.91 (d, 1H) |
| 205 | 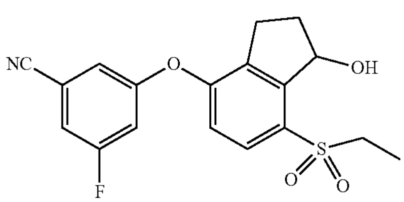 [SMILES: CCS(=O)(=O)c1ccc(Oc2cc(F)cc(C#N)c2)c2c1C(O)CC2] | | (400 MHz, CDCl$_3$): δ 7.79 (d, 1H), 7.18 (d, 1H), 7.09 (s, 1H), 6.98 (m, 2H), 5.65 (m, 1H), 3.69 (d, 1H), 3.29 (m, 2H), 3.08 (m, 1H), 2.83 (m, 1H), 2.45 (m, 1H), 2.24 (m, 1H), 1.36 (t, 3H) |
| 206 | 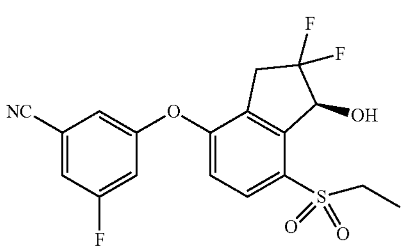 | 442 (M + HCO2) | (400 MHz, CDCl$_3$): δ 7.86 (m, 1H), 7.27-7.24 (m, 1H), 7.16-7.14 (m, 1H), 7.07-7.04 (m, 1H), 6.99 (d, 1H), 5.55-5.51 (m, 1H), 3.61-3.27 (m, 5H), 1.35 (t, 3H) |

TABLE 2-continued

| No. | Structure | Mass Characterization | ¹H NMR Data |
|---|---|---|---|
| 207 | 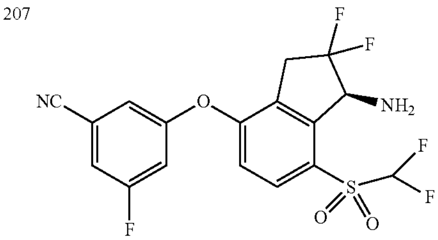 | 419 (M + H) | (400 MHz, CDCl$_3$): δ 7.94 (d, 1H), 7.32-7.28 (m, 1H), 7.22-7.19 (m, 1H), 7.12-7.07 (m, 1H), 6.94 (d, 1H), 6.83 (t, 1H), 4.91 (d, 1H), 3.60-3.40 (m, 2H), 1.91 (br s, 2H) |
| 208 | 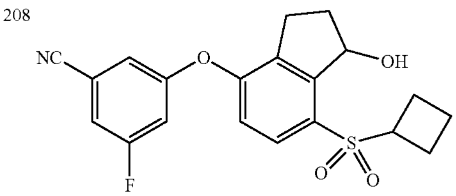 | | (400 MHz, CDCl$_3$): δ 7.73 (d, 1H), 7.18 (d, 1H), 7.08 (s, 1H), 6.95 (m, 2H), 5.62 (m, 1H), 4.02 (m, 1H), 3.77 (s, 1H), 3.07 (m, 1H), 2.81 (m, 1H), 2.61 (m, 2H), 2.45 (m 1H), 2.26 (m, 3H), 2.06 (m, 2H) |
| 209 | 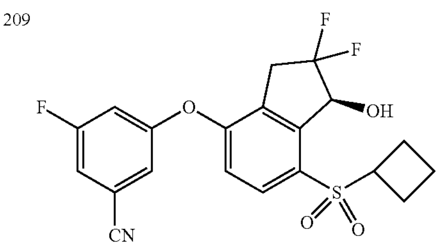 | 468 (M + HCO2) | (400 MHz, CDCl$_3$): δ 7.81 (d, 1H), 7.27-7.24 (m, 1H), 7.15-7.14 (m, 1H), 7.06-7.03 (m, 1H), 6.96 (d, 1H), 5.50-5.45 (m, 1H), 3.70 (d, 1H), 3.55-3.34 (m, 2H), 2.67-2.50 (m, 2 H), 2.29-2.17 (m, 2H), 2.08-2.01 (m, 2H) |
| 210 | 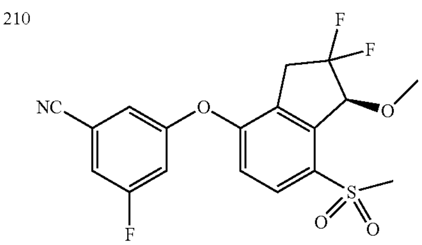 | 398 (M + H) | (400 MHz, CDCl$_3$): δ 7.95 (d, 1H), 7.24(d, 1H), 7.13 (br s, 1H), 7.05-7.01 (m, 1H), 6.99 (d, 1H), 5.31 (d, 1H), 3.78 (s, 3H), 3.53-3.32 (m, 2H), 3.19 (s, 3H) |
| 211 | 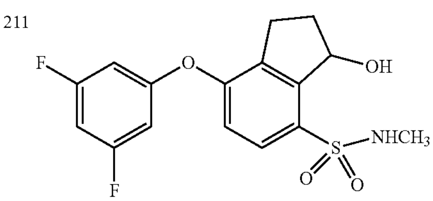 | 354 (M − H) | (400 MHz, CDCl$_3$): δ 7.75 (d, 1H), 6.94 (d, 1H), 6.65-6.60 (m, 1H), 6.54-6.52 (m, 2H), 5.77-5.71 (m, 1H), 5.02-4.95 (m, 1H), 3.23-3.18 (m, 1H), 3.12-3.04 (m, 1H), 2.84-2.70 (m, 1H), 2.65 (m, 3H), 2.57-2.47 (m, 1H), 2.19-2.11 (m, 1H) |
| 212 | 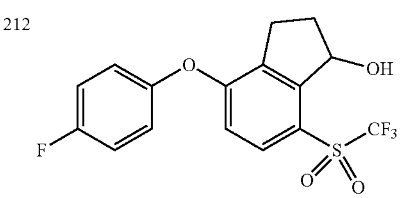 | | (400 MHz, CDCl$_3$): δ 7.77 (d, 1H), 7.05-7.26 (m, (d, 4H), 6.75 1H), 5.62 (m, 1H), 3.17-3.30 (m, 2H), 2.98-3.07 (m, 1H), 2.40-2.47 (m, 1H), 2.28-2.37 (m, 1H) |
| 213 | 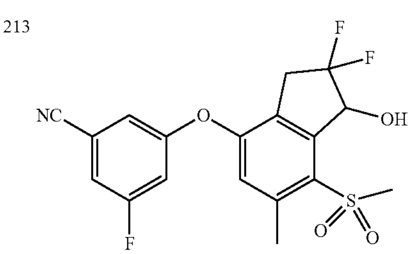 | | (400 MHz, CDCl$_3$): δ 7.22-7.25 (m, 1H), 7.08 and 7.12 (m 1H), 6.98-7.04 (m 1H), 6.80 (s, 1H), 5.58 and 5.78 (m 1H), 3.69 (d, 1H), 3.20 and 3.23 (s, 3H), 3.08-3.47 (m, 2H), 2.68 (s, 3H) |

TABLE 2-continued

| No. | Structure | Mass Characterization | ¹H NMR Data |
|---|---|---|---|
| 214 | 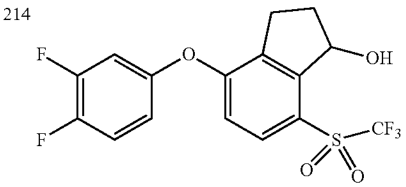 | | (400 MHz, d$_6$-DMSO): 7.87 (d, 1H), 7.51-7.64 (m, 2H), 7.11-7.16 (m, 1H), 6.96 (d, 1H), 5.51 (m, 1H), 5.30 (d, 1H), 3.04-3.31 (m, 1H), 2.87-2.95 (m, 1H), 2.11-2.30 (m, 1H), 1.99-2.09 (m, 1H) |
| 215 | 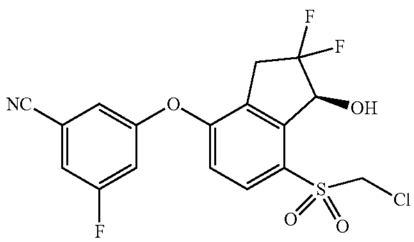 [SMILES: N#Cc1cc(F)cc(Oc2ccc(S(=O)(=O)CCl)c3c2CC(F)(F)[C@H]3O)c1] | | (400 MHz, CDCl$_3$): 7.92 (d, 1H), 7.27 (m, 2H), 7.08 (d, 1H), 6.99 (d, 1H), 5.63 (dd, 1H), 4.92 (d, 1H), 4.65 (d, 1H), 3.34-3.49 (m, 2H), 3.21 (s, 1H) |
| 216 | 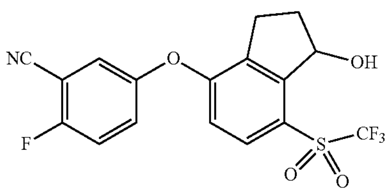 [SMILES: N#Cc1cc(Oc2ccc(S(=O)(=O)C(F)(F)F)c3c2CCC3O)ccc1F] | | (400 MHz, CDCl$_3$): 7.83 (d, 1H), 7.26-7.38 (m, 3H), 6.81 (d, 1H), 5.64 (dd, 1H), 3.16-3.25 (m, 2H), 3.00-3.04 (m 1H), 2.34-2.42 (m, 2H) |
| 217 | 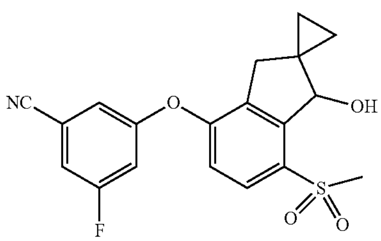 | 418 (M + HCO$_2^-$) | (400 MHz, CDCl$_3$): 7.88 (d, 1H), 7.17 (d, 1H), 7.09 (s, 1H), 7.06 (m, 2H), 5.07 (d, 1H), 3.20 (m, 5H), 2.60 (d, 1H), 1.18-1.32 (m, 2H), 0.68-0.87 (m, 2H) |
| 218 | 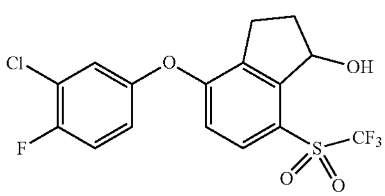 [SMILES: O=S(=O)(c1ccc(Oc2ccc(F)c(Cl)c2)c2c1C(O)CC2)C(F)(F)F] | | (400 MHz, CDCl3): 7.80 (d, 1H), 7.18-7.23 (m, 2H), 6.97-7.01 (m, 1H), 6.80 (d, 1H), 5.63 (m 1H), 3.16-3.29 (m, 2H), 2.96-3.05 (m 1H), 2.29-2.46 (m, 2H) |
| 219 | 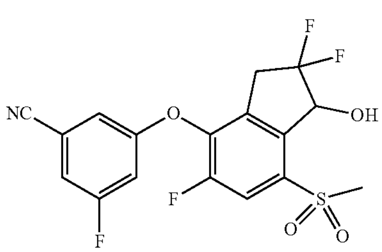 [SMILES: CS(=O)(=O)c1cc(F)c(Oc2cc(F)cc(C#N)c2)c2c1C(O)C(F)(F)C2] | | (400 MHz, d6-DMSO): δ 7.85 (d, 1H), 7.67 (m, 1H), 7.46 (d, 1H), 6.85 (d, 1H), 5.38 (dd, 1H), 3.40-3.49 (m, 2H), 3.40 (s, 3H) |
| 220 | 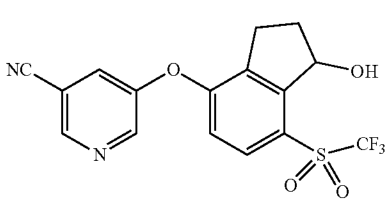 [SMILES: N#Cc1cncc(Oc2ccc(S(=O)(=O)C(F)(F)F)c3c2CCC3O)c1] | | |

TABLE 2-continued

| No. | Structure | Mass Characterization | ¹H NMR Data |
|---|---|---|---|
| 221 | 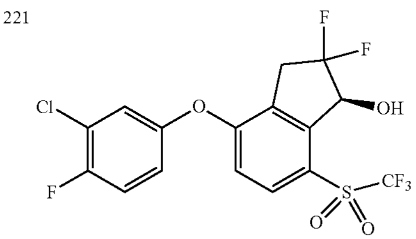 | 445, 447 (M − H) | (400 MHz, CDCl₃): δ 7.97 (d, 1H), 7.28-7.22 (m, 2H), 7.02 (d, 1H), 6.87 (d, 1H), 5.43-5.39 (m, 1H), 3.64-3.47 (m, 2H), 3.26 (d, 1H) |
| 222 | 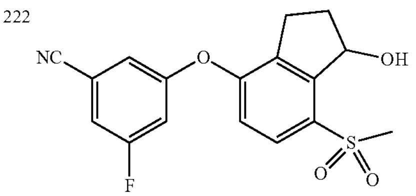 | 392 (M + HCO₂⁻) | (400 MHz, CDCl₃): δ 7.84 (d, 1H), 7.19-7.17 (m, 1H), 7.08 (s, 1H), 7.00-6.97 (m, 2H), 5.71-5.68 (m, 1H), 3.64 (d, 1H), 3.21 (s, 3H), 3.12-3.04 (m, 1H), 2.84-2.76 (m, 1H), 2.52-2.43 (m, 1H), 2.27-2.19 (m, 1H) |
| 223 | 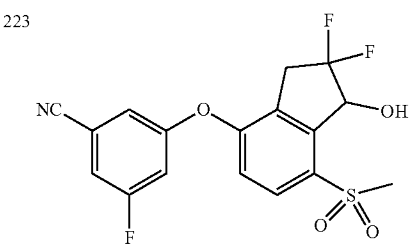 | 428 (M + HCO₂⁻) | (400 MHz, CDCl₃): δ 7.93 (d, 1H), 7.27-7.24 (m, 1H), 7.15-7.14 (m, 1H), 7.07-7.03 (m, 1H), 7.00 (d, 1H), 5.63-5.58 (m, 1H), 3.56-3.35 (m, 3H), 3.24 (s, 3H) |
| 224 | 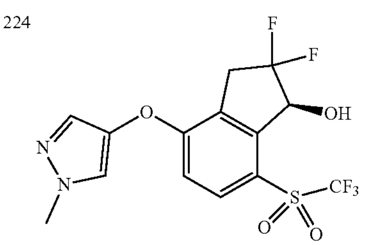 | 399 (M + H) | (400 MHz, CDCl₃): δ 7.87 (d, 1H), 7.40 (s, 1H), 7.36 (s, 1H), 7.08 (d, 1H), 5.42-5.38 (m, 1H), 3.94 (s, 3H), 3.59-3.52 (m, 2H), 3.21 (d, 1H) |
| 225 | 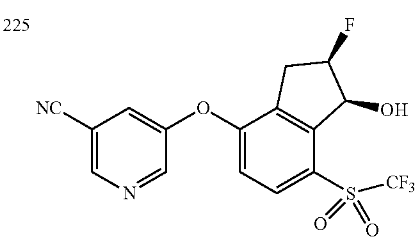 | 401 (M − H) | (400 MHz, CDCl₃): δ 8.82 (d, 1H), 8.70 (d, 1H), 7.95 (d, 1H), 7.71-7.69 (m, 1H), 6.94 (d, 1H), 5.64-5.59 (m, 1H), 5.46-5.31 (m, 1H), 3.36-3.27 (m, 2H), 3.19 (d, 1H) |
| 226 | 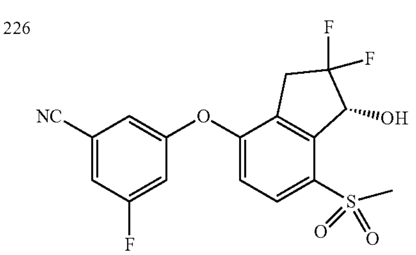 | 428 (M + HCO₂⁻) | (400 MHz, CDCl₃): δ 7.93 (d, 1H), 7.27-7.24 (m, 1H), 7.15-7.14 (m, 1H), 7.07-7.03 (m, 1H), 7.00 (d, 1H), 5.63-5.58 (m, 1H), 3.56-3.35 (m, 3H), 3.24 (s, 3H) |

TABLE 2-continued

| No. | Structure | Mass Characterization | ¹H NMR Data |
|---|---|---|---|
| 227 | 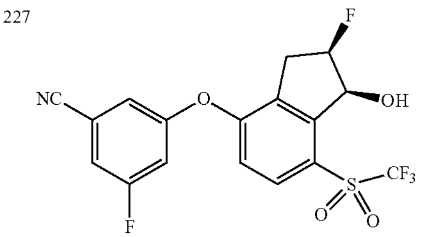 | 428 (M + HCO₂⁻) | (400 MHz, CDCl₃): δ 7.93 (d, 1H), 7.27-7.24 (m, 1H), 7.15-7.14 (m, 1H), 7.07-7.03 (m, 1H), 7.00 (d, 1H), 5.63-5.58 (m, 1H), 3.56-3.35 (m, 3H), 3.24 (s, 3H) |
| 228 | 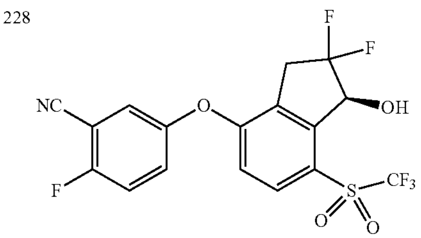 | 436 (M − H) | (400 MHz, CDCl₃): δ 7.90 (d, 1H), 7.42-7.30 (m, 3H), 6.86 (d, 1H), 5.42 (dd, 1H), 3.58-3.47 (m, 2H), 3.32 (d, 1H) |
| 229 | 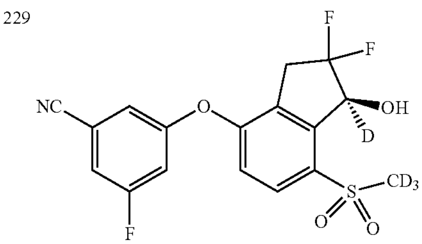 | 432 (M + HCO₂⁻) | (400 MHz, CDCl₃): δ 7.92 (d, 1H), 7.26-7.24 (m, 1H), 7.15 (s, 1H), 7.06-7.03 (m, 1H), 7.01 (d, 1H), 3.56-3.35 (m, 3H) |
| 230 | 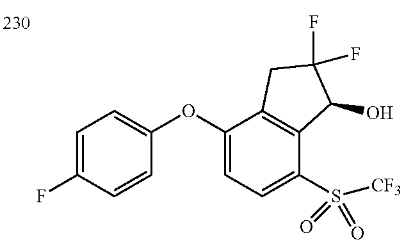 | 411 (M − H) | (400 MHz, CDCl₃): δ 7.85 (d, 1H), 7.19-7.08 (m, 4H), 6.83 (d, 1H), 5.42 (dd, 1H), 3.65-3.49 (m, 2H), 3.25 (dd, 1H) |
| 231 | 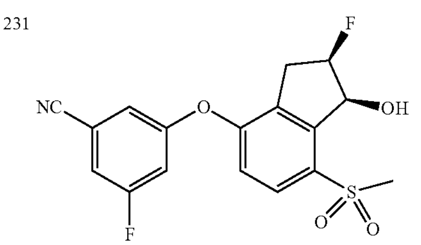 | 383 (M + NH₄⁺) | (400 MHz, CDCl₃): δ 7.92 (d, 1H), 7.21-7.20 (m, 1H), 7.12-7.11 (m, 1H), 7.03-6.98 (m, 2H), 5.71-5.65 (m, 1H), 5.46-5.33 (m, 1H), 3.66 (dd, 1H), 3.31 (s, 3H), 3.27-3.05 (m, 2H) |
| 232 | 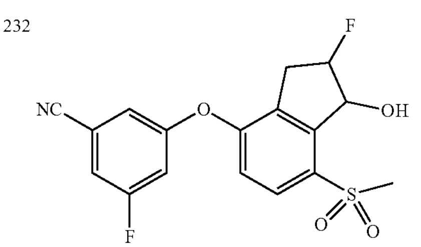 | 383 (M + NH₄⁺) | (400 MHz, CDCl₃): δ 7.92 (d, 1H), 7.21-7.20 (m, 1H), 7.12-7.11 (m, 1H), 7.03-6.98 (m, 2H), 5.71-5.65 (m, 1H), 5.46-5.33 (m, 1H), 3.66 (dd, 1H), 3.31 (s, 3H), 3.27-3.05 (m, 2H) |

TABLE 2-continued

| No. | Structure | Mass Characterization | ¹H NMR Data |
|---|---|---|---|
| 233 | 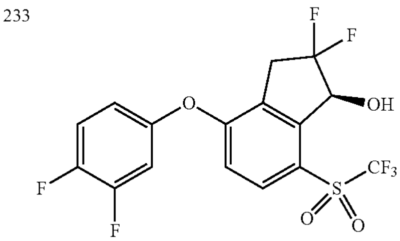 | 429 (M − H) | (400 MHz, CDCl₃): δ 7.88 (d, 1H), 7.32-7.25 (m, 1H), 7.03-6.98 (m, 1H), 6.91-6.86 (m, 2H), 5.42 (dd, 1H), 3.64-3.47 (m, 2H), 3.22 (d, 1H) |
| 234 | 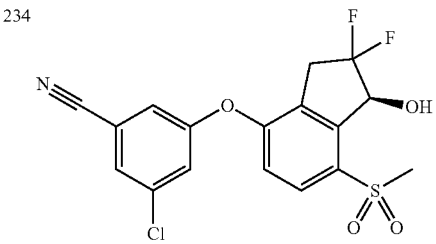 | 444 (M + HCO₂⁻) | (400 MHz, CDCl₃): δ 7.92 (d, 1H), 7.52-7.51 (m, 1H), 7.32-7.31 (m, 1H), 7.25-7.24 (m, 1H), 6.98 (d, 1H), 5.62-5.58 (m, 1H), 3.56-3.35 (m, 3H), 3.24 (s, 3H) |
| 235 | 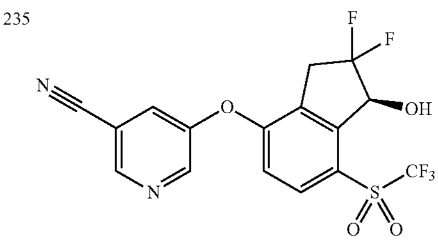 | 419 (M − H) | (400 MHz, CDCl₃): δ 8.84 (d, 1H), 8.73 (d, 1H), 7.96 (d, 1H), 7.75-7.74 (m, 1H), 6.95 (d, 1H), 5.45 (dd, 1H), 3.64-3.48 (m, 2H), 3.31 (d, 1H) |
| 236 | 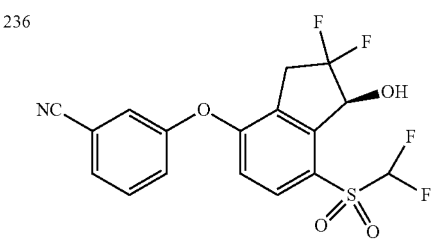 | 419 (M + NH4) | (400 MHz, CDCl₃): δ 7.89 (d, 1H), 7.62-7.57 (m, 2H), 7.42 (s, 1H), 7.39-7.34 (m, 1H), 6.90 (d, 1H), 6.44 (t, 1H), 5.51 (dd, 1H), 5.63-5.45 (m, 2H), 3.37 (d, 1H) |
| 237 | 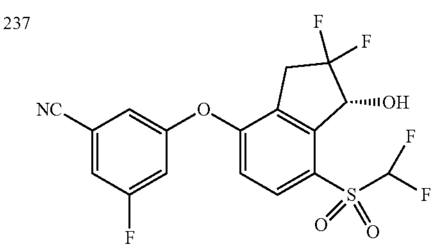 | | |
| 238 | 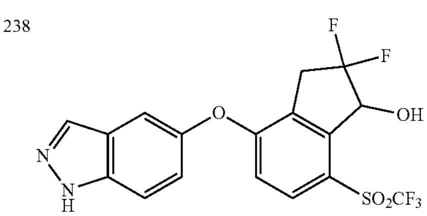 | [M + H] 435 | (400 MHz, CDCl₃): δ 10.35 (br s, 1H), 8.14 (s, 1H), 7.82 (d, 1H), 7.61 (d, 1H), 7.51 (d, 1H), 7.21-7.17 (m, 1H), 6.82 (d, 1H), 5.44 (d, 1H), 3.70-3.57 (m, 2H), 3.40 (br s, 1H) |

TABLE 2-continued

| No. | Structure | Mass Characterization | ¹H NMR Data |
|---|---|---|---|
| 239 | 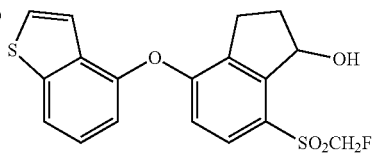 | [M + formic acid] 459 | (400 MHz, CDCl₃): δ 7.78 (d, 1H), 7.68 (d, 1H), 7.44 (d, 1H), 7.37 (t, 1H), 7.23 (d, 1H), 7.00 (d, 1H), 6.71 (d, 1H), 5.73-5.68 (m, 1H), 5.38-5.12 (m, 2H), 3.37-3.33 (m, 1H), 3.32-3.22 (m, 1H) 3.07-2.99 (m, 1H), 2.56-2.46 (m, 1H), 2.35-2.24 (m, 1H) |
| 240 | 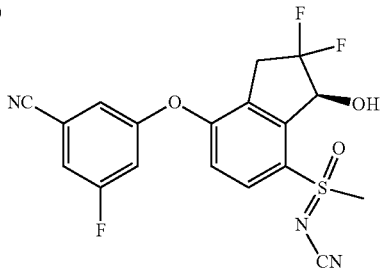 | [M + H] 408 | (400 MHz, CD₃OD): δ 8.01 (d, 1H), 7.54-7.49 (m, 1H), 7.46-7.44 (m, 1H), 7.40-7.36 (m, 1H), 7.20-7.14 (m, 1H), 5.56 (d, 1H), 3.78-3.61 (m, 1H), 3.62 (s, 3H), 3.55-3.47 (m, 1H) |
| 241 | 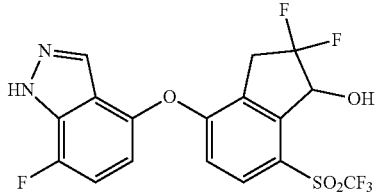 | [M + 1] 453 | (400 MHz, CDCl₃): δ 10.55 (br s, 1H), 7.94 (d, 1H), 7.83 (d, 1H), 7.16-7.10 (m, 1H), 6.86 (d, 1H), 6.83-6.78 (m, 1H), 5.46 (d, 1H), 3.72-3.59 (m, 2H), 3.34 (br s, 1H) |
| 242 | 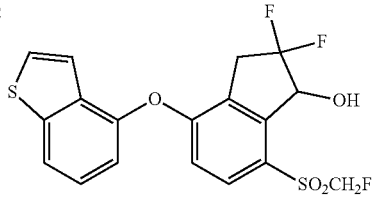 | [M + formic acid] 459 | (400 MHz, CDCl₃): δ 7.83-7.76 (m, 2H), 7.47 (d, 1H), 7.40 (t, 1H), 7.21-7.19 (m, 1H), 7.05 (d, 1H), 6.76 (d, 1H), 5.61-5.11 (m, 3H), 3.71-3.57 (m, 2H), 3.30 (br s, 1H) |
| 243 | 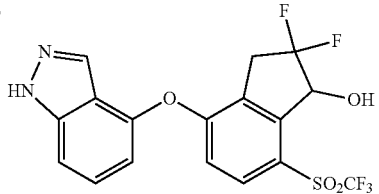 | [M + H] 435 | (400 MHz, CDCl₃): δ 10.45 (br s, 1H), 7.93 (s, 1H), 7.84 (d, 1H), 7.48-7.41 (m, 2H), 6.92 (d, 1H), 6.86 (dd, 1H), 5.46 (d, 1H), 3.72-3.59 (m, 2H), 3.44 (br s, 1H) |
| 244 | 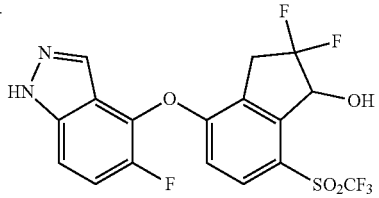 | [M + H] 453 | (400 MHz, CDCl₃): δ 10.35 (br s, 1H), 7.96 (s, 1H), 7.84 (d, 1H), 7.47-7.43 (m, 1H), 7.39-7.33 (m, 1H), 6.81 (dd, 1H), 5.46 (d, 1H), 3.74-3.59 (m, 2H), 3.36 (br s, 1H) |
| 245 | 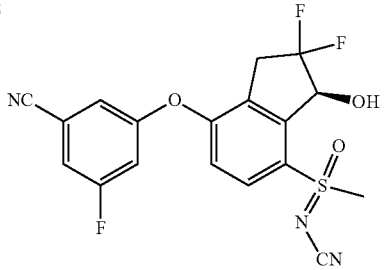 [SMILES: CS(=O)(=NC#N)c1ccc(Oc2cc(F)cc(C#N)c2)c2c1[C@H](O)C(F)(F)C2] | [M + H] 408 | (400 MHz, CDCl₃): δ 8.01 (d, 1H), 7.32-7.28 (m, 1H), 7.22-7.20 (m, 1H), 7.14-7.09 (m, 1H), 7.02 (d, 1H), 5.67 (d, 1H), 4.22 (br s, 1H), 3.65 (s, 3H), 3.60-3.40 (m, 2H) |

TABLE 2-continued

| No. | Structure | Mass Characterization | ¹H NMR Data |
|---|---|---|---|
| 246 | 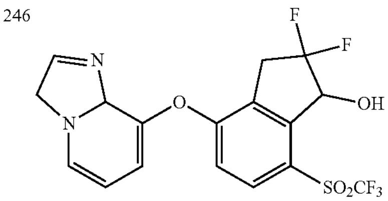 | [M + H] 435 | (400 MHz, CDCl$_3$): δ 8.15 (d, 1H), 7.82 (d, 1H), 7.72 (s, 1H), 7.65 (s, 1H), 6.99 (d, 1H), 6.88-6.81 (m, 2H), 5.43 (d, 1H), 3.76-3.63 (m, 2H), 3.51 (br s, 1H) |
| 247 | 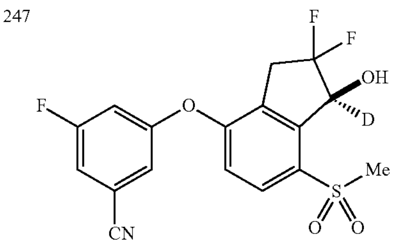 | (M + H) 385 | (400 MHz, CDCl$_3$): δ 7.93 (d, 1H), 7.27-7.23 (m, 1H), 7.16-7.13 (m, 1H), 7.07-6.98 (m, 2H), 3.56-3.34 (m, 3H), 3.24 (s, 3H) |
| 248 | 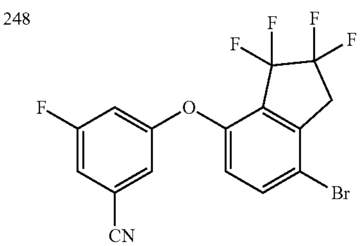 | (M − H) 402, 404 | (400 MHz, CDCl$_3$): δ 7.70 (d, 1H), 7.20-7.15 (m, 1H), 7.10-7.08 (m, 1H), 7.02 (dt, 1H), 6.86 (d, 1H), 3.50 (t, 2H) |
| 249 | 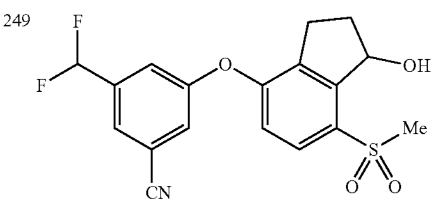 | (M + NH$_4$) 397 | (400 MHz, CDCl$_3$): δ 7.83 (d, 1H), 7.60 (s, 1H), 7.41 (s, 1H), 7.37 (s, 1H), 6.94 (d, 1H), 6.65 (t, 1H), 5.72-5.68 (m, 1H), 3.64 (br d, 1H), 3.22 (s, 3H), 3.14-3.04 (m, 1H), 2.81 (ddd, 1H), 2.54-2.43 (m, 1H), 2.28-2.19 (m, 1H) |
| 250 | 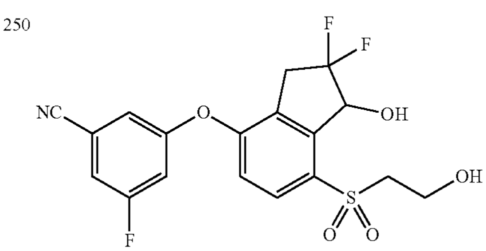 | 414 (M + H) | (400 MHz, CDCl$_3$): δ 7.90 (d, 1H), 7.27-7.24 (m, 1H), 7.16 (br s, 1H), 7.06 (d, 1H), 7.00 (d, 1H), 5.62 (d, 1H), 4.00 1.16 (m, 2H), 3.30-3.74 (m, 4H) |
| 251 | 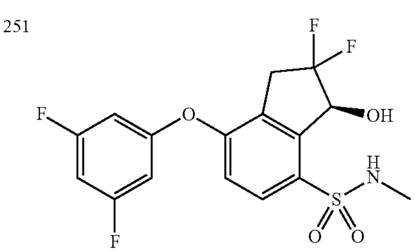 | 392 (M + H) | (400 MHz, CDCl$_3$): δ 7.82 (d, 1H), 6.97 (d, 1H), 6.69 (t, 1H), 6.64-6.54 (m, 2H), 5.62 (d, 1H), 5.04-4.96 (m, 1H), 3.50-3.30 (m, 2H), 2.64 (d, 3H) |

| No. | Structure | Mass Characterization | $^1$H NMR Data |
|---|---|---|---|
| 252 | 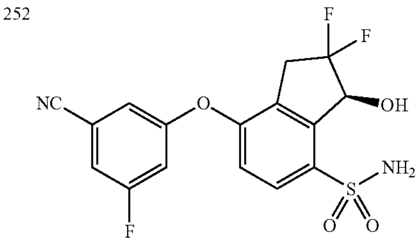 | 383 (M − H) | (400 MHz, CDCl$_3$): δ 7.93 (d, 1H), 7.26-7.20 (m, 1H), 7.12 (br s, 1H), 7.04-6.96 (m, 2H), 5.74-5.66 (m, 1H), 5.28 (br s, 2H), 3.50-3.32 (m, 2H) |
| 253 | 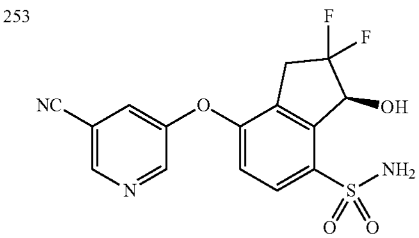 | 368 (M + H) | (400 MHz, CDCl$_3$): δ 8.67 (s, 1H), 8.58 (s, 1H), 7.85 (d, 1H), 7.58 (s, 1H), 6.89 (d, 1H), 5.54 (d, 2H), 3.50-3.24 (m, 2H) |
| 254 | 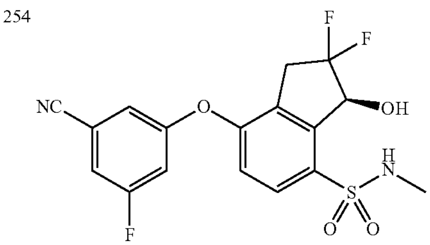 | 399 (M + H) | (400 MHz, CDCl$_3$): δ 7.85 (d, 1H), 7.25-7.18 (m, 1H), 7.13 (brs, 1H), 7.08-6.92 (m, 2H), 5.68-5.56 (m, 1H), 5.05 (br s, 1H), 3.58-3.30 (m, 2H), 2.65 (s, 3H) |
| 255 | 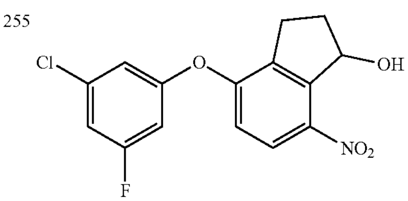 | 322 (M − H) | (400 MHz, CDCl$_3$): δ 8.06 (d, 1H), 6.97-6.93 (m, 1H), 6.85-6.83 (m, 1H), 6.69-6.66 (m, 1H), 3.37 (d, 1H), 3.20-3.12 (m, 1H), 2.93-2.85 (m, 1H), 2.52-2.43 (m, 1H), 2.32-2.25 (m, 1H) |
| 256 | 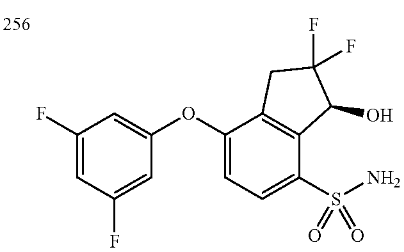 | 378 (M + H) | (400 MHz, CDCl$_3$): δ 7.89 (d, 1H), 6.98 (d, 1H), 6.72-6.60 (m, 1H), 6.62-6.52 (m, 2H), 5.72-5.64 (m, 1H), 5.29 (br s, 2H), 3.56-3.34 (m, 2H) |
| 257 | 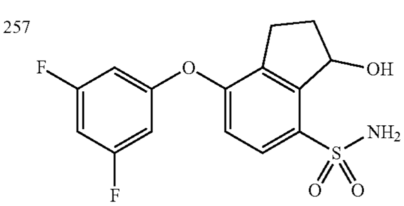 | 340 (M − H) | (400 MHz, CDCl$_3$): δ 7.82 (d, 1H), 6.95 (d, 1H), 6.62 (t, 1H), 6.55-6.50 (m, 2H), 5.84-5.80 (m, 2H), 5.34 (br s, 2H), 3.11-3.03 (m, 1H), 2.83-2.75 (m, 1H), 2.61-2.52 (m, 1H), 2.19-2.10 (m, 1H) |
| 258 | 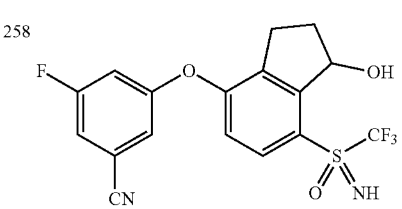 | (M − H) 399 | (400 MHz, CDCl$_3$): δ 7.96 (d, 1H), 7.27-7.22 (m, 1H), 7.18-7.15 (m, 1H), 7.07-7.03 (m, 1H), 6.97 (d, 1H), 5.59 (d, 1H), 4.59 (s, 1H), 3.89 (s, 1H), 3.18 (dt, 1H), 2.96 (ddd, 1H), 2.43-2.27 (m, 2H) |

TABLE 2-continued

| No. | Structure | Mass Characterization | ¹H NMR Data |
|---|---|---|---|
| 259 | 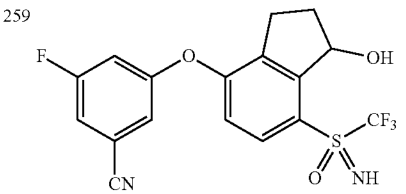 | (M − H) 399 | (400 MHz, CDCl$_3$): δ 8.01 (d, 1H), 7.25-7.21 (m, 1H), 7.17-7.14 (m, 1H), 7.06-7.01 (m, 1H), 6.96 (d, 1H), 5.78-5.73 (m, 1H), 3.96-3.93 (m, 1H), 3.73 (s, 1H), 3.13 (dt, 1H), 2.87 (ddd, 1H), 2.52-2.41 (m, 1H), 2.31-2.23 (m, 1H) |
| 260 | 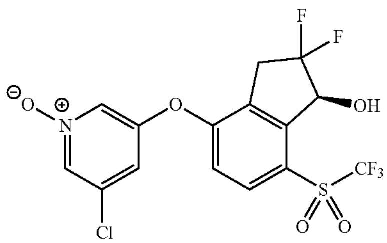 [SMILES: O=S(=O)(c1ccc(Oc2cc(Cl)c[n+]([O-])c2)c2c1[C@H](O)C(F)(F)C2)C(F)(F)F] | (M + H) 446, 448 | (400 MHz, CDCl$_3$): δ 8.17 (s, 1H), 8.03 (s, 1H), 7.99 (d, 1H), 7.11 (d, 1H), 7.08 (s, 1H), 5.44 (dd, 1H), 3.64-3.42 (m, 3H) |
| 261 | 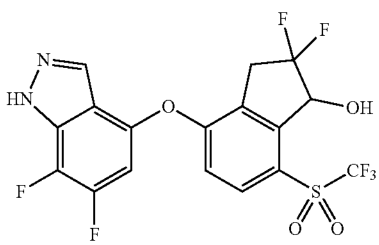 [SMILES: O=S(=O)(c1ccc(Oc2cc(F)c(F)c3[nH]ncc23)c2c1C(O)C(F)(F)C2)C(F)(F)F] | (M + H) 471 | (400 MHz, CDCl$_3$): δ 7.95 -7.87 (m, 2H), 6.95 (d, 1H), 6.77 (dd, 1H), 5.46 (d, 1H), 3.66-3.58 (m, 2H), 3.25 (m, 1H) |
| 262 | 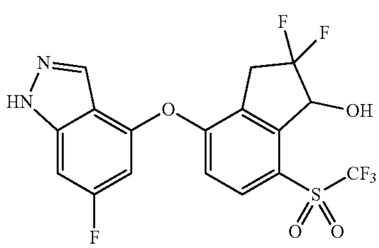 [SMILES: O=S(=O)(c1ccc(Oc2cc(F)cc3[nH]ncc23)c2c1C(O)C(F)(F)C2)C(F)(F)F] | (M + H) 453 | (400 MHz, CDCl$_3$): δ 7.91 -7.88 (m, 2H), 7.12 (d, 1H), 7.03 (d, 1H), 6.66 (d, 1H), 6.46 (d, 1H), 3.66-3.56 (m, 2H), 3.26 (br s, 1H) |
| 263 | 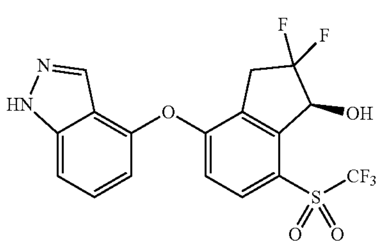 [SMILES: O=S(=O)(c1ccc(Oc2cccc3[nH]ncc23)c2c1[C@H](O)C(F)(F)C2)C(F)(F)F] | (M + H) 435 | (400 MHz, CDCl$_3$): δ 7.92 (s, 1H), 7.84 (d, 1H), 7.48-7.42 (m, 2H), 6.92 (d, 1H), 6.86 (d, 1H), 5.46 (d, 1H), 3.68-3.59 (m, 2H), 3.28 (br s, 1H) |
| 264 | 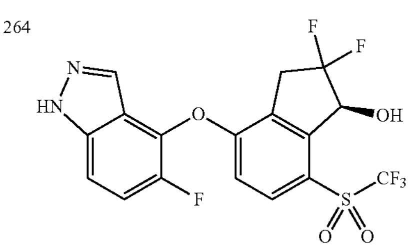 | (M + H) 453 | (400 MHz, CDCl$_3$): δ 7.93 (d, 1H), 7.84 (d, 1H), 7.13 (t, 1H), 6.81 (d, 1H), 6.86 (d, 1H), 5.46 (d, 1H), 3.68-3.69 (m, 2H), 3.29 (br s, 1H) |

TABLE 2-continued

| No. | Structure | Mass Characterization | ¹H NMR Data |
|---|---|---|---|
| 265 | 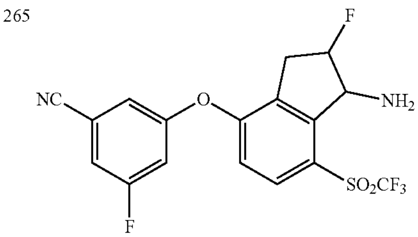 | 419 (M + H) | (400 MHz, CDCl$_3$): δ 7.90 (d, 1H), 7.30-7.28 (m, 1H), 7.19 (br s, 1H), 7.10-7.06 (m, 1H), 6.92 (d, 1H), 5.44-5.26 (m, 1H), 4.93 (t, 1H), 3.40-3.24 (m, 2H), 1.95 (br s, 2H) |
| 266 | 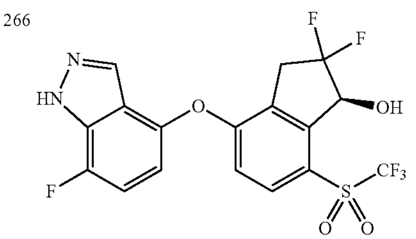 | (M + H) 453 | (400 MHz, CDCl$_3$): δ 7.96 (s, 1H), 7.83 (d, 1H), 7.36 (t, 1H), 6.81 (d, 1H), 6.68 (d, 1H), 5.47 (d, 1H), 3.74-3.65 (m, 2H), 3.28 (br s, 1H) |
| 267 | 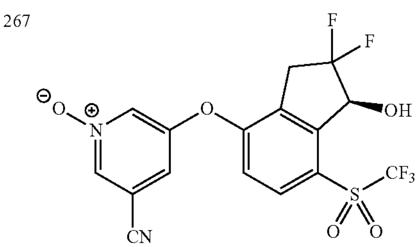 | (M − H) 435 | (400 MHz, CDCl$_3$): δ 8.32 (s, 1H), 8.23 (s, 1H), 8.03 (d, 1H), 7.23 (s, 1H), 7.13 (d, 1H), 5.46 (dd, 1H), 3.64-3.42 (m, 2H), 3.25 (d, 1H) |
| 268 | 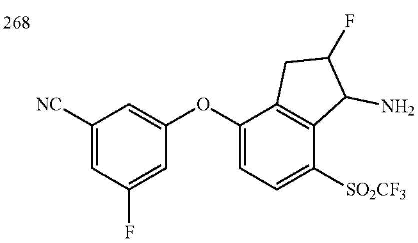 | 419 (M + H) | (400 MHz, CDCl$_3$): δ 7.90 (d, 1H), 7.30-7.28 (m, 1H), 7.22 (br s, 1H), 7.12-7.08 (m, 1H), 6.95 (d, 1H), 5.25-5.12 (m, 1H), 4.95 (d, 1H), 3.52-3.46 (m, 1H), 3.29-3.18 (m, 1H), 1.73 (br s, 2H) |
| 269 | 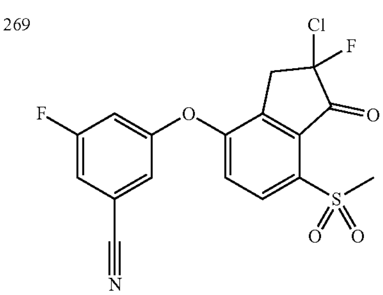 | 398/400 (M + NH$_4^+$) | (400 MHz, CDCl$_3$): δ 8.23-8.21 (m, 1H), 7.35-7.32 (m, 1H), 7.26-7.24 (m, 1H), 7.23-7.21 (m, 1H), 7.14-7.10 (m, 1H), 3.97-3.78 (m, 2H), 3.43 (s, 3H) |
| 270 | 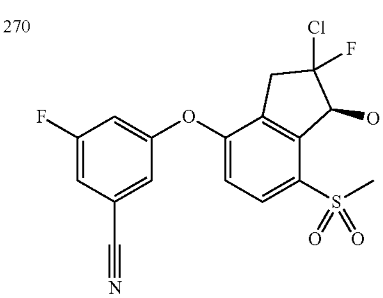 | 417/419 (M + NH$_4^+$) | (400 MHz, CDCl$_3$): δ 7.95-7.91 (m, 1H), 7.26-7.23 (m, 1H), 7.14-7.13 (m, 1H), 7.06-7.00 (m, 2H), 5.80-5.78 (m, 0.5H), 5.65-5.61 (m, 0.5H), 3.81-3.55 (m, 3.5H), 3.25 (s, 1.5H), 3.24 (s, 1.5H) |

TABLE 2-continued

| No. | Structure | Mass Characterization | $^1$H NMR Data |
|---|---|---|---|
| 271 | 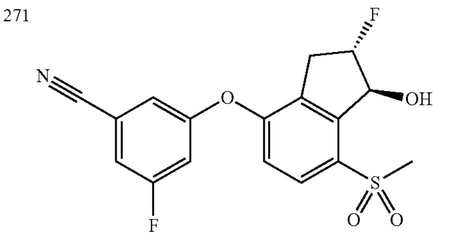 | 383 (M + NH$_4^+$) | (400 MHz, CDCl$_3$): δ 7.87 (d, 1H), 7.23-7.21 (m, 1H), 7.13-7.12 (m, 1H), 7.05-7.00 (m, 2H), 5.62-5.56 (m, 1H), 5.44-5.29 (m, 1H), 3.66 (dd, 1H), 3.49-3.35 (m, 1H), 3.20 (s, 3H), 3.17-3.06 (m, 1H) |
| 272 | 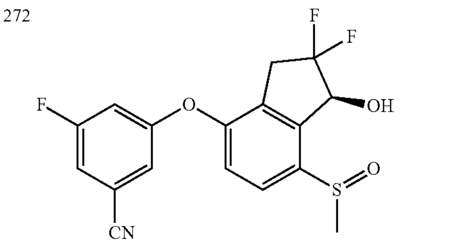 | [M + H] 368 | (400 MHz, CDCl$_3$): δ 7.84-7.80 (m, 1H), 7.19-7.16 (m, 1H), 7.10 (d, 1H), 7.08-7.06 (m, 1H), 7.00-6.96 (m, 1H), 5.40 (d, 1H), 4.48-4.36 (m, 1H), 3.49-3.27 (m, 2H), 2.93 (s, 3H) |
| 273 | 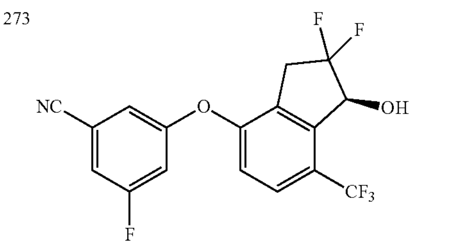 | [M + formate − H] 418 | (400 MHz, CDCl$_3$): δ 7.63 (d, 1H), 7.21-7.18 (m, 1H), 7.11-7.09 (m, 1H), 7.03-6.97 (m, 2H), 5.29 (d, 1H), 3.51-3.28 (m, 2H), 2.76 (br s, 1H) |
| 274 | 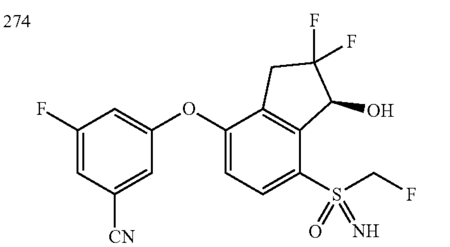 | (M + H) 401 | (400 MHz, CDCl$_3$): δ 7.95 (d, 1H), 7.28-7.25 (m, 1H), 7.17-7.15 (m, 1H), 7.06 (dt, 1H), 7.00 (d, 1H), 5.62-5.56 (m, 1H), 5.37 (dd, 1H), 5.24 (dd, 1H), 4.26 (d, 1H), 3.57-3.34 (m, 2H), 3.20 (br d, 1H) |
| 275 | 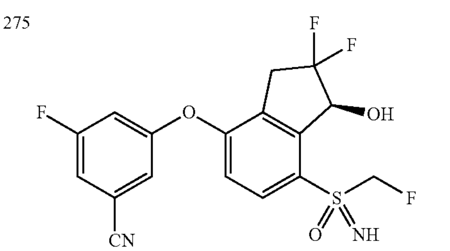 | (M + H) 401 | (400 MHz, CDCl$_3$): δ 7.96 (d, 1H), 7.28-7.25 (m, 1H), 7.18-7.16 (m, 1H), 7.06 (dt, 1H), 7.01 (d, 1H), 5.42 (dd, 1H), 5.27 (dd, 1H), 5.15 (dd, 1H), 5.04-5.02 (m, 1H), 3.62-3.38 (m, 2H), 3.33 (br s, 1H) |
| 276 | 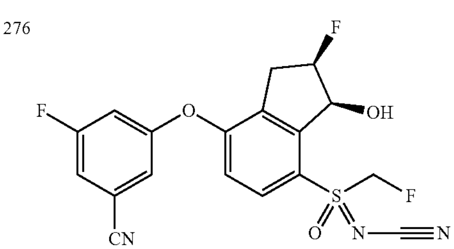 | (M + H) 408 | (400 MHz, CDCl$_3$): δ 8.00 (d, 1H), 7.30 (ddd, 1H), 7.21-7.19 (m, 1H), 7.09 (dt, 1H), 6.99 (d, 1H), 5.92 (dd, 1H), 5.76-5.69 (m, 1H), 5.65 (dd, 1H), 5.55-5.37 (m, 1H), 3.43-3.18 (m, 2H), 3.22 (dd, 1H) |

TABLE 2-continued

| No. | Structure | Mass Characterization | ¹H NMR Data |
|---|---|---|---|
| 277 | 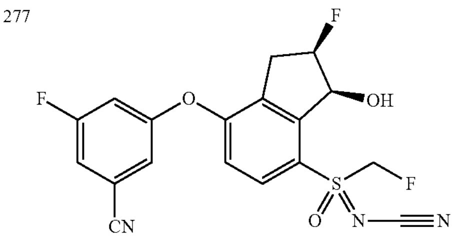 | (M + H) 408 | (400 MHz, CDCl$_3$): δ 8.04 (d, 1H), 7.31 (ddd, 1H), 7.24-7.22 (m, 1H), 7.11 (dt, 1H), 7.00 (d, 1H), 6.27 (dd, 1H), 5.75-5.69 (m, 1H), 5.55 (dd, 1H), 5.56-5.39 (m, 1H), 3.45-3.22 (m, 2H), 3.12 (t, 1H) |
| 278 | 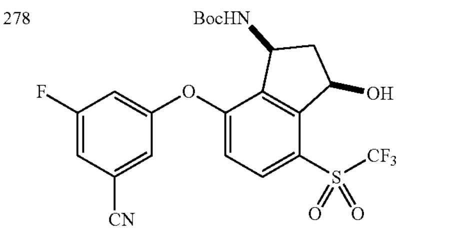 | (M + Cl⁻) 551, 553 | (400 MHz, CDCl$_3$): δ 7.97 (d, 1H), 7.27-7.23 (m, 1H), 7.17-7.13 (m, 1H), 7.07 (dt, 1H), 7.02 (d, 1H), 5.54 (dd, 1H), 5.49-5.41 (m, 1H), 5.12 (br d, 1H), 3.33 (br s, 1H), 2.73-2.64 (m, 1H), 2.22 (d, 1H), 1.35 (s, 9H) |
| 279 | 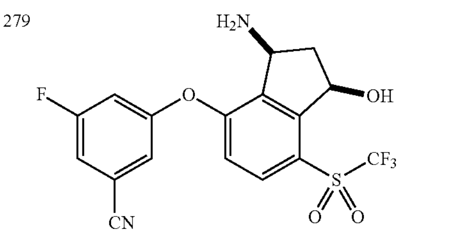 | (M + H) 417 | (400 MHz, CDCl$_3$): δ 7.93 (d, 1H), 7.31 (ddd, 1H), 7.26-7.24 (m, 1H), 7.16 (dt, 1H), 6.94 (d, 1H), 5.53 (d, 1H), 4.59 (d, 1H), 2.69-2.61 (m, 1H), 2.35-1.95 (m, 4H) |
| 280 | 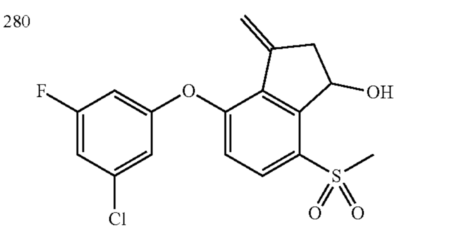 | (M + H) 369, 371 | (400 MHz, CDCl$_3$): δ 7.79 (d, 1H), 6.98 (ddd, 1H), 6.91 (d, 1H), 6.91-6.89 (m, 1H), 6.74 (dt, 1H), 5.97 (t, 1H), 5.68 (dt, 1H), 5.41 (t, 1H), 3.75 (d, 1H), 3.26-3.17 (m, 1H), 3.20 (s, 3H), 2.91-2.84 (m, 1H) |
| 281 | 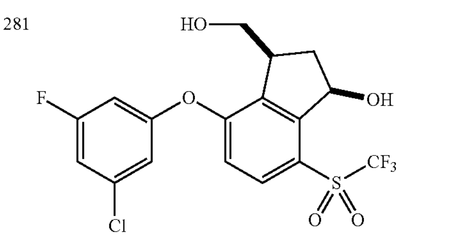 | (M + H) 387, 389 | (400 MHz, CDCl$_3$): δ 7.85 (d, 1H), 6.95 (ddd, 1H), 6.92 (d, 1H), 6.88-6.85 (m, 1H), 6.70 (dt, 1H), 5.65 (d, 1H), 4.24-4.06 (br m, 1H), 4.08 (dd, 1H), 3.88 (dd, 1H), 3.64-3.59 (m, 1H), 3.26 (s, 3H), 2.69 (ddd, 1H), 2.66-2.48 (br m, 1H), 2.12 (d, 1H) |
| 282 | 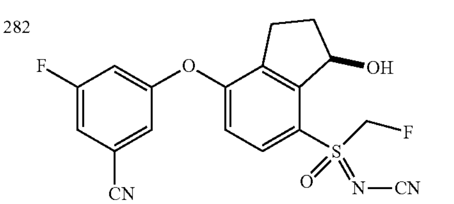 | (M + H) 390 | (400 MHz, CDCl$_3$): δ 7.93 (d, 1H), 7.27 (ddd, 1H), 7.20-7.18 (m, 1H), 7.08 (dt, 1H), 7.00 (d, 1H), 5.98 (dd, 1H), 5.80-5.75 (m, 1H), 5.49 (dd, 1H), 3.17 (dt, 1H), 2.94 (ddd, 1H), 2.86 (d, 1H), 2.62-2.51 (m, 1H), 2.29-2.20 (m, 1H) |
| 283 | 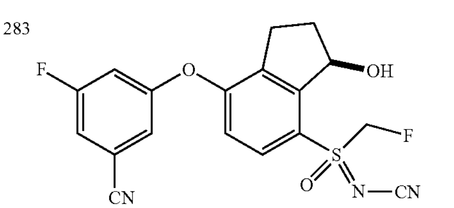 | (M + H) 390 | (400 MHz, CDCl$_3$): δ 7.91 (d, 1H), 7.27 (ddd, 1H), 7.19-7.16 (m, 1H), 7.06 (dt, 1H), 6.98 (d, 1H), 5.85-5.79 (m, 1H), 5.72 (dd, 1H), 5.61 (dd, 1H), 3.15 (ddd, 1H), 2.97 (d, 1H), 2.89 (ddd, 1H), 2.62-2.52 (m, 1H), 2.27-2.18 (m, 1H) |

TABLE 2-continued

| No. | Structure | Mass Characterization | ¹H NMR Data |
|---|---|---|---|
| 284 | 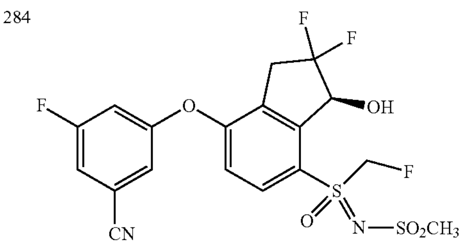 | (M + H) 479 | (400 MHz, CDCl$_3$): δ 8.04 (d, 1H), 7.30 (ddd, 1H), 7.22-7.19 (m, 1H), 7.10 (dt, 1H), 7.01 (d, 1H), 5.97 (dd, 1H), 5.70 (dd, 1H), 5.60 (dd, 1H), 3.68 (d, 1H), 3.61-3.39 (m, 2H), 3.23 (s, 3H) |
| 285 | 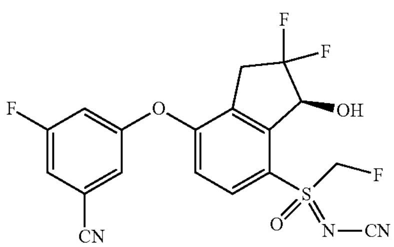 [SMILES: N#CN=S(=O)(CF)c1ccc(Oc2cc(F)cc(C#N)c2)c2c1[C@H](O)C(F)(F)C2] | (M + H) 426 | (400 MHz, CDCl$_3$): δ 8.01 (d, 1H), 7.34 (ddd, 1H), 7.25-7.22 (m, 1H), 7.12 (dt, 1H), 7.01 (d, 1H), 5.75 (dd, 1H), 5.71-5.65 (m, 1H), 5.61 (dd, 1H), 3.64-3.45 (m, 2H), 3.14 (dd, 1H) |
| 286 | 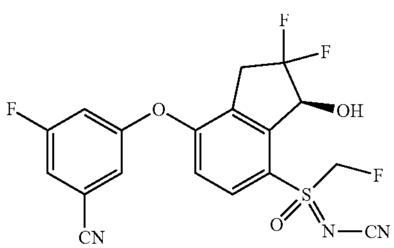 [SMILES: N#CN=S(=O)(CF)c1ccc(Oc2cc(F)cc(C#N)c2)c2c1[C@H](O)C(F)(F)C2] | (M + H) 426 | (400 MHz, CDCl$_3$): δ 8.03 (d, 1H), 7.34 (ddd, 1H), 7.26-7.24 (m, 1H), 7.14 (dt, 1H), 7.02 (d, 1H), 6.02 (dd, 1H), 5.65-5.59 (m, 1H), 5.54 (dd, 1H), 3.66-3.48 (m, 2H), 3.30 (dd, 1H) |
| 287 | 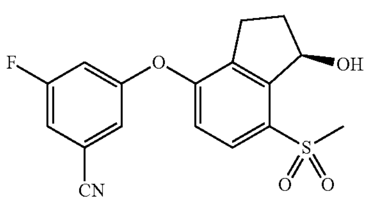 | 392 (M + HCO$_2^-$) | (400 MHz, CDCl$_3$): δ 7.83 (d, 1H), 7.19-7.16 (m, 1H), 7.09-7.07 (m, 1H), 7.01-6.96 (m, 2H), 5.71-5.67 (m, 1H), 3.64 (d, 1H), 3.21 (s, 3H), 3.12-3.02 (m, 1H), 2.84-2.75 (m, 1H), 2.52-2.42 (m, 1H), 2.27-2.18 (m, 1H) |
| 288 | 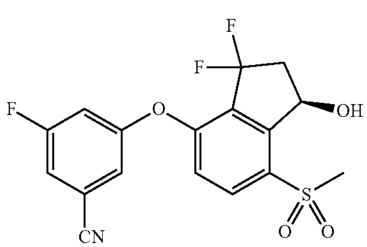 | 428 (M + HCO$_2^-$) | (400 MHz, CDCl$_3$): δ 8.08 (d, 1H), 7.29-7.23 (m, 1H), 7.19 (brs, 1H), 7.15-7.08 (m, 1H), 7.02 (d, 1H), 5.78-5.70 (m, 1H), 3.89 (d, 1H), 3.23 (s, 3H), 3.17-3.02 (m, 1H), 2.80-2.64 (m, 1H) |
| 289 | 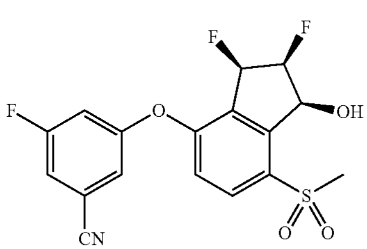 [SMILES: CS(=O)(=O)c1ccc(Oc2cc(F)cc(C#N)c2)c2c1[C@H](O)[C@H](F)[C@@H]2F] | 384 (M + H) | (400 MHz, CDCl$_3$): δ 8.13 (d, 1H), 7.31-7.25 (m, 1H), 7.23-7.19 (m, 1H), 7.14-7.09 (m, 1H), 7.04 (d, 1H), 6.09-5.91 (m, 1H), 5.87-5.80 (m, 1H), 5.25-5.05 (m, 1H), 3.32 (s, 3H), 2.95 (d, 1H) |

TABLE 2-continued

| No. | Structure | Mass Characterization | ¹H NMR Data |
|---|---|---|---|
| 290 | 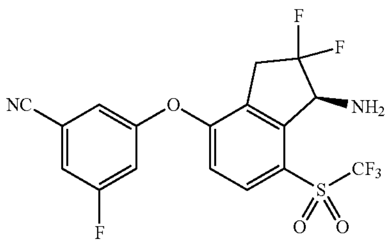 [SMILES: N#Cc1cc(F)cc(Oc2ccc(S(=O)(=O)C(F)(F)F)c3c2CC(F)(F)[C@H]3N)c1] | 437 (M + H) | (400 MHz, CDCl$_3$): δ 7.92 (d, 1H), 7.34-7.30 (m, 1H), 7.24-7.22 (m, 1H), 7.14-7.10 (m, 1H), 6.94 (d, 1H), 4.85 (d, 1H), 3.65-3.41 (m, 2H) |
| 291 | 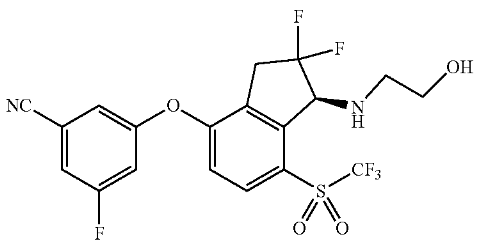 [SMILES: N#Cc1cc(F)cc(Oc2ccc(S(=O)(=O)C(F)(F)F)c3c2CC(F)(F)[C@H]3NCCO)c1] | 481 (M + H) | (400 MHz, CDCl$_3$): δ 7.95 (d, 1H), 7.35-7.31 (m, 1H), 7.24-7.22 (m, 1H), 7.14-7.10 (m, 1H), 6.95 (d, 1H), 4.59 (d, 1H), 3.77-3.52 (m, 2H), 3.42 (t, 2H), 3.06 (t, 2H) |
| 292 | 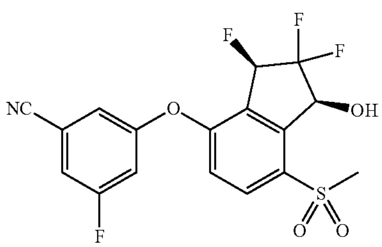 [SMILES: CS(=O)(=O)c1ccc(Oc2cc(F)cc(C#N)c2)c2c1[C@H](O)C(F)(F)[C@@H]2F] | 419 (M + NH$_4^+$) | (400 MHz, CDCl$_3$): δ 8.14-8.11 (m, 1H), 7.33-7.29 (m, 1H), 7.25-7.23 (m, 1H), 7.16-7.12 (m, 1H), 7.05 (d, 1H), 5.91-5.75 (m, 1H), 5.71-5.65 (m, 1H), 3.39 (d, 1H), 3.25 (s, 3H) |
| 293 | 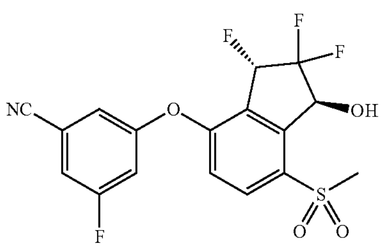 [SMILES: CS(=O)(=O)c1ccc(Oc2cc(F)cc(C#N)c2)c2c1[C@H](O)C(F)(F)[C@H]2F] | 419 (M + NH$_4^+$) | (400 MHz, CDCl$_3$): δ 8.10-8.07 (m, 1H), 7.32-7.28 (m, 1H), 7.23-7.20 (m, 1H), 7.15-7.10 (m, 1H), 7.02 (d, 1H), 6.07-5.90 (m, 1H), 5.87-5.80 (m, 1H), 3.95 (d, 1H), 3.26 (s, 3H) |
| 294 | 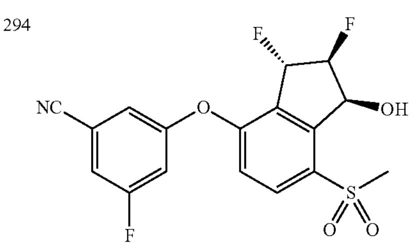 | 384 (M + H) | (400 MHz, CDCl$_3$): δ 8.09-8.06 (m, 1H), 7.27-7.24 (m, 1H), 7.19-7.17 (m, 1H), 7.10-7.07 (m, 1H), 7.04 (d, 1H), 6.30-6.12 (m, 1H), 5.96-5.89 (m, 1H), 5.46-5.27 (m, 1H), 3.53-3.51 (m, 1H), 3.27 (s, 3H) |
| 295 | 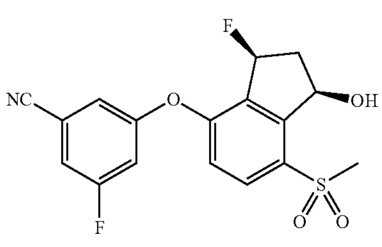 [SMILES: CS(=O)(=O)c1ccc(Oc2cc(F)cc(C#N)c2)c2c1[C@H](O)C[C@@H]2F] | 383 (M + NH$_4^+$) | (400 MHz, CDCl$_3$): δ 8.04-8.01 (m, 1H), 7.25-7.22 (m, 1H), 7.18-7.16 (m, 1H), 7.11-7.06 (m, 1H), 7.00 (d, 1H), 6.09-5.79 (m, 1H), 5.69-5.61 (m, 1H), 3.54 (d, 1H), 3.23 (s, 3H), 2.94-2.80 (m, 1H), 2.52-2.41 (m, 1H) |

TABLE 2-continued

| No. | Structure | Mass Characterization | ¹H NMR Data |
|---|---|---|---|
| 296 | 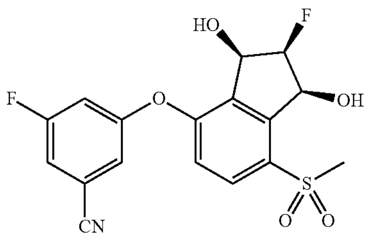 [SMILES: CS(=O)(=O)c1ccc(Oc2cc(F)cc(C#N)c2)c2c1[C@H](O)[C@H](F)[C@@H]2O] | 399 (M + NH$_4^+$) | (400 MHz, CDCl$_3$): δ 8.05 (d, 1H), 7.26-7.22 (m, 1H), 7.19-7.17 (m, 1H), 7.12-7.07 (m, 1H), 7.05 (d, 1H), 5.76-5.70 (m, 1H), 5.30-5.24 (m, 1H), 5.18-5.01 (m, 1H), 3.29 (s, 3H) |
| 297 | 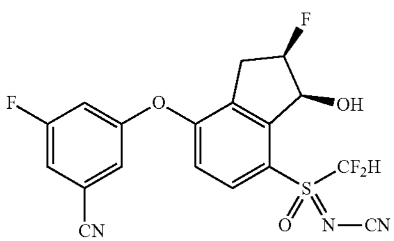 [SMILES: N#CN=S(=O)(c1ccc(Oc2cc(F)cc(C#N)c2)c2c1[C@H](O)[C@H](F)C2)C(F)F] | 426 (M + H) | (400 MHz, CDCl$_3$): δ 8.04 (d, 1H), 7.34-7.30 (m, 1H), 7.25-7.22 (m, 1H), 7.23 (t, J = 54 Hz, 1H), 7.14-7.10 (m, 1H), 7.00 (d, 1H), 5.71-5.63 (m, 1H), 5.56-5.52 (m, 0.5H), 5.43-5.39 (m, 0.5H), 3.59 (t, 1H), 3.46-3.18 (m, 2H) |
| 298 | 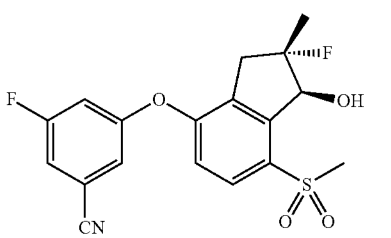 [SMILES: C[C@]1(F)Cc2c(Oc3cc(F)cc(C#N)c3)ccc(S(C)(=O)=O)c2[C@@H]1O] | 397 (M + NH$_4$) | (400 MHz, CDCl$_3$): δ 7.85 (d, 1H), 7.22-7.19 (m, 1H), 7.12-7.09 (m, 1H), 7.03-6.98 (m, 2H), 5.29-5.23 (m, 1H), 3.57-3.53 (m, 1H), 3.26-3.04 (m, 2H), 3.19 (s, 3H), 1.70 (d, J = 22 Hz, 3H) |
| 299 | 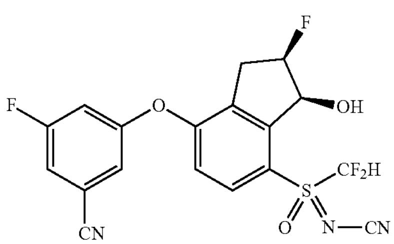 [SMILES: N#CN=S(=O)(c1ccc(Oc2cc(F)cc(C#N)c2)c2c1[C@H](O)[C@H](F)C2)C(F)F] | 426 (M + H) | (400 MHz, CDCl$_3$): δ 8.03 (d, 1H), 7.34-7.30 (m, 1H), 7.23-7.21 (m, 1H), 7.13-7.09 (m, 1H), 7.01 (t, J = 53 Hz, 1H), 6.99 (d, 1H), 5.73-5.66 (m, 1H), 5.56-5.52 (m, 0.5H), 5.43-5.39 (m, 0.5H), 3.45-3.34 (m, 1H), 3.35-3.19 (m, 2H) |
| 300 | 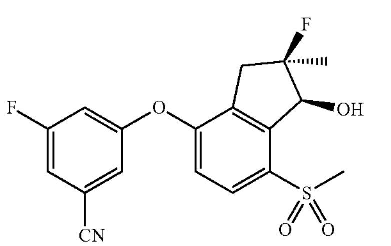 [SMILES: C[C@@]1(F)Cc2c(Oc3cc(F)cc(C#N)c3)ccc(S(C)(=O)=O)c2[C@@H]1O] | 397 (M + NH$_4$) | (400 MHz, CDCl$_3$): δ 7.90 (d, 1H), 7.21-7.19 (m, 1H), 7.10-7.08 (m, 1H), 6.99 (dt, 1H), 6.98 (d, 1H), 5.40-5.35 (m, 1H), 3.79-3.77 (m, 1H), 3.36-3.27 (m, 1H), 3.32 (s, 3H), 2.95-2.84 (m, 1H), 1.70 (d, 3H) |
| 301 | 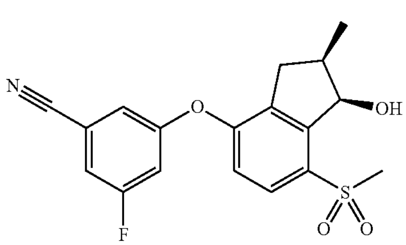 [SMILES: C[C@@H]1Cc2c(Oc3cc(F)cc(C#N)c3)ccc(S(C)(=O)=O)c2[C@@H]1O] | 379 (M + NH$_4$) | (400 MHz, CDCl$_3$): δ 7.84 (d, 1H), 7.19-7.15 (m, 1H), 7.07-7.06 (m, 1H), 6.98 (d, 1H), 6.97 (dt, 1H), 5.46-5.43 (m, 1H), 3.12 (s, 3H), 3.08 (d, 1H), 2.97-2.91 (m, 1H), 2.68-2.53 (m, 2H), 1.25 (d, 3H) |

TABLE 2-continued

| No. | Structure | Mass Characterization | ¹H NMR Data |
|---|---|---|---|
| 302 | 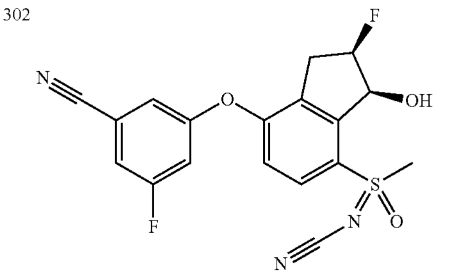 | 390 (M + H) | (400 MHz, CDCl₃): δ 8.00 (d, J = 8.7 Hz, 0.5H), 7.95 (d, J = 8.7 Hz, 0.5H), 7.29-7.25 (m, 1H), 7.19-7.16 (m, 1H), 7.10-7.05 (m, 1H), 7.01 (d, 1H), 5.78-5.69 (m, 1H), 5.54-5.50 (m, 0.5H), 5.40-5.37 (m, 0.5H), 3.50 (d, J = 42 Hz, 3H), 3.39-3.11 (m, 3H) |
| 303 | 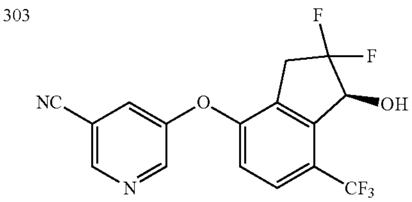 | [M + H] 357 | (400 MHz, CDCl₃): δ 8.72 (s, 1H), 8.64 (s, 1H), 7.64 (d, 1H), 7.59-7.57 (m, 1H), 6.97 (d, 1H), 5.33-5.28 (m, 1H), 3.55-3.32 (m, 2H), 2.86-2.82 (m, 1H) |
| 304 | 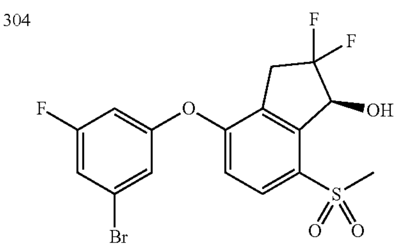 | 437, 439 (M + H) | (400 MHz, CDCl₃): δ 7.88 (d, 1H), 7.17-7.13 (m, 1H), 7.04-7.02 (m, 1H), 6.98 (d, 1H), 6.77-6.74 (m, 1H), 5.61-5.56 (m, 1H), 3.57-3.36 (m, 3H), 3.22 (s, 3H) |
| 305 | 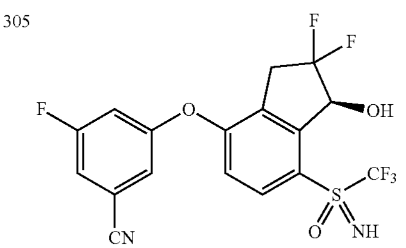 | (M + H) 437 | (400 MHz, CDCl₃): δ 8.01 (d, 1H), 7.32 (ddd, 1H), 7.24-7.22 (m, 1H), 7.12 (dt, 1H), 6.99 (d, 1H), 5.35 (dd, 1H), 4.73-4.71 (m, 1H), 3.97 (br s, 1H), 3.63-3.46 (m, 2H) |
| 306 | 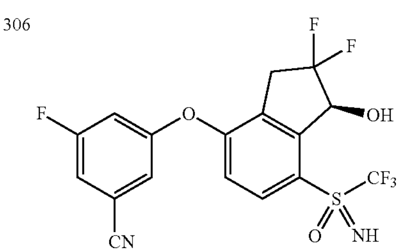 | (M + H) 437 | (400 MHz, CDCl₃): δ 8.07 (d, 1H), 7.30 (ddd, 1H), 7.23-7.21 (m, 1H), 7.11 (dt, 1H), 6.98 (d, 1H), 5.59 (ddd, 1H), 3.97 (d, 1H), 3.81 (br s, 1H), 3.61-3.39 (m, 2H) |
| 307 | 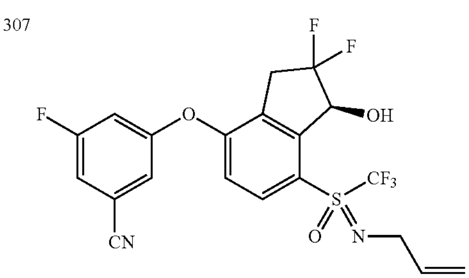 | (M + H) 477 | (400 MHz, CDCl₃): δ 7.99 (d, 1H), 7.30 (ddd, 1H), 7.23-7.20 (m, 1H), 7.10 (dt, 1H), 6.98 (d, 1H), 6.04-5.93 (m, 1H), 5.35-5.28 (m, 2H), 5.21 (dq, 1H), 4.87 (br s, 1H), 4.16-4.09 (m, 1H), 4.04-3.96 (m, 1H), 3.61-3.44 (m, 2H) |

TABLE 2-continued

| No. | Structure | Mass Characterization | ¹H NMR Data |
|---|---|---|---|
| 308 | 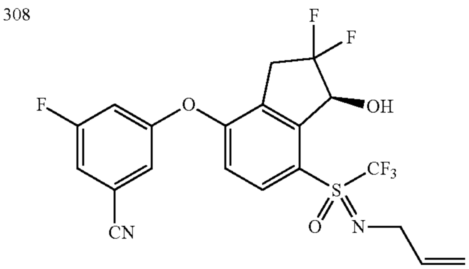 | (M + H) 477 | (400 MHz, CDCl$_3$): δ 8.04 (d, 1H), 7.29 (ddd, 1H), 7.21-7.19 (m, 1H), 7.09 (dt, 1H), 6.97 (d, 1H), 5.98 (ddt, 1H), 5.58 (dd, 1H), 5.34 (dq, 1H), 5.19 (dq, 1H), 4.13-4.05 (m, 1H), 4.03-3.95 (m, 1H), 3.59-3.33 (m, 3H) |
| 309 | 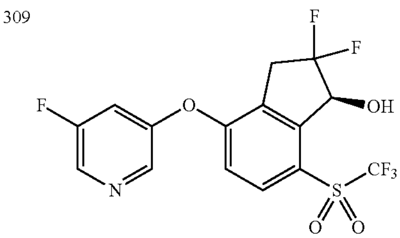 | (M + H) 414 | (400 MHz, CDCl$_3$): δ 8.49 (d, 1H), 8.37 (d, 1H), 7.93 (d, 1H), 7.26 (dt, 1H), 6.95 (d, 1H), 5.44 (dd, 1H), 3.67-3.48 (m, 2H), 3.42 (d, 1H). |
| 310 | 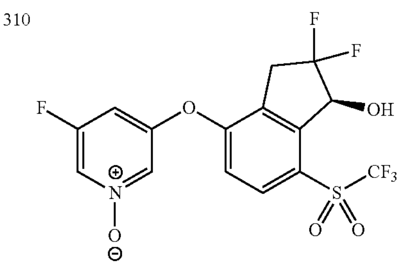 | (M + H) 430 | (400 MHz, CDCl$_3$): δ 8.11-8.08 (m, 1H), 8.01-7.97 (m, 2H), 7.14 (d, 1H), 6.90 (dt, 1H), 5.43 (dd, 1H), 3.95 (d, 1H), 3.62-3.41 (m, 2H) |
| 311 | 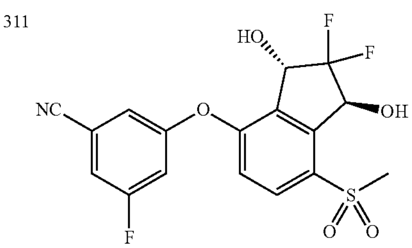 | 400 (M + H) | (400 MHz, CDCl$_3$): δ 8.00 (d, 1H), 7.27-7.25 (m, 1H), 7.20-7.18 (m, 1H), 7.12-7.07 (m, 1H), 7.03 (d, 1H), 5.81-5.74 (m, 1H), 5.43-5.36 (m, 1H), 3.81 (d, 1H), 3.25 (s, 3H), 2.71 (m, 1H) |
| 312 | 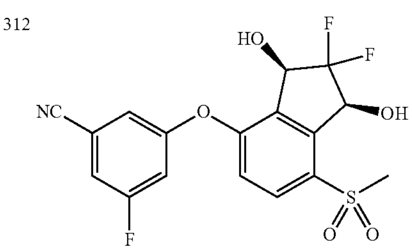 | 400 (M + H) | (400 MHz, CDCl$_3$): δ 8.05 (d, 1H), 7.29-7.20 (m, 2H), 7.15-7.10 (m, 1H), 7.05 (d, 1H), 5.63-5.57 (m, 1H), 5.22-5.15 (m, 1H), 3.53-3.48 (m, 1H), 3.24 (s, 3H), 2.73 (d, 1H) |
| 313 | 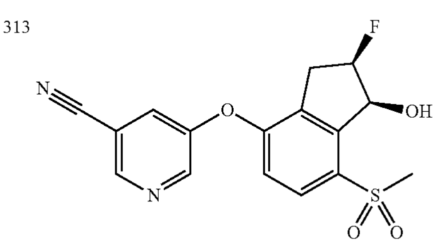 | 349 (M + H) | (400 MHz, CDCl$_3$): δ 8.75-8.72 (m, 1H), 8.66-8.64 (m, 1H), 7.92 (d, 1H), 7.61-7.59 (m, 1H), 6.95 (d, 1H), 5.73-5.65 (m, 1H), 5.51-5.47 (m, 0.5H), 5.38-5.34 (m, 0.5H), 3.71-3.68 (m, 1H), 3.36-3.38 (m, 2H), 3.31 (s, 3H) |

TABLE 2-continued

| No. | Structure | Mass Characterization | ¹H NMR Data |
|---|---|---|---|
| 314 | 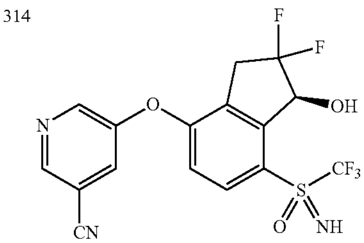 | (M + H) 420 | (400 MHz, CDCl₃): δ 8.83 (d, 1H), 8.72 (d, 1H), 8.02 (d, 1H), 7.73 (dd, 1H), 6.95 (d, 1H), 5.35 (dd, 1H), 4.73-4.70 (m s, 1H), 3.99 (br s, 1H), 3.67-3.49 (m, 2H) |
| 315 | 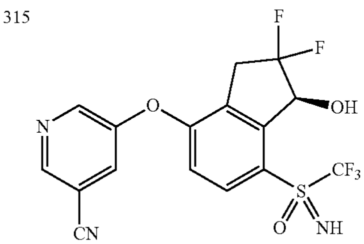 | (M + H) 420 | (400 MHz, CDCl₃): δ 8.82 (d, 1H), 8.71 (d, 1H), 8.08 (d, 1H), 7.72 (dd, 1H), 6.93 (d, 1H), 5.63-5.57 (m, 1H), 3.97 (d, 1H), 3.82 (br s, 1H), 3.65-3.43 (m, 2H) |
| 316 | 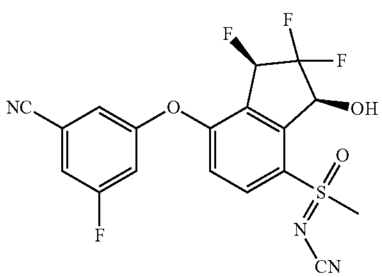 [SMILES: CS(=O)(=NC#N)c1ccc(Oc2cc(F)cc(C#N)c2)c2c1[C@H](O)C(F)(F)[C@@H]2F] | [M + H] 426 | (400 MHz, CD₃OD): δ 8.21 (dd, 1H), 7.59-7.56 (m, 1H), 7.54-7.53 (m, 1H), 7.46 (dt, 1H), 7.25 (d, 1H), 6.00 (dd, 1H), 5.60-5.56 (m, 1H), 3.64 (s, 3H) |
| 317 | 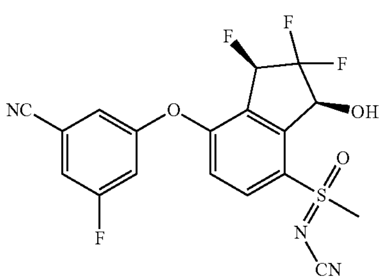 [SMILES: CS(=O)(=NC#N)c1ccc(Oc2cc(F)cc(C#N)c2)c2c1[C@H](O)C(F)(F)[C@@H]2F] | [M + H] 426 | (400 MHz, CDCl₃): δ 8.23-8.20 (m, 1H), 7.38-7.34 (m, 1H), 7.30-7.28 (m, 1H), 7.21-7.17 (m, 1H), 7.09 (d, 1H), 5.90 (dd, 1H), 5.71-5.66 (m, 1H), 3.90-3.88 (m, 1H), 3.64 (s, 3H) |
| 318 | 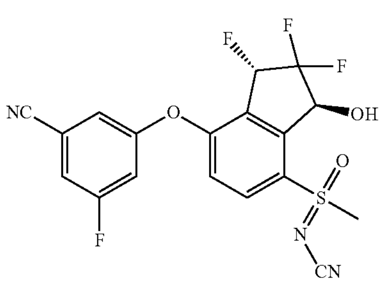 [SMILES: CS(=O)(=NC#N)c1ccc(Oc2cc(F)cc(C#N)c2)c2c1[C@H](O)C(F)(F)[C@H]2F] | [M + H] 426 | (400 MHz, CDCl₃): δ 8.13 (dd, 1H), 7.37-7.33 (m, 1H), 7.28-7.27 (m, 1H), 7.19-7.15 (m, 1H), 7.05 (d, 1H), 6.08-5.84 (m, 2H), 4.08 (d, 1H), 3.54 (s, 3H) |

TABLE 2-continued

| No. | Structure | Mass Characterization | ¹H NMR Data |
|---|---|---|---|
| 319 | | [M + H] 409 | (400 MHz, CD₃COCD₃): δ 8.95 (d, 1H), 8.94 (d, 1H), 8.34-8.32 (m, 1H), 8.23-8.20 (m, 1H), 7.45 (d, 1H), 6.43-6.40 (m, 1H), 6.15 (dd, 1H), 5.72-5.66 (m, 1H), 3.69 (s, 3H) |
| 320 | | [M + H] 409 | (400 MHz, CD₃COCD₃): δ 8.96-8.95 (m, 1H), 8.94-8.92 (m, 1H), 8.34-8.32 (m, 1H), 8.24-8.20 (m, 1H), 7.44-7.41 (m, 1H), 6.51-6.31 (m, 2H), 5.90-5.83 (m, 1H), (s, 3.81 3H) |
| 321 | | [M + H] 409 | (400 MHz, CD₃COCD₃): δ 8.97-8.96 (m, 1H), 8.96-8.94 (m, 1H), 8.35 (dd, 1H), 8.25 (dd, 1H), 7.45 (d, 1H), 6.50 (brs, 1H), 6.16 (dd, 1H), 5.68-5.30 (m, 1H), 3.80 (s, 3H) |
| 322 | | [M + H] 409 | (400 MHz, CD₃COCD₃): δ 8.95-8.94 (m, 1H), 8.94-8.92 (m, 1H), 8.33 (dd, 1H), 8.19 (dd, 1H), 7.41 (d, 1H), 6.50-6.28 (m, 2H), 5.90-5.85 (m, 1H), 3.70 (s, 3H) |
| 323 | | 418, 420 (M + H) | (400 MHz, CD₃COCD₃): δ 8.65-8.63 (m, 1H), 8.60-8.59 (m, 1H), 8.15-8.12 (m, 1H), 8.02-8.00 (m, 1H), 7.60-7.57 (m, 1H), 3.86-3.79 (m, 2H), 3.39 (s, 3H) |
| 324 | | 420, 422 (M + H) | (400 MHz, CDCl₃): δ 8.61-8.59 (m, 1H), 8.41-8.39 (m, 1H), 7.91-7.87 (d, 1H), 7.61-7.58 (m, 1H), 6.95-6.9' (d, 1H), 5.63-5.57 (m, 1H), 3.61-3.40 (m, 3H), 3.23 (s, 3H) |

TABLE 2-continued

| No. | Structure | Mass Characterization | ¹H NMR Data |
|---|---|---|---|
| 325 | 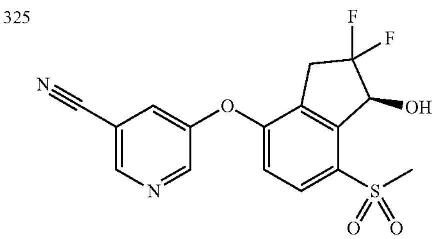 | 367 (M + H) | (400 MHz, CDCl₃): δ 8.76-8.75 (m, 1H), 8.67-8.66 (m, 1H), 7.95 (d, 1H), 7.70-7.68 (m, 1H), 6.98 (d, 1H), 5.60 (d, 1H), 3.57-3.35 (m, 3H), 3.22 (s, 3H) |
| 326 | 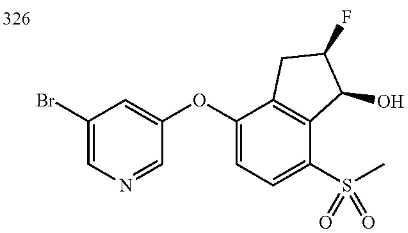 | 402, 404 (M + H) | (400 MHz, CDCl₃): δ 8.57-8.56 (m, 1H), 8.39-8.38 (m, 1H), 7.88 (d, 1H), 7.56-7.54 (m, 1H), 6.91 (d, 1H), 5.72-5.65 (m, 1H), 5.51-5.47 (m, 0.5H), 5.38-5.34 (m, 0.5H), 3.71-3.69 (m, 1H), 3.38-3.09 (m, 3H), 3.29 (s, 3H) |
| 327 | 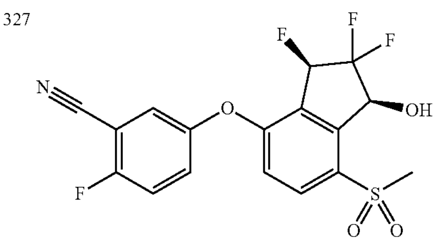 | 402 (M + H) | (400 MHz, CDCl₃): δ 8.10-8.06 (m, 1H), 7.44-7.32 (m, 3H), 6.91 (d, 1H), 5.95-5.91 (m, 0.5H), 5.81-5.78 (m, 0.5H), 5.70-5.64 (m, 1H), 4.00-3.97 (m, 1H), 3.24 (s, 3H) |
| 328 | 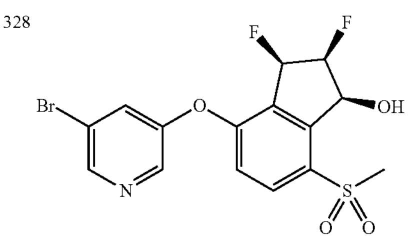 | 420, 422 (M + H) | (400 MHz, CDCl₃): δ 8.63-8.61 (m, 1H), 8.45-8.43 (m, 1H), 8.11-8.07 (m, 1H), 7.66-7.64 (m, 1H), 6.96 (d, 1H), 6.13-6.11 (m, 0.5H), 5.99-5.97 (m, 0.5H), 5.86-5.82 (m, 1H), 5.24-5.04 (m, 1H), 3.30 (s, 3H), 3.03-3.00 (m, 1H) |
| 329 | 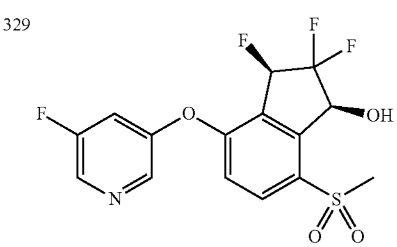 | 378 (M + H) | (400 MHz, CDCl₃): δ 8.49-8.47 (m, 1H), 8.39-8.37 (m, 1H), 8.11-8.07 (m, 1H), 7.29-7.25 (m, 1H), 7.00 (d, 1H), 5.96-5.93 (m, 0.5H), 5.83-5.79 (m, 0.5H), 5.71-5.65 (m, 1H), 3.65-3.63 (m, 1H), 3.24 (s, 3H) |
| 330 | 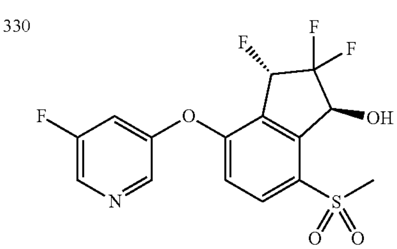 | 378 (M + H) | (400 MHz, CDCl₃): δ 8.49-8.46 (m, 1H), 8.39-8.36 (m, 1H), 8.08-8.04 (m, 1H), 8.28-8.24 (m, 1H), 6.98 (d, 1H), 6.12-6.08 (m, 0.5H), 5.99-5.95 (m, 0.5H), 5.88-5.81 (m, 1H), 4.10-4.06 (m, 1H), 3.26 (s, 3H) |

TABLE 2-continued

| No. | Structure | Mass Characterization | ¹H NMR Data |
|---|---|---|---|
| 331 | 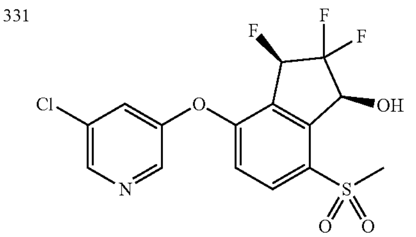 | 394, 396 (M + H) | (400 MHz, CDCl₃): δ 8.56-8.55 (m, 1H), 8.44-8.43 (m, 1H), 8.11-8.08 (m, 1H), 7.54-7.52 (m, 1H), 6.99 (d, 1H), 5.96-5.92 (m, 0.5H), 5.83-5.79 (m, 0.5H), 5.71-5.65 (m, 1H), 3.66-3.64 (m, 1H), 3.25 (s, 3H) |
| 332 | 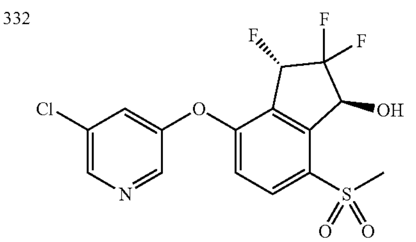 | 394, 396 (M + H) | (400 MHz, CDCl₃): δ 8.56-8.54 (m, 1H), 8.43-8.41 (m, 1H), 8.08-8.04 (m, 1H), 7.52-7.50 (m, 1H), 6.96 (d, 1H), 6.12-6.08 (m, 0.5H), 5.98-5.94 (m, 0.5H), 5.88-5.81 (m, 1H), 4.02-3.99 (m, 1H), 3.26 (s, 3H) |
| 333 | 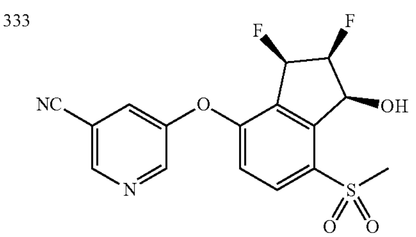 | 367 (M + H) | (400 MHz, CD₃COCD₃): δ 8.88-8.86 (m, 1H), 8.82-8.80 (m, 1H), 8.13-8.08 (m, 2H), 7.33 (d, 1H), 6.21-6.18 (m, 0.5H), 6.07-6.04 (m, 0.5H), 5.83-5.79 (m, 1H), 5.36-5.29 (m, 0.5H), 5.25-5.16 (m, 0.5H), 5.07-5.04 (m, 1H), 3.33 (s, 3H) |
| 334 | 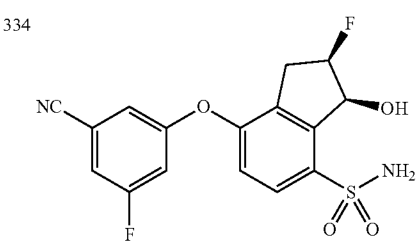 | 365 (M − H) | (400 MHz, CD₃OD): δ 7.87 (d, 1H), 7.42-7.35 (m, 1H), 7.26-7.13 (m, 2H), 7.08 (d, 1H), 5.63-5.51 (m, 1H), 5.40-5.18 (m, 1H), 3.20-3.15 (m, 2H) |
| 335 | 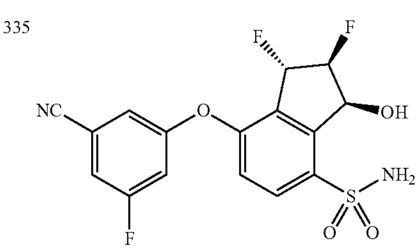 | 383 (M − H) | (400 MHz, CD₃OD): δ 8.04 (d, 1H), 7.45-7.41 (m, 1H), 7.31-7.29 (m, 1H), 7.26-7.21 (m, 1H), 7.18 (d, 1H), 6.30-6.11 (m, 1H), 5.80 (t, 1H), 5.37-5.17 (m, 1H) |
| 336 | 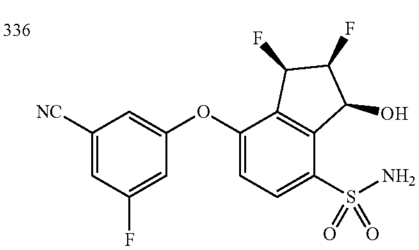 | 383 (M − H) | |

TABLE 2-continued
| No. | Structure | Mass Characterization | ¹H NMR Data |
|---|---|---|---|
| 337 | 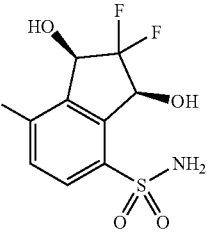 | 399 (M − H) | (400 MHz, CD₃OD): δ 8.00 (d, 1H), 7.44-7.41 (m, 1H), 7.35-7.32 (m, 1H), 7.29-7.24 (m, 1H), 7.14 (d, 1H), 5.46 (d, 1H), 5.06 (d, 1H) |
| 338 | 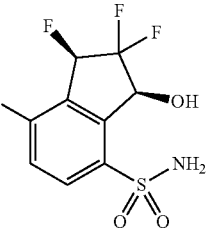 | 401 (M − H) | (400 MHz, CD₃OD): δ 8.03-8.00 (m, 1H), 7.24-7.20 (m, 1H), 7.17-7.15 (m, 1H), 7.08-7.04 (m, 1H), 6.96 (d, 1H), 5.82-5.65 (m, 1H), 5.54-5.48 (m, 1H) |
| 339 | 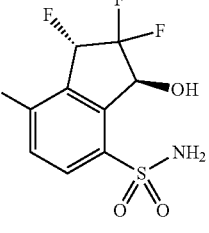 | 401 (M − H) | (400 MHz, CD₃OD): δ 8.09-8.05 (m, 1H), 7.50-7.46 (m, 1H), 7.39-7.38 (m, 1H), 7.33-7.29 (m, 1H), 7.14 (d, 1H), 6.19-6.02 (m, 1H), 5.72-5.65 (m, 1H) |
| 340 | 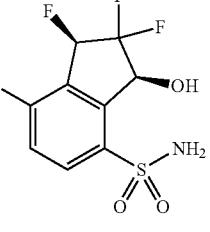 | 384 (M − H) | (400 MHz, CD₃OD): δ 8.81 (d, 1H), 8.73 (d, 1H), 8.11-8.07 (m, 1H), 8.06-8.04 (m, 1H), 7.18 (d, 1H), 6.04-5.86 (m, 1H), 5.57-5.51 (m, 1H) |
| 341 | 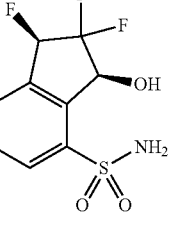 | 377 (M − H) | (400 MHz, CD₃OD): δ 8.43 (d, 1H), 8.35 (d, 1H), 8.10-8.06 (m, 1H), 7.59-7.54 (m, 1H), 7.15 (d, 1H), 6.03-5.85 (m, 1H), 5.56-5.50 (m, 1H) |
| 342 | 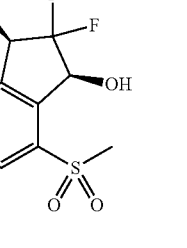 | (M + H) 385 | (400 MHz, CDCl₃): δ 8.82 (d, 1H), 8.74 (d, 1H), 8.14 (dd, 1H), 7.74 (dd, 1H), 7.02 (d, 1H), 5.87 (dd, 1H), 5.73-5.66 (m, 1H), 3.58 (d, 1H), 3.26 (s, 3H) |

TABLE 2-continued

| No. | Structure | Mass Characterization | ¹H NMR Data |
|---|---|---|---|
| 343 | 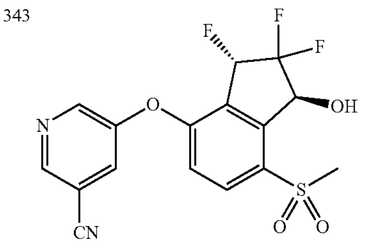 | (M + H) 385 | (400 MHz, (CD$_3$)$_2$CO): δ 8.89 (dd, 1H), 8.86 (d, 1H), 8.21 (dd, 1H), 8.11 (dd, 1H), 7.36 (d, 1H), 6.36 (ddd, 1H), 6.10 (d, 1H), 5.87-5.80 (m, 1H), 3.31 (s, 3H) |
| 344 | 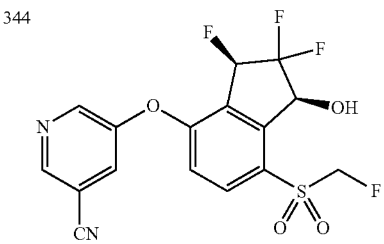 | (M + H) 403 | (400 MHz, CDCl$_3$): δ 8.84 (d, 1H), 8.75 (d, 1H), 8.15 (dd, 1H), 7.77 (dd, 1H), 7.02 (d, 1H), 5.83 (dd, 1H), 5.68-5.62 (m, 1H), 5.43 (dd, 1H), 5.31 (dd, 1H), 3.43 (dd, 1H) |
| 345 | 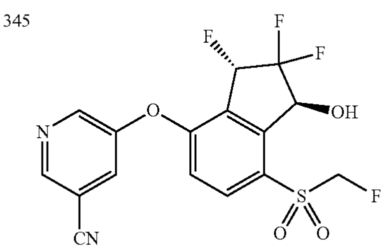 | (M + H) 403 | (400 MHz, (CD$_3$)$_2$CO): δ 8.93 (dd, 1H), 8.90 (dd, 1H), 8.26 (dd, 1H), 8.13 (dd, 1H), 7.38 (d, 1H), 6.39 (ddd, 1H), 5.73 (dd, 1H), 5.80 (ddd, 1H), 5.61 (dd, 1H) |
| 346 | 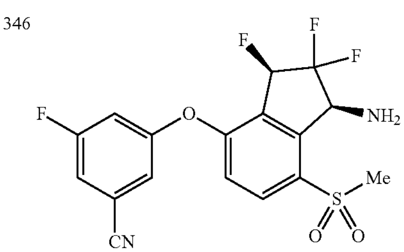 | (M + H) 401 | (400 MHz, CDCl$_3$): δ 8.14 (dd, 1H), 7.30 (ddd, 1H), 7.24-7.22 (m, 1H), 7.14 (dt, 1H), 6.98 (d, 1H), 5.77 (dd, 1H), 5.10-5.01 (m, 1H), 3.45 (s, 3H), 1.82 (br d, 2H) |
| 347 | 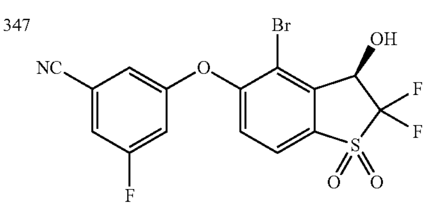 | | (400 MHz, CDCl$_3$): δ 7.86 (d, 1H), (d, 7.27 1H), 7.27-7.24 (m, 1H), 7.13-7.11 (m, 1H), 7.04-7.00 (m, 1H), 5.41-5.37 (m, 1H), 3.06 (d, 1H) |
| 348 | 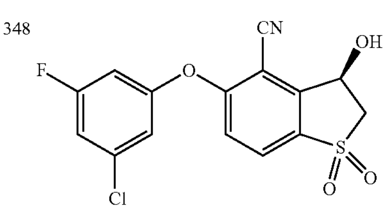 | 352, 354 (M − H) | (CDCl$_3$, 400 MHz) δ 7.89 (d, 1H), 7.13 (d, 1H), 7.09-7.06 (m, 1H), 6.96-6.94 (m, 1H), 6.80 (dt, 1H), 5.78-5.74 (m, 1H), 3.91 (dd, 1H), 3.65 (dd, 1H), 3.41 (d, 1H) |

TABLE 2-continued

| No. | Structure | Mass Characterization | ¹H NMR Data |
|---|---|---|---|
| 349 | (NC-phenyl-F)-O-(benzothiophene-CHF₂, OH, F, F, SO₂) | 404 (M − H) | (400 MHz, CDCl₃): δ 7.98 (d, 1H), 7.33-7.30 (m, 1H), 7.23 (t, 1H), 7.22-7.18 (m, 2H), 7.10-7.06 (m, 1H), 5.69-5.65 (m, 1H), 3.23 (d, 1H) |
| 350 | (Cl-phenyl-F)-O-(benzothiophene-Br, SO₂) | 391, 393, 395 (M + H) | (400 MHz, CDCl₃): δ 7.70 (d, 1H), 7.10 (d, 1H), 6.93 (ddd, 1H), 6.78-6.76 (m, 1H), 6.63 (dt, 1H), 3.62-3.58 (m, 2H), 3.42-3.37 (m, 2H) |
| 351 | (Cl-phenyl-F)-O-(benzothiophene-CN, SO₂) | 336, 338 (M + H) | (400 MHz, CDCl₃): δ 7.87 (d, 1H), 7.06 (dt, 1H), 7.03 (d, 1H), 6.94-6.92 (m, 1H), 6.78 (dt, 1H), 3.66-3.61 (m, 2H), 3.60-3.55 (m, 2H) |
| 352 | (Cl-phenyl-F)-O-(benzothiophene-Br, OH, SO₂) | 424, 426, 428 (M + NH₄) | (400 MHz, CDCl₃): δ 7.72 (d, 1H), 7.19 (d, 1H), 6.98-6.94 (ddd, 1H), 6.82-6.80 (m, 1H), 6.67 (dt, 1H), 5.60 (td, 1H), 3.80 (dd, 1H), 3.68 (dd, 1H), 2.89 (d, 1H) |
| 353 | (Cl-phenyl-F)-O-(benzothiophene-CN, OH, SO₂) | 352, 354 (M − H) | (400 MHz, CDCl₃): δ 7.89 (d, 1H), 7.13 (d, 1H), 7.07 (ddd, 1H), 6.97-6.94 (m, 1H), 6.80 (dt, 1H), 5.79-5.72 (m, 1H), 3.91 (dd, 1H), 3.64 (dd, 1H), 3.57 (br d, 1H) |
| 354 | (Cl-phenyl-F)-O-(benzothiophene-Br, =O, F, F, SO₂) | | (400 MHz, CDCl₃): δ 7.89 (d, 1H), 7.50 (d, 1H), 7.06 (ddd, 1H), 6.89-6.86 (m, 1H), 6.73 (dt, 1H) |
| 355 | (Cl-phenyl-F)-O-(benzothiophene-Br, OH, F, F, SO₂) | 425, 427, 429 (M − OH) | (400 MHz, CDCl₃): δ 7.80 (d, 1H), 7.22 (d, 1H), 7.01 (dt, 1H), 6.87-6.85 (m, 1H), 6.71 (dt, 1H), 5.38 (d, 1H), 2.98 (br s, 1H) |

TABLE 2-continued

| No. | Structure | Mass Characterization | ¹H NMR Data |
|---|---|---|---|
| 356 | | 388, 390 (M − H) | (400 MHz, CDCl$_3$): δ 7.97 (d, 1H), 7.19 (d, 1H), 7.12 (ddd, 1H), 6.99-6.97 (m, 1H), 6.83 (dt, 1H), 5.58-5.51 (m, 1H), 3.51 (br d, 1H) |
| 357 | | 397, 399 (M − H) | (400 MHz, CDCl$_3$): δ 7.76 (d, 1H), 7.26 (d, 1H), 7.01 (ddd, 1H), 6.87-6.85 (m, 1H), 6.71 (dt, 1H), 5.44 (dd, 1H), 2.94 (d, 1H) |
| 358 | | 364, 366 (M + H) | (400 MHz, CDCl$_3$): δ 7.81 (d, 1H), 7.36 (dd, 1H), 7.20 (ddd, 1H), 6.99 (ddd, 1H), 6.89-6.86 (m, 1H), 6.71 (dt, 1H), 4.73-4.61 (m, 1H), 1.79 (br d, 2H) |
| 359 | | 377, 379 (M − H) | (400 MHz, CDCl$_3$): δ 7.70 (d, 1H), 7.16 (d, 1H), 6.95 (ddd, 1H), 6.80-6.78 (m, 1H), 6.64 (dt, 1H), 5.30 (dd, 1H), 2.72 (dd, 1H), 2.43 (s, 3H) |
| 360 | | 431, 433 (M − H) | (400 MHz, CDCl$_3$): δ 8.00 (d, 1H), 7.29 (d, 1H), 7.04 (ddd, 1H), 6.91-6.89 (m, 1H), 6.74 (dt, 1H), 5.58 (d, 1H), 3.16 (br s, 1H) |
| 361 | | 377, 379 (M − H) | (400 MHz, CDCl$_3$): δ 7.85 (d, 1H), 7.22 (t, 1H), 7.14 (dt, 1H), 7.01 (ddd, 1H), 6.87-6.85 (m, 1H), 6.71 (dt, 1H), 5.90-5.85 (m, 1H), 3.77 (ddd, 1H), 3.67 (dd, 1H), 2.87 (t, 1H) |
| 362 | | 363, 365 (M − H) | (400 MHz, CDCl$_3$): δ 7.84 (d, 1H), 7.27-7.23 (m, 2H), 7.01 (dt, 1H), 6.90-6.88 (m, 1H), 6.72 (dt, 1H), 5.35 (q, 1H), 2.79 (dd, 1H) |

TABLE 2-continued

| No. | Structure | Mass Characterization | ¹H NMR Data |
|---|---|---|---|
| 363 | 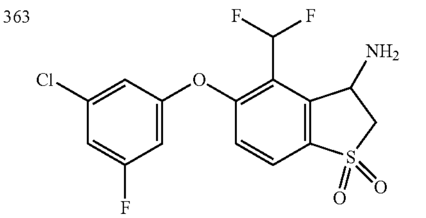 | 378, 380 (M + H) | (400 MHz, CDCl$_3$): δ 7.80 (d, 1H), 7.22 (t, 1H), 7.06 (dt, 1H), 7.00 (dt, 1H), 6.87-6.84 (m, 1H), 6.70 (dt, 1H), 5.16-5.03 (br s, 1H), 3.75 (dd, 1H), 3.49 (dd, 1H), 2.20-1.97 (br s, 2H) |
| 364 | 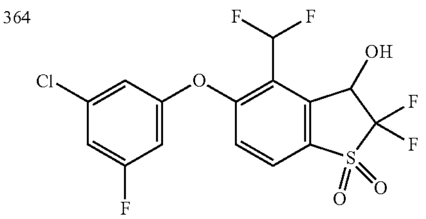 | 413, 415 (M − H) | (400 MHz, CDCl$_3$): δ 7.93 (d, 1H), 7.25 (t, 1H), 7.21-7.17 (m, 1H), 7.06 (ddd, 1H), 6.92-6.89 (m, 1H), 6.75 (dt, 1H), 5.67 (dd, 1H), 3.10 (dd, 1H) |
| 365 | 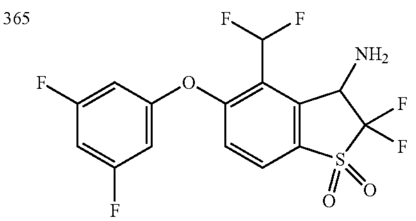 | 398 (M + H) | (400 MHz, CDCl$_3$): δ 7.90 (d, 1H), 7.28 (dd, 1H), 7.18-7.14 (m, 1H), 6.76 (tt, 1H), 6.67-6.60 (m, 2H), 4.98 (dt, 1H), 2.01 (br d, 2H) |
| 366 | 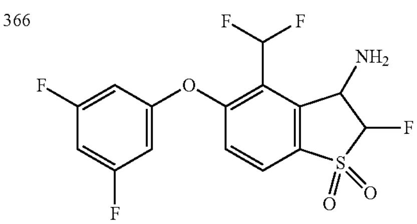 | 380 (M + H) | (400 MHz, CDCl$_3$): δ 7.87 (d, 1H), 7.44 (dd, 1H), 7.15 (d, 1H), 6.73 (tt, 1H), 6.64-6.57 (m, 2H), 5.58 (dd, 1H), 5.17-5.07 (m, 1H), 2.02-1.93 (m, 2H) |
| 367 | 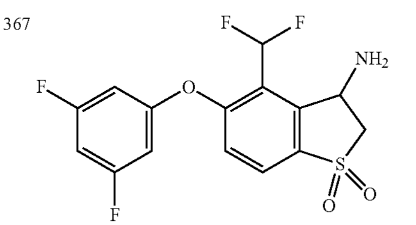 | 362 (M + H) | (400 MHz, CDCl$_3$): δ 7.81 (d, 1H), 7.22 (t, 1H), 7.10-7.06 (m, 1H), 6.72 (tt, 1H), 6.63-6.56 (m, 2H), 5.14-5.07 (m, 1H), 3.75 (dd, 1H), 3.49 (dd, 1H), 2.12-2.04 (m, 2H) |
| 368 | 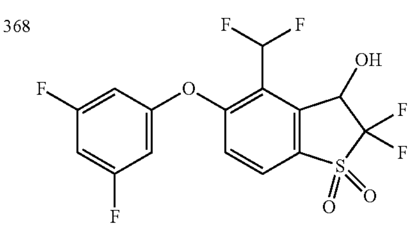 | 397 (M − H) | (400 MHz, CDCl$_3$): δ 7.93 (d, 1H), 7.25 (t, 1H), 7.23-7.19 (m, 1H), 6.78 (tt, 1H), 6.68-6.61 (m, 2H), 5.67 (dd, 1H), 3.09 (dd, 1H) |
| 369 | 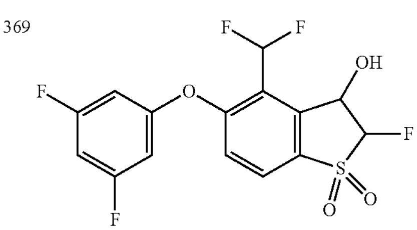 | 379 (M − H) | (400 MHz, CDCl$_3$): δ 7.89 (d, 1H), 7.29 (t, 1H), 7.19 (d, 1H), 6.74 (tt, 1H), 6.65-6.58 (m, 2H), 5.87-5.80 (m, 1H), 5.66 (dd, 1H), 2.98 (ddd, 1H) |

TABLE 2-continued

| No. | Structure | Mass Characterization | $^1$H NMR Data |
|---|---|---|---|
| 370 | 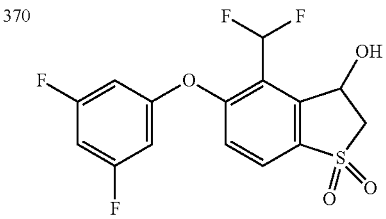 | 363 (M + H) | (400 MHz, CDCl$_3$): δ 7.85 (d, 1H), 7.25 (t, 1H), 7.16 (dt, 1H), 6.73 (tt, 1H), 6.63-6.56 (m, 1H), 5.90-5.86 (m, 1H), 5.90-5.85 (m, 1H), 3.78 (ddd, 1H), 3.67 (dd, 1H), 2.89 (t, 1H) |
| 371 | 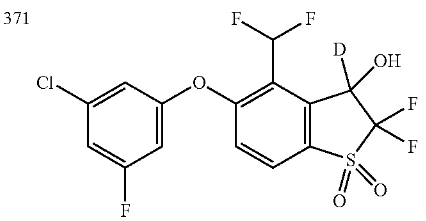 | 414, 416 (M − H) | (400 MHz, CDCl$_3$): δ 7.95-7.92 (m, 1H), 7.25 (t, 1H), 7.21-7.17 (m, 1H), 7.06 (ddd, 1H), 6.92-6.89 (m, 1H), 6.75 (dt, 1H), 3.07 (d, 1H) |
| 372 | 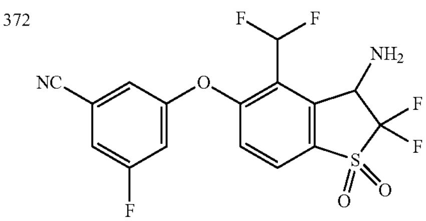 | 405 (M + H) | (400 MHz, CDCl$_3$): δ 7.95 (d, 1H), 7.31-7.27 (m, 1H), 7.30 (dd, 1H), 7.19-7.14 (m, 2H), 7.07 (dt, 1H), 5.00-4.92 (m, 1H), 2.03 (d, 2H) |
| 373 | 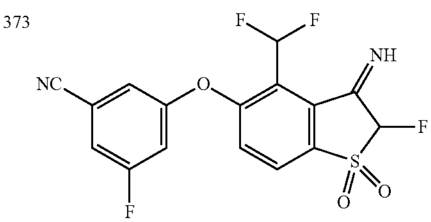 | 385 (M + H) | (400 MHz, CDCl$_3$): δ 11.26-11.22 (m, 1H), 8.09 (dd, 1H), 8.06 (d, 1H), 7.04 (d, 1H), 7.27-7.23 (m, 1H), 7.15-7.13 (m, 1H), 7.06 (dt, 1H), 5.87 (dd, 1H) |
| 374 | 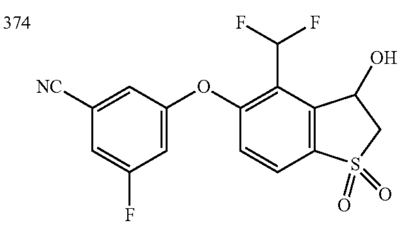 | 370 (M − H) | (400 MHz, CDCl$_3$): δ 7.89 (d, 1H), 7.28-7.25 (m, 1H), 7.20 (t, 1H), 7.17-7.13 (m, 2H), 7.04 (dt, 1H), 5.90-5.85 (m, 1H), 3.79 (dd, 1H), 3.69 (dd, 1H), 2.93 (t, 1H) |
| 375 | 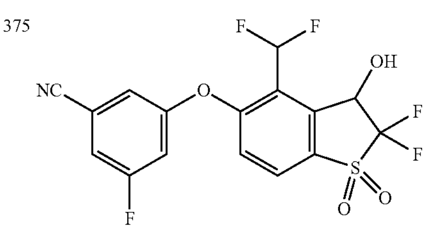 | 404 (M − H) | (400 MHz, CDCl$_3$): δ 7.98 (d, 1H), 7.31 (ddd, 1H), 7.23 (t, 1H), 7.22-7.18 (m, 2H), 7.08 (dt, 1H), 5.66 (dd, 1H), 3.23 (d, 1H) |
| 376 | 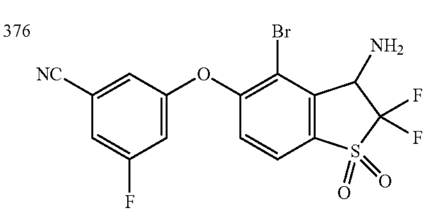 | 426, 428 (M + H) | (400 MHz, CDCl$_3$): δ 7.78 (d, 1H), 7.18 (d, 1H), 6.72 (tt, 1H), 6.63-6.54 (m, 2H), 4.70 (dt, 1H), 1.92 (d, 2H) |

TABLE 2-continued

| No. | Structure | Mass Characterization | ¹H NMR Data |
|---|---|---|---|
| 377 | 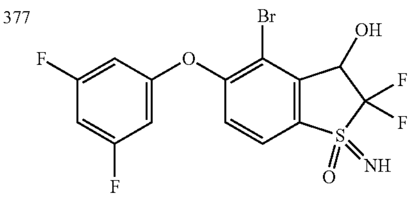 | 426, 428 (M + H) | (400 MHz, CDCl$_3$): δ 7.88 (d, 1H), 7.22 (d, 1H), 6.71 (tt, 1H), 6.62-6.55 (m, 2H), 5.31 (dd, 1H), 3.43 (br s, 1H), 3.03 (d, 1H) |
| 378 | 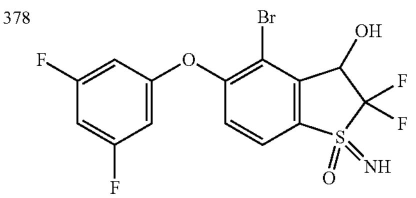 | 426, 428 (M + H) | (400 MHz, CDCl$_3$): δ 7.81 (d, 1H), 7.22 (d, 1H), 6.70 (tt, 1H), 6.61-6.54 (m, 2H), 5.35 (t, 1H), 3.75 (br s, 1H), 3.27 (d, 1H) |
| 379 | 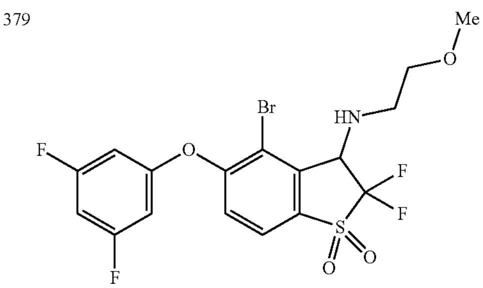 | 484, 486 (M + H) | (400 MHz, CDCl$_3$): δ 7.75 (d, 1H), 7.16 (d, 1H), 6.71 (tt, 1H), 6.62-6.55 (m, 2H), 4.60 (dd, 1H), 3.55 (t, 2H), 3.35 (s, 3H), 3.21-3.06 (m, 2H), 2.10-2.03 (m, 1H) |
| 380 | 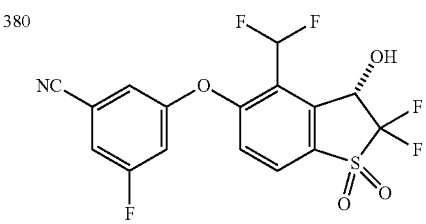 | 404 (M − H) | (400 MHz, CDCl$_3$): δ 7.98 (d, 1H), 7.31 (ddd, 1H), 7.23 (t, 1H), 7.22-7.18 (m, 2H), 7.08 (dt, 1H), 5.66 (dd, 1H), 3.23 (d, 1H) |
| 381 | 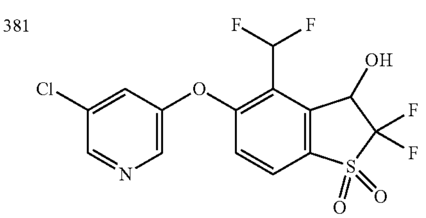 | 398, 400 (M + H) | (400 MHz, CDCl$_3$): δ 8.55 (d, 1H), 8.38 (d, 1H), 7.96 (d, 1H), 7.46 (t, 1H), 7.29 (t, 1H), 7.16-7.13 (m, 1H), 5.67 (dd, 1H), 3.24 (dd, 1H) |
| 382 | 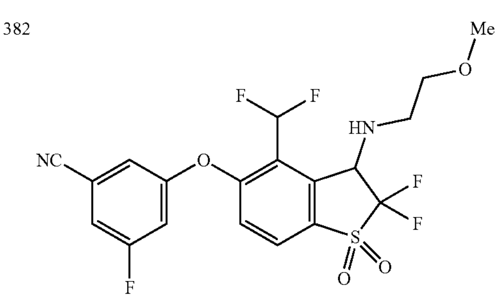 | 463 (M + H) | (400 MHz, CDCl$_3$): δ 7.91 (d, 1H), 7.39 (t, 1H), 7.29-7.24 (m, 1H), 7.19-7.14 (m, 2H), 7.05 (dt, 1H), 4.94-4.87 (m, 1H), 3.53 (t, 2H), 3.37 (s, 3H), 3.17-3.07 (m, 2H), 2.28-2.20 (m, 1H) |

TABLE 2-continued

| No. | Structure | Mass Characterization | ¹H NMR Data |
|---|---|---|---|
| 383 | 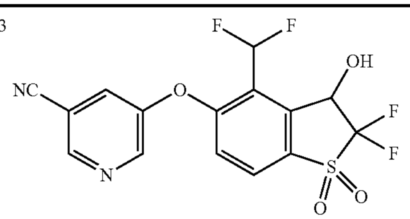 | 389 (M + H) | (400 MHz, CD₃OD): δ 8.81 (d, 1H), 8.71 (d, 1H), 8.08 (d, 1H), 8.04 (dd, 1H), 7.42 (d, 1H), 7.38 (t, 1H), 5.69 (d, 1H) |
| 384 | 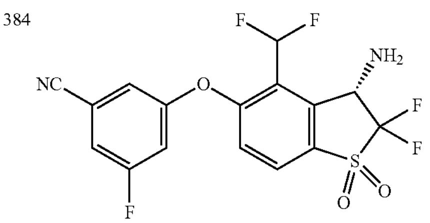 | 405 (M + H) | (400 MHz, CDCl₃): δ 7.95 (d, 1H), 7.31-7.27 (m, 1H), 7.30 (dd, 1H), 7.19-7.14 (m, 2H), 7.07 (dt, 1H), 5.01-4.91 (dd, 1H), 2.06-1.99 (m, 2H) |
| 385 | 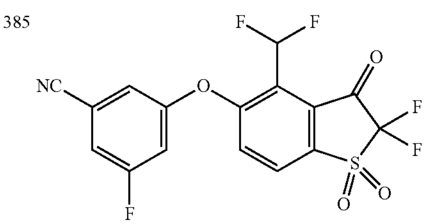 | | (400 MHz, (CD₃)₂SO): δ 8.79 (s, 2H), 8.27 (d, 1H), 7.78-7.73 (m, 1H), 7.72 (t, 1H), 7.55-7.47 (m, 3H) |
| 386 | 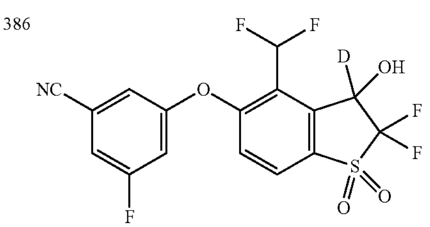 | 405 (M − H) | (400 MHz, CDCl₃): δ 7.98 (d, 1H), 7.33-7.30 (m, 1H), 7.23 (t, 1H), 7.22-7.18 (m, 2H), 7.08 (dt, 1H), 3.12 (s, 1H) |
| 387 | 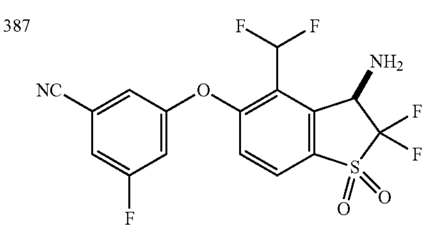 | 405 (M + H) | (400 MHz, CDCl₃): δ 7.94 (d, 1H), 7.30 (d, 1H), 7.31-7.27 (m, 1H), 7.19-7.14 (m, 2H), 7.08 (dt, 1H), 5.02-4.89 (m, 1H), 2.12-1.92 (m, 2H) |
| 388 | 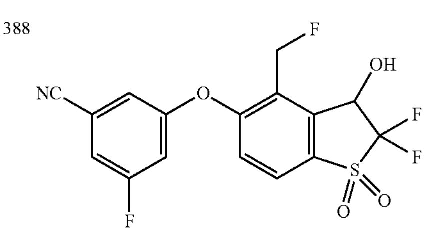 | 405 (M + NH₄) | (400 MHz, CDCl₃): δ 7.90 (d, 1H), 7.29-7.25 (m, 1H), 7.19 (d, 1H), 7.16-7.14 (m, 1H), 7.06-7.01 (m, 1H), 5.75 (d, 2H), 5.58 (br d, 1H), 3.30-3.22 (m, 1H) |
| 389 | 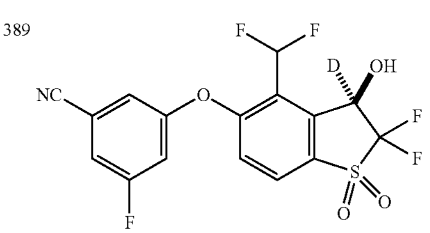 | 405 (M − H) | (400 MHz, CDCl₃): δ 7.98 (d, 1H), 7.33-7.30 (m, 1H), 7.23 (t, 1H), 7.22-7.18 (m, 2H), 7.08 (dt, 1H), 3.12 (s, 1H) |

TABLE 2-continued

| No. | Structure | Mass Characterization | ¹H NMR Data |
|---|---|---|---|
| 390 | 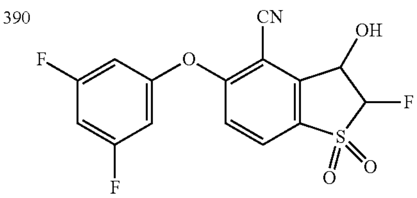 | 373 (M + NH₄) | (400 MHz, CD₃CN): δ 8.02 (d, 1H), 7.27 (d, 1H), 7.01-6.87 (m, 3H), 5.88-5.73 (m, 2H), 4.91 (d, 1H) |
| 391 | 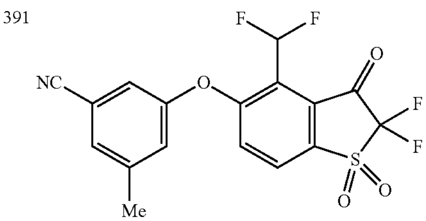 | | (400 MHz, CDCl₃): δ 8.13 (d, 1H), 7.67 (t, 1H), 7.53 (d, 1H), 7.43 (s, 1H), 7.21 (s, 1H), 7.15 (s, 1H), 2.45 (s, 3H) |
| 392 | 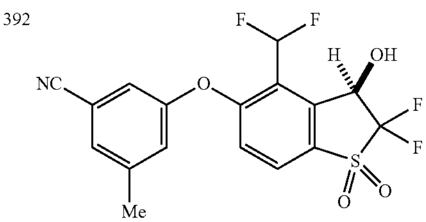 | 419 (M + NH₄) | (400 MHz, CDCl₃): δ 7.91 (d, 1H), 7.41 (s, 1H), 7.27 (t, 1H), 7.21 (s, 1H), 7.13 (s, 1H), 7.10 (d, 1H), 5.71-5.64 (m, 1H), 3.04 (br d, 1H), 2.44 (s, 3H) |
| 393 | 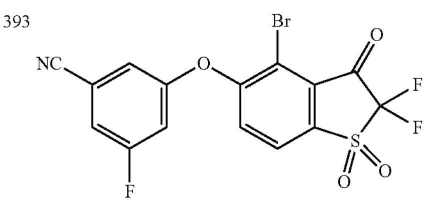 | 467, 469 (M + H2O + NH4) | (400 MHz, CDCl₃): δ 8.05 (d, 1H), 7.55 (d, 1H), 7.30 (d, 1H), 7.13 (s, 1H), 7.07-7.02 (m, 1H) |
| 394 | 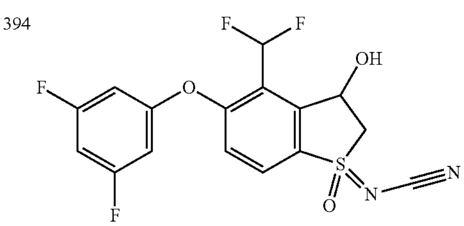 | 387 (M + H) | (400 MHz, CDCl₃): δ 8.01 (d, 1H), 7.28 (t, 1H), 7.21 (d, 1H), 6.83-6.76 (m, 1H), 6.69-6.63 (m, 2H), 6.03-5.97 (m, 1H), 4.20 (dd, 1H), 3.88 (dd, 1H), 3.15-3.11 (m, 1H) |
| 395 | 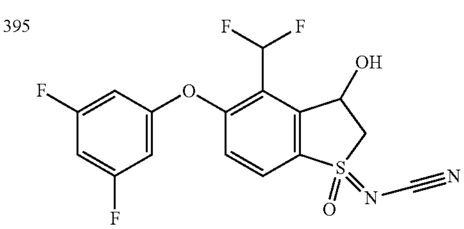 | 387 (M + H) | (400 MHz, CDCl₃): δ 7.97 (d, 1H), 7.26 (t, 1H), 7.21 (d, 1H), 6.83-6.76 (m, 1H), 6.70-6.63 (m, 2H), 5.99 (t, 1H), 4.08-4.02 (m, 1H), 3.98 (dd, 1H), 3.20-3.15 (m, 1H) |
| 396 | 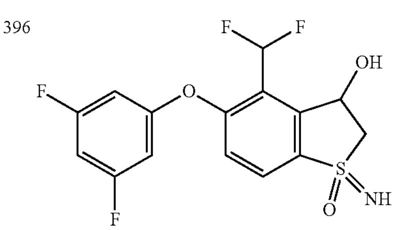 | 362 (M + H) | (400 MHz, CDCl₃): δ 7.80 (d, 1H), 7.17 (t, 1H), 7.12 (d, 1H), 6.74-6.67 (m, 1H), 6.62-6.55 (m, 2H), 5.80-5.74 (m, 1H), 3.80 (dd, 1H), 3.75-3.69 (m, 2H), 3.41-3.34 (m, 1H) |

TABLE 2-continued

| No. | Structure | Mass Characterization | ¹H NMR Data |
|---|---|---|---|
| 397 | 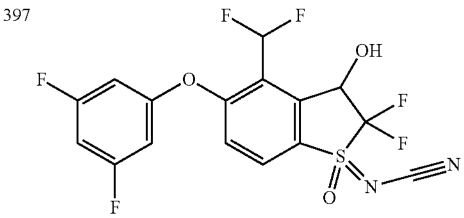 | 423 (M + H) | (400 MHz, CDCl$_3$): δ 8.07-8.00 (m, 1H), 7.42-7.13 (m, 2H), 6.87-6.80 (m, 1H), 6.73-6.66 (m, 2H), 5.83-5.76 (m, 1H), 3.78-3.66 (m, 1H) |
| 398 | 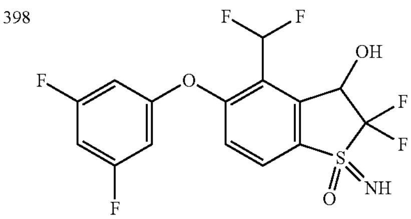 | 398 (M + H) | (400 MHz, CDCl$_3$): δ 8.02 (d, 1H), 7.22 (t, 1H), 7.19 (d, 1H), 6.79-6.72 (m, 1H), 6.66-6.59 (m, 2H), 5.60 (t, 1H), 3.39 (br s, 1H), 3.12 (d, 1H) |
| 399 | 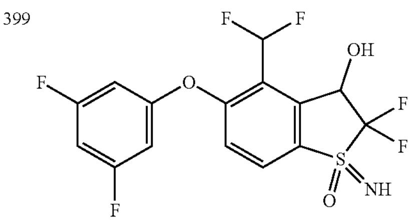 | 398 (M + H) | (400 MHz, CDCl$_3$): δ 7.95 (d, 1H), 7.23 (t, 1H), 7.19 (d, 1H), 6.79-6.72 (m, 1H), 6.66-6.59 (m, 2H), 5.64 (t, 1H), 3.68 (br s, 1H), 3.33 (d, 1H) |
| 400 | 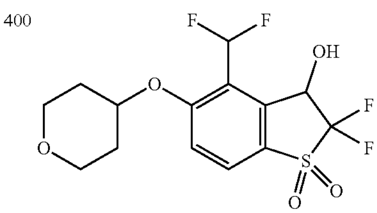 | 387 (M + H) | (400 MHz, CD$_3$OD): δ 7.99 (d, 1H), 7.57 (d, 1H), 7.26 (t, 1H), 5.57-5.52 (m, 1H), 4.95-4.88 (m, 1H), 3.98-3.91 (m, 2H), 3.67-3.60 (m, 2H), 2.32-2.03 (m, 2H), 1.86-1.76 (m, 2H) |
| 401 | 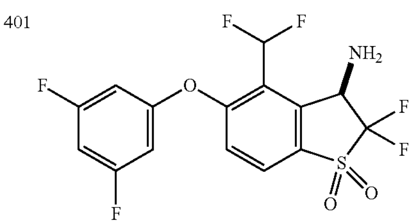 | 398 (M + H) | (400 MHz, CDCl$_3$): δ 7.90 (d, 1H), 7.29 (t, 1H), 7.16 (d, 1H), 6.76 (tt, 1H), 6.67-6.60 (m, 2H), 5.02-4.93 (m, 1H), 2.01 (br d, 2H) |
| 402 | 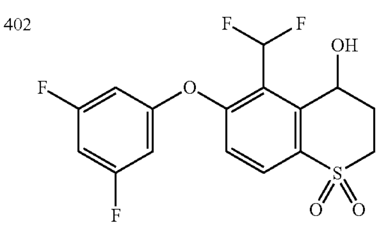 | 394 (M + NH$_4$) | (400 MHz, CDCl$_3$): δ 8.08 (d, 1H), 7.31 (t, 1H), 7.10 (d, 1H), 6.71 (tt, 1H), 6.61-6.54 (m, 2H), 5.52-5.48 (m, 1H), 4.05 (td, 1H), 3.32 (ddd, 1H), 2.84-2.74 (m, 1H), 2.73-2.64 (m, 2H) |
| 403 | 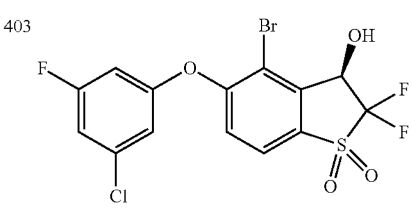 | 441, 443, 445 (M − H) | (CDCl$_3$, 400 MHz) δ: 7.80 (d, 1H), 7.22 (d, 1H), 7.02-7.00 (m, 1H), 6.87-6.86 (m, 1H), 6.72 (dt, 1H), 5.38 (d, 1H) |

TABLE 2-continued

| No. | Structure | Mass Characterization | $^1$H NMR Data |
|---|---|---|---|
| 404 | 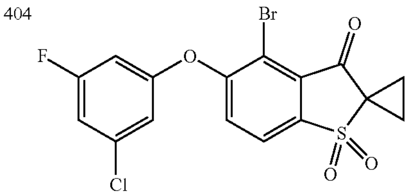 | 475, 477, 479 (M + HCO2−) | (CDCl$_3$, 400 MHz) δ: 8.00 (d, 1H), 7.46 (d, 1H), 6.99-6.96 (m, 1H), 6.81-6.80 (m, 1H), 6.67 (dt, 1H), 2.08-2.04 (m, 2H), 1.96-1.93 (m, 2H) |
| 405 | 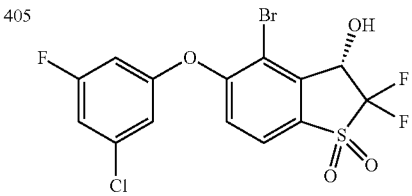 | 441, 443, 445 (M − H) | (CDCl$_3$, 400 MHz): δ 7.80 (d, 1H), 7.22 (d, 1H), 7.02-7.00 (m, 1H), 6.87-6.86 (m, 1H), 6.72 (dt, 1H), 5.38 (d, 1H) |
| 406 | 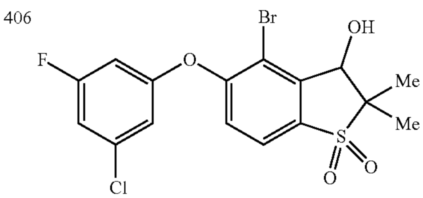 | 479, 481, 483 (M + HCO$_2^-$) | (CDCl$_3$, 400 MHz): δ 7.73 (dd, 1H), 7.16 (d, 1H), 6.98-6.95 (m, 1H), 6.83-6.82 (m, 1H), 6.66 (dt, 1H), 1.65 (s, 3H), 1.40 (s, 3H) |
| 407 | 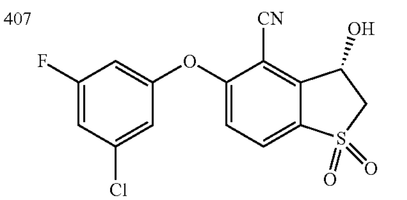 | 352, 354 (M − H) | (CDCl$_3$, 400 MHz): δ 7.89 (d, 1H), 7.13 (d, 1H), 7.09-7.06 (m, 1H), 6.96-6.94 (m, 1H), 6.80 (dt, 1H), 5.78-5.74 (m, 1H), 3.91 (dd, 1H), 3.65 (dd, 1H), 3.41 (d, 1H) |
| 408 | 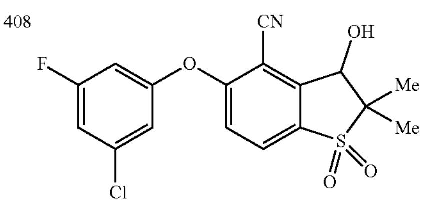 | 380, 382 (M − H) | (CDCl$_3$, 400 MHz): δ 7.91 (d, 1H), 7.10-7.06 (m, 2H), 6.97-6.96 (m, 1H), 6.81 (dt, 1H), 1.55 (s, 3H), 1.49 (s, 3H) |
| 409 | 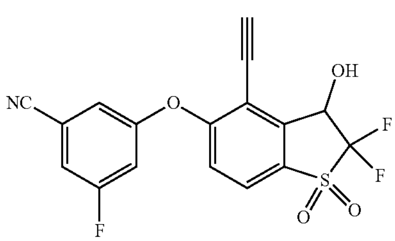 [SMILES: C#Cc1c(Oc2cc(F)cc(C#N)c2)ccc2c1C(O)C(F)(F)S2(=O)=O] | 397 (M + NH$_4$) | (400 MHz, CDCl$_3$): δ 7.85 (d, 1H), 7.27-7.23 (m, 2H), 7.15 (s, 1H), 7.04 (d, 1H), 5.46 (dd, 1H), 3.69 (s, 1H), 3.13 (d, 1H) |
| 410 | 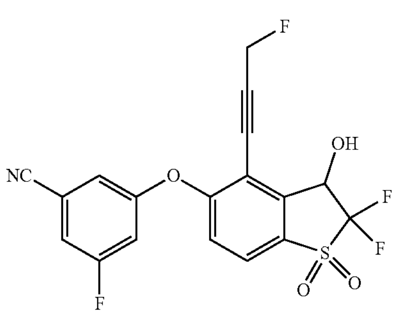 [SMILES: N#Cc1cc(F)cc(Oc2ccc3c(c2C#CCF)C(O)C(F)(F)S3(=O)=O)c1] | 410 (M − H) | (400 MHz, CDCl$_3$): δ 7.85 (d, 1H), 7.28-7.25 (m, 1H), 7.23 (d, 1H), 7.16-7.14 (m, 1H), 7.05 (dt, 1H), 5.43 (d, 1H), 5.19 (d, 2H), 3.27 (s, 1H) |

| No. | Structure | Mass Characterization | ¹H NMR Data |
|---|---|---|---|
| 411 | 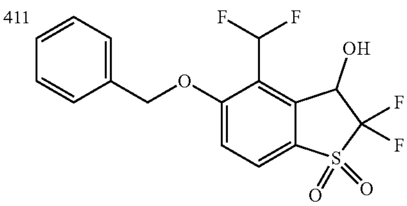 | 394 (M + NH$_4$) | (400 MHz, CDCl$_3$): δ 7.92 (d, 1H), 7.46-7.10 (m, 7H), 5.61 (d, 1H), 5.26(s, 2H), 3.00 (s, 1H) |
| 412 | 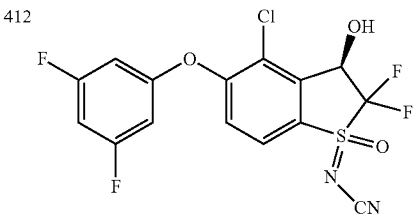 | 407, 409 (M + H) | (400 MHz, CDCl$_3$): δ 7.89-7.81 (m, 1H), 7.31-7.26 (m, 1H), 6.78 (t, 1H), 6.65 (d, 2H), 5.59-5.51 (m, 1H), 4.60-4.38 (br s, 1H) |
| 413 | 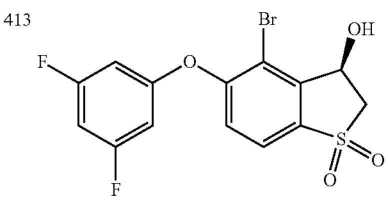 | | (400 MHz, CDCl$_3$): δ 7.72 (d, 1H), 7.21 (d, 1H), 6.71-6.64 (m, 1H), 6.57-6.52 (m, 2H), 5.60 (t, 1H), 3.83-3.78 (m, 1H), 3.71-3.67 (m, 1H), 2.88 (d, 1H) |
| 414 | 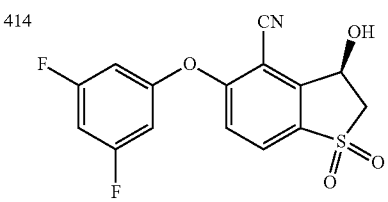 | | (400 MHz, CDCl$_3$): δ 7.89 (d, 1H), 7.15 (d, 1H), 6.83-6.76 (m, 1H), 6.71-6.67 (m, 2H), 5.78-5.74 (m, 1H), 3.94-3.89 (m, 1H), 3.67-3.63 (m, 1H), 3.27-3.24 (m, 1H) |
| 415 | 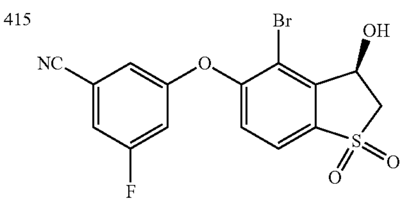 | | (400 MHz, CDCl$_3$): δ 7.77 (d, 1H), 7.25 (d, 1H), 7.22-7.19 (m, 1H), 7.06-7.05 (m, 1H), 6.99-6.96 (m, 1H), 5.62-5.59 (m, 1H), 3.85-3.80 (m, 1H), 3.71-3.69 (m, 1H), 2.90 (d, 1H) |
| 416 | 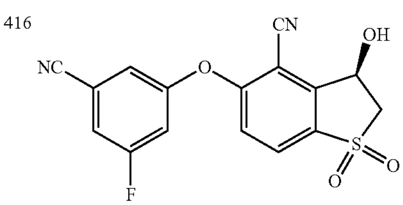 | | (400 MHz, CDCl$_3$): δ 7.94 (d, 1H), 7.35-7.31 (m, 1H), 7.24-7.22 (m, 1H), 7.16 (d, 1H), 7.16-7.12 (m, 1H), 5.80-5.73 (m, 1H), 3.96-3.90 (m, 1H), 3.68-3.63 (m, 1H), 3.48-3.46 (m, 1H) |
| 417 | 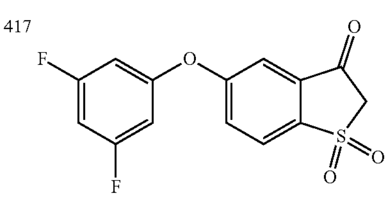 | | (400 MHz, CDCl$_3$): δ 8.24 (d, 1H), 7.89-7.86 (dd, 1H), 7.11 (d, 1H), 6.70-6.65 (m, 1H), 6.59-6.51 (m, 2H), 3.10 (s, 2H) |

TABLE 2-continued

| No. | Structure | Mass Characterization | ¹H NMR Data |
|---|---|---|---|
| 418 | 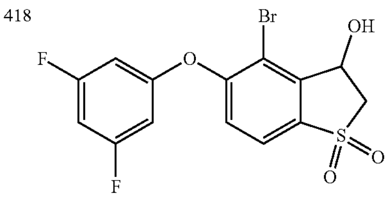 | | (400 MHz, CDCl$_3$): δ 7.72 (d, 1H), 7.20 (d, 1H), 6.70-6.65 (m, 1H), 6.58-6.52 (m, 2H), 5.62-5.58 (m, 1H), 3.83-3.78 (m, 1H), 3.71-3.67 (m, 1H), 2.93 (d, 1H) |
| 419 | 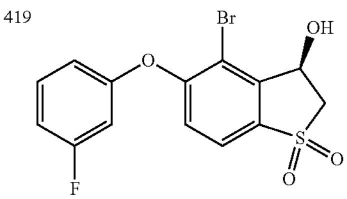 | | (400 MHz, CDCl$_3$): δ 7.66 (d, 1H), 7.40-7.35 (m, 1H), 7.10 (d, 1H), 6.97-6.93 (m, 1H), 6.83-6.76 (m, 2H), 5.62-5.59 (m, 1H), 3.82-3.77 (m, 1H), 3.70-3.66 (m, 1H), 2.96 (d, 1H) |
| 420 | 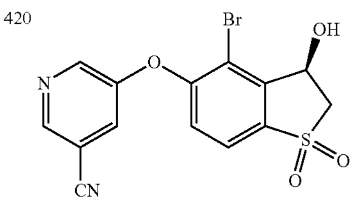 | | (400 MHz, CDCl$_3$ + CD$_3$OD): δ 8.69 (d, 1H), 8.61-8.60 (d, 1H), 7.79 (d, 1H), 7.55-7.54 (m, 1H), 7.29 (d, 1H), 5.57(d, 1H), 3.84-3.79 (m, 1H), 3.70-3.66(m, 1H) |
| 421 | 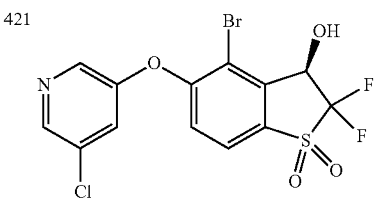 | | (400 MHz, CDCl$_3$): δ 8.50 (s, 1H), 8.33 (s, 1H), 7.81 (d, 1H), 7.41-7.40 (m, 1H), 7.19 (d, 1H), 5.41-5.37 (m, 1H), 3.45-3.40 (m, 1H) |
| 422 | 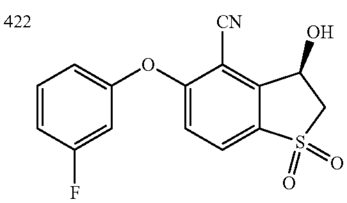 | | (400 MHz, CDCl$_3$): δ 7.83 (d, 1H), 7.48-7.42 (m, 1H), 7.08-7.03 (m, 1H), 7.06 (d, 1H), 6.94-6.87 (m, 2H), 5.78-5.73 (m, 1H), 3.93-3.88 (m, 1H), 3.66-3.62 (m, 1H), 3.56 (d, 1H) |
| 423 | 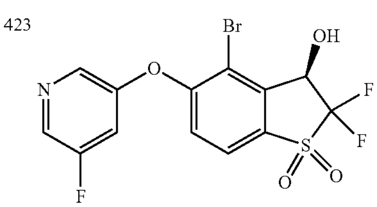 | | (400 MHz, CDCl$_3$): δ 8.43 (d, 1H), 8.29 (d, 1H), 7.82 (d, 1H), 7.21 (d, 1H), 7.18-7.14 (dt, 1H), 5.41-5.37 (m, 1H), 3.29-3.28 (m, 1H) |
| 424 | 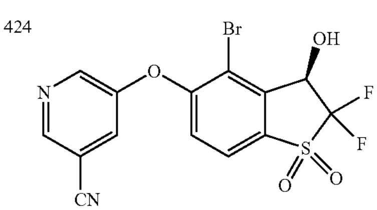 | | (400 MHz, CDCl$_3$): δ 8.76 (s, 1H), 8.64 (d, 1H), 7.87 (d, 1H), 7.59-7.58 (m, 1H), 7.27 (d, 1H), 5.42-5.36 (m, 1H), 3.36-3.32 (m, 1H) |

TABLE 2-continued

| No. | Structure | Mass Characterization | ¹H NMR Data |
|---|---|---|---|
| 425 | 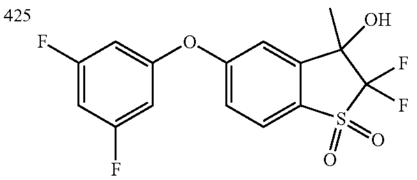 | 407 (M + HCOOH − H) | (400 MHz, CDCl$_3$): δ 7.81 (d, 1H), 7.28 (d, 1H), 7.24-7.21 (m, 1H), 6.76-6.70 (1H), 6.65-6.95 (m, 2H), 2.80 (m, 1H), 1.75 (m, 3H) |
| 426 | 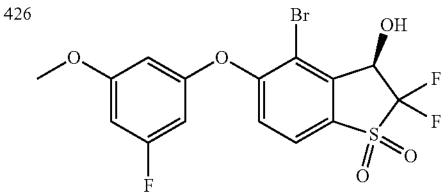 | 437, 439 (M − H) | (400 MHz, CDCl$_3$) δ 7.75 (d, 1H), 7.17 (d, 1H), 6.56-6.51 (m, 1H), 6.42-6.37 (m, 2H), 5.42-5.35 (m, 1H), 3.80 (s, 3H), 2.99-2.95 (m, 1H) |
| 427 | 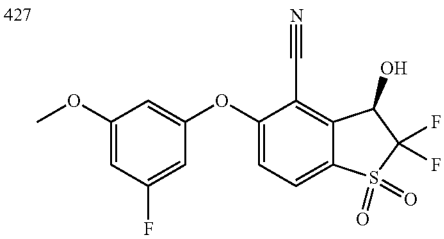 | 384 (M − H) | (400 MHz, CDCl$_3$) δ 7.92 (d, 1H), 7.17 (d, 1H), 6.64-6.60 (m, 1H), 6.50-6.45 (m, 2H), 6.57-6.51 (m, 1H), 3.82 (s, 3H), 3.80-3.74 (m, 1H) |
| 428 | 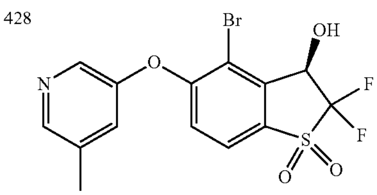 | | (400 MHz, CDCl$_3$): δ 8.38-8.36 (m, 1H), 8.14 (d, 1H), 7.72 (d, 1H), 7.24-7.22 (m, 1H), 7.01 (d, 1H), 5.41-5.37 (m, 1H), 4.14-4.08 (m, 1H), 2.40 (s, 3H) |
| 429 | 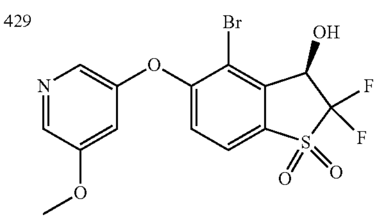 | | (400 MHz, CDCl$_3$): δ 8.26-8.23 (m, 1H), 7.95-7.93 (m, 1H), 7.73 (d, 1H), 7.06 (d, 1H), 6.95-6.92 (m, 1H), 5.42-5.35 (m, 1H), 4.03-3.97 (m, 1H), 3.88 (s, 3H) |
| 430 | 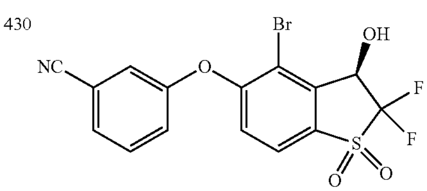 | | (400 MHz, CDCl$_3$): δ 7.80 (d, 1H), 7.59-7.54 (m, 2H), 7.37-7.35 (m, 1H), 7.32-7.27 (m, 1H), 7.15 (d, 1H), 5.42-5.37 (m, 1H), 3.11 (d, 1H) |
| 431 | 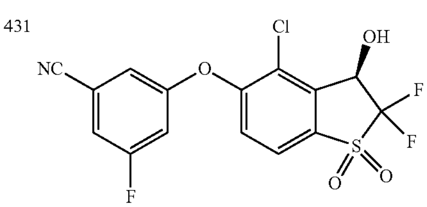 | 388, 390 (M − H) | (400 MHz, CDCl$_3$): δ 7.82 (d, 1H), 7.32 (d, 1H), 7.25-7.23 (m, 1H), 7.12-7.10 (m, 1H), 7.03-7.00 (dt, 1H), 5.44 (d, 1H), 3.39-3.25 (m, 1H) |

TABLE 2-continued

| No. | Structure | Mass Characterization | ¹H NMR Data |
|---|---|---|---|
| 432 | 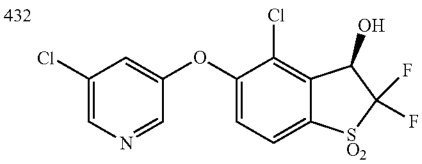 | | (400 MHz, CDCl₃): δ 8.50 (d, 1H), 8.33 (d, 1H), 7.78 (d, 1H), 7.41-7.40 (m, 1H), 7.22 (d, 1H), 5.47-5.42 (m, 1H), 3.45 (d, 1H) |
| 433 | 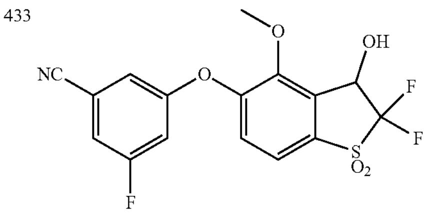 | 430 (M + HCOOH − H) | (400 MHz, CDCl₃): δ 7.62 (d, 1H), 7.32 (d, 1H), 7.21-7.18 (m, 1H), 7.08-7.06 (m, 1H), 6.97-6.93 (m, 1H), 5.47-5.43 (m, 1H), 4.02 (s, 3H), 3.10-3.08 (m, 1H) |
| 434 | 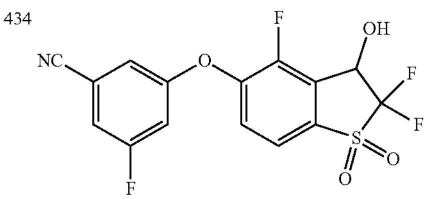 | 418 (M + HCOOH − H) | (400 MHz, CDCl₃): δ 7.72 (d, 1H), 7.44-7.40 (m, 1H), 7.25-7.22 (m, 1H), 7.13-7.10 (m, 1H), 7.05-7.01 (m, 1H), 5.51 (d, 1H) |
| 435 | 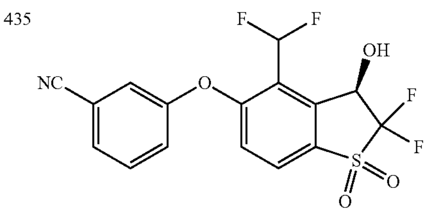 | | (400 MHz, CDCl₃): δ 7.92 (d, 1H), 7.62-7.57 (m, 2H), 7.42-7.40 (m, 1H), 7.35-7.31 (m, 1H), 7.28 (t, J = 53 Hz, 1H), 7.11 (d, 1H), 5.69-5.65 (m, 1H), 3.33-3.32 (m, 1H) |
| 436 | 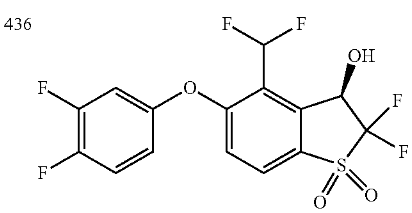 | | (400 MHz, CDCl₃ + CD₃OD): δ 7.80 (d, 1H), 7.23-7.15 (m, 1H), 7.20 (t, 1H), 7.02 (d, 1H), 6.94-6.88 (m, 1H), 6.80-6.75 (m, 1H), 5.50 (d, 1H) |
| 437 | 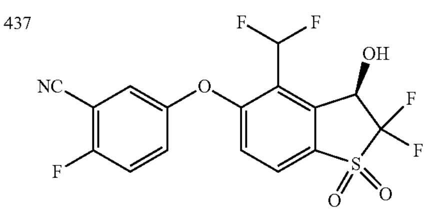 | | (400 MHz, CDCl₃ + CD₃OD): δ 7.83 (d, 1H), 7.33-7.23 (m, 3H), 7.18 (t, 1H), 7.01 (d, 1H), 5.51-5.48 (m, 1H) |
| 438 | 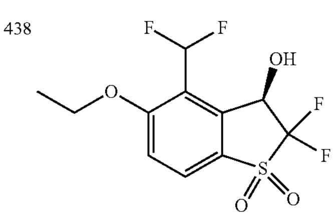 | | (400 MHz, CDCl₃): δ 7.93 (d, 1H), 7.24 (d, 1H), 7.21 (t, 1H), 5.63-5.58 (m, 1H), 4.23 (q, 2H), 2.94-2.89 (m, 1H), 1.51 (t, 3H) |

TABLE 2-continued

| No. | Structure | Mass Characterization | ¹H NMR Data |
|---|---|---|---|
| 439 | 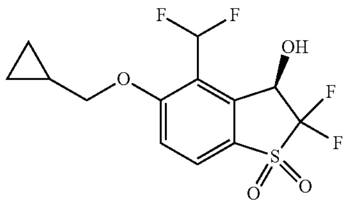 [SMILES: O=S1(=O)c2ccc(OCC3CC3)c(C(F)F)c2[C@@H](O)C1(F)F] | | (400 MHz, CDCl$_3$): δ 7.92 (d, 1H), 7.26 (t, 1H), 7.21 (d, 1H), 5.63-5.59 (m, 1H), 4.01-3.98 (m, 2H), 2.95-2.92 (m, 1H), 1.37-1.27 (m, 1H), 0.74-0.70 (m, 2H), 0.42-0.38 (m, 2H) |
| 440 | 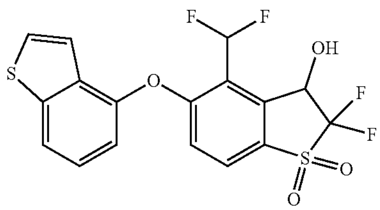 [SMILES: O=S1(=O)c2ccc(Oc3cccc4sccc34)c(C(F)F)c2C(O)C1(F)F] | | (400 MHz, CDCl$_3$): δ 7.85 (d, 1H), 7.78 (d, 1H), 7.50 (d, 1H), 7.47 (t, 1H), 7.42 (t, 1H), 7.17 (dd, 1H), 7.05 (dd, 1H), 6.96 (d, 1H), 5.73-5.67 (m, 1H), 3.20-3.13 (br s, 1H) |
| 441 | 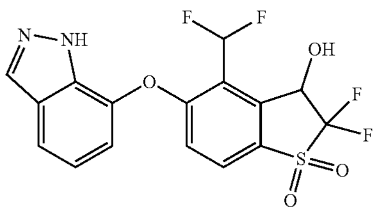 [SMILES: O=S1(=O)c2ccc(Oc3cccc4cn[nH]c34)c(C(F)F)c2C(O)C1(F)F] | | (400 MHz, CDCl$_3$): δ 8.17 (s, 1H), 7.83 (d, 1H), 7.72 (d, 1H), 7.42 (t, 1H), 7.22 (t, 1H), 7.12-7.07 (m, 2H), 5.69 (d, 1H) |
| 442 | 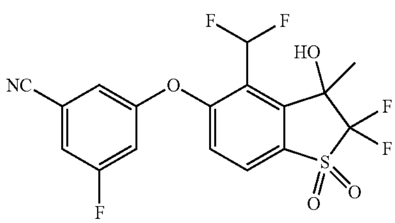 [SMILES: CC1(O)c2c(ccc(Oc3cc(F)cc(C#N)c3)c2C(F)F)S(=O)(=O)C1(F)F] | 418 (M − H) | (400 MHz, CDCl$_3$): δ 7.95-7.90 (d, 1H), 7.65 (t, 1H), 7.25-7.22 (m, 1H), 7.22-7.18 (d, 1H), 7.13-7.11 (m, 1H), 7.08-7.04 (m, 1H), 3.73 (brd s, 1H), 1.91-1.88 (m, 3H) |
| 443 | 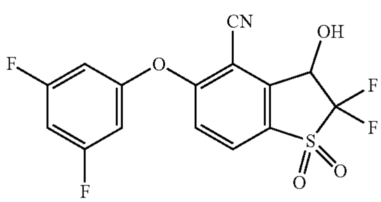 [SMILES: N#Cc1c(Oc2cc(F)cc(F)c2)ccc2c1C(O)C(F)(F)S2(=O)=O] | 372 (M − H) | (400 MHz, CDCl$_3$): δ 7.97 (d, 1H), 7.20 (d, 1H), 6.87-6.81 (m, 1H), 6.76-6.69 (m, 2H), 5.55 (dd, 1H) |
| 444 | 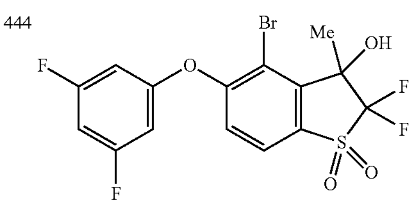 | 439, 441 (M − H) | (400 MHz, CDCl$_3$): δ 7.78 (d, 1H), 7.16 (d, 1H), 6.75-6.69 (m, 1H), 6.62-6.54 (m, 2H), 3.04-2.98 (m, 1H), 1.95 (d, 3H) |
| 445 | 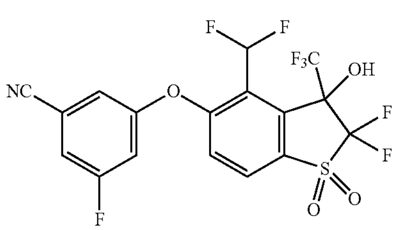 [SMILES: N#Cc1cc(F)cc(Oc2ccc3c(c2C(F)F)C(O)(C(F)(F)F)C(F)(F)S3(=O)=O)c1] | 472 (M − H) | (400 MHz, CDCl$_3$): 8.03 (d, 1H), 7.57 (t, 1H), 7.37 (d, 1H), 7.29-7.25 (m, 1H), 7.17-7.14 (m, 1H), 7.08 (dt, 1H), 5.40-5.10 (m, 1H) |

TABLE 2-continued

| No. | Structure | Mass Characterization | $^1$H NMR Data |
|---|---|---|---|
| 446 | 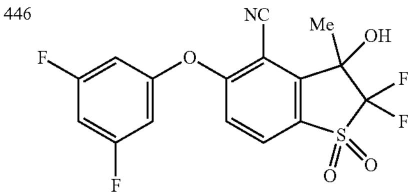 | 386 (M − H) | (400 MHz, CDCl$_3$): δ 7.93 (d, 1H), 7.13 (d, 1H), 6.83 (tt, 1H), 6.75-6.68 (m, 2H), 3.54 (s, 1H), 1.97 (d, 3H) |
| 447 | 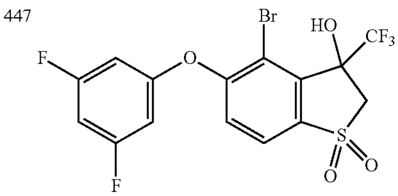 | 457, 459 (M − H) | (400 MHz, CDCl$_3$): δ 7.79 (d, 1H), 7.27 (d, 1H), 6.72 (tt, 1H), 6.62-6.55 (m, 2H), 4.71 (s, 1H), 4.16 (d, 1H), 3.83 (d, 1H) |
| 448 | 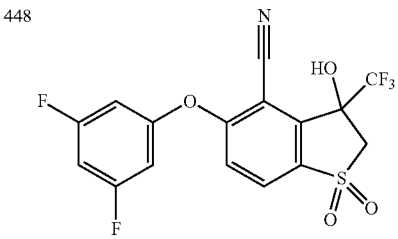 | 404 (M − H) | (400 MHz, CDCl$_3$): δ 7.94 (d, 1H), 7.26 (d, 1H), 6.83 (tt, 1H), 6.76-6.69 (m, 2H), 4.26 (br s, 1H), 4.18 (d, 1H), 3.81 (d, 1H) |
| 449 | 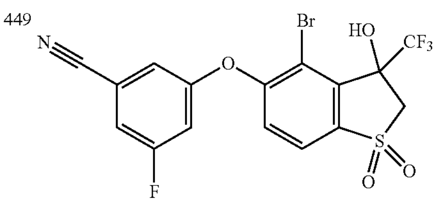 | 464, 466 (M − H) | (400 MHz, CDCl$_3$): δ 7.84 (d, 1H), 7.30 (d, 1H), 7.27-7.24 (m, 1H), 7.12-7.10 (m, 1H), 7.00 (dt, 1H), 4.63 (s, 1H), 4.18 (d, 1H), 3.85 (d, 1H) |
| 450 | 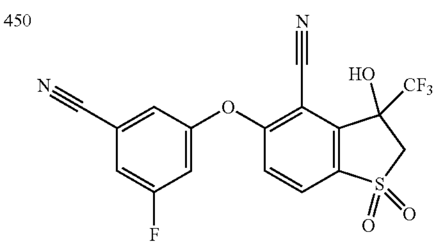 | 411 (M − H) | (400 MHz, CDCl$_3$): δ 7.99 (d, 1H), 7.38 -7.34 (m, 1H), 7.29-7.24 (m, 2H), 7.20-7.16 (dt, 1H), 4.75 (br s, 1H), 4.20 (d, 1H), 3.82 (d, 1H) |
| 451 | 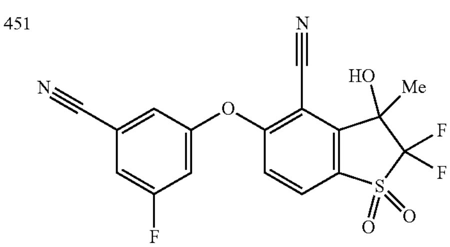 | 393 (M − H) | (400 MHz, CDCl$_3$): δ 7.98 (d, 1H), 7.39-7.35 (m, 1H), 7.27-7.25 (m, 1H), 7.17 (dt, 1H), 7.13 (d, 1H), 3.27 (d, 1H), 1.99 (d, 3H) |
| 452 | 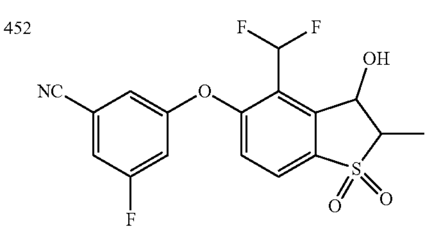 | 401 (M + NH$_4{}^+$) | (400 MHz, CDCl$_3$): δ 7.89 (d, 1H), 7.27-7.24 (m, 1H), 7.21 (t, 1H), 7.16-7.11 (m, 2H), 7.06-7.02 (m, 1H), 5.34 (br s, 1H), 3.66-3.58 (m, 1H), 3.13 (br s, 1H), 1.55 (d, 3H) |

TABLE 2-continued

| No. | Structure | Mass Characterization | ¹H NMR Data |
|---|---|---|---|
| 453 | 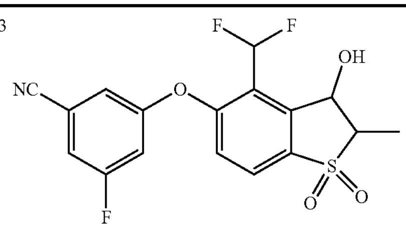 | 401 (M + NH₄⁺) | (400 MHz, DMSO-d6): δ 7.99 (d, 1H), 7.75-7.71 (m, 1H), 7.52-7.49 (m, 1H), 7.48-7.44 (m, 1H), 7.36 (d, 1H), 7.29 (t, 1H), 6.23 (d, 1H), 5.52 (t, 1H), 3.76-3.68 (m, 1H), 1.35 (d, 3H) |
| 454 | 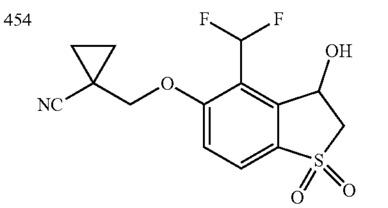 | 347 (M + NH₄⁺) | (400 MHz, CDCl₃): δ 7.84 (d, 1H), 7.31 (t, 1H), 7.09 (d, 1H), 5.87-5.79 (m, 1H), 4.17-4.04 (m, 2H), 3.75-3.68 (m, 1H), 3.65-3.59 (m, 1H), 2.91-2.84 (m, 1H), 1.54-1.48 (m, 2H), 1.22-1.14 (m, 2H) |
| 455 | 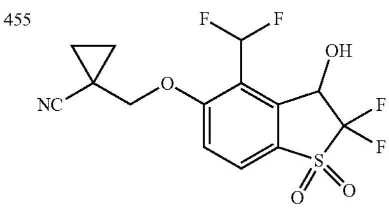 | 410 (M + HCO₂⁻) | (400 MHz, CDCl₃): δ 7.86 (d, 1H), 7.19 (t, 1H), 7.14 (d, 1H), 5.47 (d, 1H), 4.15-4.03 (m, 2H), 3.15 (s, 1H), 1.47-1.39 (m, 2H), 1.19-1.12 (m, 2H) |
| 456 | 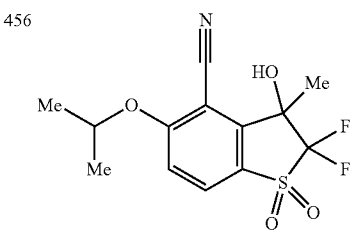 | 316 (M − H) | (400 MHz, CDCl₃): δ 7.92 (d, 1H), 7.18 (d, 1H), 4.81 (m, 1H), 3.18 (s, 1H), 1.92 (d, 3H), 1.48 (t, 6H) |
| 457 | 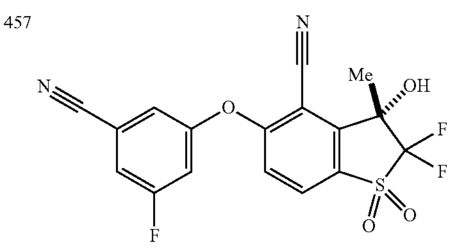 | 393 (M − H) | (400 MHz, CDCl₃): δ 7.98 (d, 1H), 7.39-7.35 (m, 1H), 7.27-7.25 (m, 1H), 7.17 (dt, 1H), 7.13 (d, 1H), 3.27 (d, 1H), 1.99 (d, 3H) |
| 458 | 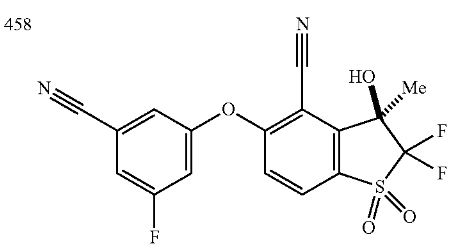 | 393 (M − H) | (400 MHz, CDCl₃): δ 7.98 (d, 1H), 7.39-7.35 (m, 1H), 7.27-7.25 (m, 1H), 7.17 (dt, 1H), 7.13 (d, 1H), 3.27 (d, 1H), 1.99 (d, 3H) |
| 459 | 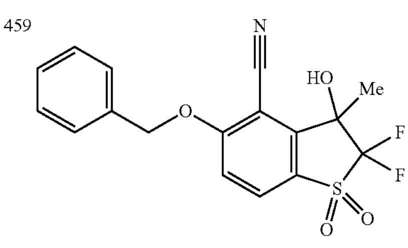 | 410 (M + HCO2−) | (400 MHz, (CD₃)₂CO): δ 8.23 (d, 1H), 7.74 (d, 1H), 7.57 (d, 2H), 7.48-7.36 (m, 3H), 6.54 (d, 1H), 5.54 (s, 2H), 1.86 (d, 3H) |

TABLE 2-continued

| No. | Structure | Mass Characterization | ¹H NMR Data |
|---|---|---|---|
| 460 | 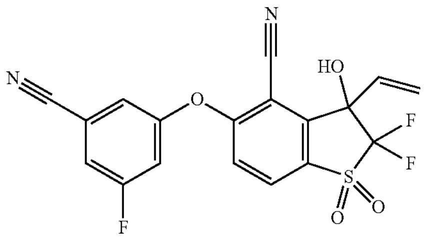 [SMILES: C=CC1(O)c2c(ccc(Oc3cc(F)cc(C#N)c3)c2C#N)S(=O)(=O)C1(F)F] | 405 (M − H) | (400 MHz, CDCl$_3$): δ 8.00 (d, 1H), 7.39-7.35 (m, 1H), 7.26-7.24 (m, 1H), 7.18-7.13 (m, 2H), 6.12 (ddd, 1H), 5.86 (d, 1H), 5.73 (d, 1H), 3.45 (d, 1H) |
| 461 | 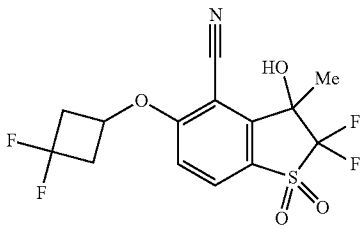 [SMILES: CC1(O)c2c(ccc(OC3CC(F)(F)C3)c2C#N)S(=O)(=O)C1(F)F] | 364 (M − H) | (400 MHz, CDCl$_3$): δ 7.97 (d, 1H), 7.02 (d, 1H), 4.90-4.81 (m, 1H), 3.29-3.17 (m, 2H), 3.10 (d, 1H), 3.02-2.87 (m, 2H), 1.93 (d, 3H) |
| 462 | 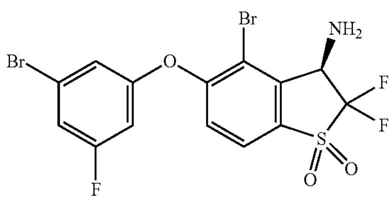 [SMILES: N[C@@H]1c2c(ccc(Oc3cc(F)cc(Br)c3)c2Br)S(=O)(=O)C1(F)F] | 486, 488, 490 (M + H) | (400 MHz, (CD$_3$)$_2$SO): δ 8.15 (d, 1H), 7.48 (d, 1H), 7.47 (ddd, 1H), 7.29-7.27 (m, 1H), 7.18 (dt, 1H), 5.04 (d, 1H) |
| 463 | 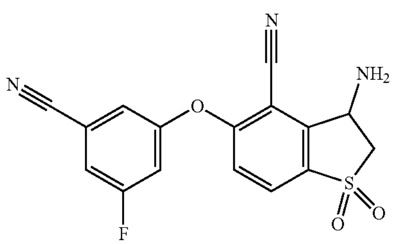 [SMILES: N#Cc1cc(F)cc(Oc2ccc3c(c2C#N)C(N)CS3(=O)=O)c1] | 342 (M − H) | (400 MHz, (CD$_3$)$_2$CO): δ 7.99 (d, 1H), 7.66-7.61 (m, 2H), 7.56 (dt, 1H), 7.42 (d, 1H), 5.03 (br s, 1H), 3.95 (dd, 1H), 3.48 (dd, 1H), 2.40 (br s, 2H) |
| 464 | 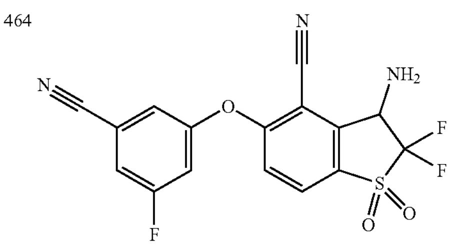 | 380 (M + H) | (400 MHz, (CD$_3$)$_2$CO): δ 8.20 (d, 1H), 7.62 (ddd, 1H), 7.55-7.53 (m, 1H), 7.45 (dt, 1H), 7.39 (d, 1H), 5.14-5.04 (m, 1H), 2.42 (br d, 2H) |
| 465 | 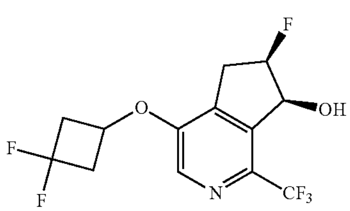 [SMILES: O[C@H]1c2c(C(F)(F)F)ncc(OC3CC(F)(F)C3)c2C[C@H]1F] | (M + H) 328 | (400 MHz, CDCl$_3$): δ 8.04 (s, 1H), 5.46-5.26 (m, 2H), 4.89-4.79 (m, 1H), 3.36-3.08 (m, 4H), 2.91-2.74 (m, 2H), 2.60 (dd, 1H) |
| 466 | 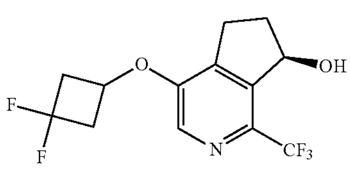 [SMILES: O[C@@H]1CCc2c(OC3CC(F)(F)C3)cnc(C(F)(F)F)c21] | (M + H) 310 | (400 MHz, CDCl$_3$): δ 7.98 (s, 1H), 5.59-5.54 (m, 1H), 4.88-4.79 (m, 1H), 3.24-3.07 (m, 3H), 2.89 (dd, 1H), 2.89-2.74 (m, 2H), 2.44-2.34 (m, 1H), 2.28-2.21 (m, 1H), 2.12-2.09 (m, 1H) |

TABLE 2-continued

| No. | Structure | Mass Characterization | ¹H NMR Data |
|---|---|---|---|
| 467 | 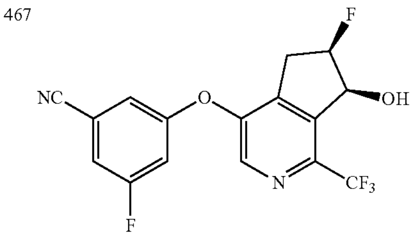 | (M + H) 357 | (400 MHz, CDCl₃): δ 8.33 (s, 1H), 7.22 (ddd, 1H), 7.10-7.08 (m, 1H), 6.99 (dt, 1H), 5.54-5.46 (m, 1H), 5.46-5.28 (m, 1H), 3.26 (ddd, 1H), 3.11 (ddd, 1H), 2.67 (dd, 1H) |
| 468 | 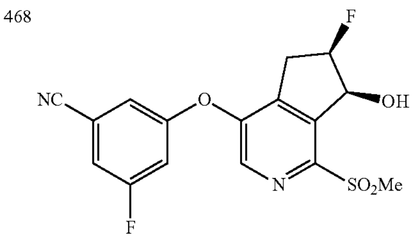 | (M + H) 367 | (400 MHz, CDCl₃): δ 8.27 (s, 1H), 7.25 (ddd, 1H), 7.14 (m, 1H), 7.03 (dt, 1H), 5.69 (dt, 1H), 5.53-5.36 (m, 1H), 4.24 (d, 1H), 3.34 (s, 3H), 3.31-3.24 (m, 1H), 3.09 (ddd, 1H) |
| 469 | 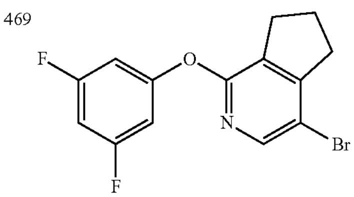 | 326/328 (M + H) | |
| 470 | 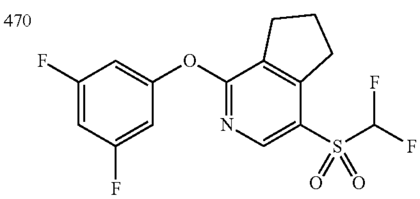 | 362 (M + H) | (400 MHz, CDCl₃): δ 7.49 (s, 1H), 6.80-6.71 (m, 3H), 6.19 (t, 1H), 3.36 (t, 2H), 3.06 (t, 2H), 2.31-2.23 (m, 2H) |
| 471 | 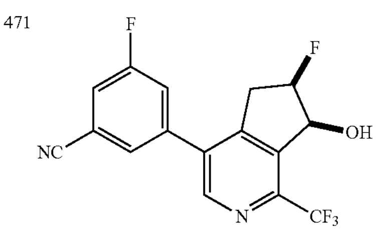 | (M + H) 341 | (400 MHz, CDCl₃): δ 8.65 (s, 1H), 7.53-7.48 (m, 2H), 7.40 (ddd, 1H), 5.56-5.48 (m, 1H), 5.35 (ddt, 1H), 3.41 (ddd, 1H), 3.21 (ddd, 1H), 2.65 (dd, 1H) |
| 472 | 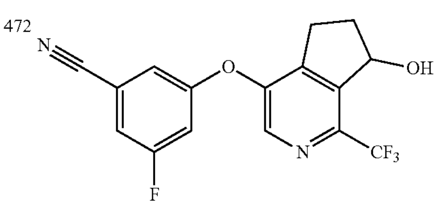 | 339 (M + H) | |
| 473 | 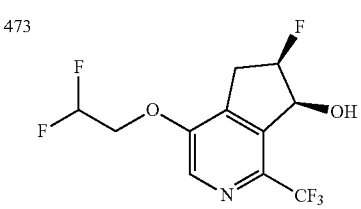 | 302 (M + H) | |

TABLE 2-continued

| No. | Structure | Mass Characterization | ¹H NMR Data |
|---|---|---|---|
| 474 | 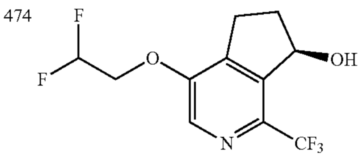 | 284 (M + H) | |
| 475 | 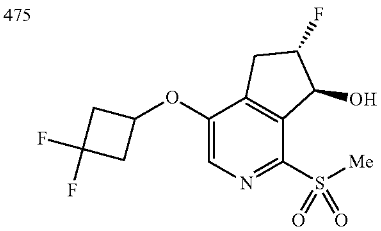 | 338 (M + H) | |
| 476 | 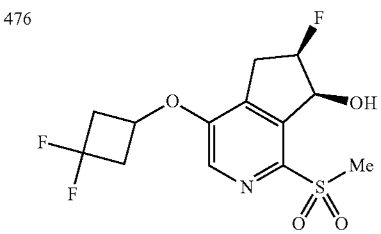 | 338 (M + H) | |
| 477 | 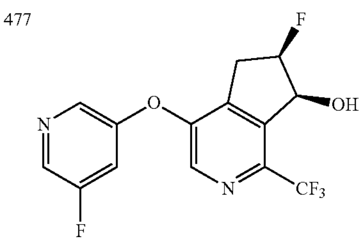 | 333 (M + H) | |
| 478 | 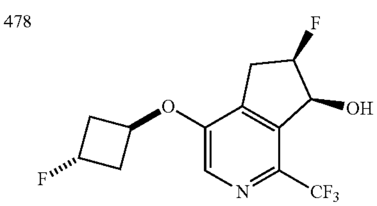 | 310 (M + H) | |
| 479 | 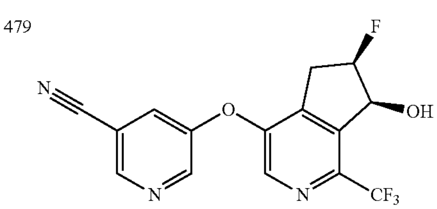 | 340 (M + H) | |
| 480 | 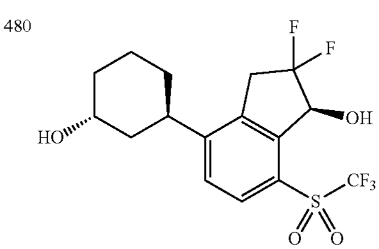 | (M + HCO₂⁻) 445 | (400 MHz, CDCl₃): δ 7.92 (d, 1H), 7.52 (d, 1H), 5.40 (dd, 1H), 4.33-4.28 (m, 1H), 3.59 (ddd, 1H), 3.49 (t, 1H), 3.22-3.13 (m, 2H), 1.97-1.82 (m, 4H), 1.75-1.58 (m, 3H), 1.46 (dd, 1H), 1.42-1.37 (m, 1H) |

TABLE 2-continued

| No. | Structure | Mass Characterization | ¹H NMR Data |
|---|---|---|---|
| 481 | 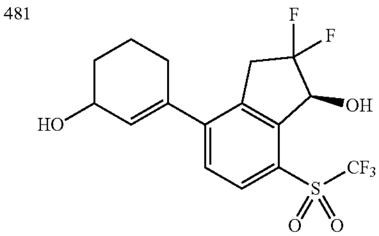 | (M − OH) 381 | (400 MHz, CDCl₃): δ 7.93 (d, 1H), 7.50 (d, 1H), 5.91-5.88 (m, 1H), 5.39 (dd, 1H), 4.49-4.43 (m, 1H), 3.64 (ddd, 1H), 3.39 (t, 1H), 3.18 (dd, 1H), 2.49-2.39 (m, 1H), 2.22-2.11 (m, 1H), 2.09-1.92 (m, 2H), 1.81-1.59 (m, 3H) |
| 482 | 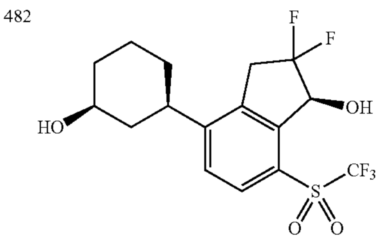 | (M + HCO₂⁻) 445 | (400 MHz, CDCl₃): δ 7.94 (d, 1H), 7.55 (d, 1H), 5.41 (dd, 1H), 3.82-3.72 (m, 1H), 3.56 (ddd, 1H), 3.42 (t, 1H), 3.20 (dd, 1H), 2.67 (tt, 1H), 2.17-2.08 (m, 2H), 2.01-1.94 (m, 1H), 1.82-1.75 (m, 1H), 1.60-1.42 (m, 3H), 1.40-1.27 (m, 2H) |
| 483 | 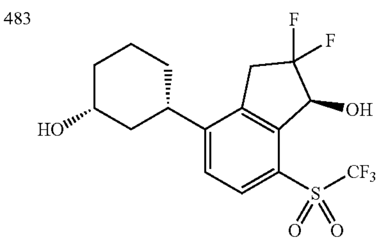 | (M + HCO₂⁻) 445 | (400 MHz, CDCl₃): δ 7.94 (d, 1H), 7.55 (d, 1H), 5.41 (dd, 1H), 3.82-3.72 (m, 1H), 3.58 (ddd, 1H), 3.40 (t, 1H), 3.18 (d, 1H), 2.67 (tt, 1H), 2.16-2.06 (m, 2H), 2.02-1.95 (m, 1H), 1.86-1.78 (m, 1H), 1.58-1.28 (m, 5H) |
| 484 | 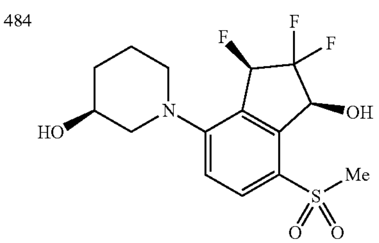 | 366 (M + H) | |
| 485 | 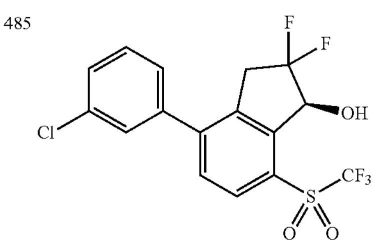 | (M − H) 411/413 | |
| 486 | 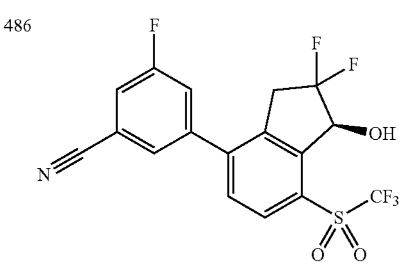 | (M − H) 420 | |

TABLE 2-continued

| No. | Structure | Mass Characterization | ¹H NMR Data |
|---|---|---|---|
| 487 | 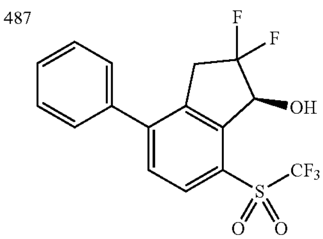 | (M − H) 377 | |
| 488 | 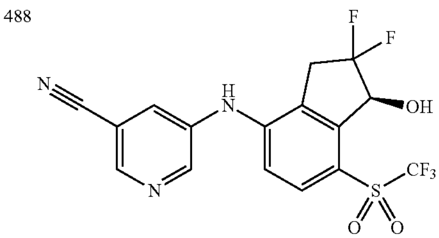 | (M + H) 420 | |
| 489 | 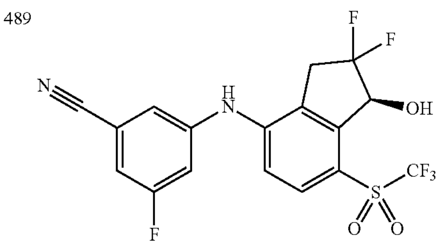 | (M − H) 435 | |
| 490 | 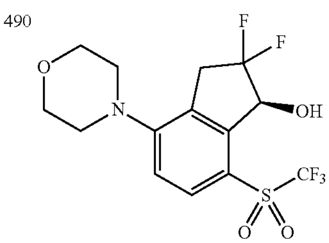 | (M + H) 388 | |
| 491 | 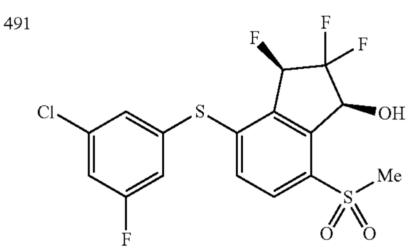 | (M + Na) 449 | |
| 492 | 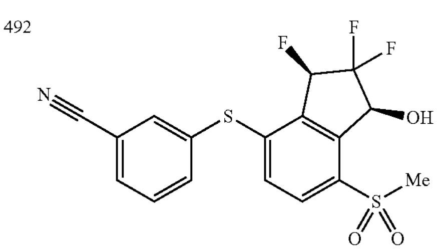 | (M + Na) 422 | |

TABLE 2-continued

| No. | Structure | Mass Characterization | ¹H NMR Data |
|---|---|---|---|
| 493 | 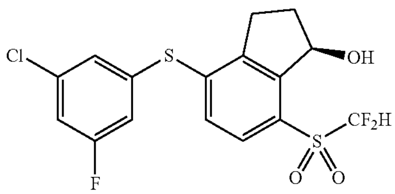 [SMILES: O=S(=O)(c1ccc(Sc2cc(F)cc(Cl)c2)c2c1[C@H](O)CC2)C(F)F] | 453/455 (M + HCO$_2^-$) | |
| 494 | 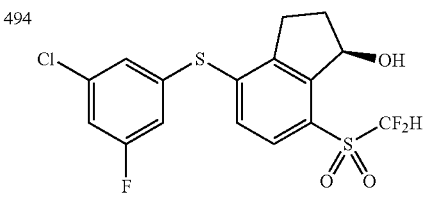 | 346 (M − H) | |
| 495 | 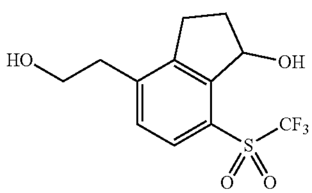 | 309 (M − H) | |
| 496 | 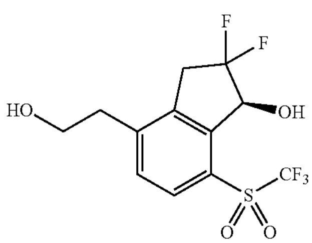 [SMILES: O=S(=O)(c1ccc(CCO)c2c1[C@H](O)C(F)(F)C2)C(F)(F)F] | 345 (M − H) | |
| 497 | 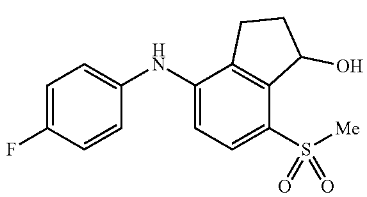 [SMILES: CS(=O)(=O)c1ccc(Nc2ccc(F)cc2)c2c1C(O)CC2] | 320 (M − H) | |
| 498 | 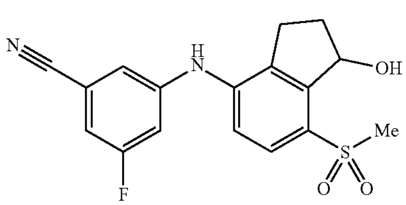 [SMILES: CS(=O)(=O)c1ccc(Nc2cc(F)cc(C#N)c2)c2c1C(O)CC2] | 345 (M − H) | |
| 499 | 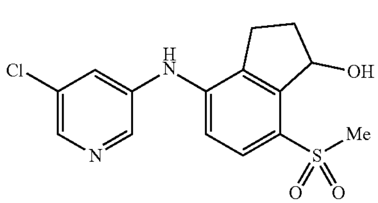 [SMILES: CS(=O)(=O)c1ccc(Nc2cncc(Cl)c2)c2c1C(O)CC2] | 337 (M − H) | |

TABLE 2-continued

| No. | Structure | Mass Characterization | ¹H NMR Data |
|---|---|---|---|
| 500 | 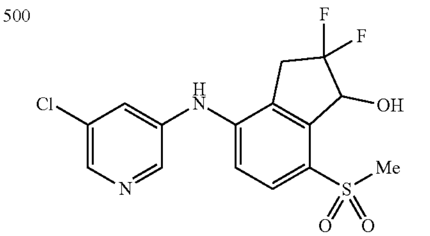 | 373 (M − H) | |
| 501 | 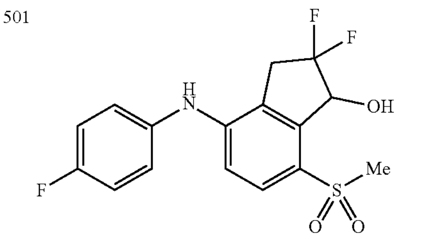 | 356 (M − H) | |
| 502 | 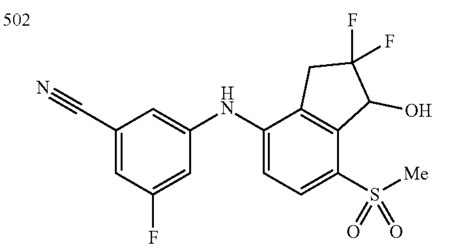 | 381 (M − H) | |
| 503 | 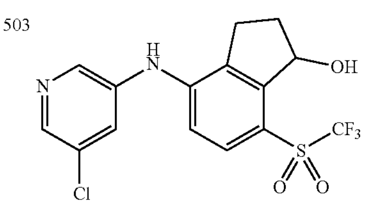 | 391 (M − H) | |
| 504 | 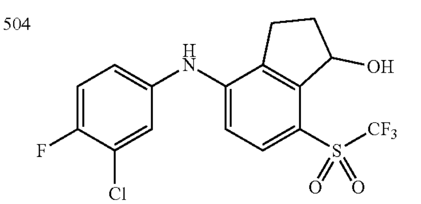 | 408 (M − H) | |
| 505 | 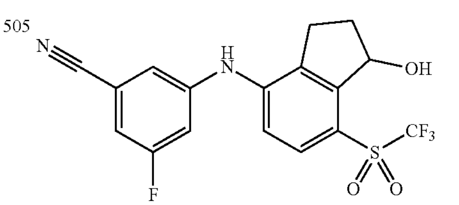 | 399 (M − H) | |
| 506 | 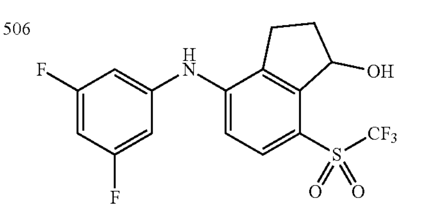 | 392 (M − H) | |

TABLE 2-continued

| No. | Structure | Mass Characterization | ¹H NMR Data |
|---|---|---|---|
| 507 | 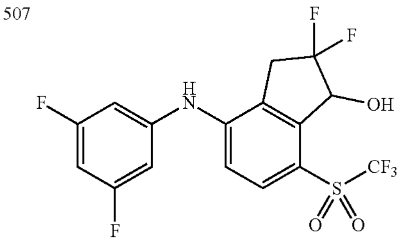 | | ¹HNMR (300 MHz, CDCl₃): δ 7.83 (d, 1H), 7.30 (d, 1H), 6.77 (m, 2H), 6.67 (m, 1H), 6.10 (s, 1H), 5.36 (m, 1H), 3.45 (m, 1H), 3.27 (m, 2H). |
| 508 | 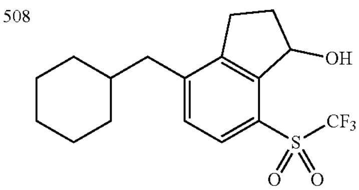 | 361 (M − H) | |
| 509 | 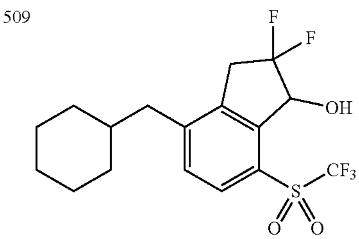 | 397 (M − H) | |
| 510 | 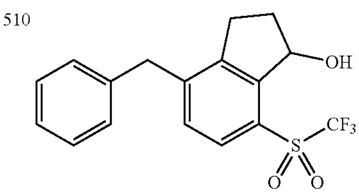 | 355 (M − H) | |
| 511 | 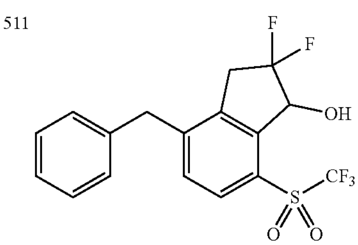 | 391 (M − H) | |
| 512 | 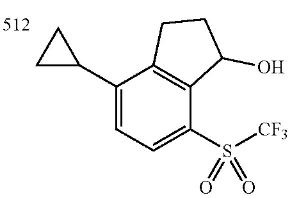 | | ¹HNMR (300 MHz, CDCl₃): δ 8.76 (d, 1H), 6.97 (d, 1H), 5.62 (m, 1H), 3.29 (m, 1H), 3.09 (m, 1H), 3.05 (m, 1H), 2.36 (m, 2H), 1.98 (m, 1H), 1.17 (m, 2H), 0.85 (m, 2H). |
| 513 | 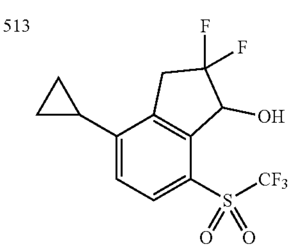 | 341 (M − H) | |

TABLE 2-continued

| No. | Structure | Mass Characterization | ¹H NMR Data |
|---|---|---|---|
| 514 | 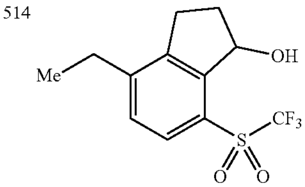 | | |
| 515 | 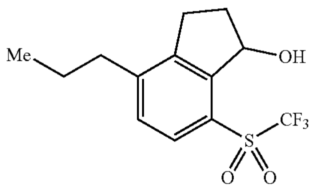 [SMILES: CCCc1ccc(S(=O)(=O)C(F)(F)F)c2c1CCC2O] | 307 (M − H) | |
| 516 | 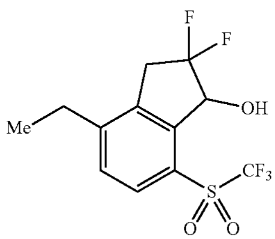 [SMILES: CCc1ccc(S(=O)(=O)C(F)(F)F)c2c1CC(F)(F)C2O] | 329 (M − H) | |
| 517 | 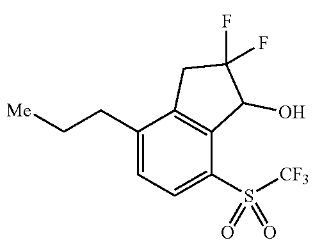 [SMILES: CCCc1ccc(S(=O)(=O)C(F)(F)F)c2c1CC(F)(F)C2O] | 343 (M − H) | |
| 518 | 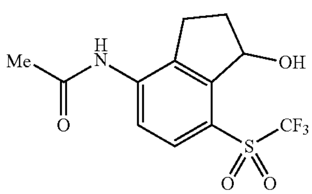 [SMILES: CC(=O)Nc1ccc(S(=O)(=O)C(F)(F)F)c2c1CCC2O] | 322 (M − H) | |
| 519 | 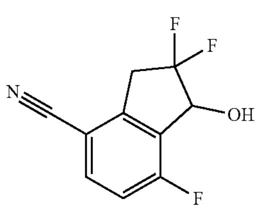 [SMILES: N#Cc1ccc(F)c2c1CC(F)(F)C2O] | 214 (M + H) | |
| 520 | 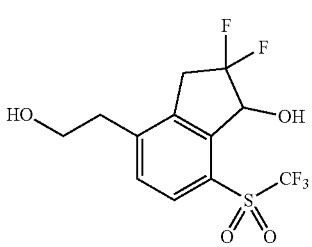 | 345 (M − H) | |

TABLE 2-continued

| No. | Structure | Mass Characterization | ¹H NMR Data |
|---|---|---|---|
| 521 | 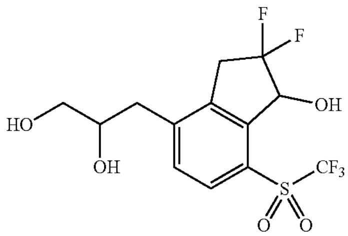 [SMILES: O=S(=O)(c1ccc(CC(O)CO)c2c1C(O)C(F)(F)C2)C(F)(F)F] | 375 (M − H) | |
| 522 | 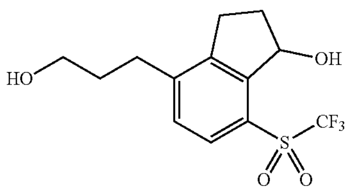 [SMILES: O=S(=O)(c1ccc(CCCO)c2c1C(O)CC2)C(F)(F)F] | 323 (M − H) | |
| 523 | 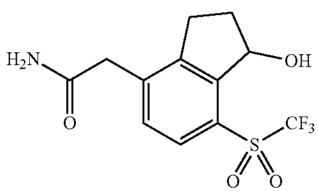 [SMILES: NC(=O)Cc1ccc(S(=O)(=O)C(F)(F)F)c2c1CCC2O] | 322 (M − H) | |
| 524 | 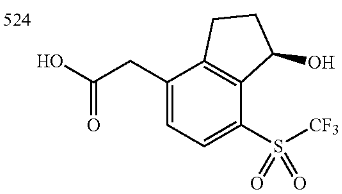 | 323 (M − H) | |
| 525 | 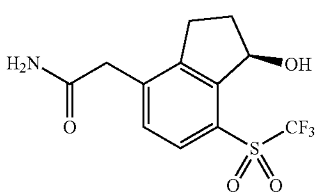 [SMILES: NC(=O)Cc1ccc(S(=O)(=O)C(F)(F)F)c2c1CC[C@H]2O] | | |
| 526 | 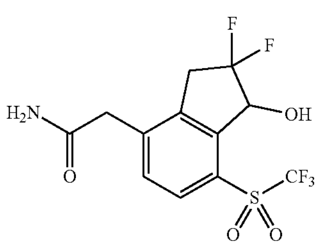 [SMILES: NC(=O)Cc1ccc(S(=O)(=O)C(F)(F)F)c2c1CC(F)(F)C2O] | 360 (M + H) | |
| 527 | 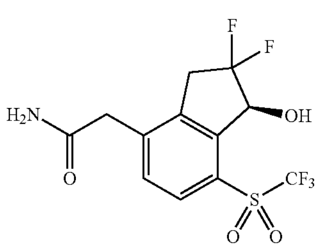 [SMILES: NC(=O)Cc1ccc(S(=O)(=O)C(F)(F)F)c2c1CC(F)(F)[C@H]2O] | 360 (M + H) | |

TABLE 2-continued

| No. | Structure | Mass Characterization | ¹H NMR Data |
|---|---|---|---|
| 528 | 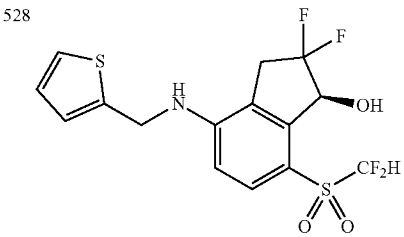 | | (400 MHz, CDCl$_3$): δ 7.79 (d, 1H), 7.29 (d, 1H), 7.07-7.00 (m, 2H), 6.78 (d, 1H), 6.33 (t, 1H), 5.40 (d, 1H), 4.66 (d, 2H), 4.64-4.58 (m, 1H), 3.38-3.24 (m, 2H), 3.14 (t, 1H) |
| 529 | 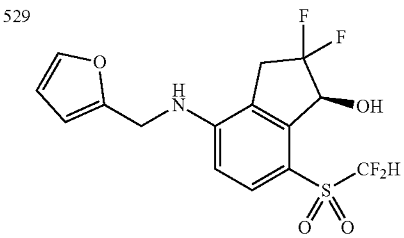 | | (400 MHz, CDCl$_3$): δ 7.79 (d, 1H), 7.40 (s, 1H), 6.80 (d, 1H), 6.46-6.20 (m, 3H), 5.39 (d, 1H), 4.64 (t, 1H), 4.47 (d, 2H), 3.46-3.24 (m, 2H), 3.14 (t, 1H) |
| 530 | 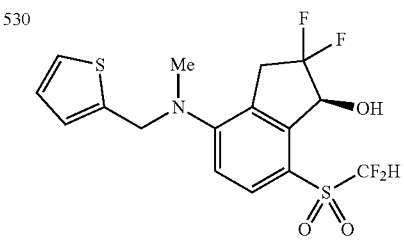 | | (400 MHz, CDCl$_3$): δ 7.79 (d, 1H), 7.28 (d, 1H), 7.01-6.94 (m, 3H), 6.35 (t, 1H), 5.38 (d, 1H), 4.61 (m, 2H), 3.70-3.58 (m, 1H), 3.52-3.44 (m, 1H), 3.23 (br s, 1H), 3.00 (s, 3H) |
| 531 | 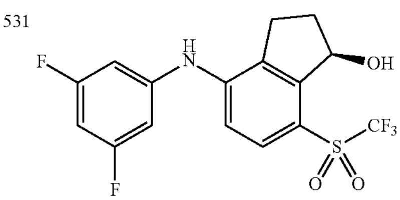 | [M − H]⁻ 392 | |
| 532 | 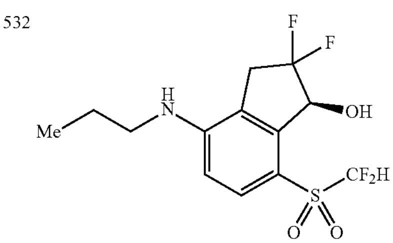 | [M + H]⁺ 343 | |
| 533 | 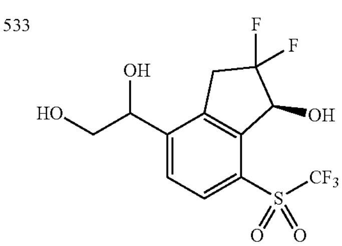 | | (400 MHz, CDCl$_3$): δ 8.00 (dd, 1H), 7.84 (dd, 1H), 5.41 (dd, 1H), 5.00-4.93 (m, 1H), 3.83 (ddd, 1H), 3.72-3.43 (m, 4H) |

TABLE 2-continued

| No. | Structure | Mass Characterization | ¹H NMR Data |
|---|---|---|---|
| 534 | 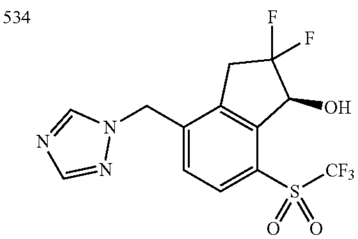 | [M − H]⁻ 382 | |
| 535 | 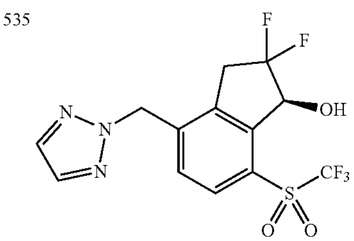 | [M − H]⁻ 382 | |
| 536 | 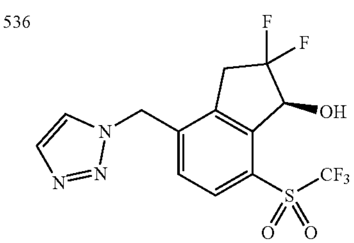 | [M − H]⁻ 382 | |
| 537 | 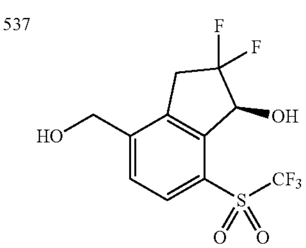 | [M − H]⁻ 331 | |
| 538 | 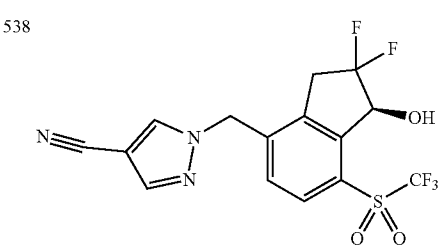 | [M − H]⁻ 406 | |
| 539 | 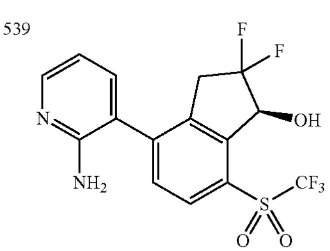 | [M + H]⁺ 395 | |

TABLE 2-continued

| No. | Structure | Mass Characterization | ¹H NMR Data |
|---|---|---|---|
| 540 | 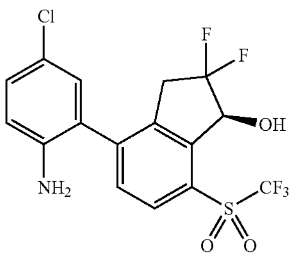 [SMILES: Nc1ccc(Cl)cc1-c1ccc(S(=O)(=O)C(F)(F)F)c2c1CC(F)(F)[C@H]2O] | [M + H]⁺ 428/430 | |
| 541 | 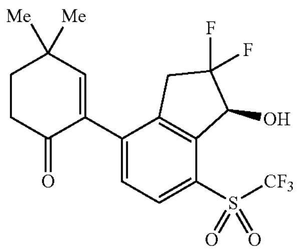 [SMILES: CC1(C)C=C(c2ccc(S(=O)(=O)C(F)(F)F)c3c2CC(F)(F)[C@H]3O)C(=O)CC1] | [M + H]⁺ 425 | |
| 542 | 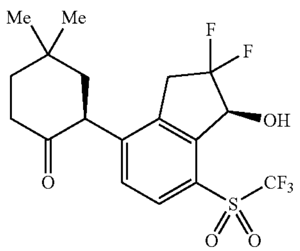 [SMILES: CC1(C)CCC(=O)[C@H](c2ccc(S(=O)(=O)C(F)(F)F)c3c2CC(F)(F)[C@H]3O)C1] | [M + NH₄]⁺ 444 | |
| 543 | 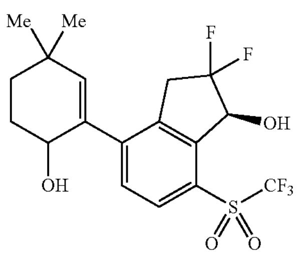 [SMILES: CC1(C)C=C(c2ccc(S(=O)(=O)C(F)(F)F)c3c2CC(F)(F)[C@H]3O)C(O)CC1] | [M − OH]⁺ 409 | |
| 544 | 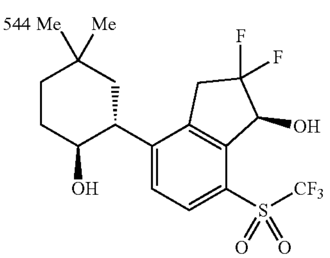 | [M + Cl]⁻ 463/465 | |
| 545 | 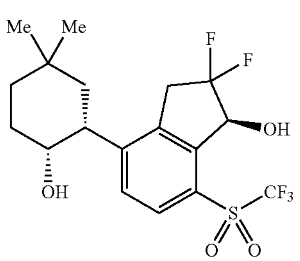 [SMILES: CC1(C)CC[C@@H](O)[C@@H](c2ccc(S(=O)(=O)C(F)(F)F)c3c2CC(F)(F)[C@H]3O)C1] | [M + Cl]⁻ 463/465 | |

TABLE 2-continued

| No. Structure | Mass Characterization | ¹H NMR Data |
|---|---|---|
| 546 | [M + NH$_4$]$^+$ 444 | |
| 547 | [M +Cl]$^-$ 463/ 465 | |
| 548 | [M + NH4]$^+$ 446 | |
| 549 | [M + NH4]$^+$ 446 | |
| 550 | [M + NH4]$^+$ 446 | |
| 551 | [M − OH]$^+$ 409 | |

TABLE 2-continued

| No. | Structure | Mass Characterization | ¹H NMR Data |
|---|---|---|---|
| 552 | 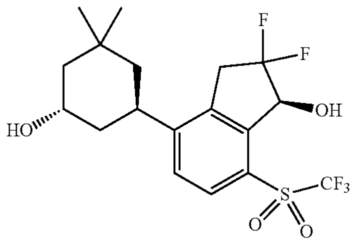 [SMILES: CC1(C)C[C@@H](O)C[C@H](c2ccc(S(=O)(=O)C(F)(F)F)c3c2CC(F)(F)[C@H]3O)C1] | [M + NH4]⁺ 446 | |
| 553 | 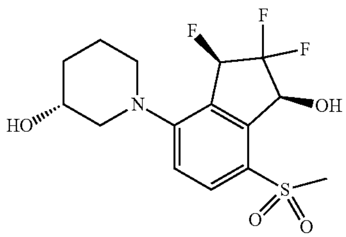 [SMILES: CS(=O)(=O)c1ccc(N2CCC[C@@H](O)C2)c2c1[C@H](O)C(F)(F)[C@@H]2F] | [M + H]⁺ 366 | |
| 554 | 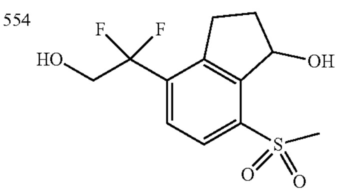 | [M + NH₄]⁺ 310 | |
| 555 | 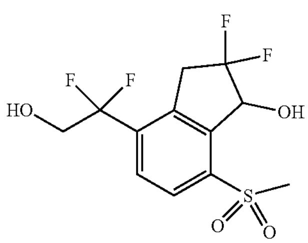 [SMILES: CS(=O)(=O)c1ccc(C(F)(F)CO)c2c1C(O)C(F)(F)C2] | [M + NH₄]⁺ 346 | |
| 556 | 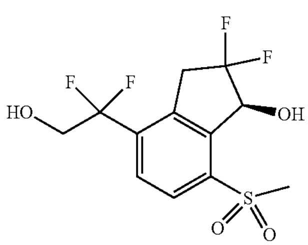 [SMILES: CS(=O)(=O)c1ccc(C(F)(F)CO)c2c1[C@H](O)C(F)(F)C2] | [M + NH₄]⁺ 346 | |
| 557 | 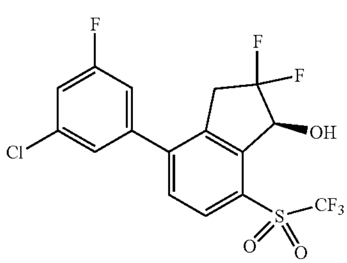 [SMILES: O=S(=O)(c1ccc(-c2cc(F)cc(Cl)c2)c2c1[C@H](O)C(F)(F)C2)C(F)(F)F] | [M + Na]⁺ 454 | |

TABLE 2-continued

| No. | Structure | Mass Characterization | ¹H NMR Data |
|---|---|---|---|
| 558 | 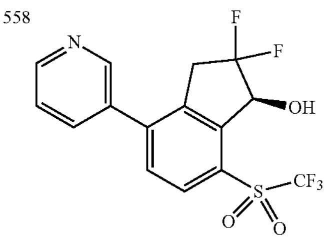 | [M + H]⁺ 380 | |
| 559 | 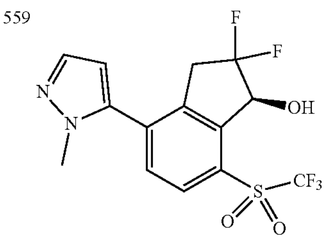 | [M + H]⁺ 383 | |
| 560 | 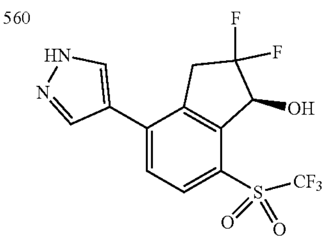 | [M + H]⁺ 369 | |
| 561 | 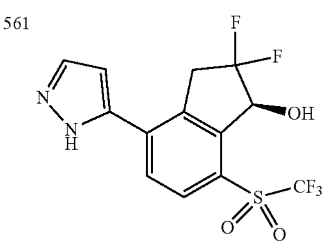 | [M + H]⁺ 369 | |
| 562 | 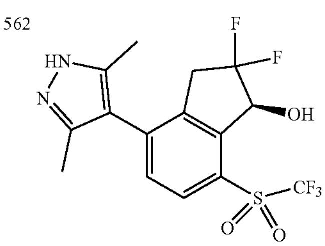 | [M + H]⁺ 397 | |
| 563 | 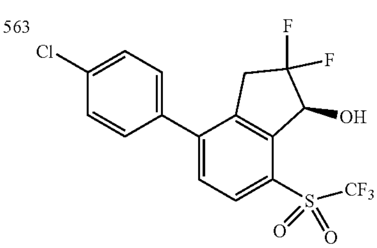 | [M + Na]⁺ 436/ 438 | |

TABLE 2-continued

| No. | Structure | Mass Characterization | ¹H NMR Data |
|---|---|---|---|
| 564 | 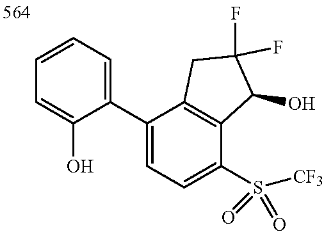 | [M − H]⁻ 393 | |
| 565 | 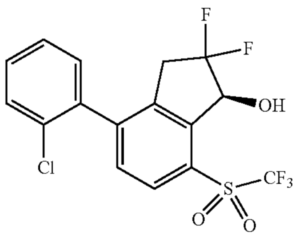 [SMILES: O=S(=O)(c1ccc(-c2ccccc2Cl)c2c1[C@H](O)C(F)(F)C2)C(F)(F)F] | [M + Na]⁺ 436/438 | |
| 566 | 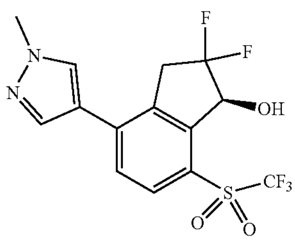 [SMILES: Cn1cc(-c2ccc(S(=O)(=O)C(F)(F)F)c3c2CC(F)(F)[C@H]3O)cn1] | [M + H]⁺ 383 | |
| 567 | 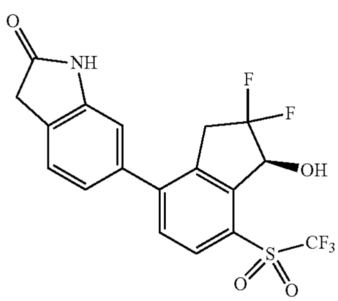 [SMILES: O=C1Cc2ccc(-c3ccc(S(=O)(=O)C(F)(F)F)c4c3CC(F)(F)[C@H]4O)cc2N1] | [M + H]⁺ 434 | |
| 568 | 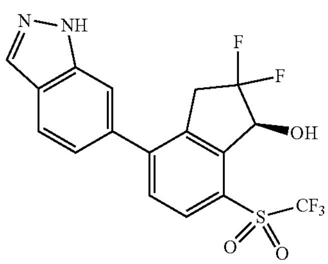 [SMILES: O=S(=O)(c1ccc(-c2ccc3cn[nH]c3c2)c2c1[C@H](O)C(F)(F)C2)C(F)(F)F] | [M + H]⁺ 419 | |
| 569 | 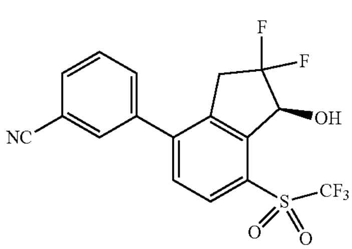 [SMILES: N#Cc1cccc(-c2ccc(S(=O)(=O)C(F)(F)F)c3c2CC(F)(F)[C@H]3O)c1] | [M − H]⁻ 402 | |

TABLE 2-continued

| No. | Structure | Mass Characterization | ¹H NMR Data |
|---|---|---|---|
| 570 | 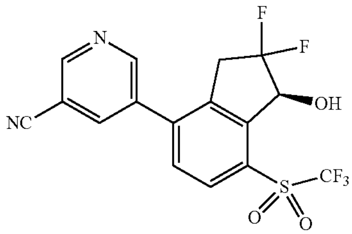 [SMILES: N#Cc1cncc(-c2ccc(S(=O)(=O)C(F)(F)F)c3c2CC(F)(F)[C@H]3O)c1] | [M + H]⁺ 405 | |
| 571 | 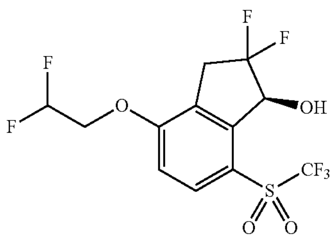 [SMILES: O=S(=O)(c1ccc(OCC(F)F)c2c1[C@H](O)C(F)(F)C2)C(F)(F)F] | [M − H]⁻ 381 | (400 MHz, CDCl₃): δ 8.00 (d, 1H), 7.07 (d, 1H), 6.15 (tt, 1H), 5.38 (dd, 1H), 4.44-4.29 (m, 2H), 3.55-3.39 (m, s, 2H), 3.16 (d, 1H) |
| 572 | 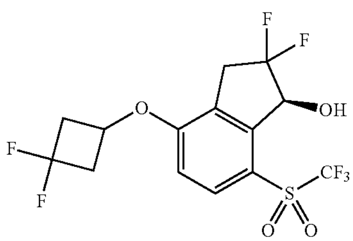 [SMILES: O=S(=O)(c1ccc(OC2CC(F)(F)C2)c2c1[C@H](O)C(F)(F)C2)C(F)(F)F] | [M − H]⁻ 407 | (400 MHz, CDCl₃): δ 7.96 (d, 1H), 6.86 (d, 1H), 5.37 (dd, 1H), 4.86-4.76 (m, 1H), 3.53-3.35 (m, 2H), 3.27-3.14 (m, 3H), 2.92-2.78 (m, 2H) |
| 573 | 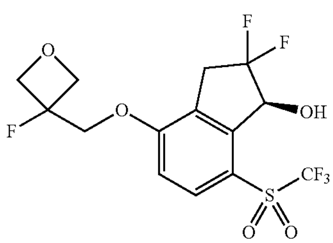 [SMILES: O=S(=O)(c1ccc(OCC2(F)COC2)c2c1[C@H](O)C(F)(F)C2)C(F)(F)F] | [M − H]⁻ 405 | (400 MHz, CDCl₃): δ 8.00 (d, 1H), 7.11 (d, 1H), 5.38 (dd, 1H), 4.92 (dd, 2H), 4.68 (dd, 2H), 4.59-4.46 (m, 2H), 3.54-3.36 (m, 2H), 3.19 (d, 1H) |
| 574 | 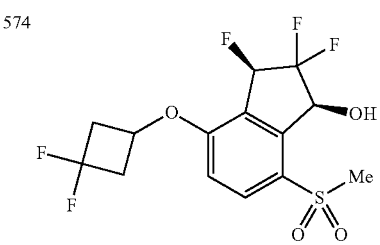 | [M + H]⁺ 373 | (400 MHz, (CD₃)₂CO): δ 8.11 (dd, 1H), 7.33 (d, 1H), 5.87 (dd, 1H), 5.65-5.59 (m, 1H), 5.17-5.08 (m, 1H), 3.40-3.26 (m, 2H), 3.27 (s, 3H), 2.98-2.81 (m, 2H), 2.80 (t, 1H) |
| 575 | 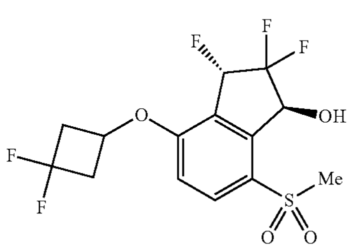 [SMILES: CS(=O)(=O)c1ccc(OC2CC(F)(F)C2)c2c1[C@H](O)C(F)(F)[C@H]2F] | [M + H]⁺ 373 | (400 MHz, CDCl₃): δ 8.06 (dd, 1H), 6.87 (d, 1H), 5.92 (dd, 1H), 5.78 (td, 1H), 4.86-4.76 (m, 1H), 3.98 (d, 1H), 3.25-3.14 (m, 2H), 3.22 (s, 3H), 2.95-2.78 (m, 2H) |

TABLE 2-continued

| No. | Structure | Mass Characterization | ¹H NMR Data |
|---|---|---|---|
| 576 | 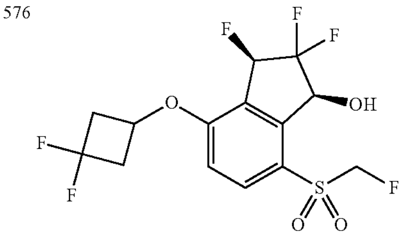 | [M + H]⁺ 391 | (400 MHz, CDCl₃): δ 8.13 (dd, 1H), 6.93 (d, 1H), 5.76 (dd, 1H), 5.59-5.53 (m, 1H), 5.47 (dd, 1H), 5.18 (dd, 1H), 4.90-4.80 (m, 1H), 3.29-3.16 (m, 2H), 3.16 (d, 1H), 2.97-2.81 (m, 2H) |
| 577 | 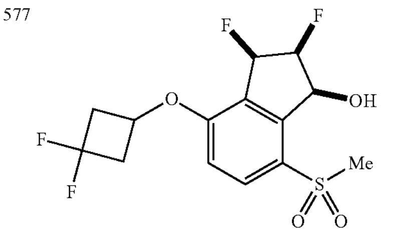 | [M + NH₄]⁺ 372 | (400 MHz, (CD₃)₂CO): δ 8.05 (dd, 1H), 7.25 (d, 1H), 5.99 (dd, 1H), 5.74 (td, 1H), 5.16 (ddt, 1H), 5.13-5.03 (m, 1H), 4.84 (dd, 1H), 3.39-3.25 (m, 2H), 3.28 (s, 3H), 2.95-2.74 (m, 2H) |
| 578 | 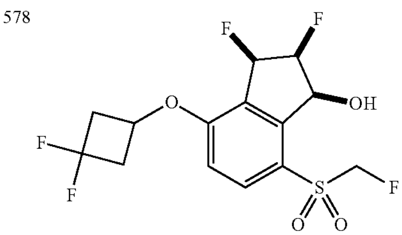 | [M + NH₄]⁺ 390 | (400 MHz, (CD₃)₂CO): δ 8.09 (dd, 1H), 7.12 (d, 1H), 5.95 (dd, 1H), 5.66 (dd, 1H), 5.61 (td, 1H), 5.34 (dd, 1H), 5.07 (ddt, 1H), 5.03-4.93 (m, 1H), 3.89 (dd, 1H), 3.33-3.18 (m, 2H), 2.95-2.72 (m, 2H) |
| 579 | 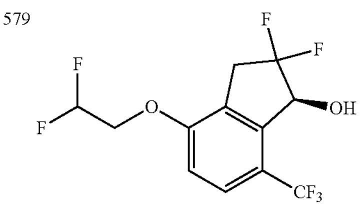 | [M − H + formate]⁻ 363 | (400 MHz, CDCl₃): δ 7.59 (d, 1H), 6.89 (d, 1H), 6.11 (tt, 1H), 5.25-5.20 (m, 1H), 4.33-4.20 (m, 2H), 3.50-3.30 (m, 2H), 2.62-2.59 (m, 1H) |
| 580 | 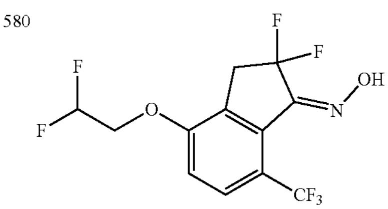 | [M + H]⁺ 332 | (400 MHz, CDCl₃): δ 8.13 (s, 1H), 7.69 (d, 1H), 6.90 (d, 1H), 6.12 (tt, 1H), 4.34-4.26 (m, 2H), 3.49 (t, 2H) |
| 581 | 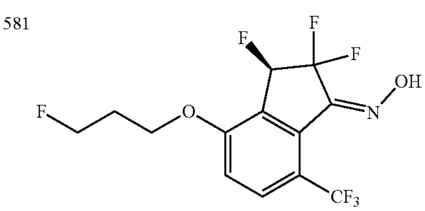 | [M − H]⁻ 344 | (400 MHz, CDCl₃): δ 8.33 (d, 1H), 7.88-7.84 (m, 1H), 7.04 (d, 1H), 5.82 (dd, 1H), 4.67 (dt, 2H), 4.33-4.24 (m, 2H), 2.32-2.20 (m, 2H) |
| 582 | 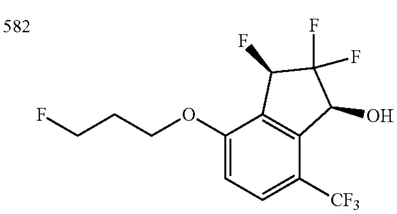 | | (400 MHz, CDCl₃): δ 7.80-7.77 (m, 1H), 7.05 (d, 1H), 5.74 (dd, 1H), 5.25-5.20 (m, 1H), 4.66 (dt, 2H), 4.33-4.22 (m, 2H), 2.52 (d, 1H), 2.32-2.19 (m, 2H) |

TABLE 2-continued

| No. | Structure | Mass Characterization | ¹H NMR Data |
|---|---|---|---|
| 583 | 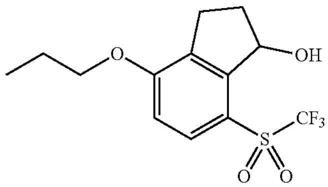 [SMILES: CCCOc1ccc(S(=O)(=O)C(F)(F)F)c2c1CCC2O] | | (300 MHz, CDCl₃): δ 7.87 (d, 1H), 6.95 (d, 1H), 5.58 (d, 1H), 4.08 (m, 2H), 2.06-3.17 (m, 2H), 2.84-2.94 (m, 1H), 2.37 (m, 1H), 2.27 (m, 1H), 1.86 (m, 2H), 1.07 (t, 3H) |
| 584 | 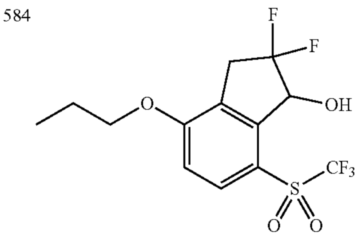 | [M − H]⁻ 359 | (300 MHz, CDCl₃): δ 7.95 (d, 1H), 7.04 (d, 1H), 5.36 (dd, 1H), 4.10 (m, 2H), 3.45 (m, 1H), 3.39 (m, 1H), 3.20 (m, 1H), 1.88 (m, 2H), 1.07 (t, 3H) |
| 585 | 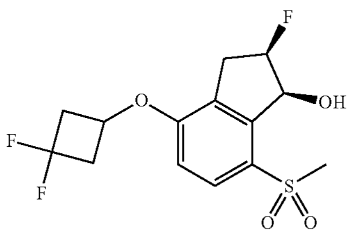 [SMILES: CS(=O)(=O)c1ccc(OC2CC(F)(F)C2)c2c1[C@H](O)[C@H](F)C2] | [M + H]⁺ 337 | |
| 586 | 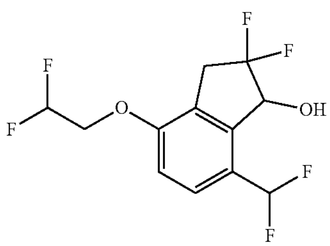 [SMILES: OC1c2c(C(F)F)ccc(OCC(F)F)c2CC1(F)F] | [M − H + HCOOH]⁻ 345 | (300 MHz, CDCl₃): δ 7.57 (d, 1H), 7.00 (t, 1H), 6.85 (t, 1H), 6.13 (t, 1H), 5.32 (m, 1H), 4.24 (t, 2H), 3.25-3.48 (m, 2H), 2.45 (d, 1H) |
| 587 | 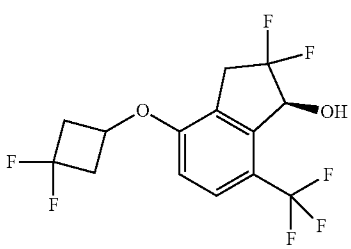 [SMILES: O[C@H]1c2c(C(F)(F)F)ccc(OC3CC(F)(F)C3)c2CC1(F)F] | 389 (M − H + HCOOH) | |
| 588 | 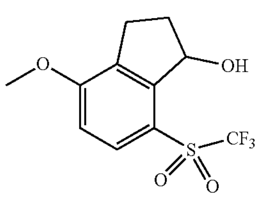 [SMILES: COc1ccc(S(=O)(=O)C(F)(F)F)c2c1CCC2O] | | (300 MHz, CDCl₃): δ 7.90 (d, 1H), 6.97 (d, 1H), 5.58 (m, 1H), 3.97 (s, 3H), 3.17 (m, 1H), 3.12 (m, 1H), 2.87 ((m, 1H), 2.37 (m, 1H), 2.27 (m, 1H). |
| 589 | 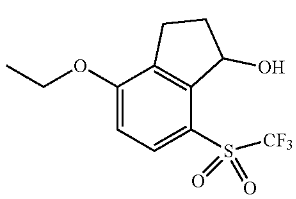 [SMILES: CCOc1ccc(S(=O)(=O)C(F)(F)F)c2c1CCC2O] | | (300 MHz, CDCl₃): δ 7.86 (d, 1H), 6.94 (d, 1H), 5.58 (m, 1H), 4.20 (m, 2H), 3.17 (m, 1H), 3.09 (m, 1H), 2.89 (m, 1H), 2.35 (m, 1H), 2.26 (m, 1H), 1.47 (t, 3H). |

TABLE 2-continued

| No. | Structure | Mass Characterization | ¹H NMR Data |
|---|---|---|---|
| 590 | 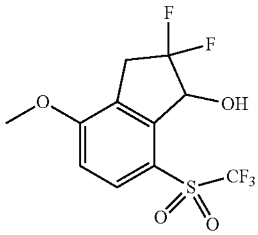 [SMILES: COc1ccc(S(=O)(=O)C(F)(F)F)c2c1CC(F)(F)C2O] | 331 (M − H) | |
| 591 | 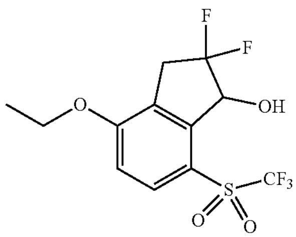 [SMILES: CCOc1ccc(S(=O)(=O)C(F)(F)F)c2c1CC(F)(F)C2O] | 345 (M − H) | |
| 592 | 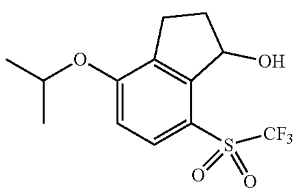 [SMILES: CC(C)Oc1ccc(S(=O)(=O)C(F)(F)F)c2c1CCC2O] | | (300 MHz, CDCl$_3$): δ 7.85 (d, 1H), 6.94 (d, 1H), 5.57 (m, 1H), 4.72 (m, 1H), 3.18 (m, 1H), 3.11 (m, 1H), 2.86 (m, 1H), 2.35 (m, 1H), 2.25 (m, 1H), 1.41 (d, 6H). |
| 593 | 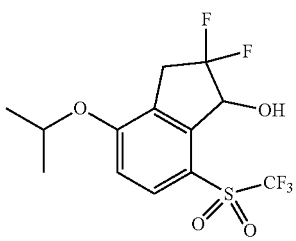 [SMILES: CC(C)Oc1ccc(S(=O)(=O)C(F)(F)F)c2c1CC(F)(F)C2O] | 359 (M − H) | |
| 594 | 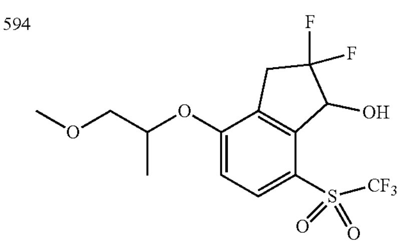 | 389 (M − H) | |
| 595 | 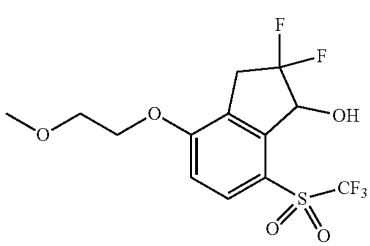 [SMILES: COCCOc1ccc(S(=O)(=O)C(F)(F)F)c2c1CC(F)(F)C2O] | 375 (M − H) | |

TABLE 2-continued

| No. | Structure | Mass Characterization | ¹H NMR Data |
|---|---|---|---|
| 596 | 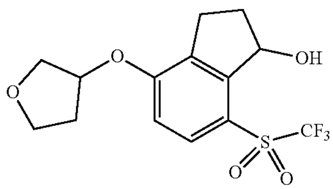 [SMILES: O=S(=O)(c1ccc(OC2CCOC2)c2c1C(O)CC2)C(F)(F)F] | | (300 MHz, CD₃OD): δ 7.89 (d, 1H), 7.28 (d, 1H), 5.44 (m, 1H), 5.27 (m, 1H), 5.14 (d, 1H), 3.77-3.96 (m 4H), 2.93 (m, 1H), 2.76 (m, 1H), 2.29 (m, 1H), 2.15 (m, 1H), 1.97 (m, 2H). |
| 597 | 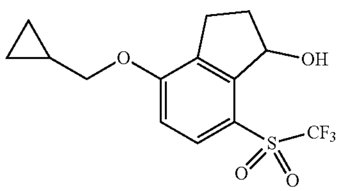 [SMILES: O=S(=O)(c1ccc(OCC2CC2)c2c1C(O)CC2)C(F)(F)F] | | (300 MHz, CDCl₃): δ 7.85 (d, 1H), 6.92 (d, 1H), 5.57 (m, 1H), 3.96 (m, 2H), 3.17 (m, 1H), 3.08 (m, 1H), 2.94 (m, 1H), 2.36 (m, 1H), 2.26 (m, 1H), 1.28 (m, 1H), 0.68 (m, 2H), 0.39 (m, 2H). |
| 598 | 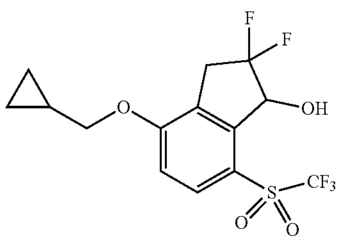 [SMILES: O=S(=O)(c1ccc(OCC2CC2)c2c1C(O)C(F)(F)C2)C(F)(F)F] | 371 (M − H) | |
| 599 | 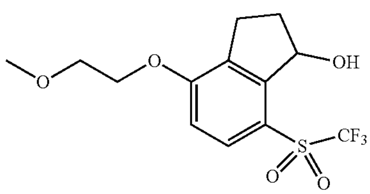 [SMILES: COCCOc1ccc(S(=O)(=O)C(F)(F)F)c2c1CCC2O] | | (300 MHz, CDCl₃): δ 7.87 (d, 1H), 6.99 (d, 1H), 5.57 (m, 1H), 4.27 (m, 2H), 3.80 (m, 2H), 3.45 (s, 3H), 3.15 (m, 1H), 3.11 (m, 1H), 2.93 (m, 1H), 2.36 (m, 1H), 2.27 (m, 1H) |
| 600 | 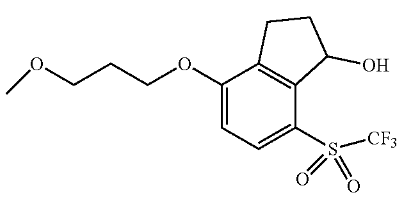 [SMILES: COCCCOc1ccc(S(=O)(=O)C(F)(F)F)c2c1CCC2O] | 372 (M + NH₄) | |
| 601 | 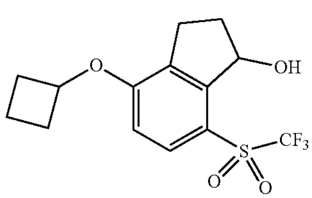 [SMILES: O=S(=O)(c1ccc(OC2CCC2)c2c1C(O)CC2)C(F)(F)F] | | (300 MHz, CDCl₃): δ 7.82 (d, 1H), 6.79 (d, 1H), 5.57 (m, 1H), 4.78 (m, 1H), 3.17 (m, 1H), 3.09 (m, 1H), 2.89 (m, 1H), 2.50 (m, 2H), 2.20-2.28 (m, 4H), 1.77 (m, 1H), 1.55 (m, 1H). |
| 602 | 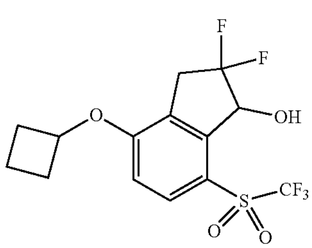 [SMILES: O=S(=O)(c1ccc(OC2CCC2)c2c1C(O)C(F)(F)C2)C(F)(F)F] | 371 (M − H) | |

TABLE 2-continued

| No. | Structure | Mass Characterization | ¹H NMR Data |
|---|---|---|---|
| 603 | 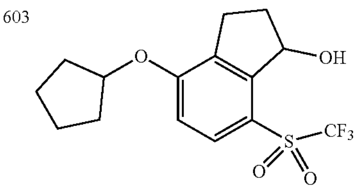 | | (300 MHz, CDCl₃): δ 7.85 (d, 1H), 6.95 (d, 1H), 5.56 (m, 1H), 4.91 (m, 1H), 3.18 (m, 1H), 3.10 (m, 1H), 2.87 (m, 1H), 2.32 (m, 1H), 2.25 (m, 1H), 1.56-1.99 (m, 8H). |
| 604 | 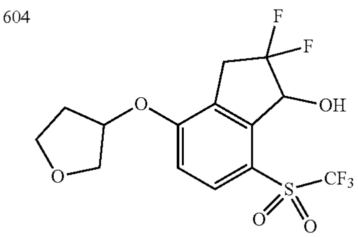 | 387 (M − H) | |
| 605 | 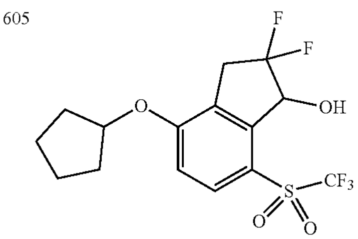 | 385 (M − H) | |
| 606 | 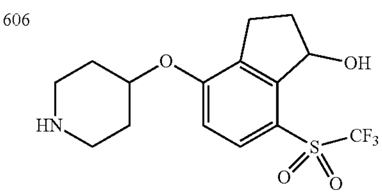 | | (300 MHz, CDCl₃): δ 7.92 (d, 1H), 7.04 (d, 1H), 5.36 (d, 1H), 4.60 (m, 1H), 3.46 (m, 1H), 3.39 (m, 1H), 3.14 (m, 2H), 2.80 (m, 2H), 2.05 (m, 2H), 1.76 (m, 2H), 1.55 (m, 4H) |
| 607 | 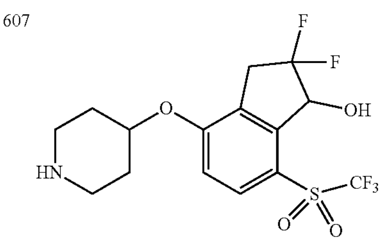 | 402 (M + H) | |
| 608 | 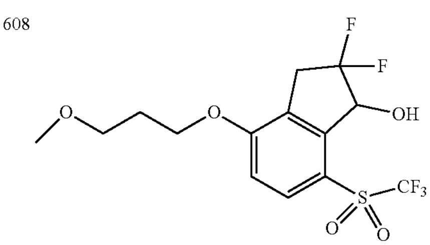 | 389 (M − H) | |
| 609 | 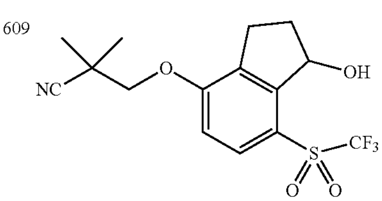 | | (300 MHz, CDCl₃): δ 7.90 (d, 1H), 6.94 (d, 1H), 5.60 (m, 1H), 4.04 (m, 2H), 3.20 (m, 1H), 3.15 (m, 1H), 2.98 (m, 1H), 2.40 (m, 1H), 2.31 (m, 1H), 1.54 (s, 3H), 1.53 (s, 3H) |

TABLE 2-continued

| No. | Structure | Mass Characterization | ¹H NMR Data |
|---|---|---|---|
| 610 | 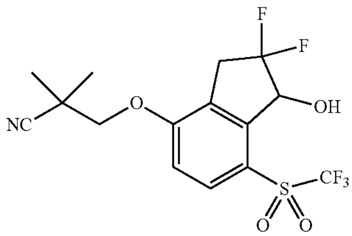 [SMILES: CC(C)(C#N)COc1ccc(S(=O)(=O)C(F)(F)F)c2c1CC(F)(F)C2O] | 398 (M − H) | |
| 611 | 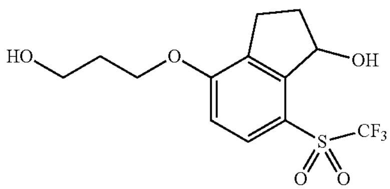 [SMILES: O=S(=O)(c1ccc(OCCCO)c2c1C(O)CC2)C(F)(F)F] | | (300 MHz, CDCl₃): δ 7.90 (d, 1H), 6.94 (d, 1H), 5.60 (m, 1H), 4.04 (m, 2H), 3.20 (m, 1H), 3.15 (m, 1H), 2.98 (m, 1H), 2.40 (m, 1H), 2.31 (m, 1H), 1.54 (s, 3H), 1.53 (s, 3H) |
| 612 | 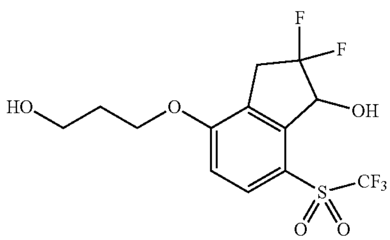 [SMILES: O=S(=O)(c1ccc(OCCCO)c2c1C(O)C(F)(F)C2)C(F)(F)F] | 377 (M + H) | |
| 613 | 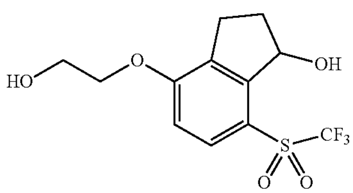 [SMILES: O=S(=O)(c1ccc(OCCO)c2c1C(O)CC2)C(F)(F)F] | 371 (M − H + HCOOH) | |
| 614 | 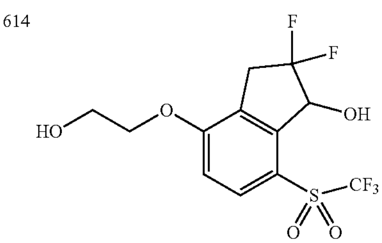 | 363 (M + H) | |
| 615 | 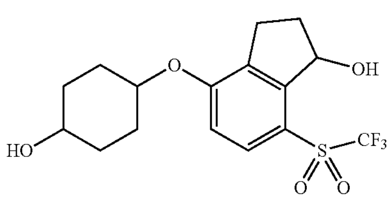 [SMILES: O=S(=O)(c1ccc(OC2CCC(O)CC2)c2c1C(O)CC2)C(F)(F)F] | 425 (M − H + HCOOH) | |
| 616 | 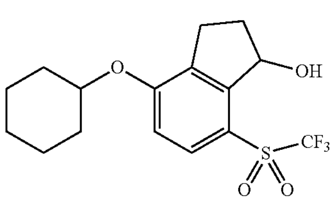 [SMILES: O=S(=O)(c1ccc(OC2CCCCC2)c2c1C(O)CC2)C(F)(F)F] | 382 (M + NH₄⁺) | |

TABLE 2-continued

| No. | Structure | Mass Characterization | ¹H NMR Data |
|---|---|---|---|
| 617 | 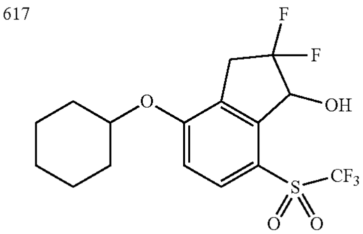 | 399 (M − H) | |
| 618 | 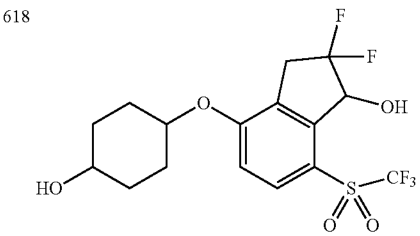 | 415 (M − H) | |
| 619 | 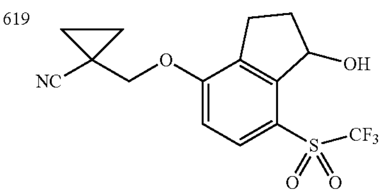 | 406 (M − H + HCOOH) | |
| 620 | 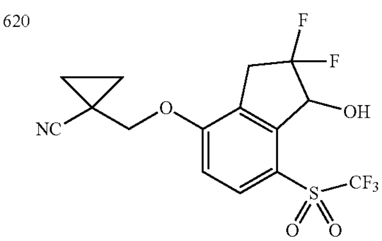 | 398 (M + H) | |
| 621 | 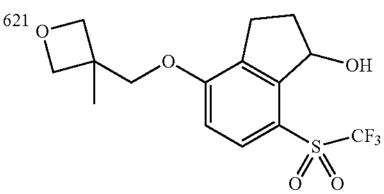 | 411 (M − H + HCOOH) | |
| 622 | 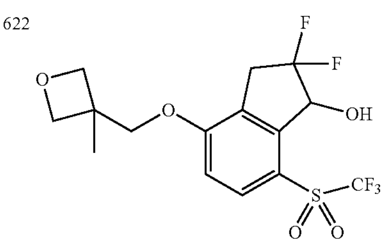 | 401 (M − H) | |
| 623 | 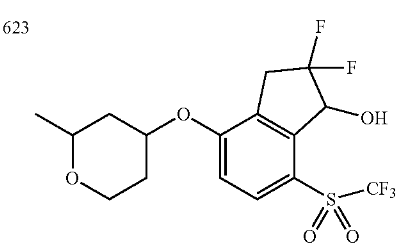 | 415 (M − H) | |

TABLE 2-continued

| No. | Structure | Mass Characterization | ¹H NMR Data |
|---|---|---|---|
| 624 | 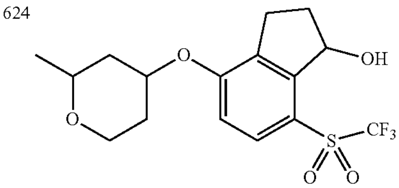 | 425 (M − H + HCOOH) | |
| 625 | 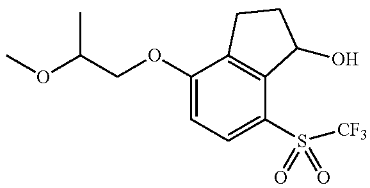 [SMILES: COC(C)COc1ccc(S(=O)(=O)C(F)(F)F)c2c1CCC2O] | 372 (M + NH₄) | |
| 626 | 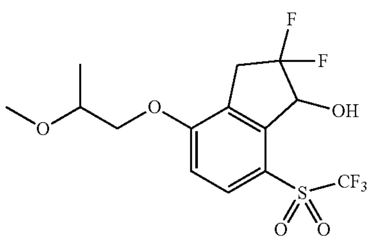 [SMILES: COC(C)COc1ccc(S(=O)(=O)C(F)(F)F)c2c1CC(F)(F)C2O] | 389 (M − H) | |
| 627 | 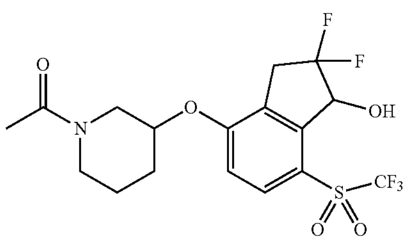 [SMILES: CC(=O)N1CCCC(Oc2ccc(S(=O)(=O)C(F)(F)F)c3c2CC(F)(F)C3O)C1] | 444 (M + H) | |
| 628 | 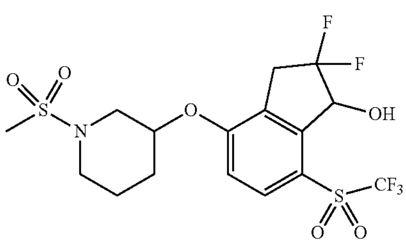 [SMILES: CS(=O)(=O)N1CCCC(Oc2ccc(S(=O)(=O)C(F)(F)F)c3c2CC(F)(F)C3O)C1] | 480 (M + H) | |
| 629 | 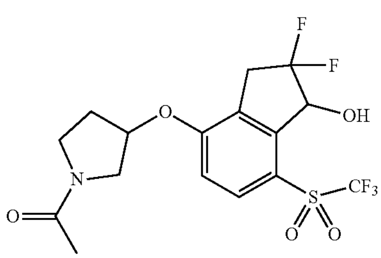 [SMILES: CC(=O)N1CCC(Oc2ccc(S(=O)(=O)C(F)(F)F)c3c2CC(F)(F)C3O)C1] | 430 (M + H) | |

TABLE 2-continued

| No. | Structure | Mass Characterization | ¹H NMR Data |
|---|---|---|---|
| 630 | 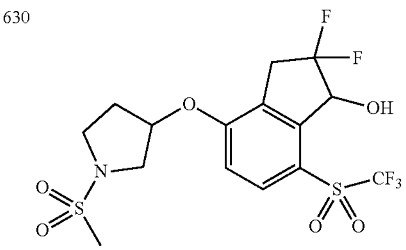 | 466 (M + H) | |
| 631 | 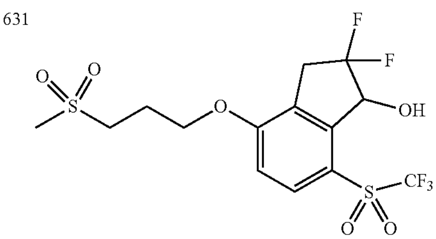 | 439 (M + H) | |
| 632 | 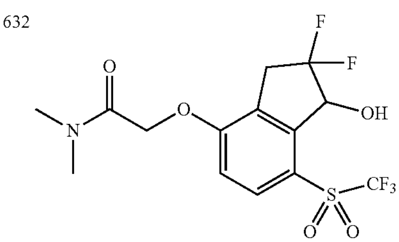 | 404 (M + H) | |
| 633 | 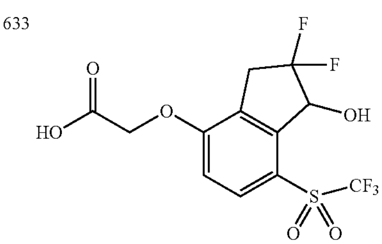 | 377 (M + H) | |
| 634 | 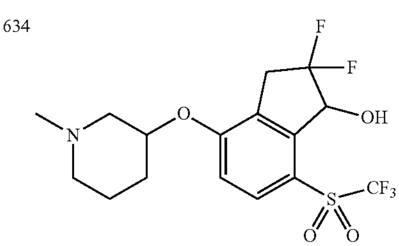 | 416 (M + H) | |
| 635 | 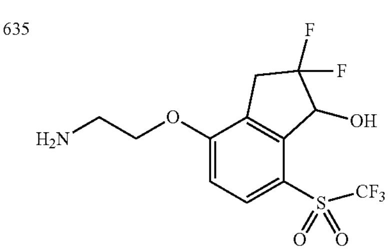 | 362 (M + H) | |

TABLE 2-continued

| No. | Structure | Mass Characterization | ¹H NMR Data |
|---|---|---|---|
| 636 | 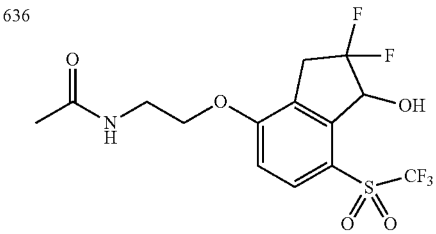 | 404 (M + H) | |
| 637 | 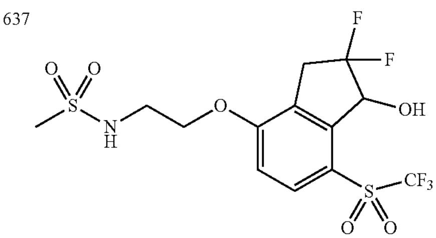 | 440 (M + H) | |
| 638 | 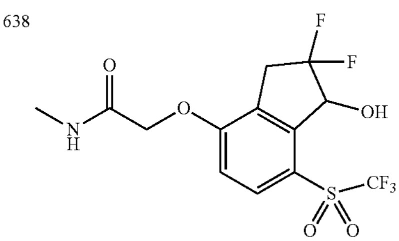 | 390 (M + H) | |
| 639 | 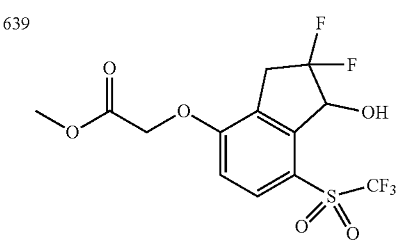 | 389 (M − H) | |
| 640 | 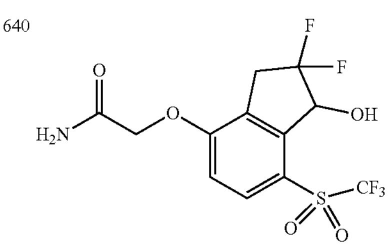 | 374 (M − H) | |
| 641 | 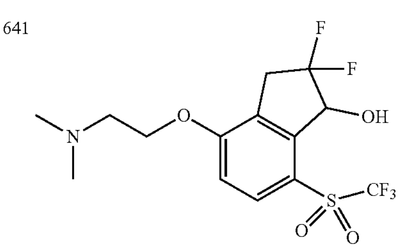 | 390 (M + H) | |

TABLE 2-continued

| No. | Structure | Mass Characterization | ¹H NMR Data |
|---|---|---|---|
| 642 | 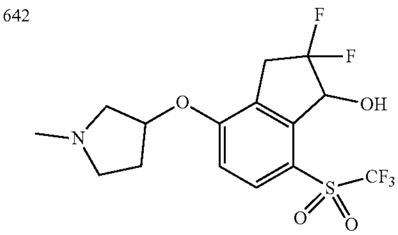 | | (300 MHz, CDCl$_3$): δ 7.93 (d, 1H), 6.94 (d, 1H), 5.35 (m, 1H), 4.96 (m, 1H), 3.38-3.47 (m, 3H), 2.82-2.92 (m 3H), 2.52 (m, 1H), 2.43 (m 1H), 2.42 (s, 3H), 2.04 (m 1H) |
| 643 | 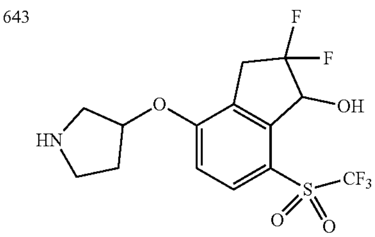 | 388 (M + H) | |
| 644 | 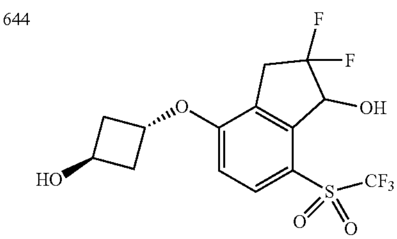 | 433 (M − H + HCOOH) | |
| 645 | 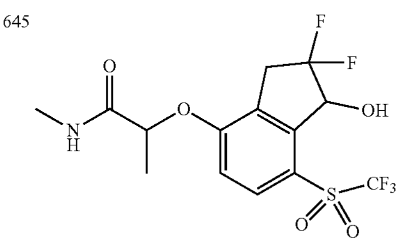 | 402 (M − H) | |
| 646 | 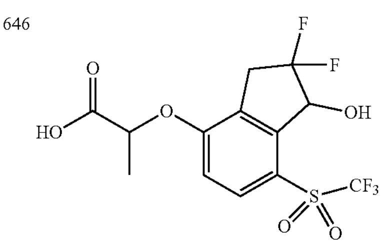 | 389 (M − H) | |
| 647 | 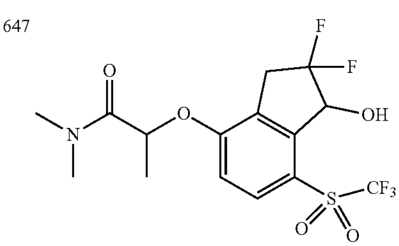 | 418 (M + H) | |

TABLE 2-continued

| No. | Structure | Mass Characterization | $^1$H NMR Data |
|---|---|---|---|
| 648 | 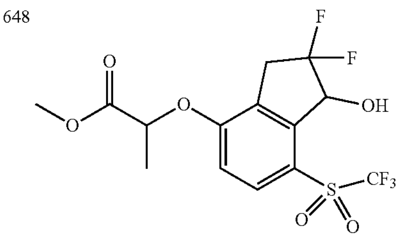 | | (300 MHz, CDCl$_3$): δ 7.92 (d, 1H), 6.87 (d, 1H), 5.36 (m, 1H), 4.93 (m, 1H), 3.80 (s, 3H), 3.44-3.60 (m, 2H), 3.22 (m, 1H), 1.71 (d, 3H) |
| 649 | 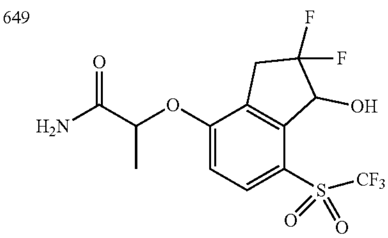 | 388 (M − H) | |
| 650 | 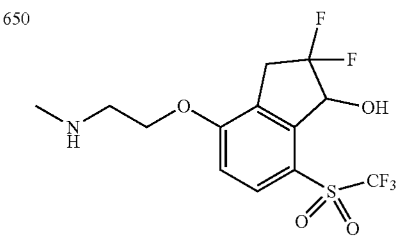 | 376 (M + H) | |
| 651 | 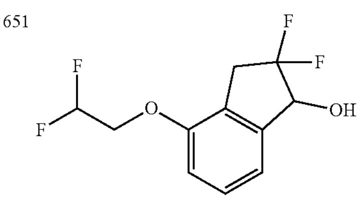 | | (400 MHz, CDCl$_3$): δ 7.31 (m, 1H), 7.17 (d, 1H), 6.82 (d, 1H), 6.09 (t, 1H), 5.15 (m, 1H), 4.20 (m, 2H), 3.45 (m, 1H), 3.27 (m, 1H), 2.27 (m, 1H) |
| 652 | 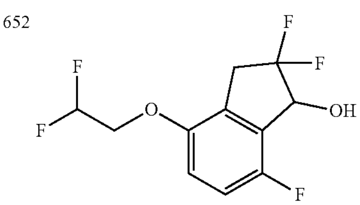 | 313 (M − H + HCOOH) | |
| 653 | 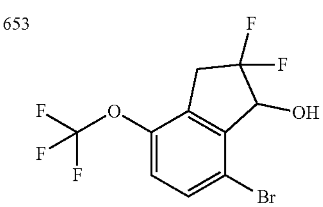 | | (400 MHz, CDCl$_3$): δ 7.56 (d, 1H), 7.17 (d, 1H), 5.13 (m, 1H), 3.56 (m, 2H), 2.50 (s, 1H) |
| 654 | 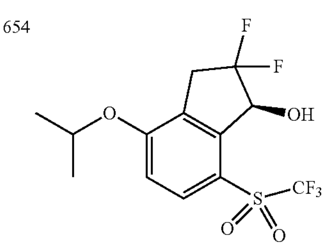 | 359 (M − H) | |

TABLE 2-continued

| No. | Structure | Mass Characterization | ¹H NMR Data |
|---|---|---|---|
| 655 | 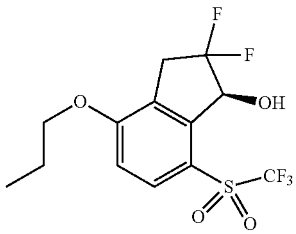 [SMILES: CCCOc1ccc(S(=O)(=O)C(F)(F)F)c2c1CC(F)(F)[C@H]2O] | 359 (M − H) | |
| 656 | 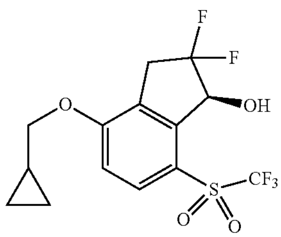 [SMILES: O=S(=O)(c1ccc(OCC2CC2)c2c1[C@H](O)C(F)(F)C2)C(F)(F)F] | 371 (M − H) | |
| 657 | 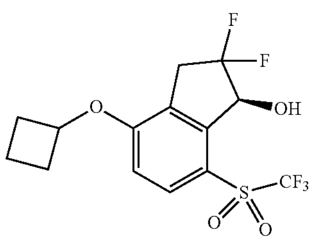 [SMILES: O=S(=O)(c1ccc(OC2CCC2)c2c1[C@H](O)C(F)(F)C2)C(F)(F)F] | 371 (M − H) | |
| 658 | 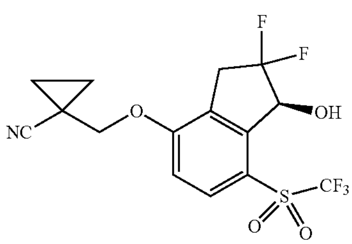 [SMILES: N#CC1(COc2ccc(S(=O)(=O)C(F)(F)F)c3c2CC(F)(F)[C@H]3O)CC1] | 442 (M + HCO₂⁻) | |
| 659 | 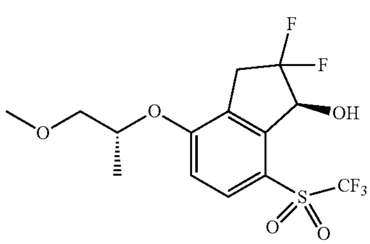 [SMILES: COC[C@@H](C)Oc1ccc(S(=O)(=O)C(F)(F)F)c2c1CC(F)(F)[C@H]2O] | 389 (M − H) | |
| 660 | 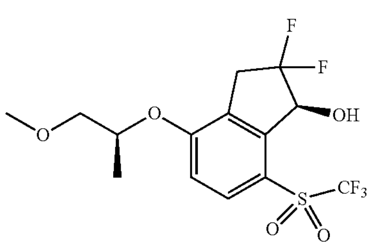 [SMILES: COC[C@H](C)Oc1ccc(S(=O)(=O)C(F)(F)F)c2c1CC(F)(F)[C@H]2O] | 389 (M − H) | |

TABLE 2-continued

| No. Structure | Mass Characterization | ¹H NMR Data |
|---|---|---|
| 661 | 424 (M + HCO₂⁻) | |
| 662 | 265 (M − OH) | |
| 663 | (M + NH4) 426 | |
| 664 | (M − H) 421 | |
| 665 | (M + H) 410 | |
| 666 | | (400 MHz, CDCl₃): δ 8.15 (s, 1H), 6.12 (t, 1H), 4.96-4.87 (1H), 4.22-4.09 (2H), 3.62-3.50 (2H), 2.49 (1H) |
| 667 | (M − OH) 467 | |

TABLE 2-continued

| No. | Structure | Mass Characterization | ¹H NMR Data |
|---|---|---|---|
| 668 | 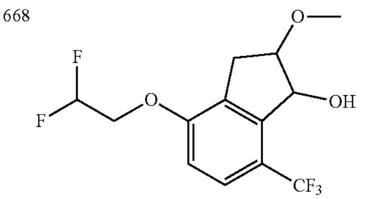 | (M + NH4) 330 | |
| 669 | 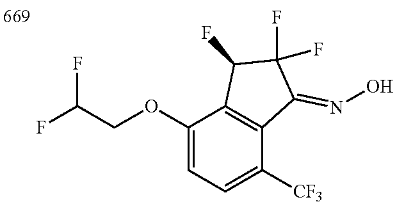 | (M + H) 350 | |
| 670 | 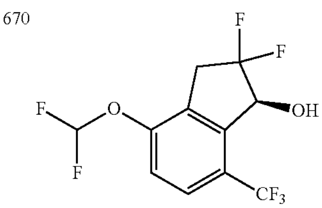 | | (400 MHz, CDCl$_3$): δ 7.63 (d, 1H), 7.25 (d, 1H), 6.62 (t, 1H), 5.30-5.25 (m, 1H), 3.58-3.37 (m, 2H), 2.54-2.51 (m, 1H) |
| 671 | 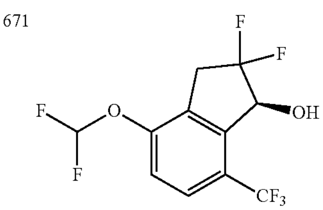 | | (400 MHz, CDCl$_3$): δ 7.59 (d, 1H), 7.18 (d, 1H), 6.60 (t, 1H), 5.40-5.23 (m, 2H), 3.40-3.12 (m, 2H), 2.55-2.51 (m, 1H) |
| 672 | 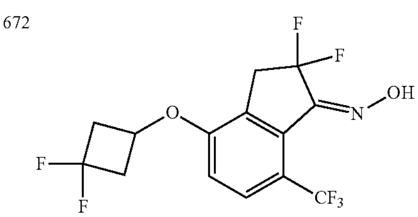 | (M + H) 358 | |
| 673 | 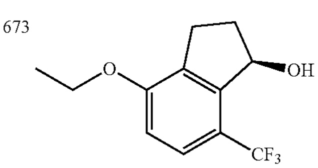 | [M − OH]$^+$ 229 | |
| 674 | 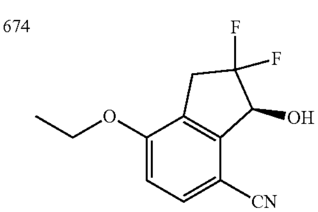 | [M − H + HCOOH]$^-$ 284 | |

TABLE 2-continued
| No. | Structure | Mass Characterization | ¹H NMR Data |
|---|---|---|---|
| 675 | 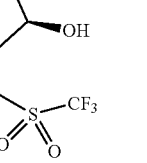 | [M − H + HCOOH]⁻ 445 | |
| 676 | 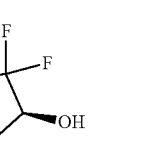 | [M + NH4]⁺ 360 | |
| 677 | 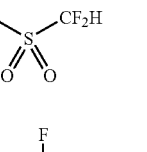 | [M + NH4]⁺ 382 | |
| 678 | 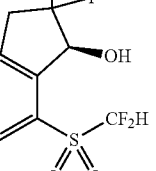 | [M + NH4]⁺ 346 | |
| 679 | 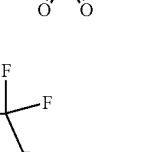 | | (400 MHz, CDCl$_3$): δ 7.62 (d, 1H), 6.63 (d, 1H), 4.94 (dd, 1H), 3.81 (s, 3H), 3.46-3.38 (m, 2H), 2.43-2.40 (m, 1H) |
| 680 | 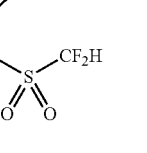 | [M + Na]⁺ 289 | |

TABLE 2-continued

| No. | Structure | Mass Characterization | ¹H NMR Data |
|---|---|---|---|
| 681 | 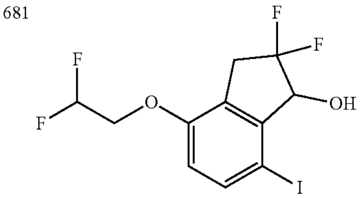 | | (400 MHz, CDCl₃): δ 7.64 (d, 1H), 6.61 (d, 1H), 6.07 (tt, 1H), 4.94 (d, 1H), 4.19 (td, 2H), 3.50-3.42 (m, 2H), 2.41 (brs, 1H) |
| 682 | 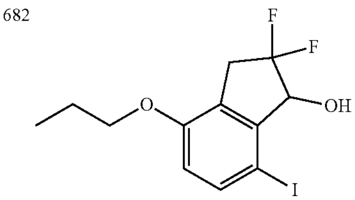 | | (400 MHz, CDCl₃): δ 7.59 (d, 1H), 6.61 (d, 1H), 4.98-4.91 (m, 1H), 3.92 (td, 2H), 3.48-3.39 (m, 2H), 2.40 (brs, 1H), 1.84-1.76 (m, 2H), 1.02 (t, 3H) |
| 683 | 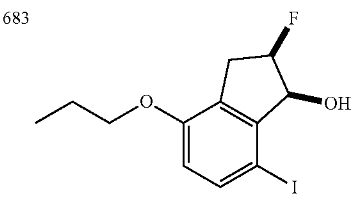 | | (400 MHz, CDCl₃): δ 7.58 (d, 1H), 6.57 (d, 1H), 5.26 (dq, 1H), 5.06-5.01 (m, 1H), 3.91 (t, 2H), 3.21 (dd, 2H), 2.42-2.38 (m, 1H), 1.84-1.74 (m, 2H), 1.03 (t, 3H) |
| 684 | 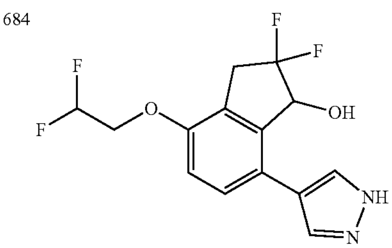 | [M + H]⁺ 317 | |
| 685 | 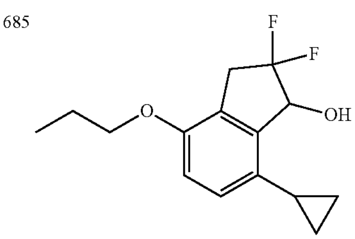 | [M + NH4]⁻ 251 | |
| 686 | 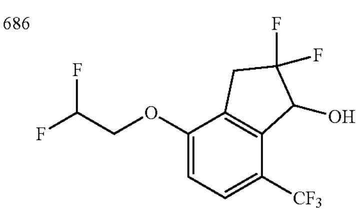 | [M − H + HCOOH]⁻ 363 | |
| 687 | 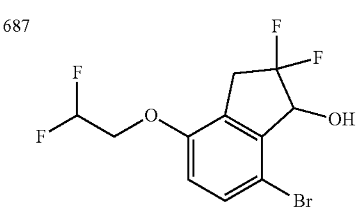 | | (400 MHz, CDCl₃): δ 7.42 (d, 1H), 6.73 (d, 1H), 6.07 (tt, 1H), 5.08 (d, 1H), 4.23-4.17 (m, 2H), 3.54-3.35 (m, 2H), 2.49 (brs, 1H) |

TABLE 2-continued

| No. | Structure | Mass Characterization | ¹H NMR Data |
|---|---|---|---|
| 688 | 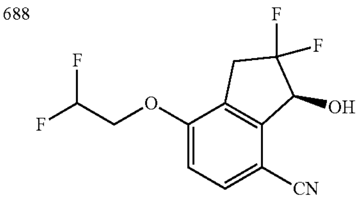 | [M + H]⁺ 276 | |
| 689 | 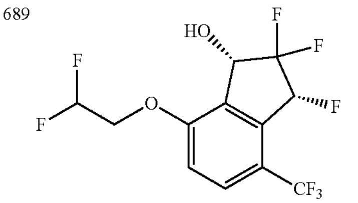 | | (400 MHz, CDCl₃): δ 7.78 (d, 1H), 7.09 (d, 1H), 6.17 (tt, 1H), 5.79 (dd, 1H), 5.24-5.18 (m, 1H), 4.42-4.31 (m, 2H), 2.47-2.44 (m, 1H) |
| 690 | 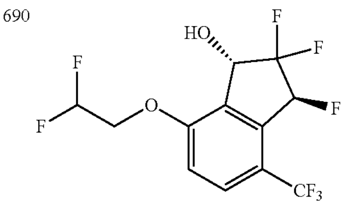 | | (400 MHz, CDCl₃): δ 7.74 (d, 1H), 7.05 (d, 1H), 6.16 (tt, 1H), 6.02 (dd, 1H), 5.54-5.48 (m, 1H), 4.35 (td, 2H), 2.68 (brd, 1H) |
| 691 | 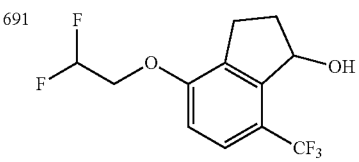 | [M − H]⁻ 290 | |
| 692 | 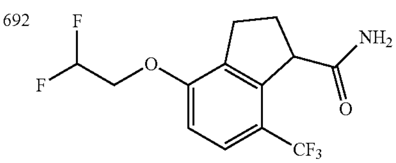 | [M + H]⁺ 310 | |
| 693 | 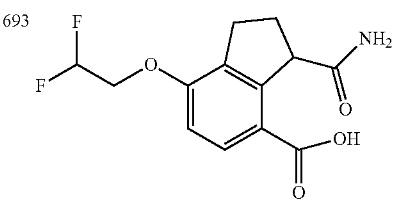 | [M + H]⁺ 286 | |
| 694 | 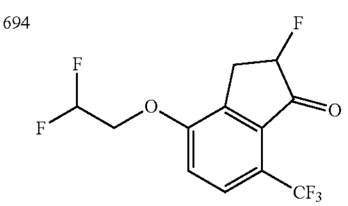 | [M − H + HCOOH]⁻ 343 | |
| 695 | 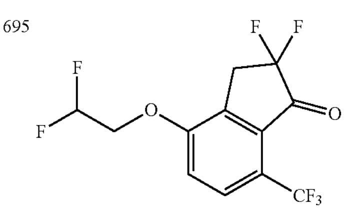 | [M + H]⁺ 317 | |

TABLE 2-continued

| No. | Structure | Mass Characterization | ¹H NMR Data |
|---|---|---|---|
| 696 | 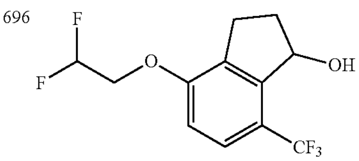 | | (400 MHz, CDCl$_3$): δ 7.56 (d, 1H), 6.84 (d, 1H), 6.11 (tt, 1H), 5.38-5.22 (m, 2H), 4.26 (td, 2H), 3.33-3.07 (m, 2H), 2.52-2.48 (m, 1H) |
| 697 | 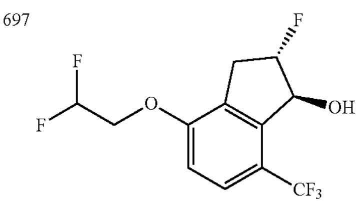 | | (400 MHz, CDCl$_3$): δ 7.56 (d, 1H), 6.87 (d, 1H), 6.12 (tt, 1H), 5.49-5.22 (m, 2H), 4.31-4.23 (m, 2H), 3.48-3.06 (m, 2H), 2.48 (brs, 1H) |
| 698 | 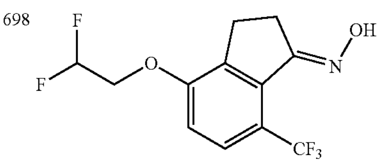 | | (400 MHz, CDCl$_3$): δ 7.62 (d, 1H), 7.61 (s, 1H), 6.81 (d, 1H), 6.13 (tt, 1H), 4.28 (td, 2H), 3.09-2.97 (m, 4H) |
| 699 | 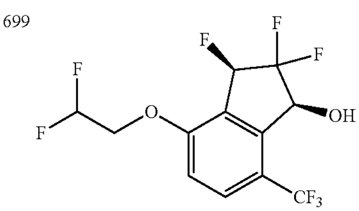 | [M − H + HCOOH]⁻ 381 | |
| 700 | 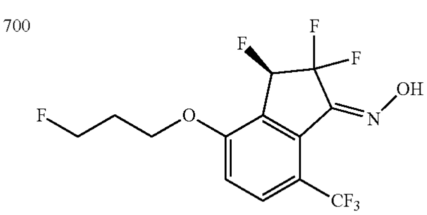 | [M − H]⁻ 344 | |
| 701 | 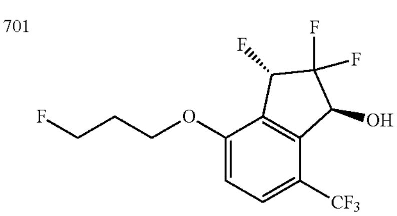 | [M − H + HCOOH]⁻ 377 | |
| 702 | 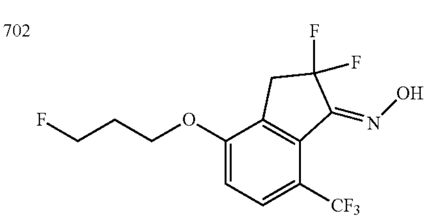 | [M + H]⁺ 328 | |

TABLE 2-continued

| No. | Structure | Mass Characterization | $^1$H NMR Data |
|---|---|---|---|
| 703 | 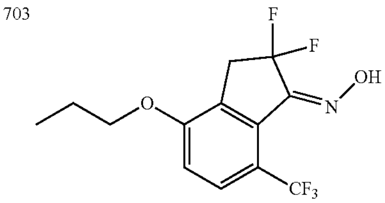 | [M + H]$^+$ 310 | |
| 704 | 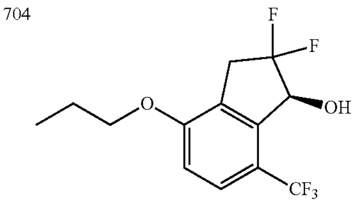 | [M + Na]$^+$ 320 | |
| 705 | 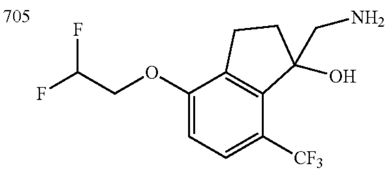 | [M + H]$^+$ 312 | |
| 706 | 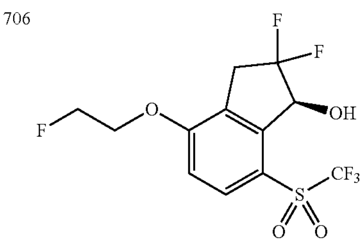 [SMILES: CCCCOc1ccc(S(=O)(=O)C(F)(F)F)c2c1CC(F)(F)[C@H]2O] | 363 (M − H)$^-$ | |
| 707 | 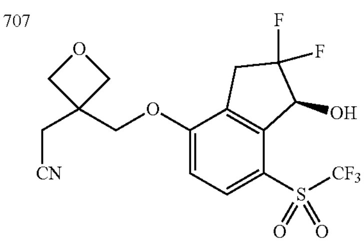 | 472 (M + HCO$_2$)$^-$ | |
| 708 | 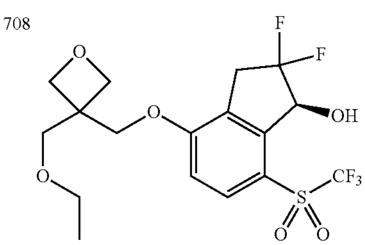 | 491 (M + HCO$_2$)$^-$ | |
| 709 | 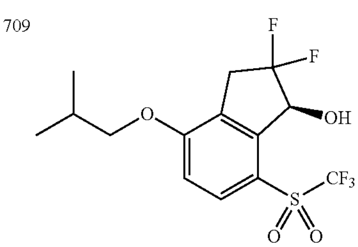 | 373 (M − H)$^-$ | |

TABLE 2-continued

| No. | Structure | Mass Characterization | ¹H NMR Data |
|---|---|---|---|
| 710 | 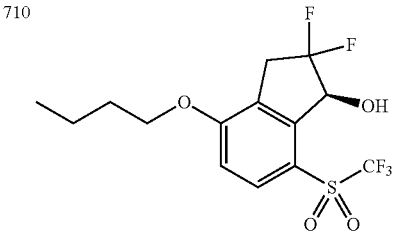 | 373 (M − H)⁻ | |
| 711 | 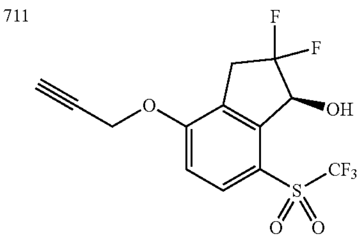 | 355 (M − H)⁻ | |
| 712 | 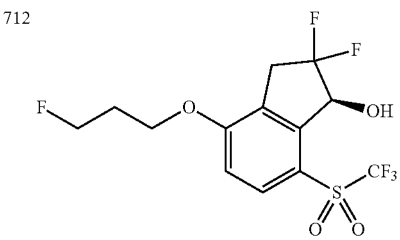 | 377 (M − H)⁻ | |
| 713 | 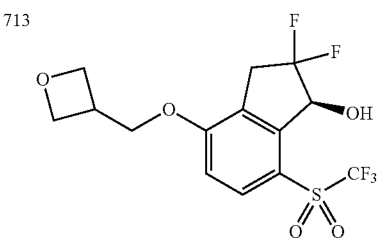 | 387 (M − H)⁻ | |
| 714 | 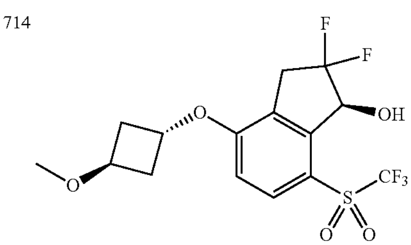 | 401 (M − H)⁻ | |
| 715 | 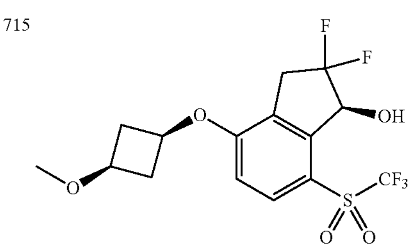 | 401 (M − H)⁻ | |

TABLE 2-continued

| No. | Structure | Mass Characterization | ¹H NMR Data |
|---|---|---|---|
| 716 | 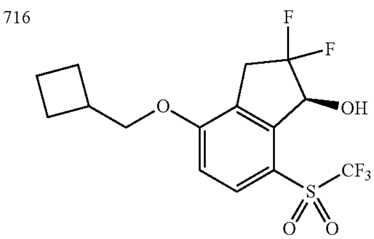 | 385 (M − H)⁻ | |
| 717 | 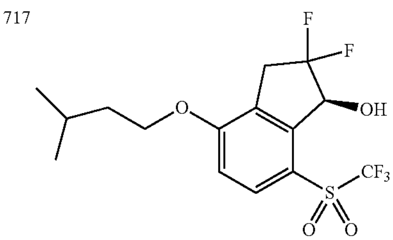 | 387 (M − H)⁻ | |
| 718 | 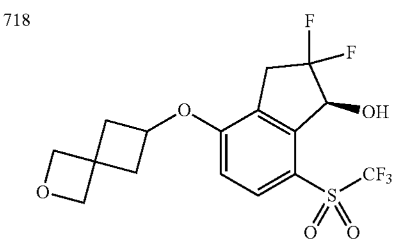 | 413 (M − H)⁻ | |
| 719 | 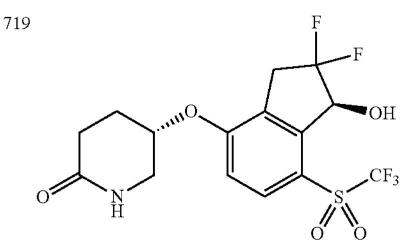 | 416 (M + H)⁻ | |
| 720 | 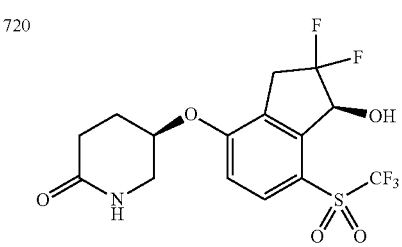 | 416 (M + H)⁺ | |
| 721 | 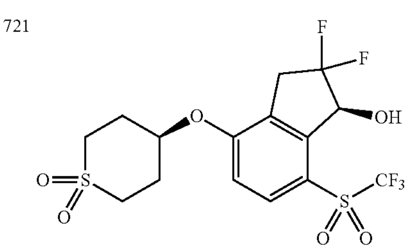 | 495 (M + HCO₂)⁻ | |

TABLE 2-continued

| No. | Structure | Mass Characterization | ¹H NMR Data |
|---|---|---|---|
| 722 | 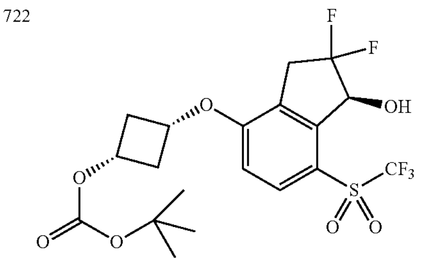 | 388 (M + H − CO₂ − C₄H₈)⁺ | |
| 723 | 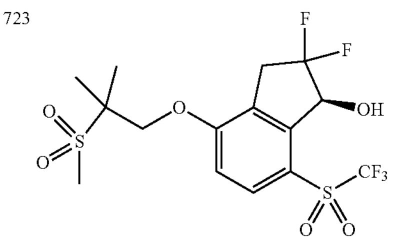 | 451 (M − H)⁻ | |
| 724 | 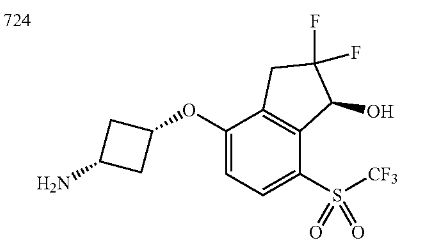 | 388 (M + H)⁺ | |
| 725 | 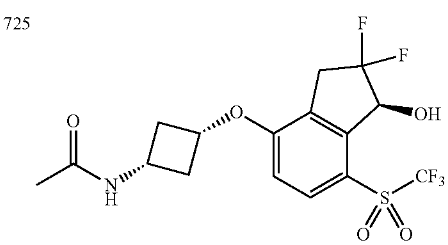 | 430 (M + H)⁺ | |
| 726 | 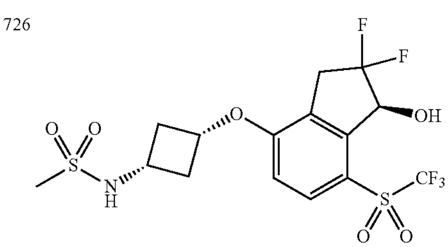 | 510 (M + HCO₂)⁻ | |
| 727 | 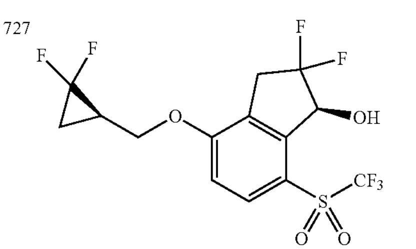 | 407 (M − H)⁻ | |

US 10,278,942 B2
TABLE 2-continued
| No. | Structure | Mass Characterization | ¹H NMR Data |
|---|---|---|---|
| 728 | 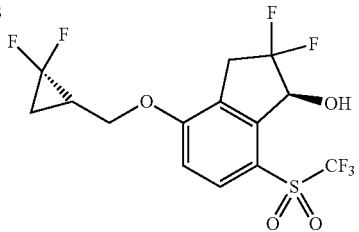 | 407 (M − H) | |
| 729 | 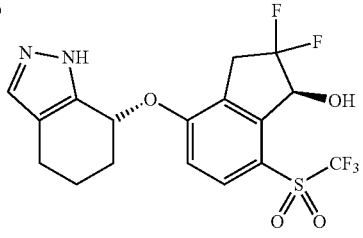 | 439 (M + H)⁺ | |
| 730 | 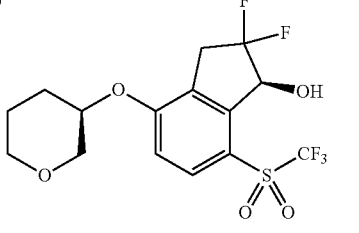 | 401 (M − H)⁻ | |
| 731 | 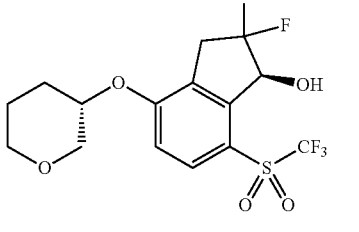 | 401 (M − H)⁻ | |
| 732 | 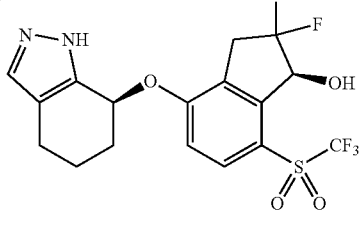 | 439 (M + H)⁺ | |
| 733 | 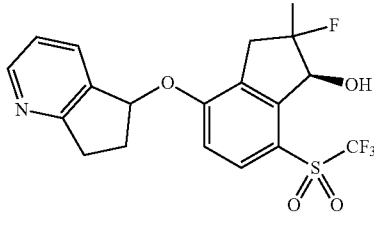 | 436 (M + H)⁺ | |

TABLE 2-continued

| No. | Structure | Mass Characterization | ¹H NMR Data |
|---|---|---|---|
| 734 | 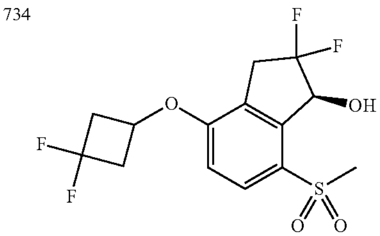 | 355 (M + H)⁺ | |
| 735 | 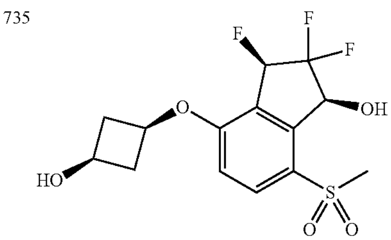 | 353 (M + H)⁺ | |
| 736 | 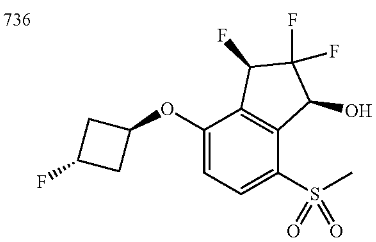 | 355 (M + H)⁺ | |
| 737 | 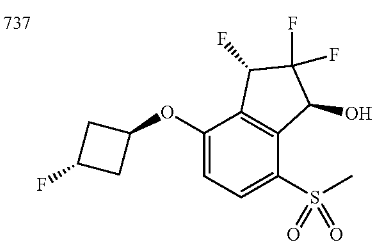 | 355 (M + H)⁺ | |
| 738 | 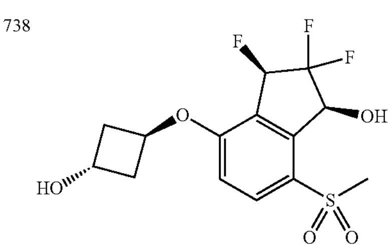 | 353 (M + H)⁺ | |
| 739 | 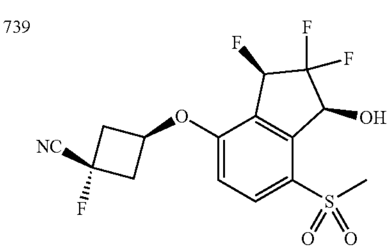 | 402 (M + Na)⁺ | |

TABLE 2-continued

| No. | Structure | Mass Characterization | ¹H NMR Data |
|---|---|---|---|
| 740 | 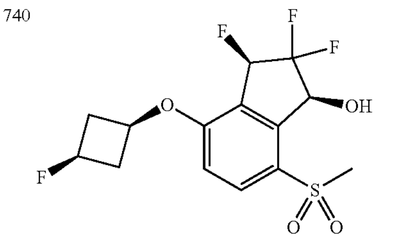 | 355 (M + H)⁺ | |
| 741 | 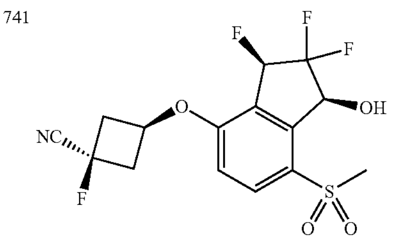 | 380 (M + H)⁺ | |
| 742 | 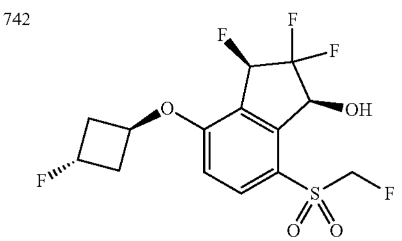 | 390 (M + NH₄)⁺ | |
| 743 | 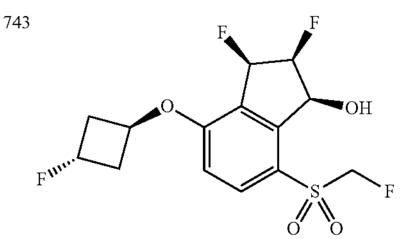 | 372 (M + NH₄)⁺ | |
| 744 | 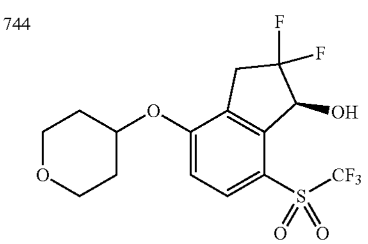 | [M + NH₄]⁺ 420 | |
| 745 | 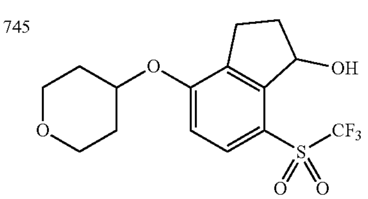 | [M + NH₄]⁺ 384 | |

TABLE 2-continued

| No. | Structure | Mass Characterization | ¹H NMR Data |
|---|---|---|---|
| 746 | 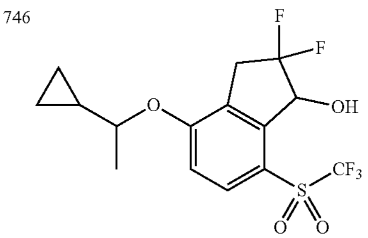 | [M + NH$_4$]$^+$ 404 | |
| 747 | 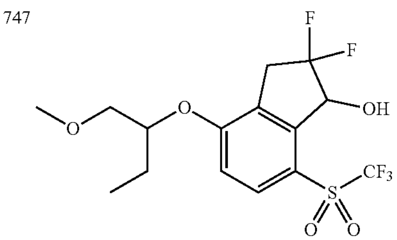 | [M + NH$_4$]$^+$ 422 | |
| 748 | 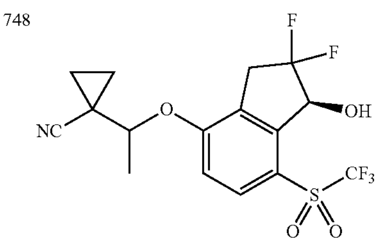 | [M + NH$_4$]$^+$ 429 | |
| 749 | 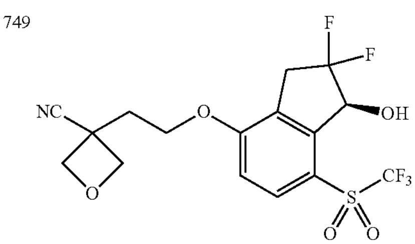 | [M + NH$_4$]$^+$ 445 | |
| 750 | 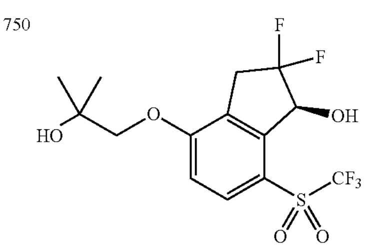 | [M + NH$_4$]$^+$ 408 | |
| 751 | 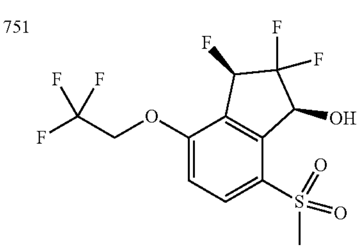 | [M + NH$_4$]$^+$ 382 | |

TABLE 2-continued

| No. | Structure | Mass Characterization | ¹H NMR Data |
|---|---|---|---|
| 752 | 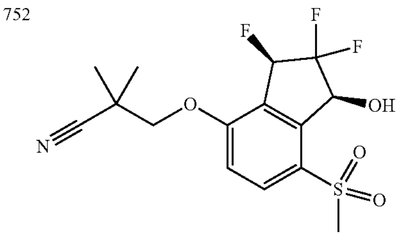 | [M + NH$_4$]$^+$ 381 | |
| 753 | 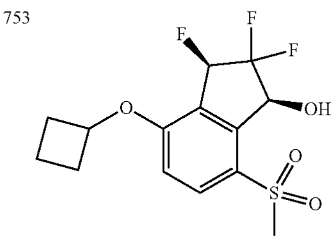 | [M + NH$_4$]$^+$ 354 | |
| 754 | 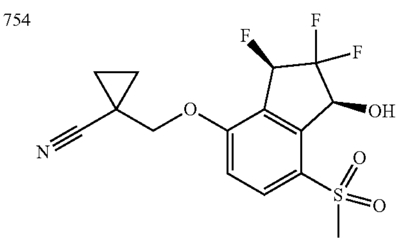 | [M + NH$_4$]$^+$ 379 | |
| 755 | 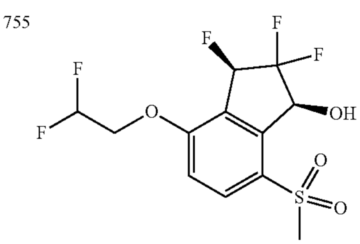 | [M + NH$_4$]$^+$ 364 | |
| 756 | 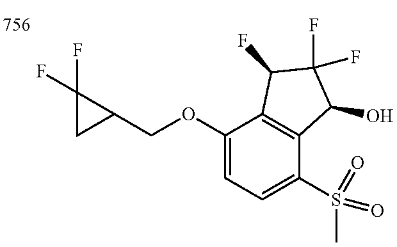 | [M + NH$_4$]$^+$ 390 | |
| 757 | 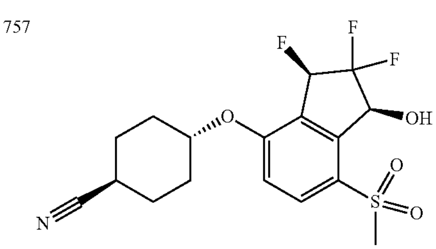 | [M + NH$_4$]$^+$ 407 | (400 MHz, CDCl$_3$): δ 8.09 (d, 1H), 7.07 (d, 1H), 5.82-5.66 (m, 1H), 5.61-5.57 (m, 1H), 4.73 (m, 1H), 3.41 (d, 1H), 3.20 (s, 3H), 2.87 (m, 1H), 2.17-1.80 (m, 8H) |

TABLE 2-continued

| No. | Structure | Mass Characterization | ¹H NMR Data |
|---|---|---|---|
| 758 | 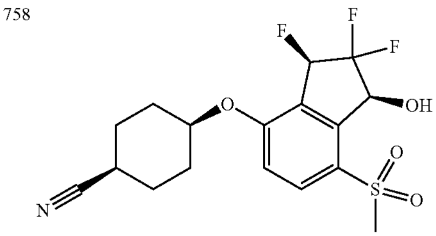 | [M + NH₄]⁺ 407 | (400 MHz, CDCl₃): δ 8.07 (dd, 1H), 7.04 (d, 1H), 5.85-5.70 (m, 1H), 5.62-5.58 (m, 1H), 4.65 (m, 1H), 3.25 (d, 1H), 3.20 (s, 3H), 2.76-2.74 (m, 1H), 2.12-1.55 (m, 8H) |
| 759 | 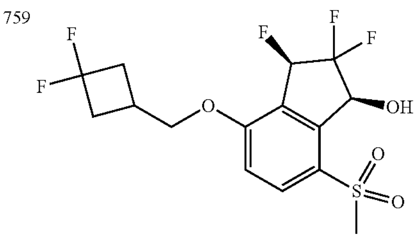 | [M + NH₄]⁺ 404 | |
| 760 | 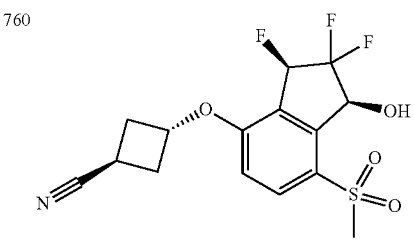 | [M + NH₄]⁺ 379 | (400 MHz, CDCl₃): δ 8.10 (dd, 1H), 6.86 (d, 1H), 5.82-5.66 (m, 1H), 5.61-5.58 (m, 1H), 5.17-5.14 (m, 1H), 3.32-3.29 (m, 1H), 3.24 (d, 1H), 3.20 (s, 3H), 2.99-2.93 (m, 2H), 2.76-2.70 (m, 2H) |
| 761 | 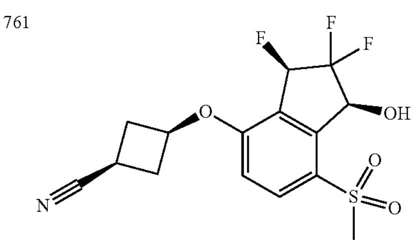 | [M + NH₄]⁺ 379 | (400 MHz, CDCl₃): δ 8.08 (dd, 1H), 6.84 (d, 1H), 5.85-5.69 (m, 1H), 5.62-5.58 (m, 1H), 4.86-4.79 (m, 1H), 3.24 (d, 1H), 3.20 (s, 3H), 3.07-3.00 (m, 2H), 2.96-2.87 (m, 1H), 2.76-2.66 (m, 2H) |
| 762 | 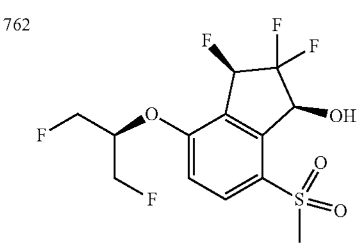 | [M + NH₄]⁺ 378 | |
| 763 | 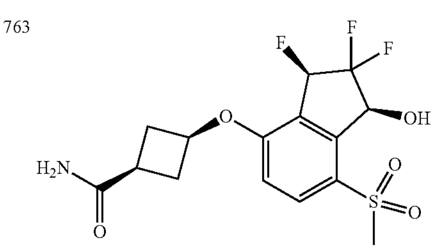 | [M + NH₄]⁺ 397 | (400 MHz, CDCl₃): δ 8.06 (dd, 1H), 6.90 (d, 1H), 5.85-5.70 (m, 1H), 5.59-5.56 (m, 1H), 5.39-5.32 (m, 2H), 4.79-4.76 (m, 1H), 3.24 (d, 1H), 3.20 (s, 3H), 2.83-2.74 (m, 3H), 2.63-2.55 (m, 2H) |

TABLE 2-continued

| No. | Structure | Mass Characterization | $^1$H NMR Data |
|---|---|---|---|
| 764 | 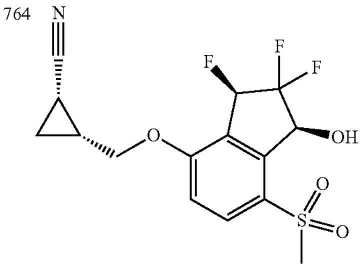 | [M + NH$_4$]$^+$ 379 | (400 MHz, CDCl$_3$): 8.10 (dd, 1H), 7.09 (d, 1H), 5.91-5.76 (m, 1H), 5.58-5.55 (m, 1H), 4.48-4.44 (m, 1H), 4.14-4.10 (m, 1H), 3.41 (d, 1H), 3.20 (s, 3H), 1.94-1.91 (m, 1H), 1.81.76 (m, 1H), 1.46-1.41 (m, 1H), 1.20-1.18 (m, 1H) |
| 765 | 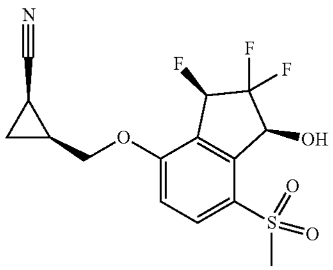 [SMILES: CS(=O)(=O)c1ccc(OC[C@H]2C[C@H]2C#N)c2c1[C@H](O)C(F)(F)[C@@H]2F] | [M + NH$_4$]$^+$ 379 | (400 MHz, CDCl$_3$): δ 8.12 (dd, 1H), 7.10 (d, 1H), 5.91-5.75 (m, 1H), 5.62-5.58 (m, 1H), 4.39-4.29 (m, 2H), 3.26 (d, 1H), 3.21 (s, 3H), 1.90-1.86 (m, 1H), 1.79-1.76 (m, 1H), 1.45-1.39 (m, 1H), 1.26-1.22 (m, 1H) |
| 766 | 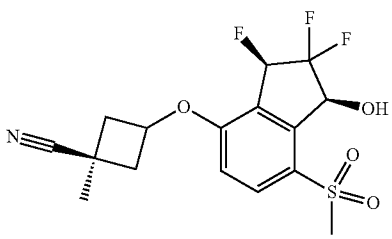 | [M + NH$_4$]$^+$ 393 | (400 MHz, CDCl$_3$): δ 8.10 (dd, 1H), 6.88 (d, 1H), 5.82-5.66 (m, 1H), 5.61-5.58 (m, 1H), 5.08-5.02 (m, 1H), 3.29 (d, 1H), 3.20 (s, 3H), 3.19-3.14 (m, 2H), 2.42-2.32 (m, 2H), 1.65 (s, 3H) |
| 767 | 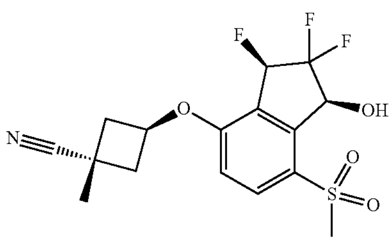 [SMILES: CS(=O)(=O)c1ccc(O[C@H]2C[C@](C)(C#N)C2)c2c1[C@H](O)C(F)(F)[C@@H]2F] | [M + NH$_4$]$^+$ 393 | (400 MHz, CDCl$_3$): 8.05 (d, 1H), 6.81 (d, 1H), 5.87-5.71 (m, 1H), 5.61-5.58 (m, 1H), 4.97-4.91 (m, 1H), 3.25 (d, 1H), 3.20 (s, 3H), 2.92-2.76 (m, 2H), 2.74-2.70 (m, 2H), 1.65 (s, 3H) |
| 768 | 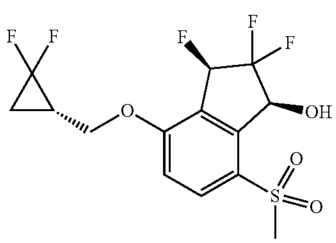 [SMILES: CS(=O)(=O)c1ccc(OC[C@@H]2CC2(F)F)c2c1[C@H](O)C(F)(F)[C@@H]2F] | [M + NH$_4$]$^+$ 390 | (400 MHz, CDCl$_3$): δ 8.11 (dd, 1H), 7.07 (d, 1H), 5.85-5.69 (m, 1H), 5.62-5.58 (m, 1H), 4.36-4.32 (m, 1H), 4.21-4.17 (m, 1H), 3.27 (d, 1H), 3.20 (s, 3H), 2.18-2.10 (m, 1H), 1.72-1.67 (m, 2H), 1.41-1.33 (m, 1H) |
| 769 | 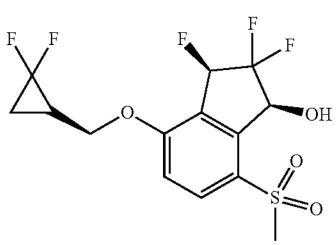 | [M + NH$_4$]$^+$ 390 | (400 MHz, CDCl$_3$): δ 8.11 (dd, 1H), 7.06 (d, 1H), 5.87-5.72 (m, 1H), 5.61-5.57 (m, 1H), 4.25-4.23 (m, 2H), 3.27 (d, 1H), 3.20 (s, 3H), 2.22-2.10 (m, 1H), 1.73-1.70 (m, 2H), 1.39-1.36 (m, 1H) |

TABLE 2-continued

| No. | Structure | Mass Characterization | ¹H NMR Data |
|---|---|---|---|
| 770 | 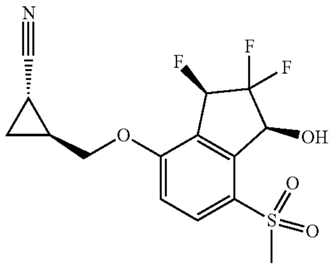 [SMILES: CS(=O)(=O)c1ccc(OC[C@H]2C[C@@H]2C#N)c2c1[C@H](O)C(F)(F)[C@@H]2F] | [M + NH₄]⁺ 379 | (400 MHz, CDCl₃): δ 8.10 (dd, 1H), 7.02 (d, 1H), 5.83-5.67 (m, 1H), 5.61-5.58 (m, 1H), 4.25-4.22 (m, 1H), 4.14-4.09 (m, 1H), 3.32-3.29 (m, 1H), 3.21 (s, 3H), 2.06-2.04 (m, 1H), 1.59-1.55 (m, 1H), 1.47-1.44 (m, 1H), 1.28-1.25 (m, 1H) |
| 771 | 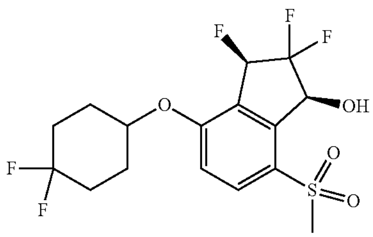 [SMILES: CS(=O)(=O)c1ccc(OC2CCC(F)(F)CC2)c2c1[C@H](O)C(F)(F)[C@@H]2F] | [M + NH₄]⁺ 418 | |
| 772 | 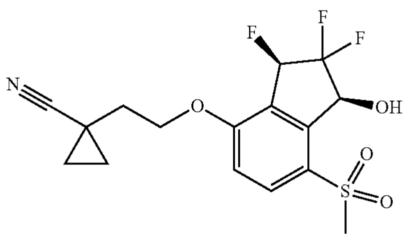 [SMILES: CS(=O)(=O)c1ccc(OCCC2(C#N)CC2)c2c1[C@H](O)C(F)(F)[C@@H]2F] | [M + NH₄]⁺ 393 | |
| 773 | 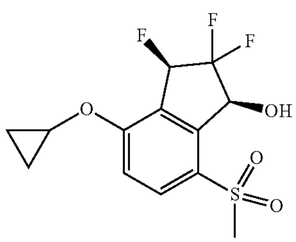 [SMILES: CS(=O)(=O)c1ccc(OC2CC2)c2c1[C@H](O)C(F)(F)[C@@H]2F] | [M + NH₄]⁺ 340 | |
| 774 | 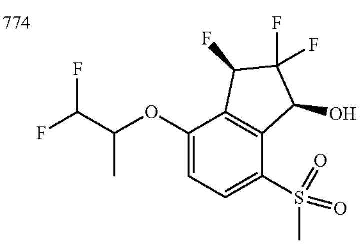 | [M + NH₄]⁺ 378 | |
| 775 | 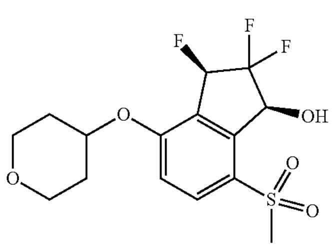 [SMILES: CS(=O)(=O)c1ccc(OC2CCOCC2)c2c1[C@H](O)C(F)(F)[C@@H]2F] | [M + NH₄]⁺ 366 | |

TABLE 2-continued
| No. | Structure | Mass Characterization | ¹H NMR Data |
|---|---|---|---|
| 776 | 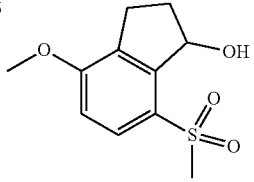 | [M + NH$_4$]$^+$ 260 | |
| 777 | 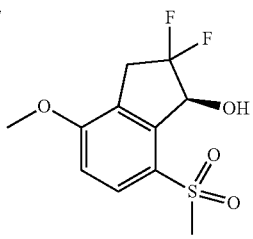 | [M + NH$_4$]$^+$ 296 | |
| 778 | 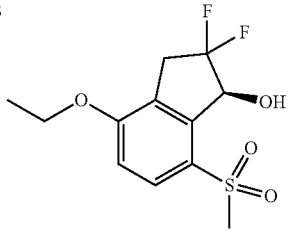 | [M + NH$_4$]$^+$ 310 | |
| 779 | 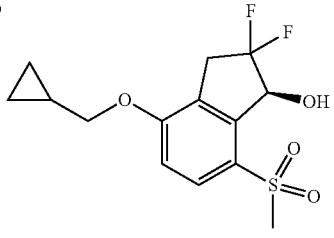 | [M + NH$_4$]$^+$ 336 | |
| 780 | 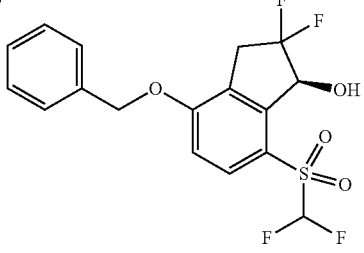 | [M + NH$_4$]$^+$ 408 | |
| 781 | 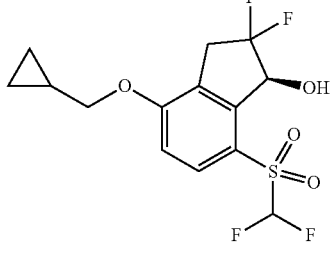 | [M + NH$_4$]$^+$ 372 | |

TABLE 2-continued

| No. | Structure | Mass Characterization | ¹H NMR Data |
|---|---|---|---|
| 782 | 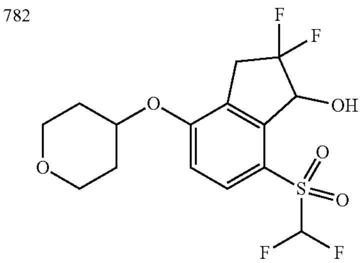 | | (400 MHz, CDCl$_3$): δ 7.89 (d, 1H), 6.98 (d, 1H), 6.55 (t, J = 54Hz, 1H), 5.41 (d, 1H), 4.68 (m, 1H), 3.98-3.88 (m, 2H), 3.66-3.54 (m, 2H), 3.48-3.26 (m, 2H), 1.87-1.74 (m, 2H), 1.62-1.51 (m, 2H) |
| 783 | 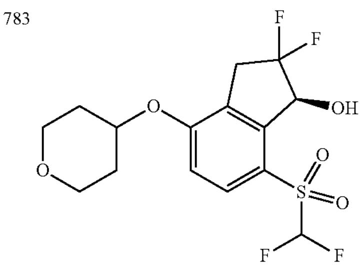 | [M + NH$_4$]$^+$ 402 | |
| 784 | 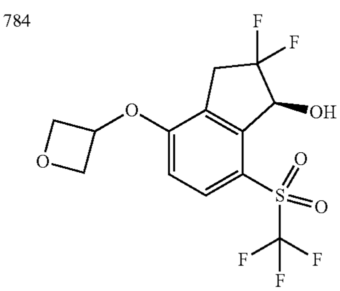 | [M + NH$_4$]$^+$ 392 | |
| 785 | 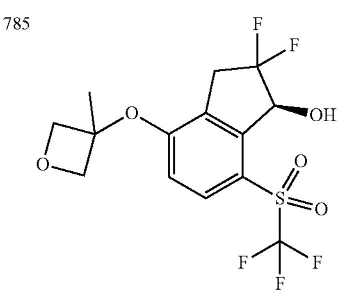 | [M + NH$_4$]$^+$ 406 | |
| 786 | 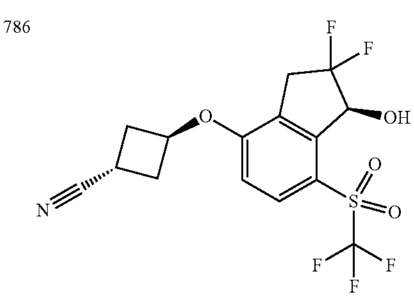 | [M + NH$_4$]$^+$ 415 | |

TABLE 2-continued

| No. | Structure | Mass Characterization | ¹H NMR Data |
|---|---|---|---|
| 787 | 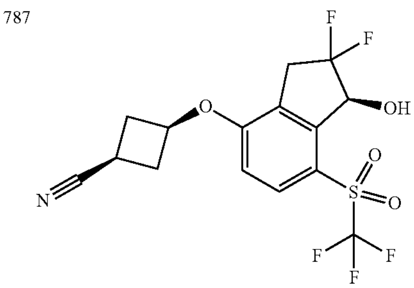 | [M + NH₄]⁺ 415 | |
| 788 | 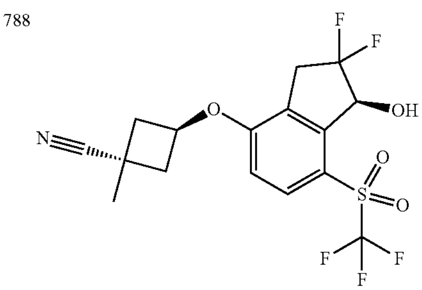 | [M + NH₄]⁺ 429 | |
| 789 | 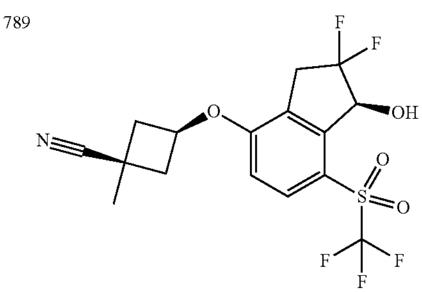 | [M + NH₄]⁺ 429 | |
| 790 | 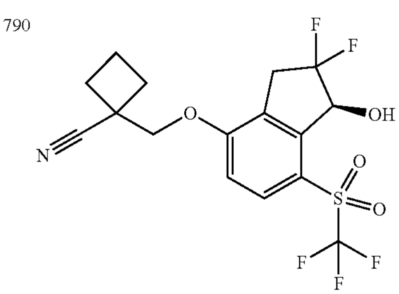 | [M + NH₄]⁺ 429 | |
| 791 | 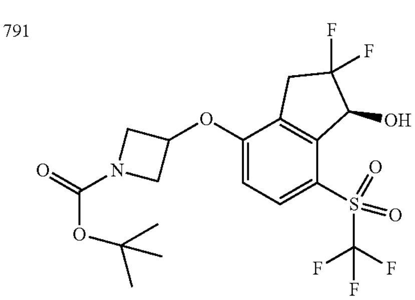 | [M + HCl − H]⁻ 508 | |

TABLE 2-continued

| No. | Structure | Mass Characterization | ¹H NMR Data |
|---|---|---|---|
| 792 | 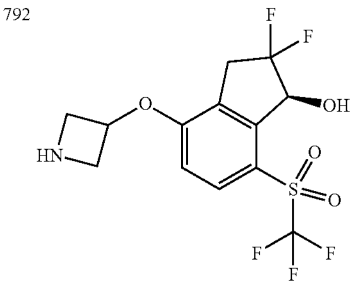 | [M + H]⁺ 374 | |
| 793 | 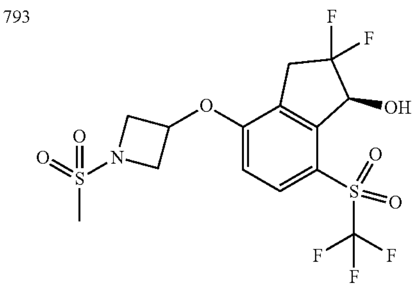 | [M + NH₄]⁺ 469 | |
| 794 | 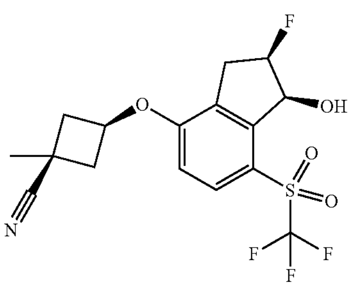 [SMILES: C[C@]1(C#N)C[C@@H](Oc2ccc(S(=O)(=O)C(F)(F)F)c3c2C[C@@H](F)[C@H]3O)C1] | [M + NH₄]⁺ 411 | |
| 795 | 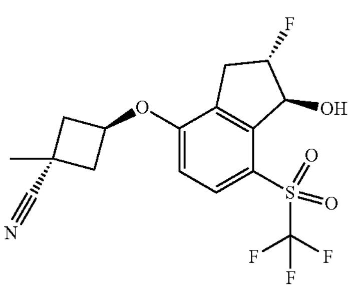 [SMILES: C[C@]1(C#N)C[C@H](Oc2ccc(S(=O)(=O)C(F)(F)F)c3c2C[C@H](F)[C@H]3O)C1] | [M + NH₄]⁺ 411 | |
| 796 | 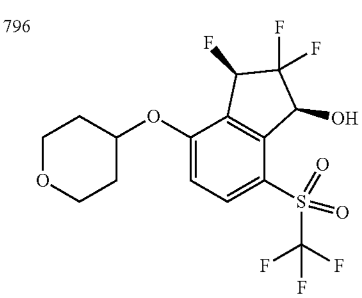 | [M + NH₄]⁺ 384 | |

TABLE 2-continued

| No. | Structure | Mass Characterization | ¹H NMR Data |
|---|---|---|---|
| 797 | 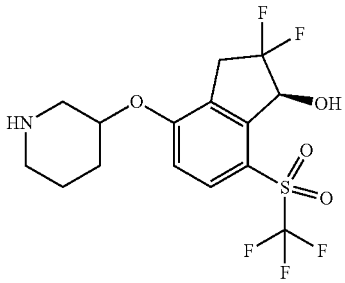 [SMILES: O=S(=O)(c1ccc(OC2CCCNC2)c2c1[C@H](O)C(F)(F)C2)C(F)(F)F] | 402 (M + H) | |
| 798 | 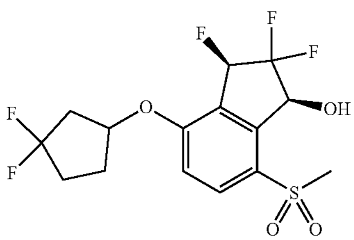 [SMILES: CS(=O)(=O)c1ccc(OC2CCC(F)(F)C2)c2c1[C@H](O)C(F)(F)[C@@H]2F] | [M + NH₄]⁺ 404 | |
| 799 | 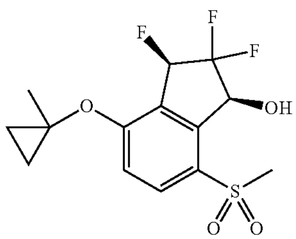 [SMILES: CC1(Oc2ccc(S(C)(=O)=O)c3c2[C@@H](F)C(F)(F)[C@H]3O)CC1] | [M + NH₄]⁺ 354 | |
| 800 | 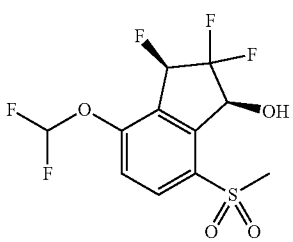 [SMILES: CS(=O)(=O)c1ccc(OC(F)F)c2c1[C@H](O)C(F)(F)[C@@H]2F] | [M + NH₄]⁺ 350 | |
| 801 | 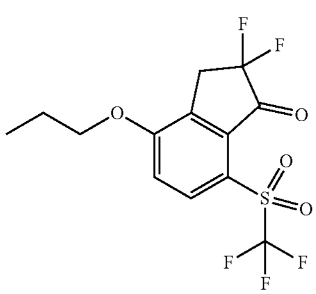 [SMILES: CCCOc1ccc(S(=O)(=O)C(F)(F)F)c2c1CC(F)(F)C2=O] | | (300 MHz, CDCl₃): δ 8.25 (d, 1H), 7.27 (d, 1H), 4.18 (t, 2H), 3.50 (t, 2H), 1.94 (m, 2H), 1.11 (t, 3H) |
| 802 | 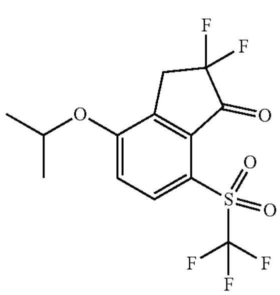 [SMILES: CC(C)Oc1ccc(S(=O)(=O)C(F)(F)F)c2c1CC(F)(F)C2=O] | | (300 MHz, CDCl₃): δ 8.23 (d, 1H), 7.25 (d, 1H), 4.83 (m, 1H), 3.47 (t, 2H), 1.48 (d, 6H) |

TABLE 2-continued

| No. | Structure | Mass Characterization | ¹H NMR Data |
|---|---|---|---|
| 803 | 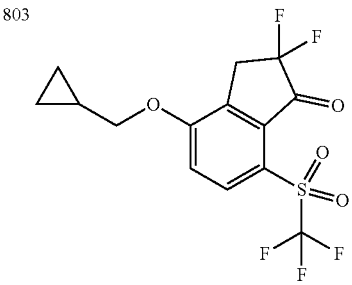 | | |
| 804 | 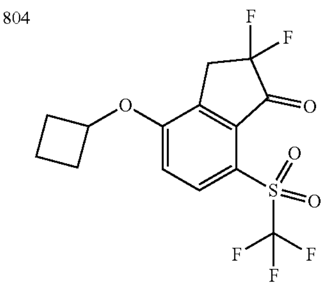 | | |
| 805 | 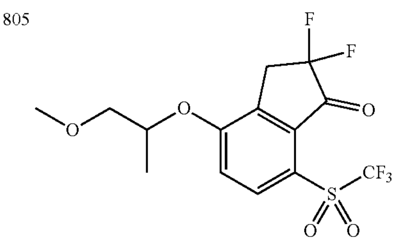 | | (400 MHz, CDCl₃): δ 8.21 (d, 1H), 7.40 (d, 1H), 4.88-4.83 (m, 1H), 3.67-3.39 (m, 7H), 1.43 (d, 3H) |
| 806 | 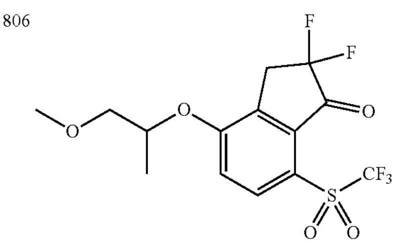 | | (400 MHz, CDCl₃): δ 8.13 (d, 1H), 7.34 (d, 1H), 4.82-4.76 (m, 1H), 3.60-3.31 (m, 7H), 1.36 (d, 3H) |
| 807 | 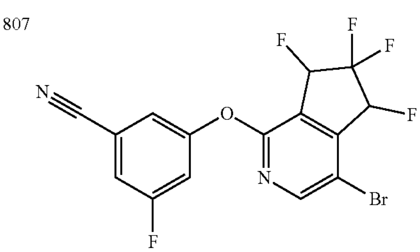 | 405/407 (M + H) | (400 MHz, CDCl₃): δ 8.38 (d, 1H), 7.37-7.36 (m, 1H), 7.30 (ddd, 1H), 7.24 (dt, 1H), 6.09 (dddd, 1H), 6.00 (dddd, 1H) |
| 808 | 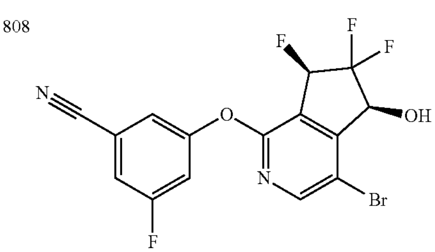 | 403/405 (M + H) | (400 MHz, CDCl₃): δ 8.36 (d, 1H), 7.37-7.35 (m, 1H), 7.29 (ddd, 1H), 7.25 (dt, 1H), 5.86 (dd, 1H), 5.11 (ddd, 1H), 2.73 (d, 1H) |

TABLE 2-continued

| No. | Structure | Mass Characterization | ¹H NMR Data |
|---|---|---|---|
| 809 | 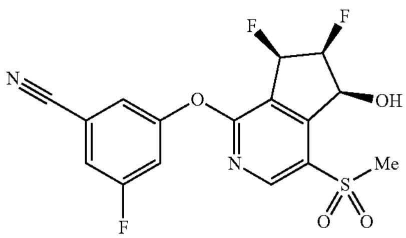 [SMILES: CS(=O)(=O)c1cnc(Oc2cc(F)cc(C#N)c2)c2c1[C@H](O)[C@H](F)[C@@H]2F] | 385 (M + H) | (400 MHz, CDCl₃): δ 8.75 (d, 1H), 7.39-7.37 (m, 1H), 7.34 (ddd, 1H), 7.29-7.25 (m, 1H), 6.25 (ddd, 1H), 5.94-5.87 (m, 1H), 5.44 (ddd, 1H), 3.66-3.58 (m, 1H), 3.29 (s, 3H) |
| 810 | 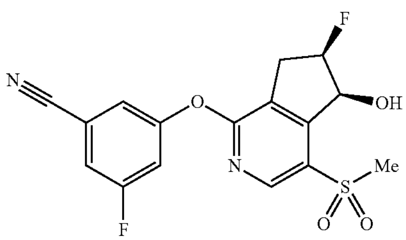 [SMILES: CS(=O)(=O)c1cnc(Oc2cc(F)cc(C#N)c2)c2c1[C@H](O)[C@H](F)C2] | 367 (M + H) | (400 MHz, CDCl₃): δ 8.60-8.59 (m, 1H), 7.35-7.33 (m, 1H), 7.31 (ddd, 1H), 7.24 (dt, 1H), 5.63 (ddd, 1H), 5.51 (dtd, 1H), 3.76 (dd, 1H), 3.47-3.35 (m, 1H), 3.31 (s, 3H), 3.29-3.15 (m, 1H) |
| 811 | 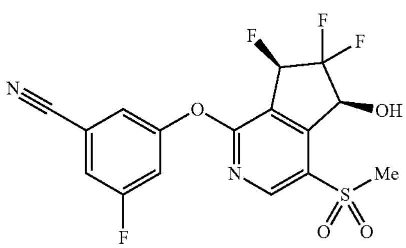 [SMILES: CS(=O)(=O)c1cnc(Oc2cc(F)cc(C#N)c2)c2c1[C@H](O)C(F)(F)[C@@H]2F] | 403 (M + H) | (400 MHz, CDCl₃): δ 8.80 (d, 1H), 7.40-7.38 (m, 1H), 7.36 (ddd, 1H), 7.28 (dt, 1H), 5.88 (dd, 1H), 5.66-5.60 (m, 1H), 3.52 (dd, 1H), 3.28 (s, 3H) |
| 812 | 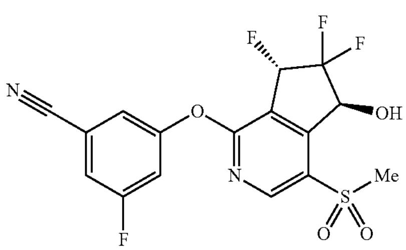 [SMILES: CS(=O)(=O)c1cnc(Oc2cc(F)cc(C#N)c2)c2c1[C@H](O)C(F)(F)[C@H]2F] | 403 (M + H) | (400 MHz, CDCl₃): δ 8.77 (d, 1H), 7.39-7.37 (m, 1H), 7.35 (ddd, 1H), 7.27 (dt, 1H), 6.00 (dd, 1H), 5.83 (tdd, 1H), 3.97 (d, 1H), 3.29 (s, 3H) |
| 813 | 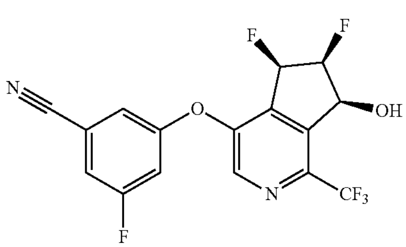 [SMILES: N#Cc1cc(F)cc(Oc2cnc(C(F)(F)F)c3c2[C@@H](F)[C@@H](F)[C@H]3O)c1] | 375 (M + H) | (400 MHz, CDCl₃): δ 8.42 (s, 1H), 7.28 (ddd, 1H), 7.20-7.18 (m, 1H), 7.09 (dt, 1H), 5.92 (dt, 1H), 5.53-5.46 (m, 1H), 5.19 (ddt, 1H), 2.66 (ddd, 1H) |
| 814 | 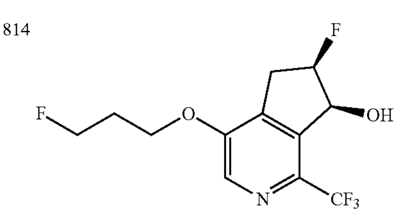 | 298 (M + H) | |

TABLE 2-continued

| No. | Structure | Mass Characterization | ¹H NMR Data |
|---|---|---|---|
| 815 | 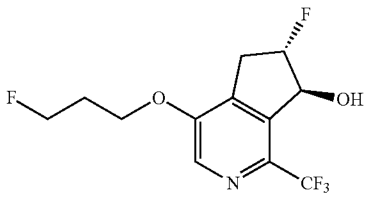 [SMILES: O[C@H]1c2c(C(F)(F)F)ncc(OCCCF)c2C[C@@H]1F] | 298 (M + H) | |
| 816 | 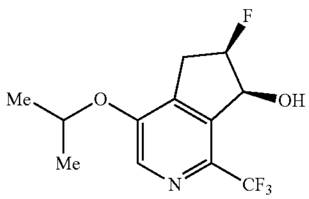 [SMILES: CC(C)Oc1cnc(C(F)(F)F)c2c1C[C@@H](F)[C@H]2O] | 280 (M + H) | |
| 817 | 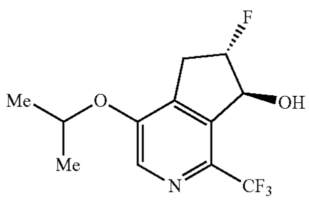 [SMILES: CC(C)Oc1cnc(C(F)(F)F)c2c1C[C@H](F)[C@H]2O] | 280 (M + H) | |
| 818 | 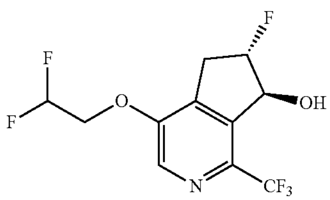 [SMILES: O[C@H]1c2c(C(F)(F)F)ncc(OCC(F)F)c2C[C@@H]1F] | 302 (M + H) | |
| 819 | 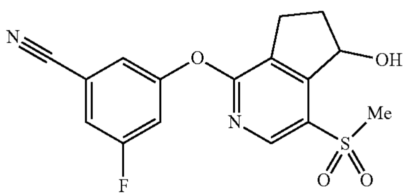 [SMILES: CS(=O)(=O)c1cnc(Oc2cc(F)cc(C#N)c2)c2c1C(O)CC2] | 349 (M + H) | (400 MHz, CDCl₃): δ 8.52-8.51 (m, 1H), 7.33 (ddd, 1H), 7.29 (ddd, 1H), 7.23 (dt, 1H), 5.71-5.66 (m, 1H), 3.64 (d, 1H), 3.26-3.17 (m, 1H), 3.22 (s, 3H), 2.99-2.90 (ddd, 1H), 2.66-2.56 (m, 1H), 2.32-2.22 (m, 1H) |
| 820 | 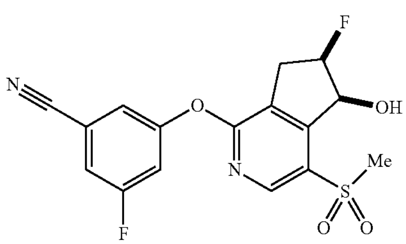 [SMILES: CS(=O)(=O)c1cnc(Oc2cc(F)cc(C#N)c2)c2c1[C@H](O)[C@H](F)C2] | 367 (M + H) | (400 MHz, CDCl₃): δ 8.60-8.59 (m, 1H), 7.35-7.33 (m, 1H), 7.31 (ddd, 1H), 7.24 (dt, 1H), 5.63 (ddd, 1H), 5.52 (dtd, 1H), 3.76 (dd, 1H), 3.47-3.35 (m, 1H), 3.31 (s, 3H), 3.29-3.15 (m, 1H) |
| 821 | 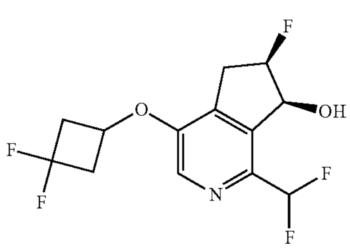 [SMILES: O[C@H]1c2c(C(F)F)ncc(OC3CC(F)(F)C3)c2C[C@H]1F] | 310 (M + H) | |

TABLE 2-continued

| No. | Structure | Mass Characterization | ¹H NMR Data |
|---|---|---|---|
| 822 | 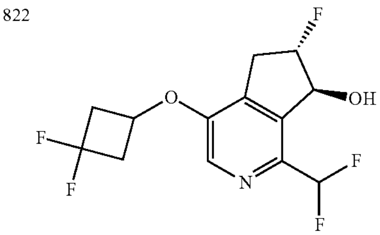 | 310 (M + H) | |
| 823 | 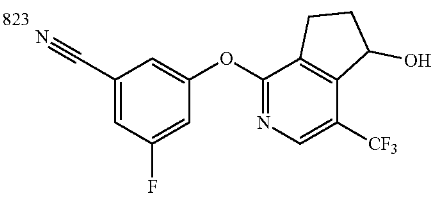 | 339 (M + H) | (400 MHz, CDCl₃): δ 8.29-8.27 (m, 1H), 7.34-7.32 (m, 1H), 7.26 (ddd, 1H), 7.22 (dt, 1H), 5.57-5.10 (m, 1H), 3.22 (dt, 1H), 2.96 (ddd, 1H), 2.56-2.45 (m, 1H), 2.33-2.25 (m, 1H), 2.22-2.18 (m, 1H) |
| 824 | 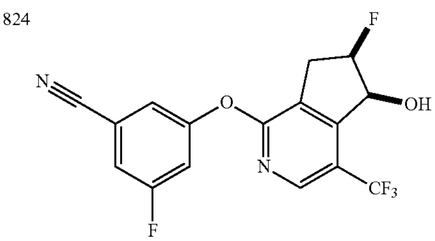 | 357 (M + H) | (400 MHz, CDCl₃): δ 8.36-8.34 (m, 1H), 7.35-7.32 (m, 1H), 7.28 (ddd, 1H), 7.23 (dt, 1H), 5.53-5.35 (m, 2H), 3.40 (ddd, 1H), 3.22 (ddd, 1H), 2.73-2.68 (m, 1H) |
| 825 | 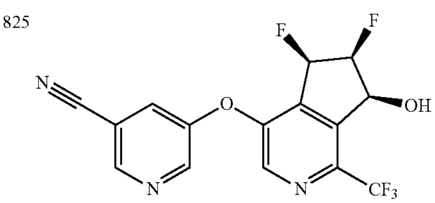 | 358 (M + H) | (400 MHz, CDCl₃): δ 8.79 (dd, 1H), 8.71 (d, 1H), 8.41 (s, 1H), 7.67 (dd, 1H), 5.94 (dt, 1H), 5.53-5.46 (m, 1H), 5.21 (ddt, 1H), 2.73 (ddd, 1H) |
| 826 | 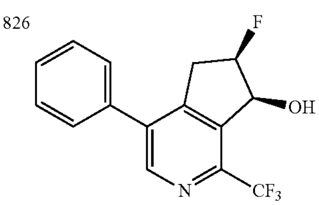 | 298 (M + H) | (400 MHz, CDCl₃): δ 8.68 (s, 1H), 7.55-7.45 (m, 3H), 7.44-7.40 (m, 2H), 5.54-5.46 (m, 1H), 5.31 (ddt, 1H), 3.46 (ddd, 1H), 3.24 (ddd, 1H), 2.61 (dd, 1H) |
| 827 | 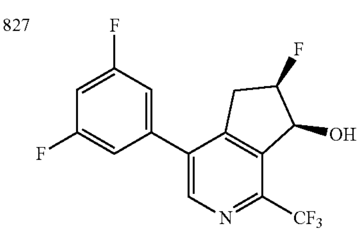 | 334 (M + H) | (400 MHz, CDCl₃): δ 8.65 (s, 1H), 6.99-6.91 (m, 3H), 5.54-5.47 (m, 1H), 5.33 (ddt, 1H), 3.44 (ddd, 1H), 3.23 (ddd, 1H), 2.63 (dd, 1H) |
| 828 | 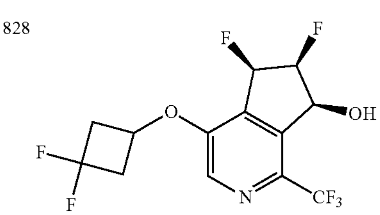 | 346 (M + H) | (400 MHz, CDCl₃): δ 8.24 (s, 1H), 5.95 (ddd, 1H), 5.47-5.41 (m, 1H), 5.07 (ddt, 1H), 4.97-4.88 (m, 1H), 3.30-3.15 (m, 2H), 2.99-2.79 (m, 2H), 2.54-2.49 (m, 1H) |

TABLE 2-continued

| No. | Structure | Mass Characterization | $^1$H NMR Data |
|---|---|---|---|
| 829 | 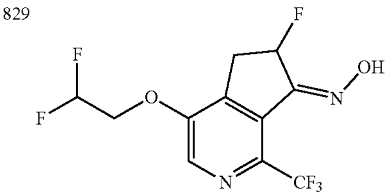 | 315 (M + H) | (400 MHz, DMSO-d$_6$): δ 8.30 (s, 1H), 6.26 (tt, 1H), 6.15 (ddd, 1H), 4.55 (td, 2H), 3.46-3.32 (m, 1H), 3.13 (ddd, 1H) |
| 830 | 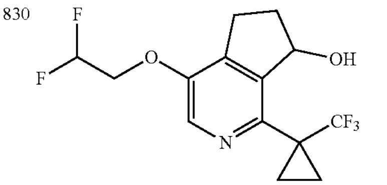 | 324 (M + H) | (400 MHz, CDCl$_3$): δ 8.14 (s, 1H), 6.10 (tt, 1H), 5.58-5.30 (m, 1H), 4.39-4.24 (m, 2H), 3.10 (dt, 1H), 2.87 (ddd, 1H), 2.37-2.27 (m, 1H), 2.20-2.12 (m, 1H), 1.90-1.86 (m, 1H), 1.47-1.39 (m, 2H), 1.27-1.21 (m, 2H) |
| 831 | 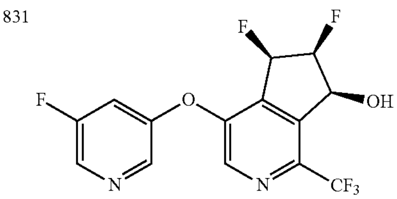 | 351 (M + H) | |
| 832 | 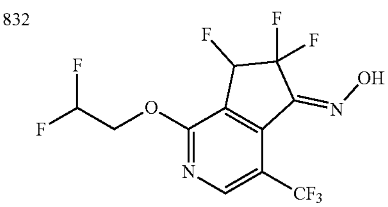 | 351 (M + H) | (400 MHz, CDCl$_3$): δ 8.75 (d, 1H), 8.65-8.62 (m, 1H), 6.17 (tt, 1H), 5.83 (dd, 1H), 4.83-4.64 (m, 2H) |
| 833 | 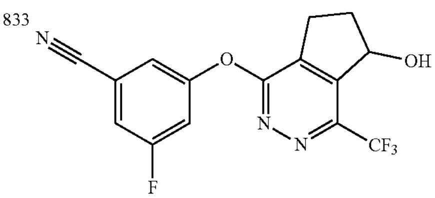 | 340 (M + H) | (400 MHz, CDCl$_3$): δ 7.43-7.41 (m, 1H), 7.33 (dt, 1H), 7.33-7.29 (m, 1H), 5.67-5.62 (m, 1H), 3.36-3.26 (m, 1H), 3.05 (ddd, 1H), 2.63-2.53 (m, 1H), 2.40-2.30 (m, 2H) |

A composition of the present disclosure may be formulated in any suitable pharmaceutical formulation. A pharmaceutical composition of the present disclosure typically contains an active ingredient (e.g., a compound of the present disclosure or a pharmaceutically acceptable salt and/or coordination complex thereof), and one or more pharmaceutically acceptable excipients, carriers, including but not limited to, inert solid diluents and fillers, diluents, sterile aqueous solution and various organic solvents, permeation enhancers, solubilizers and adjuvants. A composition of the present disclosure may be formulated in any suitable pharmaceutical formulation. In some embodiments, the pharmaceutical acceptable carriers, excipients are selected from the group consisting of water, alcohol, glycerol, chitosan, alginate, chondroitin, Vitamin E, mineral oil, and dimethyl sulfoxide (DMSO).

Pharmaceutical formulations may be provided in any suitable form, which may depend on the route of administration. In some embodiments, the pharmaceutical composition disclosed herein can be formulated in dosage form for administration to a subject. In some embodiments, the pharmaceutical composition is formulated for oral, intravenous, intraarterial, aerosol, parenteral, buccal, topical, transdermal, rectal, intramuscular, subcutaneous, intraosseous, intranasal, intrapulmonary, transmucosal, inhalation, and/or intraperitoneal administration. In some embodiments, the dosage form is formulated for oral intervention administration. For example, the pharmaceutical composition can be formulated in the form of a pill, a tablet, a capsule, an inhaler, a liquid suspension, a liquid emulsion, a gel, or a powder. In some embodiments, the pharmaceutical composition can be formulated as a unit dosage in liquid, gel, semi-liquid, semi-solid, or solid form.

In some embodiments, the disclosure provides a pharmaceutical composition comprising an amount of a HIF-2α inhibitor, e.g. Compound 231, formulated for administration to a subject in need thereof. In some embodiments, the pharmaceutical composition comprises between about 0.0001-500 g, 0.001-250 g, 0.01-100 g, 0.1-50 g, or 1-10 g of HIF-2α inhibitor. In some embodiments, the pharmaceutical composition comprises about or more than about 0.0001 g, 0.001 g, 0.01 g, 0.1, 0.5 g, 1 g, 2 g, 3 g, 4 g, 5 g, 6 g, 7 g, 8 g, 9 g, 10 g, 15 g, 20 g, 25 g, 50 g, 100 g, 200 g, 250 g, 300 g, 350 g, 400 g, 450 g, 500 g, or more of a HIF-2α inhibitor. In some embodiments, the pharmaceutical composition comprises between 0.001-2 g of a HIF-2α inhibitor in a single dose. In some embodiments, the pharmaceutical composition comprises an amount between about 50-150 g of a HIF-2α inhibitor.

In some embodiments, a therapeutically effective amount of HIF-2α inhibitor, which can be a daily amount administered over the course of a period of treatment, can sufficiently provide any one or more of the therapeutic effects described herein. As an example, the therapeutic effective amount can be in the range of about 0.001-1000 mg/kg body weight, 0.01-500 mg/kg body weight, 0.01-100 mg/kg body weight, 0.01-30 mg/kg body weight, 0.1-200 mg/kg body weight, 3-200 mg/kg body weight, 5-500 mg/kg body weight, 10-100 mg/kg body weight, 10-1000 mg/kg body weight, 50-200 mg/kg body weight, 100-1000 mg/kg body weight, 200-500 mg/kg body weight, 250-350 mg/kg body weight, or 300-600 mg/kg body weight of a HIF-2α inhibitor. In some embodiments, the therapeutic amount can be about or more than about 0.001 mg/kg body weight, 0.01 mg/kg body weight, 0.1 mg/kg body weight, 0.5 mg/kg body weight, 1 mg/kg body weight, 2 mg/kg body weight, 3 mg/kg body weight, 4 mg/kg body weight, 5 mg/kg body weight, 6 mg/kg body weight, 7 mg/kg body weight, 8 mg/kg body weight, 9 mg/kg body weight, 10 mg/kg body weight, 15 mg/kg body weight, 20 mg/kg body weight, 25 mg/kg body weight, 50 mg/kg body weight, 100 mg/kg body weight, 200 mg/kg body weight, 250 mg/kg body weight, 300 mg/kg body weight, 350 mg/kg body weight, 400 mg/kg body weight, 450 mg/kg body weight, 500 mg/kg body weight, 600 mg/kg body weight, 800 mg/kg body weight, 1000 mg/kg body weight, or more of a HIF-2α inhibitor. In some embodiments, the effective amount is at least about 0.01 mg/kg body weight of a HIF-2α inhibitor. In some embodiments, the effective amount is an amount between about 0.01-30 mg/kg body weight of a HIF-2α inhibitor. In some embodiments, the therapeutic amount can be an amount between about 50-150 mg/kg body weight of a HIF-2α inhibitor.

In some embodiments, the composition is provided in one or more unit doses. For example, the composition can be administered in 1, 2, 3, 4, 5, 6, 7, 14, 30, 60, or more doses. Such amount can be administered each day, for example in individual doses administered once, twice, or three or more times a day. However, dosages stated herein on a per day basis should not be construed to require administration of the daily dose each and every day. For example, if the HIF-2α inhibitor is provided in a suitably slow-release form, two or more daily dosage amounts can be administered at a lower frequency, e.g., as a depot every second day to once a month or even longer. Most typically and conveniently for the subject, HIF-2α inhibitor can be administered once a day, for example in the morning, in the evening or during the day.

The unit doses can be administered simultaneously or sequentially. The composition can be administered for an extended treatment period. Illustratively, the treatment period can be at least about one month, for example at least about 3 months, at least about 6 months or at least about 1 year. In some cases, administration can continue for substantially the remainder of the life of the subject.

In some embodiments, the HIF-2α inhibitor is administered as part of a therapeutic regimen that comprises administering one or more second agents (e.g. 1, 2, 3, 4, 5, or more second agents), either simultaneously or sequentially with the HIF-2α inhibitor. When administered sequentially, the HIF-2α inhibitor may be administered before or after the one or more second agents. When administered simultaneously, the HIF-2α inhibitor and the one or more second agents may be administered by the same route (e.g. injections to the same location; tablets taken orally at the same time), by a different route (e.g. a tablet taken orally while receiving an intravenous infusion), or as part of the same combination (e.g. a solution comprising the HIF-2α inhibitor and the one or more second agents).

A variety of second agents and therapies suitable for combination therapy for the treatment of PAH are available, and may be combined with one or more HIF-2α inhibitors. Examples of second agents include, but are not limited to, mitotic kinesis inhibitors, JAK2 inhibitors, prostanoids, endothelin receptor antagonists, phosphodiesterase inhibitors, prostacyclin receptor agonists (e.g., selexipag), anticoagulants, diuretics, calcium channel blockers, digoxin, oxygen therapy, nitric oxide therapy, tyrosine kinases, statins, 5-hydroxytryptamine (5-HT) receptor antagonists, phosphatidylinositol 3-kinase inhibitors, soluble guanylate cyclase activators, adrenomedullin, platelet-derived growth factor (PDGF) inhibitors, Rho-kinase inhibitors, and mTOR inhibitors, treprostinil, bosentan, iloprost, ambrisentan, sildenafil, and tadalafil.

As an example, mitotic kinesin inhibitors are compounds that act to inhibit the activity of one or more mitotic kinesins. In general, inhibition refers to a decrease in mitotic kinesin activity as a direct or indirect response to the presence of a chemical entity (e.g., a mitotic kinesin inhibitor), relative to the activity of the mitotic kinesin in the absence of the chemical entity. In some embodiments, the decrease in activity is due to the direct interaction of the chemical entity with mitotic kinesin. In other embodiments, the decrease in activity is due to the interaction of the chemical entity with one or more other factors that affect mitotic kinesin activity. For example, the presence of the chemical entity may decrease mitotic kinesin activity by directly binding to the mitotic kinesin, by causing (directly or indirectly) another factor to decrease mitotic kinesin activity, or by (directly or indirectly) decreasing the amount of mitotic kinesin present in the cell or organism. As an example, mitotic kinesin inhibitors may act by increasing or decreasing spindle pole separation, causing malformation (e.g., splaying) of mitotic spindle poles, or otherwise causing morphological perturbation of the mitotic spindle or by interfering with the normal function of the mitotic spindle (e.g. misalignment and inappropriate segregation of chromosomes). Meiotic spindles may also be disrupted. Mitotic kinesin inhibitors may be reversible or irreversible, may bind to the kinesin's active site or an allosteric site, and may act as competitive, uncompetitive or non-competitive inhibitors. In all instances, mitotic kinesin inhibitors halt or slow the normal process of cell division and proliferation.

Non-limiting examples of JAK2 inhibitors include Pacritinib, CEP-33779, SB1578, TG101348, TG101209, AZD1480, AZ960, LY2784544, BMS911543, SGI-1252, MK0457, XL019, NVP-BSK805, Ruxolitinib, Baricitinib and CYT387. Further examples are described in WO2014161046A1 and U.S. Pat. No. 8,410,173.

A second agent can be a prostanoid. Examples of prostanoids include, but are not limited to, prostacyclin (epoprostenol, epoprostenol sodium) and prostacyclin analogs such as treprostinil sodium, iloprost, cisaprost, beraprost, and ciprostene sodium.

In some embodiments, a second agent is an endothelin receptor antagonist. The endothelin receptor antagonist can be an agent that selectively or preferentially inhibits type A endothelin receptor ($ET_A$). In some embodiments, the endothelin receptor antagonist is an agent that selectively or preferentially inhibits type B endothelin receptor ($ET_B$). In some embodiments, the endothelin receptor antagonist is an agent that inhibits both $ET_A$ and $ET_B$. In some embodiments, pulmonary arterial hypertension is treated in a subject by administering to the subject a therapeutically effective amount of a mitotic kinesin inhibitor, an agent that selectively or preferentially inhibits $ET_A$, and an agent that selectively or preferentially inhibits $ET_B$. Examples of endothelin receptor antagonists include bosentan, tazosentan, BQ123, ambrisentan, atrasentan, sitaxsentan, BQ788 and macitentan.

Another example of a second agent is a phosphodiesterase (PDE) inhibitor. PDE inhibitors include selective and non-selective inhibitors of any of the PDE isoforms, including, for example, PDE1 and PDE5 inhibitors. Examples of PDE inhibitors include sildenafil, tadalafil, vardenafil, udenafil avanafil, dipyridamole, and vinpocetine.

Another example of a second agent is an anticoagulant. Anticoagulants can include, for example, coumarins (e.g., warfarin, acenocoumarol, phenprocoumon, phenindione), heparin, low molecular weight heparin, and direct thrombin inhibitors (e.g., argatroban, lepirudin, bivalirudin, dabigatran).

Another example of a second agent is a diuretic. Examples of diuretics include thiazide-like diuretics (e.g., chlorothiazide, chlorthalidone, hydrochlorothiazide, indapamide, metolazone), loop diuretics (e.g., bumetanide, furosemide, torsemide) and potassium-sparing diuretics (e.g., amiloride hydrochloride, spironolactone, triamterene).

Another example of a second agent is calcium channel blocker. Examples of calcium channel blockers include amlodipine, diltiazem, felodipine, isradipine, nicardipine, nifedipine, nisoldipine and verapamil.

Another example of a second agent is a tyrosine kinase. Tyrosine kinases include, for example, axitinib, bosutinib, cediranib, crizotinib, dasatinib, erlotinib, gefitinib, imatinib, lapatinib, lestaurtinib, neratinib, nilotinib, semaxanib, sorafenib, sunitinib, toceranib, vandetanib, and vatalanib.

In some embodiments, the second agent is a statin. Examples of statins include atorvastatin, cerivastatin, fluvastatin, lovastatin, mevastatin, pitavastatin, pravastatin, rosuvastatin, simvastatin, simvastatin/ezetimibe, lovastatin/niacin, atorvastatin/amlodipine and simvastatin/niacin.

In some embodiments, a second agent is a 5-HT receptor antagonist. 5-HT receptor antagonists include selective and non-selective antagonists of any of the 5-HT receptor isoforms, including, for example, $5\text{-}HT_{1B}$, $5\text{-}HT_{2A}$ and/or $5\text{-}HT_{2C}$ receptor antagonists. Examples of 5-HT receptor antagonists include citalopram, clozapine, fluoxetine, ketanserin and paroxetine.

Another example of a second agent is a PDGF inhibitor. Examples of PDGF inhibitors can include imatinib, sorafenib, sunitinib, lefluonamide, midostaurin, semaxanib and vatalanib.

The second agent can be a phosphatidylinositol 3-kinase inhibitor. Examples of potential PI3 kinase inhibitor can include the class I PI 3-kinase, p110δ isoform specific inhibitors, IC486068 and IC87114, ICOS Corporation and GDC-0941.

In some embodiments, a second agent can be a soluble guanylate cyclase inhibitor. An example of a soluble guanylate cyclase activator is riociguat.

In some embodiments, a second agent can be a Rho-kinase inhibitor. An example of a Rho-kinase inhibitor is fasudil (fasudil hydrochloride).

In some embodiments, a second agent can be an mTOR inhibitor. Examples of mTOR inhibitors include rapamycin, temsirolimus and resveratrol.

When the method involves combination therapy, for example, wherein a secondary agent such as a vasodilator is co-administered with a HIF-2α inhibitor, the agents may be administered separately, at the same, or at different times of the day, or they may be administered in a single composition. In the combination therapies of the invention, each agent can be administered in an "immediate release" manner or in a "controlled release manner." When the additional active agent is a vasodilator, for instance, any dosage form containing both active agents, such as both the HIF-2α inhibitor and the vasodilator, can provide for immediate release or controlled release of the vasodilator, and either immediate release or controlled release of the HIF-2α inhibitor.

As a general example, a combination dosage form for once-daily administration might contain in the range of about 0.001 mg/kg body weight to about 350 mg/kg body weight of a HIF-2α inhibitor, such as about 0.01 mg/kg body weight to about 50 mg/kg body weight of a HIF-2α inhibitor, or about 0.05 mg/kg body weight to about 15 mg/kg body weight of a HIF-2α inhibitor, or about 0.01 mg/kg body weight to about 30 mg/kg body weight in a controlled release (e.g., sustained release) or immediate release form, and either sildenafil in immediate release form, or in controlled release form, with the additional active agent present in an amount that provides a weight ratio of the HIF-2α inhibitor to sildenafil, or a weight ratio of the HIF-2α inhibitor to sildenafil, specified as above. In other formulations of the invention, two or more additional active agents, which may or may not be in the same class of drug (e.g., vasodilators), can be present in combination, along with the leukotriene inhibitor. In such a case, the effective amount of either or each individual additional active agent present will generally be reduced relative to the amount that would be required if only a single added agent were used.

Pharmaceutical Composition for Oral Administration

In some embodiments, the disclosure provides a pharmaceutical composition for oral administration containing a compound of the present disclosure, and a pharmaceutical excipient suitable for oral administration. The composition may be in the form of a solid, liquid, gel, semi-liquid, or semi-solid. In some embodiments, the composition further comprises a second agent.

Pharmaceutical composition of the disclosure suitable for oral administration can be presented as discrete dosage forms, such as hard or soft capsules, cachets, troches, lozenges, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion, or dispersible powders or granules, or syrups or elixirs. Such dosage forms can be prepared by any of the methods of pharmacy, which typically include the step of bringing the active ingredient into association with the carrier. In general, the composition are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This disclosure further encompasses anhydrous pharmaceutical composition and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical composition and dosage forms of the disclosure can be prepared using anhydrous or low moisture containing ingredients and low moisture or low humidity conditions. Pharmaceutical composition and dosage forms of the disclosure which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous composition may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the composition for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical composition and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical composition and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the composition of the disclosure to provide tablets that disintegrate when exposed to an aqueous environment. Too much of a disintegrant may produce tablets which may disintegrate in the bottle. Too little may be insufficient for disintegration to occur and may alter the rate and extent of release of the active ingredient(s) from the dosage form. A sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical composition and dosage forms of the disclosure include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical composition and dosage forms of the disclosure include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical composition and dosage forms of the disclosure include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phytosterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present disclosure and to minimize precipitation of the compound of the present disclosure. This can be especially important for composition for non-oral use, e.g., composition for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. If present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Composition for Topical (e.g., Transdermal) Delivery.

In some embodiments, the disclosure provides a pharmaceutical composition for transdermal delivery containing a compound of the present disclosure and a pharmaceutical excipient suitable for transdermal delivery. The composition may be in the form of a solid, liquid, gel, semi-liquid, or semi-solid. In some embodiments, the composition further comprises a second agent.

Composition of the present disclosure can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical composition also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Formulations for topical administration may include ointments, lotions, creams, gels (e.g., poloxamer gel), drops, suppositories, sprays, liquids and powders. Conventional pharmaceutical carriers, aqueous, powder or oily bases, thickeners and the like may be necessary or desirable. The disclosed compositions can be administered, for example, in a microfiber, polymer (e.g., collagen), nanosphere, aerosol, lotion, cream, fabric, plastic, tissue engineered scaffold, matrix material, tablet, implanted container, powder, oil, resin, wound dressing, bead, microbead, slow release bead, capsule, injectables, intravenous drips, pump device, silicone implants, or any bio-engineered materials.

Another exemplary formulation for use in the methods of the present disclosure employs transdermal delivery devices ("patches"). Such transdermal patches may be used to provide continuous or discontinuous infusion of a compound of the present disclosure in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical Composition for Injection.

In some embodiments, the disclosure provides a pharmaceutical composition for injection containing a compound of the present disclosure and a pharmaceutical excipient suitable for injection. Components and amounts of agents in the composition are as described herein.

The forms in which the novel composition of the present disclosure may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Composition for Inhalation.

Compositions for inhalation or insufflation include solutions and suspensions in pharmaceutically acceptable, aqueous or organic solvents, or mixtures thereof, and powders. The liquid or solid composition may contain suitable pharmaceutically acceptable excipients as described vide supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder composition may be administered, preferably orally or nasally, from devices that deliver the formulation in an appropriate manner.

Other Pharmaceutical Composition.

Pharmaceutical compositions may also be prepared from a composition described herein and one or more pharmaceutically acceptable excipients suitable for sublingual, buccal, rectal, intraosseous, intraocular, intranasal, epidural, or intraspinal administration. Preparations for such pharmaceutical composition are well-known in the art. See, e.g., See, e.g., Anderson, Philip O.; Knoben, James E.; Troutman, William G, eds., Handbook of Clinical Drug Data, Tenth Edition, McGraw-Hill, 2002; Pratt and Taylor, eds., *Principles of Drug Action*, Third Edition, Churchill Livingston, N.Y., 1990; Katzung, ed., *Basic and Clinical Pharmacology*, Ninth Edition, McGraw Hill, 20037ybg; Goodman and Gilman, eds., *The Pharmacological Basis of Therapeutics*, Tenth Edition, McGraw Hill, 2001; *Remingtons Pharmaceutical Sciences,* 20th Ed., Lippincott Williams & Wilkins., 2000; Martindale, *The Extra Pharmacopoeia*, Thirty-Second Edition (The Pharmaceutical Press, London, 1999); all of which are incorporated by reference herein in their entirety.

In some embodiments, the compositions and methods further comprises administering, separately or simultaneously one or more additional agents (e.g. 1, 2, 3, 4, 5, or more). Additional agents can included those useful in wound healing. Non-limiting examples of additional agents include antibiotics (e.g. Aminoglycosides, Cephalosporins, Chloramphenicol, Clindamycin, Erythromycins, Fluoroquinolones, Macrolides, Azolides, Metronidazole, Penicillin's, Tetracycline's, Trimethoprim-sulfamethoxazole, Vancomycin), steroids (e.g. Andranes (e.g. Testosterone), Cholestanes (e.g. Cholesterol), Cholic acids (e.g. Cholic acid), Corticosteroids (e.g. Dexamethasone), Estraenes (e.g. Estradiol), Pregnanes (e.g. Progesterone), narcotic and non-narcotic analgesics (e.g. Morphine, Codeine, Heroin, Hydromorphone, Levorphanol, Meperidine, Methadone, Oxydone, Propoxyphene, Fentanyl, Methadone, Naloxone, Buprenorphine, Butorphanol, Nalbuphine, Pentazocine), chemotherapy (e.g. anti-cancer drugs such as but not limited to Altretamine, Asparaginase, Bleomycin, Busulfan, Carboplatin, Carmustine, Chlorambucil, Cisplatin, Cladribine, Cyclophosphamide, Cytarabine, Dacarbazine, Diethylstilbesterol, Ethinyl estradiol, Etoposide, Floxuridine, Fludarabine, Fluorouracil, Flutamide, Goserelin, Hydroxyurea, Idarubicin, Ifosfamide, Leuprolide, Levamisole, Lomustine, Mechlorethamine, Medroxyprogesterone, Megestrol, Melphalan, Mercaptopurine, Methotrexate, Mitomycin, Mitotane, Mitoxantrone, Paclitaxel, pentastatin, Pipobroman, Plicamycin, Prednisone, Procarbazine, Streptozocin, Tamoxifen, Teniposide, Vinblastine, Vincristine), anti-inflammatory agents (e.g. Alclofenac; Alclometasone Dipropionate; Algestone Acetonide; alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Decanoate; Deflazacort; Delatestryl; Depo-Testosterone; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Loteprednol Etabonate; Meclofenamate Sodium; Meclofenamic Acid; Meclorisone Dibutyrate; Mefenamic Acid; Mesalamine; Meseclazone; Mesterolone; Methandrostenolone; Methenolone; Methenolone Acetate; Methylprednisolone Suleptanate; Morniflumate; Nabumetone; Nandrolone; Naproxen; Naproxen Sodium; Naproxol; Nimazone; Olsalazine Sodium; Orgotein; Orpanoxin; Oxandrolane; Oxaprozin; Oxyphenbutazone; Oxymetholone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Stanozolol; Sudoxicam; Sulindac; Suprofen; Talmetacin; Talniflumate; Talosalate; Tebufelone; Tenidap; Tenidap Sodium; Tenoxicam; Tesicam; Tesimide; Testosterone; Testosterone Blends; Tetrydamine; Tiopinac; Tixocortol Pivalate; Tolmetin; Tolmetin Sodium; Triclonide; Triflumidate; Zidometacin; Zomepirac Sodium), or anti-histaminic agents (e.g. Ethanolamines (like diphenhydrmine carbinoxamine), Ethylenediamine (like tripelennamine pyrilamine), Alkylamine (like chlorpheniramine, dexchlorpheniramine, brompheniramine, triprolidine), other anti-histamines like astemizole, loratadine, fexofenadine, Bropheniramine, Clemastine, Acetaminophen, Pseudoephedrine, Triprolidine).

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Synthesis of 3-[(1S)-7-(difluoromethylsulfonyl)-2,2-difluoro-1-hydroxy-indan-4-yl]oxy-5-fluoro-benzonitrile (Compound 15)

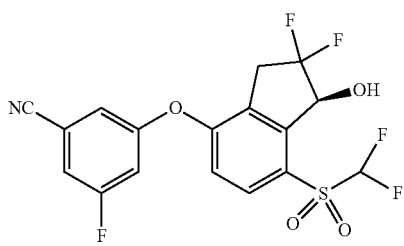 [SMILES: N#Cc1cc(F)cc(Oc2ccc(S(=O)(=O)C(F)F)c3c2CC(F)(F)[C@H]3O)c1]

Step A: Preparation of 3-((7-((difluoromethyl)sulfonyl)-2,3-dihydrospiro[indene-1,2'-[1,3]dioxolan]-4-yl)oxy)-5-fluorobenzonitrile: A mixture of 3-fluoro-5-hydroxy-benzonitrile (1.33 g, 9.7 mmol), 7'-(difluoromethylsulfonyl)-4'-fluoro-spiro[1,3-dioxolane-2,1'-indane] (1.0 g, 3.24 mmol), and cesium bicarbonate (1.26 g, 6.5 mmol) in 1-methyl-2-pyrrolidone (1.8 mL) was heated under $N_2$ at 110° C. (microwave) for 1 hour and 5 minutes. The reaction was repeated ten times. The reaction mixtures were combined, diluted with EtOAc, and washed twice with 1 N NaOH. The combined aqueous layer was extracted with EtOAc. The EtOAc extracts were combined and washed with brine, dried over $Na_2SO_4$, filtered, and concentrated to about 100 mL to give a suspension. The suspension was filtered to give 3-((7-((difluoromethyl)sulfonyl)-2,3-dihydrospiro[indene-1,2'-[1,3]dioxolan]-4-yl)oxy)-5-fluorobenzonitrile as an off-white solid (6.25 g). The filtrate was diluted with EtOAc, washed with brine (3×), dried over $Na_2SO_4$, filtered, and concentrated. The residue was purified by flash column chromatography on silica gel with EtOAc/hexane (0% to 40%) to give additional 3-((7-((difluoromethyl)sulfonyl)-2,2-difluoro-2,3-dihydrospiro[indene-1,2'-[1,3]dioxolan]-4-yl)oxy)-5-fluorobenzonitrile (3.3 g, 69% combined yield) as a white solid. LCMS ESI (+) m/z 426 (M+H).

Step B: Preparation of 3-((7-((difluoromethyl)sulfonyl)-1-oxo-2,3-dihydro-1H-inden-4-yl)oxy)-5-fluorobenzonitrile: A mixture of 3-((7-((difluoromethyl)sulfonyl)-2,3-dihydrospiro[indene-1,2'-[1,3]dioxolan]-4-yl)oxy)-5-fluorobenzonitrile (10.9 g, 25.6 mmol) and PPTS (667 mg, 2.66 mmol) in acetone (100 mL)/water (15 mL) was heated at 82° C. for 5 hours and then 75° C. overnight. The reaction mixture was cooled to room temperature, concentrated under reduced pressure, diluted with EtOAc, washed with saturated aqueous $NaHCO_3$, dried over $MgSO_4$, filtered, and concentrated. The residue was filtered and washed with water. The solid obtained was briefly dried under vacuum at 50° C. and then triturated with EtOAc/hexane to give 3-((7-((difluoromethyl)sulfonyl)-1-oxo-2,3-dihydro-1H-inden-4-yl)oxy)-5-fluorobenzonitrile (8 g). Flash column chromatography of the mother liquor on silica gel with EtOAc/hexane (0% to 80%) provided additional 3-((7-((difluoromethyl)sulfonyl)-1-oxo-2,3-dihydro-1H-inden-4-yl)oxy)-5-fluorobenzonitrile (1.3 g, combined 9.3 g, quant. yield). LCMS ESI (+) m/z 382 (M+H).

Step C: Preparation of (E, Z)-3-((1-(butylimino)-7-((difluoromethyl)sulfonyl)-2,3-dihydro-1H-inden-4-yl)oxy)-5-fluorobenzonitrile: A mixture of 3-((7-((difluoromethyl)sulfonyl)-1-oxo-2,3-dihydro-1H-inden-4-yl)oxy)-5-fluorobenzonitrile (1.42 g, 3.72 mmol), butylamine (6.0 mL) and 5 drops of trifluoroacetic acid (~0.1 mL) in benzene (40 mL) was refluxed overnight with removal of water using a Dean-Stark trap. The reaction mixture was concentrated under reduced pressure, diluted with methyl tert-butyl ether, washed with saturated aqueous $NaHCO_3$ and brine, dried over $Na_2SO_4$, filtered, and concentrated. The residue was used in the next step without further purification.

Step D: Preparation of 3-((7-((difluoromethyl)sulfonyl)-2,2-difluoro-1-oxo-2,3-dihydro-1H-inden-4-yl)oxy)-5-fluorobenzonitrile: A mixture of (E, Z)-3-((1-(butylimino)-7-((difluoromethyl)sulfonyl)-2,3-dihydro-1H-inden-4-yl)oxy)-5-fluorobenzonitrile (1.29 g, 3 mmol, crude from step C), Selectfluor® (2.62 g, 7.4 mmol) and sodium sulfate (4 g, 28.2 mmol) under $N_2$ was heated at 82° C. for 4 hours. After cooling to room temperature, concentrated HCl (37%, 3 mL) was added. The mixture was stirred at room temperature for 15 minutes and then concentrated under reduced pressure. The residue was diluted with methyl t-butyl ether, washed with half saturated aqueous NaHCO₃ and then brine, dried over Na₂SO₄, filtered, and triturated with EtOAc/hexane to give 3-((7-((difluoromethyl)sulfonyl)-2,2-difluoro-1-oxo-2,3-dihydro-1H-inden-4-yl)oxy)-5-fluorobenzonitrile as an off-white solid (0.5 g). The mother liquor was purified by flash column chromatography with EtOAc/hexane (5% to 40%) to give additional 3-((7-((difluoromethyl)sulfonyl)-2,2-difluoro-1-oxo-2,3-dihydro-1H-inden-4-yl)oxy)-5-fluorobenzonitrile (0.13 g, 51% combined yield). LCMS ESI (+) m/z 418 (M+H) and 435 (M+NH₄).

Step E: Preparation of (S)-3-((7-((difluoromethyl)sulfonyl)-2,2-difluoro-1-hydroxy-2,3-dihydro-1H-inden-4-yl)oxy)-5-fluorobenzonitrile (Compound 15): An ice cold solution of RuCl(p-cymene)[(R,R)-Ts-DPEN] (0.6 mg) in dichloromethane (0.2 mL) was added by syringe under nitrogen to an ice cold solution of 3-[7-(difluoromethylsulfonyl)-2,2-difluoro-1-oxo-indan-4-yl]oxy-5-fluoro-benzonitrile (28 mg, 0.07 mmol), triethylamine (18.7 µL, 0.13 mmol) and formic acid (7.6 µL, 0.2 mmol) in dichloromethane (0.5 mL) and then placed in a refrigerator at 4° C. overnight. The reaction mixture was directly purified on preparative TLC with EtOAc/hexane (40%) to give Compound 15 (23.4 mg, 0.06 mmol, 83% yield). The ee was determined to be greater than 95% by ¹⁹F NMR analysis of the corresponding Mosher ester. LCMS ESI (+) m/z 420 (M+H); NMR (400 MHz, CDCl₃): δ 7.94 (d, 1H), 7.33-6.98 (m, 4H), 6.44 (t, 1H), 5.51 (d, 1H), 3.61-3.45 (m, 2H).

Example 2: Synthesis of (S)-3-((2,2-Difluoro-1-hydroxy-7-(methylsulfonyl)-2,3-dihydro-1H-inden-4-yl)oxy)-5-fluorobenzonitrile (Compound 163)

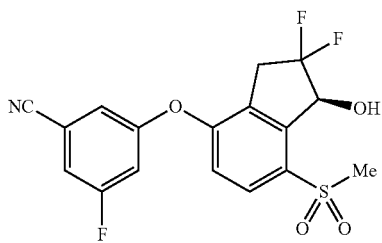 [SMILES: CS(=O)(=O)c1ccc(Oc2cc(F)cc(C#N)c2)c2c1[C@H](O)C(F)(F)C2]

Step A: Preparation of 4'-(3-bromo-5-fluoro-phenoxy)-7'-methylsulfonyl-spiro[1,3-dioxolane-2,1'-indane]: Cesium hydrogen carbonate (142 mg, 0.73 mmol) was added all at once to 4'-fluoro-7'-methylsulfonyl-spiro[1,3-dioxolane-2,1'-indane] (100 mg, 0.37 mmol) and 3-bromo-5-fluoro-phenol (105 mg, 0.55 mmol) in 1-methyl-2-pyrrolidone (1.5 mL) at room temperature in a microwave reaction vial equipped with a stir bar. The flask was flushed with nitrogen then sealed with a crimp cap. The reaction was heated to 150° C. for 7 hours, cooled to ambient temperature then purified directly on reverse phase silica gel (25+M, 14 CV, 20-100% MeCN/water) affording 4'-(3-bromo-5-fluoro-phenoxy)-7'-methylsulfonyl-spiro[1,3-dioxolane-2,1'-indane] (118 mg, 0.26 mmol, 72% yield).

Step B: Preparation of 3-fluoro-5-(7'-methylsulfonylspiro[1,3-dioxolane-2,1'-indane]-4'-yl)oxy-benzonitrile: Dichloro[1;1'-bis(diphenylphosphino)ferrocene]palladium (II) dichloromethane adduct (784 mg, 0.97 mmol) was quickly added to a degassed mixture of 4'-(3-bromo-5-fluoro-phenoxy)-7'-methylsulfonyl-spiro[1,3-dioxolane-2,1'-indane] (4.3 g, 9.7 mmol), zinc cyanide (1.14 g, 9.7 mmol) and zinc powder (761 mg, 11.6 mmol) in DMF (60 mL) under nitrogen. The reaction mixture was then warmed to 110° C. for 2 hours. After cooling, the mixture was filtered through a pad of celite. The filtrate was diluted with water (100 mL), extracted with MTBE (5×100 mL), washed with brine (100 mL), dried over MgSO₄, filtered and concentrated in vacuo. The crude product was purified on silica gel (100 g SNAP, 14 CV, 15-100% EtOAc/hexanes) then purified again on silica gel (25 g Ultra SNAP, 14 CV, 0-20% dichloromethane/EtOAc) affording 3-fluoro-5-(7'-methylsulfonylspiro[1,3-dioxolane-2,1'-indane]-4'-yl)oxy-benzonitrile (3.77 g, 9.7 mmol, 100% yield).

Step C: Preparation of 3-fluoro-5-(7-methylsulfonyl-1-oxo-indan-4-yl)oxy-benzonitrile: Pyridinium para-toluenesulfonate (354 mg, 1.4 mmol) was added all at once to a solution of 3-fluoro-5-(7'-methylsulfonylspiro[1,3-dioxolane-2,1'-indane]-4'-yl)oxy-benzonitrile (550 mg, 1.4 mmol) in acetone (6 mL)/water (2 mL) at room temperature and then warmed to reflux until completion. The mixture was concentrated in vacuo then purified on silica gel (10 g SNAP, 14 CV, 20-100% EtOAc/hexane) affording 3-fluoro-5-(7-methylsulfonyl-1-oxo-indan-4-yl)oxy-benzonitrile (450 mg, 1.3 mmol, 92% yield).

Step D: Preparation of 3-[(E,Z)-1-butylimino-7-methylsulfonyl-indan-4-yl]oxy-5-fluoro-benzonitrile: Butan-1-amine (5.15 mL, 52 mmol) was added to 3-fluoro-5-(7-methylsulfonyl-1-oxo-indan-4-yl)oxy-benzonitrile (450 mg, 1.3 mmol) and trifluoroacetic acid (19.96 µL, 0.26 mmol) in benzene (10 mL) at room temperature then warmed to reflux with the azeotropic removal of water by a Dean-Stark apparatus. Progress of the reaction was monitored by ¹H-NMR. When complete, the reaction was cooled to room temperature then concentrated in vacuo. The residue was diluted with water (10 mL), extracted with MTBE (3×10 mL), washed with brine and dried over Na₂SO₄, filtered and concentrated. Crude 3-[(E, Z)-1-butylimino-7-methylsulfonyl-indan-4-yl]oxy-5-fluoro-benzonitrile was used immediately without purification in the next step.

Step E: Preparation of 3-(2,2-difluoro-7-methylsulfonyl-1-oxo-indan-4-yl)oxy-5-fluoro-benzonitrile: Selectfluor® (1.15 g, 3.25 mmol) was added to crude 3-[(E, Z)-1-butylimino-7-methylsulfonyl-indan-4-yl]oxy-5-fluoro-benzonitrile (520 mg, 1.3 mmol) and sodium sulfate (369 mg, 2.6 mmol) in acetonitrile (10 mL) then warmed to reflux for 6 hours. The reaction was cooled to room temperature, concentrated HCl (1.0 mL, 12 mmol) was added and stirred for 15 minutes. The mixture was diluted with water (10 mL), extracted with EtOAc (3×10 mL), washed with brine (10 mL), dried over MgSO₄, filtered and concentrated in vacuo. The residue was purified on silica gel (25 g SNAP, 14 CV, 20-100% EtOAc/hexane) afforded 3-(2,2-difluoro-7-methylsulfonyl-1-oxo-indan-4-yl)oxy-5-fluoro-benzonitrile (437 mg, 1.2 mmol, 88% yield).

Step F: Preparation of (S)-3-((2,2-difluoro-1-hydroxy-7-(methylsulfonyl)-2,3-dihydro-1H-inden-4-yl)oxy)-5-fluorobenzonitrile (Compound 163): An ice cold solution of RuCl(p-cymene)[(R,R)-Ts-DPEN] (40.7 mg, 0.06 mmol) in CH₂Cl₂ (30 mL) was added by syringe under nitrogen to an ice cold solution of 3-(2,2-difluoro-7-methylsulfonyl-1-oxo-indan-4-yl)oxy-5-fluoro-benzonitrile (2.44 g, 6.4 mmol), triethylamine (1.78 mL, 12.8 mmol) and formic acid (724 µL, 19.2 mmol) in CH₂Cl₂ (30 mL). The reaction was placed in a refrigerator at 4° C. for 16 hours. The mixture was concentrated to 10 mL then purified directly on silica gel (25 g SNAP ULTRA, 14 CV, 10-50% EtOAc/hexane) affording Compound 163 (2.15 g, 5.6 mmol, 87% yield). Enantiomeric excess (98%) was determined by chiral HPLC. Retention time for (S)-enantiomer: 1.93 minutes; retention time for (R)-enantiomer: 2.32 minutes. LCMS ESI (−) 428 (M+HCO$_2^-$). $^1$HNMR (400 MHz, CDCl$_3$): δ 7.93 (d, 1H), 7.27-7.24 (m, 1H), 7.15-7.14 (m, 1H), 7.07-7.03 (m, 1H), 7.00 (d, 1H), 5.63-5.58 (m, 1H), 3.56-3.35 (m, 3H), 3.24 (s, 3H).

Example 3: Synthesis of N-(3-Chlorophenyl-4,6-t2)-4-nitrobenzo[c][1,2,5]oxadiazol-5-amine (Compound 183)

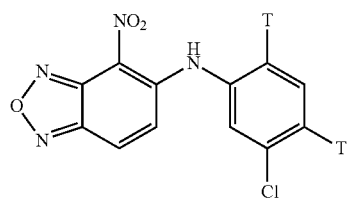

Step A: Synthesis of 3-chlorobenzen-4,6-t$_2$-amine: 3-Chloro-4,6-diiodoaniline (100 mg,) was dissolved in methanol (3 mL) and added with triethylamine (0.1 mL) and submitted for overnight tritiation using 50 Ci of tritium gas, at room temperature. Labile tritium was removed by dissolving the crude reaction mixture in methanol (3 mL) and bringing to dryness under vacuum. Labile removal was done in duplicate. The crude tritiated material was purified by preparative TLC (Silica gel, 1000μ) using hexane:ethyl acetate:AcOH (85:14:1). The product band was eluted with ethyl acetate to give 3-chlorobenzen-4,6-t$_2$-amine (yield=600 mCi, radiochemical purity was >98%).

Step B: Synthesis of Compound 183: A stirred mixture of 5-chloro-4-nitro-2,1,3-benzoxadiazole (20 mg, 0.1 mmol), 3-chlorobenzen-4,6-t$_2$-amine (600 mCi) and Cs$_2$CO$_3$ (65 mg, 0.20 mmol) in DMF (1 mL) was heated at 60° C. for 1 h. After cooling, the reaction mixture was partitioned between EtOAc and water. The aqueous layer was extracted with EtOAc. The combined organic layers were washed with water and brine, dried and concentrated. The residue was purified by preparative HPLC on an ACE-5 C18 Semi-prep column, 250×10 mm, 100 Å. Elution was carried out isocratically using 0.1% TFA in water/Acetonitrile (35:65) to give Compound 183 (478 mCi, 80%).

Example 4: Synthesis of Isomer 1 of N-((S)-7-(3-Cyano-5-fluorophenoxy)-2,2-difluoro-3-hydroxy-2,3-dihydro-1H-inden-4-yl)(methyl)(oxo)-λ$^6$-sulfanylidene)cyanamide (Compound 240)

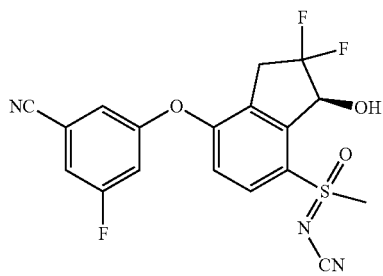 [SMILES: CS(=O)(=NC#N)c1ccc(Oc2cc(F)cc(C#N)c2)c2c1[C@H](O)C(F)(F)C2]

Step A: N-((7-(3-cyano-5-fluorophenoxy)-3-hydroxy-2,3-dihydro-1H-inden-4-yl)(methyl)(oxo)-λ$^6$-sulfanylidene) cyanamide: Sodium hydrogen carbonate (79.3 mg, 0.94 mmol) was added to a solution of 3-fluoro-5-hydroxybenzonitrile (86.27 mg, 0.63 mmol) and N-((7-fluoro-3-hydroxy-2,3-dihydro-1H-inden-4-yl)(methyl)(oxo)-λ$^6$-sulfanylidene)cyanamide (80 mg, 0.31 mmol) in DMF (3 mL). The vial was sealed and heated at 100° C. over a weekend. The reaction mixture was partitioned between EtOAc and dilute aqueous NaOH. The EtOAc was washed with water, two portions of brine, dried over MgSO$_4$, filtered, and evaporated. The residue was chromatographed on a Biotage 25M reverse phase column with a 20% to 90% ACN:water gradient to afford N-((7-(3-cyano-5-fluorophenoxy)-3-hydroxy-2,3-dihydro-1H-inden-4-yl)(methyl)(oxo)-λ$^6$-sulfanylidene)cyanamide (80 mg, 0.21 mmol, 69% yield). m/z (ES-API-pos) [M+H]=372.

Step B: N-((7-(3-cyano-5-fluorophenoxy)-3-oxo-2,3-dihydro-1H-inden-4-yl)(methyl)(oxo)-λ$^6$-sulfanylidene)cyanamide: Dess-Martin periodinane (192 mg, 0.45 mmol) was added to a solution of N-((7-(3-cyano-5-fluorophenoxy)-3-hydroxy-2,3-dihydro-1H-inden-4-yl)(methyl) (oxo)-λ$^6$-sulfanylidene)cyanamide (200 mg, 0.54 mmol) in dichloromethane (50 mL). After 10 minutes, the reaction mixture was evaporated and the residue was partitioned between EtOAc and aqueous sodium thiosulfate and saturated aqueous NaHCO$_3$. The EtOAc layer was washed with water, brine, dried over MgSO$_4$, filtered, and evaporated to afford N-((7-(3-cyano-5-fluorophenoxy)-3-oxo-2,3-dihydro-1H-inden-4-yl)(methyl)(oxo)-λ$^6$-sulfanylidene)cyanamide (174 mg, 0.47 mmol, 88% yield) as a colorless film. m/z (ES-API-pos) [M+H]=370.

Step C: (E/Z)-N-((7-(3-cyano-5-fluorophenoxy)-3-((3-methoxypropyl)imino)-2,3-dihydro-1H-inden-4-yl)(methyl) (oxo)-λ$^6$-sulfanylidene)cyanamide: Pivalic acid (9.4 mg, 0.09 mmol) was added to a mixture of N-((7-(3-cyano-5-fluorophenoxy)-3-oxo-2,3-dihydro-1H-inden-4-yl)(methyl) (oxo)-λ$^6$-sulfanylidene)cyanamide (170 mg, 0.46 mmol) and 3-methoxypropylamine (0.12 mL, 1.2 mmol) in cyclohexane (7 mL) and toluene (7 mL). The mixture was heated at reflux with a Hickman still attached. After 1 hour, the reaction mixture was evaporated and the residue was used as is in the next step.

Step D: N-((7-(3-cyano-5-fluorophenoxy)-2,2-difluoro-3-oxo-2,3-dihydro-1H-inden-4-yl)(methyl)(oxo)-λ$^6$-sulfanylidene)cyanamide: 1-Chloromethyl-4-fluoro-1,4-diazoniabicyclo[2.2.2]octane bis(tetrafluoroborate) (406 mg, 1.15 mmol) was added to a mixture of (E/Z)-N-((7-(3-cyano-5-fluorophenoxy)-3-((3-methoxypropyl)imino)-2,3-dihydro-1H-inden-4-yl)(methyl)(oxo)-λ$^6$-sulfanylidene)cyanamide (202 mg, 0.46 mmol) and sodium sulfate (162 mg, 1.15 mmol) in acetonitrile (5 mL). The mixture was heated at 70° C. After 3.5 hours, the reaction mixture was evaporated and the residue was partitioned between EtOAc and water. The EtOAc was washed with brine, dried over MgSO$_4$, filtered, and evaporated. The residue was taken up in EtOAc, absorbed on silica gel, and chromatographed on a Biotage 25 g SNAP column with a 50% to 100% EtOAc:hexane gradient to afford N-((7-(3-cyano-5-fluorophenoxy)-2,2-difluoro-3-oxo-2,3-dihydro-1H-inden-4-yl)(methyl)(oxo)-λ$^6$-sulfanylidene)cyanamide (48 mg, 0.118 mmol, 26% yield. m/z (ES-API-pos) [M+H]=406.

Step E: N-(((S)-7-(3-cyano-5-fluorophenoxy)-2,2-difluoro-3-hydroxy-2,3-dihydro-1H-inden-4-yl)(methyl)(oxo)-λ$^6$-sulfanylidene)cyanamide (Compound 240): RuCl(p-cymene)[(R,R)-Ts-DPEN] (1.5 mg, 0.020 mmol) was added to a nitrogen-sparged, ice-cold solution of N-((7-(3-cyano-5-fluorophenoxy)-2,2-difluoro-3-oxo-2,3-dihydro-1H-inden-4-yl)(methyl)(oxo)-λ$^6$-sulfanylidene)cyanamide (49 mg, 0.120 mmol), triethylamine (0.022 mL, 0.16 mmol), and formic acid (0.01 mL, 0.24 mmol) in dichloromethane (5 mL). The flask was placed in a 4° C. refrigerator over a weekend. The reaction mixture was evaporated and the residue was chromatographed on a Biotage 10 g SNAP Ultra column with a 20% to 80% EtOAc:hexane gradient to afford a solid, which was triturated twice with chloroform to afford Compound 240 (8.6 mg, 0.021 mmol, 18% yield) as a single diastereomer in 93% d.e. by chiral chromatography. $^1$H NMR (400 MHz, CD$_3$OD): δ 8.01 (d, 1H), 7.54-7.49 (m, 1H), 7.46-7.44 (m, 1H), 7.40-7.36 (m, 1H), 7.20-7.14 (m, 1H), 5.56 (d, 1H), 3.78-3.61 (m, 1H), 3.62 (s, 3H), 3.55-3.47 (m, 1H). m/z (ES-API-pos) [M+H]=408.

Example 5: Synthesis of 3-[(1S,2S,3R)-2,3-difluoro-1-hydroxy-7-methylsulfonyl-indan-4-yl]oxy-5-fluoro-benzonitrile (Compound 289)

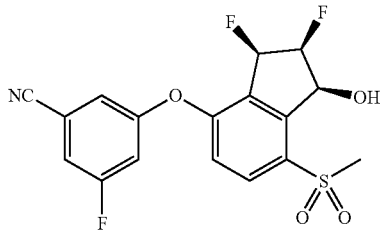 [SMILES: CS(=O)(=O)c1ccc(Oc2cc(F)cc(C#N)c2)c2c1[C@H](O)[C@H](F)[C@@H]2F]

Step A: [(1S,2R)-4-(3-cyano-5-fluoro-phenoxy)-2-fluoro-7-methylsulfonyl-indan-1-yl] acetate: To a stirred solution of 3-fluoro-5-[(1S,2R)-2-fluoro-1-hydroxy-7-methylsulfonyl-indan-4-yl]oxy-benzonitrile (2.00 g, 5.47 mmol) in DCM (27 mL) was added 4-(dimethylamino)pyridine (0.2 g, 1.64 mmol) and triethylamine (1.53 mL, 10.9 mmol). Acetic anhydride (1.00 mL, 10.9 mmol) was added dropwise at 0° C. under nitrogen. The reaction mixture was stirred at ambient temperature overnight. The reaction mixture was diluted with DCM, washed with saturated aqueous NaHCO$_3$ and brine, dried and concentrated. The residue was purified by flash chromatography on silica gel (20-40% EtOAc/hexane) to give [(1S,2R)-4-(3-cyano-5-fluoro-phenoxy)-2-fluoro-7-methylsulfonyl-indan-1-yl] acetate (1.95 g, 87%). LCMS ESI (+) m/z 408 (M+H).

Step B: [(1S,2S,3S)-3-bromo-4-(3-cyano-5-fluoro-phenoxy)-2-fluoro-7-methylsulfonyl-indan-1-yl] acetate and [(1S,2S,3R)-3-bromo-4-(3-cyano-5-fluoro-phenoxy)-2-fluoro-7-methylsulfonyl-indan-1-yl] acetate: To a stirred solution of [(1S,2R)-4-(3-cyano-5-fluoro-phenoxy)-2-fluoro-7-methylsulfonyl-indan-1-yl] acetate (1.95 g, 4.79 mmol) in 1,2-dichloroethane (24 mL) was added N-bromosuccinimide (0.94 g, 5.27 mmol) and 2,2'-azobisisobutyronitrile (8 mg, 0.05 mmol). The reaction mixture was heated at 80° C. for 3 hours. After cooling, the reaction mixture was diluted with DCM, washed with saturated aqueous NaHCO$_3$ and brine, dried and concentrated. The residue was purified by column chromatography on silica gel (20-30% EtOAc/hexane) to give [(1S,2S,3S)-3-bromo-4-(3-cyano-5-fluoro-phenoxy)-2-fluoro-7-methylsulfonyl-indan-1-yl] acetate (1.52 g, 65%). LCMS ESI (+) m/z 486, 488 (M+H). Further elution with 30-50% EtOAc/hexane gave the more polar product [(1S,2S,3R)-3-bromo-4-(3-cyano-5-fluoro-phenoxy)-2-fluoro-7-methylsulfonyl-indan-1-yl] acetate (0.583 g, 25%). LCMS ESI (+) m/z 486, 488 (M+H).

Step C: [(1S,2R,3S)-4-(3-cyano-5-fluoro-phenoxy)-2-fluoro-3-hydroxy-7-methylsulfonyl-indan-1-yl] acetate: To a combined mixture of [(1S,2S,3S)-3-bromo-4-(3-cyano-5-fluoro-phenoxy)-2-fluoro-7-methylsulfonyl-indan-1-yl] acetate and [(1S,2S,3R)-3-bromo-4-(3-cyano-5-fluoro-phenoxy)-2-fluoro-7-methylsulfonyl-indan-1-yl] acetate prepared in Step B (2.05 g, 4.22 mmol) were added 1,2-dimethoxyethane (28 mL) and water (0.050 mL) followed by silver perchlorate hydrate (1.42 g, 6.32 mmol). The reaction mixture was heated at 70° C. for 2 hours. After cooling, the reaction mixture was diluted with EtOAc and filtered through Celite. The filtrate was washed with water and brine, dried and concentrated. The residue was purified by flash chromatography on silica gel (20-50%) to give [(1S,2R,3S)-4-(3-cyano-5-fluoro-phenoxy)-2-fluoro-3-hydroxy-7-methylsulfonyl-indan-1-yl] acetate (0.416 g, 23%) as the less polar product. LCMS ESI (+) m/z 441 (M+NH$_4^+$). Further elution with 60% EtOAc/hexane gave [(1S,2R,3R)-4-(3-cyano-5-fluoro-phenoxy)-2-fluoro-3-hydroxy-7-methylsulfonyl-indan-1-yl] acetate (0.58 g, 32%). LCMS ESI (+) m/z 441 (M+NH$_4^+$).

Step D: [(1S,2S,3R)-4-(3-cyano-5-fluoro-phenoxy)-2,3-difluoro-7-methylsulfonyl-indan-1-yl] acetate: To a stirred solution of [(1S,2R,3S)-4-(3-cyano-5-fluoro-phenoxy)-2-fluoro-3-hydroxy-7-methylsulfonyl-indan-1-yl] acetate (416 mg, 0.98 mmol) in DCM (10 mL) was added (diethylamino)sulfur trifluoride (DAST) (0.26 mL, 2.0 mmol) at −78° C. under nitrogen. The reaction mixture was allowed to warm to 0° C. and stirred for 15 minutes. The reaction was quenched by saturated aqueous NaHCO$_3$. The mixture was partitioned between EtOAc and water. The aqueous layer was extracted with EtOAc. The combined organic layers were washed with brine, dried and concentrated. The residue was purified by flash chromatography on silica gel (20-40% EtOAc/hexane) to give [(1S,2S,3R)-4-(3-cyano-5-fluoro-phenoxy)-2,3-difluoro-7-methylsulfonyl-indan-1-yl] acetate (310 mg, 74%). LCMS ESI (+) m/z 426 (M+H).

Step E: 3-[(1S,2S,3R)-2,3-difluoro-1-hydroxy-7-methylsulfonyl-indan-4-yl]oxy-5-fluoro-benzonitrile (Compound 289): To a stirred solution of [(1S,2S,3R)-4-(3-cyano-5-fluoro-phenoxy)-2,3-difluoro-7-methylsulfonyl-indan-1-yl] acetate (0.23 mmol) in tetrahydrofuran (1.5 mL) was added 0.5 N LiOH solution (0.68 mL, 0.34 mmol) at 0° C. under nitrogen. The reaction mixture was stirred at 0° C. for 1 hour. The reaction was then partitioned between EtOAc and water. The aqueous layer was extracted with EtOAc. The combined organic layers were washed with water and brine, dried and concentrated. The residue was purified by flash chromatography on silica gel (30-70% EtOAc/hexane) to give Compound 289. LCMS ESI (+) m/z 384 (M+H); $^1$H NMR (400 MHz, CDCl$_3$): δ 8.13 (d, 1H), 7.31-7.25 (m, 1H), 7.23-7.19 (m, 1H), 7.14-7.09 (m, 1H), 7.04 (d, 1H), 6.09-5.91 (m, 1H), 5.87-5.80 (m, 1H), 5.25-5.05 (m, 1H), 3.32 (s, 3H), 2.95 (d, 1H).

Example 6: Synthesis of 3-fluoro-5-[(1S,3R)-2,2,3-trifluoro-1-hydroxy-7-methylsulfonyl-indan-4-yl]oxy-benzonitrile (Compound 292)

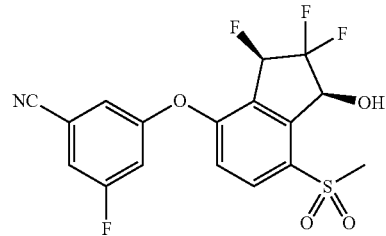 [SMILES: CS(=O)(=O)c1ccc(Oc2cc(F)cc(C#N)c2)c2c1[C@H](O)C(F)(F)[C@@H]2F]

Step A: [(1S,3S)-4-(3-cyano-5-fluoro-phenoxy)-2,2-difluoro-3-hydroxy-7-methylsulfonyl-indan-1-yl] acetate and [(1S,3R)-4-(3-cyano-5-fluoro-phenoxy)-2,2-difluoro-3-hydroxy-7-methylsulfonyl-indan-1-yl] acetate: To a stirred solution of [(1S)-4-(3-cyano-5-fluoro-phenoxy)-2,2-difluoro-7-methylsulfonyl-indan-1-yl] acetate (1.0 g, 2.35 mmol) in DCE (24 mL) were added N-bromosuccinimide (0.46 g, 2.59 mmol) and 2,2'-azobisisobutyronitrile (4 mg, 0.02 mmol). The reaction mixture was heated at 80° C. overnight. After cooling, the reaction mixture was diluted with DCM, washed with saturated aqueous NaHCO$_3$ and brine, dried and concentrated. The crude product was dissolved in 1,2-dimethoxyethane (11 mL) and water (0.11 mL). Silver perchlorate hydrate (0.35 g, 1.55 mmol) was added. The reaction mixture was heated at 70° C. overnight. After cooling, the reaction mixture was diluted with EtOAc and filtered through Celite. The filtrate was washed with water and brine, dried and concentrated. The residue was purified by flash chromatography on silica gel (20-60% EtOAc/hexane) to give [(1S,3S)-4-(3-cyano-5-fluoro-phenoxy)-2,2-difluoro-3-hydroxy-7-methylsulfonyl-indan-1-yl] acetate (39 mg, 9% yield) as the less polar product. LCMS ESI (+) m/z 459 (M+NH$_4^+$). Further elution gave [(1S,3R)-4-(3-cyano-5-fluoro-phenoxy)-2,2-difluoro-3-hydroxy-7-methylsulfonyl-indan-1-yl] acetate (80 mg, 18%). LCMS ESI (+) m/z 459 (M+NH$_4^+$).

Step B: [(1S,3R)-4-(3-cyano-5-fluoro-phenoxy)-2,2,3-trifluoro-7-methylsulfonyl-indan-1-yl] acetate: Prepared as described in Example 5 Step D substituting [(1S,2R,3S)-4-(3-cyano-5-fluoro-phenoxy)-2-fluoro-3-hydroxy-7-methylsulfonyl-indan-1-yl] acetate with [(1S,3S)-4-(3-cyano-5-fluoro-phenoxy)-2,2-difluoro-3-hydroxy-7-methylsulfonyl-indan-1-yl] acetate. LCMS ESI (+) m/z 444 (M+H).

Step C: 3-fluoro-5-[(1S,3R)-2,2,3-trifluoro-1-hydroxy-7-methylsulfonyl-indan-4-yl]oxy-benzonitrile (Compound 292): Prepared as described in Example 5 Step E substituting [(1R)-4-(3-cyano-5-fluoro-phenoxy)-3,3-difluoro-7-methylsulfonyl-indan-1-yl] acetate with [(1S,3R)-4-(3-cyano-5-fluoro-phenoxy)-2,2,3-trifluoro-7-methylsulfonyl-indan-1-yl] acetate. LCMS ESI (+) m/z 419 (M+NH$_4^+$); $^1$H NMR (400 MHz, CDCl$_3$): δ 8.14-8.11 (m, 1H), 7.33-7.29 (m, 1H), 7.25-7.23 (m, 1H), 7.16-7.12 (m, 1H), 7.05 (d, 1H), 5.91-5.75 (m, 1H), 5.71-5.65 (m, 1H), 3.39 (d, 1H), 3.25 (s, 3H).

Example 7: Synthesis of (R)-3-((4-(Difluoromethyl)-2,2-difluoro-3-hydroxy-1,1-dioxido-2,3-dihydrobenzo[b]thiophen-5-yl)oxy)-5-fluorobenzonitrile (Compound 349)

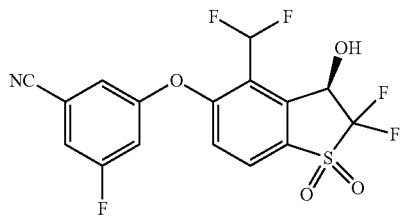 [SMILES: N#Cc1cc(F)cc(Oc2ccc3c(c2C(F)F)[C@@H](O)C(F)(F)S3(=O)=O)c1]

Step A: Preparation of 2-bromo-3-(difluoromethyl)-1,4-difluorobenzene: A solution of 2-bromo-3,6-difluorobenzaldehyde (40.0 g, 181 mmol) dissolved in dichloromethane (800 mL) was cooled to 0° C., then treated with (diethylamino)sulfur trifluoride (70.0 g, 454 mmol). After the addition, the reaction mixture was warmed to ambient temperature and stirred at this temperature for 4 hours. Saturated aqueous sodium bicarbonate solution was added slowly until the pH was 8-9. The organic layer was separated, dried over sodium sulfate, filtered and concentrated under reduced pressure to give 2-bromo-3-(difluoromethyl)-1,4-difluorobenzene (44.0 g, quant.) as solid which was used immediately in the next step without purification. $^1$H NMR (400 MHz, CDCl$_3$): δ 7.28-7.22 (m, 1H), 7.17-7.10 (m, 1H), 7.04 (t, 1H).

Step B: Preparation of 2-(difluoromethyl)-3,6-difluorobenzonitrile: A suspension of 2-bromo-3-(difluoromethyl)-1,4-difluorobenzene (44.0 g, 181 mmol) and copper (I) cyanide (21.1 g, 235 mmol) in 1-methyl-2-pyrrolidinone (400 mL) was heated to 180° C. for 2 hours. After cooling to ambient temperature, the reaction mixture was poured into water and extracted with diethyl ether. The organic layer was washed with brine, dried over sodium sulfate, filtered and then concentrated under reduced pressure. The crude product was purified by flash chromatography on silica gel eluting with hexane/ethyl acetate to give 2-(difluoromethyl)-3,6-difluorobenzonitrile as a solid (23 g, 67%). $^1$H NMR (400 MHz, CDCl$_3$): δ 7.48-7.35 (m, 2H), 6.98 (t, 1H).

Step C: Preparation of 2-(difluoromethyl)-3-fluoro-6-(methylthio)benzonitrile: A solution of 2-(difluoromethyl)-3,6-difluorobenzonitrile (31.3 g, 65.5 mmol) in acetonitrile (500 mL) was cooled to −30° C., then treated with sodium methanethiolate (12.8 g, 174 mmol). After addition of the solid, the reaction mixture was stirred for 7 hours while maintaining the temperature between −30° C. and −40° C. A mixture of water (200 mL) and methyl t-butyl ether (500 mL) were added and the reaction mixture was warmed to ambient temperature. The organic layer was separated, washed with brine, dried over sodium sulfate, filtered and concentrated under reduced pressure to give 2-(difluoromethyl)-3-fluoro-6-methylsulfanyl-benzonitrile as yellow solid (36.3 g, 150 mmol, 91%). $^1$H NMR (400 MHz, CDCl$_3$): δ 7.47-7.44 (m, 1H), 7.36-7.32 (m, 1H), 6.99 (t, 1H), 2.58 (s, 3H).

Step D: Preparation of 2-(difluoromethyl)-3-fluoro-6-(methylsulfonyl)benzonitrile: A slurry of 2-(difluoromethyl)-3-fluoro-6-methylsulfanyl-benzonitrile (36.3 g, 167 mmol) in acetonitrile (350 mL) and water (175 mL) was treated with Oxone® (257 g, 418 mmol), then the mixture was heated at 56° C. for 4 hours. After cooling to ambient temperature, the remaining solids were removed by filtration and washed with dichloromethane (300 mL). The filtrate was concentrated in vacuo to remove volatile solvents. The resulting aqueous solution was extracted with dichloromethane (400 mL). The organic layer was dried over sodium sulfate, filtered and concentrated under reduced pressure. The resulting solid was suspended in 4:1 hexane/methyl t-butyl ether (200 mL) and stirred for 10 minutes at ambient temperature. The undissolved solid was collected by filtration and air-dried to give 2-(difluoromethyl)-3-fluoro-6-(methylsulfonyl)benzonitrile (29.9 g, 71%). $^1$H NMR (400 MHz, CDCl$_3$): δ 8.41-8.37 (m, 1H), 7.66-7.61 (m, 1H), 7.11 (t, 1H), 3.34 (s, 3H).

Step E: Preparation of 3-(3-cyano-5-fluorophenoxy)-2-(difluoromethyl)-6-(methylsulfonyl)benzonitrile: A suspension of 2-(difluoromethyl)-3-fluoro-6-(methylsulfonyl)benzonitrile (9.52 g, 38.2 mmol), 3-fluoro-5-hydroxybenzonitrile (5.23 g, 38.2 mmol), and cesium carbonate (7.77 g, 40.1 mmol) in N,N-dimethylformamide (76 mL) was heated to 45° C. for 3 hours. Additional cesium carbonate (0.46 g, 1.4 mmol) was added and the reaction mixture was heated at 45° C. for three hours, then stirred at ambient temperature for 54 hours. The reaction mixture was vigorously stirred while water (800 mL) was added. The resulting suspension was stirred for 30 minutes, then the solids were collected by filtration, washed with water (1.2 L), and dried under high vacuum to give 3-(3-cyano-5-fluorophenoxy)-2-(difluoromethyl)-6-(methylsulfonyl)benzonitrile as a white solid (13.3 g, 96%). LCMS ESI (+) m/z 384 (M+NH$_4$). $^1$H NMR (400 MHz, DMSO-d$_6$): δ 8.22 (d, 1H), 7.86-7.82 (m, 1H), 7.72-7.62 (m, 3H), 7.49 (t, 1H), 3.44 (s, 3H).

Step F: Preparation of 3-((4-(difluoromethyl)-1,1-dioxido-3-oxo-2,3-dihydrobenzo[b]thiophen-5-yl)oxy)-5-fluorobenzonitrile: A solution of 3-(3-cyano-5-fluorophenoxy)-2-(difluoromethyl)-6-(methylsulfonyl)benzonitrile (13.3 g, 36 mmol) was dissolved in tetrahydrofuran (380 mL) and treated with sodium hydride (60% in mineral oil, 2.26 g, 56 mmol) in two equal portions at five minute intervals. The resulting suspension was stirred at ambient temperature for 60 minutes. The reaction mixture was quenched by addition of a mixture of 4:1 methanol/10% aqueous HCl (200 mL) and the resulting suspension was stirred for 1 hour. The mixture was concentrated to remove volatile solvents, then the remaining slurry was diluted with additional water (800 mL) and stirred for an additional 30 minutes. The solids were recovered by filtration and washed with additional water and the resulting beige solid was dried under high vacuum in the presence of solid NaOH. 3-((4-(Difluoromethyl)-1,1-dioxido-3-oxo-2,3-dihydrobenzo[b]thiophen-5-yl)oxy)-5-fluorobenzonitrile was obtained as a beige solid (13.3 g, quant.) and was used without further purification. LCMS ESI (–) m/z 366 (M–H). $^1$H NMR (400 MHz, DMSO-d$_6$): δ 8.35 (d, 1H), 7.79 (d, 1H), 7.76 (t, 1H), 7.76-7.72 (m, 1H), 7.56-7.50 (m, 2H), 4.72 (s, 2H).

Step G: Preparation of 3-((4-(difluoromethyl)-2,2-difluoro-1,1-dioxido-3-oxo-2,3-dihydrobenzo[b]thiophen-5-yl)oxy)-5-fluorobenzonitrile: A solution of 3-((4-(difluoromethyl)-1,1-dioxido-3-oxo-2,3-dihydrobenzo[b]thiophen-5-yl)oxy)-5-fluorobenzonitrile (1.40 g, 3.82 mmol) dissolved in acetonitrile (38 mL) was treated at ambient temperature with sodium carbonate (890 mg, 8.4 mmol) followed by Selectfluor® (2.98 g, 8.4 mmol). The reaction mixture was stirred at ambient temperature for 90 minutes. The reaction mixture was concentrated in vacuo to remove volatile solvents, then the residue was diluted with water (100 mL) and extracted three times with ethyl acetate (50 mL portions). The combined organic layers were washed with saturated NaCl, dried over MgSO$_4$, filtered and concentrated in vacuo to give 3-((4-(difluoromethyl)-2,2-difluoro-1,1-dioxido-3-oxo-2,3-dihydrobenzo[b]thiophen-5-yl)oxy)-5-fluorobenzonitrile as a solid (1.48 g, quant.). $^1$H NMR (400 MHz, DMSO-d$_6$, sample exists as hydrate): δ 8.81 (s, 2H), 8.29 (d, 1H), 7.80-7.76 (m, 1H), 7.74 (t, 1H), 7.57-7.50 (m, 3H).

Step H: Preparation of 3-((4-(difluoromethyl)-2,2-difluoro-3-hydroxy-1,1-dioxido-2,3-dihydrobenzo[b]thiophen-5-yl)oxy)-5-fluorobenzonitrile: A solution of 3-((4-(difluoromethyl)-2,2-difluoro-1,1-dioxido-3-oxo-2,3-dihydro benzo[b]thiophen-5-yl)oxy)-5-fluorobenzonitrile (1.48 g, 3.67 mmol) in methanol (37 mL) was cooled to 0° C., then treated with sodium borohydride (139 mg, 3.7 mmol) and stirred for 1 hour. The reaction was quenched by addition of water (0.5 mL) and saturated NH$_4$Cl (0.25 mL). The reaction mixture was concentrated in vacuo to remove volatile solvents, then diluted with 0.5 M NaOH (10 mL). The aqueous was extracted three times with ethyl acetate and the combined organic layers were washed with saturated NaCl, dried over MgSO$_4$, filtered and concentrated in vacuo. The crude product was chromatographed on SiO$_2$ eluting with a gradient of ethyl acetate/hexane to give 3-((4-(difluoromethyl)-2,2-difluoro-3-hydroxy-1,1-dioxido-2,3-dihydrobenzo[b]thiophen-5-yl)oxy)-5-fluorobenzonitrile as a white solid (1.24 g, 83%).

Step I: Preparation of (R)-3-((4-(difluoromethyl)-2,2-difluoro-3-hydroxy-1,1-dioxido-2,3-dihydrobenzo[b]thiophen-5-yl)oxy)-5-fluorobenzonitrile: 3-((4-(Difluoromethyl)-2,2-difluoro-3-hydroxy-1,1-dioxido-2,3-dihydrobenzo[b]thiophen-5-yl)oxy)-5-fluorobenzonitrile was resolved using preparative SFC chromatography under the following conditions: ChiralPak AS(–H) (2×15 cm) column, 20% ethanol with carbon dioxide at 100 bar, 60 mL/min flow rate, injection volume was 0.5 mL of a 20 mg/mL solution in ethanol, peak detection at 220 nm. Compound 349 was recovered as the first peak (1.50 minutes) to elute from the column. LCMS ESI (–) m/z 404 (M–H). $^1$H NMR (400 MHz, CDCl$_3$): δ 7.98 (d, 1H), 7.33-7.30 (m, 1H), 7.23 (t, 1H), 7.22-7.18 (m, 2H), 7.10-7.06 (m, 1H), 5.69-5.65 (m, 1H), 3.23 (d, 1H).

Example 8: Synthesis of (6R,7S)-4-(3,3-difluorocyclobutoxy)-6-fluoro-1-(trifluoromethyl)-6,7-dihydro-5H-cyclopenta[c]pyridin-7-ol (Compound 465) and (R)-4-(3,3-difluorocyclobutoxy)-1-(trifluoromethyl)-6,7-dihydro-5H-cyclopenta[c]pyridin-7-ol (Compound 466)

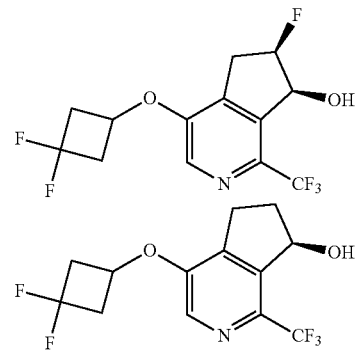

Step A: Preparation of 4-bromo-1-(trifluoromethyl)-5,6-dihydro-7H-cyclopenta[c]pyridin-7-one: A suspension of 4-bromo-5,6-dihydrocyclopenta[c]pyridin-7-one (1.0 g, 4.72 mmol) and bis(((trifluoromethyl)sulfinyl)oxy)zinc (4.69 g, 14.15 mmol) in a mixture of dichloromethane (30 mL) and water (15 mL) at 0° C. was treated with tert-butyl hydroperoxide (~70% in water, 2.58 mL, 18.86 mmol, added via pipette using a plastic tip) and stirred overnight. Additional portions of bis(((trifluoromethyl)sulfinyl)oxy)zinc (2.35 g, 7.07 mmol) and tert-butyl hydroperoxide (2.58 mL, 18.86 mmol) were added sequentially to drive the reaction to completion. After stirring for an additional day, the reaction vessel was placed into a water bath and carefully quenched by the addition of saturated NaHCO$_3$. Once effervescence ceased, the reaction mixture filtered through a pad of celite to remove. The pad of celite was rinsed with additional dichloromethane. The filtrate was separated and the aqueous portion extracted further with 2×20 mL CH$_2$Cl$_2$. The combined organics were rinsed with 10 mL of brine, dried with MgSO$_4$, filtered, and concentrated to dryness. Purification was achieved by chromatography on silica using 30-90% CH$_2$Cl$_2$/hexane to afford 4-bromo-1-(trifluoromethyl)-5,6-dihydro-7H-cyclopenta[c]pyridin-7-one as an off-white solid (390 mg, 30%). The desired regioisomer elutes first. LCMS ESI (+) (M+H) m/z 280/282.

Step B: Preparation of 4-bromo-1-(trifluoromethyl)-5,6-dihydrospiro[cyclopenta[c]pyridine-7,2'-[1,3]dioxolane] and 4-bromo-1-(trifluoromethyl)-7-(2-((trimethylsilyl)oxy)ethoxy)-5H-cyclopenta[c]pyridine: Trimethylsilyl trifluoromethanesulfonate (75.9 µL, 0.42 mmol) was added to a solution of 4-bromo-1-(trifluoromethyl)-5,6-dihydrocyclopenta[c]pyridin-7-one (389 mg, 1.39 mmol) and trimethyl (2-trimethylsilyloxyethoxy)silane (1.37 mL, 5.56 mmol) in dichloromethane (13.6 mL) cooled in an ice bath. The mixture was allowed to slowly warm to ambient temperature. After 5 h, an additional 1.3 mL of trimethyl(2-trimethylsilyloxyethoxy)silane and 76 µL of trimethylsilyl trifluoromethanesulfonate were added. After another 16 h, the reaction mixture was treated with triethylamine (770 µL, 5.56 mmol), stirred for 10 min, and then concentrated. The residue was treated with 20 mL EtOAc and 20 mL of water and the layers separated. The aqueous portion was extracted further with 2×20 mL of EtOAc. The combined organic extracts were washed with brine, dried over MgSO$_4$, filtered, and evaporated. Purification was achieved by chromatography on silica using 5-20% EtOAc/hexane to afford 4-bromo-1-(trifluoromethyl)-5,6-dihydrospiro[cyclopenta[c]pyridine-7,2'-[1,3]dioxolane] as a shite solid (262 mg, 58%) and 4-bromo-1-(trifluoromethyl)-7-(2-((trimethylsilyl)oxy)ethoxy)-5H-cyclopenta[c]pyridine as a white solid (170 mg, 31%). Data for 4-bromo-1-(trifluoromethyl)-5,6-dihydrospiro[cyclopenta[c]pyridine-7,2'-[1,3]dioxolane]: LCMS ESI (+) (M+H) m/z 324/326. Data for 4-bromo-1-(trifluoromethyl)-7-(2-((trimethylsilyl)oxy)ethoxy)-5H-cyclopenta[c]pyridine: $^1$H NMR (400 MHz, CDCl$_3$): δ 8.56 (s, 1H), 5.59 (t, 1H), 4.10 (t, 2H), 3.96 (t, 2H), 3.36 (d, 2H), 0.15 (s, 9H).

Step C: Preparation of 4-bromo-6-fluoro-1-(trifluoromethyl)-5,6-dihydrospiro[cyclopenta[c]pyridine-7,2'-[1,3]dioxolane]: A solution of 2-[[4-bromo-1-(trifluoromethyl)-5H-cyclopenta[c]pyridin-7-yl]oxy]ethoxy-trimethyl-silane (146.6 mg, 0.37 mmol) and sodium sulfate (262.7 mg, 1.85 mmol) in acetonitrile (3.7 mL) was stirred for 10 min and then treated with Selectfluor® (145.2 mg, 0.41 mmol) and stirred at 25° C. for 1 h. Volatiles were removed by concentration under reduced pressure. The reaction mixture was poured into 30 mL of water and extracted with 3×15 mL EtOAc. The combined organics were rinsed with 10 mL of brine, dried with MgSO$_4$, filtered, and concentrated to dryness. Purification was achieved by chromatography on silica using 5-20% EtOAc/hexane to afford 4-bromo-6-fluoro-1-(trifluoromethyl)-5,6-dihydrospiro[cyclopenta[c]pyridine-7,2'-[1,3]dioxolane] as a white solid (96.2 mg, 76%). LCMS ESI (+) (M+H) m/z 342/344.

Step D: Preparation of 6-fluoro-1-(trifluoromethyl)-5,6-dihydrospiro[cyclopenta[c]pyridine-7,2'-[1,3]dioxolan]-4-ol and 1-(trifluoromethyl)-5,6-dihydrospiro[cyclopenta[c]pyridine-7,2'-[1,3]dioxolan]-4-ol: A solution of 4'-bromo-6'-fluoro-1'-(trifluoromethyl)spiro[1,3-dioxolane-2,7'-5,6-dihydrocyclopenta[c]pyridine] (96.2 mg, 0.2800 mmol) and 2-(di-t-butylphosphino)-3,6-dimethoxy-2',4',6'-tri-i-propyl-1,1'-biphenyl (3.4 mg, 0.007 mmol) in 1,4-dioxane (5.0 mL) was sparged with nitrogen for 3 mins. The reaction mixture was then treated sequentially with potassium hydroxide (47.3 mg, 0.84 mmol), water (101 µL, 5.62 mmol) and [2-(2-aminophenyl)phenyl]-methylsulfonyloxy-palladium; di-t-butyl-[3,6-dimethoxy-2-(2,4,6-triisopropylphenyl)phenyl]phosphane (6.0 mg, 0.007 mmol) under continuous nitrogen stream. The vessel was sealed and heated to 80 C for 1 h and 30 min. The reaction mixture was quenched by the addition of acetic acid (64.3 µL, 1.13 mmol). The reaction mixture was poured into 75 mL of water and extracted with 4×20 mL EtOAc. The combined organics were dried with MgSO$_4$, filtered, and concentrated to dryness. The product was used without further purification (87 mg). During the reaction, some of the hydrodefluorinated product formed as an impurity. Data for 6-fluoro-1-(trifluoromethyl)-5,6-dihydrospiro[cyclopenta[c]pyridine-7,2'-[1,3]dioxolan]-4-ol: LCMS ESI (+) (M+H) m/z 280. Data for 1-(trifluoromethyl)-5,6-dihydrospiro[cyclopenta[c]pyridine-7,2'-[1,3]dioxolan]-4-ol: LCMS ESI (+) (M+H) m/z 262.

Step E: Preparation of 4-(3,3-difluorocyclobutoxy)-6-fluoro-1-(trifluoromethyl)-5,6-dihydrospiro[cyclopenta[c]pyridine-7,2'-[1,3]dioxolane] and 4-(3,3-difluorocyclobutoxy)-1-(trifluoromethyl)-5,6-dihydrospiro[cyclopenta[c]pyridine-7,2'-[1,3]dioxolane]: A solution of impure 6'-fluoro-1'-(trifluoromethyl)spiro[1,3-dioxolane-2,7'-5,6-dihydrocyclopenta[c]pyridine]-4'-ol (44.0 mg, 0.16 mmol), polymer supported triphenylphosphine (~2.06 mmol/g, 306.2 mg, 0.63 mmol), and 3,3-difluoro-cyclobutanol (68.1 mg, 0.63 mmol) in tetrahydrofuran (3.2 mL) was treated with diisopropyl azodicarboxylate (120 µL, 0.61 mmol) and stirred at 60° C. for 2 h. The reaction mixture was filtered and the filter cake rinsed with 20 mL EtOAc. The filtrate was concentrated and purified by chromatography on silica using 10-30% EtOAc/hexane to afford a clear solid (39.0 mg, 67%) that was a 2:1 mixture of the fluorinated and hydrodefluorinated products. LCMS ESI (+) (M+H) m/z 370. Data for 4-(3,3-difluorocyclobutoxy)-6-fluoro-1-(trifluoromethyl)-5,6-dihydrospiro[cyclopenta[c]pyridine-7,2'-[1,3]dioxolane]: LCMS ESI (+) (M+H) m/z 370. Data for 4-(3,3-difluorocyclobutoxy)-1-(trifluoromethyl)-5,6-dihydrospiro[cyclopenta[c]pyridine-7,2'-[1,3]dioxolane]: LCMS ESI (+) (M+H) m/z 352.

Step F: Preparation of 4-(3,3-difluorocyclobutoxy)-6-fluoro-1-(trifluoromethyl)-5,6-dihydro-7H-cyclopenta[c]pyridin-7-one and 4-(3,3-difluorocyclobutoxy)-1-(trifluoromethyl)-5,6-dihydro-7H-cyclopenta[c]pyridin-7-one: A solution of impure 4'-(3,3-difluorocyclobutoxy)-6'-fluoro-1'-(trifluoromethyl)spiro[1,3-dioxolane-2,7'-5,6-dihydrocyclopenta[c]pyridine] (39.0 mg, 0.106 mmol) in dichloromethane (2.0 mL) at 0 C was treated with perchloric acid (70% in water, 200 µL) and stirred at 0 C for 3 h. The reaction mixture was quenched by the addition of 5 mL of saturated aqueous NaHCO$_3$. The resulting mixture was extracted with 3×15 mL CH$_2$Cl$_2$. The combined organics were rinsed with 10 mL of brine, dried with MgSO$_4$, filtered, and concentrated to dryness. The product was used without further purification as a 2:1 mixture of fluorinated and hydrodefluorinated ketones. LCMS ESI (+) (M+H) m/z 326. Data for 4-(3,3-difluorocyclobutoxy)-6-fluoro-1-(trifluoromethyl)-5,6-dihydro-7H-cyclopenta[c]pyridin-7-one: LCMS ESI (+) (M+H) m/z 326. Data for 4-(3,3-difluorocyclobutoxy)-1-(trifluoromethyl)-5,6-dihydro-7H-cyclopenta[c]pyridin-7-one: LCMS ESI (+) (M+H) m/z 308.

Step G: Preparation of (6R,7S)-4-(3,3-difluorocyclobutoxy)-6-fluoro-1-(trifluoromethyl)-6,7-dihydro-5H-cyclopenta[c]pyridin-7-ol (Compound 465) and (R)-4-(3,3-difluorocyclobutoxy)-1-(trifluoromethyl)-6,7-dihydro-5H-cyclopenta[c]pyridin-7-ol (Compound 466): A solution of impure 4-(3,3-difluorocyclobutoxy)-6-fluoro-1-(trifluoromethyl)-5,6-dihydrocyclopenta[c]pyridin-7-one (33.8 mg, 0.10 mmol) in dichloromethane (4.0 mL) was cooled to 0° C. and sparged with nitrogen for 5 min. During this time formic acid (11.8 µL, 0.31 mmol) and triethylamine (28.8

µL, 0.21 mmol) were sequentially added. Once sparging was complete, RuCl(p-cymene)[(R,R)-Ts-DPEN] (1.3 mg, 0.002 mmol) was added under a continuous stream of nitrogen. The reaction vessel was sealed and placed into the refrigerator to react overnight. Volatiles were removed by concentration under reduced pressure. The residue was purified by chromatography on silica using 4-18% EtOAc/CH$_2$Cl$_2$ to afford (6R,7S)-4-(3,3-difluorocyclobutoxy)-6-fluoro-1-(trifluoromethyl)-6,7-dihydro-5H-cyclopenta[c]pyridin-7-ol (Compound 465) as a clear solid (5.4 mg, 16%) and (R)-4-(3,3-difluorocyclobutoxy)-1-(trifluoromethyl)-6,7-dihydro-5H-cyclopenta[c]pyridin-7-ol (Compound 466) as a clear solid (7.4 mg, 23%). Data for (6R,7S)-4-(3,3-difluorocyclobutoxy)-6-fluoro-1-(trifluoromethyl)-6,7-dihydro-5H-cyclopenta[c]pyridin-7-ol (Compound 465): Retention time HPLC (14 min)=3.59 min; LCMS ESI (+) (M+H) m/z 328; $^1$H NMR (400 MHz, CDCl$_3$): δ 8.04 (s, 1H), 5.46-5.26 (m, 2H), 4.89-4.79 (m, 1H), 3.36-3.08 (m, 4H), 2.91-2.74 (m, 2H), 2.60 (dd, 1H). Data for (R)-4-(3,3-difluorocyclobutoxy)-1-(trifluoromethyl)-6,7-dihydro-5H-cyclopenta[c]pyridin-7-ol (Compound 466): Retention time HPLC (14 min)=3.95 min; LCMS ESI (+) (M+H) m/z 310; $^1$H NMR (400 MHz, CDCl$_3$): δ 7.98 (s, 1H), 5.59-5.54 (m, 1H), 4.88-4.79 (m, 1H), 3.24-3.07 (m, 3H), 2.89 (dd, 1H), 2.89-2.74 (m, 2H), 2.44-2.34 (m, 1H), 2.28-2.21 (m, 1H), 2.12-2.09 (m, 1H).

Example 9: Synthesis of 3-fluoro-5-(((6R,7S)-6-fluoro-7-hydroxy-1-(trifluoromethyl)-6,7-dihydro-5H-cyclopenta[c]pyridin-4-yl)oxy)benzonitrile (Compound 467)

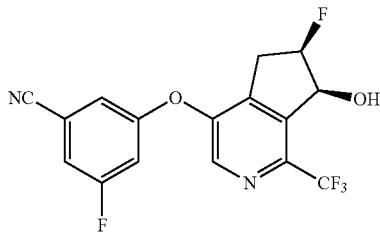 [SMILES: N#Cc1cc(F)cc(Oc2cnc(C(F)(F)F)c3c2C[C@@H](F)[C@H]3O)c1]

Step A: Preparation of 1-(trifluoromethyl)-5,6-dihydrospiro[cyclopenta[c]pyridine-7,2'-[1,3]dioxolan]-4-ol: A solution of 4'-bromo-1'-(trifluoromethyl)spiro[1,3-dioxolane-2,7'-5,6-dihydrocyclopenta[c]pyridine] (226.4 mg, 0.70 mmol) and 2-(di-t-butylphosphino)-3,6-dimethoxy-2',4',6'-tri-i-propyl-1,1'-biphenyl (8.5 mg, 0.017 mmol) in 1,4-dioxane (7.0 mL) was sparged with nitrogen for 3 mins. The reaction mixture was then treated sequentially with potassium hydroxide (117.6 mg, 2.10 mmol), water (252 µL, 13.97 mmol) and [2-(2-aminophenyl)phenyl]-methylsulfonyloxy-palladium; ditert-butyl-[3,6-dimethoxy-2-(2,4,6-triisopropylphenyl)phenyl]phosphane (14.9 mg, 0.017 mmol) under continuous nitrogen stream. The vessel was sealed and heated to 80 C for 1 h and 30 min. The reaction mixture was quenched by the addition of acetic acid (160 µL, 2.79 mmol). The reaction mixture was poured into 75 mL of water and extracted with 4×20 mL EtOAc. The combined organics were dried with MgSO4, filtered, and concentrated to dryness. The brown solid was used without further purification. LCMS ESI (−) (M−H) m/z 260.

Step B: Preparation of 3-fluoro-5-((1-(trifluoromethyl)-5,6-dihydrospiro[cyclopenta[c]pyridine-7,2'-[1,3]dioxolan]-4-yl)oxy)benzonitrile: A suspension of potassium tert-butoxide (28.4 mg, 0.25 mmol) in tetrahydrofuran (1.5 mL) at 0 C was treated with 1'-(trifluoromethyl)spiro[1,3-dioxolane-2,7'-5,6-dihydrocyclopenta[c]pyridine]-4'-ol (60.0 mg, 0.23 mmol) and stirred at 0 C for 15 min. The resulting mixture was treated with (3-cyano-5-fluoro-phenyl)-(4-methoxyphenyl)iodonium; 4-methylbenzenesulfonate (144.8 mg, 0.28 mmol) and heated to 40 C. The reaction mixture was filtered through a plastic filter cup using EtOAc to rinse. Volatiles were removed by concentration under reduced pressure. Purification was achieved by chromatography on silica using 10-40% EtOAc/hexane to afford a solid (42 mg, 48%). LCMS ESI (+) (M+H) m/z 381.

Step C: Preparation of 3-fluoro-5-((7-oxo-1-(trifluoromethyl)-6,7-dihydro-5H-cyclopenta[c]pyridin-4-yl)oxy)benzonitrile: A solution of 3-fluoro-5-[1'-(trifluoromethyl)spiro[1,3-dioxolane-2,7'-5,6-dihydrocyclopenta[c]pyridine]-4'-yl]oxy-benzonitrile (42.0 mg, 0.11 mmol) in dichloromethane (2.0 mL) at 0 C was treated with perchloric acid (70% in water, 240 µL) and stirred at 0 C for 30 min. The reaction mixture was carefully quenched by the addition of 15 mL of saturated NaHCO$_3$ and extracted with 3×15 mL CH$_2$Cl$_2$. The combined organics were rinsed with 10 mL of brine, dried with MgSO$_4$, filtered, and concentrated to dryness. The solid residue was used immediately in the next step without further purification. LCMS ESI (+) (M+H) m/z 337.

Step D: Preparation of 3-((7-((tert-butyldimethylsilyl)oxy)-1-(trifluoromethyl)-5H-cyclopenta[c]pyridin-4-yl)oxy)-5-fluorobenzonitrile: A solution of triethylamine (122 µL, 0.88 mmol) and 3-fluoro-5-[[7-oxo-1-(trifluoromethyl)-5,6-dihydrocyclopenta[c]pyridin-4-yl]oxy]benzonitrile (37.0 mg, 0.11 mmol) in dichloromethane (2.2 mL) at 0° C. was treated with tert-butyldimethylsilyl triflate (152 ul, 0.66 mmol). The ice bath was removed and the reaction mixture left to stir for 2 h. The reaction mixture was poured into 30 mL of saturated NaHCO$_3$ and extracted with 3×20 mL CH$_2$Cl$_2$. The combined organics were rinsed with 10 mL of brine, dried with MgSO$_4$, filtered, and concentrated to dryness. The product was used without further purification. LCMS ESI (+) (M+H) m/z 451.

Step E: Preparation of 3-fluoro-5-((6-fluoro-7-oxo-1-(trifluoromethyl)-6,7-dihydro-5H-cyclopenta[c]pyridin-4-yl)oxy)benzonitrile: A solution of 3-[[7-[tert-butyl(dimethyl)silyl]oxy-1-(trifluoromethyl)-5H-cyclopenta[c]pyridin-4-yl]oxy]-5-fluoro-benzonitrile (49.56 mg, 0.1100 mmol) in acetonitrile (2.2 mL) at 25° C. was treated with Selectfluor® (42.9 mg, 0.12 mmol) and stirred at 25° C. for 1 h. Volatiles were removed by concentration under reduced pressure The reaction mixture was poured into 30 mL of water and extracted with 3×10 mL EtOAc. The combined organics were rinsed with 10 mL of brine, dried with MgSO$_4$, filtered, and concentrated to dryness. Purification was achieved by chromatography on silica using 10-25% EtOAc/hexane to afford a thin film (37.8 mg, 97%). LCMS ESI (+) (M+H) m/z 355.

Step F: Preparation of 3-fluoro-5-((((6R,7S)-6-fluoro-7-hydroxy-1-(trifluoromethyl)-6,7-dihydro-5H-cyclopenta[c]pyridin-4-yl)oxy)benzonitrile (Compound 467): A solution of 3-fluoro-5-[[6-fluoro-7-oxo-1-(trifluoromethyl)-5,6-dihydrocyclopenta[c]pyridin-4-yl]oxy]benzonitrile (15.3 mg, 0.043 mmol) in dichloromethane (1.5 mL) was cooled to 0° C. and sparged with nitrogen for 5 min. During this time formic acid (4.9 µL, 0.13 mmol) and triethylamine (12.0 µL, 0.086 mmol) were sequentially added. Once the sparging was complete, RuCl(p-cymene)[(R,R)-Ts-DPEN] (0.5 mg, 0.00086 mmol) was added under a continuous stream of nitrogen. The reaction vessel was sealed and placed into the refrigerator to react overnight. Volatiles were removed by concentration under reduced pressure. The residue was purified by chromatography on silica using 10-30% EtOAc/hexane to afford 3-fluoro-5-(((6R,7S)-6-fluoro-7-hydroxy-1-(trifluoromethyl)-6,7-dihydro-5H-cyclopenta[c]pyridin-4-yl)oxy)benzonitrile (Compound 467) as a clear solid (11.8 mg, 77%). Retention time HPLC (14 min)=4.19 min; LCMS ESI (+) (M+H) m/z 357; $^1$H NMR (400 MHz, CDCl$_3$): δ 8.33 (s, 1H), 7.22 (ddd, 1H), 7.10-7.08 (m, 1H), 6.99 (dt, 1H), 5.54-5.46 (m, 1H), 5.46-5.28 (m, 1H), 3.26 (ddd, 1H), 3.11 (ddd, 1H), 2.67 (dd, 1H).

Example 10: Synthesis of 3-fluoro-5-(((6R,7S)-6-fluoro-7-hydroxy-1-(methylsulfonyl)-6,7-dihydro-5H-cyclopenta[c]pyridin-4-yl)oxy)benzonitrile (Compound 468)

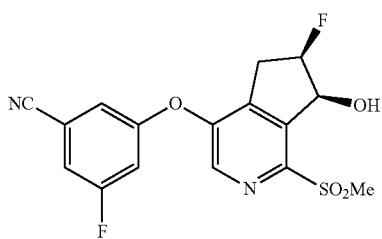 [SMILES: CS(=O)(=O)c1ncc(Oc2cc(F)cc(C#N)c2)c2c1[C@H](O)[C@H](F)C2]

Step A: Preparation of 5-bromo-2-(methylthio)nicotinic acid: A solution of 5-bromo-2-fluoro-pyridine-3-carboxylic acid (3.50 g, 15.91 mmol) in DMF (62 mL) at 0° C. was treated with potassium carbonate (2.42 g, 17.5 mmol) and vigorously stirred at 0° C. for 7 minutes. During this time, nitrogen was sparged through the solution. Then sodium thiomethoxide (1.23 g, 16.7 mmol) was added in one portion to the reaction vessel under continuous nitrogen stream. The reaction vessel was sealed and the ice bath removed. The solution turned from a tan color to faint yellow. The reaction mixture was left to stir overnight. The reaction mixture was poured onto 10% citirc acid solution inducing precipitation of a white solid. The solid was filtered and rinsed exhaustively with water. Finally, the white solid was dried overnight under high vacuum in the presence of solid NaOH and used without further purification (3.63 g, 92%). LCMS ESI (+) (M+H) m/z 248/250.

Step B: Preparation of 5-bromo-4-formyl-2-(methylthio)nicotinic acid: A solution of 2,2,6,6-tetramethyl-piperidine (3.26 mL, 19.35 mmol) in tetrahydrofuran (40.3 mL) at −50 C was treated with n-butyllithium (~2.5M in hexanes, 7.09 mL, 17.73 mmol) and stirred for 5 min. Then 5-bromo-2-methylsulfanyl-pyridine-3-carboxylic acid (2.00 g, 8.06 mmol) was added via cannula over 30 min as a solution in 60 mL of THF. The resulting mixture stirred for 30 min at −50 C. The reaction mixture was quenched by the addition of N,N-dimethylformamide (0.94 mL, 12.09 mmol). 15 minutes following addition of the DMF, the reaction mixture was quenched by the addition of 40 mL of 10% citric acid solution (aqueous) and the reaction warmed to room temperature. After stirring for 30 min, excess THF removed by concentration under reduced pressure. The leftover mixture was poured into 120 mL of 3% citric acid (aqueous) and extracted with 3×50 mL EtOAc. The combined organics were dried with MgSO$_4$, filtered, and concentrated to dryness. 2.41 g of an orange solid was isolated and used without further purification. The material was contaminated with about 22% citric acid based on proton integration of the unpurified NMR spectra. LCMS ESI (+) (M+H) m/z 276/278.

Step C: Preparation of methyl (E)-5-bromo-4-(3-ethoxy-3-oxoprop-1-en-1-yl)-2-(methylthio)nicotinate: A solution of 7-bromo-1-hydroxy-4-methylsulfanyl-1H-furo[3,4-c]pyridin-3-one (2.21 g, 8.00 mmol), lithium chloride (anhydrous, 339.1 mg, 8.00 mmol) and ethyl 2-diethoxyphosphorylacetate (1.60 mL, 8.00 mmol) in acetonitrile (80 mL) at 25 C was treated with 1;8-Diazabicyclo[5.4.0]undec-7-ene (2.87 mL, 19.20 mmol) and stirred at 25 C for 2 h. Initially, the solution is heterogenous with the pyridine being insoluble. Upon addition of the DBU the solution becomes homogeneous and darkens in color. After 1 h, the reaction appears to be mostly complete. In addition a precipitate has formed. Volatiles were removed by concentration under reduced pressure. The product residue was solubilized with 25 mL of DMF and treated with dimethyl sulfate (1.89 mL, 20.00 mmol). After 2 h, the reaction mixture was poured into 300 mL of water and extracted with 4×40 mL Et$_2$O. The combined organics were rinsed with 20 mL of brine, dried with MgSO$_4$, filtered, and concentrated to dryness. Purification was achieved by chromatography on silica using 5-20% EtOAc/hexane to afford methyl (E)-5-bromo-4-(3-ethoxy-3-oxoprop-1-en-1-yl)-2-(methylthio)nicotinate as a white solid (1.90 g, 66%). LCMS ESI (+) (M+H) m/z 360/362.

Step D: Preparation of methyl 5-bromo-4-(3-ethoxy-3-oxopropyl)-2-(methylthio)nicotinate: A solution of methyl 5-bromo-4-[(E)-3-ethoxy-3-oxo-prop-1-enyl]-2-methylsulfanyl-pyridine-3-carboxylate (1.87 g, 5.19 mmol) and cobalt (ii) chloride hexahydrate (123.5 mg, 0.52 mmol) in methanol (20.8 mL) at 0° C. was sparged with nitrogen for 3 min and treated with sodium borohydride (98.2 mg, 2.60 mmol) under continuous nitrogen stream. The vessel was sealed and the contents stirred at 0° C. for 10 min. LCMS at this time indicated partial consumption of the olefin. An additional portion of sodium borohydride (98.2 mg, 2.60 mmol) was added to drive the reaction to completion. The reaction mixture was quenched by the addition of 30 mL of saturated aqueous NH$_4$Cl. Volatiles were removed by concentration under reduced pressure. The reaction mixture was poured into 30 mL of water and extracted with 3×40 mL EtOAc. The combined organics were rinsed with 10 mL of brine, dried with MgSO$_4$, filtered, and concentrated to dryness. Purification was achieved by chromatography on silica using 5-15% EtOAc/hexane to afford the desired product as a solid (1.08 g, 57%). LCMS ESI (+) (M+H) m/z 362/364.

Step E: Preparation of ethyl 4-bromo-1-(methylthio)-5,6-dihydro-7H-cyclopenta[c]pyridin-7-one: A solution of methyl 5-bromo-4-(3-ethoxy-3-oxo-propyl)-2-methylsulfanyl-pyridine-3-carboxylate (1.08 g, 2.98 mmol) in tetrahydrofuran (29.8 mL) at −78° C. was treated with lithium bis(trimethylsilyl)amide (~1.0 M in THF, 7.16 mL, 7.16 mmol) by dropwise addition over 30 minutes. Once the addition was complete, LCMS indicated a small amount of starting material remained so an additional 1 mL of lithium bis(trimethylsilyl)amide was added and the reaction allowed to stir for a further 15 minutes. The reaction mixture was quenched by the addition of 30 mL of saturated aqueous NH$_4$Cl. THF was removed by concentration under reduced pressure. The reaction mixture diluted with 60 mL of EtOAc and an additional 30 mL of water. A thick precipitate formed that could be eliminated by the addition of 10% citric acid solution. The reaction mixture was extracted with 3×30 mL EtOAc. The combined organics were rinsed with 10 mL of brine, dried with MgSO$_4$, filtered, and concentrated to dryness. The intermediate product was transferred into a microwave tube using 9.1 mL of DMSO. The resulting mixture was diluted with 900 μL of water. The vessel was sealed and heated to 150 C by microwave irradiation for 40 min. The reaction mixture was diluted with 120 mL of water to induce precipitation of the product and vigorously stirred for 30 min. The precipitate was collected, dried overnight under high vacuum in the presence of solid NaOH, and used without further purification. Beige solid (705 mg, 92%). LCMS ESI (+) (M+H) m/z 258/260.

Step F: Preparation of 4-bromo-1-(methylsulfonyl)-5,6-dihydro-7H-cyclopenta[c]pyridin-7-one: A solution of 4-bromo-1-methylsulfanyl-5,6-dihydrocyclopenta[c]pyridin-7-one (364.5 mg, 1.41 mmol) in methanol (11.3 mL) at 0° C. was treated with a solution of Oxone® (1.91 g, 3.11 mmol) in water (11.3 mL). The reaction was left to stir for 24 h. Volatiles were removed by concentration under reduced pressure. The reaction mixture was poured into 40 mL of water and extracted with 3×20 mL EtOAc. The combined organics were rinsed with 10 mL of brine, dried with MgSO$_4$, filtered, and concentrated to dryness. The off white solid was used without further purification. LCMS ESI (+) (M+H) m/z 290/292.

Step G: Preparation of 4-bromo-1-(methylsulfonyl)-5,6-dihydrospiro[cyclopenta[c]pyridine-7,2'-[1,3]dioxolane]: Trimethylsilyl trifluoromethanesulfonate (331 μL, 1.83 mmol) was added to a solution of 4-bromo-1-methylsulfonyl-5,6-dihydrocyclopenta[c]pyridin-7-one (354 mg, 1.22 mmol) and trimethyl(2-trimethylsilyloxyethoxy)silane (1.20 mL, 4.88 mmol) in dichloromethane (14 mL) cooled in an ice bath. The ice bath was removed. After 3 h, an additional portion of trimethyl(2-trimethylsilyloxyethoxy)silane (1.20 mL, 4.88 mmol) was added. The reaction was left to stir overnight. After stirring, for the rest of the day, the reaction was quenched by the addition of triethylamine (1.02 mL, 7.32 mmol). The reaction mixture stirred for 10 min. Volatiles were removed and the residue suspended into 30 mL of saturated aqueous NaHCO$_3$ and extracted with 3×20 mL EtOAc. The combined organics were rinsed with 10 mL of brine, dried with MgSO4, filtered, and concentrated to dryness. Purification was achieved by chromatography on silica using 15-50% EtOAc/hexane to afford 4-bromo-1-(methylsulfonyl)-5,6-dihydrospiro[cyclopenta[c]pyridine-7,2'-[1,3]dioxolane] as a white solid (74.5 mg, 18%). LCMS ESI (+) (M+H) m/z 334/336. The bulk of the product was isolated as the enol ether (295 mg, 59%).

Step H: Preparation of 1-(methylsulfonyl)-5,6-dihydrospiro[cyclopenta[c]pyridine-7,2'-[1,3]dioxolan]-4-ol: A solution of 4'-bromo-1'-methylsulfonyl-spiro[1,3-dioxolane-2,7'-5,6-dihydrocyclopenta[c]pyridine] (74.5 mg, 0.22 mmol) and 2-(di-t-butylphosphino)-3,6-dimethoxy-2',4',6'-tri-i-propyl-1,1'-biphenyl (5.4 mg, 0.011 mmol) in 1,4-dioxane (1.5 mL) was sparged with nitrogen for 3 mins. The reaction mixture was then treated sequentially with potassium hydroxide (37.5 mg, 0.67 mmol), water (80.3 μL, 4.46 mmol) and [2-(2-aminophenyl)phenyl]-methylsulfonyloxypalladium; ditert-butyl-[3,6-dimethoxy-2-(2,4,6-triisopropylphenyl)phenyl]phosphane (9.5 mg, 0.011 mmol) under continuous nitrogen stream. The vessel was sealed and heated to 80 C for 1 h and 30 min. The reaction mixture was quenched by the addition of acetic acid (51.0 μL, 0.89 mmol). The reaction mixture was poured into 75 mL of water and extracted with 4×20 mL EtOAc. The combined organics were dried with MgSO$_4$, filtered, and concentrated to dryness. The product was used without further purification (77.9 mg). LCMS ESI (+) (M+H) m/z 272.

Step I: Preparation of 3-fluoro-5-((1-(methylsulfonyl)-5,6-dihydrospiro[cyclopenta[c]pyridine-7,2'-[1,3]dioxolan]-4-yl)oxy)benzonitrile: A suspension of potassium carbonate (30.6 mg, 0.22 mmol) in acetonitrile (1.5 mL) at 25 C was treated with 1'-methylsulfonylspiro[1,3-dioxolane-2,7'-5,6-dihydrocyclopenta[c]pyridine]-4'-ol (40.0 mg, 0.15 mmol) and stirred at 25 C for 10 min. The resulting mixture was treated with (3-cyano-5-fluoro-phenyl)-(4-methoxyphenyl)iodonium; 4-methylbenzenesulfonate (116.2 mg, 0.22 mmol) and heated to 50 C for 3 h. Volatiles were removed by concentration under reduced pressure. The reaction mixture was poured into 20 mL of water and extracted with 3×15 mL EtOAc. The combined organics were rinsed with 10 mL of brine, dried with MgSO$_4$, filtered, and concentrated to dryness. Purification was achieved by chromatography on silica using 20-50% EtOAc/hexane to afford (3-fluoro-5-((1-(methylsulfonyl)-5,6-dihydrospiro[cyclopenta[c]pyridine-7,2'-[1,3]dioxolan]-4-yl)oxy)benzonitrile as a solid (25.1 mg, 44%). LCMS ESI (+) (M+H) m/z 391.

Step J: Preparation of 3-fluoro-5-((1-(methylsulfonyl)-7-oxo-6,7-dihydro-5H-cyclopenta[c]pyridin-4-yl)oxy)benzonitrile: A solution of 4'-(3,3-difluorocyclobutoxy)-6'-fluoro-1'-methylsulfonyl-spiro[1,3-dioxolane-2,7'-5,6-dihydrocyclopenta[c]pyridine] (25.1 mg, 0.064 mmol) in dichloromethane (3.0 mL) at 0 C was treated with perchloric acid (70% in water, 330 μL) and stirred at 0 C for 2 h and then at room temperature for 30 min. The reaction mixture was carefully quenched with 5 mL of saturated NaHCO$_3$/10 mL of water and extracted with 3×15 mL CH$_2$Cl$_2$. The combined organics were rinsed with 10 mL of brine, dried with MgSO$_4$, filtered, and concentrated to dryness. The product was used without further purification. LCMS ESI (+) (M+H) m/z 347.

Step K: Preparation of 3-((7-((tert-butyldimethylsilyl)oxy)-1-(methylsulfonyl)-5H-cyclopenta[c]pyridin-4-yl)oxy)-5-fluorobenzonitrile: A solution of triethylamine (71.4 μL, 0.51 mmol) and 3-fluoro-5-[[7-oxo-1-(trifluoromethyl)-5,6-dihydrocyclopenta[c]pyridin-4-yl]oxy]benzonitrile (22.2 mg, 0.064 mmol) in dichloromethane (3.0 mL) at 0° C. was treated with tert-butyldimethylsilyl trifluoromethanesulfonate (58.2 μL, 0.38 mmol). The ice bath was removed and the reaction mixture stirred for 2 h. The reaction mixture was poured into 30 mL of saturated NaHCO$_3$ and extracted with 3×20 mL CH$_2$Cl$_2$. The combined organics were rinsed with 10 mL of brine, dried with MgSO$_4$, filtered, and concentrated to dryness. The product was used without further purification. LCMS ESI (+) (M+H) m/z 461.

Step L: Preparation of 3-fluoro-5-((6-fluoro-1-(methylsulfonyl)-7-oxo-6,7-dihydro-5H-cyclopenta[c]pyridin-4-yl)oxy)benzonitrile: A solution of 3-[[7-tert-butyl(dimethyl)silyl]oxy-1-(trifluoromethyl)-5H-cyclopenta[c]pyridin-4-yl]oxy]-5-fluoro-benzonitrile (29.5 mg, 0.064 mmol) in acetonitrile (2.6 mL) at 25° C. was treated with Selectfluor® (24.9 mg, 0.070 mmol) and stirred at 25° C. for 1 h. Volatiles were removed by concentration under reduced pressure. The reaction mixture was poured into 30 mL of water and extracted with 3×10 mL EtOAc. The combined organics were rinsed with 10 mL of brine, dried with MgSO$_4$, filtered, and concentrated to dryness. Purification was achieved by chromatography on silica using 10-25% EtOAc/hexane to afford 3-fluoro-5-((6-fluoro-1-(methylsulfonyl)-7-oxo-6,7-dihydro-5H-cyclopenta[c]pyridin-4-yl)oxy)benzonitrile as a thin film (11.1 mg, 48%). LCMS ESI (+) (M+H) m/z 365.

Step M: Preparation of 3-fluoro-5-(((6R,7S)-6-fluoro-7-hydroxy-1-(methylsulfonyl)-6,7-dihydro-5H-cyclopenta[c]pyridin-4-yl)oxy)benzonitrile (Compound 468): A solution of 6-fluoro-4-[(5-fluoro-3-pyridyl)oxy]-1-(trifluoromethyl)-

5,6-dihydrocyclopenta[c]pyridin-7-one (11.1 mg, 0.031 mmol) in dichloromethane (2.0 mL) was cooled to 0° C. and sparged with nitrogen for 5 min. During this time formic acid (3.4 μL, 0.091 mmol) and triethylamine (8.4 μL, 0.061 mmol) were sequentially added. Once the sparging was complete, RuCl(p-cymene)[(R,R)-Ts-DPEN] (0.4 mg, 0.0006 mmol) was added under a continuous stream of nitrogen. The reaction vessel was sealed and put into the refrigerator to react overnight. Volatiles were removed by concentration under reduced pressure. The residue was purified by chromatography on silica using 20-60% EtOAc/hexane to afford 3-fluoro-5-(((6R,7S)-6-fluoro-7-hydroxy-1-(methylsulfonyl)-6,7-dihydro-5H-cyclopenta[c]pyridin-4-yl)oxy)benzonitrile (Compound 468) as a white solid (7.0 mg, 63%). Retention time HPLC (14 min)=3.16 min; LCMS ESI (+) (M+H) m/z 367; $^1$HNMR (400 MHz, CDCl$_3$): δ 8.27 (s, 1H), 7.25 (ddd, 1H), 7.14 (m, 1H), 7.03 (dt, 1H), 5.69 (dt, 1H), 5.53-5.36 (m, 1H), 4.24 (d, 1H), 3.34 (s, 3H), 3.31-3.24 (m, 1H), 3.09 (ddd, 1H).

Example 11: Synthesis of 4-bromo-1-(3,5-difluorophenoxy)-6,7-dihydro-5H-cyclopenta[c]pyridine (Compound 469) and 4-(difluoromethylsulfonyl)-1-(3,5-difluorophenoxy)-6,7-dihydro-5H-cyclopenta[c]pyridine (Compound 470)

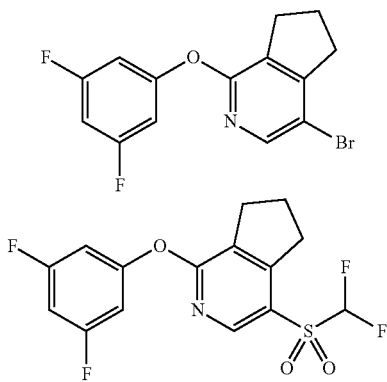

Step A: 4-bromo-1-chloro-6,7-dihydro-5H-cyclopenta[c]pyridine: A mixture of 4-bromo-2,5,6,7-tetrahydrocyclopenta[c]pyridin-1-one (420 mg, 1.96 mmol) and POCl$_3$ (2.20 mL, 23.6 mmol) was heated at reflux for 40 hours. After cooling, excess POCl$_3$ was removed under reduced pressure. The residue was taken up in EtOAc, washed with saturated aqueous NaHCO$_3$ and brine, dried and concentrated. The residue was purified by column chromatography on silica gel (2-10% EtOAc/hexanes) to give 4-bromo-1-chloro-6,7-dihydro-5H-cyclopenta[c]pyridine (207 mg, 45%). LCMS ESI (+) m/z 232/234/236 (M+H)$^+$.

Step B: 4-bromo-1-(3,5-difluorophenoxy)-6,7-dihydro-5H-cyclopenta[c]pyridine (Compound 469): A mixture of 4-bromo-1-chloro-6,7-dihydro-5H-cyclopenta[c]pyridine (62 mg, 0.27 mmol), 3,5-difluorophenol (38 mg, 0.29 mmol), cesium carbonate (130 mg, 0.400 mmol) and NMP (1.8 mL) was heated at 90° C. overnight under nitrogen. The reaction mixture was heated to 140° C. and stirred overnight again. After cooling, the reaction mixture was partitioned between EtOAc and water. The aqueous layer was extracted with EtOAc. The combined organic layers were washed with brine, dried and concentrated. The residue was purified by Biotage C18 reverse phase flash chromatography (20-95% acetonitrile/water) to give 4-bromo-1-(3,5-difluorophenoxy)-6,7-dihydro-5H-cyclopenta[c]pyridine (Compound 469, 21 mg, 24%) as a pale yellow solid. LCMS ESI (+) m/z 326/328 (M+H)$^+$.

Step C: S-[1-(3,5-difluorophenoxy)-6,7-dihydro-5H-cyclopenta[c]pyridin-4-yl]ethanethioate: To a vial containing a solution of 4-bromo-1-(3,5-difluorophenoxy)-6,7-dihydro-5H-cyclopenta[c]pyridine (20 mg, 0.060 mmol) in 1,4-dioxane (0.3 mL) were added acetylsulfanylpotassium (8.8 mg, 0.080 mmol) and (5-diphenylphosphanyl-9,9-dimethylxanthen-4-yl)-diphenyl-phosphane (4.3 mg, 0.010 mmol). The mixture was sparged with nitrogen. Then tris(dibenzylideneacetone)dipalladium(0) (3.4 mg, 0.004 mmol) was added, and the vial was sealed and heated at 110° C. for 4 hours. After cooling, the reaction mixture was filtered through Celite. The filtrate was concentrated. The residue was purified by Biotage C18 reverse phase flash chromatography (10-80% acetonitrile/water) to give S-[1-(3,5-difluorophenoxy)-6,7-dihydro-5H-cyclopenta[c]pyridin-4-yl]ethanethioate (10 mg, 51%). LCMS ESI (+) m/z 322 (M+H)$^+$.

Step D: 1-(3,5-difluorophenoxy)-6,7-dihydro-5H-cyclopenta[c]pyridine-4-thiol: To a stirred solution of S-[1-(3,5-difluorophenoxy)-6,7-dihydro-5H-cyclopenta[c]pyridin-4-yl] ethanethioate (10 mg, 0.030 mmol) in MeOH (0.3 mL) was added 1 N LiOH solution (0.050 mL, 0.050 mmol). The reaction mixture was stirred at ambient temperature for 30 minutes and then concentrated. To the residue was added water. The pH was added to 2-3 using 0.1 N HCl. The mixture was extracted with EtOAc. The combined organic layers were washed with brine, dried and concentrated. The crude was used in the next step without further purification. LCMS ESI (+) m/z 280 (M+H)$^+$.

Step E: 4-(difluoromethylsulfanyl)-1-(3,5-difluorophenoxy)-6,7-dihydro-5H-cyclopenta[c]pyridine: To a stirred solution of crude 1-(3,5-difluorophenoxy)-6,7-dihydro-5H-cyclopenta[c]pyridine-4-thiol (9 mg, 0.03 mmol) in acetonitrile (0.3 mL) was added potassium hydroxide (36 mg, 0.64 mmol) in water (0.3 mL). The reaction mixture was purged with nitrogen and then cooled to −78° C. Bromodifluoromethyl diethylphosphonate (17 mg, 0.060 mmol) was added. The resulting mixture was allowed to warm to ambient temperature and stirred for 3 hours. The reaction mixture was partitioned between EtOAc and water. The aqueous layer was extracted with EtOAc. The combined organics were washed with water and brine, dried over Na$_2$SO4, filtered, and concentrated to dryness. The crude was used in the next step without further purification. LCMS ESI (+) m/z 330 (M+H)$^+$.

Step F: 4-(difluoromethylsulfonyl)-1-(3,5-difluorophenoxy)-6,7-dihydro-5H-cyclopenta[c]pyridine (Compound 470): Sodium periodate (18 mg, 0.080 mmol) was added all at once to crude 4-(difluoromethylsulfanyl)-1-(3,5-difluorophenoxy)-6,7-dihydro-5H-cyclopenta[c]pyridine (11 mg, 0.030 mmol) and ruthenium(III) chloride (0.2 mg, 0.001 mmol) in acetonitrile (0.2 mL)/CCl$_4$ (0.2 mL)/water (0.4 mL). The reaction mixture was stirred at ambient temperature for 3 hours. Solids were removed by filtration and rinsed with CH$_2$Cl$_2$. The organic layer was separated. The aqueous layer was extracted with CH$_2$Cl$_2$. The combined organics were washed with brine, dried over Na$_2$SO$_4$, filtered and concentrated in vacuo. The crude product was purified by column chromatography on silica gel (4-12% EtOAc/hexanes) affording Compound 470 (3 mg, 25% overall yield for three steps) as a white solid. LCMS ESI (+) m/z 362

(M+H)⁺. ¹HNMR (400 MHz, CDCl₃): δ 7.49 (s, 1H), 6.80-6.71 (m, 3H), 6.19 (t, 1H), 3.36 (t, 2H), 3.06 (t, 2H), 2.31-2.23 (m, 2H).

Example 12: Synthesis of racemic 3-fluoro-5-((6R, 7S)-6-fluoro-7-hydroxy-1-(trifluoromethyl)-6,7-dihydro-5H-cyclopenta[c]pyridin-4-yl)benzonitrile (Compound 471)

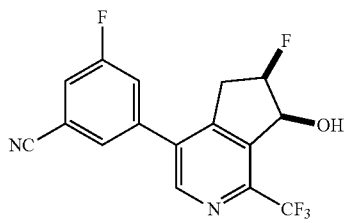 [SMILES: N#Cc1cc(F)cc(-c2cnc(C(F)(F)F)c3c2C[C@@H](F)[C@H]3O)c1]

Step A: Preparation of racemic (6R,7S)-4-bromo-6-fluoro-1-(trifluoromethyl)-6,7-dihydro-5H-cyclopenta[c]pyridin-7-ol: A solution of 4-bromo-6-fluoro-1-(trifluoromethyl)-5,6-dihydrocyclopenta[c]pyridin-7-one (6.7 mg, 0.022 mmol) in methanol (0.8 mL) at 0° C. was treated with sodium borohydride (0.9 mg, 0.022 mmol) and stirred at 0° C. for 10 min. The reaction mixture was quenched by the addition of 0.2 mL of saturated NH₄Cl. Volatiles were removed by concentration under reduced pressure. The reaction mixture was poured into 20 mL of water and extracted with 3×10 mL EtOAc. The combined organics were rinsed with 10 mL of brine, dried with MgSO₄, filtered, and concentrated to dryness. The product was used without further purification. LCMS ESI (+) (M+H) m/z 300/302.

Step B: Preparation of racemic 3-fluoro-5-((6R,7S)-6-fluoro-7-hydroxy-1-(trifluoromethyl)-6,7-dihydro-5H-cyclopenta[c]pyridin-4-yl)benzonitrile (Compound 471): A suspension of racemic (6R,7S)-4-bromo-6-fluoro-1-(trifluoromethyl)-6,7-dihydro-5H-cyclopenta[c]pyridin-7-ol (6.7 mg, 0.022 mmol), 3-cyano-5-fluorophenylboronic acid (5.5 mg, 0.033 mmol), cesium fluoride (10.5 mg, 0.069 mmol) and bis(di-tert-butyl(4-dimethylaminophenyl)phosphine)dichloropalladium(II) (0.8 mg, 0.0011 mmol) in a mixture 1,4-dioxane (0.8 mL) and water (80 µL) was sparged with nitrogen for 3 mins. The vessel was sealed and heated to 80° C. for 1 h. LCMS indicates product formation. The reaction mixture was poured into 60 mL of water and extracted with 3×20 mL EtOAc. The combined organics were rinsed with 10 mL of brine, dried with MgSO₄, filtered, and concentrated to dryness. Purification was achieved by chromatography on silica using 10-30% EtOAc/hexane to afford racemic 3-fluoro-5-((6R,7S)-6-fluoro-7-hydroxy-1-(trifluoromethyl)-6,7-dihydro-5H-cyclopenta[c]pyridin-4-yl)benzonitrile (Compound 471) as an orange solid (1.8 mg, 24%). Retention time HPLC (14 min)=3.80 min; LCMS ESI (+) (M+H) m/z 341; NMR (400 MHz, CDCl₃): δ 8.65 (s, 1H), 7.53-7.48 (m, 2H), 7.40 (ddd, 1H), 5.56-5.48 (m, 1H), 5.35 (ddt, 1H), 3.41 (ddd, 1H), 3.21 (ddd, 1H), 2.65 (dd, 1H).

Example 13: Synthesis of (S)-1-((1S,3R)-2,2,3-trifluoro-1-hydroxy-7-(methylsulfonyl)-2,3-dihydro-1H-inden-4-yl)piperidin-3-ol (Compound 484)

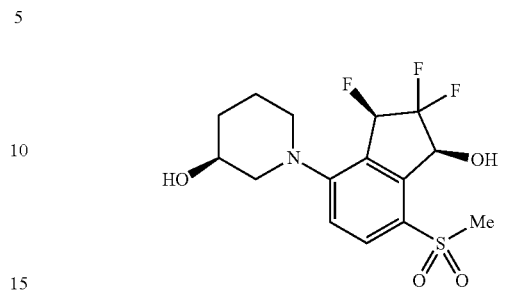

Step A: Preparation of 4,7-difluoro-1H-indene-1,3(2H)-dione: A solution of 3,6 difluorophthalic anhydride (4.25 g, 23.1 mmol), tert-butyl 3-oxobutanoate (4.29 mL, 25.9 mmol) and acetic anhydride (21.0 mL, 221.6 mmol) at 25° C. was treated with triethylamine (11.7 mL, 84.3 mmol) and stirred at ambient temperature for 18 hours. The reaction mixture was cooled to 0° C. and treated with 10% hydrochloric acid (65 mL, 211 mmol) by dropwise addition. Once the addition was complete, the ice bath was removed and the mixture stirred at ambient for 10 minutes. The mixture was then heated to 75° C. for 10 minutes. During this time gas evolution was observed. The suspension slowly broke up to form a clear red mixture. The reaction mixture was poured into 100 mL of water and extracted with 3×50 mL CH₂Cl₂. The combined organics were dried with MgSO₄, filtered, and concentrated to dryness. The product was used without further purification.

Step B: Preparation of 2,2,4,7-tetrafluoro-1H-indene-1,3 (2H)-dione: A solution of the unpurified 4,7-difluoro-1H-indene-1,3(2H)-dione (4.2 g, 23.1 mmol) in acetonitrile (100 mL) cooled in a 25° C. water bath was treated with sodium carbonate (5.38 g, 50.7 mmol). Selectfluor® (17.97 g, 50.7 mmol) was added and the reaction mixture was stirred at ambient temperature for 1 hour. Volatiles were removed under reduced pressure and the residue was poured into 100 mL of 0.1% HCl and extracted with 3×50 mL EtOAc. The combined organics were rinsed with 40 mL of brine, dried with MgSO₄, filtered, and concentrated to dryness. The residue was purified by flash chromatography on silica gel 1:1 hexane/ethyl acetate to give 2,2,4,7-tetrafluoro-1H-indene-1,3(2H)-dione (3.5 g, 70%) as a solid. ¹H NMR (400 MHz, CDCl₃): δ 7.70 (t, 2H).

Step C: Preparation of (S)-2,2,4,7-tetrafluoro-3-hydroxy-2,3-dihydro-1H-inden-1-one: To a solution of 2,2,4,7-tetrafluoro-1H-indene-1,3(2H)-dione (3.48 g, 16.0 mmol) in dichloromethane (150 mL) at 0° C. was added formic acid (600 µL, 16.0 mmol) and triethylamine (1.55 mL, 11.2 mmol). The resulting mixture was sparged with nitrogen for 5 minutes and then RuCl(p-cymene)[(S,S)-Ts-DPEN] (203.6 mg, 0.32 mmol) was added. The reaction vessel was sealed and put into a 4° C. refrigerator to stand for 18 hours. The reaction mixture was poured into 40 mL 1 N HCl. The CH₂Cl₂ layer was separated and the aqueous layer extracted with ethyl acetate (2×50 mL). The combined organics were dried with Na₂SO₄, filtered and concentrated under reduced pressure. The residue was purified by flash chromatography on silica gel using 25% EtOAc/hexane to give (S)-2,2,4,7-tetrafluoro-3-hydroxy-2,3-dihydro-1H-inden-1-one (2.9 g, 83%) as an oil. ¹H NMR (400 MHz, CDCl₃): δ 7.51 (ddd, 1H), 7.29-7.23 (m, 1H), 5.44 (dd, 1H), 2.79 (dd, 1H).

Step D: Preparation of (S)-2,2,4-trifluoro-3-hydroxy-7-(methylthio)-2,3-dihydro-1H-inden-1-one: A solution of (S)-2,2,4,7-tetrafluoro-3-hydroxy-2,3-dihydro-1H-inden-1-one (966 mg, 4.39 mmol) in acetonitrile (40 mL) at 0° C. was sparged with nitrogen for 5 minutes and treated with sodium thiomethoxide (353.7 mg, 5.05 mmol). The ice bath was removed and the reaction mixture was allowed to stir at ambient temperature for 2 hours. The reaction mixture was evaporated and the residue partitioned between 40 mL of EtOAc and 40 mL of water. The aqueous layer was further extracted with 2×40 mL of EtOAc. The combined organic extracts were washed with brine, dried over MgSO₄, filtered, and evaporated. The residue was chromatographed on silica using 10-60% EtOAc/hexane to afford (S)-2,2,4-trifluoro-3-hydroxy-7-(methylthio)-2,3-dihydro-1H-inden-1-one (870 mg, 80%) as a yellow solid. LCMS ESI (+) m/z 249 (M+H).

Step E: Preparation of (S)-2,2,4-trifluoro-3-hydroxy-7-(methylsulfonyl)-2,3-dihydro-1H-inden-1-one: (S)-2,2,4-trifluoro-3-hydroxy-7-(methylthio)-2,3-dihydro-1H-inden-1-one (400 mg, 1.6 mmol) was dissolved in MeOH (10 mL) and the reaction was treated dropwise with a solution of Oxone® (2.18 g, 3.55 mmol) dissolved in water (10 mL). The mixture was stirred at ambient temperature for 14 hours. The reaction mixture was filtered, the solids were washed with ethyl acetate and the filtrate was concentrated in vacuo. The aqueous filtrate was extracted 3×30 mL of EtOAc and then the combined organics were washed with saturated NaCl, dried over Na₂SO₄ and concentrated in vacuo to a yellow solid that was used without further purification (467 mg). LCMS ESI (+) m/z 281.1 (M+H).

Step F: Preparation of (R)-2,2,3,4-tetrafluoro-7-(methylsulfonyl)-2,3-dihydro-1H-inden-1-one: (S)-2,2,4-trifluoro-3-hydroxy-7-(methylsulfonyl)-2,3-dihydro-1H-inden-1-one (450 mg, 1.6 mmol) was dissolved in dichloromethane (16 mL), cooled to 0° C. and treated dropwise with diethylaminosulfur trifluoride (0.32 mL, 2.4 mmol) and the mixture was stirred at 0° C. for 2 hours, then the whole homogeneous reaction mixture was placed into the refrigerator overnight. The reaction was treated with additional diethylaminosulfur trifluoride (0.32 mL, 2.4 mmol) and stirring continued for 6 hours at 0° C. The cold reaction was treated with saturated NaHCO₃ (10 mL) and stirred vigorously for 20 minutes. The mixture was diluted with additional methylene chloride and the layers were separated. The aqueous was re-extracted with methylene chloride and the combined organic layers were dried over Na₂SO₄ and concentrated in vacuo to a yellow solid. The crude material was chromatographed on SiO₂ (Biotage SNAP Ultra) and eluted with a gradient of ethyl acetate/hexanes. The desired material was concentrated to a pale yellow solid (258 mg). LCMS ESI (+) m/z 283 (M+H).

Step G: Preparation of (R)-2,2,3-trifluoro-4-((S)-3-hydroxypiperidin-1-yl)-7-(methylsulfonyl)-2,3-dihydro-1H-inden-1-one: A solution of (3R)-2,2,3,4-tetrafluoro-7-methylsulfonyl-indan-1-one (28.7 mg, 0.10 mmol) and (3S)-3-piperidinol, hydrochloride (14.0 mg, 0.10 mmol) in DMF (700 µL) was treated with cesium bicarbonate (59.2 mg, 0.31 mmol) and stirred at 35° C. for 3 h. The reaction mixture was poured into 30 mL of water and extracted with 3×10 mL Et₂O. The combined organics were rinsed with 10 mL of brine, dried with MgSO₄, filtered, and concentrated to dryness. The product was used without further purification. LCMS ESI (+) m/z 364 (M+H).

Step H: Preparation of (S)-1-((1S,3R)-2,2,3-trifluoro-1-hydroxy-7-(methylsulfonyl)-2,3-dihydro-1H-inden-4-yl)piperidin-3-ol (Compound 484): A solution of (3R)-2,2,3-trifluoro-4-[(3S)-3-hydroxy-1-piperidyl]-7-methylsulfonyl-indan-1-one (36.3 mg, 0.10 mmol) in dichloromethane (4 mL) was cooled to 0° C. and sparged with nitrogen for 5 min. During this time formic acid (12.1 µL, 0.32 mmol) and triethylamine (27.9 µL, 0.20 mmol) were sequentially added. Once the sparging was complete, RuCl(p-cymene)[(R,R)-Ts-DPEN] (1.3 mg, 2 mol %) was added under a continuous stream of nitrogen. The reaction vessel was sealed and put into the refrigerator to react overnight. Volatiles were removed by concentration under reduced pressure. The residue was purified by chromatography on silica using 45-75% EtOAc/hexane to afford (S)-1-((1S,3R)-2,2,3-trifluoro-1-hydroxy-7-(methylsulfonyl)-2,3-dihydro-1H-inden-4-yl)piperidin-3-ol (Compound 484) as a white solid (23.9 mg, 65%). Retention time HPLC (14 min)=2.63 min; LCMS ESI (+) m/z 366 (M+H); ¹H NMR (400 MHz, CDCl₃): δ 7.97 (dd, 1H), 7.07 (d, 1H), 5.74 (dd, 1H), 5.55 (dd, 1H), 4.01-3.93 (m, 1H), 3.46-3.34 (m, 3H), 3.33 (d, 1H), 3.20-3.13 (m, 1H), 3.18 (s, 3H), 2.01-1.91 (m, 2H), 1.89 (d, 1H), 1.82-1.62 (m, 2H).

Example 14: Synthesis of (S)-2,2-difluoro-4-((1R,3R)-3-hydroxycyclohexyl)-7-((trifluoromethyl)sulfonyl)-2,3-dihydro-1H-inden-1-ol (Compound 480) and (1S)-2,2-difluoro-4-(3-hydroxycyclohex-1-en-1-yl)-7-((trifluoromethyl)sulfonyl)-2,3-dihydro-1H-inden-1-ol (Compound 481) and (S)-2,2-difluoro-4-((1R,3S)-3-hydroxycyclohexyl)-7-((trifluoromethyl)sulfonyl)-2,3-dihydro-1H-inden-1-ol (Compound 482) and (S)-2,2-difluoro-4-((1S,3R)-3-hydroxycyclohexyl)-7-(methylsulfonyl)-2,3-dihydro-1H-inden-1-ol (Compound 483)

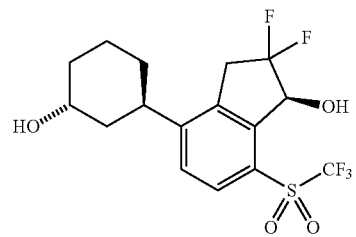

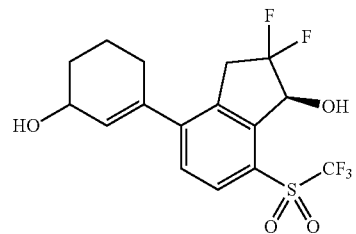

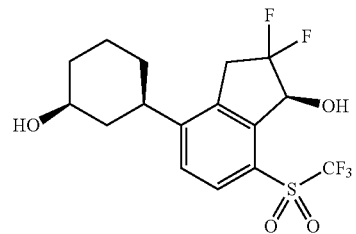

-continued

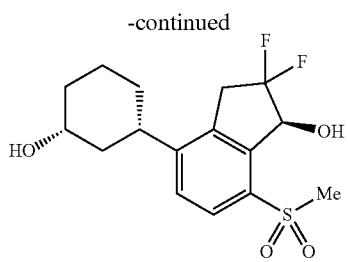

Step A: Preparation of (S)-3-(2,2-difluoro-1-hydroxy-7-((trifluoromethyl)sulfonyl)-2,3-dihydro-1H-inden-4-yl)cyclohex-2-en-1-one: A suspension of (1S)-4-bromo-2,2-difluoro-7-(trifluoromethylsulfonyl)indan-1-ol (102.0 mg, 0.27 mmol), 3-(4,4,5,5-tetramethyl-1,3,2-dioxaborolan-2-yl)cyclohex-2-en-1-one (89.2 mg, 0.40 mmol), cesium fluoride (126.0 mg, 0.83 mmol) and bis(di-tert-butyl(4-dimethylaminophenyl)phosphine)dichloropalladium(II) (9.5 mg, 0.013 mmol) in 1,4-dioxane (4.5 mL) was sparged with nitrogen for 3 mins. The vessel was sealed and heated to 80° C. for 1 h. The reaction mixture was poured into 60 mL of water and extracted with 3×20 mL EtOAc. The combined organics were rinsed with 10 mL of brine, dried with MgSO$_4$, filtered, and concentrated to dryness. Purification was achieved by chromatography on silica using 20-50% EtOAc/hexane. LCMS ESI (−) (M−H) m/z 395.

Step B: Preparation of (S)-2,2-difluoro-4-((1R,3R)-3-hydroxycyclohexyl)-7-((trifluoromethyl)sulfonyl)-2,3-dihydro-1H-inden-1-ol (Compound 480) and (1S)-2,2-difluoro-4-(3-hydroxycyclohex-1-en-1-yl)-7-((trifluoromethyl)sulfonyl)-2,3-dihydro-1H-inden-1-ol (Compound 481) and (S)-2,2-difluoro-4-((1R,3S)-3-hydroxycyclohexyl)-7-((trifluoromethyl)sulfonyl)-2,3-dihydro-1H-inden-1-ol (Compound 482) and (S)-2,2-difluoro-4-((1S,3R)-3-hydroxycyclohexyl)-7-(methylsulfonyl)-2,3-dihydro-1H-inden-1-ol (Compound 483): A solution of 3-[(1S)-2,2-difluoro-1-hydroxy-7-(trifluoromethylsulfonyl)indan-4-yl]cyclohex-2-en-1-one (60.0 mg, 0.15 mmol) in methanol (3.0 mL) at 0° C. was treated with sodium borohydride (11.5 mg, 0.30 mmol) and stirred at 0° C. for 1 h. The reaction mixture was quenched by the addition of 0.5 mL of saturated NH$_4$Cl. Volatiles were removed by concentration under reduced pressure. The reaction mixture was poured into 30 mL of water and extracted with 3×10 mL EtOAc. The combined organics were rinsed with 10 mL of brine, dried with MgSO$_4$, filtered, and concentrated to dryness. Initial purification was achieved by chromatography on silica using 10-40% EtOAc/CH$_2$Cl$_2$ to isolate 2 components. A second purification was necessary on the first eluting component by chromatography on silica using 20-45% EtOAc/hexanes. Finally, each product was purified individually, as described in the characterization section. Data for (S)-2,2-difluoro-4-((1R,3R)-3-hydroxycyclohexyl)-7-((trifluoromethyl)sulfonyl)-2,3-dihydro-1H-inden-1-ol (Compound 480): Final purification was achieved by chromatography on silica using 30-70% EtOAc/hexanes to afford the desired product as a white solid (1.5 mg, 2%). Retention time HPLC (14 min)=4.69 min; LCMS ESI (−) (M+HCO$_2^-$) m/z 445; $^1$H NMR (400 MHz, CDCl$_3$): δ 7.92 (d, 1H), 7.52 (d, 1H), 5.40 (dd, 1H), 4.33-4.28 (m, 1H), 3.59 (ddd, 1H), 3.49 (t, 1H), 3.22-3.13 (m, 2H), 1.97-1.82 (m, 4H), 1.75-1.58 (m, 3H), 1.46 (dd, 1H), 1.42-1.37 (m, 1H). Data for (1S)-2,2-difluoro-4-(3-hydroxycyclohex-1-en-1-yl)-7-((trifluoromethyl)sulfonyl)-2,3-dihydro-1H-inden-1-ol (Compound 481): Final purification was achieved by chromatography on silica using 30-70% EtOAc/hexanes to afford the desired product as a clear solid (3.5 mg, 6%). Retention time HPLC (14 min)= 4.70 min; LCMS ESI (+) (M-OH) m/z 381; $^1$H NMR (400 MHz, CDCl$_3$): δ 7.93 (d, 1H), 7.50 (d, 1H), 5.91-5.88 (m, 1H), 5.39 (dd, 1H), 4.49-4.43 (m, 1H), 3.64 (ddd, 1H), 3.39 (t, 1H), 3.18 (dd, 1H), 2.49-2.39 (m, 1H), 2.22-2.11 (m, 1H), 2.09-1.92 (m, 2H), 1.81-1.59 (m, 3H). Data for (S)-2,2-difluoro-4-((1R,3S)-3-hydroxycyclohexyl)-7-((trifluoromethyl)sulfonyl)-2,3-dihydro-1H-inden-1-ol (Compound 482): Final purification was achieved by chromatography on silica using 30-70% EtOAc/hexanes to afford the desired product as a clear solid (6.7 mg, 11%). Retention time HPLC (14 min)=4.27 min; LCMS ESI (−) (M+HCO$_2^-$) m/z 445; $^1$H NMR (400 MHz, CDCl$_3$): δ 7.94 (d, 1H), 7.55 (d, 1H), 5.41 (dd, 1H), 3.82-3.72 (m, 1H), 3.56 (ddd, 1H), 3.42 (t, 1H), 3.20 (dd, 1H), 2.67 (tt, 1H), 2.17-2.08 (m, 2H), 2.01-1.94 (m, 1H), 1.82-1.75 (m, 1H), 1.60-1.42 (m, 3H), 1.40-1.27 (m, 2H). Data for (S)-2,2-difluoro-4-((1S,3R)-3-hydroxycyclohexyl)-7-(methylsulfonyl)-2,3-dihydro-1H-inden-1-ol (Compound 483): Final purification was achieved by chromatography on silica using 20-60% EtOAc/hexanes to afford the desired product as a white solid (8.6 mg, 14%). Retention time HPLC (14 min)=4.77 min; LCMS ESI (−) (M+HCO$_2^-$) m/z 445; $^1$H NMR (400 MHz, CDCl$_3$): δ 7.94 (d, 1H), 7.55 (d, 1H), 5.41 (dd, 1H), 3.82-3.72 (m, 1H), 3.58 (ddd, 1H), 3.40 (t, 1H), 3.18 (d, 1H), 2.67 (tt, 1H), 2.16-2.06 (m, 2H), 2.02-1.95 (m, 1H), 1.86-1.78 (m, 1H), 1.58-1.28 (m, 5H).

Example 15: (S)-3-((2,2-difluoro-1-hydroxy-7-((trifluoromethyl)sulfonyl)-2,3-dihydro-1H-inden-4-yl)amino)-5-fluorobenzonitrile (Compound 489)

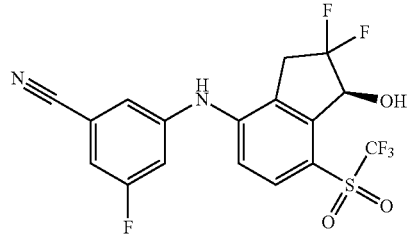 [SMILES: N#Cc1cc(F)cc(Nc2ccc(S(=O)(=O)C(F)(F)F)c3c2CC(F)(F)[C@H]3O)c1]

Step A: Preparation of 4-bromophenyl 3-chloropropanoate: A solution of 4-bromophenol (45.0 g, 260 mmol) in dichloromethane (1.0 L) was cooled to 0° C., treated with triethylamine (44.7 g, 442 mmol). A solution of 3-chloropropionyl chloride (36.3 g, 286 mmol) dissolved in dichloromethane (100 mL) was added dropwise to the reaction vessel. The reaction mixture was allowed to warm to ambient temperature and stirred overnight. Saturated NaCl was added to the reaction mixture, (300 mL). After stirring for 1 hour, the organic layer was separated. The aqueous layer was extracted with dichloromethane. The combined organics were washed with saturated NaCl, dried over Na$_2$SO$_4$, and concentrated in vacuo. The crude product was used without further purification.

Step B: Preparation of 4-bromo-7-hydroxy-2,3-dihydro-1H-inden-1-one: A flask containing crude (4-bromophenyl) 3-chloropropanoate (68.0 g, 258 mmol) was cooled to 0° C., then treated in several portions with aluminum trichloride (275 g, 2060 mmol). The reaction mixture was then heated at 155° C. under N$_2$ for 3 hours. Stirring became difficult as the reaction proceeded. HCl (g) which was generated from the reaction was trapped by a beaker containing 1 N NaOH. After cooling to ambient temperature, the reaction mixture was further cooled in an ice bath. Water was added very carefully (dropwise initially and then added in small volumes) to the reaction to quench excess AlCl$_3$. The mixture was then extracted with twice with ethyl acetate. The combined organic layers were washed with water and brine, dried and concentrated. The crude product was used without additional purification.

Step C: Preparation of O-(7-bromo-3-oxo-2,3-dihydro-1H-inden-4-yl) dimethylcarbamothioate: A mixture of 4-bromo-7-hydroxy-2,3-dihydro-1H-inden-1-one (900 mg, 4.0 mmol) dissolved in DMF (15 mL) was treated with DABCO 33LV (1.3 mL, 12 mmol) and N,N-diethylcarbamothioyl chloride (1.5 g, 12 mmol) was stirred overnight at ambient temperature. The reaction was treated with water and ethyl acetate and separated. The aqueous layer was extracted with ethyl acetate then the combined organic layers were washed with water and saturated NaCl. After drying, the organic layer was concentrated in vacuo and purified by chromatography on SiO2 eluting with a gradient of ethyl acetate/hexanes, (670 mg, 54%). $^1$H NMR (400 MHz, CDCl$_3$): δ 7.78-7.76 (d, 1H), 6.97-6.95 (d, 1H), 3.44 (s, 3H), 3.41 (s, 3H), 3.08 (m, 2H), 2.76-2.69 (m, 2H).

Step D: Preparation of S-(7-bromo-3-oxo-2,3-dihydro-1H-inden-4-yl) dimethylcarbamothioate: A mixture of O-(7-bromo-3-oxo-2,3-dihydro-1H-inden-4-yl) dimethylcarbamothioate (670 mg, 2.1 mmol) and diphenyl ether (15 mL) was heated at 220° C. under N$_2$ for 30 minutes. After cooling to ambient temperature, the mixture was diluted with hexanes and the mixture was applied to a pad of SiO$_2$ and eluted with hexanes. After removal of the diphenyl ether, the desired product was eluted with ethyl acetate. After concentration in vacuo, the crude product was used without further purification.

Step E: Preparation of 4-bromo-7-mercapto-2,3-dihydro-1H-inden-1-one: A solution of S-(7-bromo-3-oxo-2,3-dihydro-1H-inden-4-yl) dimethylcarbamothioate (670 mg, 2.1 mmol) dissolved in ethanol (25 mL) was treated with 3N sodium hydroxide) 10.7 mL, 32.1 mmol). The mixture was heated to reflux for 1 hour then cooled to 0° C. Aqueous HCl (3M) was added dropwise to neutralize the reaction. Ethanol was removed by concentration in vacuo followed by addition of aqueous HCl (1M) to adjust to pH 3-4. The aqueous was extracted twice with ethyl acetate and the combined organic layers were washed with saturated NaCl, dried and concentrated in vacuo. The crude product was used without further purification.

Step F: Preparation of 4-bromo-7-((trifluoromethyl)thio)-2,3-dihydro-1H-inden-1-one: Methyl viologen dichloride hydrate (0.11 g, 0.41 mmol), 4-bromo-7-mercapto-2,3-dihydro-1H-inden-1-one (2.0 g, 8.2 mmol) and triethylamine (1.25 g, 12.3 mmol) were dissolved in DMF (50 mL) and cooled to −50° C. The flask was placed under gentle vacuum then trifluoromethyl iodide (3.2 g, 16 mmol) gas was introduced using a balloon. This reaction was warmed to ambient temperature and stirred at overnight. The reaction mixture was diluted with ethyl acetate and water, filtered through a celite pad, and the layers were partitioned. The organic layer was washed with water, brine, dried over Na$_2$SO$_4$, filtered, and evaporated. The crude oil was then purified by flash column chromatography on SiO$_2$ eluting with petroleum ether/ethyl acetate, (0.96 g, 51.7%). $^1$H NMR (400 MHz, CDCl$_3$): δ 7.72 (d, 1H), 7.41 (d, 1H), 3.10-3.07 (m, 2H), 2.79-2.77 (m, 2H).

Step G: Preparation of 4-bromo-7-((trifluoromethyl)sulfonyl)-2,3-dihydro-1H-inden-1-one: Ruthenium(III) chloride (19 mg, 0.09 mmol) was added to a mixture of 4-bromo-7-((trifluoromethyl)thio)-2,3-dihydro-1H-inden-1-one (0.96 g, 3.1 mmol) and sodium periodate (1.98 g, 9.26 mmol) in a mixture of carbon tetrachloride (20 mL), acetonitrile (20 mL), and water (40 mL). The mixture was stirred at ambient temperature for 3 hours. The reaction mixture was partitioned between dichloromethane and water. The organic layer was washed with brine, dried over MgSO$_4$, filtered, and concentrated in vacuo. The crude product was purified by flash column chromatography on SiO$_2$ eluting with petroleum ether/ethyl acetate, (1.7 g, 79%). $^1$H NMR (400 MHz, CDCl$_3$): δ 8.05-8.02 (m, 2H), 3.21-3.18 (m, 2H), 2.89-2.86 (m, 2H).

Step H: Preparation of 4-bromo-7-((trifluoromethyl)sulfonyl)-2,3-dihydrospiro[indene-1,2'-[1,3]dioxolane]: Trimethylsilyl trifluoromethanesulfonate (177 mg, 0.80 mmol) was added dropwise to a pre-cooled (−78° C.) solution of 4-bromo-7-((trifluoromethyl)sulfonyl)-2,3-dihydro-1H-inden-1-one and trimethyl(2-trimethylsilyloxyethoxy)silane (410 mg, 2.0 mmol) dissolved in dichloromethane (50 mL). The reaction mixture was warmed to ambient temperature and stirred for 2 hours. The reaction was quenched by addition of triethylamine then concentrated in vacuo. The residue was redissolved in ethyl acetate and washed twice with water, and saturated NaCl. The organic layer was separated, dried over Na$_2$SO$_4$ and concentrated in vacuo. The crude product was purified by chromatography on SiO$_2$ eluting with ethyl acetate/isohexane, (600 mg, 77%).

Step I: Preparation of 4-bromo-7-((trifluoromethyl)sulfonyl)-2,3-dihydro-1H-inden-1-one: 4-Bromo-7-((trifluoromethyl)sulfonyl)-2,3-dihydrospiro[indene-1,2'-[1,3]dioxolane] (3.5 g, 9.1 mmol) was dissolved in THF (72 mL) and treated with 10% aqueous HCl (27 mL, 27 mmol). The mixture was stirred for several minutes then warmed to 60° C. for 2 hours. The mixture was cooled, diluted with diethyl ether and separated. The aqueous was washed with diethyl ether and the combined organics were washed with water, saturated NaHCO$_3$, saturated NaCl, dried over Na$_2$SO$_4$ and concentrated in vacuo to a yellowish solid, (3.09 g, quant.). $^1$H NMR (400 MHz, CDCl$_3$): δ 8.05-8.02 (m, 2H), 3.21-3.18 (m, 2H), 2.89-2.86 (m, 2H).

Step J: Preparation of (E.Z)-3-((4-bromo-7-((trifluoromethyl)sulfonyl)-2,3-dihydro-1H-inden-1-ylidene)amino) propan-1-ol: 4-Bromo-7-(trifluoromethylsulfonyl)indan-1-one (3.09 g, 9.02 mmol] was slurried in toluene (35 mL) and cyclohexane (35 mL) then treated with 3-methoxypropylamine (2.15 mL, 27.1 mmol) and pivalic acid (46 mg, 0.45 mmol). The mixture was refluxed through a Dean-Stark trap (sidearm pre-filled with cyclohexane) for 8 hours. The reaction mixture was cooled and concentrated in vacuo. The crude material was taken directly into the fluorination.

Step K: Preparation of 4-bromo-2,2-difluoro-7-((trifluoromethyl)sulfonyl)-2,3-dihydro-1H-inden-1-one: Crude (E.Z)-3-((4-bromo-7-((trifluoromethyl)sulfonyl)-2,3-dihydro-1H-inden-1-ylidene)amino)propan-1-ol (3.75 g, 9.1 mmol) was dissolved in dry acetonitrile (23 mL) and added dropwise to a warm (60° C.), suspension of Selectfluor (9.6 g, 27.2 mmol) and sodium sulfate (12.9 g, 90.5 mmol) slurried in acetonitrile (10 mL). After the addition, the mixture was heated to 60° C. for 10 minutes then cooled to ambient temperature and treated with 10% HCl (15 mL) and stirred for 20 minutes. The mixture was adjusted to pH 8 with solid NaHCO$_3$ then diluted with ethyl acetate and separated. The aqueous was washed with ethyl acetate and the combined organics were washed with saturated NaHCO$_3$, saturated NaCl, dried over Na$_2$SO$_4$ filtered, and concentrated in vacuo to dark oil. The crude material was chromatographed on SiO₂ eluting with a gradient of ethyl acetate/hexanes. The desired product was concentrated to a light yellow solid, (2.27 g, 66%). ¹H NMR (400 MHz, CDCl₃): δ 8.22-8.14 (m, 2H), 3.60-3.55 (t, 2H).

Step L: Preparation of (S)-4-bromo-2,2-difluoro-7-((trifluoromethyl)sulfonyl)-2,3-dihydro-1H-inden-1-ol: 4-Bromo-2,2-difluoro-7-((trifluoromethyl)sulfonyl)-2,3-dihydro-1H-inden-1-one (1.65 g, 4.35 mmol) was dissolved in isopropanol (21 mL) and treated with triethylamine (1.2 mL, 8.7 mmol), formic acid (0.49 mL, 13.1 mmol) and RuCl(p-cymene)[(R,R)-Ts-DPEN] (27.7 mg, 0.040 mmol). The reaction mixture was stirred at ambient temperature for 4 hours. The solvent was removed in vacuo then the crude material was chromatographed on SiO₂ eluting with a gradient of ethyl acetate/hexanes. The product was isolated as a more pure fraction (1.83 g) and a slightly less pure fraction. Both of these fractions were successfully utilized in the coupling reaction. ¹H NMR (400 MHz, CDCl₃): 7.88-7.80 (m, 2H), 5.50-5.45 (m, 1H), 3.66-3.58 (m, 1H), 3.20 (m, 1H).

Step M: Preparation of (S)-3-((2,2-difluoro-1-hydroxy-7-((trifluoromethyl)sulfonyl)-2,3-dihydro-1H-inden-4-yl)amino)-5-fluorobenzonitrile: (S)-4-Bromo-2,2-difluoro-7-((trifluoromethyl)sulfonyl)-2,3-dihydro-1H-inden-1-ol (98 mg, 0.26 mmol) was dissolved in 1,4-dioxane (0.80 mL) and treated with benzonitrile, 3-amino-5-fluoro- (42 mg, 0.31 mmol), palladium (II) acetate (2.9 mg, 0.010 mmol), and Xantphos (14.9 mg, 0.030 mmol). The mixture was heated to 120° C. for 1.5 hours in the microwave reactor. The reaction mixture was cooled, diluted with ethyl acetate and water then separated. The aqueous was washed with ethyl acetate and the combined organics were washed with saturated NaHCO₃, saturated NaCl, dried over Na₂SO₄ and concentrated in vacuo. The crude dark oil was chromatographed on SiO₂ eluting with a gradient of ethyl acetate/hexanes. The desired material was recovered in a slightly impure form. This material was re-chromatographed on reversed-phase SiO₂ eluting with a gradient of MeCN/water. A single fraction was collected and to light tan solid, (35 mg, 31%). LCMS ESI (−) m/z (M−H) 435; NMR (400 MHz, CDCl₃): δ 7.87 (d, 1H), 7.31-7.29 (m, 2H), 7.21-7.19 (m, 2H), 6.18 (m, 1H), 5.42-5.38 (m, 1H), 3.52-3.41 (m, 1H), 3.32-3.24 (m, 1H).

Example 16: Synthesis of (S)-5-((2,2-difluoro-1-hydroxy-7-((trifluoromethyl)sulfonyl)-2,3-dihydro-1H-inden-4-yl)amino)nicotinonitrile (Compound 488)

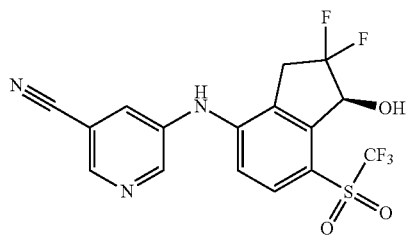 [SMILES: N#Cc1cncc(Nc2ccc(S(=O)(=O)C(F)(F)F)c3c2CC(F)(F)[C@H]3O)c1]

(S)-4-Bromo-2,2-difluoro-7-((trifluoromethyl)sulfonyl)-2,3-dihydro-1H-inden-1-ol (23 mg, 0.060 mmol) was dissolved in 1,4-dioxane (0.20 mL) and treated with 3-pyridinecarbonitrile, 5-amino- (8.6 mg, 0.070 mmol), cesium carbonate (27.5 mg, 0.080 mmol), palladium (II) acetate (0.68 mg, 0.003 mmol), and Xantphos (3.5 mg, 0.010 mmol). After cooling, the mixture was diluted with water and ethyl acetate then separated. This mixture didn't separate well and there was insoluble yellow solid present, which was removed by filtration. The aqueous was washed with ethyl acetate and the combined organics were washed with saturated NaHCO₃, saturated NaCl, dried over Na2SO4, and concentrated in vacuo to a dark residue. The crude material was chromatographed on SiO₂ eluting with a gradient of ethyl acetate/hexanes. The product was recovered as light tan solid, (12 mg, 47%). LCMS ESI (+) m/z (M+H) 420; NMR (400 MHz, CDCl₃ plus CD₃OD): δ 8.66 (s, 1H), 8.60 (s, 1H), 7.79-7.75 (m, 2H), 7.22-7.20 (m, 1H), 5.30 (d, 1H), 3.92-3.90 (m, 1H), 3.46-3.32 (m, 1H), 3.31-3.21 (m, 1H).

Example 17: Synthesis of (S)-2,2-difluoro-4-morpholino-7-((trifluoromethyl)sulfonyl)-2,3-dihydro-1H-inden-1-ol (Compound 490)

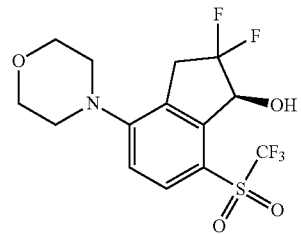 [SMILES: O=S(=O)(c1ccc(N2CCOCC2)c2c1[C@H](O)C(F)(F)C2)C(F)(F)F]

Step A: Preparation of (S)-((4-bromo-2,2-difluoro-7-((trifluoromethyl)sulfonyl)-2,3-dihydro-1H-inden-1-yl)oxy)(tert-butyl)dimethylsilane: (S)-4-bromo-2,2-difluoro-7-((trifluoromethyl)sulfonyl)-2,3-dihydro-1H-inden-1-ol (0.30 g, 0.78 mmol) was dissolved in methylene chloride (3.3 mL) and treated with 2,6-lutidine (0.40 mL, 3.1 mmol), cooled to 0° C., followed by treatment with t-butyldimethylsilyl triflate (0.45 mL, 1.9 mmol). The mixture was warmed to ambient temperature and stirred for two hours. The reaction mixture was re-cooled to 0° C. and cold 10% KHSO₄ was added along with additional methylene chloride then the layers were separated. The organic layer was washed with 10% KHSO₄, water, then with one-half saturated NaHCO₃. The organic layer was dried over Na₂SO₄ and concentrated in vacuo to a light yellow oil. The crude product was chromatographed on SiO₂ eluting with a gradient of methylene chloride/hexanes. The product was concentrated to colorless oil, (466 mg, 92%).

Step B: Preparation of (S)-4-(1-((tert-butyldimethylsilyl)oxy)-2,2-difluoro-7-((trifluoromethyl)sulfonyl)-2,3-dihydro-1H-inden-4-yl)morpholine: (S)-((4-bromo-2,2-difluoro-7-((trifluoromethyl)sulfonyl)-2,3-dihydro-1H-inden-1-yl)oxy)(tert-butyl)dimethylsilane (0.030 g, 0.060 mmol) was dissolved in DMF (0.25 mL) and treated with sodium acetate (14 mg, 0.17 mmol) followed by morpholine (0.020 mL, 0.17 mmol). The mixture was heated at 120° C. for 1 hour in the microwave reactor. After cooling, the mixture was diluted with ethyl acetate then washed 7 times with water, saturated NaCl, dried over Na₂SO₄ and concentrated in vacuo. The residue was chromatographed on SiO₂ eluting with a gradient of ethyl acetate/hexanes. The product was recovered as a colorless film, (17 mg, 58%). LCMS ESI (+) m/z (M+H) 502.

Step C: Preparation of (S)-2,2-difluoro-4-morpholino-7-((trifluoromethyl)sulfonyl)-2,3-dihydro-1H-inden-1-ol: (S)-4-(1-((tert-butyldimethylsilyl)oxy)-2,2-difluoro-7-((trifluoromethyl)sulfonyl)-2,3-dihydro-1H-inden-4-yl)morpholine (0.02 g, 0.04 mmol) was dissolved in THF (0.25 mL) and treated with glacial acetic acid (2 µL, 0.04 mmol) followed by a solution of 1 M tetrabutylammonium fluoride in THF (0.04 mL, 0.04 mmol). The mixture was heated to 60° C. for 45 minutes. The darkened reaction mixture was cooled and added into saturated aqueous NaHCO$_3$. The mixture was vortexed vigorously then diluted with ethyl acetate and separated. The organic layer was washed with saturated NaHCO$_3$, saturated NaCl, dried over Na$_2$SO$_4$ and concentrated in vacuo. The crude material was chromatographed on SiO$_2$ eluting with a gradient of ethyl acetate/hexanes. Compound 490 was recovered as light orange oil, (10.8 mg, 78%). LCMS ESI (+) m/z (M+H) 388; $^1$H NMR (400 MHz, CDCl$_3$): δ 7.87 (d, 1H), 7.01 (d, 1H), 5.35-5.31 (m, 1H), 3.93-3.81 (m, 4H), 3.56-3.45 (m, 1H), 3.35-3.23 (m, 3H), 3.16-3.09 (m, 3H).

Example 18: Synthesis of (1S,3R)-4-((3-chloro-5-fluorophenyl)thio)-2,2,3-trifluoro-7-(methylsulfonyl)-2,3-dihydro-1H-inden-1-ol (Compound 491)

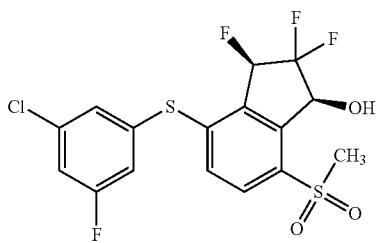 [SMILES: CS(=O)(=O)c1ccc(Sc2cc(F)cc(Cl)c2)c2c1[C@H](O)C(F)(F)[C@@H]2F]

Step A: Preparation of 4,7-difluoro-1H-indene-1,3(2H)-dione (0.52 g, 2.8 mmol) was slurried acetic anhydride (2.5 mL, 27 mmol) and treated with tert-butyl 3-oxobutanoate (0.52 mL, 3.1 mmol) and triethylamine (1.4 mL, 10 mmol). The mixture was stirred at ambient temperature for 60 hours. The reaction was cooled to 0° C. and treated with 10% aqueous hydrochloric acid (8.6 mL, 25 mmol) by dropwise addition. After the addition, the mixture was warmed to ambient temperature then heated to 75° C. for 10 minutes. After cooling, the mixture was diluted with water (20 mL) and extracted three times with methylene chloride (20 mL portions). The combined organics were dried over Na$_2$SO$_4$ and concentrated in vacuo to crude orange solid. This material was carried forward without purification.

Step B: Preparation of 2,2,4,7-tetrafluoro-1H-indene-1,3 (2H)-dione: 4,7-difluoro-1H-indene-1,3(2H)-dione (0.51 g, 2.8 mmol) was dissolved in acetonitrile (27 mL), placed in an ambient temperature water bath then treated with solid sodium carbonate (950 mg, 9.0 mmol) followed by Selectfluor® (2.18 g, 6.2 mmol). The mixture was stirred at ambient temperature for 1 hour. The mixture was filtered to removed undissolved solids, the solids were washed with ethyl acetate and the filtrate was concentrated in vacuo. The residue was redissolved in water (ca. 20 mL) and extracted four times with ethyl acetate (20 mL each). The combined organics were washed with saturated NaCl, dried over Na$_2$SO$_4$ and concentrated in vacuo to orange solid. The crude solid was chromatographed on SiO$_2$ eluting with an aggressive gradient of ethyl acetate/hexanes. The desired material concentrated to orange solid, (493 mg, 81%). $^1$H NMR (400 MHz, CDCl$_3$): δ 7.70-7.65 (2H).

Step C: Preparation of (S)-2,2,4,7-tetrafluoro-3-hydroxy-2,3-dihydro-1H-inden-1-one: 2,2,4,7-tetrafluoro-1H-indene-1,3(2H)-dione (5.81 g, 26.6 mmol) was suspended in methylene chloride (260 mL), cooled to 0° C., and treated with formic acid (1.01 mL, 26.6 mmol), triethylamine (2.60 mL, 18.6 mmol), then the reaction mixture was sparged with argon for 5 minutes. RuCl(p-cymene)[(S,S)-Ts-DPEN] (339 mg, 0.530 mmol) was added and the reaction was transferred to the refrigerator and allowed to stand at 4° C. for 20 hours. The cold reaction mixture was poured into cold 1N aqueous HCl (70 mL) and separated. The aqueous was washed twice with ethyl acetate then the combined organic layers were dried over Na$_2$SO$_4$ and concentrated in vacuo to a brown semi-solid. The crude material was chromatographed on SiO$_2$ eluting with a gradient of ethyl acetate/hexanes. The product was recovered as yellow solid, (3.48 g, 59%). $^1$H NMR (400 MHz, CDCl$_3$): δ 7.86-7.80 (m, 1H), 7.60-7.54 (m, 1H), 5.79-5.74 (m, 1H), 3.23-3.18 (m, 1H).

Step D: Preparation of (S)-2,2,4-trifluoro-3-hydroxy-7-(methylthio)-2,3-dihydro-1H-inden-1-one: (S)-2,2,4,7-tetrafluoro-3-hydroxy-2,3-dihydro-1H-inden-1-one (0.40 g, 1.8 mmol) was dissolved in dry acetonitrile (18 mL), cooled to 0° C., and sparged with argon for 5 minutes. The solution was treated in a single portion with sodium thiomethoxide (144 mg, 2.06 mmol) and after 5 minutes, the ice bath was removed and the reaction was stirred at ambient temperature for 3 hours. The reaction mixture was concentrated in vacuo and the residue was redissolved in water and ethyl acetate. After separation, the aqueous was washed twice with ethyl acetate and the combined organics were washed with saturated NaCl, dried over Na$_2$SO$_4$ and concentrated in vacuo. The orange residue was chromatographed on SiO$_2$ eluting with a gradient of ethyl acetate/hexanes. The desired material was recovered as bright yellow solid, (314 mg, 70%). LCMS ESI (+) m/z (M+H) 249.

Step E: Preparation of (S)-2,2,4-trifluoro-3-hydroxy-7-(methylsulfonyl)-2,3-dihydro-1H-inden-1-one: (S)-2,2,4-trifluoro-3-hydroxy-7-(methylthio)-2,3-dihydro-1H-inden-1-one (0.40 g, 1.6 mmol) was dissolved in MeOH (10 mL) and the reaction was treated dropwise with a solution of Oxone® (2.2 g, 3.6 mmol) dissolved in water (10 mL). The mixture was stirred at ambient temperature for 14 hours. The reaction mixture was filtered, the solids were washed with ethyl acetate and the filtrate was concentrated in vacuo to remove volatile solvents. The aqueous filtrate was extracted three times with ethyl acetate then the combined organics were washed with saturated NaCl, dried over Na$_2$SO$_4$ and concentrated in vacuo to yellow solid, (467 mg, quant.). LCMS ESI (+) m/z (M+H) 281.

Step F: Preparation of (R)-2,2,3,4-tetrafluoro-7-(methylsulfonyl)-2,3-dihydro-1H-inden-1-one: (S)-2,2,4-trifluoro-3-hydroxy-7-(methylsulfonyl)-2,3-dihydro-1H-inden-1-one (0.45 g, 1.6 mmol) was dissolved in dichloromethane (16 mL), cooled to 0° C., and treated dropwise with diethylaminosulfur trifluoride (DAST) (0.32 mL, 2.4 mmol) and stirred at 0° C. for 14 hours. The reaction was treated with additional diethylaminosulfur trifluoride (0.32 mL, 2.4 mmol) and stirring continued for 6 hours at 0° C. The cold reaction was treated with saturated NaHCO$_3$ (10 mL) and stirred vigorously for 20 minutes. The mixture was diluted with additional methylene chloride and the layers were separated. The aqueous was re-extracted with methylene chloride and the combined organic layers were dried over Na$_2$SO$_4$ and concentrated in vacuo to a yellow solid. The crude material was chromatographed on SiO$_2$ eluting with a gradient of ethyl acetate/hexanes. The desired material was recovered as pale yellow solid, (258 mg, 53%). LCMS ESI (+) m/z (M+H) 283.

Step G: Preparation of (1S,3R)-2,2,3,4-tetrafluoro-7-(methylsulfonyl)-2,3-dihydro-1H-inden-1-ol: (R)-2,2,3,4-tetrafluoro-7-(methylsulfonyl)-2,3-dihydro-1H-inden-1-one: (0.098 g, 0.35 mmol) was suspended in methylene chloride (3.3 mL), cooled to 0° C., and treated with triethylamine (97 µL, 0.69 mmol), formic acid (39 µL, 1.0 mmol) and RuCl(p-cymene)[(R,R)-Ts-DPEN] (2.2 mg, 0.003 mmol). The solution was allowed to stand at 4° C. in the refrigerator for 60 hours. The reaction mixture was concentrated in a stream of nitrogen gas then chromatographed on SiO$_2$ eluting with a gradient of ethyl acetate/hexanes. The desired fractions were concentrated to colorless film, (53 mg, 53%). LCMS ESI (+) m/z (M+H) 285.

Step H: Preparation of (1S,3R)-4-((3-chloro-5-fluorophenyl)thio)-2,2,3-trifluoro-7-(methylsulfonyl)-2,3-dihydro-1H-inden-1-ol: (1S,3R)-2,2,3,4-tetrafluoro-7-(methylsulfonyl)-2,3-dihydro-1H-inden-1-ol (0.005 g, 0.02 mmol) was treated with cesium bicarbonate (17 mg, 0.090 mmol) and suspended in DMF (0.1 mL) then stirred at ambient temperature for 1 hour. 3-Chloro-5-fluorothiophenol (14 mg, 0.090 mmol) was added and the mixture was stirred at ambient temperature for 18 hours. The reaction was concentrated in a stream of nitrogen gas to remove DMF. The residue was chromatographed on SiO$_2$ eluting with a stepped gradient of ethyl acetate/hexanes. Compound 491 was concentrated to light pink oil, (7 mg, 93%). LCMS ESI (+) m/z (M+Na) 449; $^1$H NMR (400 MHz, CDCl$_3$): δ 7.99-7.95 (m, 1H), 7.33-7.32 (m, 1H), 7.24-7.19 (m, 2H), 7.16-7.13 (m, 1H), 5.75 (dd, 1H), 5.68-5.65 (m, 1H), 3.37-3.36 (m, 1H), 3.23 (s, 3H).

Example 19: Synthesis of 3-(((1S,3R)-2,2,3-trifluoro-1-hydroxy-(methylsulfonyl)-2,3-dihydro-1H-inden-4-yl)thio)benzonitrile (Compound 492)

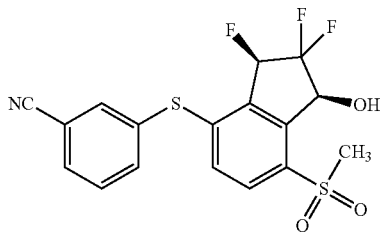 [SMILES: CS(=O)(=O)c1ccc(Sc2cccc(C#N)c2)c2c1[C@H](O)C(F)(F)[C@@H]2F]

(1S,3R)-2,2,3,4-tetrafluoro-7-(methylsulfonyl)-2,3-dihydro-1H-inden-1-ol (0.0073 g, 0.030 mmol) was treated with cesium bicarbonate (25 mg, 0.13 mmol) and suspended in DMF (0.1 mL) then 3-mercapto-benzonitrile (17 mg, 0.13 mmol) was added and the mixture was stirred at ambient temperature for 60 hours. The reaction was concentrated in a stream of nitrogen gas to remove DMF. The residue was chromatographed on SiO$_2$ eluting with a stepped gradient of ethyl acetate/hexanes. The product was concentrated to light oil, (7 mg, 91%). LCMS ESI (+) m/z (M+Na) 422; $^1$H NMR (400 MHz, CDCl$_3$): δ 7.97-7.87 (m, 1H), 7.81 (m, 1H), 7.77-7.74 (m, 2H), 7.61-7.57 (m, 1H), 7.16-7.14 (m, 1H), 5.77 (dd, 1H), 5.69-5.65 (m, 1H), 3.40-3.39 (m, 1H), 3.23 (s, 3H).

Example 20: Synthesis of (S)-4-(3-chlorophenyl)-2,2-difluoro-7-((trifluoromethyl)sulfonyl)-2,3-dihydro-1H-inden-1-ol (Compound 485)

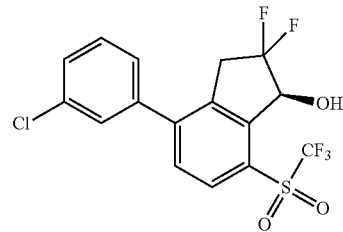 [SMILES: O=S(=O)(c1ccc(-c2cccc(Cl)c2)c2c1[C@H](O)C(F)(F)C2)C(F)(F)F]

Step A: Preparation of 4-((4-methoxybenzyl)oxy)-7-((trifluoromethyl)sulfonyl)-2,3-dihydrospiro[indene-1,2'-[1,3]dioxolane]: A solution of 4'-fluoro-7'-(trifluoromethylsulfonyl)spiro[1,3-dioxolane-2,1'-indane] (1.0 g, 3.07 mmol) and 4-methoxybenzyl alcohol (760 µL, 6.13 mmol) in acetonitrile (9.3 mL) at 25° C. was treated with potassium hydroxide (516 mg, 9.2 mmol) and stirred at 25° C. for 1.5 h. The reaction mixture was poured into 150 mL of water and extracted with 3×40 mL EtOAc. The combined organics were rinsed with 20 mL of brine, dried with MgSO$_4$, filtered, and concentrated to dryness. Purification was achieved by chromatography on silica using 10-25% EtOAc/hexane to afford 4-((4-methoxybenzyl)oxy)-7-((trifluoromethyl)sulfonyl)-2,3-dihydrospiro[indene-1,2'-[1,3]dioxolane] as a solid (1.08 g, 79%). LCMS ESI (+) [M+H]$^+$ m/z 445.

Step B: Preparation of 4-((4-methoxybenzyl)oxy)-7-((trifluoromethyl)sulfonyl)-2,3-dihydro-1H-inden-1-one: In a glass pressure vessel, a solution of 4'-[(4-methoxyphenyl)methoxy]-7'-(trifluoromethylsulfonyl)spiro[1,3-dioxolane-2,1'-indane] (1.08 g, 2.43 mmol) in a mixture acetone (20 mL) and water (20 mL) was treated with pyridinium p-toluenesulfonate (122 mg, 0.49 mmol), sealed and stirred at 80° C. overnight. Volatiles were removed by concentration under reduced pressure. The residue was poured into 40 mL of saturated aqueous NaHCO$_3$ and extracted with 3×50 mL EtOAc. The combined organics were rinsed with 30 mL of brine, dried with MgSO$_4$, filtered, and concentrated to dryness. The product was used without further purification. LCMS ESI (+) [M+H]$^+$ m/z 401.

Step C: Preparation of 2,2-difluoro-4-((4-methoxybenzyl)oxy)-7-((trifluoromethyl)sulfonyl)-2,3-dihydro-1H-inden-1-one: 2,2-Dimethylpropanoic acid (50 mg, 0.46 mmol) was added to a flask containing a suspension of 4-[(4-methoxyphenyl)methoxy]-7-(trifluoromethylsulfonyl)indan-1-one (922 mg, 2.3 mmol) and 3-methoxypropan-1-amine (0.35 mL, 3.45 mmol) in a mixture of toluene (14 mL) and cyclohexane (14 mL). This was refluxed with a Dean-Stark trap attached at 104° C. After 2.5 h, the reaction mixture was cooled and volatiles removed by concentration under reduced pressure. The residue was dissolved in acetonitrile (24 mL) and treated sequentially with sodium sulfate (850 mg, 6.0 mmol) and 1-(chloromethyl)-4-fluoro-1,4-diazoniabicyclo[2.2.2]octane ditetrafluoroborate (2.13 g, 6.0 mmol). The resulting suspension stirred at 60° C. for 2 h. After cooling to room temperature, the reaction mixture was treated with concentrated hydrochloric acid (600 µL, 7.2 mmol) and water (10 mL). The resulting mixture stirred for 20 min. Volatiles were removed by concentration under reduced pressure. The reaction mixture was poured into 20 mL of water and extracted with 3×30 mL EtOAc. The combined organics were rinsed with 20 mL of brine, dried with MgSO$_4$, filtered, and concentrated to dryness. Purification was achieved by chromatography on silica using 5-40% EtOAc/hexane to afford 2,2-difluoro-4-((4-methoxybenzyl)oxy)-7-((trifluoromethyl)sulfonyl)-2,3-dihydro-1H-inden-1-one as a solid (520 mg, 50%). LCMS ESI (+) [M+H]$^+$ m/z 437.

Step D: Preparation of (S)-2,2-difluoro-4-((4-methoxybenzyl)oxy)-7-((trifluoromethyl)sulfonyl)-2,3-dihydro-1H-inden-1-ol: A solution of 2,2-difluoro-4-[(4-methoxyphenyl)methoxy]-7-(trifluoromethylsulfonyl)indan-1-one (520 mg, 1.19 mmol) in dichloromethane (11.9 mL) was cooled to 0° C. and sparged with nitrogen for 5 minutes. During this time, formic acid (130 µL, 3.58 mmol) and triethylamine (330 µL, 2.38 mmol) were sequentially added. Once the sparging was complete, RuCl(p-cymene)[(R,R)-Ts-DPEN] (22.8 mg, 0.036 mmol) was added under a continuous stream of nitrogen. The reaction vessel was sealed and put into the refrigerator to react overnight. Once complete, the reaction mixture was poured into 30 mL of saturated aqueous NaHCO$_3$ and extracted with 3×30 mL CH$_2$Cl$_2$. The combined organics were rinsed with 20 mL of brine, dried with MgSO$_4$, filtered, and concentrated to dryness. Purification was achieved by chromatography on silica using 10-40% EtOAc/hexane to afford (S)-2,2-difluoro-4-((4-methoxybenzyl)oxy)-7-((trifluoromethyl)sulfonyl)-2,3-dihydro-1H-inden-1-ol as a solid (370 mg, 71%). LCMS ESI (+) [M+NH$_4$]$^+$ m/z 456.

Step E: Preparation of (S)-tert-butyl((2,2-difluoro-4-((4-methoxybenzyl)oxy)-7-((trifluoromethyl)sulfonyl)-2,3-dihydro-1H-inden-1-yl)oxy)dimethylsilane: A solution of (1S)-2,2-difluoro-4-[(4-methoxyphenyl)methoxy]-7-(trifluoromethylsulfonyl)indan-1-ol (370 mg, 0.84 mmol) and 2,6-lutidine (780 µL, 7.76 mmol) in dichloromethane (8.4 mL) at −78° C. was treated with tert-butyldimethylsilyl trifluoromethanesulfonate (980 µL, 4.22 mmol) and allowed to warm to room temperature over 2 h. The reaction mixture was poured into 30 mL of saturated aqueous NaHCO$_3$ and extracted with 3×20 mL CH$_2$Cl$_2$. The combined organics were rinsed with 10 mL of brine, dried with MgSO$_4$, filtered, and concentrated to dryness. Purification was achieved by chromatography on silica using 5-20% EtOAc/hexane to afford (S)-tert-butyl((2,2-difluoro-4-((4-methoxybenzyl)oxy)-7-((trifluoromethyl)sulfonyl)-2,3-dihydro-1H-inden-1-yl)oxy)dimethylsilane (460 mg, quant). LCMS ESI (−) [M−H]$^-$ m/z 551.

Step F: Preparation of (S)-1-((tert-butyldimethylsilyl)oxy)-2,2-difluoro-7-((trifluoromethyl)sulfonyl)-2,3-dihydro-1H-inden-4-ol: A solution of tert-butyl-[(1S)-2,2-difluoro-4-[(4-methoxyphenyl)methoxy]-7-(trifluoromethylsulfonyl)indan-1-yl]oxy-dimethyl-silane (460 mg, 0.83 mmol) in dichloromethane (3.0 mL) at 25° C. was treated with trifluoroacetic acid (3.0 mL) and stirred at 25° C. After 1 h, volatiles were removed by concentration under reduced pressure. To the resulting residue was added 6 mL of toluene and the organic volatiles were once again removed by concentration under reduced pressure. This process was repeated twice. Purification was achieved by chromatography on reverse phase by injection of a DMF solution of the product residue. 40-100% CH$_3$CN/Water was used as eluent. (S)-1-((tert-butyldimethylsilyl)oxy)-2,2-difluoro-7-((trifluoromethyl)sulfonyl)-2,3-dihydro-1H-inden-4-ol was isolated a thick orange oil (236 mg, 89%). LCMS ESI (−) [M−H]$^-$ m/z 431.

Step G: Preparation of (S)-2,2-difluoro-1-hydroxy-7-((trifluoromethyl)sulfonyl)-2,3-dihydro-1H-inden-4-yl trifluoromethanesulfonate: A solution of (S)-1-(((tert-butyldimethylsilyl)oxy)-2,2-difluoro-7-((trifluoromethyl)sulfonyl)-2,3-dihydro-1H-inden-4-ol (215 mg, 0.50 mmol) and 2,6-bis(1,1-dimethylethyl)-4-methyl-pyridine (408 mg, 1.99 mmol) in dichloromethane (10 mL) was cooled to −78° C. and treated with trifluoromethanesulfonic anhydride (0.17 mL, 0.99 mmol). The mixture was stirred at −78° C. for 1 h. The reaction mixture was poured into 20 mL of saturated NaHCO$_3$ and extracted with 3×20 mL EtOAc. The combined organics were rinsed with 10 mL of brine, dried with MgSO$_4$, filtered, and concentrated to dryness. Purification was achieved by chromatography on SiO$_2$ eluting with a gradient of ethyl acetate/hexanes.

Step H: Preparation of tributyl(3-chlorophenyl)stannane: A solution of 3-chlorophenylmagnesium bromide (0.5 M in THF) (1.40 mL, 0.70 mmol) was cooled to −78° C. and treated dropwise with a solution of tributyl(chloro)stannane (230 mg, 0.70 mmol) dissolved in THF (0.5 mL). The solution was stirred for 5 minutes then allowed to warm to ambient temperature slowly without the bath and stirred at ambient temperature for 45 hours. The reaction was quenched by addition of saturated NH$_4$Cl and water. Diethyl ether was added and the mixture was separated. The aqueous was washed twice with diethyl ether and the combined organics were washed saturated NaCl, dried over Na$_2$SO$_4$ and concentrated in vacuo. The crude material was chromatographed on SiO$_2$ eluting with cyclohexane. The desired product was concentrated to colorless liquid, (234 mg, 84%). $^1$H NMR (400 MHz, CDCl$_3$): δ 7.58-7.30 (m, 4H), 1.60-1.45 (m, 6H), 1.40-1.28 (m, 6H), 1.17-1.00 (m, 6H), 0.92-0.85 (m, 9H).

Step I: Preparation of (S)-tert-butyl((4-(3-chlorophenyl)-2,2-difluoro-7-((trifluoromethyl)sulfonyl)-2,3-dihydro-1H-inden-1-yl)oxy)dimethylsilane: (S)-2,2-difluoro-1-hydroxy-7-((trifluoromethyl)sulfonyl)-2,3-dihydro-1H-inden-4-yl trifluoromethanesulfonate (17 mg, 0.030 mmol) was dissolved in toluene (0.4 mL) then tributyl-(3-chlorophenyl)stannane (23 mg, 0.060 mmol), tetrakis(triphenylphosphine)palladium (1.7 mg, 0.001 mmol), and lithium chloride (4 mg, 0.09 mmol) were added. The reaction mixture was sparged with argon then heated to reflux for 16 hours. After cooling, the mixture was concentrated in a stream of nitrogen gas. The crude material was chromatographed on SiO$_2$ eluting with a gradient of ethyl acetate/hexanes. The less polar UV-active spot was recovered as colorless oil, (9.8 mg, 63%).

Step J: Preparation of (S)-4-(3-chlorophenyl)-2,2-difluoro-7-((trifluoromethyl)sulfonyl)-2,3-dihydro-1H-inden-1-ol: (S)-tert-butyl((4-(3-chlorophenyl)-2,2-difluoro-7-((trifluoromethyl)sulfonyl)-2,3-dihydro-1H-inden-1-yl)oxy)dimethylsilane (9.8 mg, 0.020 mmol) was dissolved in THF (0.2 mL) containing glacial acetic acid (3.2 µL, 0.060 mmol) and the mixture was treated with a 1M solution of tetrabutylammonium fluoride in THF (28 µL, 0.030 mmol). The mixture was heated to 60° C. for 2 hours, then the reaction was cooled, treated with one-half saturated NaHCO$_3$, diluted with ethyl acetate and separated. The aqueous was washed twice with ethyl acetate and the combined organics were washed with saturated NaHCO$_3$, saturated NaCl, dried over Na$_2$SO$_4$ and concentrated in vacuo to dark oil. The crude material was chromatographed on SiO$_2$ eluting with a stepped gradient of ethyl acetate/hexanes. The desired product was concentrated to light yellow solid, (2.5 mg, 32%). LCMS ESI (−) m/z (M−H) 411/413; $^1$H NMR (400 MHz, CDCl$_3$): δ 8.06-8.04 (d, 1H), 7.66-7.64 (d, 1H), 7.48-7.41

(m, 3H), 7.29-7.26 (m, 1H), 5.47-5.43 (m, 1H), 3.78-3.65 (m, 1H), 3.33 (t, 1H), 3.19-3.17 (m, 1H).

Example 21: Synthesis of (S)-2,2-difluoro-4-phenyl-7-((trifluoromethyl)sulfonyl)-2,3-dihydro-1H-inden-1-ol (Compound 487)

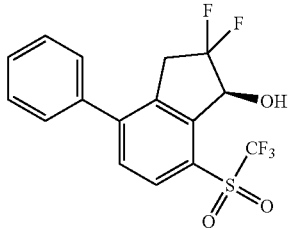 [SMILES: O=S(=O)(c1ccc(-c2ccccc2)c2c1[C@H](O)C(F)(F)C2)C(F)(F)F]

(S)-4-bromo-2,2-difluoro-7-((trifluoromethyl)sulfonyl)-2,3-dihydro-1H-inden-1-ol (20 mg, 0.050 mmol) was dissolved in 1,4-dioxane (0.20 mL) and treated with phenylboronic acid (9.6 mg, 0.080 mmol), Pd(dppf)Cl$_2$-DCM adduct (3 mg, 0.004 mmol), and potassium fluoride (6.1 mg, 0.10 mmol). The mixture was heated to 100° C. for 10 hours. After cooling, the reaction mixture was concentrated in a stream of nitrogen gas then chromatographed on SiO$_2$ eluting with a gradient of ethyl acetate/hexanes. The desired material was concentrated to white solid, (17 mg, 86%). LCMS ESI (−) m/z (M−H) 377; $^1$H NMR (400 MHz, CDCl$_3$): 8.03 (d, 1H), 7.67 (d, 1H), 7.54-7.47 (m, 3H), 7.42-7.39 (m, 2H), 5.47-5.43 (m, 1H), 3.80-3.67 (m, 1H), 3.40-3.31 (t, 1H), 3.22-3.21 (m, 1H).

Example 22: Synthesis of (S)-3-(2,2-difluoro-1-hydroxy-7((trifluoromethyl)sulfonyl)-2,3-dihydro-1H-inden-4-yl)-5-fluorobenzonitrile (Compound 486)

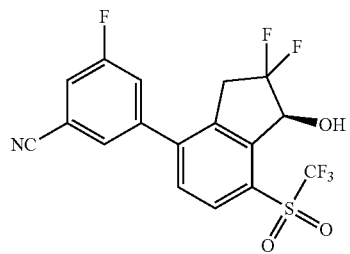 [SMILES: N#Cc1cc(F)cc(-c2ccc(S(=O)(=O)C(F)(F)F)c3c2CC(F)(F)[C@H]3O)c1]

(S)-4-bromo-2,2-difluoro-7-((trifluoromethyl)sulfonyl)-2,3-dihydro-1H-inden-1-ol (20 mg, 0.050 mmol) was dissolved in 1,4-dioxane (0.20 mL) and treated with 3-cyano-5-fluorophenylboronic acid (10 mg, 0.060 mmol), Pd(dppf)Cl$_2$-DCM adduct (3 mg, 0.004 mmol), and potassium fluoride (6.1 mg, 0.10 mmol). The mixture was heated to 100° C. for 10 hours. After cooling, the mixture was concentrated in a stream of nitrogen gas, then directly chromatographed on SiO$_2$ eluting with a gradient of ethyl acetate/hexanes. The desired product was recovered as colorless film, (12 mg, 54%). LCMS ESI (−) m/z (M−H) 420; $^1$H NMR (400 MHz, CDCl$_3$): δ 8.09 (d, 1H), 7.65 (d, 1H), 7.61-7.60 (m, 2H), 7.40-7.37 (m, 1H), 5.49-5.46 (m, 1H), 3.78-3.65 (m, 1H), 3.33-3.25 (t, 1H), 3.20 (m, 1H).

Example 23: Synthesis of (R)-4-((3-chloro-5-fluorophenyl)thio)-7-((difluoromethyl)sulfonyl)-2,3-dihydro-1H-inden-1-ol (Compound 493)

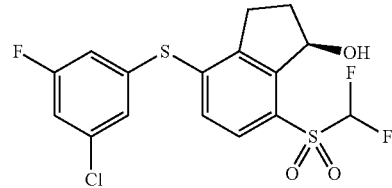 [SMILES: O=S(=O)(c1ccc(Sc2cc(F)cc(Cl)c2)c2c1[C@H](O)CC2)C(F)F]

Sodium bicarbonate (18.9 mg, 0.23 mmol) was added all at once to (1R)-7-(difluoromethylsulfonyl)-4-fluoro-indan-1-ol (20.0 mg, 0.08 mmol) and 3-chloro-5-fluoro-benzenethiol (24.4 mg, 0.15 mmol) in 1-methyl-2-pyrrolidone (0.5 mL) at room temperature then the reaction vial was sealed with a threaded cap. The reaction mixture was then warmed to 90° C. and continued to stir at this temperature until complete as judged by LC-MS (4 h). Cooled to room temperature then purified directly on reverse phase silica gel (25+M, 14 CV, 20-100% MeCN/water) affording (1R)-4-(3-chloro-5-fluoro-phenyl)sulfanyl-7-(difluoromethylsulfonyl) indan-1-ol (25.5 mg, 0.062 mmol, 83% yield). LC-MS ESI (−) m/z 453/455 (M+HCO$_2^-$). $^1$H-NMR (400 MHz, CDCl$_3$): δ 7.84 (d, 1H), 7.19-7.17 (m, 1H), 7.08 (s, 1H), 7.00-6.97 (m, 2H), 5.71-5.68 (m, 1H), 3.64 (d, 1H), 3.21 (s, 3H), 3.12-3.04 (m, 1H), 2.84-2.76 (m, 1H), 2.52-2.43 (m, 1H), 2.27-2.19 (m, 1H).

Example 24: Synthesis of (1R)-7-(difluoromethylsulfonyl)-4-(tetrahydropyran-4-ylamino)indan-1-ol (Compound 494)

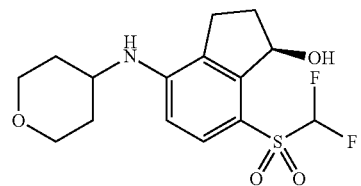 [SMILES: O=S(=O)(c1ccc(NC2CCOCC2)c2c1[C@H](O)CC2)C(F)F]

4-Piperidone (8.4 mg, 0.08 mmol) was added all at once to (1R)-7-(difluoromethylsulfonyl)-4-fluoro-indan-1-ol (22.0 mg, 0.08 mmol) in 1-methyl-2-pyrrolidone (0.5 mL) at room temperature. The reaction mixture was then stirred at 50° C. for 24 h. Additional 4-piperidone (8.4 mg, 0.08 mmol) was added at room temperature and then warmed to 90° C. for an additional 4 h. Cooled to room temperature and added additional 4-piperidone (8.4 mg, 0.08 mmol). Warmed to 90° C. for an additional 4 h. Cooled to room temperature then purified directly on reverse phase silica gel (12+M, 14 CV, 20-100% MeCN/water) affording (1R)-7-(difluoromethylsulfonyl)-4-(tetrahydropyran-4-ylamino)indan-1-ol (15.8 mg, 0.046 mmol, 55% yield). LC-MS ESI (−) m/z 346 (M−H). $^1$H-NMR (400 MHz, CDCl$_3$): δ 7.69 (d, 1H), 6.64 (d, 1H), 6.26 (t, 1H), 5.57-5.56 (m, 1H), 4.14 (d, 1H), 4.06-4.01 (m, 2H), 3.72-3.62 (m, 1H), 3.58-3.51 (m, 2H), 3.32 (d, 1H), 2.95-2.84 (m, 1H), 2.61-2.55 (m, 1H), 2.47-2.38 (m, 1H), 2.28-2.20 (m, 1H), 2.09-2.03 (m, 2H), 1.62-1.52 (m, 2H).

Example 25: Synthesis of 4-(2-hydroxyethyl)-7-((trifluoromethyl)sulfonyl)-2,3-dihydro-1H-inden-1-ol (Compound 495)

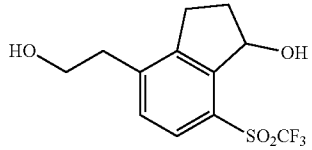

Step A: Preparation of diethyl 2-[7'-(trifluoromethylsulfonyl)spiro[1,3-dioxolane-2,1'-indane]-4'-yl]propanedioate: Tetrahydrofuran (12.0 mL) was added all at once to sodium hydride (735.6 mg, 18.39 mmol) at 0° C. under nitrogen followed by the slow addition of diethyl malonate (1.86 mL, 12.26 mmol). Stirred for 15 min then a solution of 4'-fluoro-7'-(trifluoromethylsulfonyl)spiro[1,3-dioxolane-2,1'-indane] (1.0 g, 3.07 mmol) in tetrahydrofuran (3.0 mL) was added by syringe over 2 minutes. The reaction mixture was then removed from the cooling bath and stirred at room temperature overnight. Additional sodium hydride (200 mg) was added as well as diethyl malonate (0.5 mL) and stirred an additional 6 h. Cooled to 0° C., quenched with water, extracted with ethyl acetate, washed with brine, dried over sodium sulfate, filtered and concentrated in vacuo. Purified on silica gel (25 g SNAP Ultra, 10-100% ethyl acetate/hexanes) affording diethyl 2-[7'-(trifluoromethylsulfonyl)spiro[1,3-dioxolane-2,1'-indane]-4'-yl]propanedioate (940.0 mg, 2.01 mmol, 66% yield).

Step B: Preparation of 2-[1-oxo-7-(trifluoromethylsulfonyl)indan-4-yl]acetic acid: HCl (4.84 mL, 29.03 mmol) was added to diethyl 2-[7'-(trifluoromethylsulfonyl)spiro[1,3-dioxolane-2,1'-indane]-4'-yl]propanedioate (300.0 mg, 0.64 mmol) then warmed to 100° C. for 6 h. Cooled to room temperature, extracted with MTBE, washed with water, brine, dried over $Na_2SO_4$, filtered and concentrated in vacuo affording 2-[1-oxo-7-(trifluoromethylsulfonyl)indan-4-yl]acetic acid (200.0 mg, 0.62 mmol, 96% yield). Used without further purification.

Step C: Preparation of 4-(2-hydroxyethyl)-7-(trifluoromethylsulfonyl)indan-1-ol: Borane dimethylsulfide complex (434.4 μL, 0.87 mmol) was added slowly to 2-[1-oxo-7-(trifluoromethylsulfonyl)indan-4-yl]acetic acid (70.0 mg, 0.22 mmol) in tetrahydrofuran (1.5 mL) at room temperature and stirred for 2 h. Cooled to 0° C. and quenched with 1 N HCl, extracted with ethyl acetate, washed with brine, dried over $MgSO_4$, filtered and concentrated in vacuo. Purified on silica gel (10 g SNAP Ultra, 14 CV, 60-100% ethyl acetate/hexanes) affording 4-(2-hydroxyethyl)-7-(trifluoromethylsulfonyl)indan-1-ol (36.0 mg, 0.12 mmol, 53% yield). Hexanes was added to the clear oil and then cooled to −78° C. with scratching until a white gum was observed, warmed to room temperature and continued scratching until a white powder formed. Hexanes was then removed under a stream of nitrogen to afford Compound 495. LC-MS (−) ESI m/z 309 (M−H). $^1$H-NMR (400 MHz, $CDCl_3$): δ 7.83 (d, 1H), 7.47 (d, 1H), 5.61 (d, 1H), 3.95-3.92 (m, 1H), 3.27-3.18 (m, 1H), 3.10 (s, 1H), 2.99-2.96 (m, 3H), 2.41-2.26 (m, 2H).

Example 26: Synthesis of (S)-2,2-difluoro-4-(2-hydroxyethyl)-7-((trifluoromethyl)sulfonyl)-2,3-dihydro-1H-inden-1-ol (Compound 496)

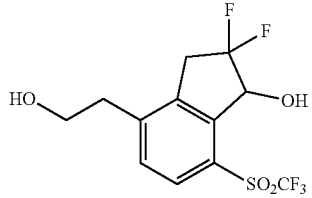

Step A: Borane dimethylsulfide complex (439.0 μL, 0.88 mmol) was added dropwise to 2-[7'-(trifluoromethylsulfonyl)spiro[1,3-dioxolane-2,1'-indane]-4'-yl]acetic acid (268.0 mg, 0.73 mmol) in tetrahydrofuran (7.0 mL) at 0° C. under nitrogen then slowly warmed to room temperature. Stirred until complete as judged by LC-MS. Quenched carefully with saturated sodium bicarbonate, extracted with ethyl acetate, washed with brine, dried over $MgSO_4$, filtered and concentrated in vacuo. Purified on silica gel (10 g SNAP Ultra, 14 CV, 40-100% ethyl acetate/hexanes) affording 2-[7'-(trifluoromethylsulfonyl)spiro[1,3-dioxolane-2,1'-indane]-4'-yl]ethanol (95.0 mg, 0.27 mmol, 37% yield).

Step B: HCl (1.0 mL, 1.0 mmol) was added all at once to 2-[7'-(trifluoromethylsulfonyl)spiro[1,3-dioxolane-2,1'-indane]-4'-yl]ethanol (95.0 mg, 0.27 mmol) in acetone (4.0 mL) at room temperature then stirred until complete as judged by LC-MS. Diluted with water, extracted with ethyl acetate, washed with saturated sodium bicarbonate, washed with brine, dried over $MgSO_4$, filtered and concentrated in vacuo. Used without further purification.

Step C: Tert-Butyldimethylsilyl chloride (46.9 mg, 0.31 mmol) was added all at once to a solution of 4-(2-hydroxyethyl)-7-(trifluoromethylsulfonyl)indan-1-one (80.0 mg, 0.26 mmol) and imidazole (53.0 mg, 0.78 mmol) in dichloromethane (2.0 mL) at room temperature then stirred overnight. Diluted with water, extracted with MTBE, washed with brine, dried over $Na_2SO_4$, filtered and concentrated in vacuo. Purified on silica gel (10 g SNAP, 12 CV, 5-60% ethyl acetate/hexanes) affording 4-[2-[tert-butyl(dimethyl)silyl]oxyethyl]-7-(trifluoromethylsulfonyl)indan-1-one (89.0 mg, 0.21 mmol, 81% yield).

Step D: Pivalic acid (2.2 mg, 0.02 mmol) was added to a mixture of 4-[2-[tert-butyl(dimethyl)silyl]oxyethyl]-7-(trifluoromethylsulfonyl)indan-1-one (89.0 mg, 0.21 mmol) and 3-methoxypropylamine (37.6 mg, 0.42 mmol) in cyclohexane (1.5 mL):toluene (1.5 mL) at room temperature then warmed to reflux with the azeotropic removal of water by Dean-Stark trap. Monitored by $^1$H-NMR. Cooled to room temperature then concentrated in vacuo. Used without further purification.

Step E: Crude 4-[2-[tert-butyl(dimethyl)silyl]oxyethyl]-N-(3-methoxypropyl)-7-(trifluoromethylsulfonyl)indan-1-imine (103.0 mg, 0.21 mmol) in acetonitrile (1.5 mL) was added to 1-chloromethyl-4-fluoro-1,4-diazoniabicyclo[2.2.2]octane bis(tetrafluoroborate) (184.8 mg, 0.52 mmol) and sodium Sulfate (59.3 mg, 0.42 mmol) in acetonitrile (1.5 mL) at 60° C. and stirred for 1 h. Cooled to room temperature then 1 N HCl (3.0 mL) was added and stirred overnight. Extracted with ethyl acetate, washed with brine, dried over $MgSO_4$, filtered and concentrated in vacuo. Purified on reverse phase silica gel (12+M, 14 CV, 20-100% acetonitrile/water) affording 2,2-difluoro-4-(2-hydroxyethyl)-7-(trifluoromethylsulfonyl)indan-1-one (40.0 mg, 0.12 mmol, 56% yield).

Step F: Chloro{[(1R,2R)-(−)-2-amino-1,2-diphenylethyl](4-toluenesulfonyl)amido}(p-cymene)ruthenium(II) (1.5 mg, 0.002 mmol) was added all at once to an ice cold solution of 2,2-difluoro-4-(2-hydroxyethyl)-7-(trifluoromethylsulfonyl)indan-1-one (40.0 mg, 0.12 mmol), triethylamine (32.4 µL, 0.23 mmol) and formic acid (13.2 µL, 0.35 mmol) in dichloromethane (1.0 mL) then sealed with a threaded teflon cap and placed in a 4° C. fridge over the weekend. Purified directly on silica gel (10 g SNAP Ultra, 14 CV, 25-100% ethyl acetate/hexanes) affording (1S)-2,2-difluoro-4-(2-hydroxyethyl)-7-(trifluoromethylsulfonyl)indan-1-ol (Compound 496) (28.0 mg, 0.081 mmol, 70% yield) as a clear oil. Swirled with hexanes to yield a white solid. LC-MS ESI (−) m/z 345 (M−H).

Example 27: Synthesis of 3-(2,2-difluoro-1-hydroxy-7-((trifluoromethyl)sulfonyl)-2,3-dihydro-1H-inden-4-yl)propane-1,2-diol (Compound 521)

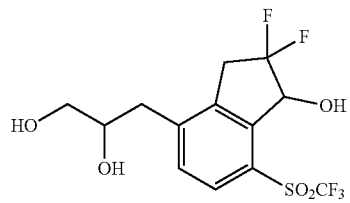

Step A: Tetrakis(triphenylphosphine)palladium(0) (59.69 mg, 0.0500 mmol) was added all at once to a degassed solution of 4'-bromo-7'-(trifluoromethylsulfonyl)spiro[1,3-dioxolane-2,1'-indane] (200.0 mg, 0.52 mmol) and allyltributyltin (0.19 mL, 0.62 mmol) in DMF (5.0 mL) under nitrogen then warmed to 90° C. until complete as judged by LC-MS. Cooled to room temperature, saturated KF (5.0 mL) was added and stirred for 30 min, extracted with MTBE, washed with brine, dried over MgSO$_4$, filtered and concentrated in vacuo. Purified on silica gel (10 g SNAP Ultra, 14 CV, 5-50% ethyl acetate/hexanes) affording 4'-allyl-7'-(trifluoromethylsulfonyl)spiro[1,3-dioxolane-2,1'-indane] (145.0 mg, 0.42 mmol, 81% yield).

Step B: HCl (2.0 mL, 2.0 mmol) was added all at once to a solution of 4'-allyl-7'-(trifluoromethylsulfonyl)spiro[1,3-dioxolane-2,1'-indane] (145.0 mg, 0.42 mmol) in acetone (5.0 mL) then stirred overnight at room temperature. Diluted with water, extracted with MTBE, washed with brine, dried over MgSO$_4$, filtered and concentrated in vacuo. Used without further purification.

Step C: Pivalic acid (2.6 mg, 0.02 mmol) was added all at once to 4-allyl-7-(trifluoromethylsulfonyl)indan-1-one (76.0 mg, 0.25 mmol) and 3-methoxypropylamine (76.4 µL, 0.75 mmol) in cyclohexane (1.5 mL):toluene (1.5 mL) at room temperature then warmed to reflux with azeotropic removal of water via a Dean-Stark trap until complete as judged by $^1$H-NMR. Cooled to room temperature then concentrated in vacuo. Used without further purification.

Step D: 1-chloromethyl-4-fluoro-1,4-diazoniabicyclo[2.2.2]octane bis(tetrafluoroborate) (219.4 mg, 0.62 mmol) was added all at once to crude 4-allyl-N-(3-methoxypropyl)-7-(trifluoromethylsulfonyl)indan-1-imine (93.0 mg, 0.25 mmol) and sodium sulfate (70.4 mg, 0.50 mmol) in acetonitrile (3.0 mL) at 60° C. then stirred for 1 h. Cooled to room temperature, 1 N HCl was added (3.0 mL) and stirred for 15 min, extracted with MTBE, washed with brine, dried over MgSO$_4$, filtered and concentrated in vacuo. Used without further purification.

Step E: Sodium borohydride (25.0 mg, 0.66 mmol) was added all at once to a solution of 4-allyl-2,2-difluoro-7-(trifluoromethylsulfonyl)indan-1-one (75.0 mg, 0.22 mmol) and 2,2-difluoro-4-[(E)-prop-1-enyl]-7-(trifluoromethylsulfonyl)indan-1-one (75.0 mg, 0.22 mmol) in methanol (2.0 mL) at room temperature and stirred for 30 min. Quenched with 1 N HCl (2.0 mL), diluted with water, extracted with MTBE, washed with brine, dried over Na$_2$SO$_4$, filtered and concentrated in vacuo. Used without further purification.

Step F: Osmium tetroxide, 4 wt. % solution (27.9 µL, 0.004 µL mmol) was added all at once to a solution of 4-allyl-2,2-difluoro-7-(trifluoromethylsulfonyl)indan-1-ol (75.0 mg, 0.22 mmol), 4-methylmorpholine N-oxide (51.3 mg, 0.44 mmol) in acetone (2.0 mL) then stirred over the weekend in a sealed vial. Diluted with water, extracted with ethyl acetate, washed with brine dried over Na$_2$SO$_4$, filtered and concentrated in vacuo. Purified on silica gel (10 g SNAP Ultra, 14 CV, 50-100% ethyl acetate/hexanes) affording Compound 521 (17.4 mg, 0.046 mmol, 21% yield). LC-MS ESI (−) m/z 375 (M−H)

Example 28: Synthesis of 4-(3-hydroxypropyl)-7-((trifluoromethyl)sulfonyl)-2,3-dihydro-1H-inden-1-ol (Compound 522)

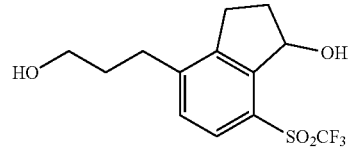

Step A: 3-Ethoxy-3-oxopropylzinc bromide (0.77 mL, 0.39 mmol) was added to a solution of 4'-bromo-7'-(trifluoromethylsulfonyl)spiro[1,3-dioxolane-2,1'-indane] (50.0 mg, 0.13 mmol), palladium(II) acetate (2.9 mg, 0.01 mmol) and SPhos (10.6 mg, 0.03 mmol) in tetrahydrofuran (0.5 mL) at room temperature under nitrogen in a sealed microwave vial then warmed to 60° C. until complete as judged by LC-MS. Cooled to room temperature, quenched with saturated ammonium chloride, extracted with ethyl acetate, washed with brine, dried over MgSO$_4$, filtered and concentrated in vacuo. Purified on silica gel (10 g SNAP Ultra, 14 CV, 5-50% ethyl acetate/hexanes) affording ethyl 3-[7'-(trifluoromethylsulfonyl)spiro[1,3-dioxolane-2,1'-indane]-4'-yl]propanoate (25.0 mg, 0.061 mmol, 47% yield).

Step B: 1 N HCl (1.0 mL, 1.0 mmol) was added all at once to a solution of ethyl 3-[7'-(trifluoromethylsulfonyl)spiro[1,3-dioxolane-2,1'-indane]-4'-yl]propanoate (25.0 mg, 0.06 mmol) in acetone (2.0 mL) then stirred at room temperature until complete as judged by LC-MS (30 min). Diluted with brine, extracted with ethyl acetate, dried over Na$_2$SO$_4$, filtered and concentrated in vacuo. Used without further purification.

Step C: Lithium borohydride solution (0.2 mL, 0.40 mmol) was added to a solution of crude ethyl 3-[1-oxo-7-(trifluoromethylsulfonyl)indan-4-yl]propanoate (22.0 mg, 0.06 mmol) in tetrahydrofuran (0.50 mL) at room temperature under nitrogen then stirred until complete as judged by LC-MS. Warmed to 75° C. after 5 h at room temperature and held for 3 h. Cooled to room temperature, poured into 1 N HCl, extracted with ethyl acetate, washed with brine, dried over MgSO₄, filtered and concentrated in vacuo. Purified on silica gel (10 g SNAP Ultra, 14 CV, 50%-100% EtOAc/hexanes) affording Compound 522 (4.4 mg, 0.014 mmol, 22% yield). LC-MS ESI (−) m/z 323 (M−H).

Example 29: Synthesis of 2-[1-oxo-7-(trifluoromethylsulfonyl)indan-4-yl]acetamide (Compound 523)

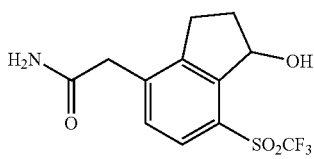

Step A: Preparation of 2-[7'-(trifluoromethylsulfonyl)spiro[1,3-dioxolane-2,1'-indane]-4'-yl]acetic acid: Sodium hydroxide (0.55 mL, 1.66 mmol) added by syringe to diethyl 2-[7'-(trifluoromethylsulfonyl)spiro[1,3-dioxolane-2,1'-indane]-4'-yl]propanedioate (515.0 mg, 1.10 mmol) in ethanol 95% (2.2 mL) at room temperature and stirred for 30 min. Warmed to 60° C. for 3 h. Added additional sodium hydroxide (0.55 mL, 1.66 mmol) and stirred until complete as judged by LC-MS. Acidified to pH 2 with 1 N HCl, diluted with brine, extracted with ethyl acetate, dried over Na₂SO₄, filtered and concentrated in vacuo affording 2-[7'-(trifluoromethylsulfonyl)spiro[1,3-dioxolane-2,1'-indane]-4'-yl]acetic acid (368 mg, 1.00 mmol, 91% yield). Used without further purification.

Step B: Preparation of 2-[1-oxo-7-(trifluoromethylsulfonyl)indan-4-yl]acetamide: N,N-Diisopropylethylamine (142.7 μL, 0.82 mmol) added all at once to 2-[7'-(trifluoromethylsulfonyl)spiro[1,3-dioxolane-2,1'-indane]-4'-yl]acetic acid (100.0 mg, 0.27 mmol), ammonium chloride (73.0 mg, 1.4 mmol) and HATU (156.1 mg, 0.41 mmol) in DMF (2.0 mL) at room temperature then stirred until complete as judged by LC-MS. Purified directly on reverse phase silica gel (12+M, 14 CV, 20-100% acetonitrile/water) affording 2-[1-oxo-7-(trifluoromethylsulfonyl)indan-4-yl]acetamide (12.0 mg, 0.037 mmol, 14% yield). LC-MS ESI (+) m/z 322 (M+H).

Step C: Preparation of 2-[1-hydroxy-7-(trifluoromethylsulfonyl)indan-4-yl]acetamide: Sodium borohydride (4.2 mg, 0.11 mmol) was added all at once to 2-[1-oxo-7-(trifluoromethylsulfonyl)indan-4-yl]acetamide (12.0 mg, 0.04 mmol) in methanol (1.0 mL) at room temperature and stirred for 20 min. Quenched with 1 N HCl, extracted with ethyl acetate, washed with brine, dried over Na₂SO₄, filtered and concentrated in vacuo. A portion was purified by preparative TLC (ethyl acetate) affording Compound 523 (1.6 mg, 0.005 mmol, 13% yield). LC-MS ESI (−) m/z 322 (M−H).

Example 30: Synthesis of (R)-2-(1-hydroxy-7-((trifluoromethyl)sulfonyl)-2,3-dihydro-1H-inden-4-yl)acetic acid (Compound 524)

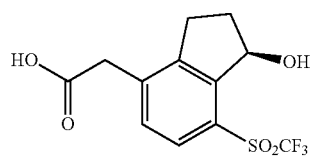

Chloro {[(1R,2R)-(−)-2-amino-1,2-diphenylethyl](4-toluenesulfonyl)amido}(p-cymene)ruthenium(II) (2.0 mg, 0.003 mmol) was added all at once to an ice cold solution of 2-[1-oxo-7-(trifluoromethylsulfonyl)indan-4-yl]acetic acid (102.0 mg, 0.32 mmol), triethylamine (88.2 μL, 0.63 mmol) and formic acid (35.8 μL, 0.95 mmol) in dichloromethane (3.0 mL), sealed with a teflon lined cap and placed in a 4° C. fridge overnight. Warmed to room temperature then stirred for an additional 3 days. Concentrated in vacuo then purified on reverse phase silica gel (25+M, 14 CV, 20-100% acetonitrile/water), diluted with ethyl acetate, washed with 1 N HCl to remove triethylamine, washed with brine, dried over Na₂SO₄, filtered and concentrated in vacuo affording 2-[(1R)-1-hydroxy-7-(trifluoromethylsulfonyl)indan-4-yl]acetic acid (45.0 mg, 0.14 mmol, 44% yield). LC-MS ESI (−) m/z 323 (M−H).

Example 31: Synthesis of (1S,3R)-4-(3,3-difluorocyclobutoxy)-2,2,3-trifluoro-7-(methylsulfonyl)-2,3-dihydro-1H-inden-1-ol (Compound 574) and (1S,3S)-4-(3,3-difluorocyclobutoxy)-2,2,3-trifluoro-7-(methylsulfonyl)-2,3-dihydro-1H-inden-1-ol (Compound 575)

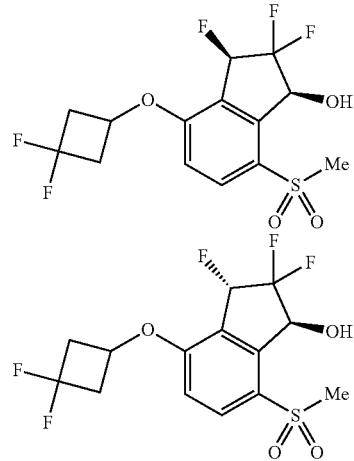

Step A: Preparation of 4,7-difluoro-1H-indene-1,3(2H)-dione: A solution of 3,6 difluorophthalic anhydride (4.25 g, 23.1 mmol), tert-butyl 3-oxobutanoate (4.29 mL, 25.9 mmol) and acetic anhydride (21.0 mL, 221.6 mmol) at 25° C. was treated with triethylamine (11.7 mL, 84.3 mmol) and stirred at ambient temperature for 18 h. The reaction mixture was cooled to 0° C. and treated with 10% hydrochloric acid (65 mL, 211 mmol) by dropwise addition. Once the addition was complete, the ice bath was removed and the mixture stirred at ambient for 10 minutes. The mixture was then heated to 75° C. for 10 minutes. During this time gas evolution was observed. The suspension slowly broke up to form a clear red mixture. The reaction mixture was poured into 100 mL of water and extracted with 3×50 mL CH₂Cl₂. The combined organics were dried with MgSO₄, filtered, and concentrated to dryness. The product was used without further purification.

Step B: Preparation of 2,2,4,7-tetrafluoro-1H-indene-1,3(2H)-dione: A solution of the unpurified 4,7-difluoro-1H-indene-1,3(2H)-dione (4.2 g, 23.1 mmol) in acetonitrile (100 mL) cooled in a 25° C. water bath was treated with sodium carbonate (5.38 g, 50.7 mmol). Selectfluor® (17.97 g, 50.7 mmol) was added and the reaction mixture was stirred at ambient temperature for 1 hour. Volatiles were removed under reduced pressure and the residue was poured into 100 mL of 0.1% HCl and extracted with 3×50 mL EtOAc. The combined organics were rinsed with 40 mL of brine, dried with $MgSO_4$, filtered, and concentrated to dryness. The residue was purified by flash chromatography on silica gel 1:1 hexane/ethyl acetate to give 2,2,4,7-tetrafluoro-1H-indene-1,3(2H)-dione (3.5 g, 70%) as a solid. $^1$H NMR (400 MHz, $CDCl_3$): δ 7.70 (t, 2H).

Step C: Preparation of (S)-2,2,4,7-tetrafluoro-3-hydroxy-2,3-dihydro-1H-inden-1-one: To a solution of 2,2,4,7-tetrafluoro-1H-indene-1,3(2H)-dione (3.48 g, 16.0 mmol) in dichloromethane (150 mL) at 0° C. was added formic acid (600 μL, 16.0 mmol) and triethylamine (1.55 mL, 11.2 mmol). The resulting mixture was sparged with nitrogen for 5 minutes and then RuCl(p-cymene)[(S,S)-Ts-DPEN] (203.6 mg, 0.32 mmol) was added. The reaction vessel was sealed and put into a 4° C. refrigerator to stand for 18 hours. The reaction mixture was poured into 40 mL 1 N HCl. The $CH_2Cl_2$ layer was separated and the aqueous layer extracted with ethyl acetate (2×50 mL). The combined organics were dried with $Na_2SO_4$, filtered and concentrated under reduced pressure. The residue was purified by flash chromatography on silica gel using 25% EtOAc/hexane to give (S)-2,2,4,7-tetrafluoro-3-hydroxy-2,3-dihydro-1H-inden-1-one (2.9 g, 83%) as an oil. $^1$H NMR (400 MHz, $CDCl_3$): δ 7.51 (ddd, 1H), 7.29-7.23 (m, 1H), 5.44 (dd, 1H), 2.79 (dd, 1H).

Step D: Preparation of (S)-2,2,4-trifluoro-3-hydroxy-7-(methylthio)-2,3-dihydro-1H-inden-1-one: A solution of (S)-2,2,4,7-tetrafluoro-3-hydroxy-2,3-dihydro-1H-inden-1-one (966 mg, 4.39 mmol) in acetonitrile (40 mL) at 0° C. was sparged with nitrogen for 5 minutes and treated with sodium thiomethoxide (353.7 mg, 5.05 mmol). The ice bath was removed and the reaction mixture was allowed to stir at ambient temperature for 2 hours. The reaction mixture was evaporated and the residue partitioned between 40 mL of EtOAc and 40 mL of water. The aqueous layer was further extracted with 2×40 mL of EtOAc. The combined organic extracts were washed with brine, dried over $MgSO_4$, filtered, and evaporated. The residue was chromatographed on silica using 10-60% EtOAc/hexane to afford (S)-2,2,4-trifluoro-3-hydroxy-7-(methylthio)-2,3-dihydro-1H-inden-1-one (870 mg, 80%) as a yellow solid. LCMS ESI (+)[M+H]$^+$ m/z 249.

Step E: Preparation of (S)-2,2,4-trifluoro-3-hydroxy-7-(methylsulfonyl)-2,3-dihydro-1H-inden-1-one: (S)-2,2,4-trifluoro-3-hydroxy-7-(methylthio)-2,3-dihydro-1H-inden-1-one (400 mg, 1.6 mmol) was dissolved in MeOH (10 mL) and the reaction was treated dropwise with a solution of Oxone® (2.18 g, 3.55 mmol) dissolved in water (10 mL). The mixture was stirred at ambient temperature for 14 hours. The reaction mixture was filtered, the solids were washed with ethyl acetate and the filtrate was concentrated in vacuo. The aqueous filtrate was extracted 3×30 mL of EtOAc and then the combined organics were washed with saturated NaCl, dried over $Na_2SO_4$ and concentrated in vacuo to a yellow solid that was used without further purification (467 mg). LCMS ESI (+) [M+H]$^+$ m/z 281.

Step F: Preparation of (R)-2,2,3,4-tetrafluoro-7-(methylsulfonyl)-2,3-dihydro-1H-inden-1-one: (S)-2,2,4-trifluoro-3-hydroxy-7-(methylsulfonyl)-2,3-dihydro-1H-inden-1-one (450 mg, 1.6 mmol) was dissolved in dichloromethane (16 mL), cooled to 0° C. and treated dropwise with diethylaminosulfur trifluoride (0.32 mL, 2.4 mmol) and the mixture was stirred at 0° C. for 2 hours, then the whole homogeneous reaction mixture was placed into the refrigerator overnight. The reaction was treated with additional diethylaminosulfur trifluoride (0.32 mL, 2.4 mmol) and stirring continued for 6 h at 0° C. The cold reaction was treated with saturated $NaHCO_3$ (10 mL) and stirred vigorously for 20 minutes. The mixture was diluted with additional methylene chloride and the layers were separated. The aqueous was re-extracted with methylene chloride and the combined organic layers were dried over $Na_2SO_4$ and concentrated in vacuo to a yellow solid. The crude material was chromatographed on $SiO_2$ (Biotage SNAP Ultra) and eluted with a gradient of ethyl acetate/hexane. The desired material was concentrated to a pale yellow solid (258 mg). LCMS ESI (+) [M+H]$^+$ m/z 283.

Step G: Preparation of (R)-2,2,3,4-tetrafluoro-7-(methylsulfonyl)-2,3-dihydrospiro[indene-1,2'-[1,3]dioxolane]: A solution of (3R)-2,2,3,4-tetrafluoro-7-methylsulfonyl-indan-1-one (2.03 g, 7.2 mmol) and 2-bromoethanol (1.53 mL, 21.6 mmol) in DMF (16 mL) at 25° C. was treated with potassium carbonate (2.98 g, 21.6 mmol) and stirred at 25° C. for 30 min. The reaction mixture was poured into 200 mL of water and extracted with 3×50 mL Et2O. The combined organics were rinsed with 30 mL of brine, dried with MgSO4, filtered, and concentrated to dryness. The off-white solid was used without further purification. LCMS ESI (+) [M+H]$^+$ m/z 327.

Step H: Preparation of (R)-4-(3,3-difluorocyclobutoxy)-2,2,3-trifluoro-7-(methylsulfonyl)-2,3-dihydrospiro[indene-1,2'-[1,3]dioxolane]: A solution of (3'R)-2',2',3',4'-tetrafluoro-7'-methylsulfonyl-spiro[1,3-dioxolane-2,1'-indane] (1.95 g, 5.98 mmol) and 3,3-difluoro-cyclobutanol (770 μL, 7.95 mmol) in acetonitrile (30 mL) at 25° C. was treated with potassium hydroxide (402.4 mg, 7.17 mmol) and stirred at 25° C. for 1 h. Excess acetonitrile was removed by concentration under reduced pressure. The reaction mixture was poured into 40 mL of water and extracted with 3×40 mL EtOAc. The combined organics were rinsed with 10 mL of brine, dried with $MgSO_4$, filtered, and concentrated to dryness. Purification was achieved by chromatography on silica using 15-45% EtOAc/hexane to afford a white solid (2.2 g, 89%). LCMS ESI (+) [M+H]$^+$ m/z 415.

Step I: Preparation of (R)-4-(3,3-difluorocyclobutoxy)-2,2,3-trifluoro-7-(methylsulfonyl)-2,3-dihydro-1H-inden-1-one: A solution of (3'R)-4'-(3,3-difluorocyclobutoxy)-2',2',3'-trifluoro-7'-methylsulfonyl-spiro[1,3-dioxolane-2,1'-indane] (2.2 g, 5.31 mmol) in dichloromethane (40 mL) at 25° C. was treated with perchloric acid (70% in water, 10 mL) and left to stir for 2 days. The reaction mixture was carefully quenched by the addition of 100 mL of saturated aqueous $NaHCO_3$ and extracted with 3×50 mL $CH_2Cl_2$. The combined organics were rinsed with 10 mL of brine, dried with $MgSO_4$, filtered, and concentrated to dryness. Purification was achieved by chromatography on silica using 25-65% EtOAc/hexane to afford a solid (1.41 g, 72%). LCMS ESI (+) [M+H]$^+$ m/z 371.

Step J: Preparation of (1S,3R)-4-(3,3-difluorocyclobutoxy)-2,2,3-trifluoro-7-(methylsulfonyl)-2,3-dihydro-1H-inden-1-ol (Compound 574) and (1S,3S)-4-(3,3-difluorocyclobutoxy)-2,2,3-trifluoro-7-(methylsulfonyl)-2,3-dihydro-1H-inden-1-ol (Compound 575): A solution of (3R)-4-(3,3-difluorocyclobutoxy)-2,2,3-trifluoro-7-methylsulfonyl-indan-1-one (1.41 g, 3.81 mmol) in dichloromethane (40 mL) was cooled to 0° C. and sparged with nitrogen for 5 minutes. During this time formic acid (430 μL, 11.42 mmol) and triethylamine (1.06 mL, 7.62 mmol) were sequentially added. Once the sparging was complete, RuCl(p-cymene)[(R,R)-Ts-DPEN] (48.5 mg, 0.076 mmol) was added under a continuous stream of nitrogen. The reaction vessel was sealed and put into the refrigerator to react overnight. Volatiles were removed by concentration under reduced pressure. The residue was purified by chromatography on silica using 25-55% EtOAc/hexane. Additional purifications by chromatography on silica using 20-50% EtOAc/hexane were necessary to isolate material of sufficient purity. A flash crystallization was preformed from $CHCl_3$. The sample was dissolved in a minimum of refluxing $CHCl_3$ and then cooled to 0° C. The collected solid was rinsed with $CHCl_3$ and dried under high vacuum overnight to afford Compound 574 as a white solid (550 mg, 39%). From the repeated purifications, Compound 575 was isolated as a white solid. Data for Compound 574: LCMS ESI (+) $[M+H]^+$ m/z 373; $^1$H NMR (400 MHz, $(CD_3)_2CO$): δ 8.11 (dd, 1H), 7.33 (d, 1H), 5.87 (dd, 1H), 5.65-5.59 (m, 1H), 5.17-5.08 (m, 1H), 3.40-3.26 (m, 2H), 3.27 (s, 3H), 2.98-2.81 (m, 2H), 2.80 (t, 1H). Data for Compound 575: LCMS ESI (+) $[M+H]^+$ m/z 373; $^1$H NMR (400 MHz, $CDCl_3$): δ 8.06 (dd, 1H), 6.87 (d, 1H), 5.92 (dd, 1H), 5.78 (td, 1H), 4.86-4.76 (m, 1H), 3.98 (d, 1H), 3.25-3.14 (m, 2H), 3.22 (s, 3H), 2.95-2.78 (m, 2H).

Example 32: Synthesis of (1S,3R)-4-(3,3-difluoro-cyclobutoxy)-2,2,3-trifluoro-7-((fluoromethyl)sulfonyl)-2,3-dihydro-1H-inden-1-ol (Compound 576)

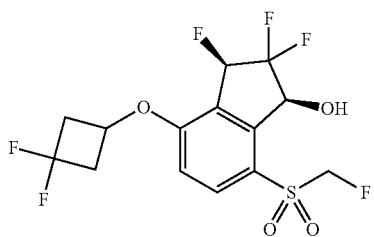 [SMILES: O=S(=O)(CF)c1ccc(OC2CC(F)(F)C2)c2c1[C@H](O)C(F)(F)[C@@H]2F]

Step A: Preparation of (R)-2,2,3,4-tetrafluoro-7-(methylthio)-2,3-dihydro-1H-inden-1-one: A solution of (S)-2,2,4-trifluoro-3-hydroxy-7-(methylthio)-2,3-dihydro-1H-inden-1-one (402 mg, 1.62 mmol) in dichloromethane (16.2 mL) at 0° C. was treated with diethylaminosulfur trifluoride (390 µL, 2.92 mmol). The ice bath was removed from the resulting reaction mixture and the reaction mixture was stirred for 2 hours at room temperature. Volatiles were removed by concentration under reduced pressure. The residue was suspended in 30 mL of EtOAc, cooled to 0° C., and quenched by the addition of 20 mL of saturated aqueous $NaHCO_3$. The reaction mixture was vigorously stirred for 30 minutes and then extracted with 3×20 mL EtOAc. The combined organics were rinsed with 10 mL of brine, dried with $MgSO_4$, filtered, and concentrated to dryness. The product was used without further purification. LCMS ESI (+) $[M+H]^+$ m/z 251.

Step B: Preparation of (R)-2,2,3,4-tetrafluoro-7-((fluoromethyl)thio)-2,3-dihydro-1H-inden-1-one: A solution of (R)-2,2,3,4-tetrafluoro-7-(methylthio)-2,3-dihydro-1H-inden-1-one (393 mg, 1.57 mmol) in acetonitrile (15.7 mL) at 0° C. was treated with Selectfluor® (584.3 mg, 1.65 mmol) and stirred at 0° C. for 2 hours. Volatiles were removed by concentration under reduced pressure. The reaction mixture was poured into 30 mL of water and extracted with 3×20 mL EtOAc. The combined organics were rinsed with 10 mL of brine, dried with $MgSO_4$, filtered, and concentrated to dryness. Purification was achieved by chromatography on silica using 10-30% EtOAc/hexane to afford (R)-2,2,3,4-tetrafluoro-7-((fluoromethyl)thio)-2,3-dihydro-1H-inden-1-one (153 mg, 36%) as a yellow oil. LCMS ESI (+) $[M-F]^+$ m/z 249.

Step C: Preparation of (R)-2,2,3,4-tetrafluoro-7-((fluoromethyl)sulfonyl)-2,3-dihydro-1H-inden-1-one: A solution of (R)-2,2,3,4-tetrafluoro-7-((fluoromethyl)thio)-2,3-dihydro-1H-inden-1-one (91.8 mg, 0.34 mmol) in a mixture of methanol (3.4 mL) and water (3.4 mL) was treated with Oxone® (252.5 mg, 0.41 mmol). The resulting suspension was heated to 60° C. overnight. Additional Oxone® (252.5 mg, 0.41 mmol) was added and the reaction mixture heated for an additional 6 hours. Volatiles were removed by concentration under reduced pressure. The reaction mixture was poured into 100 mL of water and extracted with 3×25 mL EtOAc. The combined organics were rinsed with 10 mL of brine, dried with $MgSO_4$, filtered, and concentrated to dryness. Purification was achieved by chromatography on silica using 10-40% EtOAc/hexane to afford (R)-2,2,3,4-tetrafluoro-7-((fluoromethyl)sulfonyl)-2,3-dihydro-1H-inden-1-one as a white solid (73 mg, 71%). LCMS ESI (+) $[M+H]^+$ m/z 301.

Step D: Preparation of (1S,3R)-4-(3,3-difluorocyclobutoxy)-2,2,3-trifluoro-7-((fluoromethyl)sulfonyl)-2,3-dihydro-1H-inden-1-ol (Compound 576): Prepared similarly as described in Example 31, Steps G-J. Purification was achieved by chromatography on silica using 15-30% EtOAc/hexane to afford Compound 576 (29.8 mg, 49%) as a white solid. Retention time HPLC (14 min)=4.63 min; LCMS ESI (+) $[M+H]^+$ m/z 391; $^1$H NMR (400 MHz, $CDCl_3$): δ 8.13 (dd, 1H), 6.93 (d, 1H), 5.76 (dd, 1H), 5.59-5.53 (m, 1H), 5.47 (dd, 1H), 5.18 (dd, 1H), 4.90-4.80 (m, 1H), 3.29-3.16 (m, 2H), 3.16 (d, 1H), 2.97-2.81 (m, 2H).

Example 33: HIF-2α Scintillation Proximity Assay (SPA)

The total assay volume was about 100 µL in the following configuration: 2 µL compound in 100% DMSO, 88 µL buffer with protein and probe and 10 µL of SPA beads. The compound was diluted in a master plate consisting of a 10-point dose response with a 3-fold compound dilution from 100 µM to 5 nM. Assays were run on a 96-well plate in which one column, designated as the high signal control, contained DMSO with no compound and another column, designated as the low signal control, contained no protein. Prior to plating out of compound, a buffer solution, consisting of 25 mM TRIS pH 7.5 (Sigma), 150 mM NaCl (Sigma), 15% Glycerol (Sigma), 0.15% BSA (Sigma), 0.001% Tween-20 (Sigma), 150 nM N-(3-Chlorophenyl-4,6-$t_2$)-4-nitrobenzo[c][1,2,5]oxadiazol-5-amine (Compound 183) and 100 nM HIF-2α HIS TAG-PASB Domain, was made and allowed to equilibrate for 30 minutes. Compounds that were to be tested were then plated in to a 96-well white clear bottom Isoplate-96 SPA plate (Perkin Elmer). To the compounds was added 88 µL of the buffer solution, then the plate covered with a plastic cover and aluminum foil, placed onto a shaker and equilibrated for 1 hour. After equilibration, 10 µL of a 2 mg/mL solution of YSi Cu His tagged SPA beads (Perkin Elmer) were then added to each well of the plate, covered and equilibrated for another 2 hours. The plates were then removed from the shaker, placed into a 1450 LSC and luminescence counter MicroBeta Trilux (Perkin Elmer) to measure the extent of probe displacement. The percent inhibition was determined and $IC_{50}$ values were calculated using the Dotmatics system on the following equation: % inhibition=[(high control−sample)/(high control−low control)]×100.

Example 34: VEGF ELISA Assay

Figure 28:
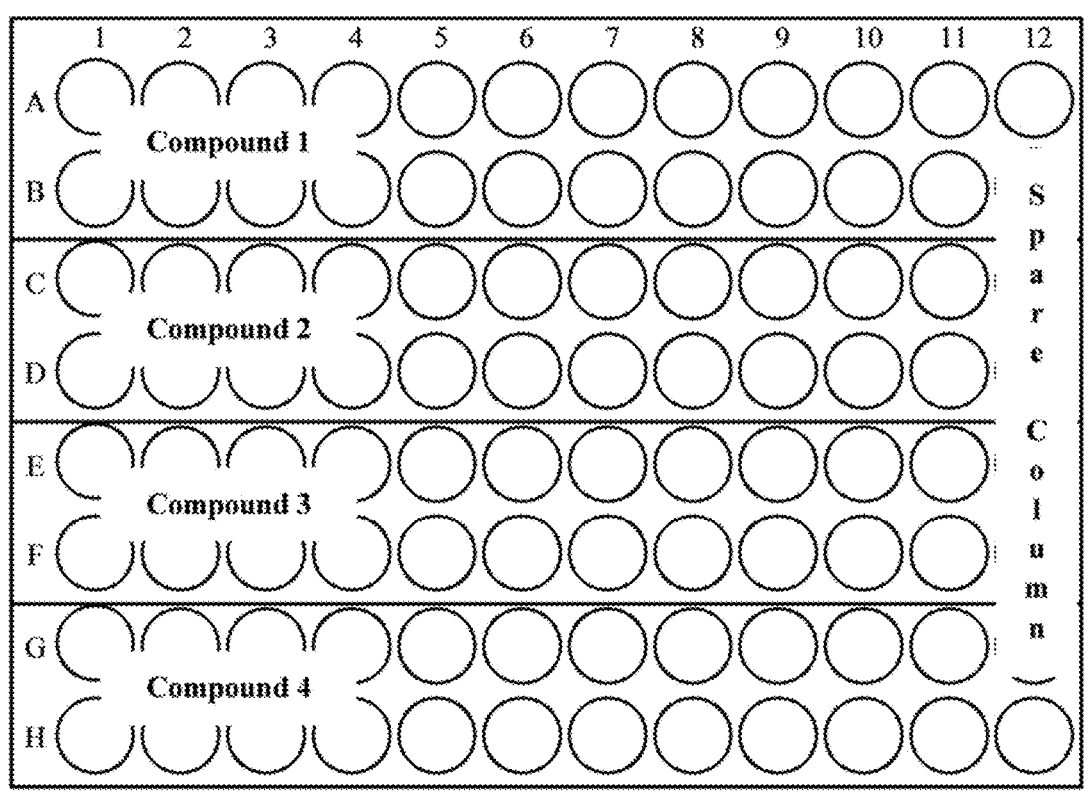
FIG. 28 depicts a 96-well plate layout of an ELISA assay.

About 7500 786-O cells in 180 μL of growth medium were seeded into each well of a 96-well, white, clear bottom plate (07-200-566, Fisher Scientific) on day one in the layout presented in FIG. 28. Four hours later, serial dilutions of 10× compound stocks were made in growth medium from 500× DMSO stocks, and 20 μL of those 10× stocks were added to each well to make final concentrations as follows (μM): 20, 6.67, 2.22, 0.74, 0.25, 0.082, 0.027, 0.009, 0.003, 0.001, and 0. Each concentration was plated in duplicate. About 20 hours later, medium was removed by suction and each well was supplied with 180 μL of growth medium. About 20 μl freshly-made 10× compound stocks were added to each well. About 24 hours later, cell culture medium was removed and the VEGF concentration determined using an ELISA kit purchased from R&D systems, following the manufacturer's suggested method. The $EC_{50}$ was calculated by GraphPad Prism using the dose-response-inhibition (four parameter) equation. The cell-seeded plate was then subjected to Cell-Titer-Glo luminescence cell viability assay (Promega) by adding 50 μL of Celltiter Glo reagent into each well and shaking the plate for 8 minutes at 550 rpm (Thermomixer R, Eppendorf) then the luminescence signal immediately read in a plate reader (3 second delay, 0.5 second/well integration time, Synergy 2 multi Detection Microplate reader).

Example 35: Luciferase Assay

Figure 29:
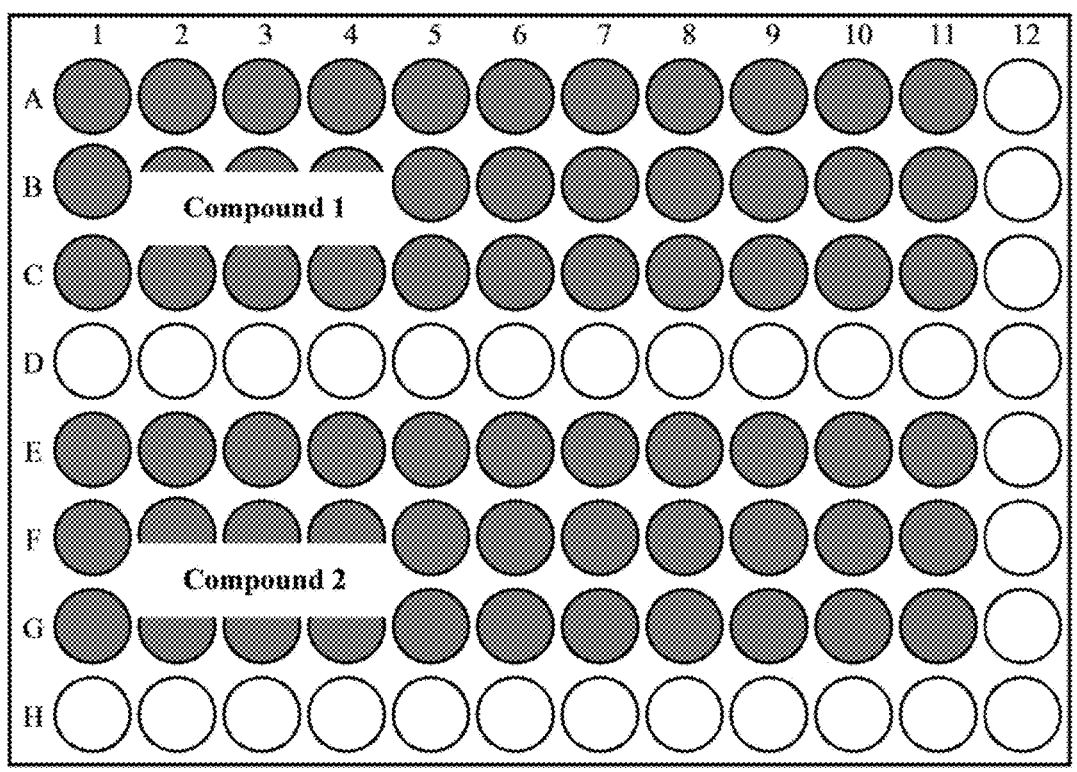
FIG. 29 depicts a 96-well plate layout of a luciferase assay.

786-O-Hif-Luc single clone cells were obtained by infecting 786-O cells (ATCC® CRL-1932™) with commercial lentivirus that delivers a luciferase gene driven by multiple HIF responsive elements (Cignal Lenti HIF Reporter (luc): CLS-007L, Qiagen) at Multiplicity of Infection (MOI) of 25 for 24 hours. The cells were replenished with fresh medium (Dulbecco's Modified Eagle's Medium (DMEM, D5796, Sigma) supplemented with 10% FBS (F6178, Sigma), 100 units penicillin and 100 μg streptomycin/mL (P4333, Sigma)) for another 24 hours. A pool of infected cells were then selected against 2 μg/mL of puromycin (P8833, Sigma) for 10 days followed by limited dilution to select single clones. The clones were tested for their response to HIF-2 inhibitors and the ones that showed the biggest dynamic range (786-0-Hif-Luc) were expanded and used for the luciferase assay. For the luciferase assay, about 7500 786-O-Hif-Luc cells in 90 μL growth medium were seeded into each well of a 96-well white opaque plate (08-771-26, Fisher scientific) a day before treatment with the layout presented in FIG. 29. On treatment day, serial dilutions of 10× compound stocks were made in growth medium from 500× DMSO stocks, and 10 μL of the 10× stocks were added to each well to make final concentrations as follows (μM): 20, 6.67, 2.22, 0.74, 0.25, 0.08, 0.027, 0.009, 0.003, 0.001, and 0. Each concentration was tested in triplicate. After about 24 hours, luciferase activity was determined using ONE-Glo Luciferase Assay Reagent (E6110, Promega) following the manufacturer's recommended procedure. $EC_{50}$ were calculated using Dotmatics software.

Table 3 shows biological activities of selected compounds in Luciferase, VEGF ELISA and Scintillation Proximity assays. Compound numbers correspond to the numbers and structures provided in Table 2 and Examples 1-32.

TABLE 3

| | Less than 50 nM (++++) | 50 nM to 249 nM (+++) | 250 nM to 1000 nM (++) | Greater than 1000 nM (+) |
|---|---|---|---|---|
| Scintillation Proximity Assay $IC_{50}$ (nM) | 1, 2, 6, 7a, 8, 9, 11, 15, 25, 26, 29, 30, 32, 34, 52, 55, 56, 57, 58, 59, 60, 61, 62, 63, 64, 65, 67, 80, 92, 98, 101, 111, 112, 123, 124, 140, 143, 144, 155, 158, 159, 160, 161, 163, 166, 167, 168, 179, 185, 186, 188, 191, 194, 196, 198, 200, 201, 206, 215, 221, 223, 225, 227, 228, 229, 230, 231, 232, 233, 234, 235, 236, 240, 245, 247, 251, 256, 263, 266, 273, 286, 289, 290, 292, 303, 304, 305, 306, 309, 310, 314, 315, 316, 317, 319, 321, 327, 328, 329, 331, 338, 340, 341, 342, 344, 347, 348, 349, 355, 356, 357, 359, 360, 364, 365, 368, 371, | 17, 18, 21, 33, 38, 39, 41, 50, 54, 74, 75, 90, 93, 94, 99, 100, 102, 107, 116, 117, 118, 119, 128, 136, 141, 145, 146, 147, 148, 153, 156, 162, 165, 187, 192, 195, 203, 204, 214, 224, 237, 241, 242, 252, 254, 260, 265, 267, 270, 274, 275, 276, 277, 285, 295, 302, 308, 312, 324, 325, 333, 334, 336, 353, 358, 361, 370, 378, 381, 383, 387, 388, 399, 405, 409, 412, 414, 421, 424, 426, 427, 437, 442, 444, 462, 468, 477, 480, 488, 517, 545, 547, 551, 554, 563, 569, 584, 586, 598, 604, 609, 614, 616, 620, 660, 663, 669, 672, 676, 681, 682, | 3, 5, 16, 22, 24, 27, 31, 40, 42, 43, 46, 48, 53, 70, 71, 72, 76, 78, 81, 91, 103, 104, 106, 115, 120, 131, 132, 133, 134, 135, 137, 152, 157, 172, 178, 182, 184, 190, 193, 197, 202, 207, 209, 212, 213, 218, 220, 243, 244, 249, 258, 261, 264, 269, 271, 281, 287, 293, 307, 339, 346, 369, 374, 411, 422, 423, 432, 433, 434, 471, 476, 481, 482, 487, 496, 505, 506, 511, 513, 522, 523, 531, 542, 575, 580, 591, 595, 601, 603, 612, 622, 637, 644, 648, 678, 703, 707, 711, 735, 748, 749, 750, 754, 762, 765, 770, 775, 781, 812, 816, 827 | 4, 7b, 12, 13, 14, 19, 20, 23, 28, 35, 36, 37, 44, 45, 47, 49, 51, 66, 68, 69, 73, 77, 79, 82, 83, 84, 85, 86, 87, 88, 89, 95, 96, 97, 105, 108, 109, 110, 113, 114, 121, 122, 125, 126, 127, 129, 130, 138, 139, 142, 149, 150, 151, 154, 164, 169, 170, 171, 173, 174, 175, 176, 177, 180, 181, 189, 199, 205, 208, 210, 211, 216, 217, 219, 222, 226, 238, 239, 246, 248, 250, 253, 255, 257, 259, 262, 268, 272, 278, 279, 280, 282, 283, 284, 288, 291, 294, 296, 297, 298, 299, 300, 301, 311, 313, 318, 320, 322, 323, 326, 330, 332, 335, 337, 343, 345, 350, 351, |

TABLE 3-continued

| Less than 50 nM (++++) | 50 nM to 249 nM (+++) | 250 nM to 1000 nM (++) | Greater than 1000 nM (+) |
|---|---|---|---|
| 372, 375, 376, 379, 386, 389, 392, 397, 398, 401, 403, 430, 431, 435, 436, 440, 443, 446, 451, 458, 465, 466, 467, 472, 473, 478, 483, 485, 486, 489, 491, 507, 509, 532, 549, 550, 557, 571, 572, 573, 574, 576, 577, 578, 579, 581, 582, 585, 587, 593, 594, 602, 605, 607, 608, 610, 617, 623, 626, 654, 655, 656, 657, 658, 659, 661, 675, 677, 699, 704, 709, 710, 712, 713, 715, 716, 727, 728, 731, 736, 739, 740, 741, 742, 743, 744, 746, 753, 756, 760, 761, 766, 774, 778, 783, 786, 787, 789, 790, 794, 796, 811, 813, 814, 825, 828, 831 | 686, 696, 697, 700, 701, 706, 714, 717, 718, 730, 734, 737, 747, 751, 755, 759, 768, 769, 771, 782, 784, 788, 795, 808, 815, 818 | | 352, 354, 362, 363, 366, 367, 373, 377, 380, 382, 384, 385, 390, 391, 393, 394, 395, 396, 400, 402, 404, 406, 407, 408, 410, 413, 415, 416, 417, 418, 419, 420, 425, 428, 429, 438, 439, 441, 445, 447, 448, 449, 450, 452, 453, 454, 455, 456, 457, 459, 460, 461, 463, 464, 469, 470, 474, 475, 484, 490, 492, 493, 494, 495, 497, 498, 499, 500, 501, 502, 503, 504, 508, 510, 512, 514, 515, 516, 518, 519, 520, 521, 524, 525, 526, 527, 528, 529, 530, 533, 534, 535, 536, 537, 538, 539, 540, 541, 543, 544, 546, 548, 552, 553, 555, 556, 558, 559, 560, 561, 562, 564, 565, 566, 567, 568, 570, 583, 588, 589, 590, 592, 596, 597, 599, 600, 606, 611, 613, 615, 618, 619, 621, 624, 625, 627, 628, 629, 630, 631, 632, 633, 634, 635, 636, 638, 639, 640, 641, 642, 643, 645, 646, 647, 649, 650, 651, 652, 653, 662, 664, 665, 666, 667, 668, 670, 671, 673, 674, 679, 680, 683, 684, 685, 687, 688, 689, 690, 691, 692, 693, 694, 695, 698, 702, 705, 708, 719, 720, 721, 722, 723, 724, 725, 726, 729, 732, 733, 738, 745, 752, 757, 758, 763, 764, 767, 772, 773, 776, 777, 779, 780, 785, 791, 792, 793, 797, 807, 809, 810, 817, 819, 820, 821, 822, 823, 824, 826, 829, 830, 833 |

TABLE 3-continued

| | Less than 50 nM (++++) | 50 nM to 249 nM (+++) | 250 nM to 1000 nM (++) | Greater than 1000 nM (+) |
|---|---|---|---|---|
| Mean VEGF ELISA EC$_{50}$ (nM) | 8, 9, 11, 15, 25, 55, 60, 63, 64, 158, 159, 161, 163, 167, 185, 186, 196, 228, 230, 233, 235, 236, 251, 273, 289, 292, 305, 306, 309, 316, 317, 364, 368, 375, 389, 403, 446, 451, 458, 465, 478, 489, 571, 572, 579, 617, 654, 655, 656, 657, 658, 709, 712, 742, 744, 813, 828 | 2, 17, 67, 155, 166, 188, 191, 225, 231, 234, 240, 245, 252, 254, 256, 303, 304, 310, 325, 342, 347, 349, 355, 357, 360, 365, 372, 398, 399, 421, 431, 467, 507, 574, 576, 578, 605, 610, 620, 659, 706, 710, 713, 736, 740, 743, 760, 761, 783, 784, 825 | 1, 34, 41, 74, 78, 80, 99, 102, 124, 132, 165, 203, 267, 353, 387, 424, 473, 495, 577, 734 | 98, 133, 179, 274 |
| Mean Luciferase EC$_{50}$ (nM) | 8, 9, 11, 15, 25, 55, 63, 64, 65, 158, 159, 160, 161, 163, 166, 167, 185, 186, 196, 215, 221, 225, 227, 228, 229, 230, 231, 232, 233, 234, 235, 236, 240, 247, 256, 266, 273, 289, 292, 303, 304, 305, 306, 309, 316, 317, 338, 347, 349, 364, 368, 371, 375, 380, 386, 389, 399, 403, 430, 431, 435, 446, 451, 458, 465, 467, 478, 489, 571, 572, 576, 579, 582, 584, 602, 605, 617, 654, 655, 656, 657, 658, 661, 675, 704, 709, 710, 712, 716, 727, 728, 742, 743, 744, 746, 783, 786, 787, 789, 790, 794, 813, 828, 831 | 1, 2, 6, 17, 26, 27, 56, 57, 58, 59, 60, 61, 62, 67, 155, 162, 165, 187, 188, 191, 200, 206, 223, 224, 237, 241, 245, 251, 252, 254, 260, 267, 270, 274, 276, 277, 285, 286, 290, 302, 310, 314, 315, 334, 336, 342, 348, 355, 357, 360, 365, 369, 372, 381, 383, 387, 388, 392, 398, 401, 405, 409, 421, 423, 424, 436, 473, 477, 480, 486, 488, 507, 523, 547, 549, 573, 574, 578, 593, 594, 598, 604, 610, 620, 623, 626, 659, 676, 677, 681, 686, 696, 697, 699, 706, 713, 715, 717, 730, 731, 734, 736, 740, 760, 761, 781, 782, 784, 795, 814, 818, 825 | 3, 5, 7a, 34, 38, 39, 41, 42, 43, 52, 54, 74, 80, 81, 90, 92, 93, 94, 99, 101, 107, 112, 115, 124, 144, 145, 146, 156, 168, 192, 194, 198, 203, 207, 213, 242, 243, 263, 265, 271, 275, 287, 293, 294, 295, 308, 312, 324, 325, 339, 353, 359, 361, 370, 377, 378, 390, 411, 414, 416, 422, 426, 432, 434, 437, 440, 443, 444, 462, 466, 468, 471, 472, 482, 483, 505, 517, 531, 532, 550, 557, 563, 569, 577, 585, 591, 595, 608, 616, 622, 644, 660, 663, 669, 678, 682, 707, 711, 714, 718, 747, 748, 750, 753, 756, 759, 762, 766, 768, 769, 771, 774, 775, 788, 796 | 16, 18, 20, 21, 22, 31, 32, 33, 35, 40, 46, 50, 53, 75, 85, 91, 98, 100, 103, 104, 110, 111, 114, 116, 117, 118, 119, 120, 128, 131, 132, 134, 135, 136, 140, 143, 147, 148, 151, 152, 157, 172, 181, 182, 190, 195, 201, 202, 209, 212, 214, 218, 220, 222, 226, 244, 249, 250, 253, 255, 258, 259, 261, 264, 268, 269, 272, 279, 291, 296, 300, 301, 307, 313, 352, 356, 358, 363, 374, 376, 379, 385, 394, 397, 400, 412, 427, 428, 433, 439, 441, 455, 456, 464, 470, 474, 476, 481, 485, 487, 491, 492, 495, 496, 506, 509, 511, 513, 516, 534, 538, 542, 545, 551, 554, 558, 565, 570, 575, 580, 581, 586, 601, 603, 607, 609, 612, 614, 618, 619, 637, 639, 665, 670, 672, 683, 692, 700, 701, 703, 721, 722, 723, 724, 725, 726, 735, 737, 739, 741, 749, 751, 752, 754, 755, 764, 765, 767, 770, 778, 779, 780, 808, 811, 812, 833 |

Example 36: Prevention of PAH by a HIF-2α Inhibitor

The preventive effects of sildenafil and Compound 231 were evaluated in rats with hypoxia/semaxanib induced pulmonary arterial hypertension. Male Sprague-Dawley rats (n=10 in each group) were orally administered vehicle (0.5% methylcellulose, 0.5% Tween80 in water, administered once daily), Compound 231 (100 or 300 mg/kg, administered once daily), or sildenafil (30 mg/kg, administered twice daily) daily for 28 consecutive days. Two rats not exposed to either semaxanib or hypoxia served as hypertrophic sentinels for this study. Rats received a single injection of semaxanib (200 mg/kg, s.c.) on the same day as initiation of test article dosing and introduction to the hypoxic chamber. Rats were kept in hypoxic conditions for the duration of this study. On the twenty-eighth day of test article dosing, the rats were anesthetized with ketamine/xylazine for terminal monitoring of pulmonary and systemic arterial pressures along with heart rate. In addition, histopathology and muscularization of pulmonary arterioles were evaluated in lungs from thirty-eight male (Sprague Dawley) rats in groups 1 (seven rats), 2 (nine rats), 3 (ten rats), 4 (ten rats), and 5 (two rats). Table 4 is a summary of the experimental design. Compound 231 has the following formula:

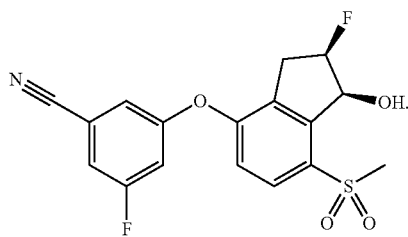 [SMILES: CS(=O)(=O)c1ccc(Oc2cc(F)cc(C#N)c2)c2c1[C@H](O)[C@H](F)C2]

There were substantive differences in systolic and mean pulmonary arterial pressures after 28 days in rats treated with Compound 231 compared to the vehicle group (Table 5). The low and high doses of Compound 231 showed a 38% and 56% reduction in systolic pulmonary arterial pressure—the variable used as the arbiter of protection. The 300 mg/kg QD Compound 231 systolic pulmonary artery pressures were also significantly reduced compared to sildenafil. The sildenafil group also showed protection versus vehicle. There was a significant protective effect with respect to right ventricular hypertrophy (as measured by Fulton's Index, RV/LV+S) in the Compound 231 cohort compared to vehicle. Rats treated with Compound 231 at 100 mg/kg QD presented with a 28% reduction in Fulton's right ventricular hypertrophy ratio, while animals treated with 300 mg/kg QD reduced this parameter by 40%. The 300 mg/kg QD dose was also superior to sildenafil with respect to Fulton's Index. Mean arterial pressure was also significantly increased in Compound 231 rats compared to vehicle treated animals, a finding that may represent improved health of the rats in the Compound 231 cohorts. No notable differences in heart rate were noted for rats treated with Compound 231 or sildenafil compared to vehicle. FIGS. 1-8 illustrate the bar graphs of systolic pulmonary artery pressure, mean pulmonary artery pressure, diastolic pulmonary artery pressure, heart rate, systolic arterial pressure, mean arterial pressure, diastolic arterial pressure, and Fulton's index, respectively. Bars from left to right correspond to groups listed in the legend from top to bottom.

Both histopathology evaluation and counts of completely, partially, and non-muscularized arterioles showed a dose-related decrease in pulmonary arteriolar smooth muscle hypertrophy in rats injected with Semaxanib, exposed to hypoxia, and treated with Compound 231 compared to those injected with Semaxanib, exposed to hypoxia, and treated with vehicle (compare FIGS. 9-13). In this study, Sildenafil treatment (FIG. 13) led to a slight decrease in pulmonary arteriolar smooth muscle hypertrophy compared to vehicle treatment (FIG. 10), based on histopathology evaluation.

TABLE 4

Experimental design of Example 36.

| Group/ Test Compound | Test Compound Dose Level (mg/kg) | Stock Concentration (mg/mL) | Dose Volume (mL/kg) | Dose Route | Number of Male Rats |
|---|---|---|---|---|---|
| 1-4/Semaxanib[1] | 200 | 60 | 3.33 | subcutaneous | 40 |
| 1/Vehicle[2,3] | 0 | 0 | 5 | oral gavage | 5 |
| 2/Compound 231[3] | 100 | 20 | 5 | oral gavage | 10 |
| 3/Compound 231[3] | 300 | 60 | 5 | oral gavage | 10 |
| 4/Sildenafil[4] | 60/day | 6 | 5/dose | oral gavage | 10 |
| 5/NA | NA | NA | NA | NA | 2 |

[1]Single dose in DMSO (J.T. Baker, Catalog 9224-01) administered 28 days prior to terminal procedure.
[2]Vehicle is 0.5% methylcellulose, 0.5% Tween80 in water.
[3]Administered once daily for 28 days (Days 1 to 28). Hypoxia during Days 1-28.
[4]Administered twice daily for 28 days (Days 1 to 28). Vehicle is saline. Hypoxia during Days 1-28.

TABLE 5

Summary of endpoint parameters of Example 36.

| Parameter Mean ± SEM | Treatment Cohort (mg/kg) | | | | |
|---|---|---|---|---|---|
| | Vehicle | Compound 231 100 | Compound 231 300 | Sildenafil 60/day bid | Sentinel n = 2 |
| Systolic PAP (mm Hg) | 71 ± 8 | 44 ± 7* | 31 ± 4**,# | 55 ± 5 | — |
| Mean PAP (mm Hg) | 47 ± 4 | 33 ± 4 | 23 ± 3***,# | 38 ± 3 | — |
| MAP (mm Hg) | 78 ± 7 | 96 ± 3* | 104 ± 3** | 92 ± 2 | — |
| HR (bpm) | 271 ± 15 | 283 ± 6 | 283 ± 7 | 289 ± 11 | — |
| Heart Wt (g) | 1.41 ± 0.1 | 1.29 ± 0.05 | 1.24 ± 0.05 | 1.23 ± 0.03 | 1.04 ± 0.03 |
| LV Wt (g) | 0.77 ± 0.05 | 0.80 ± 0.02 | 0.81 ± 0.03 | 0.71 ± 0.02 | 0.71 ± 0.00 |
| RV Wt (g) | 0.44 ± 0.04 | 0.34 ± 0.03 | 0.28 ± 0.02** | 0.36 ± 0.03 | 0.21 ± 0.01 |
| Lung Wt (g) | 2.30 ± 0.11 | 2.57 ± 0.10 | 2.31 ± 0.09 | 2.39 ± 0.07 | 1.60 ± 0.13 |
| RV/LV + S | 0.58 ± 0.05 | 0.42 ± 0.03* | 0.35 ± 0.02***,# | 0.52 ± 0.04 | 0.30 ± 0.02 |
| RV/BW | 1.34 ± 0.12 | 0.93 ± 0.09* | 0.79 ± 0.05** | 1.12 ± 0.10 | 0.57 ± 0.00 |
| Body Weight (kg) | 0.33 ± 0.01 | 0.37 ± 0.01# | 0.36 ± 0.01 | 0.33 ± 0.01 | 0.38 ± 0.02 |

\* = $p < 0.05$, ANOVA - Tukey vs Vehicle
\*\* = $p < 0.01$, ANOVA - Tukey vs Vehicle
\*\*\* = $p < 0.001$, ANOVA - Tukey vs Vehicle
\# = $p < 0.05$, ANOVA - Tukey vs Sildenafil Histopathology evaluation showed that smooth muscle hypertrophy was greatest in Group 1 (Semaxanib/Vehicle) and there was a dose-related decrease in smooth muscle hypertrophy in Groups 2 (Semaxanib/100 mg/kg QD Compound 231) and 3 (Semaxanib/300 mg/kg QD Compound 231) compared to Group 1. There was a slight decrease in smooth muscle hypertrophy in Group 4 (Semaxanib/30 mg/kg BID Sildenafil) compared to Group 1. Group mean scores for smooth muscle hypertrophy were 3.7, 3.0, 2.2, 3.4, and 0 in Groups 1, 2, 3, 4, and 5, respectively.

Figure 14:
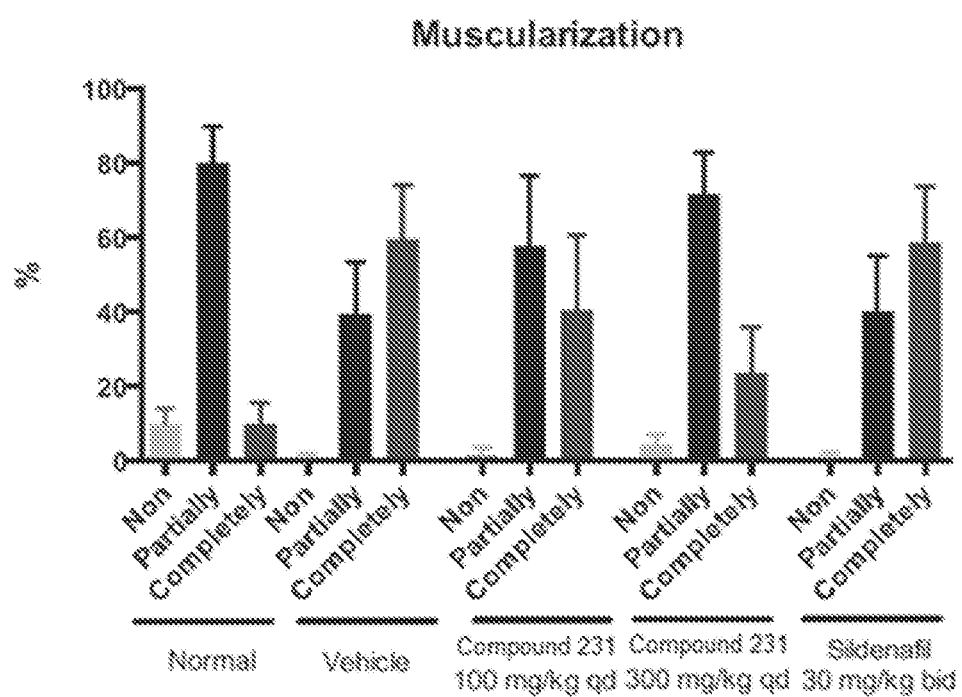
FIG. 14 illustrates effects of HIF-2α inhibitors on preventing pulmonary vascular muscularization.
Figure 15:
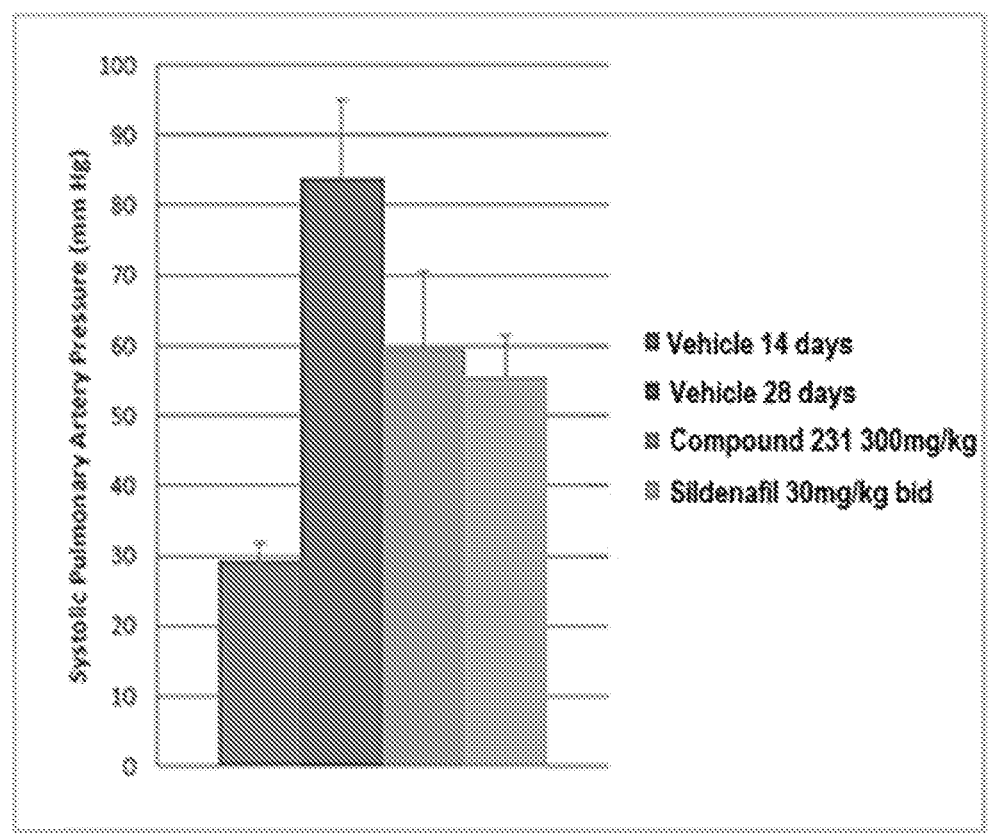
FIG. 15 is a bar graph illustrating effects of HIF-2α inhibitors on treating PAH. HIF-2α inhibitors reduce systolic pulmonary artery pressure in a model of active PAH. Bars from left to right correspond to groups listed in the legend from top to bottom. The dose for Compound 231 was in the indicated amount per day (QD).
Figure 16:
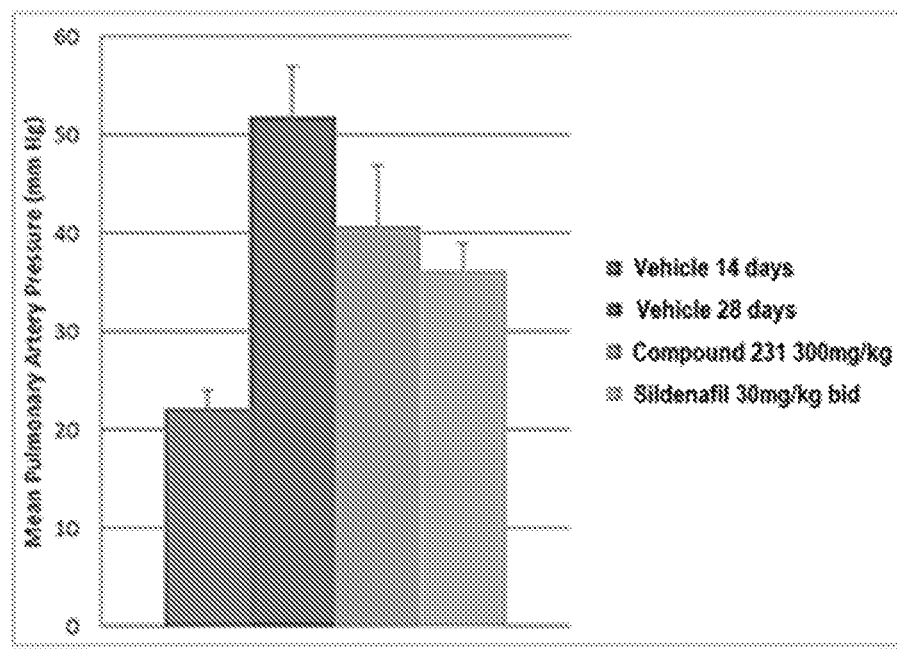
FIG. 16 is a bar graph illustrating effects of HIF-2α inhibitors on treating PAH. HIF-2α inhibitors reduce mean pulmonary artery pressure in a model of active PAH. Bars from left to right correspond to groups listed in the legend from top to bottom. The dose for Compound 231 was in the indicated amount per day (QD).
Figure 17:
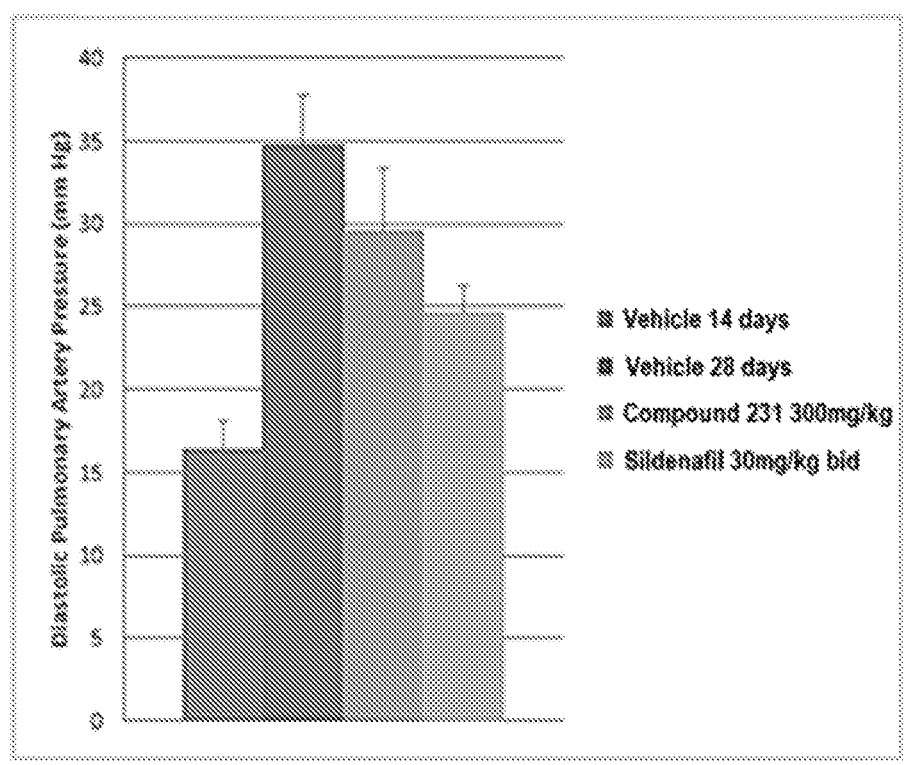
FIG. 17 is a bar graph illustrating effects of HIF-2α inhibitors on treating PAH. HIF-2α inhibitors reduce diastolic pulmonary artery pressure in a model of active PAH. Bars from left to right correspond to groups listed in the legend from top to bottom. The dose for Compound 231 was in the indicated amount per day (QD).
Figure 18:
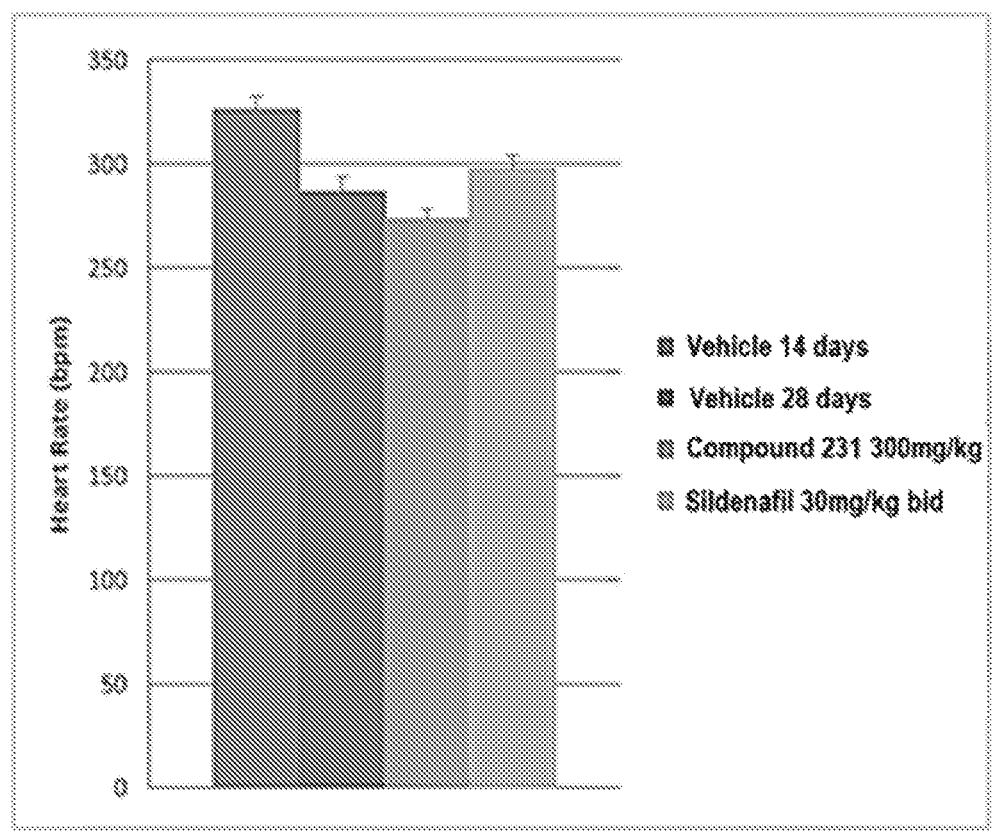
FIG. 18 illustrates effects of HIF-2α inhibitors on heart rate in a model of active PAH. Bars from left to right correspond to groups listed in the legend from top to bottom. The dose for Compound 231 was in the indicated amount per day (QD).
Figure 19:
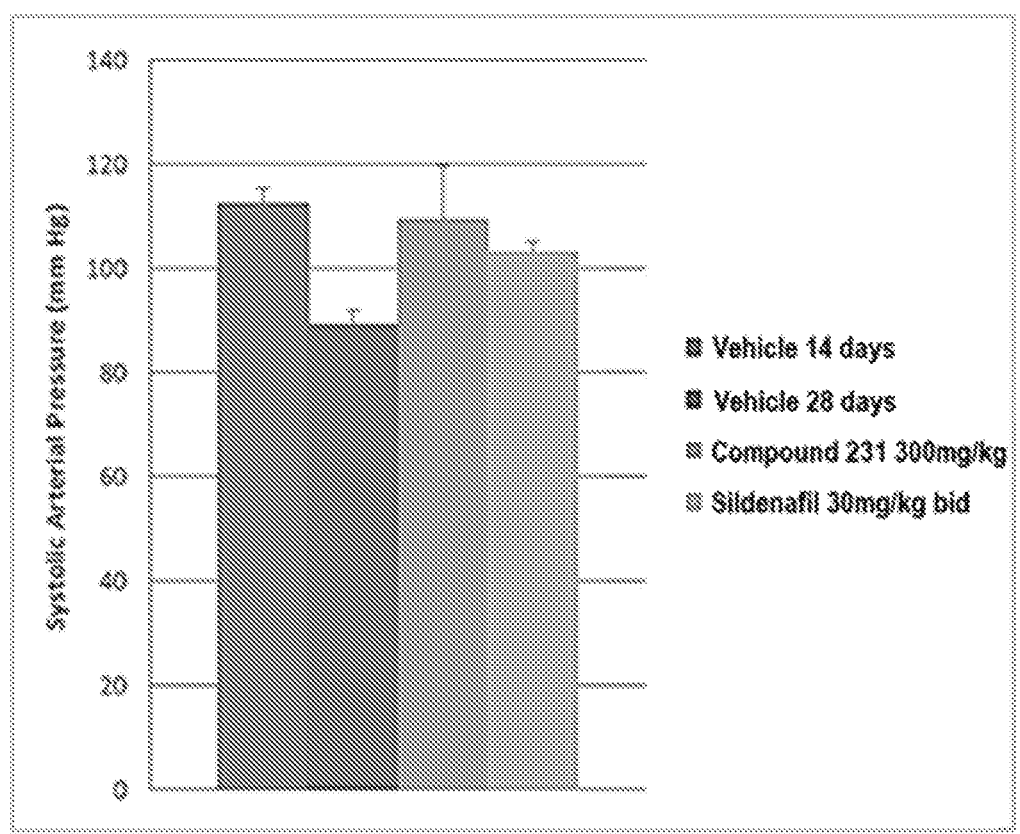
FIG. 19 illustrates effects of HIF-2α inhibitors on systolic arterial pressure in a model of active PAH. Bars from left to right correspond to groups listed in the legend from top to bottom. The dose for Compound 231 was in the indicated amount per day (QD).
Figure 20:
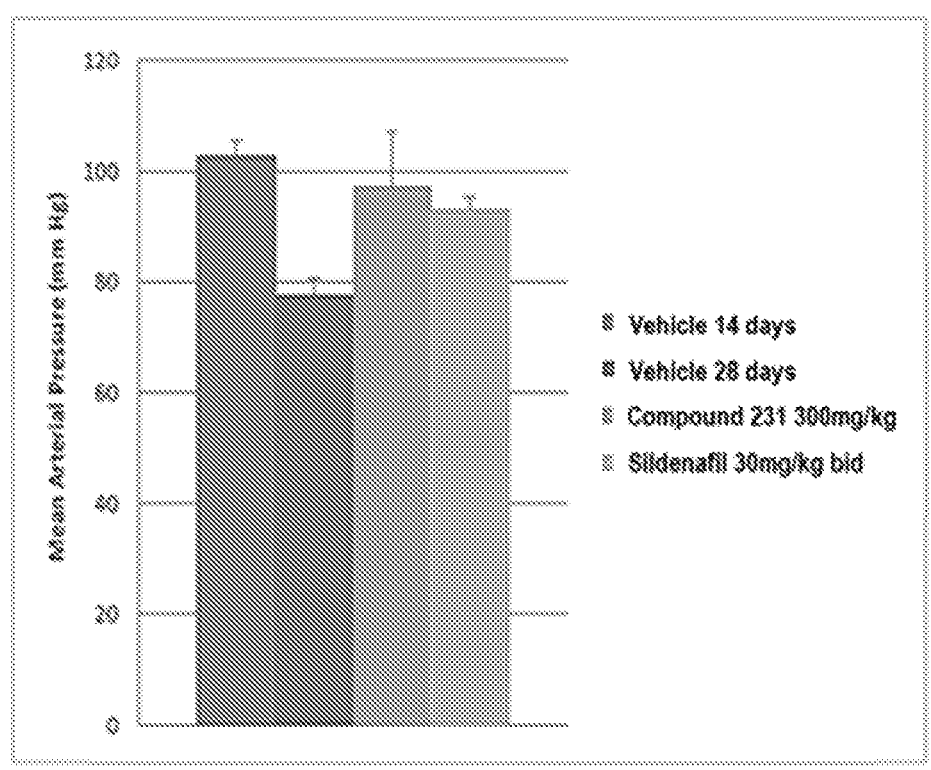
FIG. 20 illustrates effects of HIF-2α inhibitors on mean arterial pressure in a model of active PAH. Bars from left to right correspond to groups listed in the legend from top to bottom. The dose for Compound 231 was in the indicated amount per day (QD).
Figure 21:
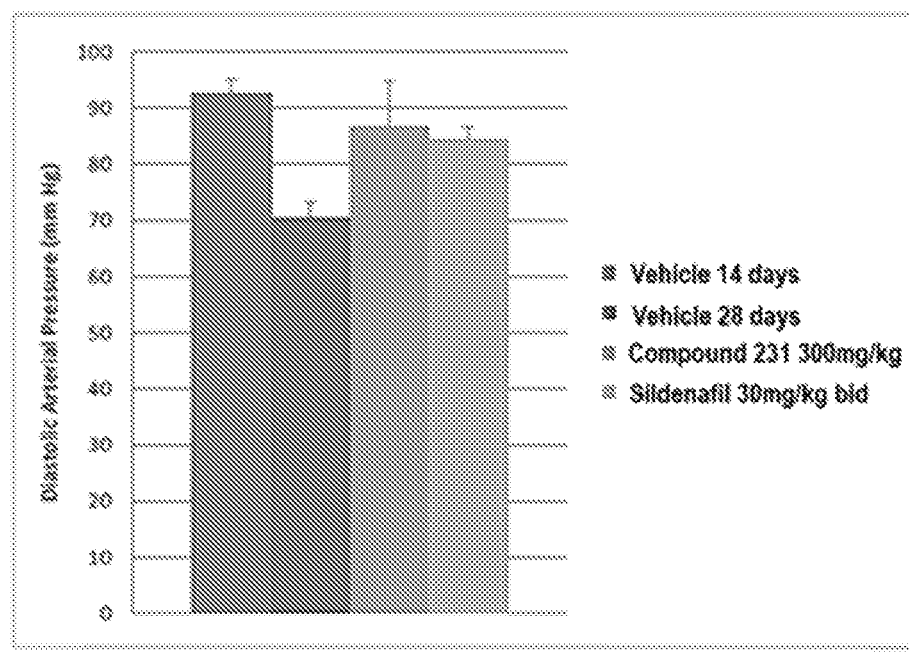
FIG. 21 illustrates effects of HIF-2α inhibitors on diastolic arterial pressure in a model of active PAH. Bars from left to right correspond to groups listed in the legend from top to bottom. The dose for Compound 231 was in the indicated amount per day (QD).

Counts of completely, partially, or non-muscularized arterioles showed that the greatest percentage of completely muscularized arterioles and lowest percentages of non-muscularized and partially muscularized arterioles were in Group 1. Groups 2 and 3 showed dose-related decreases in completely muscularized arterioles and corresponding increases in non-muscularized and partially muscularized arterioles (FIG. 14). Muscularization of arterioles was similar in Groups 1 and 4. The mean percentages of completely muscularized arterioles were 59.6%, 40.6%, 23.8%, 58.7%, and 10.0% in Groups 1, 2, 3, 4, and 5. The mean percentages of partially muscularized arterioles were 39.6%, 57.8%, 71.7%, 40.2%, and 80.0% in Groups 1, 2, 3, 4, and 5, respectively. The mean percentages of non-muscularized arterioles were 0.9%, 1.7%, 4.5%, 1.1%, and 10.0% in Groups 1, 2, 3, 4, and 5, respectively.

Example 37: Effect of HIF-2α Inhibition in a Model of Active PAH

The interventional effects of sildenafil and Compound 231 were evaluated in rats with hypoxia/semaxanib induced pulmonary arterial hypertension. Male Sprague-Dawley rats (n=10 in each group) were orally administered vehicle (0.5% methylcellulose, 0.5% Tween80 in water, administered once daily), Compound 231 (300 mg/kg, administered once daily), or sildenafil (30 mg/kg, administered twice daily) daily for 14 consecutive days starting on Study Day 14 after the initiation of PAH. Four rats not exposed to either semaxanib or hypoxia served as hypertrophic sentinels for this study, while five rats served as a breakout group that were developing PAH only for 14 days. Rats in Groups 2-4 received a single injection of semaxanib (200 mg/kg, s.c.) 28 days prior to terminal assessment. Rats were kept in hypoxic conditions for the duration of this study. On the fourteenth day of test article dosing, the rats were anesthetized with ketamine/xylazine for terminal monitoring of pulmonary and systemic arterial pressures along with heart rate. In addition, lungs from thirty-one male (Sprague Dawley) rats in groups 1 (five rats), 2 (nine rats), 3 (eight rats), and 4 (ten rats) were provided to Seventh Wave for evaluation of histopathology and muscularization of pulmonary arterioles. Table 6 is a summary of the experimental design.

TABLE 6

Experimental design of Example 37.

| Group/ Test Compound | Test Compound Dose Level (mg/kg) | Stock Concentration (mg/mL) | Dose Volume (mL/kg) | Dose Route | Number of Male Rats |
|---|---|---|---|---|---|
| 1-4/Semaxanib[1] | 200 | 60 | 3.33 | subcutaneous | 35 |
| 1/Vehicle[2] | 0 | 0 | 5 | oral gavage | 5 |
| 2/Vehicle[3] | 0 | 0 | 5 | oral gavage | 10 |

TABLE 6-continued

Experimental design of Example 37.

| Group/<br>Test<br>Compound | Test<br>Compound<br>Dose Level<br>(mg/kg) | Stock<br>Concentration<br>(mg/mL) | Dose<br>Volume<br>(mL/kg) | Dose Route | Number of<br>Male Rats |
|---|---|---|---|---|---|
| 3/Compound 231[3] | 300 | 60 | 5 | oral gavage | 10 |
| 4/Sildenafil[4] | 60/day | 6 | 5/dose | oral gavage | 10 |
| 5/NA | NA | NA | NA | NA | 4 |

[1]Single dose in DMSO (J.T. Baker, Catalog 9224-01) administered 14 days (Group 1) or 28 days (Groups 2-4) prior to terminal procedure.
[2]Vehicle is 0.5% methylcellulose, 0.5% Tween80 in water. Administered once daily for 14 days (Days 1 to 14). Hypoxia during Days 1-14. Terminal procedure on Day 14.
[3]Vehicle is 0.5% methylcellulose, 0.5% Tween80 in water. Administered once daily for 14 days (Days 15 to 28). Hypoxia during Days 1-28. Terminal procedure on Day 28.
[4]Administered twice daily for 14 days (Days 15 to 28). Vehicle is saline. Hypoxia during Days 1-28. Terminal, procedure on Day 28.

Moderate reductions in systolic and mean pulmonary arterial pressures were observed after 14 days of interventional treatment with Compound 231 compared to the vehicle group (Table 7). The 300 mg/kg QD dose of Compound 231 showed a 29% reduction in systolic pulmonary arterial pressure—the variable used as the arbiter of protection. The 300 mg/kg QD Compound 231 systolic pulmonary artery pressures were not significantly different from sildenafil-treated rats. Rats treated with Compound 231 at 300 mg/kg QD presented with an 8% reduction in Fulton's right ventricular hypertrophy ratio. When correcting RV weight by body weight, 300 mg/kg QD Compound 231 rats only showed a 7% decrease in this ratio compared to vehicle. However, pulmonary hypertrophy was significantly reduced with Compound 231 treatment. Sildenafil rats presented with a 21% reduction ($p<0.05$) in RV/BW ratio, along with reductions in pulmonary hypertrophy. Mean arterial pressure was also significantly increased in Compound 231 rats compared to vehicle treated animals. No substantive differences in heart rate were noted for rats treated with Compound 231 or sildenafil compared to vehicle. FIGS. 15-21 illustrate the bar graphs of systolic pulmonary artery pressure, mean pulmonary artery pressure, diastolic pulmonary artery pressure, heart rate, systolic arterial pressure, mean arterial pressure, and diastolic arterial pressure. Bars from left to right correspond to groups listed in the legend from top to bottom.

TABLE 7

Summary of endpoint parameters of Example 37.

| Parameter<br>Mean ± SEM | Treatment Cohort (mg/kg) | | |
|---|---|---|---|
| | Vehicle | Compound 231<br>300 | Sildenafil<br>60/day bid |
| Systolic PAP<br>(mm Hg) | 84 ± 11 | 60 ± 11 | 56 ± 6 |
| Mean PAP<br>(mm Hg) | 52 ± 5 | 41 ± 6 | 36 ± 3* |
| MAP<br>(mm Hg) | 77 ± 3 | 97 ± 10 | 93 ± 2 |
| HR<br>(bpm) | 286 ± 8 | 274 ± 5 | 298 ± 6 |
| Heart Wt<br>(g) | 1.41 ± 0.1 | 1.39 ± 0.07 | 1.25 ± 0.04 |
| LV Wt<br>(g) | 0.81 ± 0.04 | 0.83 ± 0.03 | 0.75 ± 0.02 |
| RV Wt<br>(g) | 0.39 ± 0.02 | 0.37 ± 0.04 | 0.35 ± 0.02 |
| Lung Wt<br>(g) | 2.40 ± 0.07 | 2.09 ± 0.08*,+ | 2.36 ± 0.07 |
| LW/BW | 7.57 ± 0.30 | 6.26 ± 0.20* | 6.68 ± 0.15 |
| RV/LV + S | 0.48 ± 0.02 | 0.44 ± 0.04 | 0.46 ± 0.02 |
| RV/BW | 1.24 ± 0.07 | 1.15 ± 0.08 | 0.98 ± 0.07* |
| Body Weight<br>(kg) | 0.32 ± 0.01 | 0.34 ± 0.02 | 0.35 ± 0.01 |

Figure 22:
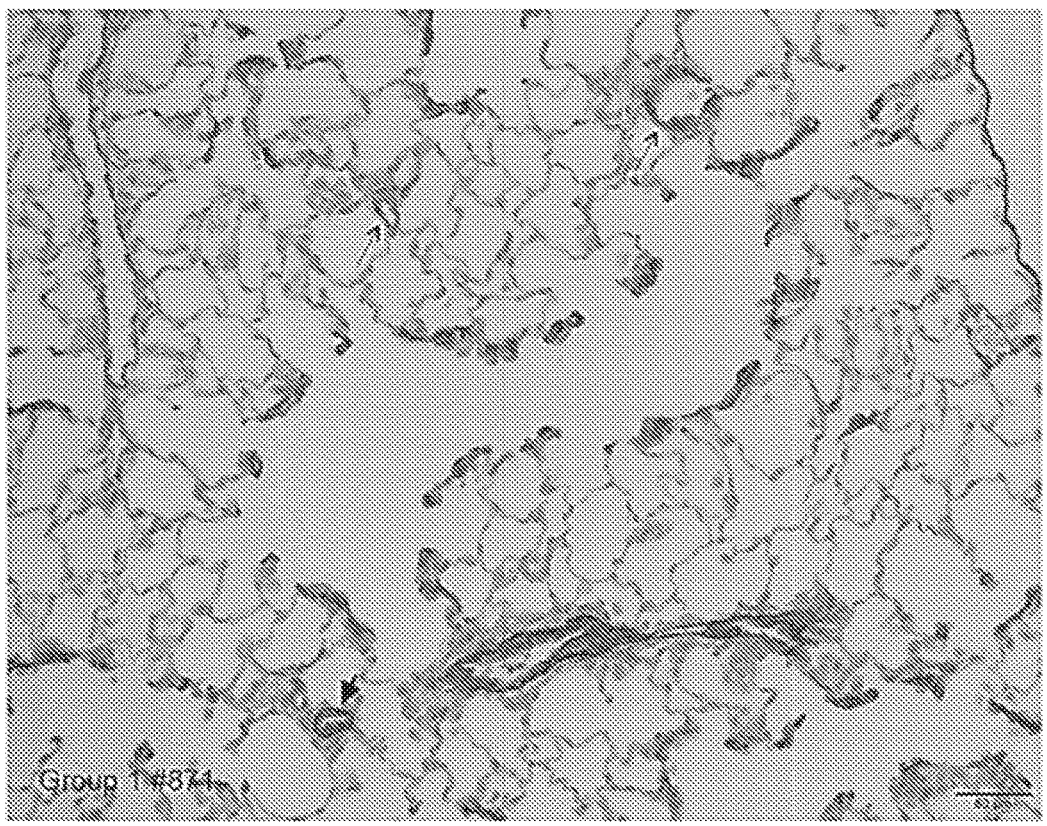
FIG. 22 shows the histopathology of lung tissues in a model of active PAH treated with a vehicle for 14 days. Short arrow points to a completely muscularized small pulmonary arteriole. Long, thin arrows point to a partially muscularized small pulmonary arterioles.
Figure 23:
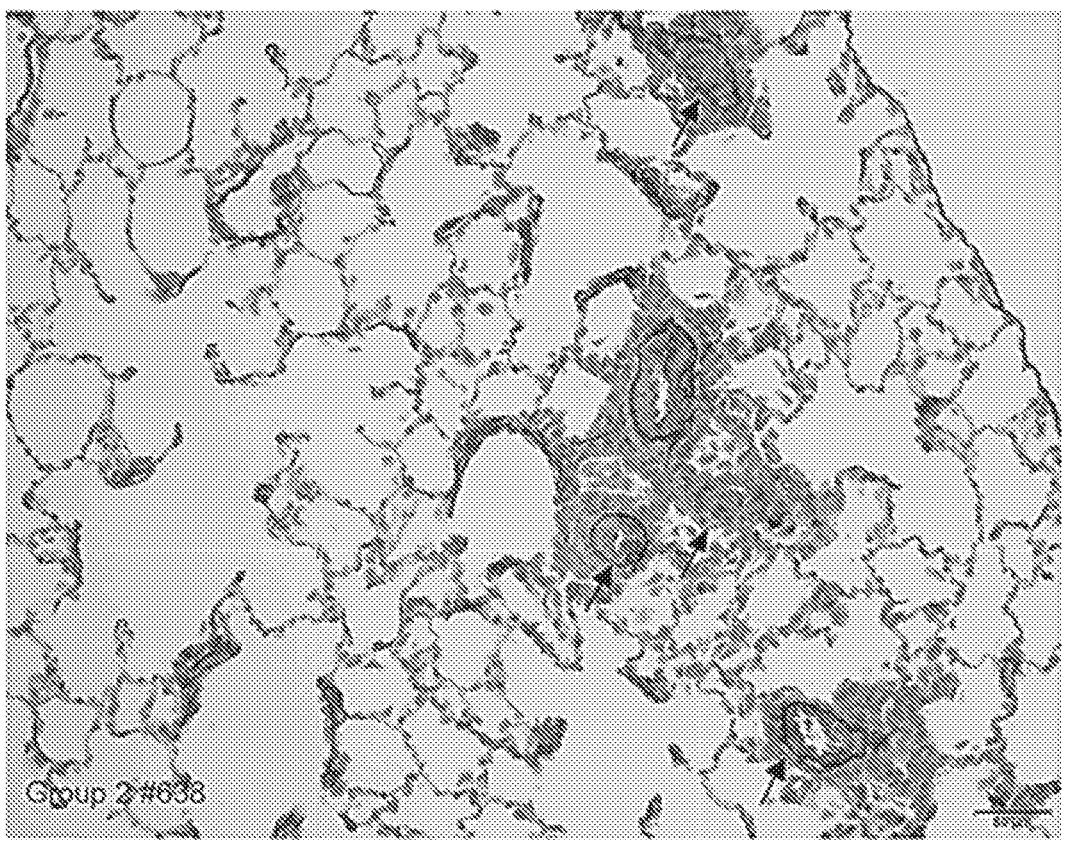
FIG. 23 shows the histopathology of lung tissues in a model of active PAH treated with a vehicle for 28 days. Arrows point to completely muscularized small pulmonary arterioles. The arteriolar walls are thick relative to the size of the lumens. There are minimal inflammatory infiltrates surrounding the arterioles.
Figure 24:
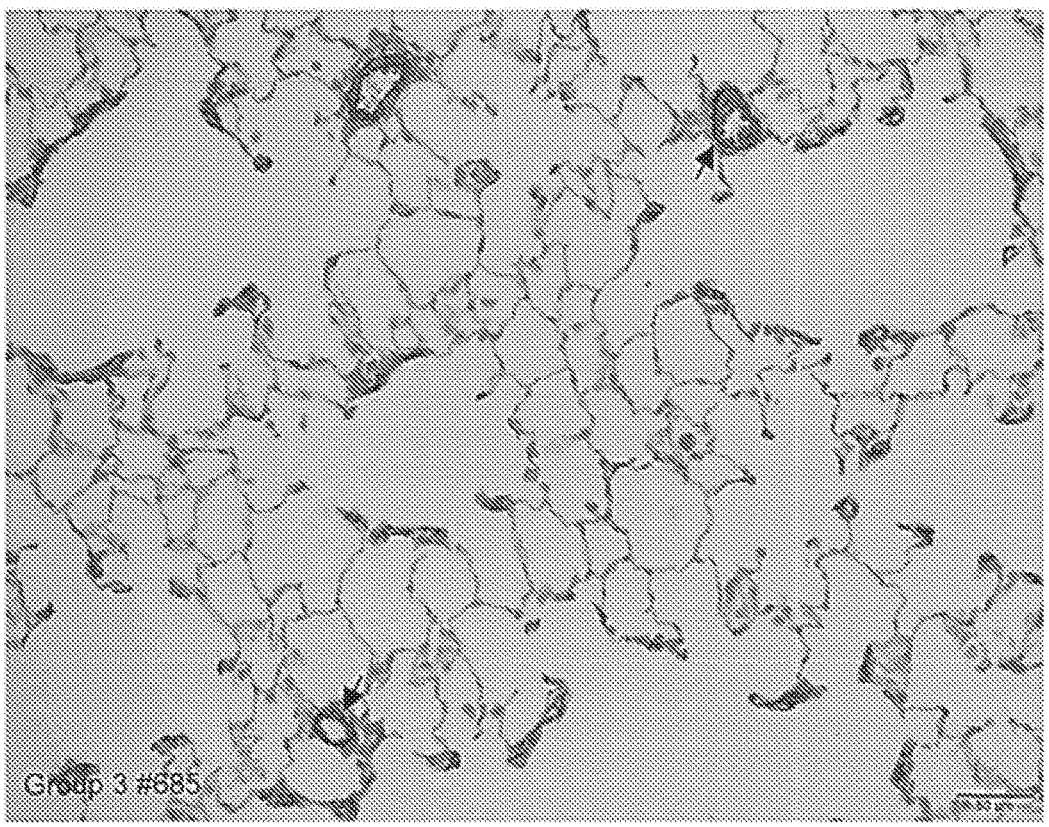
FIG. 24 shows the histopathology of lung tissues in a model of active PAH treated with 300 mg/kg Compound 231. Arrows point to completely muscularized small pulmonary arterioles.
Figure 25:
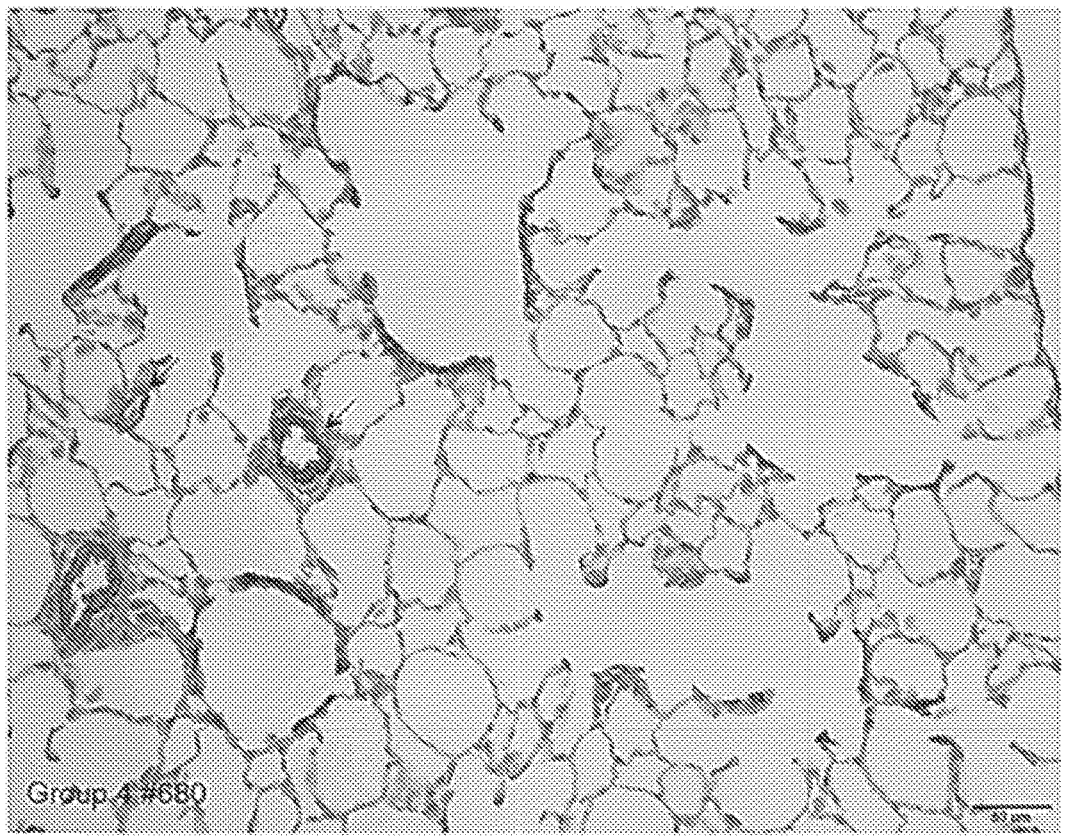
FIG. 25 shows the histopathology of lung tissues in a model of active PAH treated with 30 mg/kg bid sildenafil. Arrows point to partially muscularized small pulmonary arterioles. There are minimal inflammatory infiltrates around one partially muscularized arteriole and the completely muscularized arteriole in the lower left corner of the image.
Figure 26:
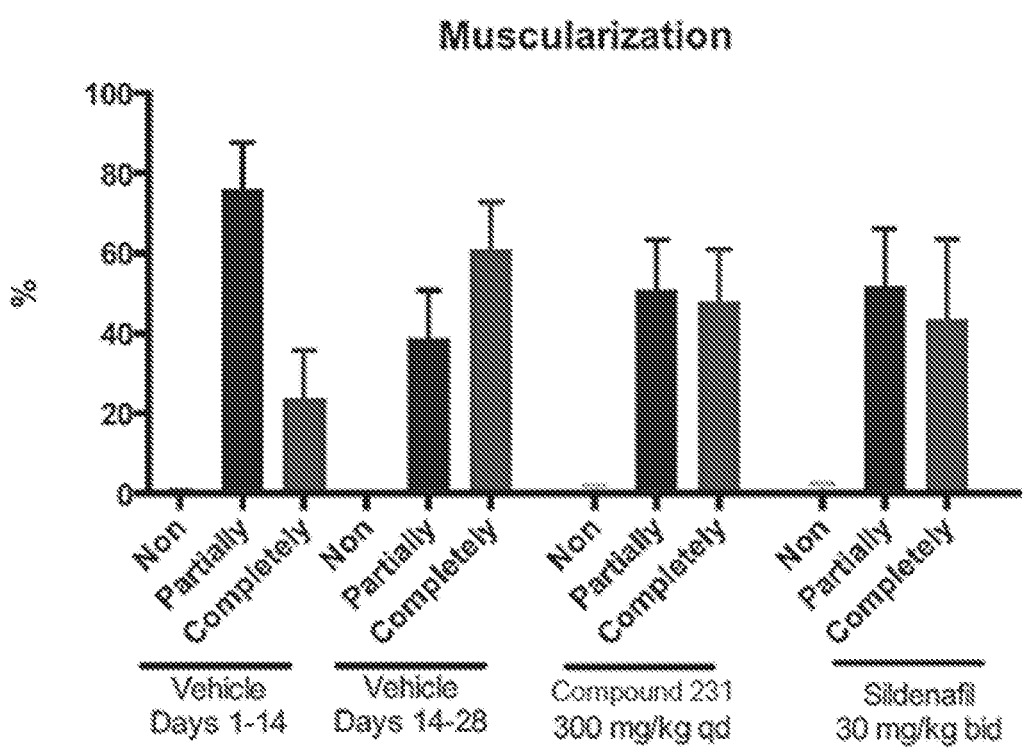
FIG. 26 depicts effects of HIF-2α inhibitors on treating pulmonary vascular muscularization in a model of active PAH.

* = $p < 0.05$, ANOVA - Tukey vs Vehicle
+ = $p < 0.05$, ANOVA - Tukey vs Sildenafil Both histopathology evaluation and counts of completely, partially, and non-muscularized arterioles showed a similar decrease in pulmonary arteriolar smooth muscle hypertrophy in rats injected with Semaxanib, exposed to hypoxia, and treated for 14 days with 300 mg/kg/day Compound 231 or 60 mg/kg/day Sildenafil compared to those injected with Semaxanib, exposed to hypoxia, and treated with vehicle for 28 days. Rats in Group 2 (28 days of vehicle treatment, FIG. 23) also exhibited slightly more perivascular inflammation and perivascular fibrosis, based on severity scores and/or incidence, than those in other groups. Group 1 (14 days of vehicle treatment, FIG. 22) showed the least amount of pulmonary arteriolar smooth muscle hypertrophy based on histopathology and counts of arterioles in each category. FIGS. 24 and 25 show histopathology of Compound 231 and sildenafil treated rats, respectively. Histopathology scoring of pulmonary vascular muscularization are illustrated in FIG. 26. Lungs from rats in Group 1 did not exhibit perivascular inflammation or perivascular fibrosis.

Group mean scores for smooth muscle hypertrophy were 1.4, 3.8, 2.8, and 2.6 in Groups 1, 2, 3, and 4, respectively. The mean percentages of completely muscularized arterioles were 23.8, 61.0, 48.0, and 47.2 in Groups 1, 2, 3, and 4, respectively. The mean percentages of partially muscularized arterioles were 76.0, 38.9, 50.9, and 51.7 in Groups 1, 2, 3, and 4, respectively. The mean percentages of non-muscularized arterioles were 0.2, 0.1, 0.9, and 1.1 in Groups 1, 2, 3, and 4, respectively.

Example 38: Effects of HIF-2α Inhibition in a Human Subject with PAH

A HIF-2α inhibitor can be administered to a human subject suffering from PAH, such as about 0.05 to 50 mg/kg. Prior to administering the HIF-2α inhibitor, a baseline can be established for one or more of pulmonary vascular resistance, pulmonary arterial pressure, systemic arterial pressure, mixed venous oxygen saturation, arterial oxygen saturation, cardiac index, pulmonary capillary wedge pressure, right atrial pressure, six-minute walk distance, brain natriuretic peptide level, and lung diffusion capacity. Upon beginning treatment with the HIF-2α inhibitor, the parameters for which a baseline is established can be monitored over time for any improvement in one or more of these parameters (e.g. an increase in six-minute walk distance, or a decrease in pulmonary vascular resistance).

Example 39: Assay for Testing Inhibition of HIF-2α Dimerization

This example describes an example assay for testing inhibition of HIF-2α dimerization using co-immunoprecipitation.

Cell Culture and Compound Treatment

786-O cells were cultured in Dulbecco's Modified Eagle's Medium (DMEM, D5796, Sigma) supplemented with 10% FBS (F6178, Sigma), 100 units penicillin, and 100 µg/mL streptomycin (P4333, Sigma). About $5 \times 10^5$ cells were plated into 6-well cell culture plates (Corning Cat#3506) in 2 mL of media and were placed in a 37° C. cell culture incubator with atmospheric levels of oxygen and 5% $CO_2$. As the cultures reached confluence, 2 µl of Compound 163 or 226 diluted in DMSO at 1000× of final concentration was added.

Co-Immunoprecipitation Analysis of HIF and ARNT

Cells in a 6-well plate were washed with 1 ml of DPBS and lysed in 1 ml of cell lysis buffer (Tris-HCl 20 mM, pH 7.5, Triton X100 1%, NaCl 150 mM, Glycerol 5%, EDTA 1 mM, DTT 1 mM and 1 tablet per 10 mls of Roche Proteinase Inhibitor Tablet Complete). The cell lysate was transferred to a 1.5 mL Eppendorf tube, and was incubated on ice for 15 to 20 min. The debris was spun down in an Eppendorf microfuge tube at 15,000 RPM for 15 min at 4° C., and the supernatant was transferred into a new tube. 1 µg of mouse mAb against human ARNT (Santa Cruz, sc-55526) or 1 µg of antibody against HIF-2α (Abcam Ab199) and 50 µl of Protein AG beads (Santa Cruse, 50% slurry in lysis buffer) were added. The tubes were rotated at 4° C. for 2 to 16 hours. The beads were spun down and washed three times with 1 ml cold lysis buffer and resuspended in 30 µl of SDS sample buffer (10% Glycerol, 60 mM Tri-HCl pH6.8, 2% Sodium Dodecyl Sulfate, 0.01% Bromophenol Blue and 1.25% β-mercaptoethanol). The tubes were boiled for 3 min. The beads were spun down, and supernatant was loaded on a denaturing acrylamide gel (Bio-Rad precasted gel) for electrophoresis. The proteins in the gels were then transferred to 0.2 µM PVDF membrane (Bio-Rad) using Bio-Rad Trans-Blot Turbo transfer system.

For Western Blotting, the membranes were incubated in TBST (10 mM Tris-HCl pH 7.4, 150 mM Sodium Chloride and 0.1% Tween 20) containing 5% dry milk for 1 hour. The membranes were incubated with antibody to HIF-2α (Abcam Ab199) at 1:500 dilutions in the blocking buffer overnight. The membrane was washed three times in TBST then incubated in TBST with 5% dry milk with HPR-conjugated goat anti rabbit (Bio-Rad 172-1019) at 1:5000 dilution for ARNT detection. The Western blot signals were developed using Thermo Super-Western Pico Lumino/Enhancer Solution following the protocol provided by the manufacturer.

Disruption of HIF-2α and ARNT Dimerization

Figure 27:
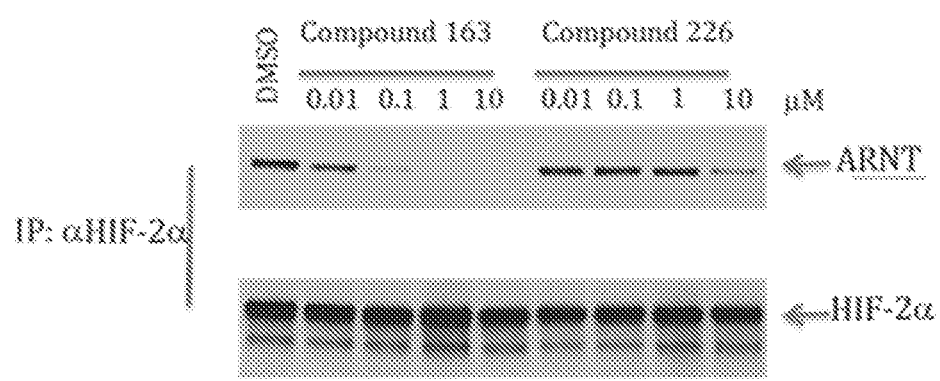
FIG. 27 depicts results of a co-immunoprecipitation assay for measuring inhibition of HIF-2α and ARNT dimerization.
Figure 27:
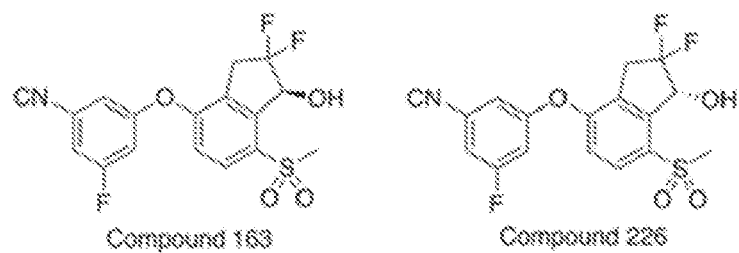

Total protein was extracted from 786-O cells treated with the indicated concentration of Compound 163 and Compound 226. HIF-2α protein complex was immunoprecipitated with antibody to HIF-2α. The immunoprecipitants were blotted with antibody against ARNT. ARNT protein coprecipitated with HIF-2α was reduced in a lysate of cells treated with Compound 163 in a dose-dependent manner (FIG. 27). Compound 226 reduced ARNT protein in complex with HIF-2α only at the highest concentration (10 µM).

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure It should be understood that various alternatives to the embodiments of the disclosure described herein may be employed in practicing the disclosure. It is intended that the appended claims define the scope of the disclosure and that methods and structures within the scope of these claims and their equivalents be covered thereby.

A composition of the present disclosure may be formulated in any suitable pharmaceutical formulation. A pharmaceutical composition of the present disclosure typically contains an active ingredient (e.g., a compound of the present disclosure or a pharmaceutically acceptable salt and/or coordination complex thereof), and one or more pharmaceutically acceptable excipients, carriers, including but not limited to, inert solid diluents and fillers, diluents, sterile aqueous solution and various organic solvents, permeation enhancers, solubilizers and adjuvants. A composition of the present disclosure may be formulated in any suitable pharmaceutical formulation. In some embodiments, the pharmaceutical acceptable carriers, excipients are selected from the group consisting of water, alcohol, glycerol, chitosan, alginate, chondroitin, Vitamin E, mineral oil, and dimethyl sulfoxide (DMSO).

Pharmaceutical formulations may be provided in any suitable form, which may depend on the route of administration. In some embodiments, the pharmaceutical composition disclosed herein can be formulated in dosage form for administration to a subject. In some embodiments, the pharmaceutical composition is formulated for oral, intravenous, intraarterial, aerosol, parenteral, buccal, topical, transdermal, rectal, intramuscular, subcutaneous, intraosseous, intranasal, intrapulmonary, transmucosal, inhalation, and/or intraperitoneal administration. In some embodiments, the dosage form is formulated for oral intervention administration. For example, the pharmaceutical composition can be formulated in the form of a pill, a tablet, a capsule, an inhaler, a liquid suspension, a liquid emulsion, a gel, or a powder. In some embodiments, the pharmaceutical composition can be formulated as a unit dosage in liquid, gel, semi-liquid, semi-solid, or solid form.

In some embodiments, the disclosure provides a pharmaceutical composition

What is claimed is:

1. A method of treating pulmonary arterial hypertension (PAH), comprising administering to a subject in need thereof a composition comprising an effective amount of a HIF-2α inhibitor, wherein the HIF-2α inhibitor is a compound of Formula I-C:

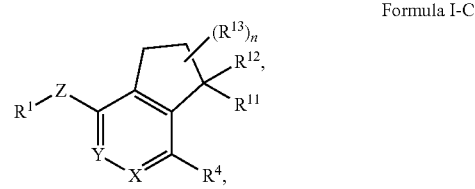

Formula I-C or a pharmaceutically acceptable salt thereof, wherein:

X is $CR^5$ or N;
Y is $CR^6$ or N;
Z is O, S, $CHR^7$, $NR^8$ or absent;
$R^1$ is alkyl, heteroalkyl, cycloalkyl, heterocycloalkyl, aryl, heteroaryl, acyl or cyano;
$R^4$ is nitro, halo, cyano, alkyl, cycloalkyl, heteroaryl, carboxyl, sulfinyl, sulfonamidyl, sulfonyl, sulfoximinyl or fluoroalkylsulfonyl;
$R^5$, $R^6$, $R^7$ and $R^8$ are independently hydrogen, halo, hydroxy, cyano, alkyl or alkoxy;
$R^{11}$ is hydroxy, alkoxy or amino;
$R^{12}$ is hydrogen;
each of $R^{13}$ is independently selected from the group consisting of hydrogen, fluoro, chloro, hydroxy, alkyl and heteroalkyl; or two $R^{13}$s and the carbon atom(s) to which they are attached form a 3- to 8-membered cycloalkyl or heterocycloalkyl moiety; and
n is 0, 1, 2, 3 or 4.

2. The method of claim 1, wherein:
$R^4$ is cyano, fluoroalkyl, sulfinyl, sulfonamidyl, sulfonyl or sulfoximinyl;
$R^{11}$ is hydroxy or amino; and
$R^{12}$ is hydrogen.

3. The method of claim 1, wherein $R^{13}$ is fluoro and n is 1, 2 or 3.

4. The method of claim 1, wherein the HIF-2α inhibitor is a compound of Formula I-H, I-I, I-J or I-K:

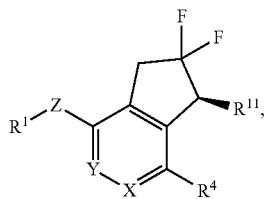
I-H

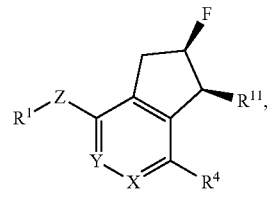
I-I

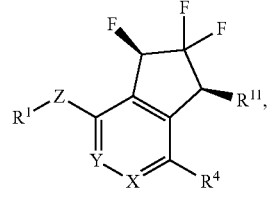
I-J

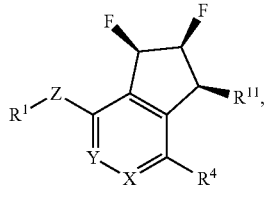
I-K or a pharmaceutically acceptable salt thereof.

5. The method of claim 1, wherein $R^{11}$ is hydroxy or amino.

6. The method of claim 1, wherein $R^1$ is phenyl, monocyclic heteroaryl or bicyclic heteroaryl.

7. The method of claim 6, wherein $R^1$ is phenyl or pyridyl.

8. The method of claim 1, wherein $R^1$ is substituted with at least one substituent selected from the group consisting of halo, $C_1$-$C_4$ alkyl, $C_1$-$C_4$ alkoxy and cyano.

9. The method of claim 1, wherein $R^4$ is cyano, fluoroalkyl, sulfinyl, sulfonamidyl, sulfonyl or sulfoximinyl.

10. The method of claim 1, wherein Z is O.

11. The method of claim 1, wherein:
$R^4$ is fluoroalkyl or sulfonyl;
n is 0, 1, 2 or 3;
Z is O;
$R^{11}$ is hydroxy; and
$R^{12}$ is hydrogen.

12. The method of claim 11, wherein $R^1$ is phenyl, pyridyl, cycloalkyl or heterocycloalkyl.

13. The method of claim 1, wherein X is $CR^5$ and Y is $CR^6$.

14. The method of claim 1, wherein the HIF-2α inhibitor is selected from the group consisting of:

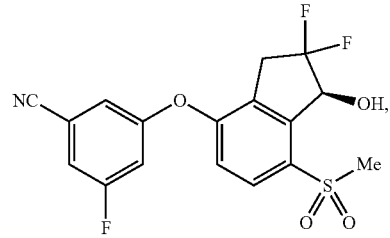

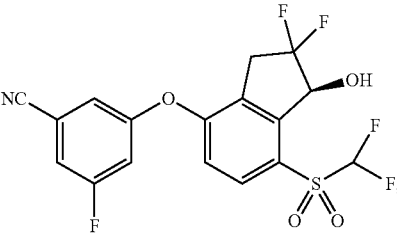

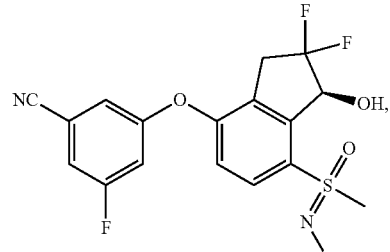

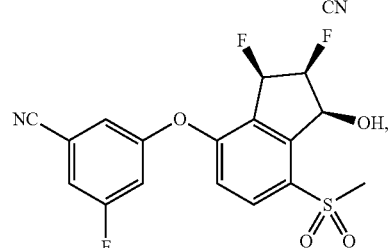

441
-continued

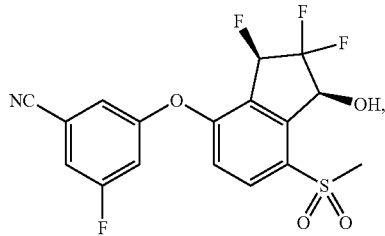

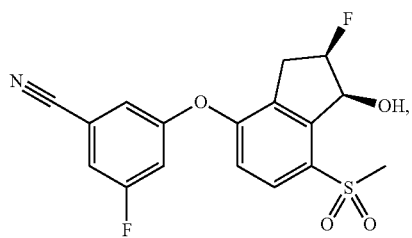

442
-continued

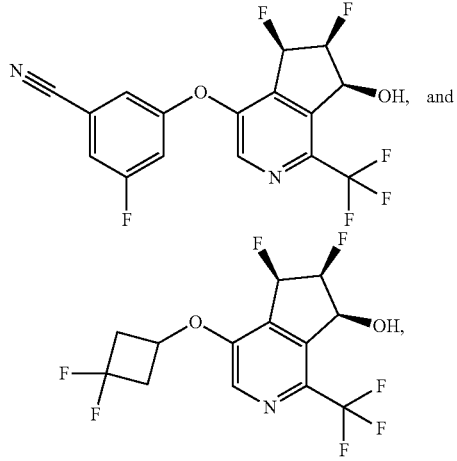

or a pharmaceutically acceptable salt thereof.

15. The method of claim 1, wherein a second therapeutic agent is administered simultaneously or sequentially with the HIF-2α inhibitor.

16. The method of claim 1, further comprising (a) measuring a physiological indicator of PAH before and after the administering, and (b) adjusting dosage or discontinuing use of the HIF-2α inhibitor based on a result of step (a).

* * * * *